United States Patent
Bhowmik et al.

(10) Patent No.: US 12,384,773 B2
(45) Date of Patent: Aug. 12, 2025

(54) THIAZOLE COMPOUNDS AND METHODS OF USE THEREOF

(71) Applicant: Arcus Biosciences, Inc., Hayward, CA (US)

(72) Inventors: Srijita Bhowmik, Hayward, CA (US); Karen Yir Jing Chen, Hayward, CA (US); Jenna Leigh Jeffrey, Hayward, CA (US); Manjunath Lamani, Hayward, CA (US); Manmohan Reddy Leleti, Hayward, CA (US); Guillaume Mata, Hayward, CA (US); Hyunyoung Moon, Hayward, CA (US); Pradeep Nareddy, Hayward, CA (US); Srinivas Paladugu, Hayward, CA (US); Zhang Wang, Foster City, CA (US); Xuelei Yan, Hayward, CA (US); Monika Yadav, Hayward, CA (US); Jiang Zhu, Hayward, CA (US)

(73) Assignee: Arcus Biosciences, Inc., Hayward, CA (US)

( * ) Notice: Subject to any disclaimer, the term of this patent is extended or adjusted under 35 U.S.C. 154(b) by 0 days.

(21) Appl. No.: 18/934,931

(22) Filed: Nov. 1, 2024

(65) Prior Publication Data

US 2025/0145606 A1 May 8, 2025

Related U.S. Application Data

(60) Provisional application No. 63/563,078, filed on Mar. 8, 2024, provisional application No. 63/595,707, filed on Nov. 2, 2023.

(51) Int. Cl.
| | |
|---|---|
| C07D 417/12 | (2006.01) |
| A61K 31/426 | (2006.01) |
| A61K 31/427 | (2006.01) |
| A61K 31/429 | (2006.01) |
| A61K 31/433 | (2006.01) |
| A61K 31/4355 | (2006.01) |
| A61K 31/436 | (2006.01) |
| A61K 31/4439 | (2006.01) |
| A61K 31/496 | (2006.01) |
| A61K 31/497 | (2006.01) |
| A61K 31/4985 | (2006.01) |
| A61K 31/501 | (2006.01) |
| A61K 31/506 | (2006.01) |
| A61K 31/5377 | (2006.01) |
| C07D 277/56 | (2006.01) |
| C07D 417/14 | (2006.01) |
| C07D 487/04 | (2006.01) |
| C07D 491/048 | (2006.01) |
| C07D 491/052 | (2006.01) |
| C07D 513/04 | (2006.01) |

(52) U.S. Cl.
CPC .......... *C07D 417/12* (2013.01); *A61K 31/426* (2013.01); *A61K 31/427* (2013.01); *A61K 31/429* (2013.01); *A61K 31/433* (2013.01); *A61K 31/4355* (2013.01); *A61K 31/436* (2013.01); *A61K 31/4439* (2013.01); *A61K 31/496* (2013.01); *A61K 31/497* (2013.01); *A61K 31/4985* (2013.01); *A61K 31/501* (2013.01); *A61K 31/506* (2013.01); *A61K 31/5377* (2013.01); *C07D 277/56* (2013.01); *C07D 417/14* (2013.01); *C07D 487/04* (2013.01); *C07D 491/048* (2013.01); *C07D 491/052* (2013.01); *C07D 513/04* (2013.01)

(58) Field of Classification Search
CPC .................................................... C07D 417/12
USPC ...................................................... 514/210.18
See application file for complete search history.

(56) References Cited

U.S. PATENT DOCUMENTS

| | | | |
|---|---|---|---|
| 7,169,771 B2 | 1/2007 | Hynes et al. | |
| 7,323,482 B2 | 1/2008 | Hynes et al. | |
| 8,067,638 B2 | 11/2011 | Kai et al. | |
| 8,168,825 B2 | 5/2012 | Yoshida et al. | |
| 2005/0176965 A1 | 8/2005 | Chen et al. | |
| 2006/0069132 A1 | 3/2006 | Armel et al. | |

(Continued)

FOREIGN PATENT DOCUMENTS

| | | |
|---|---|---|
| CN | 114805294 A | 7/2022 |
| EP | 4 074 376 A1 | 10/2022 |
| WO | WO-2004/035545 A2 | 4/2004 |

(Continued)

OTHER PUBLICATIONS

Chen et al., "Discovery of a potent and selective c-Kit inhibitor for the treatment of inflammatory diseases", Bioorganic & Medicinal Chemistry Letters, 18(14):4137-4141 (Jul. 15, 2008).

(Continued)

*Primary Examiner* — Kahsay Habte
(74) *Attorney, Agent, or Firm* — Foley & Lardner LLP; Brittany J. Perla

(57) ABSTRACT

The present disclosure is directed to compounds having a structure according to Formula I, and compositions containing those compounds. Methods of using the compounds for the treatment of diseases, disorders, or conditions are also described.

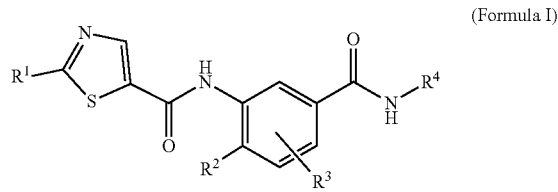

(Formula I)

14 Claims, No Drawings

(56) References Cited

U.S. PATENT DOCUMENTS

2011/0301181 A1    12/2011    Maue et al.

FOREIGN PATENT DOCUMENTS

| WO | WO-2004/071440 A2 | 8/2004 |
| WO | WO-2005/077945 A2 | 8/2005 |
| WO | WO-2006/067445 A2 | 6/2006 |
| WO | WO-2006/067446 A1 | 6/2006 |
| WO | WO-2006/081172 A2 | 8/2006 |
| WO | WO-2007/022380 A2 | 2/2007 |
| WO | WO-2007/071955 A1 | 6/2007 |
| WO | WO-2008/075465 A1 | 6/2008 |
| WO | WO-2010/133312 A1 | 11/2010 |
| WO | WO-2013/033070 A1 | 3/2013 |
| WO | WO-2018/183122 A1 | 10/2018 |
| WO | WO-2021/214117 A1 | 10/2021 |
| WO | WO-2022/136509 A1 | 6/2022 |
| WO | WO-2022/150384 A1 | 7/2022 |
| WO | WO-2023/194458 A1 | 10/2023 |
| WO | WO-2024/118887 A1 | 6/2024 |
| WO | WO-2024/123966 A1 | 6/2024 |
| WO | WO-2024/124002 A1 | 6/2024 |

OTHER PUBLICATIONS

Database accession No. 1626657-23-5 compound with the Registry No. 1626657-23-5, Database Registry [online] Chemical Abstract Service, Columbus, Ohio, 1 page, Sep. 26, 2014.

International Search Report and Written Opinion on PCT/US2024/054166 dated Jan. 30, 2025, 12 pages.

Pathania et al., "A holistic view on c-Kit in cancer: Structure, signaling, pathophysiology and its inhibitors," Biochimica et Biophysica ACTA (BBA)—Reviews on Cancer, 1876(2):188631, 21 pages (Oct. 1, 2021).

THIAZOLE COMPOUNDS AND METHODS OF USE THEREOF

CROSS-REFERENCE TO RELATED APPLICATIONS

This application claims the benefit of priority to U.S. Provisional Patent Application No. 63/595,707 filed on Nov. 2, 2023, and U.S. Provisional Patent Application No. 63/563,078, filed on Mar. 8, 2024, the entire contents of each of which are incorporated by reference herein.

BACKGROUND

The following discussion is provided to aid the reader in understanding the disclosure and is not admitted to describe or constitute prior art thereto.

Mast cells contain granules containing proinflammatory and immunomodulatory mediators. Upon activation, degranulation occurs, releasing these proinflammatory and immunomodulatory mediators into the surrounding tissues, generally in response to a perceived pathogen (e.g., parasitic, bacterial and viral infections, allergens, toxins, etc.). The activation of mast cells serves to induce an immune response to protect the body from pathogens, and to aid in wound healing, and tissue repair. However, misfunctioning mast cells underlie the etiology of many allergic and chronic inflammatory diseases and are implicated in a broad spectrum of conditions.

The activation of receptor tyrosine kinase KIT on mast cells by its ligand, Stem Cell Factor (SCF), is required for mast cell differentiation, maturation, and survival. For certain diseases, mast cell activation may play a central role in the onset and progression of the disease. Accordingly, inhibition of KIT may lead to mast cell depletion, and provide a promising therapeutic approach for mast cell-driven diseases. Thus, there is a need to develop inhibitors of KIT.

SUMMARY

In one aspect, the present disclosure relates to compounds represented by Formula I.

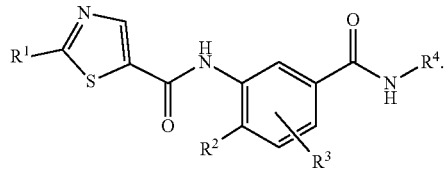

(Formula I)

In another aspect, this disclosure is directed to methods of inhibiting KIT in a subject comprising administering to the subject an effective amount of a compound of Formula I described herein.

In another aspect, this disclosure is directed to methods of reducing the activity and/or quantity of systemic mast cells in a subject comprising administering to the subject an effective amount of a compound of Formula I described herein.

In yet another aspect, this disclosure provides methods for treating a disease, disorder, or condition mediated at least in part by KIT in a subject, comprising administering to the subject a therapeutically effective amount of a compound of Formula I described herein. Diseases, disorders, and conditions mediated by KIT include e.g., an allergic disease, disorder, or condition; an inflammatory disease, disorder, or condition; a neuroinflammatory disease, disorder, or condition; a neurological disease, disorder, or condition; an immune related disease, disorder, or condition; an autoimmune related disease, disorder, or condition; a dermatological disease, disorder, or condition; a respiratory disease, disorder, or condition; a metabolic disease, disorder, or condition; a cardiovascular disease, disorder, or condition; a fibrotic disease, disorder, or condition; or cancer.

Certain aspects of the present disclosure further comprise the administration of one or more additional therapeutic agents as set forth herein below.

DETAILED DESCRIPTION OF THE DISCLOSURE

Before the present disclosure is further described, it is to be understood that the disclosure is not limited to the particular embodiments set forth herein, and it is also to be understood that the terminology used herein is for the purpose of describing particular embodiments only, and is not intended to be limiting.

Definitions

Unless otherwise defined, all terms of art, notations and other scientific terms or terminology used herein are intended to have the meanings commonly understood by those of skill in the art to which this disclosure pertains.

The term "about" as used herein has its original meaning of approximately and is to provide literal support for the exact number that it precedes, as well as a number that is near to or approximately the number that the term precedes. In determining whether a number is near to or approximately a specifically recited number, the near or approximating unrecited number can be a number which, in the context in which it is presented, provides the substantial equivalent of the specifically recited number. For example, if the degree of approximation is not otherwise clear from the context, "about" means either within plus or minus 10% of the provided value, or rounded to the nearest significant figure, in all cases inclusive of the provided value. Where ranges are provided, they are inclusive of the boundary values.

The term "alkyl", by itself or as part of another substituent, means, unless otherwise stated, a saturated hydrocarbon radical, having, in some embodiments, one to eight (e.g., $C_1$-$C_8$-alkyl), or one to six (e.g., $C_1$-$C_6$-alkyl), or one to four carbon atoms (e.g., $C_1$-$C_4$-alkyl), or one to three carbon atoms (e.g., $C_1$-$C_3$-alkyl), respectively. The term "alkyl" encompasses straight and branched-chain hydrocarbon groups. Examples of alkyl groups include, but are not limited to, methyl (Me, —$CH_3$), ethyl (Et, —$CH_2CH_3$), n-propyl, isopropyl (iPr, —$CH(CH_3)_2$), n-butyl, t-butyl (—$C(CH_3)_3$), isobutyl (—$CH_2CH(CH_3)_2$), sec-butyl, isopentyl, tert-pentyl, n-pentyl, isohexyl, n-hexyl, n-heptyl, 4-isopropylheptane, n-octyl, and the like. In some embodiments, the alkyl groups are $C_1$-$C_4$ alkyl groups (e.g., methyl, ethyl, n-propyl, isopropyl, n-butyl, isobutyl, sec-butyl, or t-butyl).

The term "alkylene" refers to a straight or branched, saturated, hydrocarbon radical having, in some embodiments, one to six carbon atoms (e.g., $C_1$-$C_6$-alkylene), or one to four carbon atoms (e.g., $C_1$-$C_4$-alkylene), or one to three carbon atoms (e.g., $C_1$-$C_3$-alkylene) and linking at least two other groups, i.e., a divalent hydrocarbon radical. When two moieties are linked to the alkylene they can be linked to the same carbon atom (i.e., geminal), or different carbon atoms of the alkylene group. For instance, a straight chain alkylene can be the bivalent radical of —(CH$_2$)$_n$—, where n is 1, 2, 3, 4, 5 or 6 (i.e., a C$_1$-C$_6$-alkylene). Representative alkylene groups include, but are not limited to, methylene, ethylene, propylene, isopropylene, butylene, isobutylene, secbutylene, pentylene, hexylene and the like. In some embodiments, the alkylene groups are C$_{1-3}$ alkylene groups (e.g., methylene, ethylene, or propylene).

The term "cycloalkyl" refers to a monocyclic, bicyclic or polycyclic hydrocarbon ring system having, in some embodiments, 3 to 14 carbon atoms (e.g., C$_3$-C$_{14}$-cycloalkyl), or 3 to 10 carbon atoms (e.g., C$_3$-C$_{10}$-cycloalkyl), or 3 to 8 carbon atoms (e.g., C$_3$-C$_8$-cycloalkyl), or 3 to 6 carbon atoms (e.g., C$_3$-C$_6$-cycloalkyl) or 5 to 6 carbon atoms (e.g., C$_5$-C$_6$-cycloalkyl). Cycloalkyl groups can be saturated or characterized by one or more points of unsaturation (i.e., carbon-carbon double and/or triple bonds), provided that the points of unsaturation do not result in an aromatic system. Examples of monocyclic cycloalkyl groups include, but are not limited to, cyclopropyl, cyclobutyl, cyclopentyl, cyclohexyl, cyclohexenyl, cyclohexynyl, cycloheptyl, cycloheptenyl, cycloheptadienyl, cyclooctyl, cyclooctenyl, cyclooctadienyl and the like. The rings of bicyclic and polycyclic cycloalkyl groups can be fused, bridged, or spirocyclic. Non-limiting examples of bicyclic, spirocyclic and polycyclic hydrocarbon groups include bicyclo[1.1.1]pentane, bicyclo[2.1.1]hexane, bicyclo[2.2.1]heptane, bicyclo[2.2.2]octane, adamantyl, spiro[5.5]undecane, spiro[2.2]pentane, spiro[2.2]pentadiene, spiro[2.5]octane, spiro[2.2]pentadiene, and the like. In some embodiments, the cycloalkyl groups of the present disclosure are monocyclic C$_3$-C$_6$-cycloalkyl moieties (e.g., cyclopropyl, cyclobutyl, cyclopentyl, or cyclohexyl). In some embodiments, the cycloalkyl groups of the present disclosure are monocyclic C$_3$-C$_4$-cycloalkyl moieties (e.g., cyclopropyl or cyclobutyl).

As used herein, a wavy line, "〜", that intersects a single, double or triple bond in any chemical structure depicted herein, represents that the point of attachment of the single, double, or triple bond to the remainder of the molecule is through either one of the atoms that make up the single, double or triple bond. Additionally, a bond extending from a substituent to the center of a ring (e.g., a phenyl ring or heteroaryl ring) is meant to indicate attachment of that substituent to the ring at any of the available ring vertices, i.e., such that attachment of the substituent to the ring results in a chemically stable arrangement.

The terms "halogen," or "halo" are used interchangeably and refer to, unless otherwise stated, a fluorine, chlorine, bromine, or iodine atom. Additionally, terms such as "haloalkyl," refer to alkyl groups, as defined herein, that are substituted with one or more halogen(s) (e.g., 1-3 halogen(s)). For example, the term "C$_1$-C$_6$ haloalkyl" is meant to include trifluoromethyl (—CF$_3$), difluoromethyl (—CF$_2$H), 2,2,2-trifluoroethyl (—CH$_2$CF$_3$), 2,2-difluoroethyl (—CH$_2$CF$_2$H), 4-chlorobutyl, 3-bromopropyl, and the like. The term "haloalkylene" refers to an alkylene group, as defined above, that is substituted with one or more halogen(s) (e.g., 1-3 halogen(s)).

The term "hydroxyalkyl" refers to an alkyl group, as defined herein, that is substituted with one or more hydroxyl groups (e.g., 1-3 hydroxyl groups). Exemplary hydroxyalkyl groups include methanol, ethanol, 1,2-propanediol, 1,2-hexanediol, glycerol, and the like. The term "hydroxyhaloalkyl" refers to an alkyl group, as defined above, that is substituted with one or more hydroxyl groups (e.g., 1-3 hydroxyl groups) and one or more halogen(s) (e.g., 1-3 halogen(s)).

As used herein, the term "alkoxy" refers to an alkyl group, as defined herein, that is attached to the remainder of the molecule via an oxygen atom (e.g., —O—C$_1$-C$_{12}$ alkyl, —O—C$_1$-C$_8$ alkyl, —O—C$_1$-C$_6$ alkyl, or —O—C$_1$-C$_3$ alkyl). Non-limiting examples of alkoxy groups include methoxy (OMe, —OCH$_3$), ethoxy (OEt, —OCH$_2$CH$_3$), n-propoxy, iso-propoxy, n-butoxy, sec-butoxy, n-pentoxy, n-hexoxy, and the like. The term "haloalkoxy" refers to an alkoxy group as defined above, wherein the alkyl portion of the substituent is substituted with one or more halogen(s) (e.g., 1-3 halogen(s). Exemplary haloalkoxy groups include, but are not limited to, trifluoromethoxy (—OCF$_3$), difluoromethoxy (—OCF$_2$H), trifluoroethoxy, difluoroethoxy, and the like.

The term "heteroaryl" refers to monocyclic or fused bicyclic aromatic groups (or rings) having, in some embodiments, from 5 to 14 (i.e., 5- to 14-membered heteroaryl), or from 5 to 10 (i.e., 5- to 10-membered heteroaryl), or from 5 to 6 (i.e., 5- to 6-membered heteroaryl) members (i.e., ring vertices), and containing from one to five, one to four, one to three, one to two or one ring heteroatom independently selected from nitrogen (N), oxygen (O), and sulfur (S). A heteroaryl group can be attached to the remainder of the molecule through a carbon atom or a heteroatom of the heteroaryl group, when chemically permissible. Non-limiting examples of heteroaryl groups include pyridyl, pyridazinyl, pyrazinyl, pyrimidinyl, triazinyl, purinyl, thienopyridinyl, thienopyrimidinyl, pyrazolopyrimidinyl, imidazopyridines, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. In some embodiments, the heteroaryl groups of the present disclosure are monocyclic 5- to 6-membered heteroaryl moieties having 1-3 ring heteroatoms independently selected from N, O, and S (e.g., pyridinyl, pyrimidinyl, pyrazinyl, pyridazinyl, triazinyl, imidazolyl, pyrazolyl, thiazolyl, oxazolyl, thiadiazolyl, oxadiazolyl, and the like).

The term "heterocycloalkyl" refers to a non-aromatic monocyclic, bicyclic or polycyclic cycloalkyl ring having, in some embodiments, 3 to 14 members (e.g., 3- to 14-membered heterocycle), or 3 to 10 members (e.g., 3- to 10-membered heterocycle), or 4 to 8 members (e.g., 4- to 8-membered heterocycle), or 4 to 6 members (e.g., 4- to 6-membered heterocycle), or 5 to 6 members (e.g., 5- to 6-membered heterocycle), and having from one to five, one to four, one to three, one to two or one ring heteroatom independently selected from nitrogen (N), oxygen (O), and sulfur (S). Heterocycloalkyl groups are saturated or characterized by one or more points of unsaturation (e.g., one or more carbon-carbon double bonds, carbon-carbon triple bonds, carbon-nitrogen double bonds, and/or nitrogen-nitrogen double bonds), provided that the points of unsaturation do not result in an aromatic system. The rings of bicyclic and polycyclic heterocycloalkyl groups can be fused, bridged, or spirocyclic. Non-limiting examples of heterocycloalkyl groups include aziridine, oxirane, thiirane, azetidine, oxetane, pyrrolidine, imidazolidine, pyrazolidine, dioxolane, phthalimide, piperidine, 1,4-dioxane, morpholine, thiomorpholine, thiomorpholine-S-oxide, thiomorpholine-S,S-oxide, piperazine, 3,4,5,6-tetrahydropyridazine, pyran, decahydroisoquinoline, 3-pyrroline, thiopyran, tetrahydrofuran, tetrahydrothiophene, quinuclidine, 2,6-diazaspiro[3.3]heptane, 2-azaspiro[3.3]heptane, 1-oxaspiro[3.3]heptane, 4-oxaspiro[2.4]heptane, 6-azaspiro[3.4]octane, and the like. A heterocycloalkyl group can be attached to the remainder of the molecule through a ring carbon atom, or a ring heteroatom, when chemically permissible. In some embodiments, the heterocycloalkyl groups of the present disclosure are monocyclic or bicyclic 4- to 8-membered heterocycloalkyl moieties having one or two heteroatoms independently selected from N, O, and S, (e.g., azetidine, oxetane, pyrrolidine, tetrahydrofuran, tetrahydropyran, piperidine, piperazine, morpholine, 4-oxaspiro[2.4]heptane, and the like).

As referred to herein, "pharmaceutically acceptable salt" is meant to include salts of the compounds according to this disclosure that are prepared with suitably nontoxic acids or bases, depending on the particular substituents found on the compounds described herein. When compounds of the present disclosure contain suitably acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present disclosure contain suitably basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from suitably nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, for example, Berge, S. M., et al, "Pharmaceutical Salts", *Journal of Pharmaceutical Science*, 1977, 66, 1-19). Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present disclosure.

This disclosure also contemplates isomers of the compounds described herein (e.g., stereoisomers and/or atropisomers). For example, certain compounds of the present disclosure possess asymmetric carbon atoms (chiral centers), or hindered rotation about a single bond; the racemates, diastereomers, and enantiomers, and atropisomers (e.g., Ra, Sa, P and M isomers) of which are all intended to be encompassed within the scope of the present disclosure. Stereoisomeric forms may be defined, in terms of absolute stereochemistry, as (R) or (S), depicted uses dashes and/or wedges, and/or in terms of the direction the stereoisomer rotates plane-polarized light (e.g., dextrorotary ((+) or (d)), or levorotary ((or (l))). When a stereochemical depiction (e.g., using dashes, ⦀⦀⦀⦀, and/or wedges, ▬▬◀ ) is shown in a chemical structure, or a stereochemical assignment (e.g., using (R) and (S) notation, or (d) and (l) notation) is made in a chemical name, it is meant to indicate that the depicted/referred to isomer is present and substantially free of one or more other isomer(s) (e.g., enantiomers and diastereomers, when present). "Substantially free of" other isomer(s) indicates at least an 70/30 ratio of the indicated isomer to the other isomer(s), more preferably 80/20, 90/10, or 95/5 or more. In some embodiments, the indicated isomer will be present in an amount of at least 99%. A chemical bond to an asymmetric carbon that is depicted as a solid line ( ──── ) indicates that all possible stereoisomers (e.g., enantiomers, diastereomers, racemic mixtures, etc.) at that carbon atom are included. In such instances, the compound may be present as a racemic mixture, scalemic mixture, or a mixture of diastereomers.

The compounds of the present disclosure may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium (3H), iodine-125 ($^{125}$I) or carbon-14 ($^{14}$C), or non-radioactive isotopes, such as deuterium (2H) or carbon-13 ($^{13}$C). Such isotopic variations can provide additional utilities to those described elsewhere herein. For instance, isotopic variants of the compounds of the disclosure may find additional utility, including but not limited to, as diagnostic and/or imaging reagents, or as cytotoxic/radiotoxic therapeutic agents. Additionally, isotopic variants of the compounds of the disclosure can have altered pharmacokinetic and pharmacodynamic characteristics which can contribute to enhanced safety, tolerability or efficacy during treatment. In some embodiments, the compounds according to this disclosure are characterized by one or more deuterium atoms.

The compounds according to this disclosure may also be in a prodrug form. A "prodrug" refers to any compound that when administered to a biological system generates the drug substance, or active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically active compound. Non-limiting examples of prodrugs include ester moieties, quaternary ammonium moieties, glycol moieties, and the like.

The terms "treat", "treating", treatment" and the like refer to a course of action that eliminates, reduces, suppresses, mitigates, ameliorates, or prevents the worsening of, either temporarily or permanently, a disease, disorder or condition to which the term applies, or at least one of the symptoms associated therewith. Treatment includes alleviation of symptoms, diminishment of extent of disease, inhibiting (e.g., arresting the development or further development of the disease, disorder or condition or clinical symptoms association therewith) an active disease, delaying or slowing of disease progression, improving the quality of life, and/or prolonging survival of a subject as compared to expected survival if not receiving treatment or as compared to a published standard of care therapy for a particular disease.

The term "in need of treatment" as used herein refers to a judgment made by a physician or similar professional that a subject requires or will benefit from treatment. This judgment is made based on a variety of factors that are in the realm of the physician's expertise, which may include a positive diagnosis of a disease, disorder or condition.

The terms "prevent", "preventing", "prevention", "prophylaxis" and the like refer to a course of action initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition. In certain instances, the terms also refer to slowing the progression of the disease, disorder or condition or inhibiting progression thereof to a harmful or otherwise undesired state. Prevention also refers to a course of action initiated in a subject after the subject has been treated for a disease, disorder, condition or a symptom associated therewith in order to prevent relapse of that disease, disorder, condition or symptom. In one or more embodiments, the preventative course of action is taken based on anticipation of a condition or event. In one embodiment, prevention refers to the prevention, suppression, inhibition or reduction of an allergic, immune, or autoimmune response in a subject suffering from an allergic, inflammatory, neuroinflammatory, neurological, immune, autoimmune, dermatological, respiratory, metabolic, cardiovascular or fibrotic disease, disorder, or condition.

As used herein, the term "response" may refer to a symptom initiated by an irritant or trigger (e.g., an antigen originating from within the body, or from the external environment) in a subject. For example, "response" may refer to a reaction (e.g., hives, rash, welts, itchy skin, stinging skin, skin fissures, skin lesions, skin blisters, swelling (e.g., in joints, glands, or tissues), vertigo, fatigue, dizziness, fainting, lightheadedness, muscle weakness, headache, dry skin, dry eyes, hair loss, numbness or tingling in extremities, joint pain and/or stiffness, sneezing, runny nose, stuffy nose, chest tightness and/or pain, shortness of breath, wheezing, itchy eyes, watery eyes, blurred vision, sensitivity to light, stomach cramping, abdominal pain, bloating, diarrhea, constipation, indigestion, heartburn, excessive flatulence, frequent urination, difficulty swallowing, muscle spasm, muscle tremor, unexpected weight gain or loss, increased thirst, increased hunger, irritability, temperature sensitivity, low blood pressure, constriction of airways, weak pulse, rapid pulse, nausea, vomiting, anemia, depression, and the like) caused by an external or internal trigger in a subject susceptible to the trigger. Subjects susceptible to a trigger are generally those suffering from an allergic, inflammatory, neuroinflammatory, neurological, immune, autoimmune, dermatological, respiratory, metabolic, cardiovascular or fibrotic disease, disorder, or condition, such as those described elsewhere herein.

The term "in need of prevention" as used herein refers to a judgment made by a physician or other caregiver that a subject requires or will benefit from preventative care. This judgment is made based on a variety of factors that are in the realm of a physician's or caregiver's expertise.

"Substantially pure" indicates that a component (e.g., a compound according to this disclosure) makes up greater than about 50% of the total content of the composition, and typically greater than about 60% of the total content. More typically, "substantially pure" refers to compositions in which at least 75%, at least 85%, at least 90% or more of the total composition is the component of interest. In some cases, the component of interest will make up greater than about 90%, or greater than about 95% of the total content of the composition.

The terms "inhibitor of KIT" and "KIT inhibitor" may be used interchangeably, and refer to the ability of a molecule to decrease the activation of KIT either directly or indirectly, thereby decreasing activation and/or quantity of systemic mast cells.

Compounds that are selective for KIT may be particularly useful in the treatment of certain disorders or may offer a reduced likelihood of undesired side effects. In some embodiments, compounds of the present disclosure are selective over one or more other kinases. Specific examples include, but are not limited to, type III receptor tyrosine kinases (RTKs), such as, for example, PDGFRα, PDGFRγ, CSF1R, and FLT3. Selectivity may be determined, for example, by comparing the inhibition (e.g., IC50) of a compound as described herein against KIT against the inhibition of a compound as described herein against one or more other kinase(s). In some embodiments, the selective inhibition of a compound of Formula I is at least 1000 times greater, 500 times greater, 100 times greater, 50 times greater, or 20 times greater than inhibition of one or more kinases selected from PDGFRα, PDGFRβ, CSF1R, and FLT3. Alternatively or in addition, selectivity may be measured by testing the inhibitory activity of the compound against a panel of kinases at a concentration that is above the KIT IC50 for that compound (e.g., 50 times the KIT IC50, 100 times the KIT IC50, 150 times the KIT IC50, etc.). In some embodiments, a compound selective for KIT reduces the activity of no more than 1, 2, 3, 4, or 5 kinases of the panel, each by 50% or more as compared to a suitable control. In some embodiments, a compound selective for KIT reduces the activity of no more than 5, 10, 15, 16, 17, 18, 19 or 20 kinases of the panel, each by 20% or more as compared to a suitable control. A suitable control may be the activity of the kinase in the absence of an inhibitor. In some embodiments, the kinase panel comprises between 350 to 380 kinases. The panel of kinases can include kinases from various kinase groups, including, for example, the tyrosine kinase (TK) group, the casein kinase 1 (CK1) group, the tyrosine kinase-like (TKL) group, the STE kinase group (e.g., serine/threonine kinases), the AGC kinase group (including serine/threonine protein kinase families PKA, PKC, and PKG), the $Ca^{2+}$/calmodulin-dependent protein kinase (CAMK) group, and the CMGC group (including cyclin-dependent kinases (CDKs), mitogen-activated protein kinases (MAP kinases), glycogen synthase kinases (GSK) and CDK-like kinases), among others. In some embodiments, the kinase panel is a Wild Type Kinase Panel.

Compounds provided herein may have advantageous pharmacokinetic profiles including, for example, hepatocyte stability, clearance, inhibition against CYP, bioavailability, susceptibility to bioactivation, and/or inhibition against hERG.

Compounds of the Disclosure

In one aspect, this disclosure is directed to a compound having a structure according to Formula I:

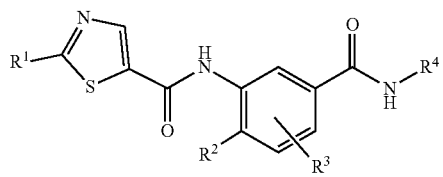

(Formula I)

or a pharmaceutically acceptable salt thereof, wherein:
$R^1$ is —H, —NR$^{1a}$R$^{1b}$, —C$_1$-C$_6$ alkyl, —C$_1$-C$_6$ haloalkyl, —C$_3$-C$_6$ cycloalkyl, or 4- to 6-membered heterocycloalkyl having 1-3 ring heteroatoms independently selected from N, O, and S;
$R^{1a}$ and $R^{1b}$ are independently —H, —C$_1$-C$_6$ haloalkyl, —C(O)R$^{1c}$, —C(O)OR$^{1d}$, or —C(O)NR$^{1e}$R$^{1f}$;
$R^{1c}$ is —C$_1$-C$_3$ alkyl, —C$_1$-C$_3$ haloalkyl, —C$_1$-C$_3$ hydroxyalkyl, —C$_3$-C$_6$ cycloalkyl, phenyl, or 4 to 6-membered heterocycloalkyl having 1 to 3 ring heteroatoms independently selected from N, O, and S; wherein said phenyl and 4- to 6-membered heterocycloalkyl are unsubstituted or substituted with 1-3 substituents independently selected from the group consisting of halo, —OH, and C$_1$-C$_3$ alkyl;
$R^{1d}$ is —C$_1$-C$_3$ alkyl or —C$_3$-C$_6$ cycloalkyl;
$R^{1e}$ and $R^{1f}$ are independently —H or —C$_1$-C$_3$ alkyl;
$R^2$ and $R^3$ are independently halo or —C$_1$-C$_3$ alkyl;
$R^4$ is selected from:
  a) —C$_1$-C$_6$ haloalkyl, —C$_1$-C$_6$ hydroxyalkyl, —C$_1$-C$_6$ hydroxyhaloalkyl, —(C$_1$-C$_3$ alkylene)-O—(C$_1$-C$_3$ alkyl), and —(C$_1$-C$_3$ haloalkylene)-O—(C$_1$-C$_3$ alkyl);
  b) —C$_1$-C$_6$ alkyl substituted with a substituent selected from the group consisting of —C$_3$-C$_6$ cycloalkyl, phenyl, 4- to 8-membered heterocycloalkyl, and 5- to 6-membered heteroaryl, wherein said 4- to 8-membered heterocycloalkyl and 5- to 6-membered heteroaryl have 1-3 ring heteroatoms independently selected from N, O, and S; and wherein said —C$_3$-C$_6$ cycloalkyl, phenyl, 4- to 8-membered heterocycloalkyl, and 5- to 6-membered heteroaryl are unsubstituted or substituted with 1-3 R$^{4b}$;
  c) —C$_3$-C$_6$ cycloalkyl, wherein said —C$_3$-C$_6$ cycloalkyl is unsubstituted or substituted with a substituent selected from the group consisting of halo, —CN, —C(O)NH$_2$, —C$_1$-C$_3$ haloalkyl, —C$_1$-C$_3$ alkoxy, —(C$_1$-C$_3$ alkylene)-O—(C$_1$-C$_3$ alkyl), and phenyl; wherein said phenyl is unsubstituted or substituted with 1-3 halo;
  d) 4- to 8-membered heterocycloalkyl having 1-3 ring heteroatoms independently selected from N, O, and S; wherein said 4- to 8-membered heterocycloalkyl is unsubstituted or substituted with —C(O)R$^{4d}$ or 5- to 6-membered heteroaryl having 1-3 ring heteroatoms independently selected from N, O, and S; and
  e) phenyl or 5- to 6-membered heteroaryl having 1-3 ring heteroatoms independently selected from N, O, and S; wherein said phenyl and 5- to 6-membered heteroaryl are unsubstituted or substituted with 1-3 R$^{4e}$;

each R$^{4b}$ is independently selected from the group consisting of halo, —C$_1$-C$_3$ alkyl, —C$_1$-C$_3$ haloalkyl, —C$_1$-C$_3$ alkoxy, and —C$_1$-C$_3$ haloalkoxy;
R$^{4d}$ is —C$_1$-C$_3$ alkyl or —C$_3$-C$_6$ cycloalkyl;
each R$^{4e}$ is independently selected from the group consisting of halo, —CN, —S(O)$_2$—(C$_1$-C$_3$ alkyl), —S(O)$_2$—(C$_3$-C$_6$ cycloalkyl), —NR$^{4f}$R$^{4g}$, —C$_1$-C$_6$ alkyl, —C$_1$-C$_6$ haloalkyl, —C$_1$-C$_6$ hydroxyalkyl, —C$_1$-C$_6$ hydroxyhaloalkyl, —C$_1$-C$_3$ alkoxy, —C$_1$-C$_3$ haloalkoxy, —C$_3$-C$_6$ cycloalkyl, 4- to 8-membered heterocycloalkyl, phenyl, 5- to 6-membered heteroaryl, —(C$_1$-C$_3$ alkylene)-(C$_3$-C$_6$ cycloalkyl), —(C$_1$-C$_3$ alkylene)-O—(C$_1$-C$_3$ alkyl), —(C$_1$-C$_3$ alkylene)-O—(C$_1$-C$_3$ haloalkyl), —(C$_1$-C$_3$ alkylene)-(4- to 8-membered heterocycloalkyl), —(C$_1$-C$_3$ alkylene)-O—(C$_1$-C$_3$ alkylene)-(C$_3$-C$_6$ cycloalkyl), —O—(C$_1$-C$_3$ alkylene)-O—(C$_1$-C$_3$ alkyl), —O—(C$_3$-C$_6$ cycloalkyl), —O-(4- to 8-membered heterocycloalkyl), —O—(C$_1$-C$_3$ alkylene)-(C$_3$-C$_6$ cycloalkyl), and —O—(C$_1$-C$_3$ alkylene)-phenyl; wherein said 4- to 8-membered heterocycloalkyl and 5- to 6-membered heteroaryl have 1-3 ring heteroatoms independently selected from N, O, and S; wherein said —C$_3$-C$_6$ cycloalkyl, —(C$_1$-C$_3$ alkylene)-(C$_3$-C$_6$ cycloalkyl), 4- to 8-membered heterocycloalkyl, phenyl, and —(C$_1$-C$_3$ alkylene)-(4- to 8-membered heterocycloalkyl), are unsubstituted or substituted with 1-3 R*; and wherein said —O—(C$_3$-C$_6$ cycloalkyl) and —O—(C$_1$-C$_3$ alkylene)-(C$_3$-C$_6$ cycloalkyl) are unsubstituted or substituted with 1-3 R**; or
two adjacent R$^{4e}$ groups taken together with the atoms to which they are attached form a fused 5-to 6-membered heterocycloalkyl having 1-3 ring heteroatoms independently selected from N, O, and S; and wherein said 5- to 6-membered heterocycloalkyl is unsubstituted or substituted with 1-3 substituents independently selected from oxo, halo, and —C$_1$-C$_3$ alkyl;
R$^{4f}$ and R$^{4g}$ are independently selected from —H, —(C$_1$-C$_3$ alkylene)-(C$_3$-C$_6$ cycloalkyl), and 4- to 6-membered heterocycloalkyl having 1-3 ring heteroatoms independently selected from N, O, and S;
each R* is independently halo, —OH, —CN, —C$_1$-C$_3$ alkyl, —C$_1$-C$_3$ haloalkyl, —C$_1$-C$_3$ alkoxy, or —(C$_1$-C$_3$ alkylene)-O—(C$_1$-C$_3$ alkyl); and
each R** is independently halo or —C$_1$-C$_3$ alkyl.

In another aspect, this disclosure is directed to a compound having a structure according to Formula I:

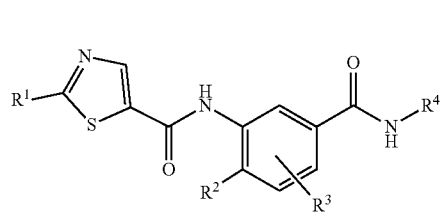

(Formula I)

or a pharmaceutically acceptable salt thereof, wherein:
$R^1$ is —H, —NR$^{1a}$R$^{1b}$, —C$_1$-C$_6$ alkyl, —C$_1$-C$_6$ haloalkyl, —C$_3$-C$_6$ cycloalkyl, or 4- to 6-membered heterocycloalkyl having 1-3 ring heteroatoms independently selected from N, O, and S;
$R^{1a}$ and $R^{1b}$ are independently —H, —C$_1$-C$_6$ haloalkyl, —C(O)R$^{1c}$, —C(O)OR$^{1d}$, or —C(O)NR$^{1e}$R$^{1f}$;

$R^{1c}$ is —$C_1$-$C_3$ alkyl, —$C_1$-$C_3$ haloalkyl, —$C_1$-$C_3$ hydroxyalkyl, —$C_3$-$C_6$ cycloalkyl, phenyl, or 4 to 6-membered heterocycloalkyl having 1 to 3 ring heteroatoms independently selected from N, O, and S; wherein said phenyl and 4- to 6-membered heterocycloalkyl are unsubstituted or substituted with 1-3 substituents independently selected from the group consisting of halo, —OH, and $C_1$-$C_3$ alkyl;

$R^{1d}$ is —$C_1$-$C_3$ alkyl or —$C_3$-$C_6$ cycloalkyl;

$R^{1e}$ and $R^{1f}$ are independently —H or —$C_1$-$C_3$ alkyl;

$R^2$ and $R^3$ are independently halo or —$C_1$-$C_3$ alkyl;

$R^4$ is selected from:
  a) —$C_1$-$C_6$ haloalkyl, —$C_1$-$C_6$ hydroxyalkyl, —$C_1$-$C_6$ hydroxyhaloalkyl, —($C_1$-$C_3$ alkylene)-O—($C_1$-$C_3$ alkyl), and —($C_1$-$C_3$ haloalkylene)-O—($C_1$-$C_3$ alkyl);
  b) —$C_1$-$C_6$ alkyl substituted with a substituent selected from the group consisting of —$C_3$-$C_6$ cycloalkyl, phenyl, 4- to 8-membered heterocycloalkyl, and 5- to 6-membered heteroaryl, wherein said 4- to 8-membered heterocycloalkyl and 5- to 6-membered heteroaryl have 1-3 ring heteroatoms independently selected from N, O, and S; and wherein said —$C_3$-$C_6$ cycloalkyl, phenyl, 4- to 8-membered heterocycloalkyl, and 5- to 6-membered heteroaryl are unsubstituted or substituted with 1-3 $R^{4b}$;
  c) —$C_3$-$C_6$ cycloalkyl substituted with a substituent selected from the group consisting of halo, —CN, —C(O)NH$_2$, —$C_1$-$C_3$ haloalkyl, —$C_1$-$C_3$ alkoxy, —($C_1$-$C_3$ alkylene)-O—($C_1$-$C_3$ alkyl), and phenyl; wherein said phenyl is unsubstituted or substituted with 1-3 halo;
  d) 4- to 8-membered heterocycloalkyl having 1-3 ring heteroatoms independently selected from N, O, and S; wherein said 4- to 8-membered heterocycloalkyl is unsubstituted or substituted with —C(O)$R^{4d}$ or 5- to 6-membered heteroaryl having 1-3 ring heteroatoms independently selected from N, O, and S; and
  e) phenyl or 5- to 6-membered heteroaryl having 1-3 ring heteroatoms independently selected from N, O, and S; wherein said phenyl and 5- to 6-membered heteroaryl are unsubstituted or substituted with 1-3 $R^{4e}$;

each $R^{4b}$ is independently selected from the group consisting of halo, —$C_1$-$C_3$ alkyl, —$C_1$-$C_3$ haloalkyl, —$C_1$-$C_3$ alkoxy, and —$C_1$-$C_3$ haloalkoxy;

$R^{4d}$ is —$C_1$-$C_3$ alkyl or —$C_3$-$C_6$ cycloalkyl;

each $R^{4e}$ is independently selected from the group consisting of halo, —CN, —S(O)$_2$—($C_1$-$C_3$ alkyl), —S(O)$_2$—($C_3$-$C_6$ cycloalkyl), —NR$^{4f}$R$^{4g}$, —$C_1$-$C_6$ alkyl, —$C_1$-$C_6$ haloalkyl, —$C_1$-$C_6$ hydroxyalkyl, —$C_1$-$C_6$ hydroxyhaloalkyl, —$C_1$-$C_3$ alkoxy, —$C_1$-$C_3$ haloalkoxy, —$C_3$-$C_6$ cycloalkyl, 4- to 8-membered heterocycloalkyl, phenyl, 5- to 6-membered heteroaryl, —($C_1$-$C_3$ alkylene)-($C_3$-$C_6$ cycloalkyl), —($C_1$-$C_3$ alkylene)-O—($C_1$-$C_3$ alkyl), —($C_1$-$C_3$ alkylene)-O—($C_1$-$C_3$ haloalkyl), —($C_1$-$C_3$ alkylene)-(4- to 8-membered heterocycloalkyl), —($C_1$-$C_3$ alkylene)-O—($C_1$-$C_3$ alkylene)-($C_3$-$C_6$ cycloalkyl), —O—($C_1$-$C_3$ alkylene)-O—($C_1$-$C_3$ alkyl), —O—($C_3$-$C_6$ cycloalkyl), —O-(4- to 8-membered heterocycloalkyl), —O—($C_1$-$C_3$ alkylene)-($C_3$-$C_6$ cycloalkyl), and —O—($C_1$-$C_3$ alkylene)-phenyl; wherein said 4- to 8-membered heterocycloalkyl and 5- to 6-membered heteroaryl have 1-3 ring heteroatoms independently selected from N, O, and S; wherein said —$C_3$-$C_6$ cycloalkyl, —($C_1$-$C_3$ alkylene)-($C_3$-$C_6$ cycloalkyl), 4- to 8-membered heterocycloalkyl, phenyl, and —($C_1$-$C_3$ alkylene)-(4- to 8-membered heterocycloalkyl), are unsubstituted or substituted with 1-3 R*; and wherein said —O—($C_3$-$C_6$ cycloalkyl) and —O—($C_1$-$C_3$ alkylene)-($C_3$-$C_6$ cycloalkyl) are unsubstituted or substituted with 1-3 R**; or two adjacent $R^{4e}$ groups taken together with the atoms to which they are attached form a fused 5- to 6-membered heterocycloalkyl having 1-3 ring heteroatoms independently selected from N, O, and S; and wherein said 5- to 6-membered heterocycloalkyl is unsubstituted or substituted with 1-3 substituents independently selected from oxo, halo, and —$C_1$-$C_3$ alkyl;

$R^{4f}$ and $R^{4g}$ are independently selected from —H, —($C_1$-$C_3$ alkylene)-($C_3$-$C_6$ cycloalkyl), and 4- to 6-membered heterocycloalkyl having 1-3 ring heteroatoms independently selected from N, O, and S;

each R* is independently halo, —OH, —CN, —$C_1$-$C_3$ alkyl, —$C_1$-$C_3$ haloalkyl, —$C_1$-$C_3$ alkoxy, or —($C_1$-$C_3$ alkylene)-O—($C_1$-$C_3$ alkyl); and each R** is independently halo or —$C_1$-$C_3$ alkyl.

In some embodiments, $R^1$ is —H. In some embodiments, $R^1$ is —$C_1$-$C_6$ alkyl or —$C_1$-$C_3$ alkyl. In some embodiments, $R^1$ is —$C_1$-$C_6$ haloalkyl or —$C_1$-$C_3$ haloalkyl. In some embodiments, $R^1$ is —$C_3$-$C_6$ cycloalkyl. In some embodiments, $R^1$ is 4- to 6-membered heterocycloalkyl having 1-3 ring heteroatoms independently selected from N, O, and S.

In some embodiments, $R^1$ is —NR$^{1a}$R$^{1b}$ In some embodiments, at least one of $R^{1a}$ and $R^{1b}$ is —H. In some embodiments, $R^{1a}$ and $R^{1b}$ are —H. In some embodiments, one of $R^{1a}$ and $R^{1b}$ is —H, and the other is —$C_1$-$C_6$ haloalkyl. In some embodiments, one of $R^{1a}$ and $R^{1b}$ is —H, and the other is —C(O)$R^{1c}$. In some embodiments, one of $R^{1a}$ and $R^{1b}$ is —H, and the other is —C(O)O$R^{1d}$. In some embodiments, one of $R^{1a}$ and $R^{1b}$ is —H, and the other is —C(O)NR$^{1e}$R$^{1f}$.

In some embodiments, $R^{1c}$ is $C_1$-$C_3$ alkyl. In some embodiments, $R^{1c}$ is —$C_1$-$C_3$ haloalkyl. In some embodiments, $R^{1c}$ is —$C_1$-$C_3$ hydroxyalkyl. In some embodiments, $R^{1c}$ is $C_3$-$C_6$ cycloalkyl. In some embodiments, $R^{1c}$ is phenyl, wherein said phenyl is unsubstituted or substituted with 1-3 substituents independently selected from the group consisting of halo, —OH, and $C_1$-$C_3$ alkyl. In some embodiments, $R^{1c}$ is 4 to 6-membered heterocycloalkyl having 1 to 3 ring heteroatoms independently selected from N, O, and S; wherein said 4- to 6-membered heterocycloalkyl is unsubstituted or substituted with 1-3 substituents independently selected from the group consisting of halo, —OH, and $C_1$-$C_3$ alkyl.

In some embodiments, $R^{1d}$ is —$C_1$-$C_3$ alkyl. In some embodiments, $R^{1d}$ is $C_3$-$C_6$ cycloalkyl.

In some embodiments, $R^{1e}$ and $R^{1f}$ are both H. In some embodiments, $R^{1e}$ and $R^{1f}$ are both —$C_1$-$C_3$ alkyl. In some embodiments, $R^{10}$ is H, and $R^{1f}$ is —$C_1$-$C_3$ alkyl.

In some embodiments, $R^1$ is selected from the group consisting of —CH$_3$, —CF$_2$H,

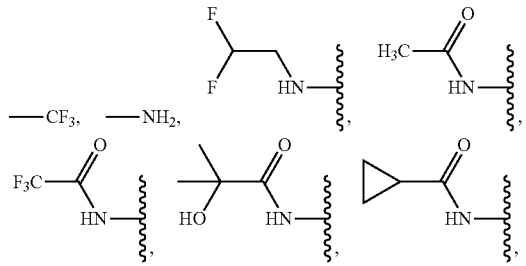

-continued

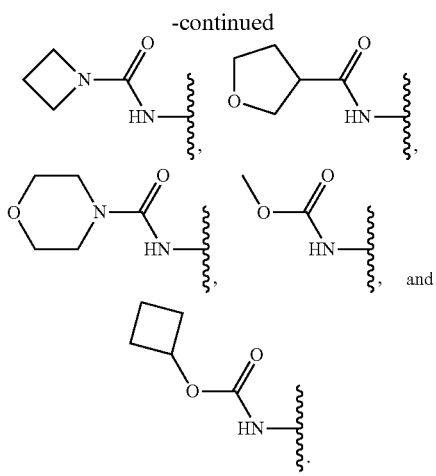

In some embodiments, $R^1$ is —$C_1$-$C_6$ alkyl, or —$NR^{1a}R^{1b}$. In some embodiments, $R^1$ is —$C_1$-$C_6$ alkyl or —$NR^{1a}R^{1b}$, wherein $R^{1a}$ and $R^{1b}$ are each independently —H or —C(O)-(4- to 6-membered heterocycloalkyl), wherein said 4- to 6-membered heterocycloalkyl has 1-2 ring heteroatoms independently selected from N and O. In some embodiments, $R^1$ is —$CH_3$, —$NH_2$, or

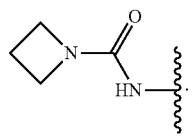 [SMILES: *NC(=O)N1CCC1]

In some embodiments, $R^1$ is —$CH_3$ or —$NH_2$. In some embodiments, $R^1$ is —$CH_3$. In some embodiments, $R^1$ is —$NH_2$.

In some embodiments, $R^2$ is halo. In some embodiments, $R^2$ is —$C_1$-$C_3$ alkyl. In some embodiments, $R^2$ is methyl.

In some embodiments, $R^3$ is halo. In some embodiments, $R^3$ is —$C_1$-$C_3$ alkyl. In some embodiments, $R^3$ is —F.

In some embodiments, both $R^2$ and $R^3$ are halo. In some embodiments, both $R^2$ and $R^3$ are —$C_1$-$C_3$ alkyl. In some embodiments, one of $R^2$ and $R^3$ is halo, and the other is —$C_1$-$C_3$ alkyl. In some embodiments, $R^2$ is —$C_1$-$C_3$ alkyl, and $R^3$ is halo. In some embodiments, one of $R^2$ and $R^3$ is —F, —Cl, or —Br, and the other is methyl or ethyl. In some embodiments, one of $R^2$ and $R^3$ is —F or —Cl, and the other is methyl or ethyl. In some embodiments, one of $R^2$ and $R^3$ is —F and the other is methyl. In some embodiments, $R^2$ is methyl and $R^3$ is —F.

In some embodiments, the compound has a structure according to Formula Ia:

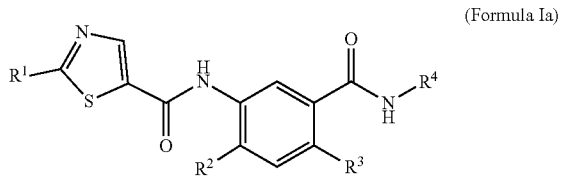

(Formula Ia)

or a pharmaceutically acceptable salt thereof.

In some embodiments, the compound has a structure according to Formula Ib:

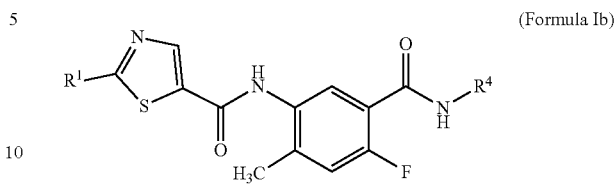

(Formula Ib)

or a pharmaceutically acceptable salt thereof.

In some embodiments, $R^4$ is —$C_1$-$C_6$ haloalkyl, —$C_1$-$C_6$ hydroxyalkyl, —$C_1$-$C_6$ hydroxyhaloalkyl, —($C_1$-$C_3$ alkylene)-O—($C_1$-$C_3$ alkyl), or —($C_1$-$C_3$ haloalkylene)-O—($C_1$-$C_3$ alkyl). In some embodiments, $R^4$ is —$C_1$-$C_6$ haloalkyl. In some embodiments, $R^4$ is —$C_1$-$C_6$ hydroxyalkyl. In some embodiments, $R^4$ is —$C_1$-$C_6$ hydroxyhaloalkyl. In some embodiments, $R^4$ is —($C_1$-$C_3$ alkylene)-O—($C_1$-$C_3$ alkyl). In some embodiments, $R^4$ is —($C_1$-$C_3$ haloalkylene)-O—($C_1$-$C_3$ alkyl).

In some embodiments, $R^4$ is —$C_1$-$C_6$ haloalkyl, —$C_1$-$C_6$ hydroxyhaloalkyl, or —($C_1$-$C_3$ haloalkylene)-O—($C_1$-$C_3$ alkyl). In some embodiments, $R^4$ is

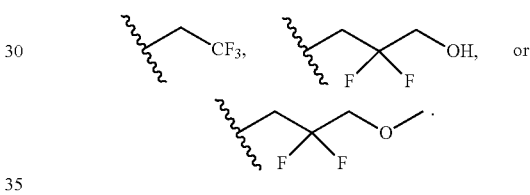

In some embodiments, $R^4$ is

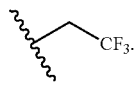 [SMILES: *CC(F)(F)F]

In some embodiments, $R^4$ is —$C_1$-$C_6$ alkyl substituted with a substituent selected from the group consisting of —$C_3$-$C_6$ cycloalkyl, phenyl, 4- to 8-membered heterocycloalkyl, and 5- to 6-membered heteroaryl, wherein said 4- to 8-membered heterocycloalkyl and 5- to 6-membered heteroaryl have 1-3 ring heteroatoms independently selected from N, O, and S; and wherein said —$C_3$-$C_6$ cycloalkyl, phenyl, 4- to 8-membered heterocycloalkyl, and 5- to 6-membered heteroaryl are unsubstituted or substituted with 1-3 $R^{4b}$. In some embodiments, $R^4$ is —$C_1$-$C_6$ alkyl substituted with —$C_3$-$C_6$ cycloalkyl, wherein said —$C_3$-$C_6$ cycloalkyl is unsubstituted or substituted with 1-3 $R^{4b}$. In some embodiments, $R^4$ is —$C_1$-$C_6$ alkyl substituted with phenyl, wherein said phenyl is unsubstituted or substituted with 1-3 $R^{4b}$. In some embodiments, $R^4$ is —$C_1$-$C_6$ alkyl substituted with 4- to 8-membered heterocycloalkyl, wherein said 4- to 8-membered heterocycloalkyl has 1-3 ring heteroatoms independently selected from N, O, and S; and wherein said 4- to 8-membered heterocycloalkyl is unsubstituted or substituted with 1-3 $R^{4b}$. In some embodiments, $R^4$ is —$C_1$-$C_6$ alkyl substituted with 5- to 6-membered heteroaryl, wherein said 5- to 6-membered heteroaryl has 1-3 ring heteroatoms independently selected from N, O, and S; and wherein said 5- to 6-membered heteroaryl is unsubstituted or substituted with 1-3 $R^{4b}$.

In some embodiments, $R^4$ is —$C_1$-$C_6$ alkyl substituted with a substituent selected from the group consisting of phenyl, —$C_3$-$C_4$ cycloalkyl, 5- to 6-membered heterocycloalkyl having 1-2 ring heteroatoms independently selected from N and O, and 5- to 6-membered heteroaryl having 1-3 ring nitrogen heteroatoms, each of which is unsubstituted or substituted with 1-3 $R^{4b}$. In some embodiments, $R^4$ is —$C_1$-$C_3$ alkyl substituted with a substituent selected from the group consisting of phenyl, cyclopropyl, cyclobutyl, morpholinyl, pyrazolyl, and pyridinyl, each of which is unsubstituted or substituted with 1-3 $R^{4b}$.

In some embodiments, each $R^{4b}$ is independently selected from the group consisting of halo, —$C_1$-$C_3$ alkyl, —$C_1$-$C_3$ haloalkyl, and —$C_1$-$C_3$ haloalkoxy. In some embodiments, $R^4$ is —$C_1$-$C_3$ alkyl substituted with a substituent selected from the group consisting of phenyl, cyclopropyl, cyclobutyl, morpholinyl, pyrazolyl, and pyridinyl, each of which is unsubstituted or substituted with 1-3 $R^{4b}$; wherein each $R^{4b}$ is independently selected from the group consisting of halo, —$C_1$-$C_3$ alkyl, —$C_1$-$C_3$ haloalkyl, and —$C_1$-$C_3$ haloalkoxy.

In some embodiments, $R^4$ is

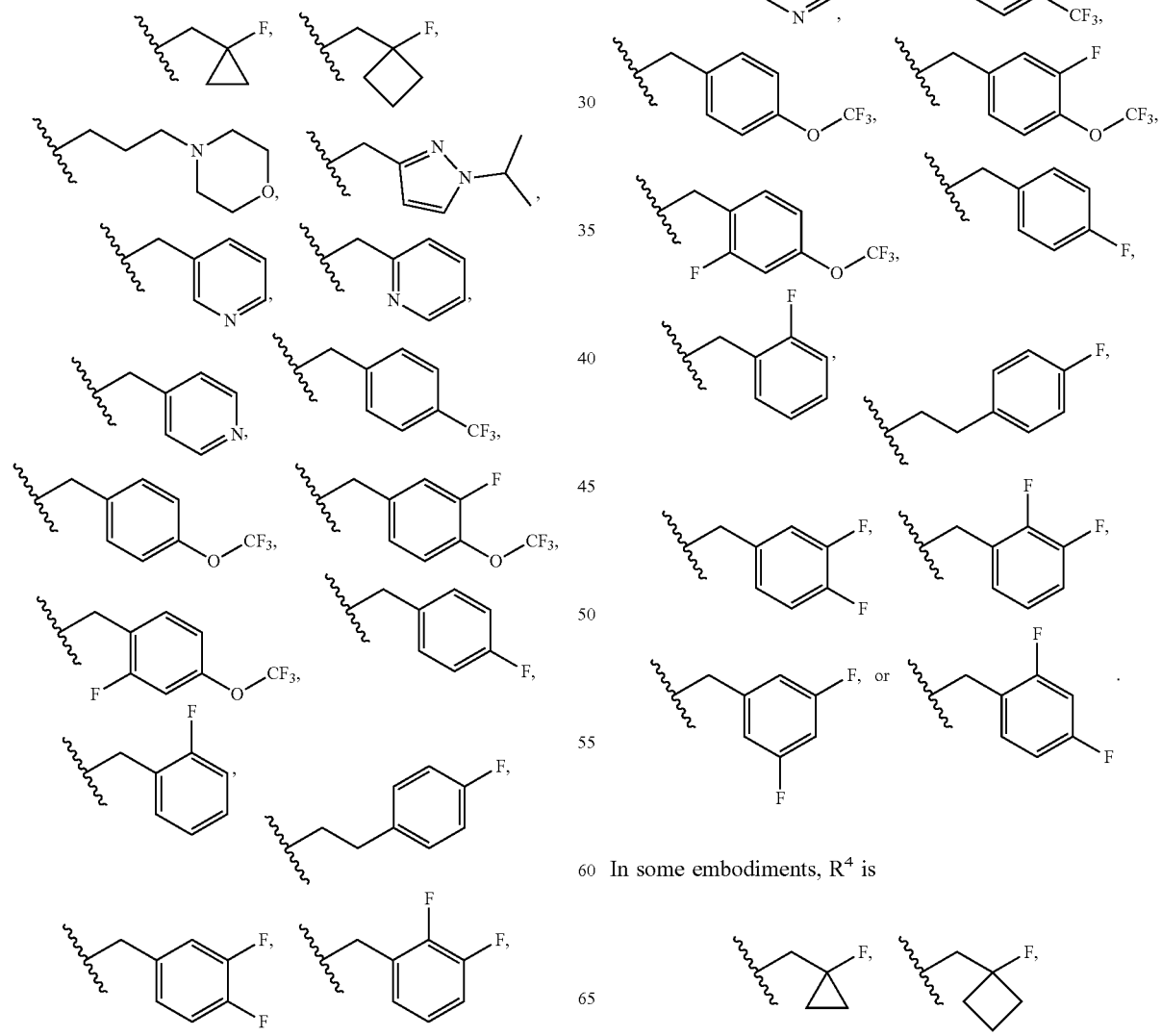

In some embodiments, $R^4$ is

17

-continued

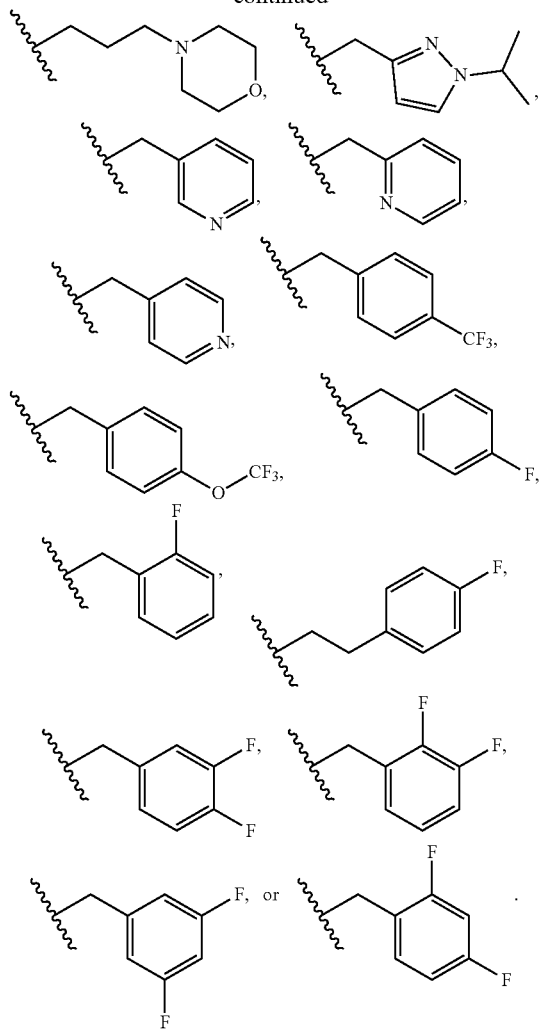

In some embodiments, $R^4$ is $-C_3-C_6$ cycloalkyl, wherein said $-C_3-C_6$ cycloalkyl is unsubstituted or substituted with a substituent selected from the group consisting of halo, $-CN$, $-C(O)NH_2$, $-C_1-C_3$ haloalkyl, $-C_1-C_3$ alkoxy, $-(C_1-C_3$ alkylene)-O-$(C_1-C_3$ alkyl), and phenyl; wherein said phenyl is unsubstituted or substituted with 1-3 halo. In some embodiments, $R^4$ is unsubstituted $-C_3-C_6$ cycloalkyl. In some embodiments, $R^4$ is $-C_3-C_6$ cycloalkyl substituted with a substituent selected from the group consisting of halo, $-CN$, $-C(O)NH_2$, $-C_1-C_3$ haloalkyl, $-C_1-C_3$ alkoxy, $-(C_1-C_3$ alkylene)-O-$(C_1-C_3$ alkyl), and phenyl; wherein said phenyl is unsubstituted or substituted with 1-3 halo. In some embodiments, $R^4$ is $-C_3-C_6$ cycloalkyl substituted with halo. In some embodiments, $R^4$ is $-C_3-C_6$ cycloalkyl substituted with $-CN$. In some embodiments, $R^4$ is $-C_3-C_6$ cycloalkyl substituted with $-C(O)NH_{12}$. In some embodiments, $R^4$ is $-C_3-C_6$ cycloalkyl substituted with $-C_1-C_3$ haloalkyl. In some embodiments, $R^4$ is $-C_3-C_6$ cycloalkyl substituted with $-C_1-C_3$ alkoxy. In some embodiments, $R^4$ is $-C_3-C_6$ cycloalkyl substituted with $-(C_1-C_3$ alkylene)-O-$(C_1-C_3$ alkyl). In some embodiments, $R^4$ is $-C_3-C_6$ cycloalkyl substituted with phenyl; wherein said phenyl is unsubstituted or substituted with 1-3 halo.

In some embodiments, $R^4$ is $-C_3-C_4$ cycloalkyl substituted with a substituent selected from the group consisting of halo, $-CN$, $-C(O)NH_2$, $-C_1-C_3$ alkoxy, and phenyl; wherein said phenyl is unsubstituted or substituted with halo. In some embodiments, $R^4$ is

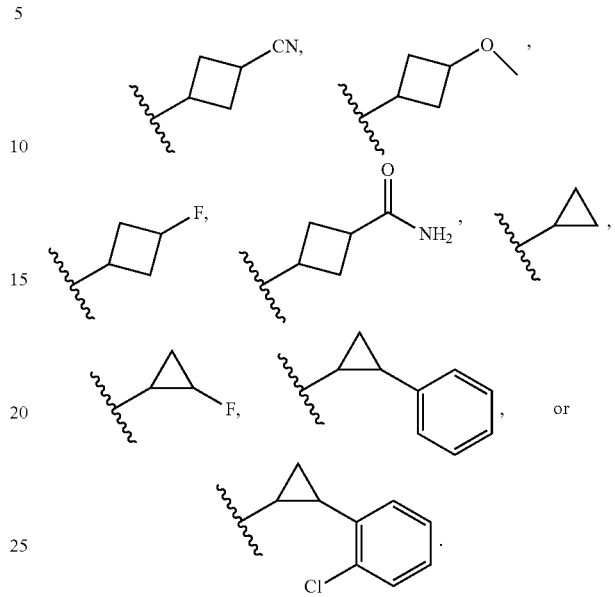

In some embodiments, $R^4$ is

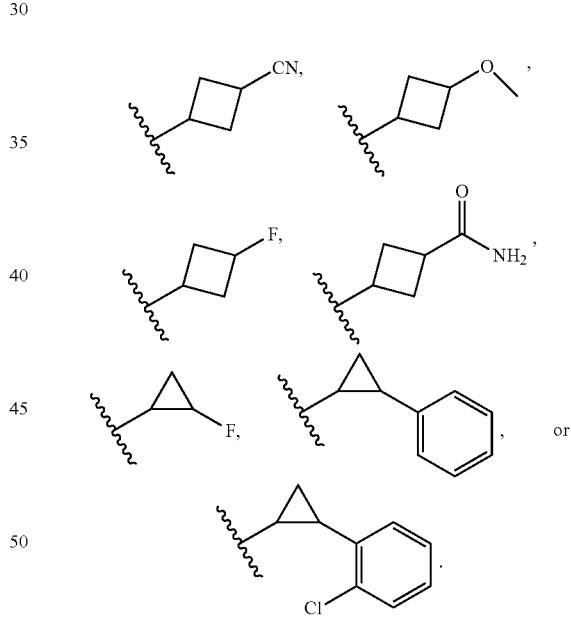

In some embodiments, $R^4$ is 4- to 8-membered heterocycloalkyl having 1-3 ring heteroatoms independently selected from N, O, and S; wherein said 4- to 8-membered heterocycloalkyl is unsubstituted or substituted with $-C(O)R^{4d}$ or 5- to 6-membered heteroaryl having 1-3 ring heteroatoms independently selected from N, O, and S. In some embodiments, $R^4$ is 4- to 8-membered heterocycloalkyl having 1-3 ring heteroatoms independently selected from N, O, and S; wherein said 4- to 8-membered heterocycloalkyl is unsubstituted. In some embodiments, $R^4$ is 4- to 8-membered heterocycloalkyl having 1-3 ring heteroatoms independently selected from N, O, and S; wherein said 4- to 8-membered heterocycloalkyl is substituted with $-C(O)R^{4d}$ or 5- to 6-membered heteroaryl having 1-3 ring heteroatoms independently selected from N, O, and S. In some embodiments, $R^4$ is 4- to 8-membered heterocycloalkyl having 1-3 ring heteroatoms independently selected from N, O, and S; wherein said 4- to 8-membered heterocycloalkyl is substituted with —C(O)$R^{4d}$. In some embodiments, $R^4$ is 4- to 8-membered heterocycloalkyl having 1-3 ring heteroatoms independently selected from N, O, and S; wherein said 4- to 8-membered heterocycloalkyl is substituted with —C(O)$R^{4d}$; and $R^{4d}$ is —$C_1$-$C_3$ alkyl. In some embodiments, $R^4$ is 4- to 8-membered heterocycloalkyl having 1-3 ring heteroatoms independently selected from N, O, and S; wherein said 4- to 8-membered heterocycloalkyl is substituted with —C(O)$R^{4d}$; and $R^{4d}$ is —$C_3$-$C_6$ cycloalkyl. In some embodiments, $R^4$ is 4- to 8-membered heterocycloalkyl having 1-3 ring heteroatoms independently selected from N, O, and S; wherein said 4- to 8-membered heterocycloalkyl is substituted with 5- to 6-membered heteroaryl having 1-3 ring heteroatoms independently selected from N, O, and S.

In some embodiments, $R^4$ is 4- to 5-membered heterocycloalkyl having 1 ring heteroatom selected from N and O; wherein said 4- to 5-membered heterocycloalkyl is unsubstituted or substituted with —C(O)—($C_3$-$C_6$ cycloalkyl), or 6-membered heteroaryl having 1-3 ring nitrogen heteroatoms. In some embodiments, $R^4$ is tetrahydrofuranyl, or azetidinyl each of which is unsubstituted or substituted with —C(O)—($C_3$-$C_6$ cycloalkyl), or 6-membered heteroaryl having 1-3 ring nitrogen heteroatoms. In some embodiments, $R^4$ is

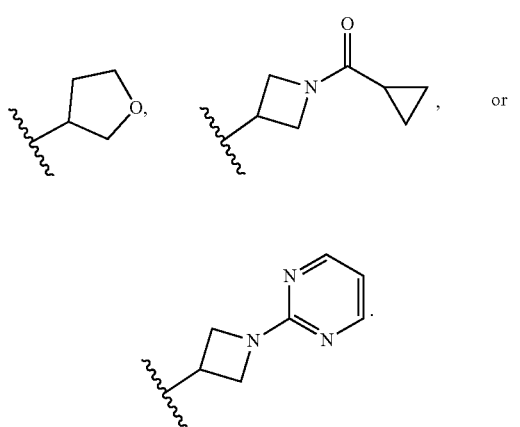

In some embodiments, $R^4$ is phenyl or 5- to 6-membered heteroaryl having 1-3 ring heteroatoms independently selected from N, O, and S; wherein said phenyl and 5- to 6-membered heteroaryl are unsubstituted or substituted with 1-3 $R^{4e}$. In some embodiments, $R^4$ is phenyl, wherein said phenyl is unsubstituted or substituted with 1-3 $R^{4e}$. In some embodiments, $R^4$ is phenyl, wherein said phenyl is unsubstituted or substituted with 1-2 $R^{4e}$. In some embodiments, $R^4$ is phenyl, wherein said phenyl is unsubstituted or substituted with 1 $R^{4e}$. In some embodiments, $R^4$ is 5- to 6-membered heteroaryl having 1-3 ring heteroatoms independently selected from N, O, and S; wherein said 5- to 6-membered heteroaryl is unsubstituted or substituted with 1-3 $R^{4e}$. In some embodiments, $R^4$ is 5-membered heteroaryl having 1-3 ring heteroatoms independently selected from N, O, and S; wherein said 5-membered heteroaryl is unsubstituted or substituted with 1-3 $R^{4e}$. In some embodiments, $R^4$ is 5-membered heteroaryl having 1-3 ring heteroatoms independently selected from N, O, and S; wherein said 5-membered heteroaryl is unsubstituted or substituted with 1-2 $R^{4e}$. In some embodiments, $R^4$ is 5-membered heteroaryl having 1-3 ring heteroatoms independently selected from N, O, and S; wherein said 5-membered heteroaryl is unsubstituted or substituted with 1 $R^{4e}$. In some embodiments, $R^4$ is 6-membered heteroaryl having 1-3 ring nitrogen atoms; wherein said 6-membered heteroaryl is unsubstituted or substituted with 1-3 $R^{4e}$. In some embodiments, $R^4$ is 6-membered heteroaryl having 1-3 ring nitrogen atoms; wherein said 6-membered heteroaryl is unsubstituted or substituted with 1-2 $R^{4e}$. In some embodiments, $R^4$ is 6-membered heteroaryl having 1-3 ring nitrogen atoms; wherein said 6-membered heteroaryl is unsubstituted or substituted with 1 $R^{4e}$. In some embodiments, $R^4$ is 5- to 6-membered heteroaryl having 1-3 ring heteroatoms independently selected from N, O, and S; wherein said 5- to 6-membered heteroaryl is unsubstituted or substituted with 1-2 $R^{4e}$. In some embodiments, $R^4$ is 5- to 6-membered heteroaryl having 1-3 ring heteroatoms independently selected from N, O, and S; wherein said 5- to 6-membered heteroaryl is unsubstituted or substituted with 1 $R^{4e}$.

In some embodiments, $R^4$ is phenyl, triazolyl, thiazolyl, thiadiazolyl, pyrazolyl, pyridinyl, pyrimidinyl, pyrazinyl, or pyridazinyl, each of which is unsubstituted or substituted with 1-3 $R^{4e}$. In some embodiments, $R^4$ is triazolyl, thiazolyl, thiadiazolyl, pyrazolyl, pyridinyl, pyrimidinyl, pyrazinyl, or pyridazinyl, each of which is unsubstituted or substituted with 1-3 $R^{4e}$.

In some embodiments, $R^4$ is

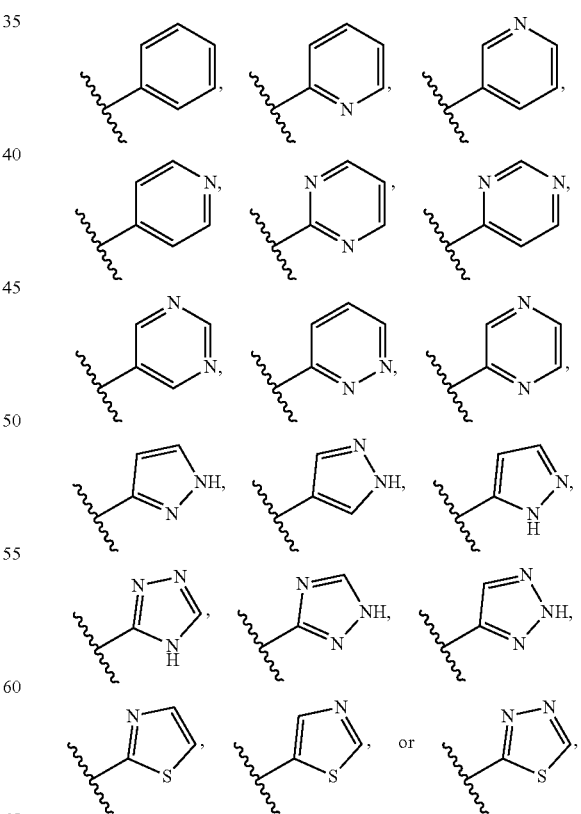

each of which is substituted with 1-2 $R^{4e}$. In some embodiments, $R^4$ is

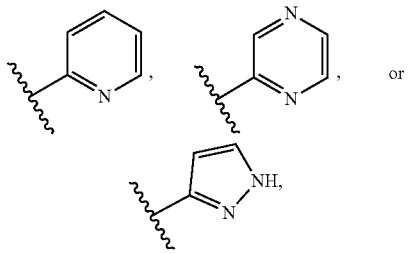

each of which is substituted with 1-2 $R^{4e}$. In some embodiments, $R^4$ is

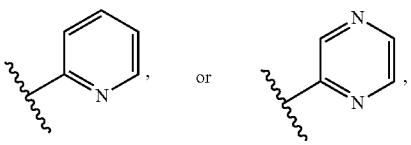 [SMILES: *c1ccccn1 ; *c1cnccn1]

each of which is substituted with 1-2 $R^{4e}$. In some embodiments, $R^4$ is

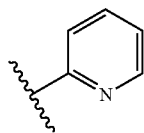

substituted with 1-2 $R^{4e}$. In some embodiments, $R^4$ is

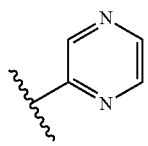 [SMILES: *c1cnccn1]

substituted with 1-2 $R^{4e}$. In some embodiments, $R^4$ is

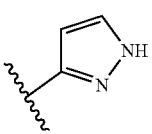

substituted with 1-2 $R^{4e}$. In some embodiments, $R^4$ is

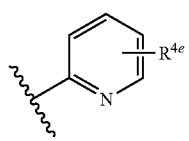

or

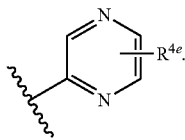

In some embodiments, $R^4$ is

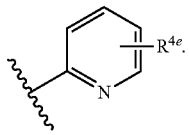

In some embodiments, $R^4$ is

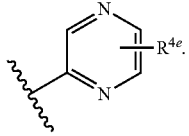

In some embodiments, $R^4$ is

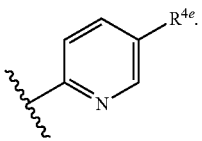

In some embodiments, $R^4$ is

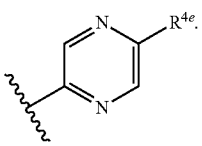

In some embodiments, each $R^{4e}$ is independently selected from the group consisting of halo, —CN, —S(O)$_2$—(C$_1$-C$_3$ alkyl), —S(O)$_2$—(C$_3$-C$_6$ cycloalkyl), —NR$^{4f}$R$^{4g}$, —C$_1$-C$_6$ alkyl, —C$_1$-C$_6$ haloalkyl, —C$_1$-C$_6$ hydroxyalkyl, —C$_1$-C$_6$ hydroxyhaloalkyl, —C$_1$-C$_3$ alkoxy, —C$_1$-C$_3$ haloalkoxy, —C$_3$-C$_6$ cycloalkyl, 4- to 8-membered heterocycloalkyl, phenyl, 5- to 6-membered heteroaryl, —(C$_1$-C$_3$ alkylene)-(C$_3$-C$_6$ cycloalkyl), —(C$_1$-C$_3$ alkylene)-O—(C$_1$-C$_3$ alkyl), —(C$_1$-C$_3$ alkylene)-O—(C$_1$-C$_3$ haloalkyl), —(C$_1$-C$_3$ alkylene)-(4- to 8-membered heterocycloalkyl), —(C$_1$-C$_3$ alkylene)-O—(C$_1$-C$_3$ alkylene)-(C$_3$-C$_6$ cycloalkyl), —O—(C$_1$-C$_3$ alkylene)-O—(C$_1$-C$_3$ alkyl), —O—(C$_3$-C$_6$ cycloalkyl), —O-(4- to 8-membered heterocycloalkyl), —O—(C$_1$-C$_3$ alkylene)-(C$_3$-C$_6$ cycloalkyl), and —O—(C$_1$-C$_3$ alkylene)-phenyl; wherein said 4- to 8-membered heterocycloalkyl and 5- to 6-membered heteroaryl have 1-3 ring heteroatoms independently selected from N, O, and S; wherein said —C$_3$-C$_6$ cycloalkyl, —(C$_1$-C$_3$ alkylene)-(C$_3$-C$_6$ cycloalkyl), 4- to 8-membered heterocycloalkyl, phenyl, and —(C₁-C₃ alkylene)-(4- to 8-membered heterocycloalkyl), are unsubstituted or substituted with 1-3 R*; and wherein said —O—(C₃-C₆ cycloalkyl) and —O—(C₁-C₃ alkylene)-(C₃-C₆ cycloalkyl) are unsubstituted or substituted with 1-3 R**.

In some embodiments, two adjacent $R^{4e}$ groups taken together with the atoms to which they are attached form a fused 5- to 6-membered heterocycloalkyl having 1-3 ring heteroatoms independently selected from N, O, and S; and wherein said 5- to 6-membered heterocycloalkyl is unsubstituted or substituted with 1-3 substituents independently selected from oxo, halo, and —C₁-C₃ alkyl. In some embodiments, two adjacent $R^{4e}$ groups taken together with the atoms to which they are attached form a fused 5- to 6-membered heterocycloalkyl having 1-3 ring heteroatoms independently selected from N, O, and S; and wherein said 5- to 6-membered heterocycloalkyl is unsubstituted. In some embodiments, two adjacent $R^{4e}$ groups taken together with the atoms to which they are attached form a fused 5- to 6-membered heterocycloalkyl having 1-3 ring heteroatoms independently selected from N, O, and S; and wherein said 5- to 6-membered heterocycloalkyl is substituted with 1-3 substituents independently selected from oxo, halo, and —C₁-C₃ alkyl.

In some embodiments, each $R^{4e}$, when present, is independently:

a) —F, —Cl, —CN, —CH₃, —OCH₃, —OCF₃, —OCF₂H, —OCH₂CH₃, —S(O)₂CH₃, —CH₂CH₃, —CH(CH₃)₂, —C(CH₃)₃, —CH₂CH(CH₃)₂, —CF₂H, —CF₃, —CH₂CF₂H, —CH₂CF₃,

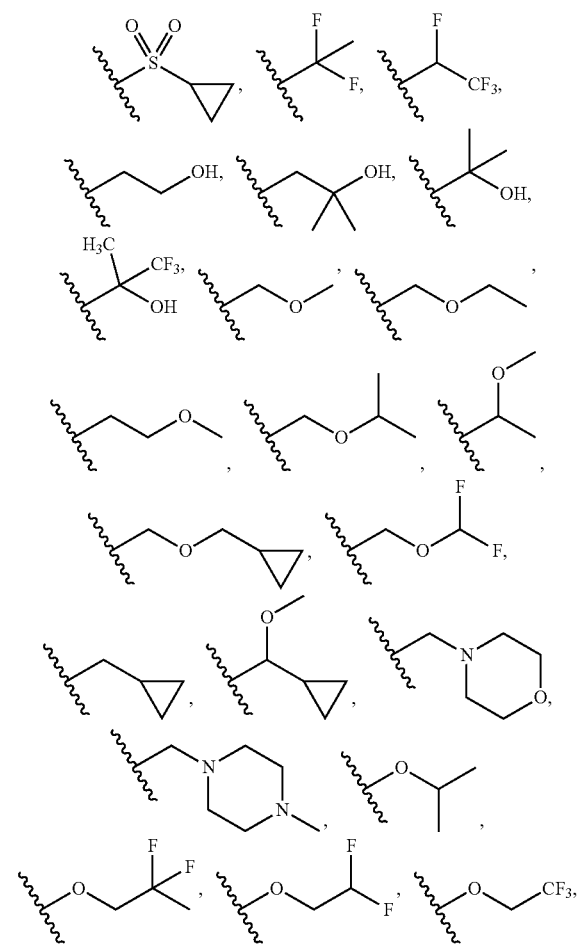

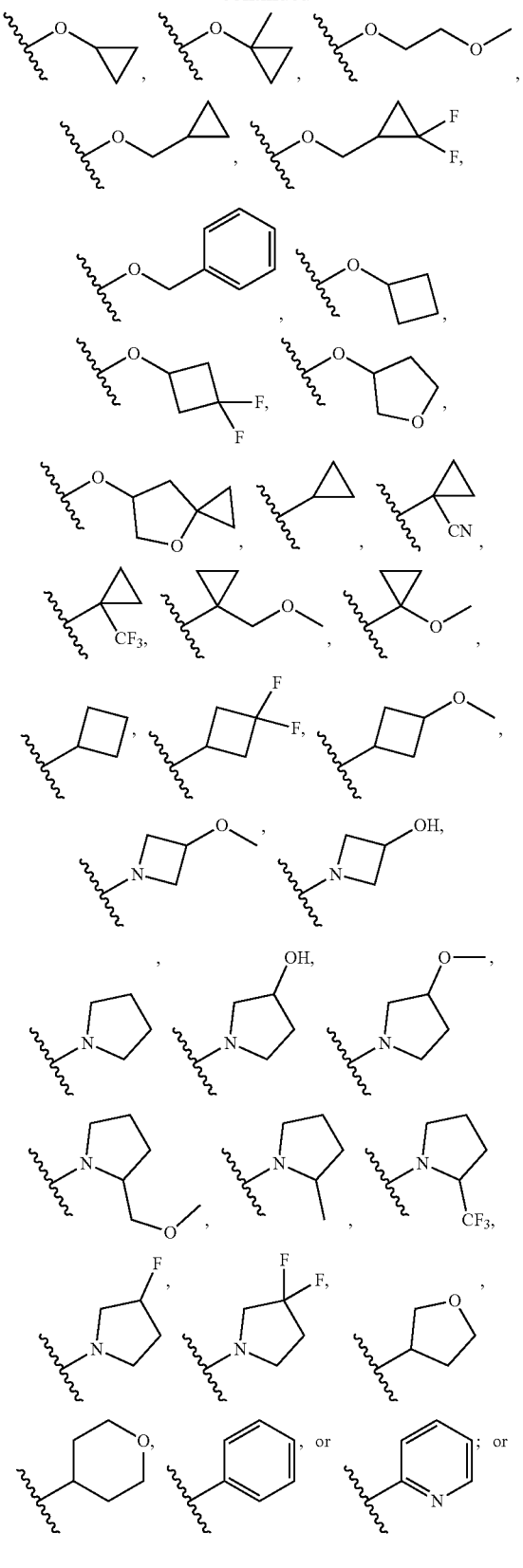

b) two adjacent $R^{4e}$ groups taken with the atoms to which they are attached form a fused heterocycloalkyl ring selected from the group consisting of:

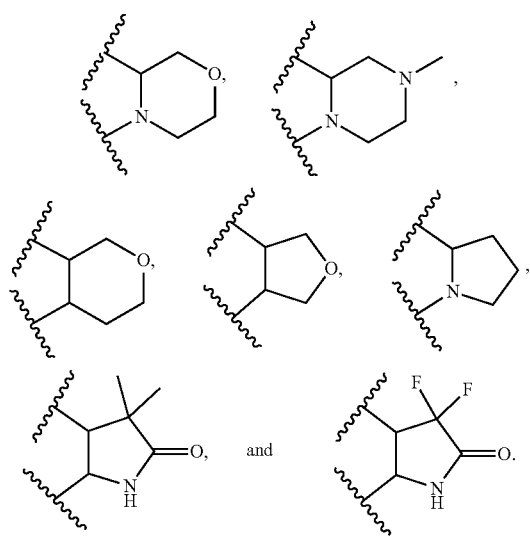
In some embodiments, each $R^{4e}$, when present, is independently:
a) —F, —Cl, —CN, —CH$_3$, —OCH$_3$, —OCF$_3$, —OCF$_2$H, —OCH$_2$CH$_3$, —S(O)$_2$CH$_3$, —CH$_2$CH$_3$, —CH(CH$_3$)$_2$, —C(CH$_3$)$_3$, —CH$_2$CH(CH$_3$)$_2$, —CF$_2$H, —CF$_3$, —CH$_2$CF$_2$H, —CH$_2$CF$_3$,
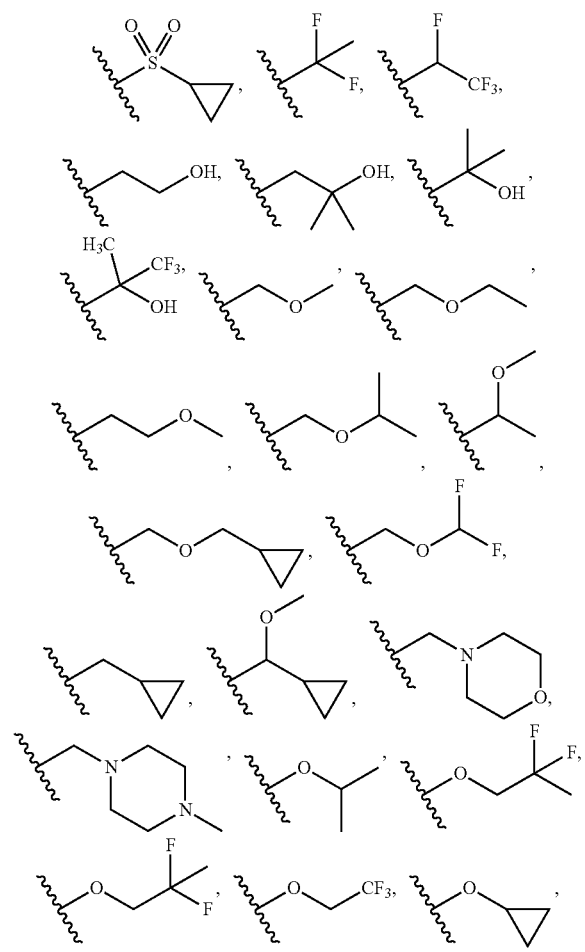
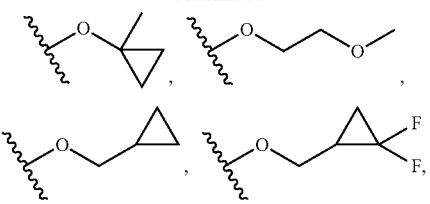
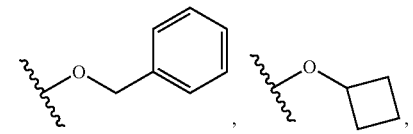
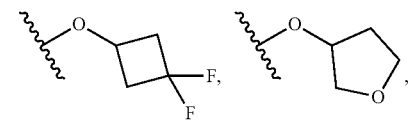
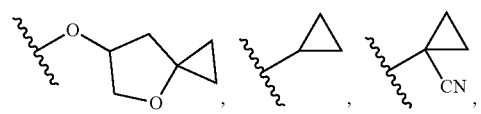
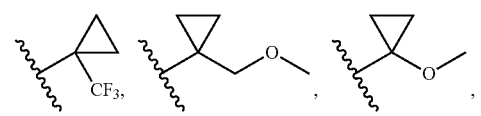
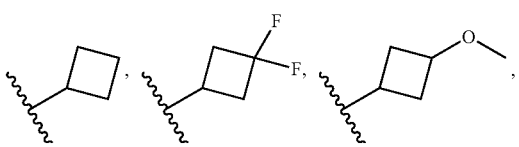
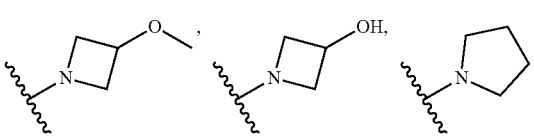
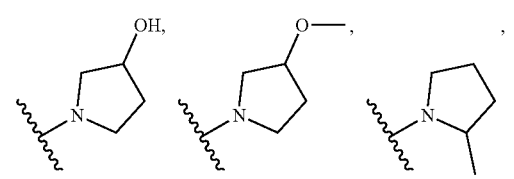
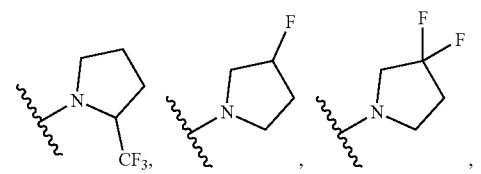
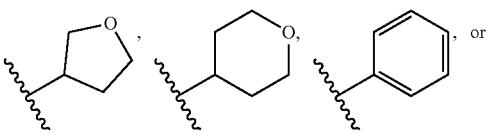
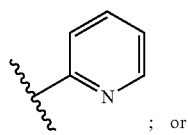
; or
b) two adjacent $R^{4e}$ groups taken with the atoms to which they are attached form a fused heterocycloalkyl ring selected from the group consisting of:

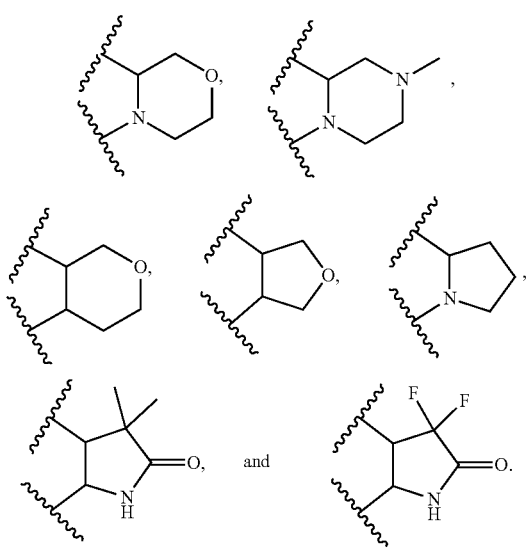

When two adjacent $R^{4e}$ groups are taken with the atoms to which they are attached to form a fused heterocycloalkyl ring, it is to be understood that the aromaticity of the ring to which they are attached (i.e., when $R^4$ is phenyl or 5- to 6-membered heteroaryl) is not disrupted. Accordingly, the resulting fused heterocycloalkyl rings have a point of unsaturation. In some embodiments, two adjacent $R^{4e}$ groups taken with the atoms to which they are attached form a fused heterocycloalkyl ring to form $R^4$ selected from the group consisting of:

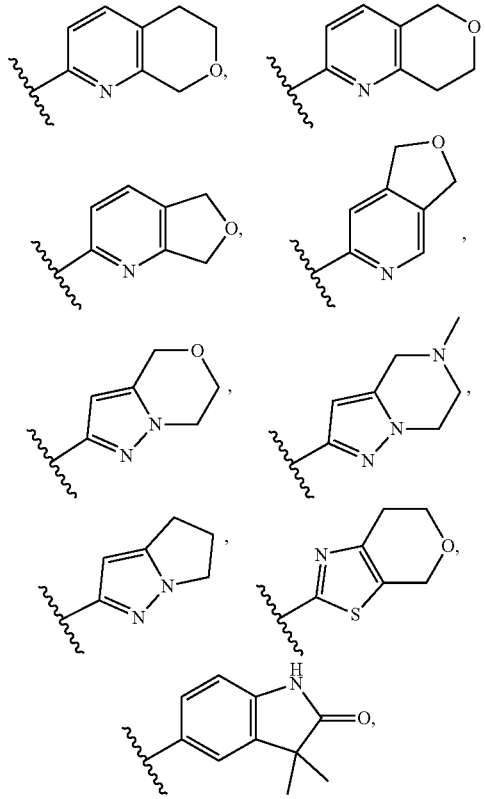

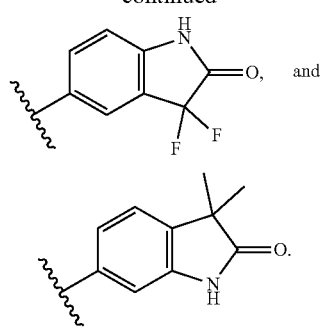

In some embodiments, $R^{4e}$ is —$C_1$-$C_3$ haloalkyl, —$C_3$-$C_6$ cycloalkyl, —($C_1$-$C_3$ alkylene)-($C_3$-$C_6$ cycloalkyl), —$C_1$-$C_3$ haloalkoxy, —O—($C_3$-$C_6$ cycloalkyl), or —($C_1$-$C_3$ alkylene)-O—($C_1$-$C_3$ alkyl).

In some embodiments, $R^4$ is

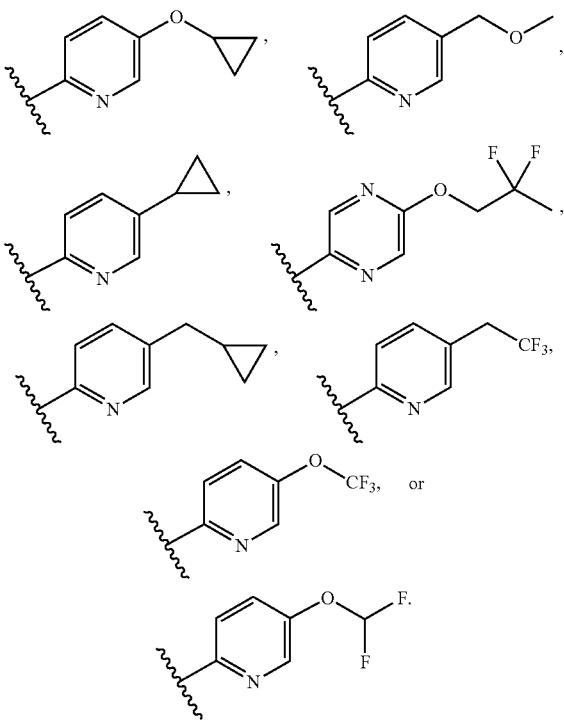

In some embodiments, $R^4$ is

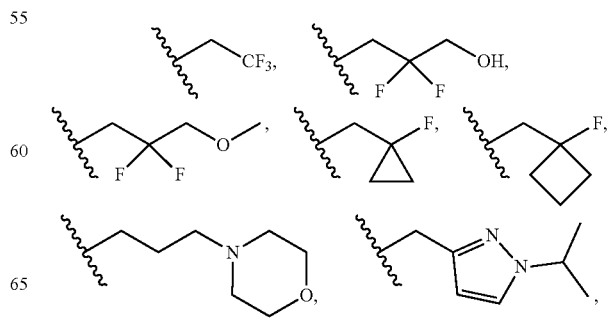

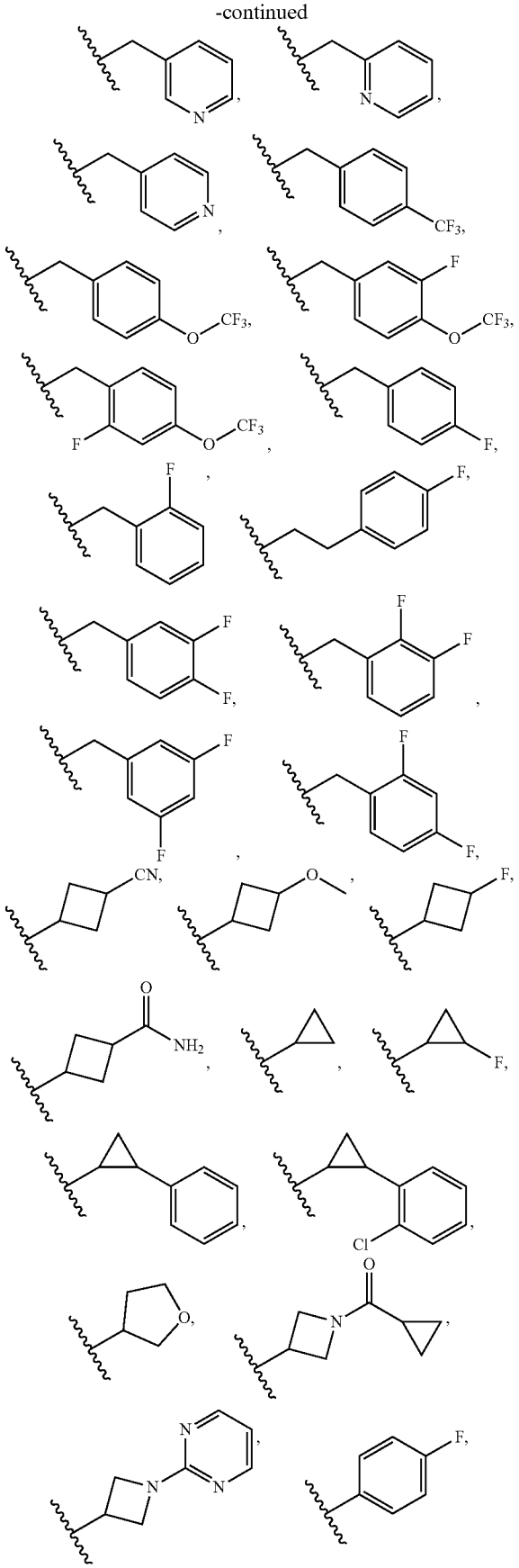
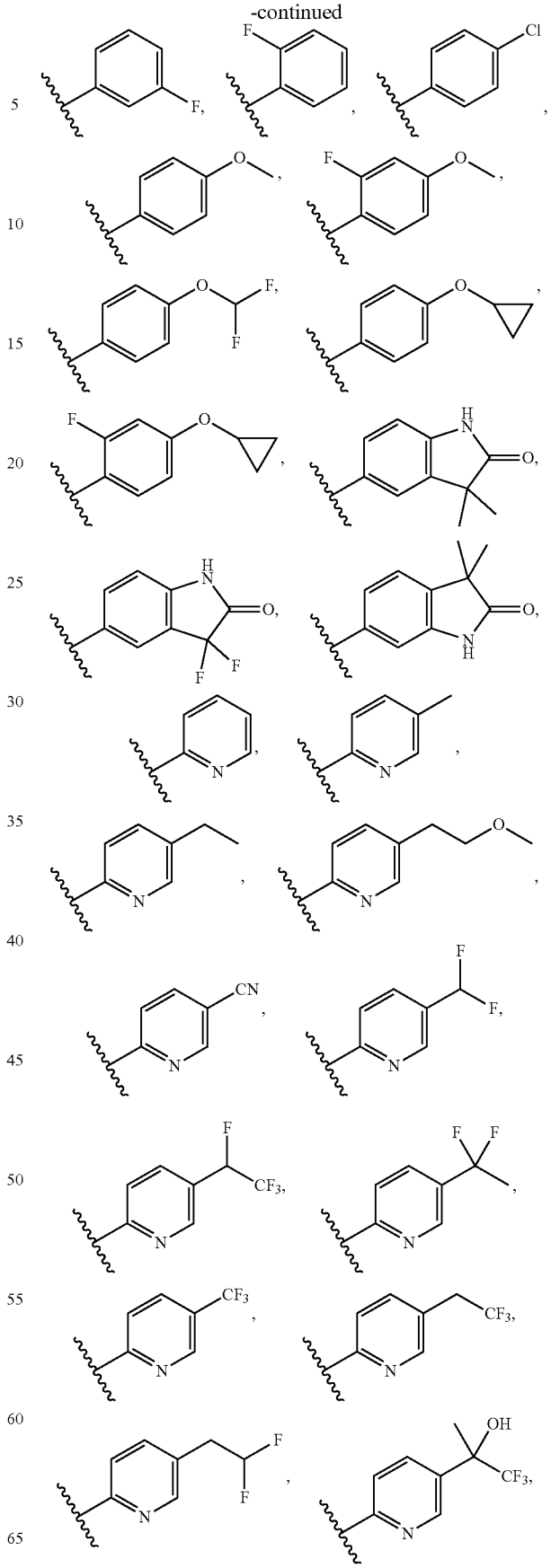

-continued
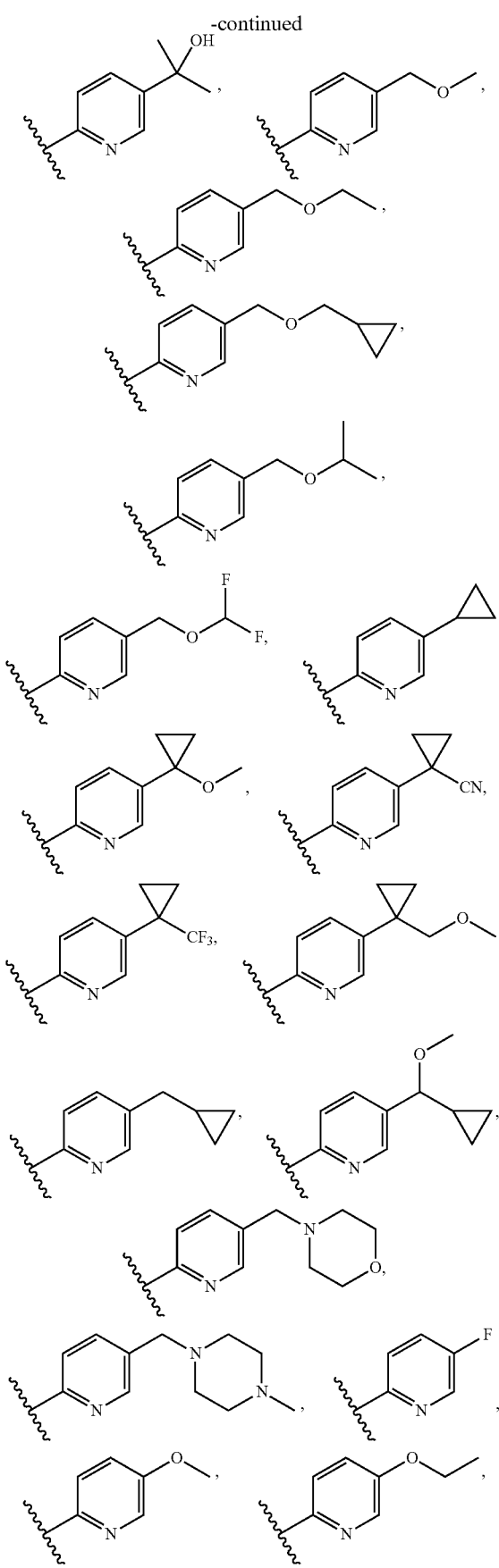
-continued
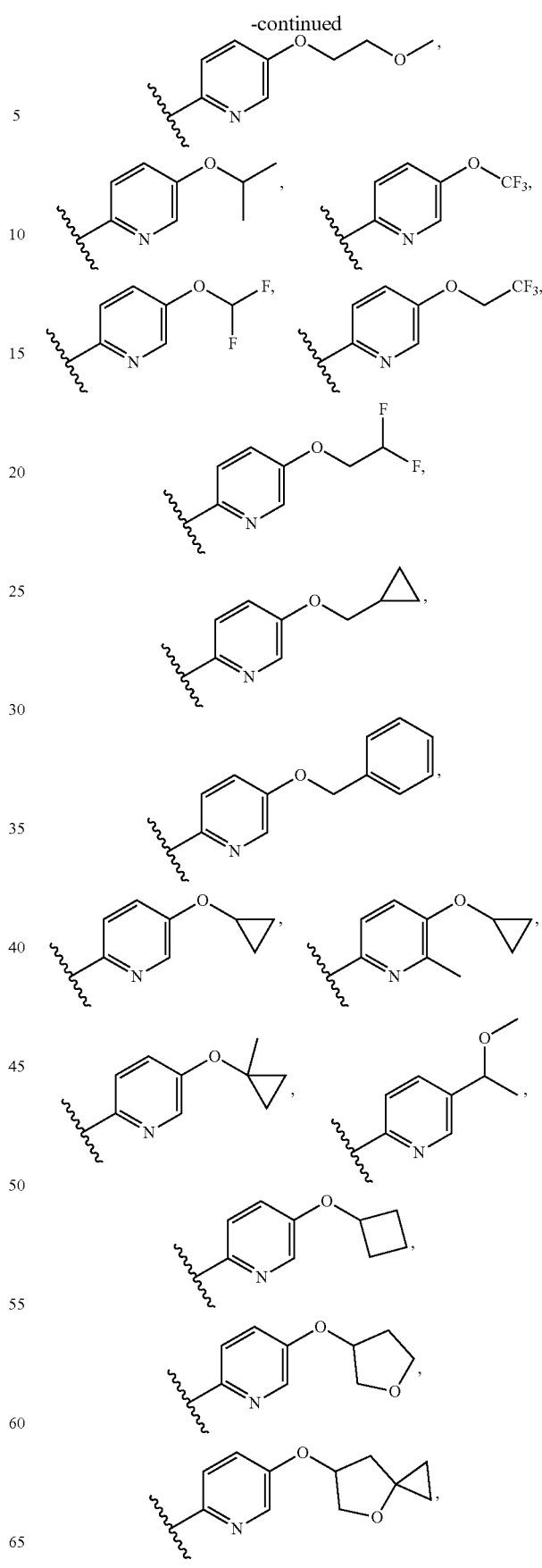

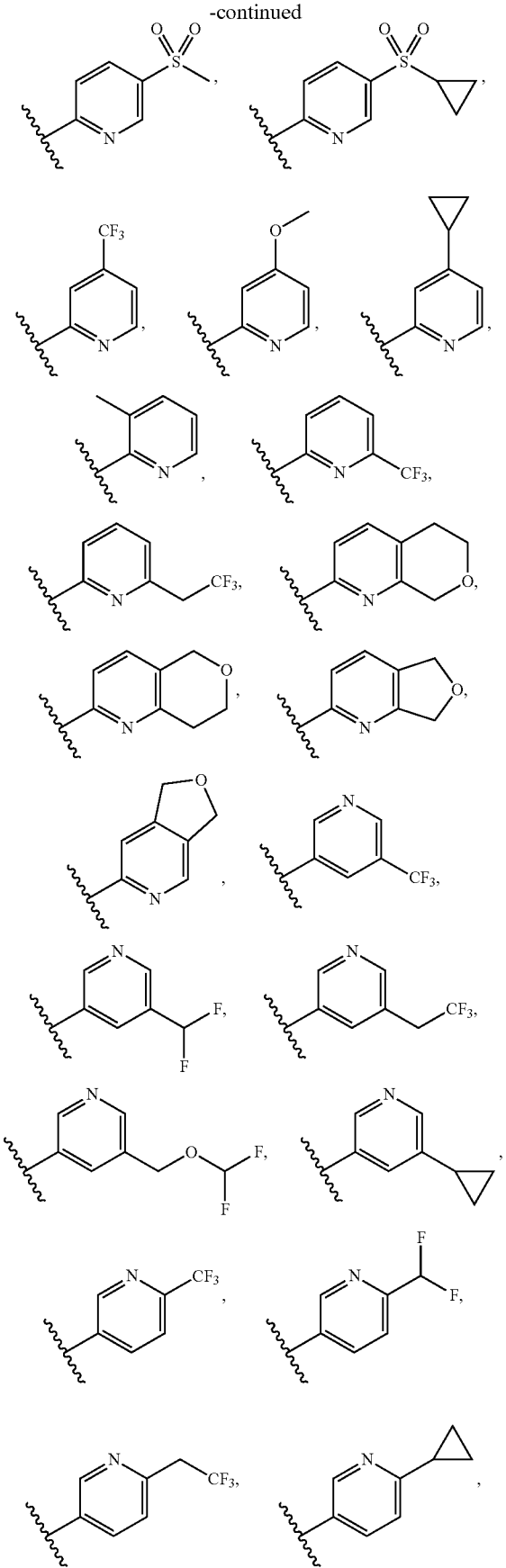
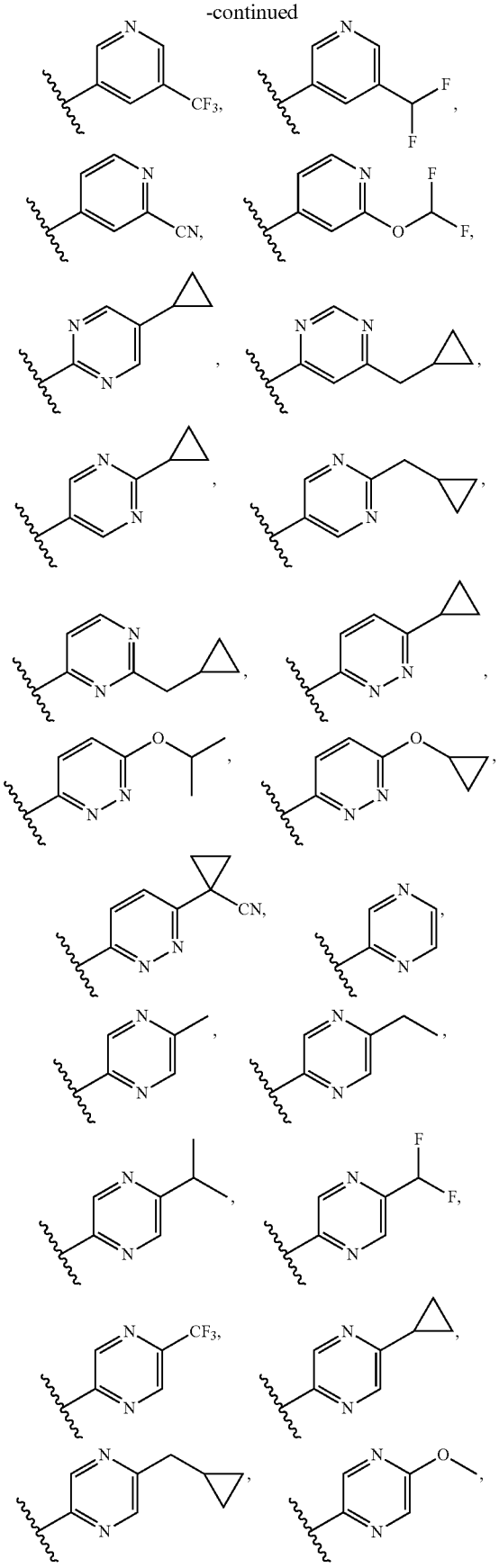

-continued
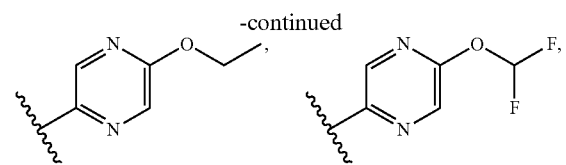 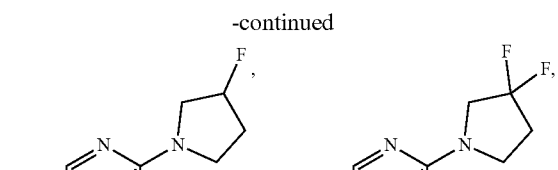
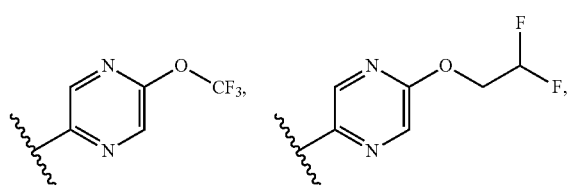 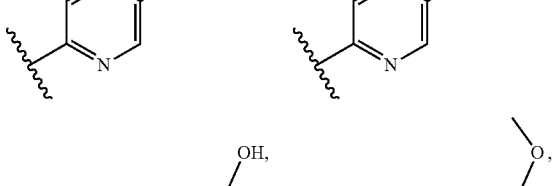
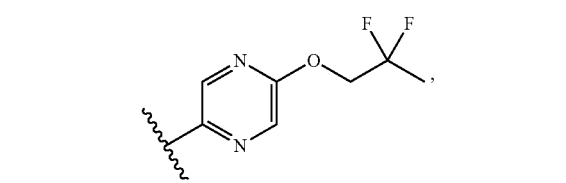 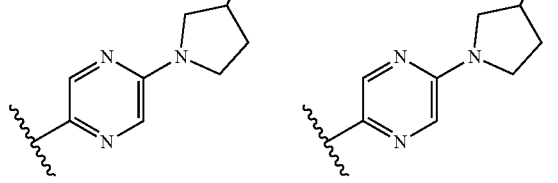
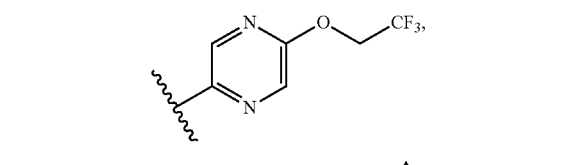 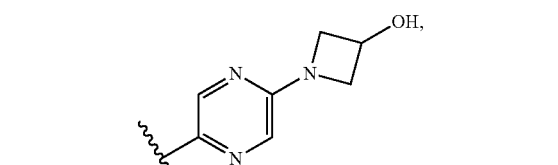
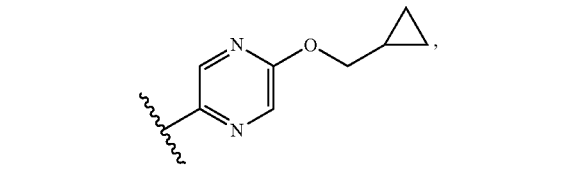 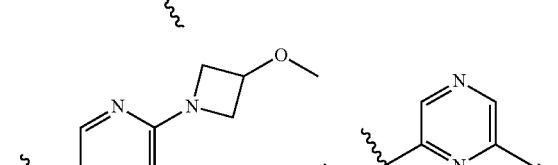
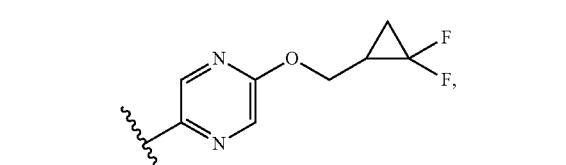 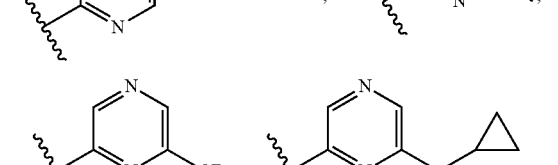
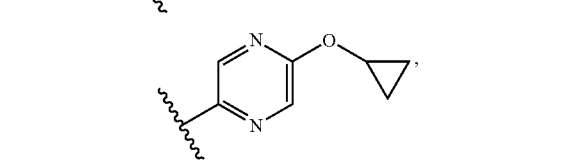 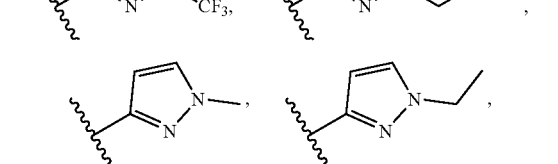
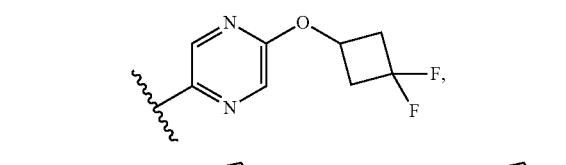 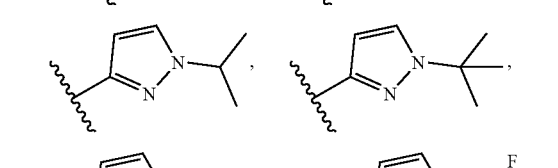
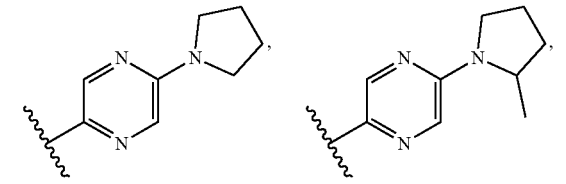 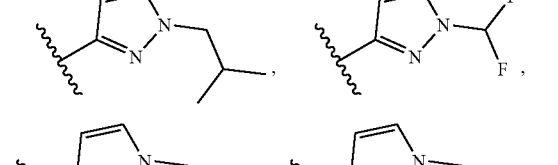
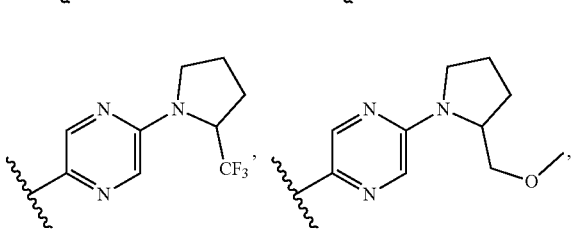 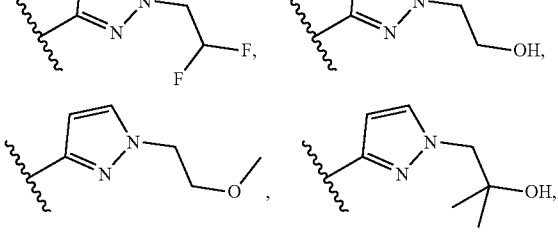

-continued
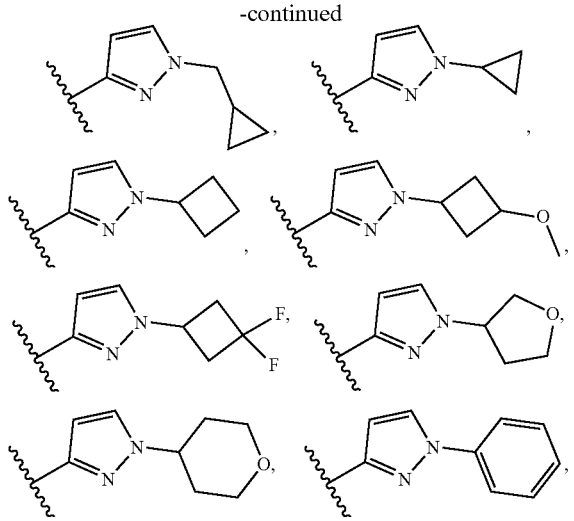
In embodiments, $R^4$ is
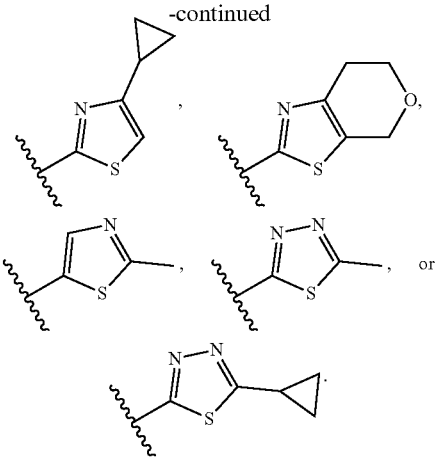

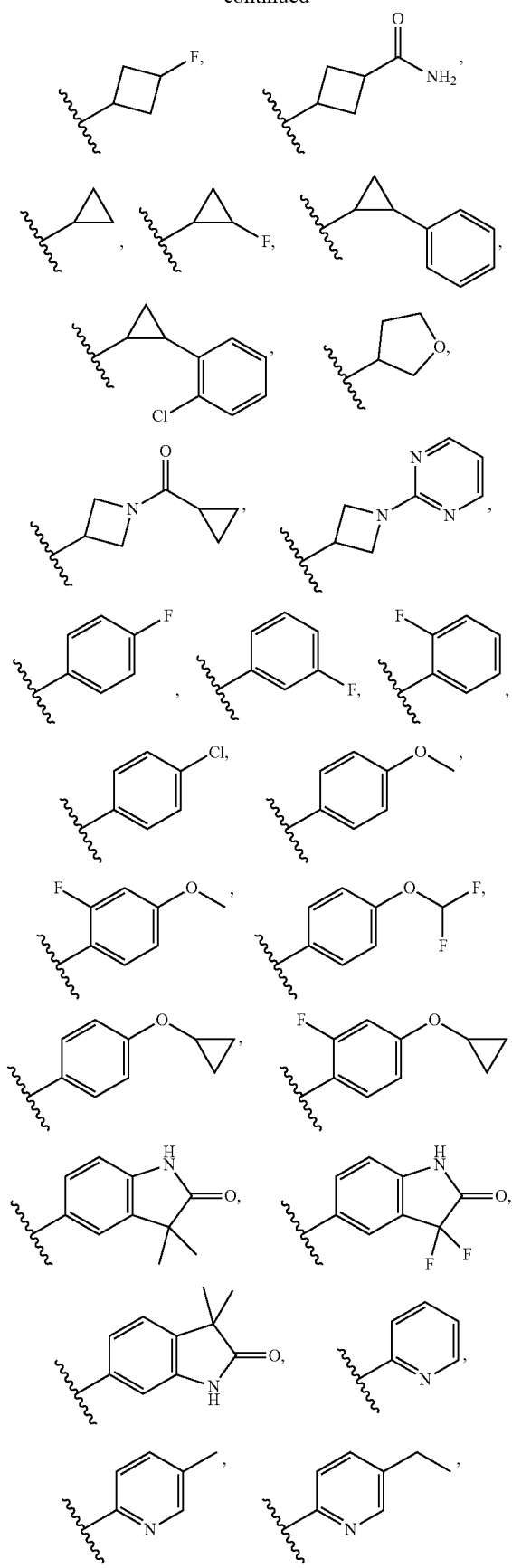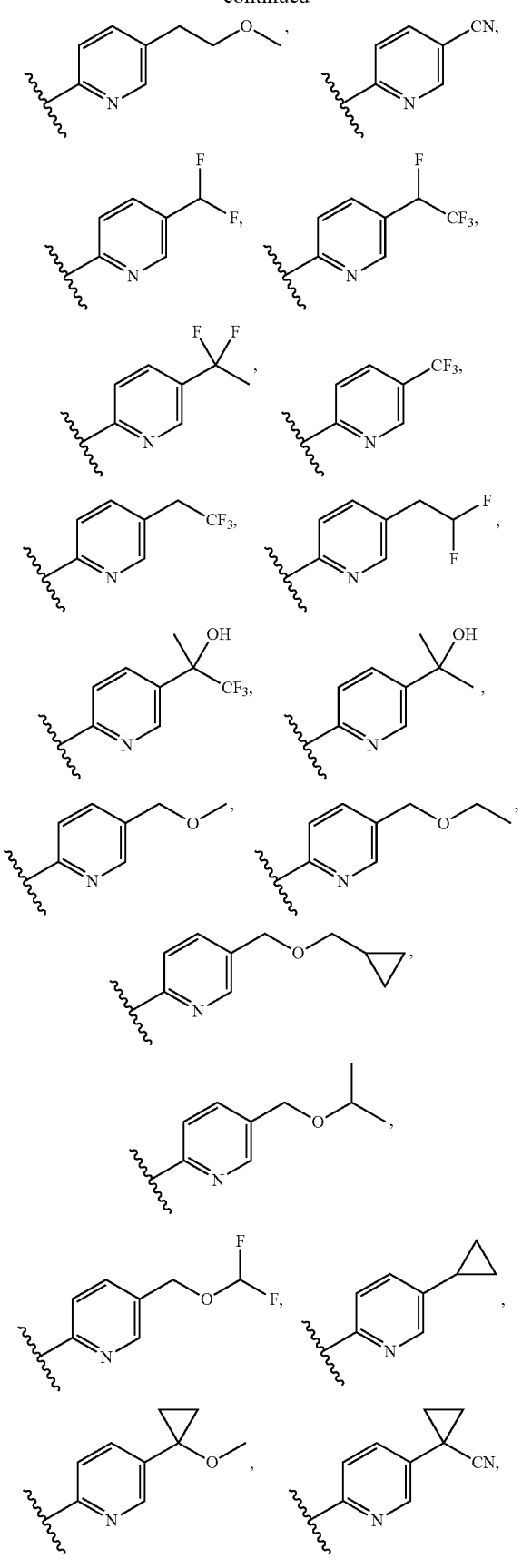

-continued
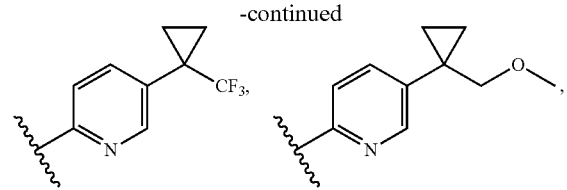
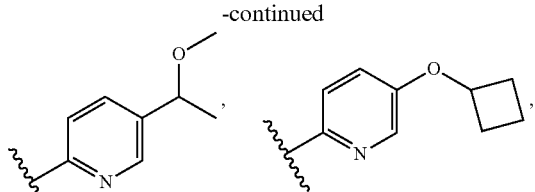
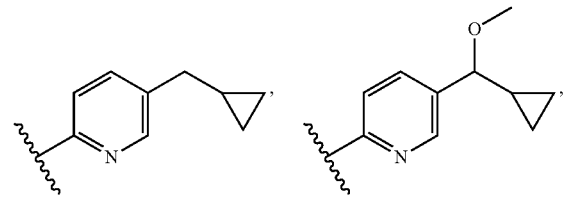
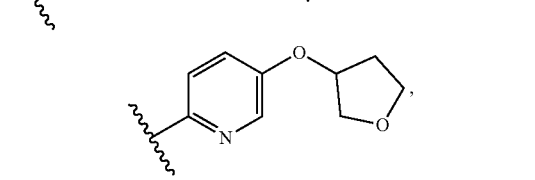
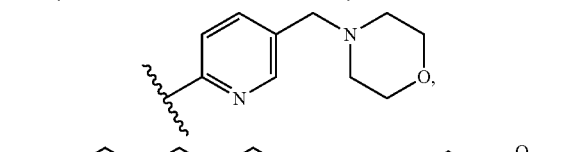

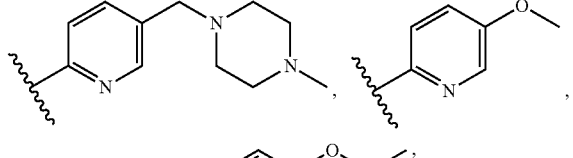
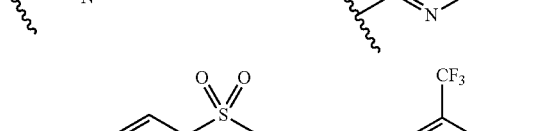
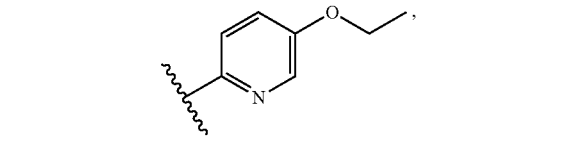
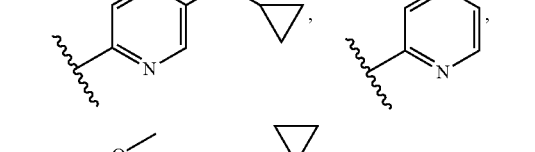
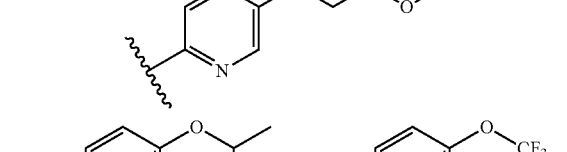

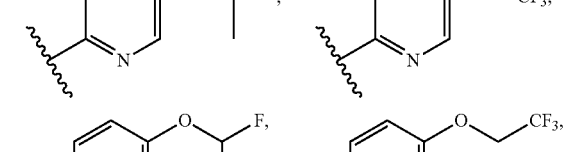
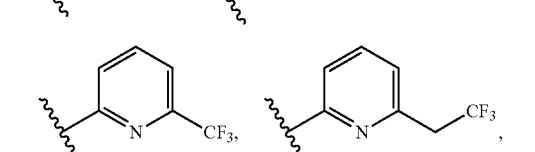

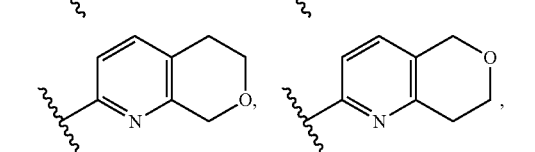
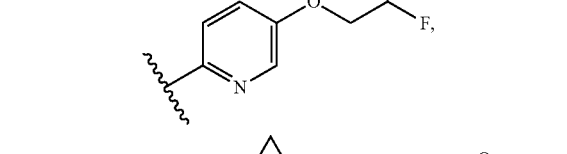
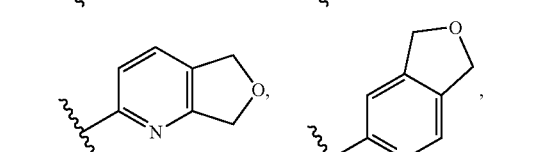
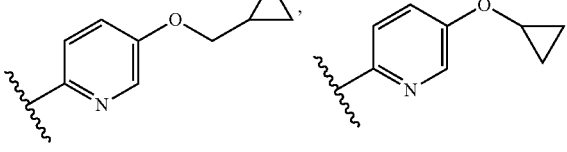
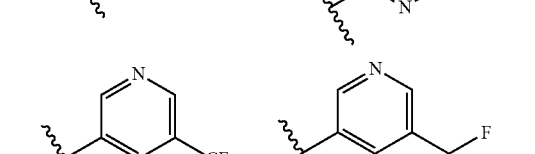
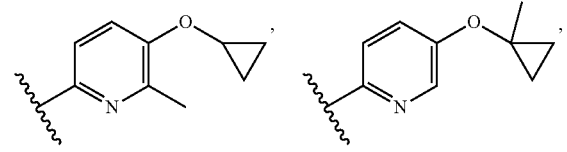
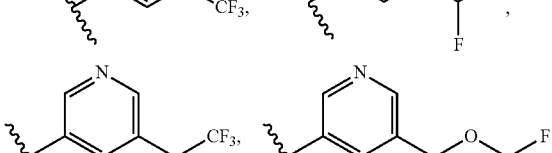

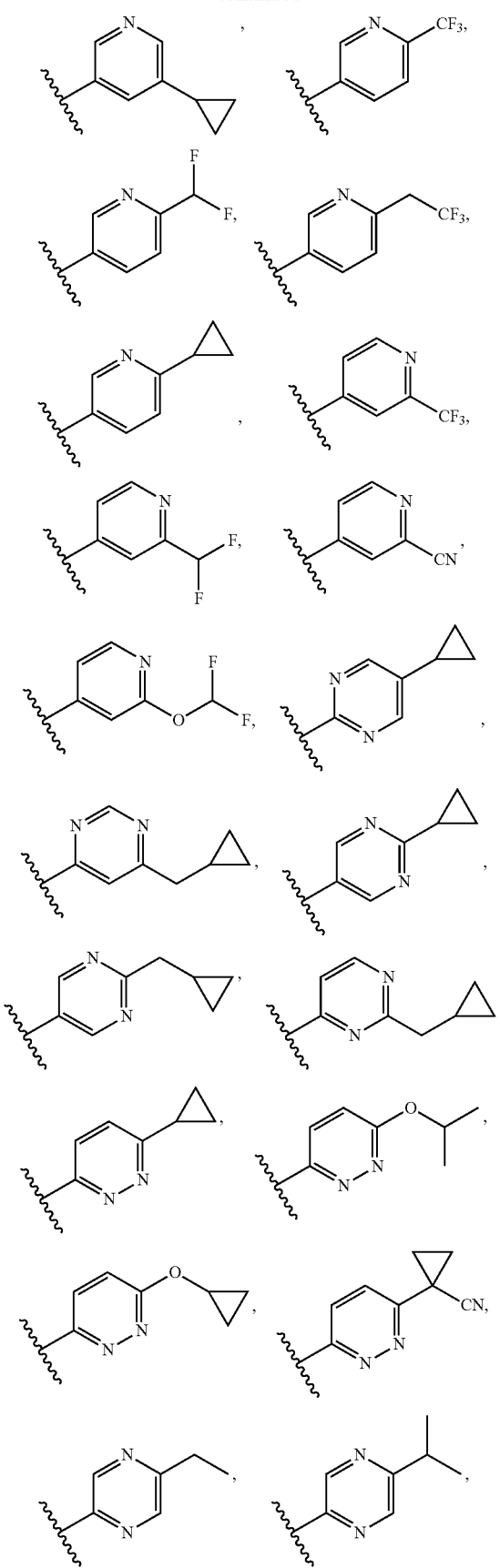
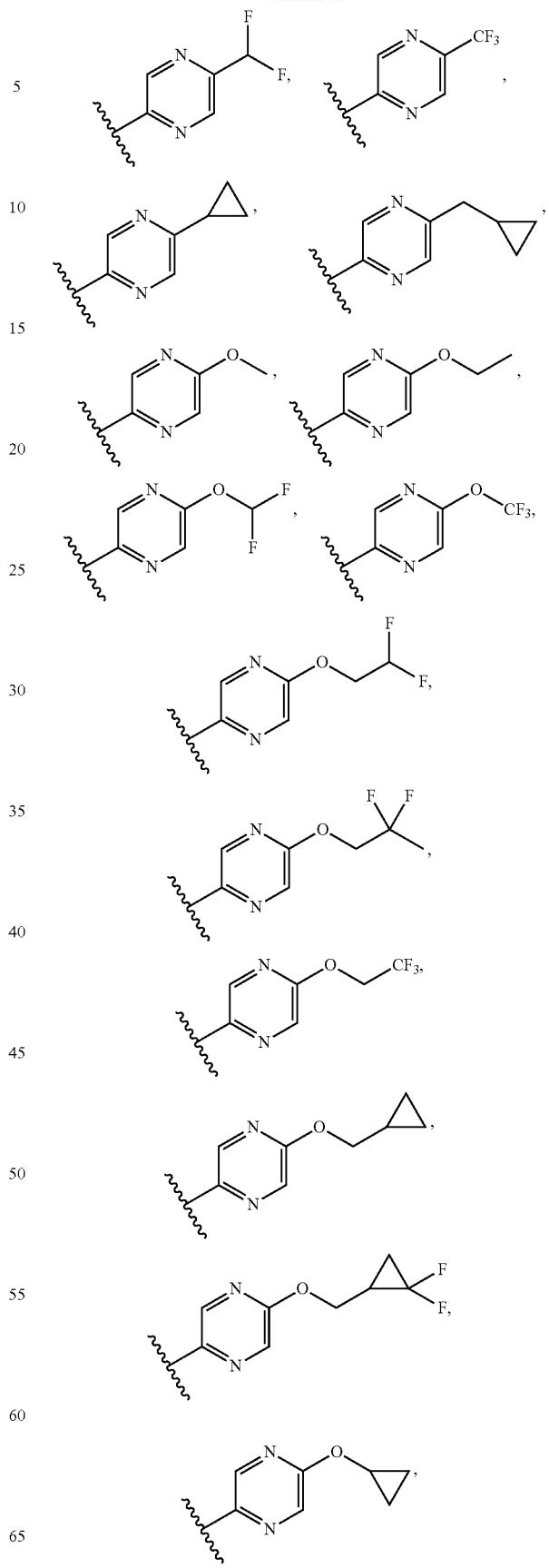

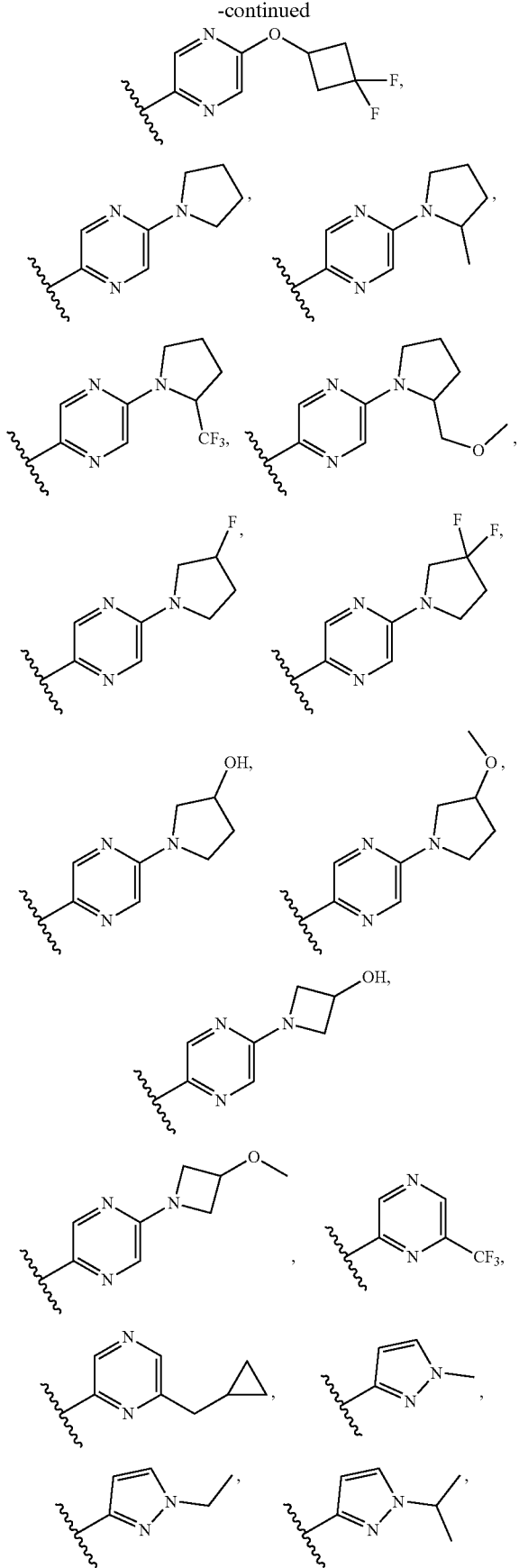
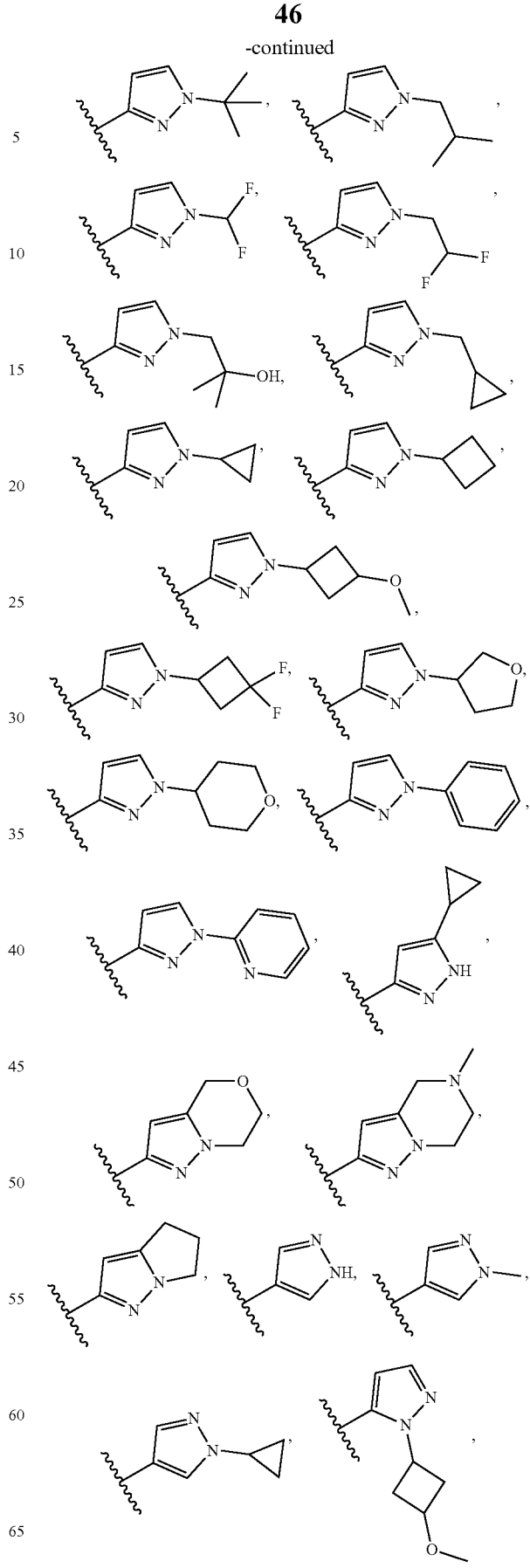

-continued
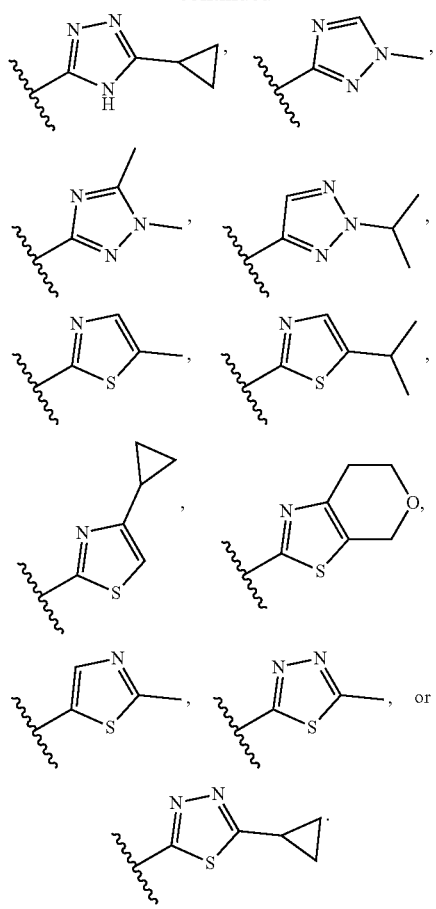
In some embodiments R⁴ is
-continued
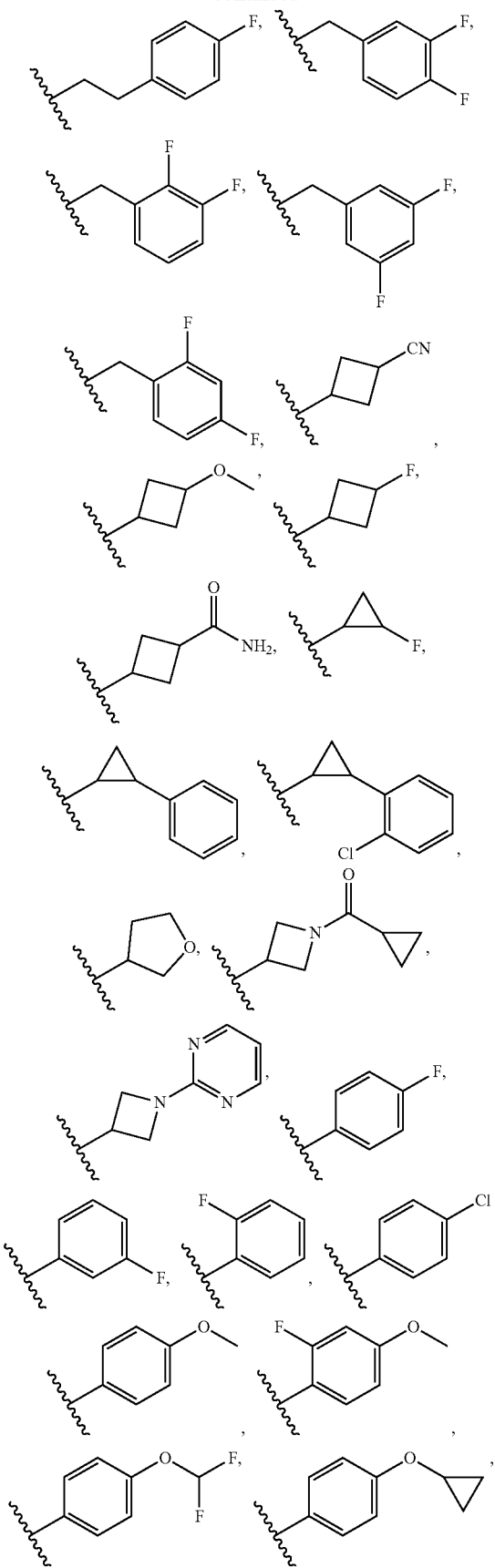

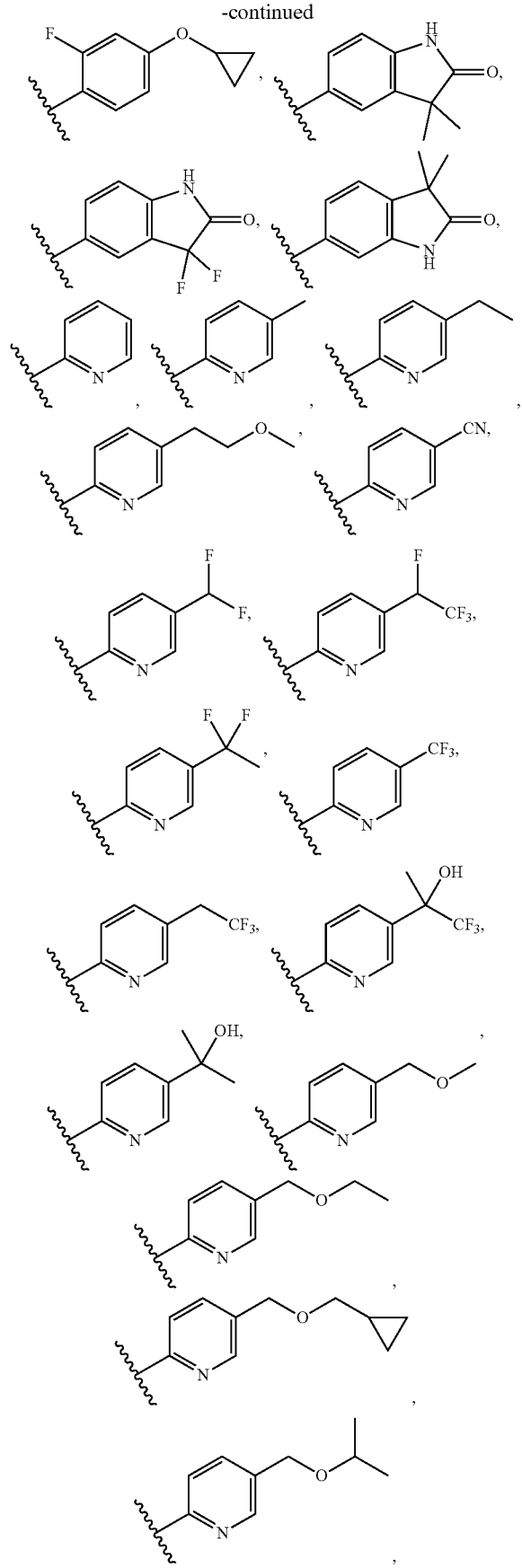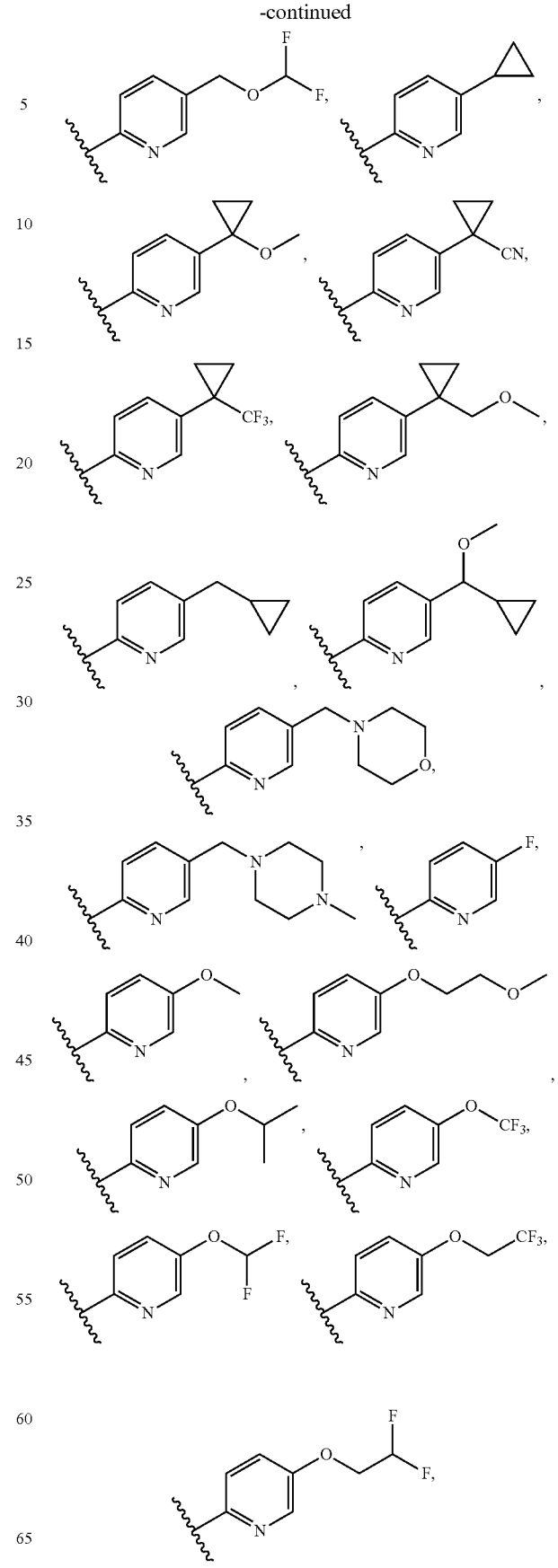

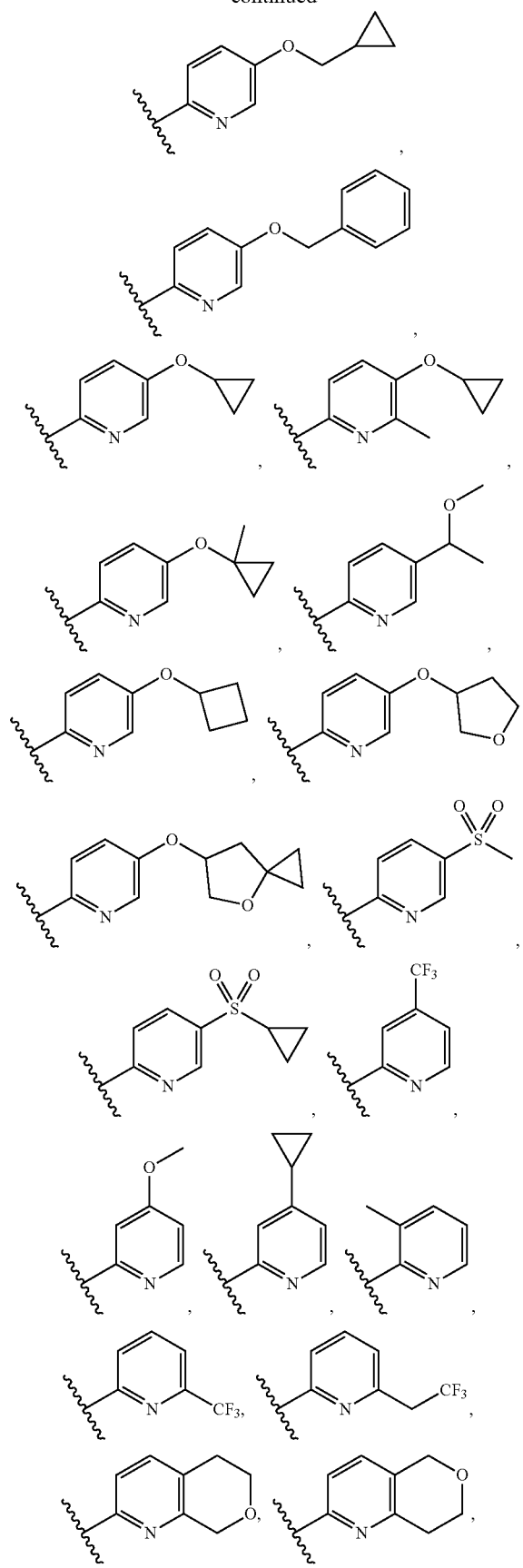
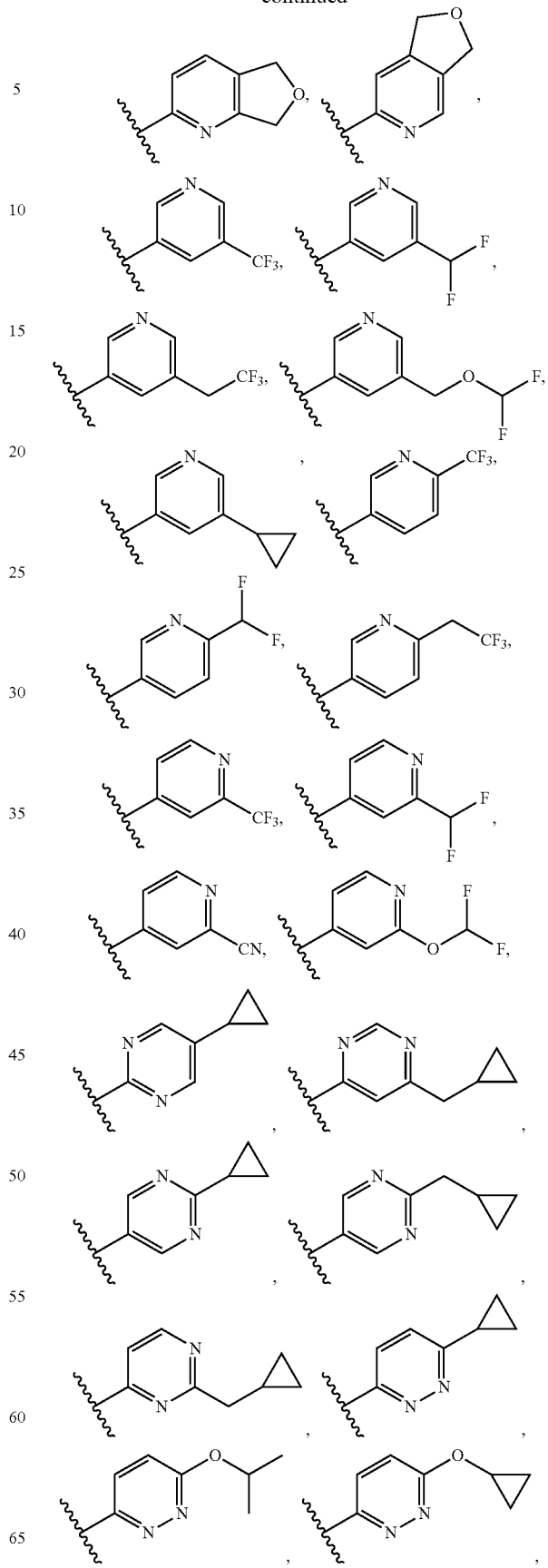

-continued
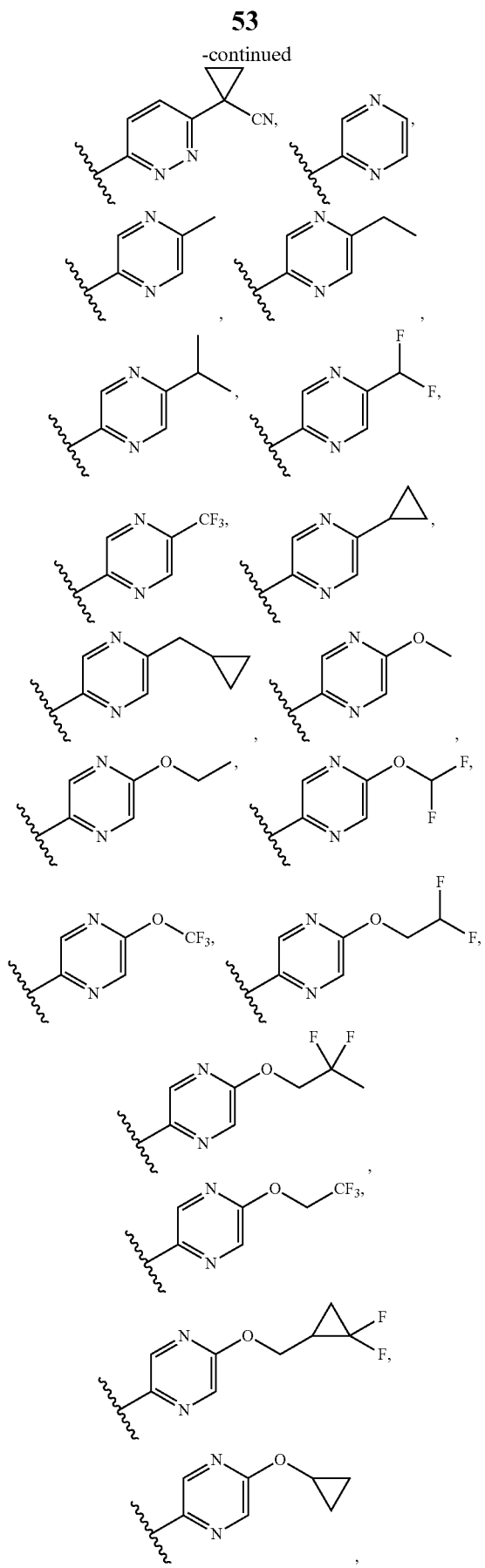
-continued
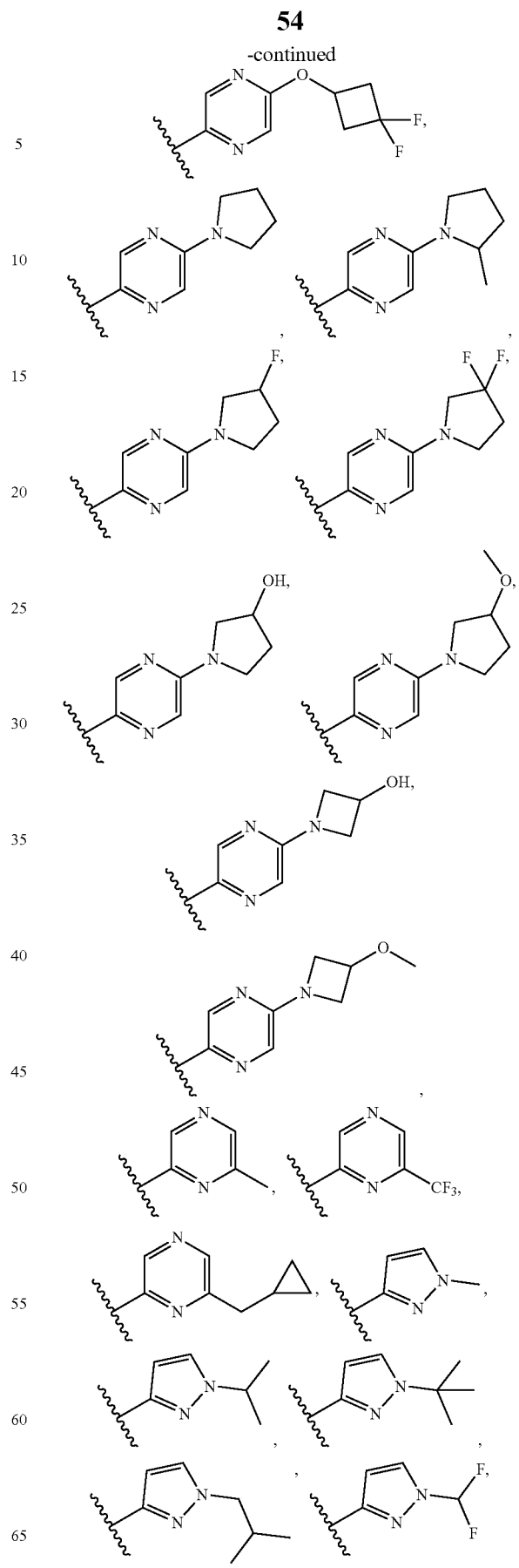

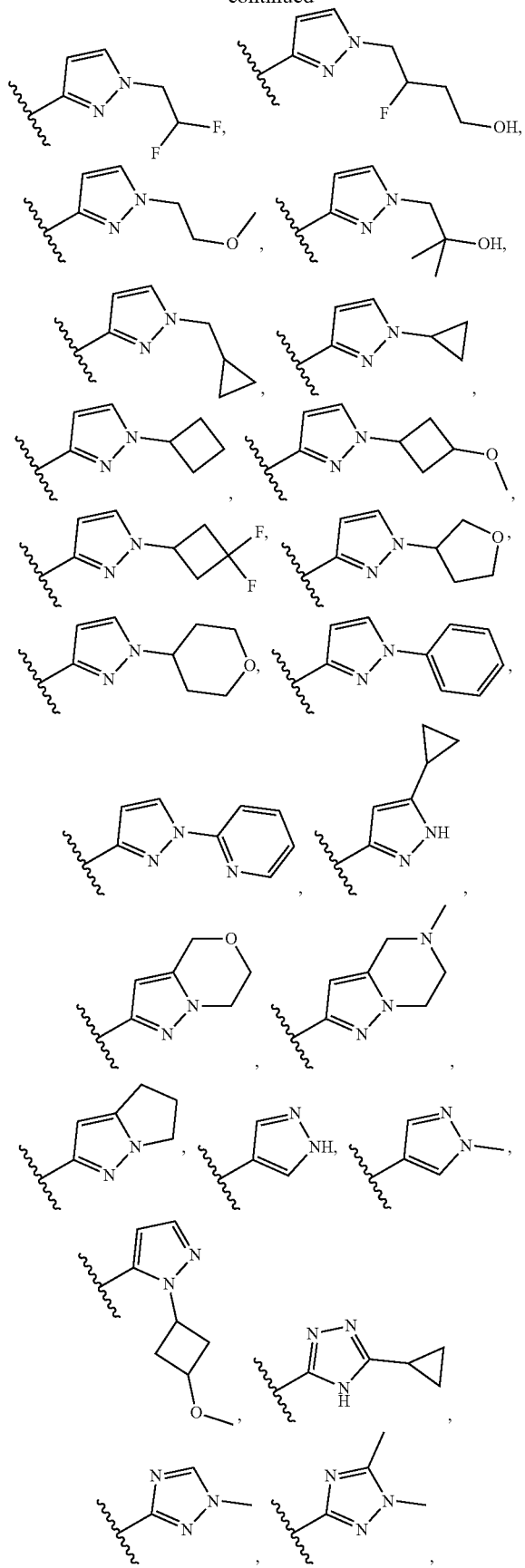
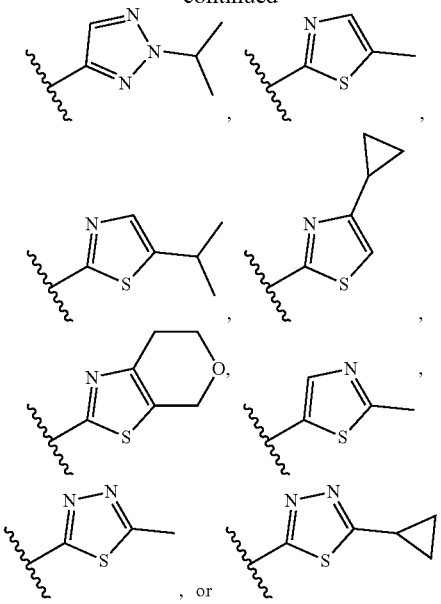

In some embodiments, the compound has a structure according to Formula R

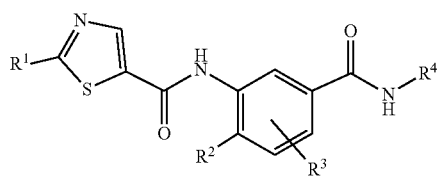

(Formula I)

or a pharmaceutically acceptable salt thereof, wherein:
R$^1$ is —H, —NR$^{1a}$R$^{1b}$, —C$_1$-C$_6$ alkyl, —C$_1$-C$_6$ haloalkyl, —C$_3$-C$_6$ cycloalkyl, or 4- to 6-membered heterocycloalkyl having 1-3 ring heteroatoms independently selected from N, O, and S;
R$^{1a}$ and R$^{1b}$ are independently —H, —C$_1$-C$_6$ haloalkyl, —C(O)R$^{1c}$, —C(O)OR$^{1d}$, or —C(O)NR$^{1e}$R$^{1f}$—;
R$^{1c}$ is —C$_1$-C$_3$ alkyl, —C$_1$-C$_3$ haloalkyl, —C$_1$-C$_3$ hydroxyalkyl, —C$_3$-C$_6$ cycloalkyl, phenyl, or 4 to 6-membered heterocycloalkyl having 1 to 3 ring heteroatoms independently selected from N, O, and S; wherein said phenyl and 4- to 6-membered heterocycloalkyl are unsubstituted or substituted with 1-3 substituents independently selected from the group consisting of halo, —OH, and C$_1$-C$_3$ alkyl;
R$^{1d}$ is —C$_1$-C$_3$ alkyl or —C$_3$-C$_6$ cycloalkyl;
R$^{1e}$ and R$^{1f}$ are independently —H or —C$_1$-C$_3$ alkyl;
R$^2$ and R$^3$ are independently halo or —C$_1$-C$_3$ alkyl;
R$^4$ is selected from:
   a) —C$_1$-C$_6$ alkyl substituted with a substituent selected from the group consisting of —C$_3$-C$_6$ cycloalkyl, phenyl, 4- to 8-membered heterocycloalkyl, and 5- to 6-membered heteroaryl, wherein said 4- to 8-membered heterocycloalkyl and 5- to 6-membered heteroaryl have 1-3 ring heteroatoms independently selected from N, O, and S; and wherein said —C$_3$-C$_6$ cycloalkyl, phenyl, 4- to 8-membered heterocycloalkyl, and 5- to 6-membered heteroaryl are unsubstituted or substituted with 1-3 R$^{4b}$;

b) —C₃-C₆ cycloalkyl substituted with a substituent selected from the group consisting of halo, —CN, —C(O)NH₂, —C₁-C₃ haloalkyl, —C₁-C₃ alkoxy, —(C₁-C₃ alkylene)-O—(C₁-C₃ alkyl), and phenyl; wherein said phenyl is unsubstituted or substituted with 1-3 halo;

c) 4- to 8-membered heterocycloalkyl having 1-3 ring heteroatoms independently selected from N, O, and S; wherein said 4- to 8-membered heterocycloalkyl is unsubstituted or substituted with —C(O)R$^{4d}$ or 5- to 6-membered heteroaryl having 1-3 ring heteroatoms independently selected from N, O, and S; and d) phenyl or 5- to 6-membered heteroaryl having 1-3 ring heteroatoms independently selected from N, O, and S; wherein said phenyl and 5- to 6-membered heteroaryl are unsubstituted or substituted with 1-3 R$^{4e}$;

each R$^{4b}$ is independently selected from the group consisting of halo, —C₁-C₃ alkyl, —C₁-C₃ haloalkyl, C₁-C₃ alkoxy, and —C₁-C₃ haloalkoxy;

R$^{4d}$ is —C₁-C₃ alkyl or —C₃-C₆ cycloalkyl;

each R$^{4e}$ is independently selected from the group consisting of halo, —CN, —S(O)₂—(C₁-C₃ alkyl), —S(O)₂—(C₃-C₆ cycloalkyl), —NR$^{4f}$R$^{4g}$, —C₁-C₆ alkyl, —C₁-C₆ haloalkyl, —C₁-C₆ hydroxyalkyl, —C₁-C₆ hydroxyhaloalkyl, —C₁-C₃ alkoxy, —C₁-C₃ haloalkoxy, —C₃-C₆ cycloalkyl, 4- to 8-membered heterocycloalkyl, phenyl, 5- to 6-membered heteroaryl, —(C₁-C₃ alkylene)-(C₃-C₆ cycloalkyl), —(C₁-C₃ alkylene)-O—(C₁-C₃ alkyl), —(C₁-C₃ alkylene)-O—(C₁-C₃ haloalkyl), —(C₁-C₃ alkylene)-(4- to 8-membered heterocycloalkyl), —(C₁-C₃ alkylene)-O—(C₁-C₃ alkylene)-(C₃-C₆ cycloalkyl), —O—(C₁-C₃ alkylene)-O—(C₁-C₃ alkyl), —O—(C₃-C₆ cycloalkyl), —O-(4- to 8-membered heterocycloalkyl), —O—(C₁-C₃ alkylene)-(C₃-C₆ cycloalkyl), and —O—(C₁—C₃ alkylene)-phenyl; wherein said 4- to 8-membered heterocycloalkyl and 5- to 6-membered heteroaryl have 1-3 ring heteroatoms independently selected from N, O, and S; wherein said —C₃-C₆ cycloalkyl, —(C₁-C₃ alkylene)-(C₃-C₆ cycloalkyl), 4- to 8-membered heterocycloalkyl, phenyl, and —(C₁-C₃ alkylene)-(4- to 8-membered heterocycloalkyl), are unsubstituted or substituted with 1-3 R*; and wherein said —O—(C₃-C₆ cycloalkyl) and —O—(C₁-C₃ alkylene)-(C₃-C₆ cycloalkyl) are unsubstituted or substituted with 1-3 R**; or two adjacent R$^{4e}$ groups taken together with the atoms to which they are attached form a fused 5- to 6-membered heterocycloalkyl having 1-3 ring heteroatoms independently selected from N, O, and S; and wherein said 5- to 6-membered heterocycloalkyl is unsubstituted or substituted with 1-3 substituents independently selected from oxo, halo, and —C₁-C₃ alkyl;

R$^{4f}$ and R$^{4g}$ are independently selected from —H, —(C₁-C₃ alkylene)-(C₃-C₆ cycloalkyl), and 4- to 6-membered heterocycloalkyl having 1-3 ring heteroatoms independently selected from N, O, and S;

each R* is independently halo, —OH, —CN, —C₁-C₃ alkyl, —C₁-C₃ haloalkyl, —C₁-C₃ alkoxy, or —(C₁-C₃ alkylene)-O—(C₁-C₃ alkyl); and each R** is independently halo or —C₁-C₃ alkyl.

In some embodiments, the compound has a structure according to Formula I:

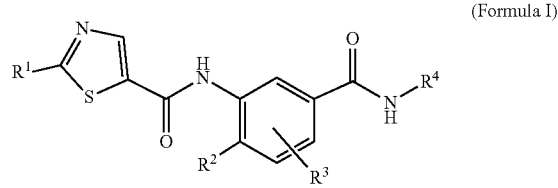

(Formula I)

or a pharmaceutically acceptable salt thereof, wherein:

R$^1$ is —H, —NR$^{1a}$R$^{1b}$, —C₁-C₆ alkyl, —C₁-C₆ haloalkyl, —C₃-C₆ cycloalkyl, or 4- to 6-membered heterocycloalkyl having 1-3 ring heteroatoms independently selected from N, O, and S; R$^{1a}$ and R$^{1b}$ are independently —H, —C₁-C₆ haloalkyl, —C(O)R$^{1c}$, —C(O)OR$^{1d}$, or —C(O)NR$^{1e}$R$^{1f}$;

R$^{1c}$ is —C₁-C₃ alkyl, —C₁-C₃ haloalkyl, —C₁-C₃ hydroxyalkyl, —C₃-C₆ cycloalkyl, phenyl, or 4 to 6-membered heterocycloalkyl having 1 to 3 ring heteroatoms independently selected from N, O, and S; wherein said phenyl and 4- to 6-membered heterocycloalkyl are unsubstituted or substituted with 1-3 substituents independently selected from the group consisting of halo, —OH, and C₁-C₃ alkyl;

R$^{1d}$ is —C₁-C₃ alkyl or —C₃-C₆ cycloalkyl;

R$^{1e}$ and R$^{1f}$ are independently —H or —C₁-C₃ alkyl;

R$^2$ and R$^3$ are independently halo or —C₁-C₃ alkyl;

R$^4$ is 4- to 8-membered heterocycloalkyl having 1-3 ring heteroatoms independently selected from N, O, and S; wherein said 4- to 8-membered heterocycloalkyl is unsubstituted or substituted with —C(O)R$^{4d}$ or 5- to 6-membered heteroaryl having 1-3 ring heteroatoms independently selected from N, O, and S;

each R$^{4b}$ is independently selected from the group consisting of halo, —C₁-C₃ alkyl, —C₁-C₃ haloalkyl, C₁-C₃ alkoxy, and —C₁-C₃ haloalkoxy;

R$^{4d}$ is —C₁-C₃ alkyl or —C₃-C₆ cycloalkyl;

each R$^{4e}$ is independently selected from the group consisting of halo, —CN, —S(O)₂—(C₁-C₃ alkyl), —S(O)₂—(C₃-C₆ cycloalkyl), —NR$^{4f}$R$^{4g}$, —C₁-C₆ alkyl, —C₁-C₆ haloalkyl, —C₁-C₆ hydroxyalkyl, —C₁-C₆ hydroxyhaloalkyl, —C₁-C₃ alkoxy, —C₁-C₃ haloalkoxy, —C₃-C₆ cycloalkyl, 4- to 8-membered heterocycloalkyl, phenyl, 5- to 6-membered heteroaryl, —(C₁-C₃ alkylene)-(C₃-C₆ cycloalkyl), —(C₁-C₃ alkylene)-O—(C₁-C₃ alkyl), —(C₁-C₃ alkylene)-O—(C₁-C₃ haloalkyl), —(C₁-C₃ alkylene)-(4- to 8-membered heterocycloalkyl), —(C₁-C₃ alkylene)-O—(C₁-C₃ alkylene)-(C₃-C₆ cycloalkyl), —O—(C₁-C₃ alkylene)-O—(C₁-C₃ alkyl), —O—(C₃-C₆ cycloalkyl), —O-(4- to 8-membered heterocycloalkyl), —O—(C₁-C₃ alkylene)-(C₃-C₆ cycloalkyl), and —O—(C₁-C₃ alkylene)-phenyl; wherein said 4- to 8-membered heterocycloalkyl and 5- to 6-membered heteroaryl have 1-3 ring heteroatoms independently selected from N, O, and S; wherein said —C₃-C₆ cycloalkyl, —(C₁-C₃ alkylene)-(C₃-C₆ cycloalkyl), 4- to 8-membered heterocycloalkyl, phenyl, and —(C₁-C₃ alkylene)-(4- to 8-membered heterocycloalkyl), are unsubstituted or substituted with 1-3 R*; and wherein said —O—(C₃-C₆ cycloalkyl) and —O—(C₁-C₃ alkylene)-(C₃-C₆ cycloalkyl) are unsubstituted or substituted with 1-3 R**; or two adjacent R$^{4e}$ groups taken together with the atoms to which they are attached form a fused 5- to 6-membered heterocycloalkyl having 1-3 ring heteroatoms independently selected from N, O, and S; and wherein said 5- to 6-membered heterocycloalkyl is unsubstituted or substituted with 1-3 substituents independently selected from oxo, halo, and —$C_1$-$C_3$ alkyl;

$R^{4f}$ and $R^{4g}$ are independently selected from —H, —($C_1$-$C_3$ alkylene)-($C_3$-$C_6$ cycloalkyl), and 4- to 6-membered heterocycloalkyl having 1-3 ring heteroatoms independently selected from N, O, and S;

each R* is independently halo, —OH, —CN, —$C_1$-$C_3$ alkyl, —$C_1$-$C_3$ haloalkyl, —$C_1$-$C_3$ alkoxy, or —($C_1$-$C_3$ alkylene)-O—($C_1$-$C_3$ alkyl); and each R** is independently halo or —$C_1$-$C_3$ alkyl.

In some embodiments, the compound, or pharmaceutically acceptable salt thereof, has a structure according to Formula Ic:

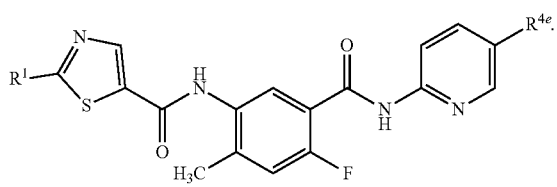

(Formula Ic)

In some embodiments, the compound, or pharmaceutically acceptable salt thereof, has a structure according to Formula Id:

(Formula Id)

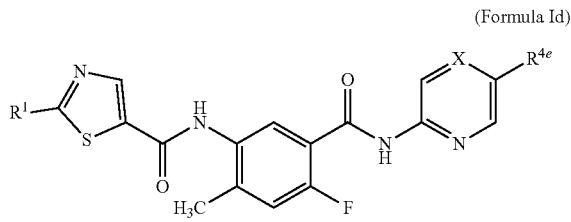

In some embodiments, the compound, or pharmaceutically acceptable salt thereof, has a structure according to Formula Ie:

(Formula Ie)

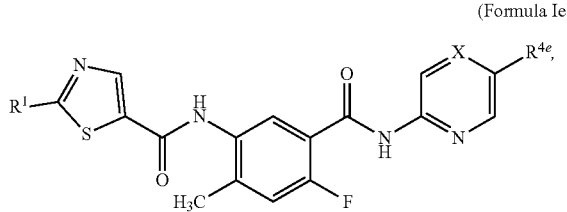

wherein X is N or CH.

In some embodiments, the compound has a structure according to Formula Id:

(Formula Id)

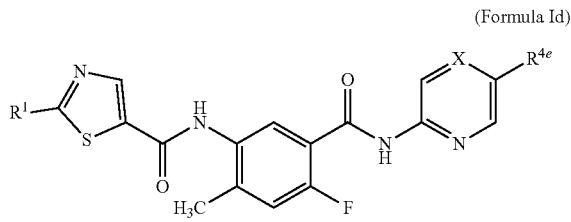

or a pharmaceutically acceptable salt thereof, wherein:
X is N or CH;
$R^1$ is —$C_1$-$C_6$ alkyl, or —$NR^{1a}R^{1b}$;
$R^{1a}$ and $R^{1b}$ are each independently —H or —C(O)-(4- to 6-membered heterocycloalkyl), wherein said 4- to 6-membered heterocycloalkyl has 1-2 ring heteroatoms independently selected from N and O; and
$R^{4e}$ is selected from the group consisting of —$C_1$-$C_6$ haloalkyl, —$C_3$-$C_6$ cycloalkyl, —$C_1$-$C_3$ haloalkoxy, —O—($C_3$-$C_6$ cycloalkyl), —($C_1$-$C_3$ alkylene)-($C_3$-$C_6$ cycloalkyl), and —($C_1$-$C_3$ alkylene)-O—($C_1$-$C_3$ alkyl).

In some embodiments, the compound is selected from the group consisting of:

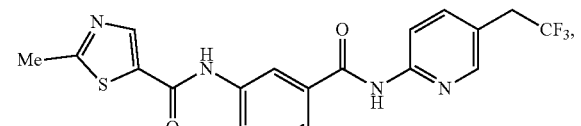

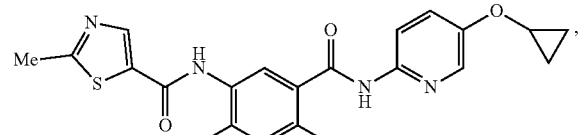

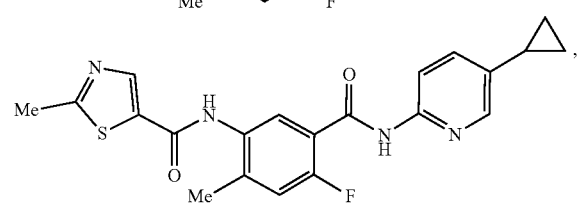

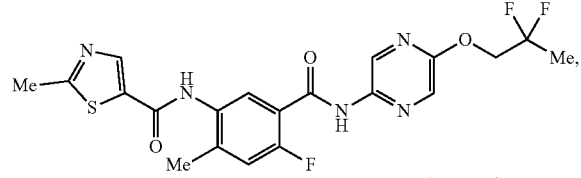

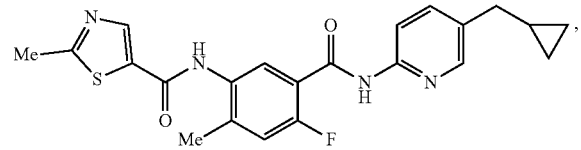

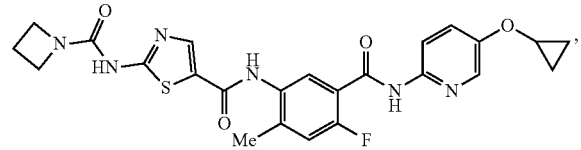

-continued
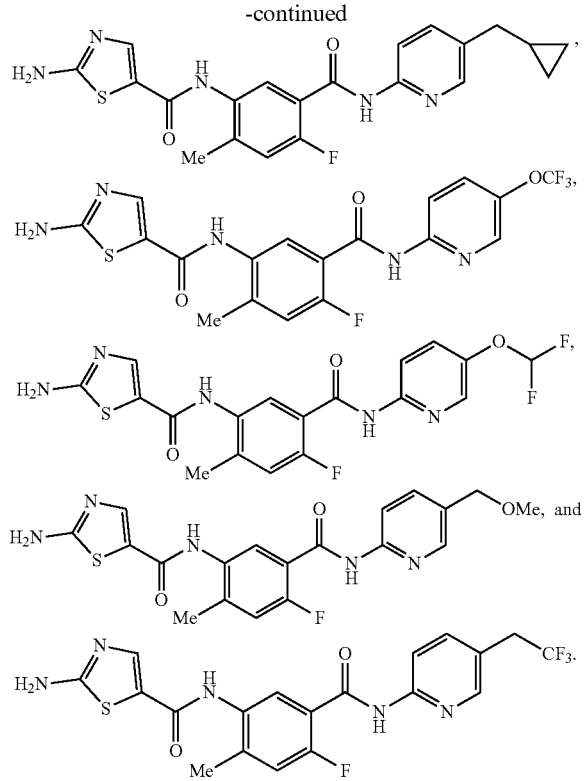
In some embodiments, the compound is selected from the group consisting of:
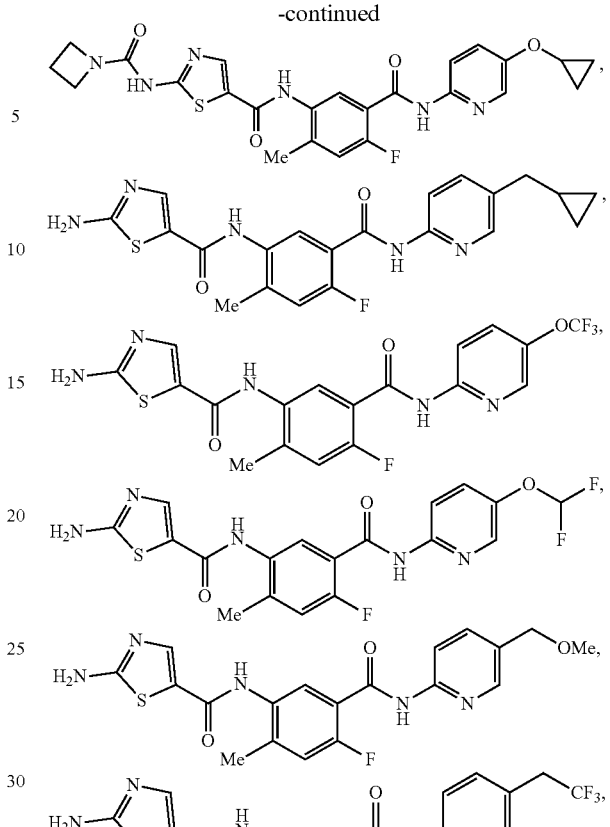
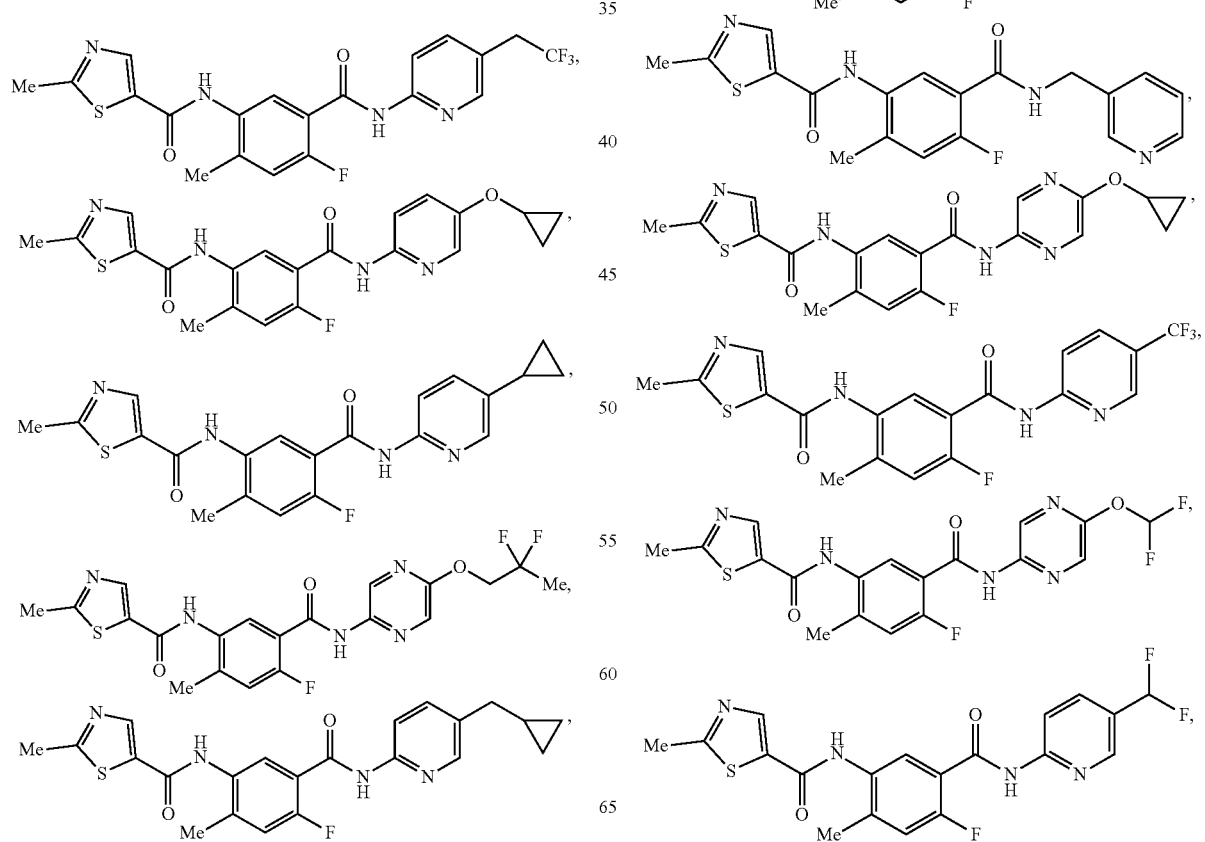

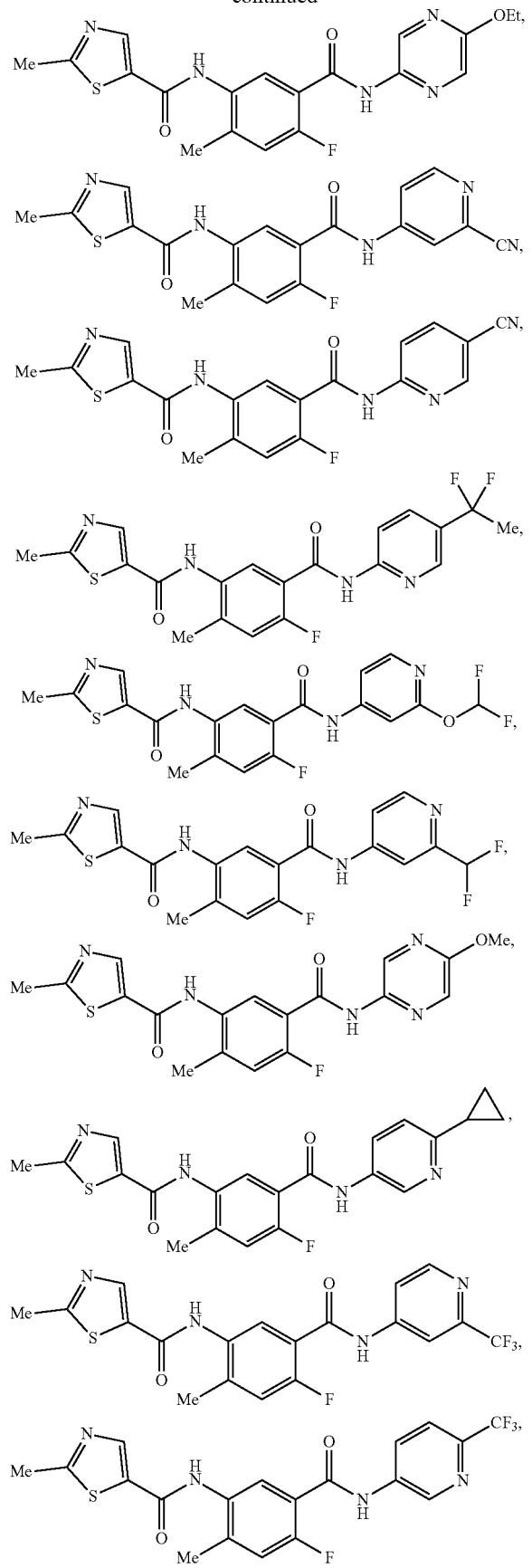
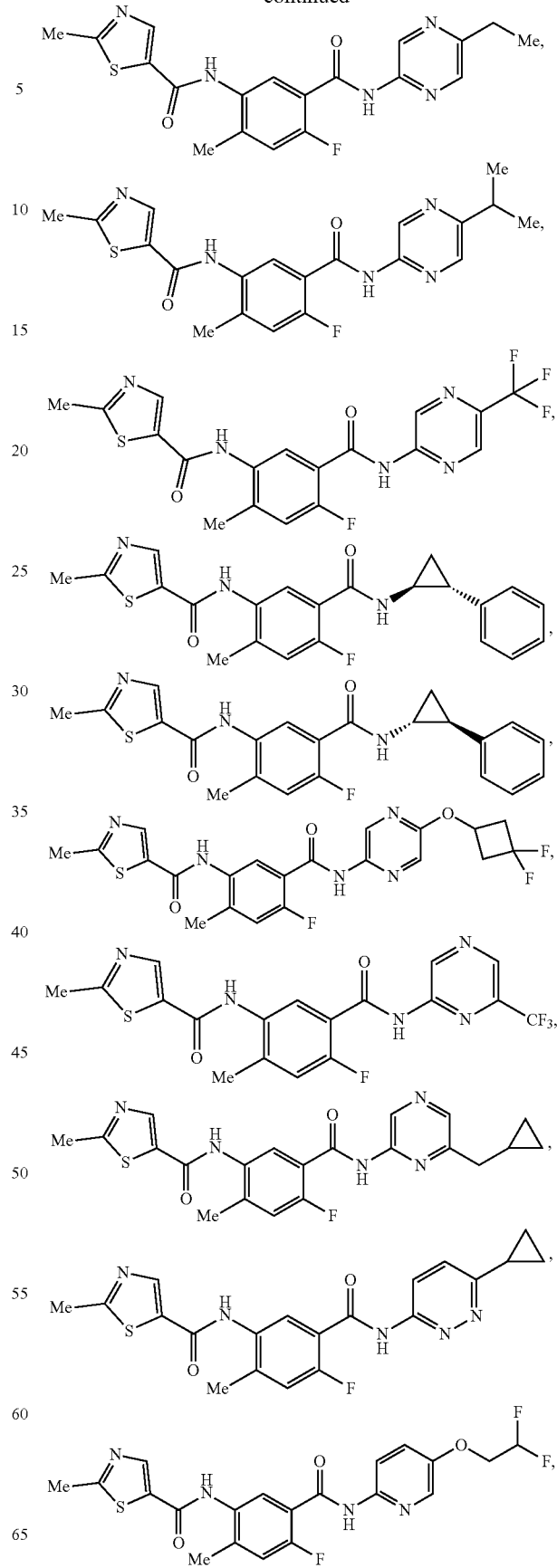

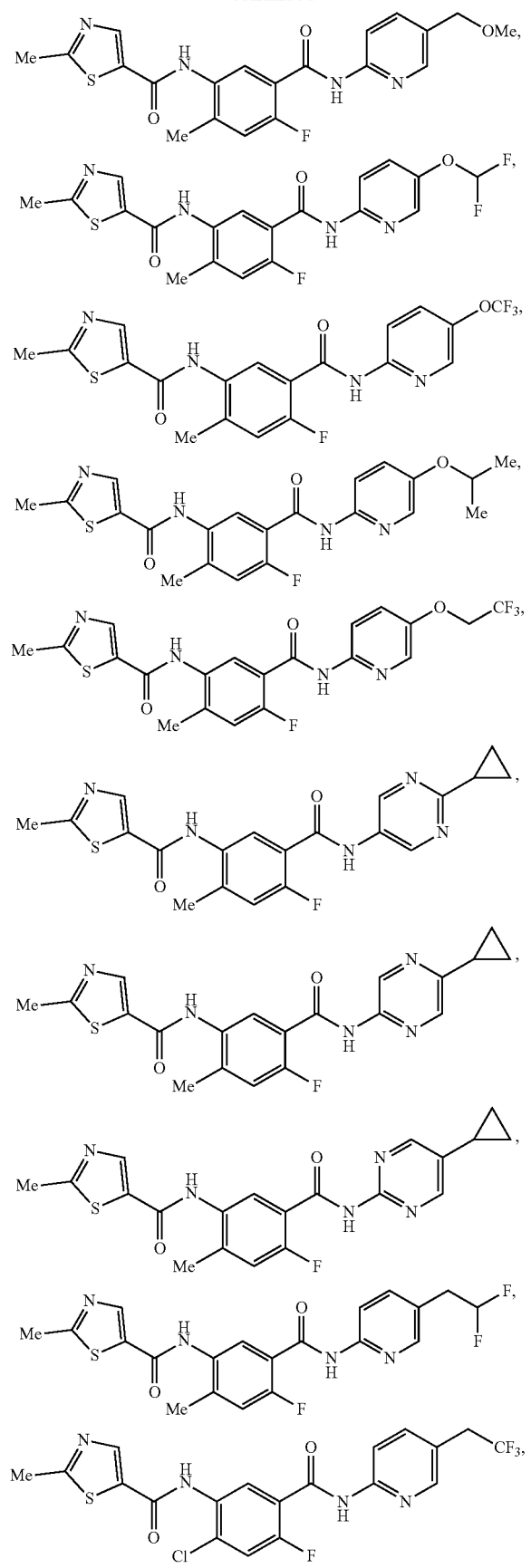
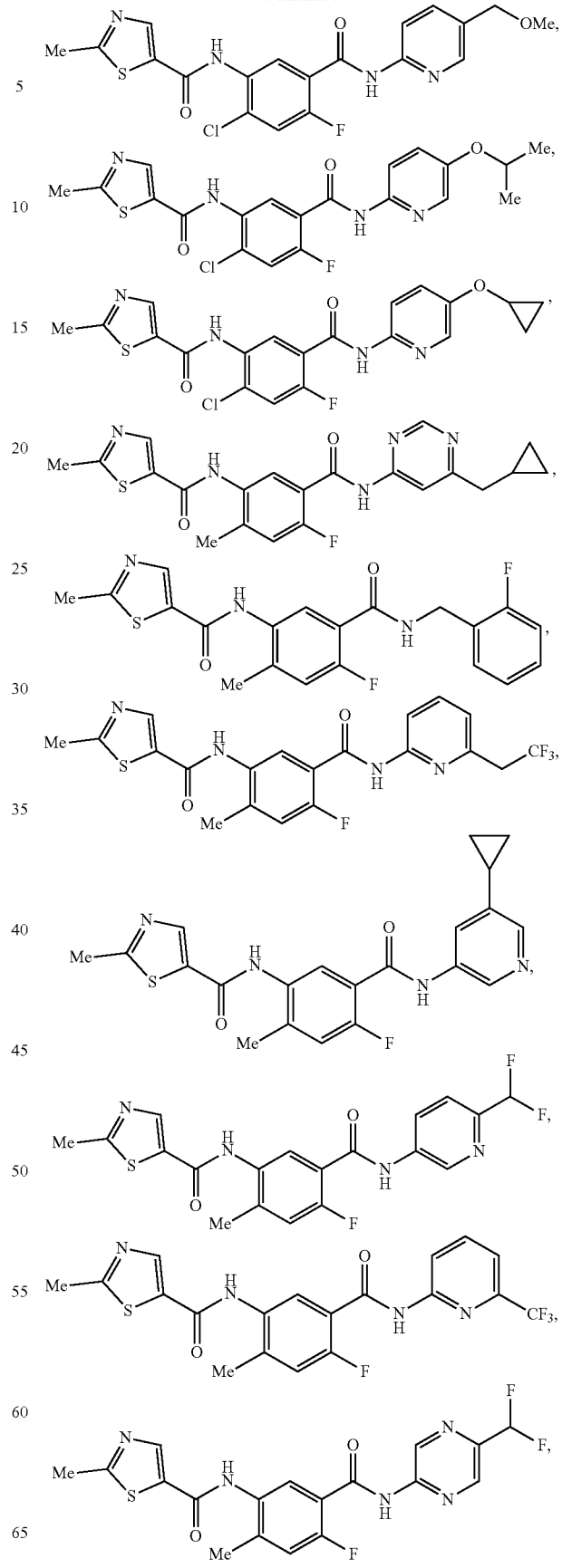

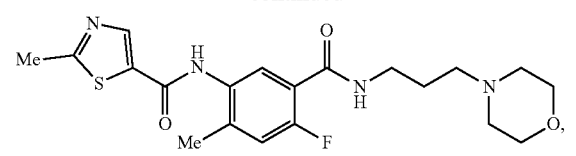
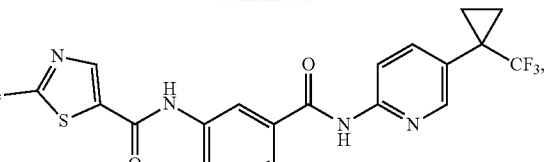

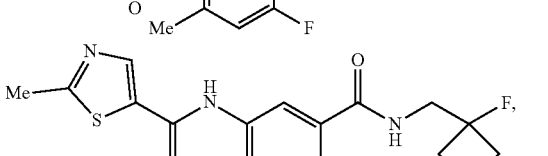
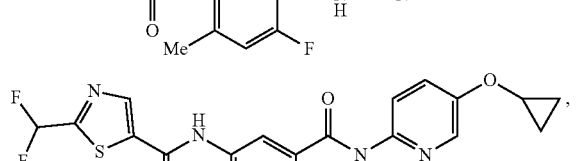
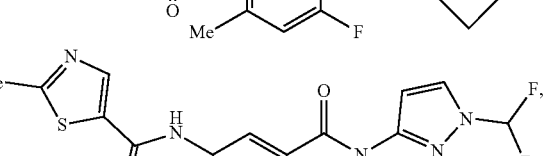
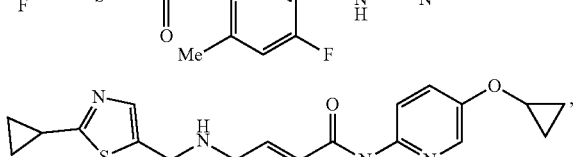
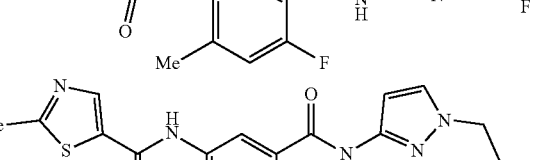
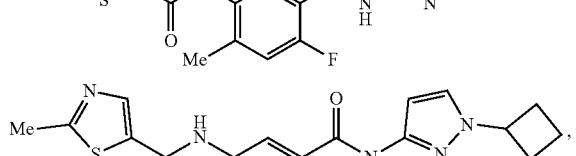
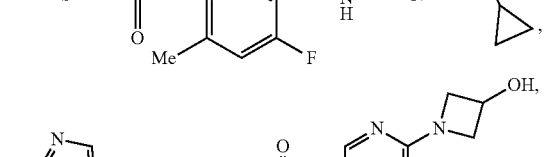
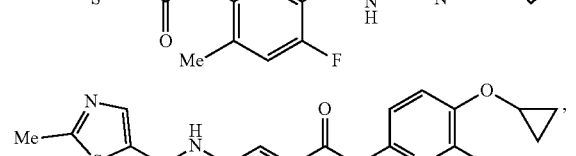
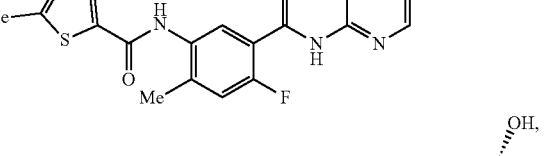
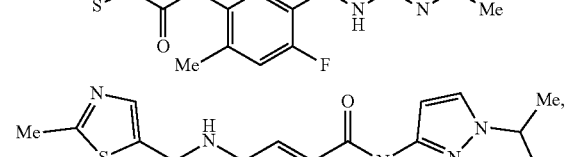
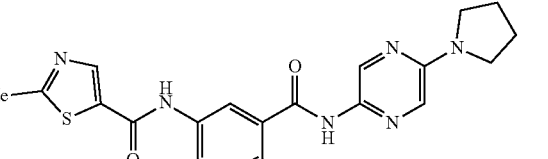
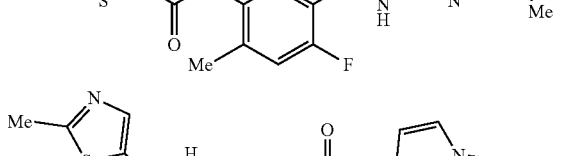
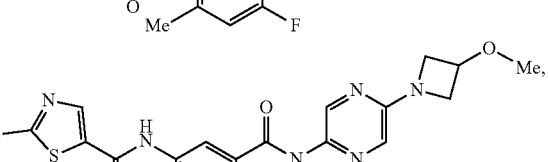
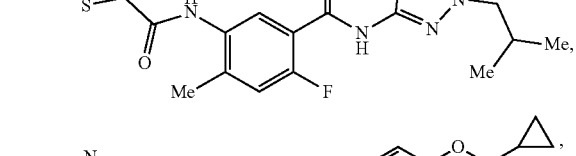
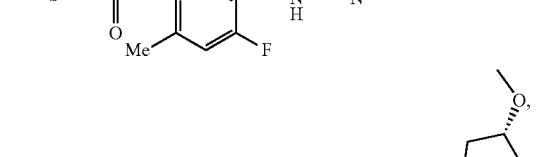
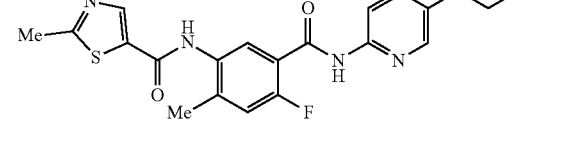
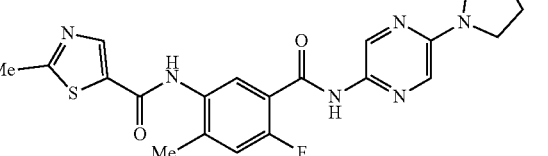
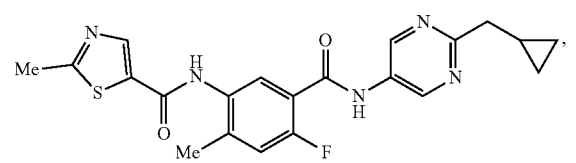
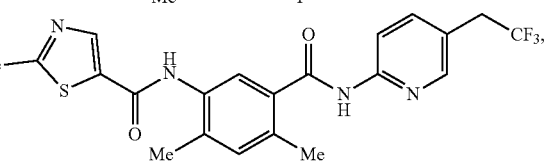

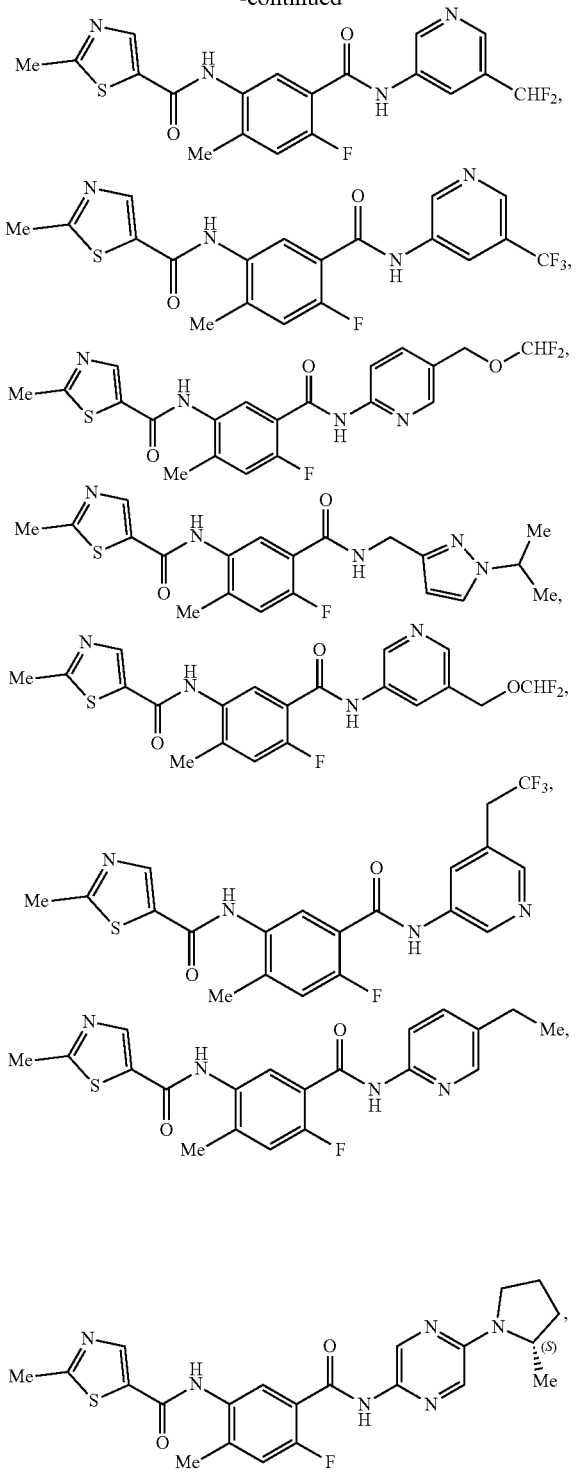
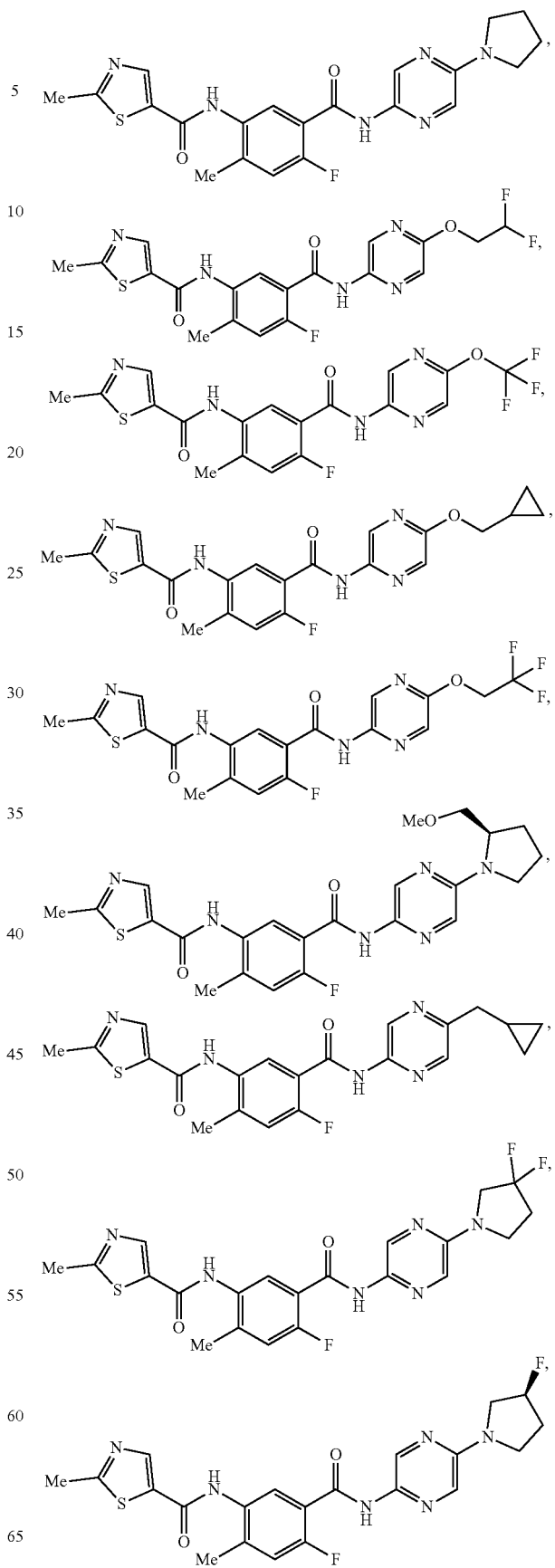

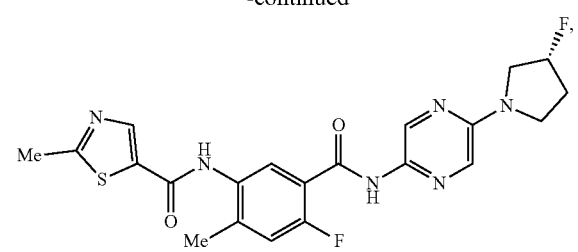
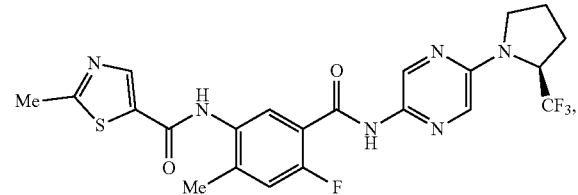
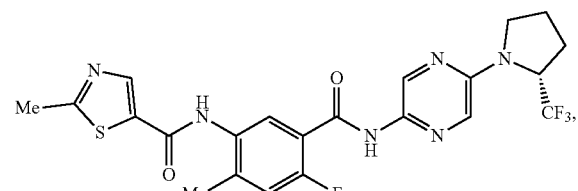
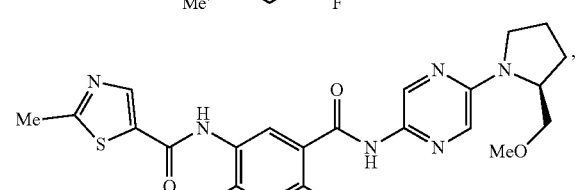
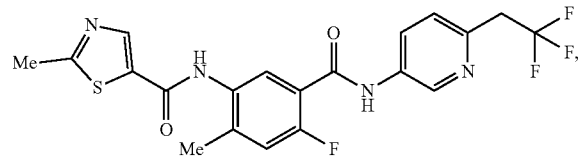
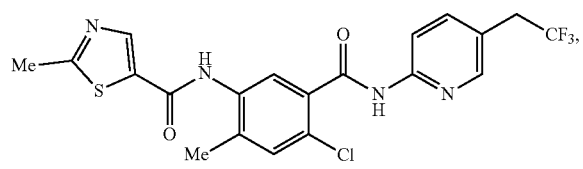
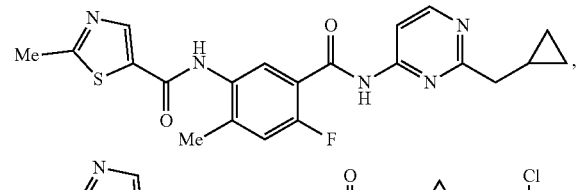
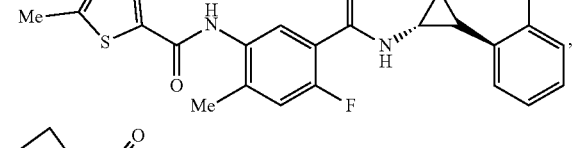
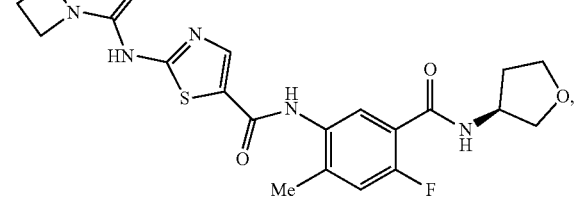
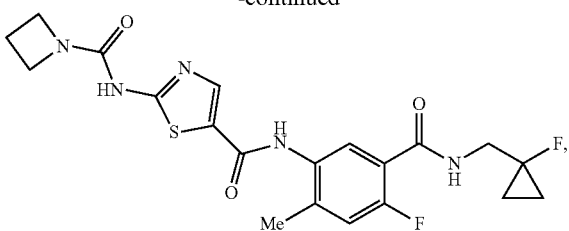
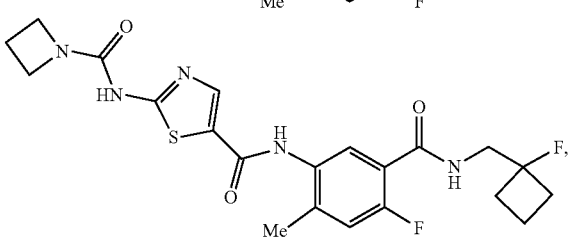
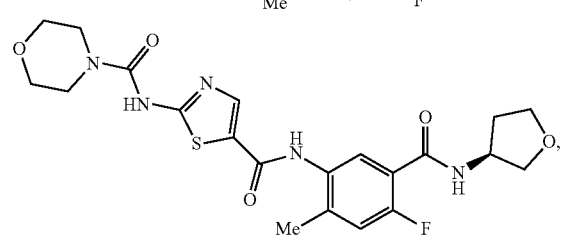
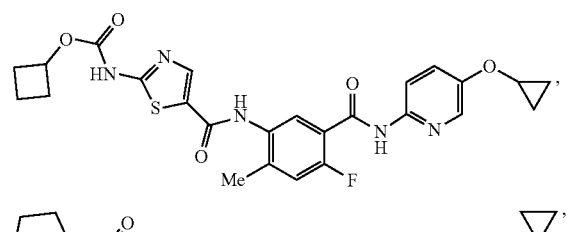
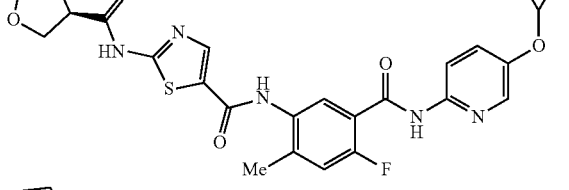
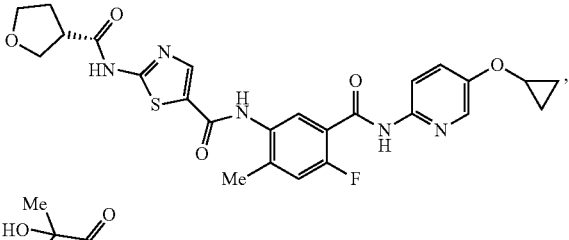
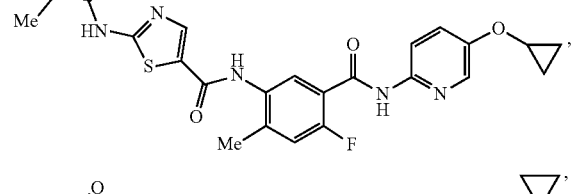
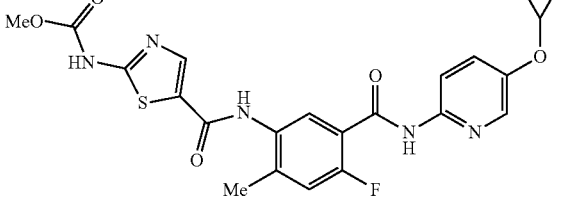

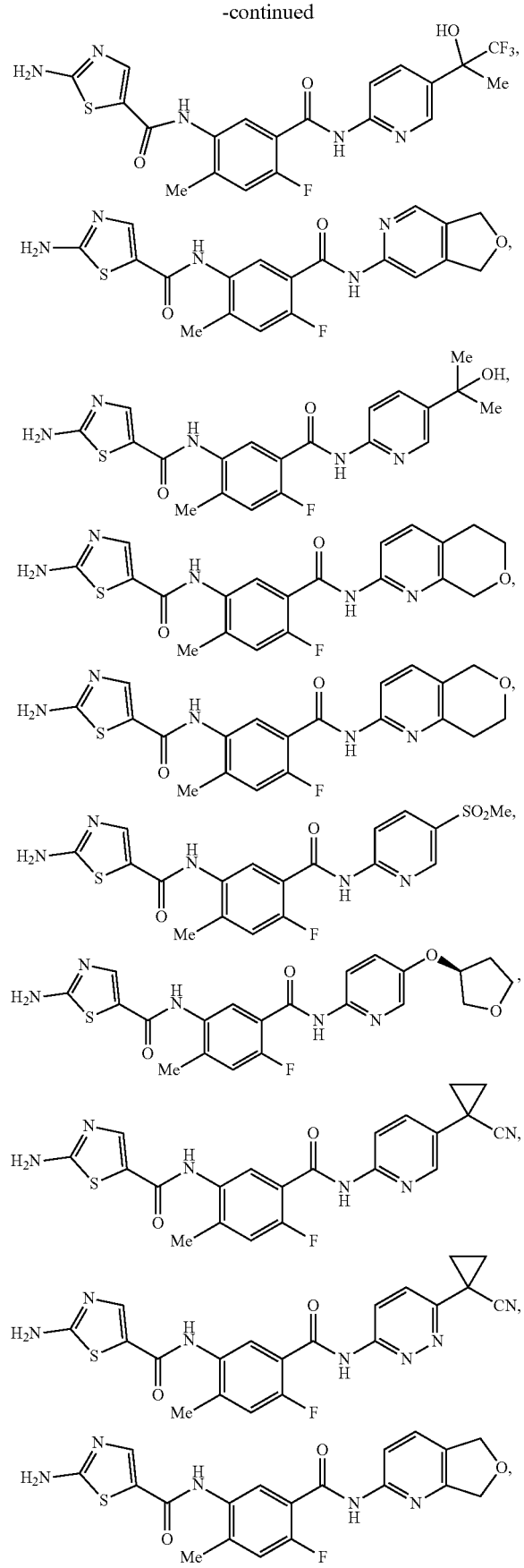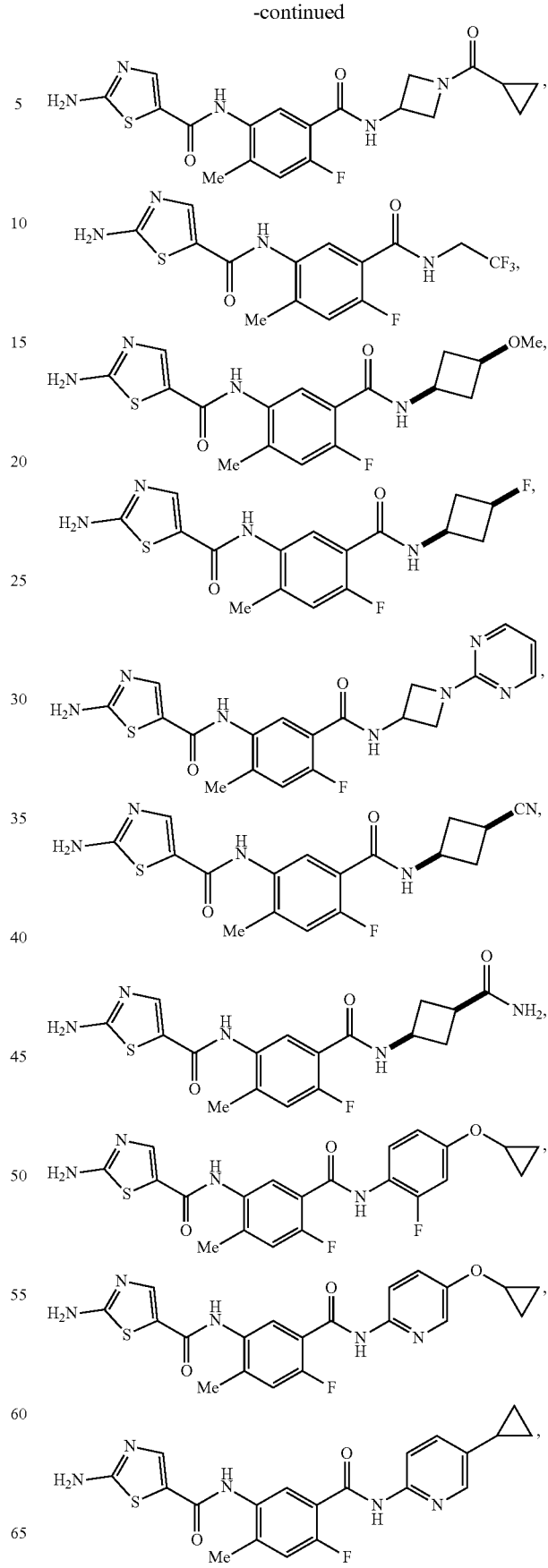

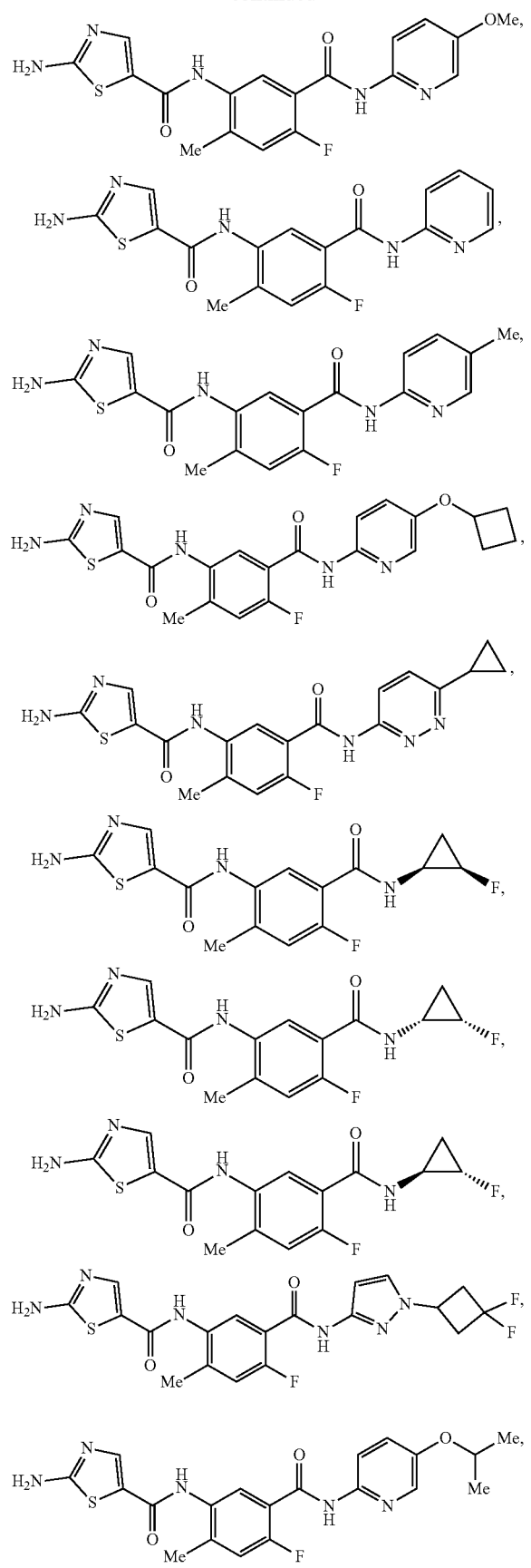
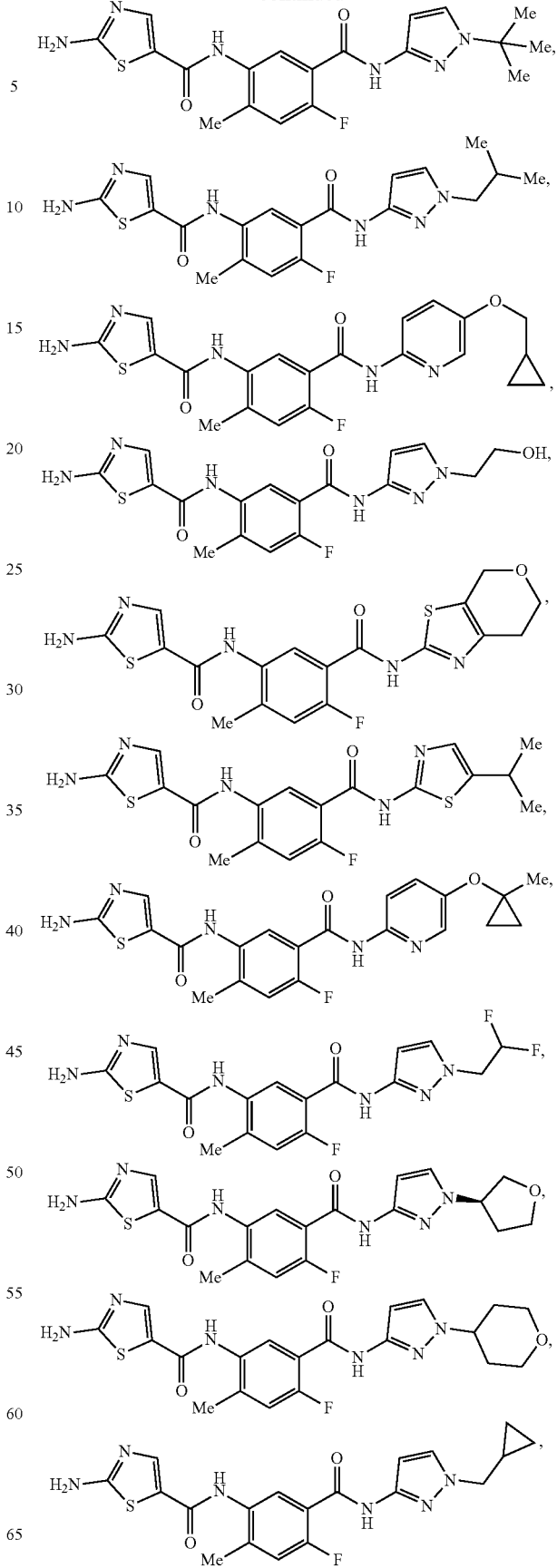

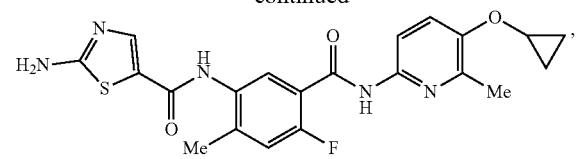
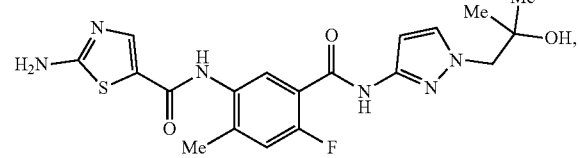
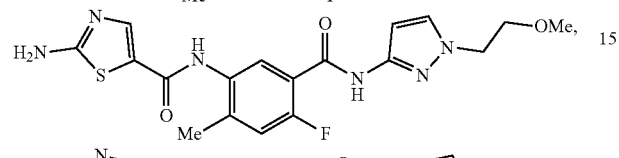
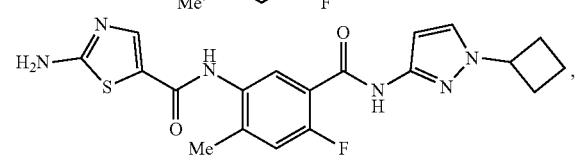
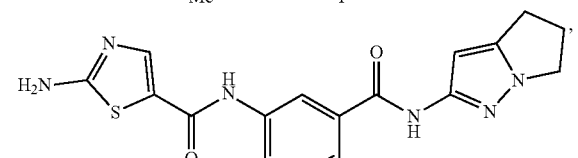
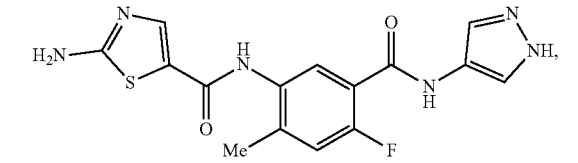
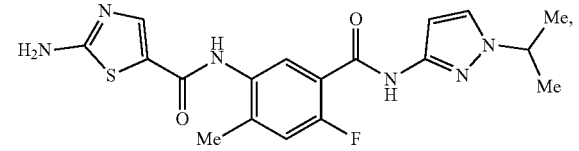
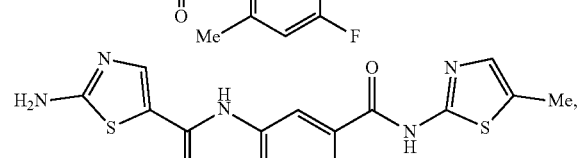
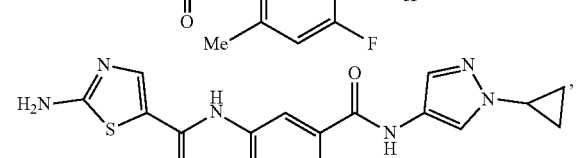
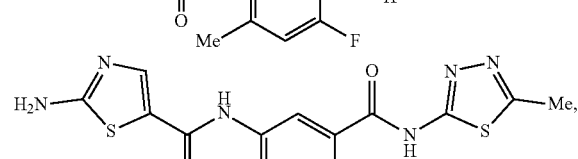
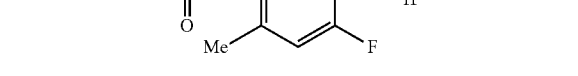
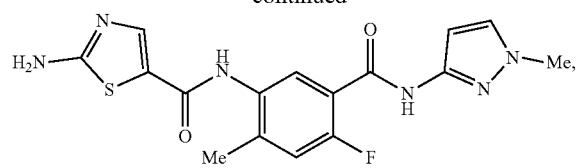
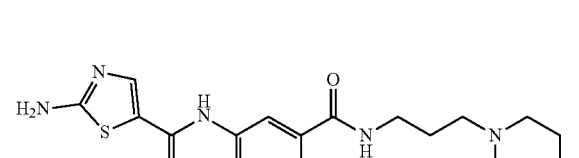
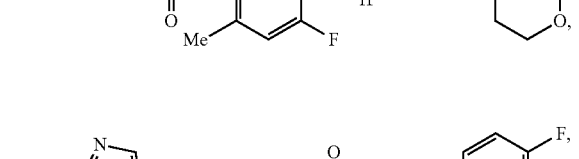
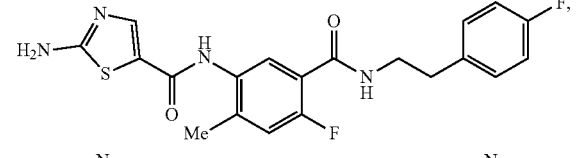
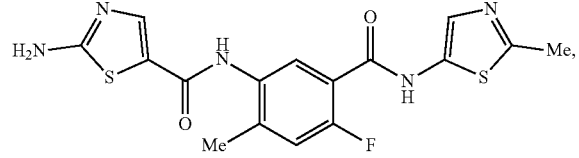
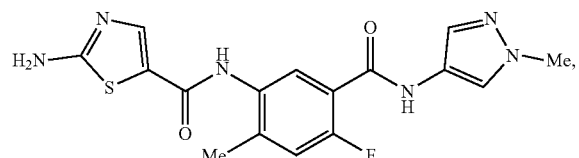
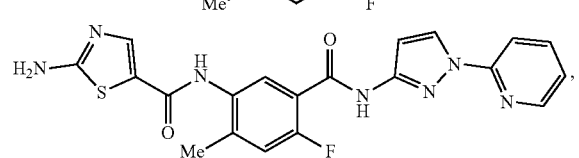
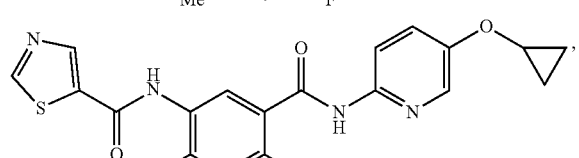
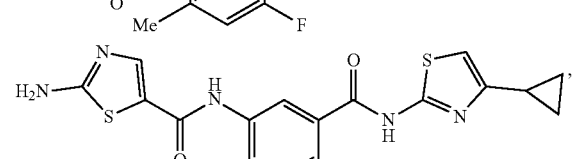
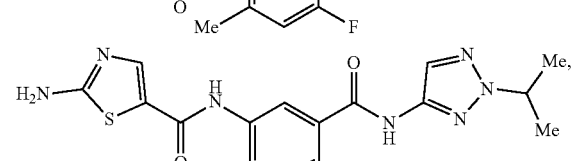
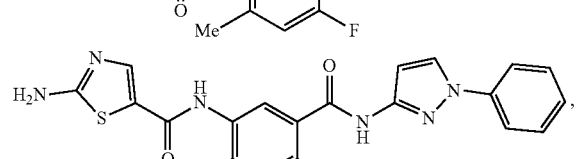
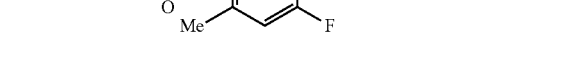

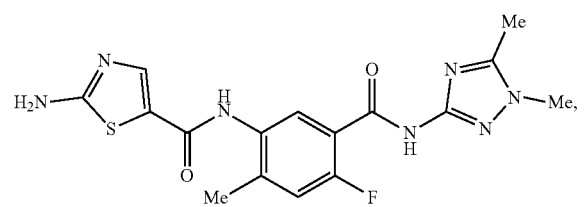
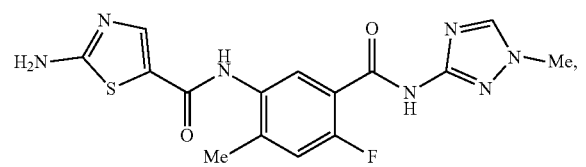
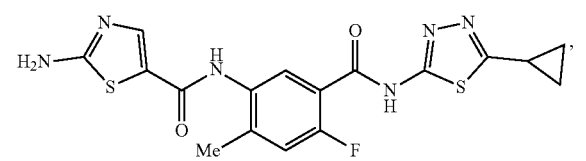
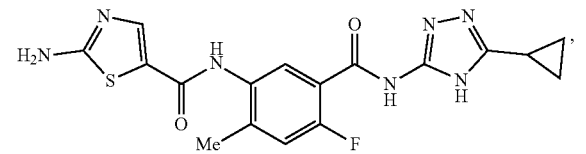
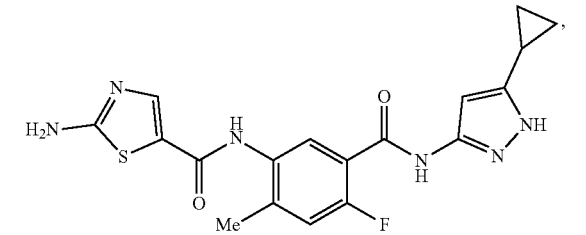
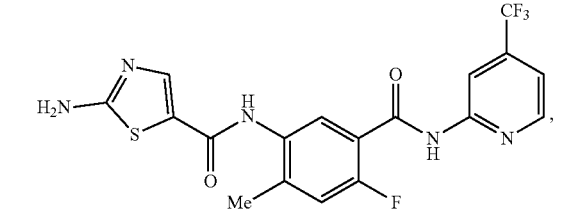
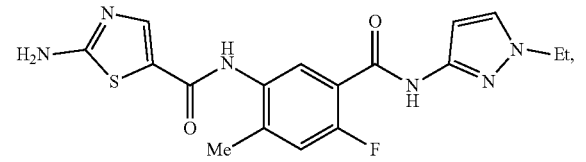
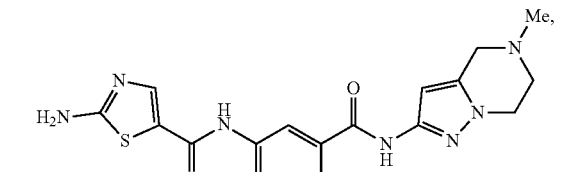
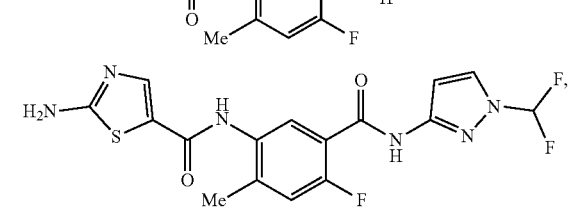
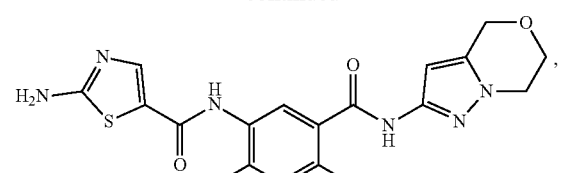
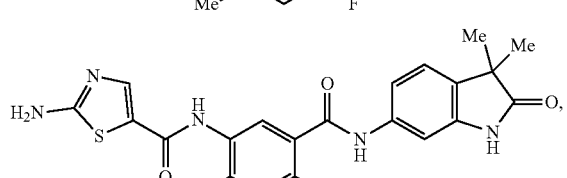
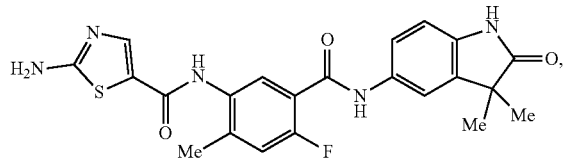
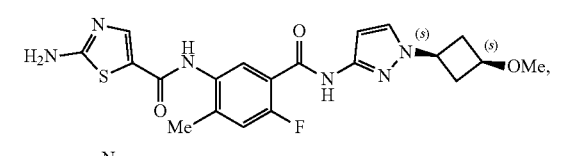
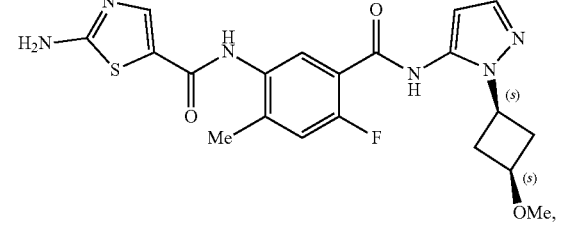
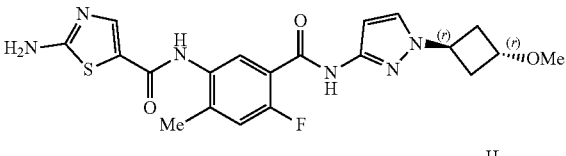
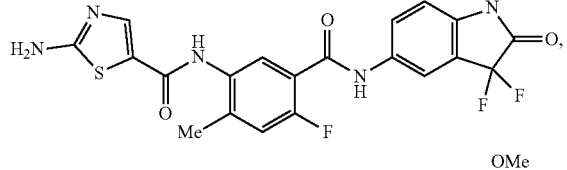
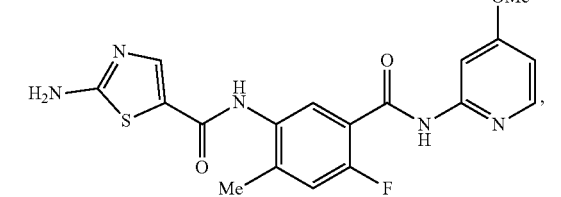
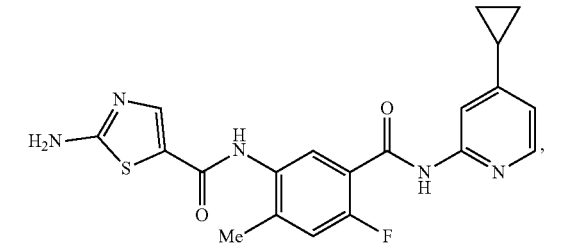

81
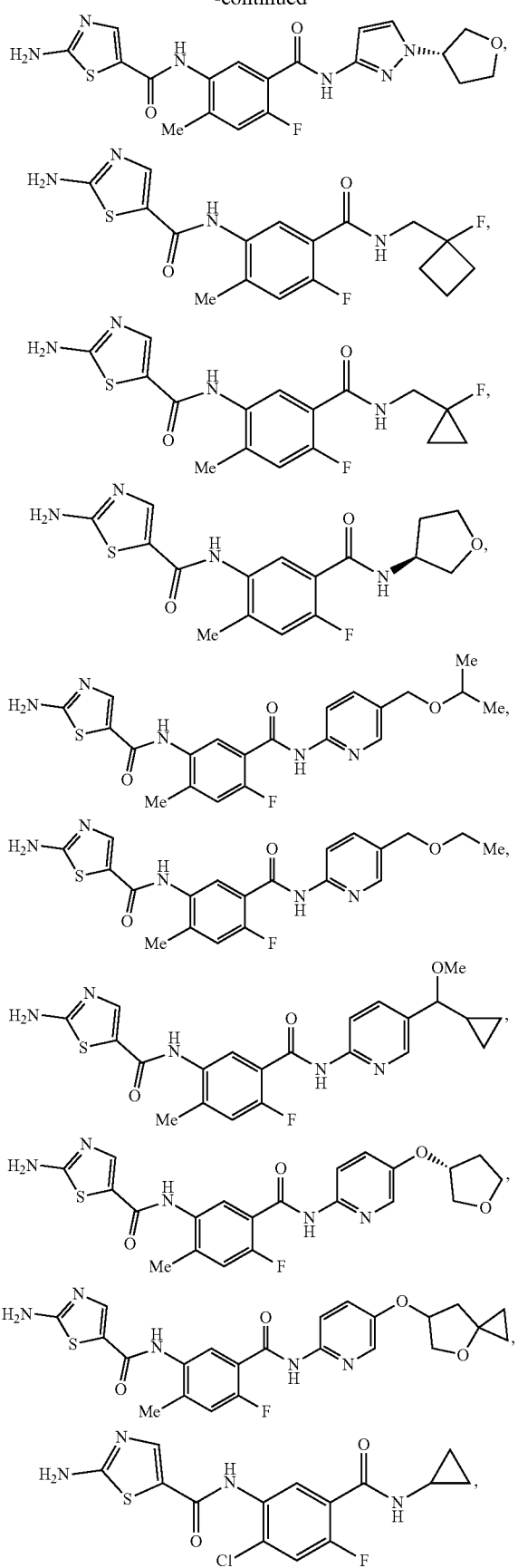
82
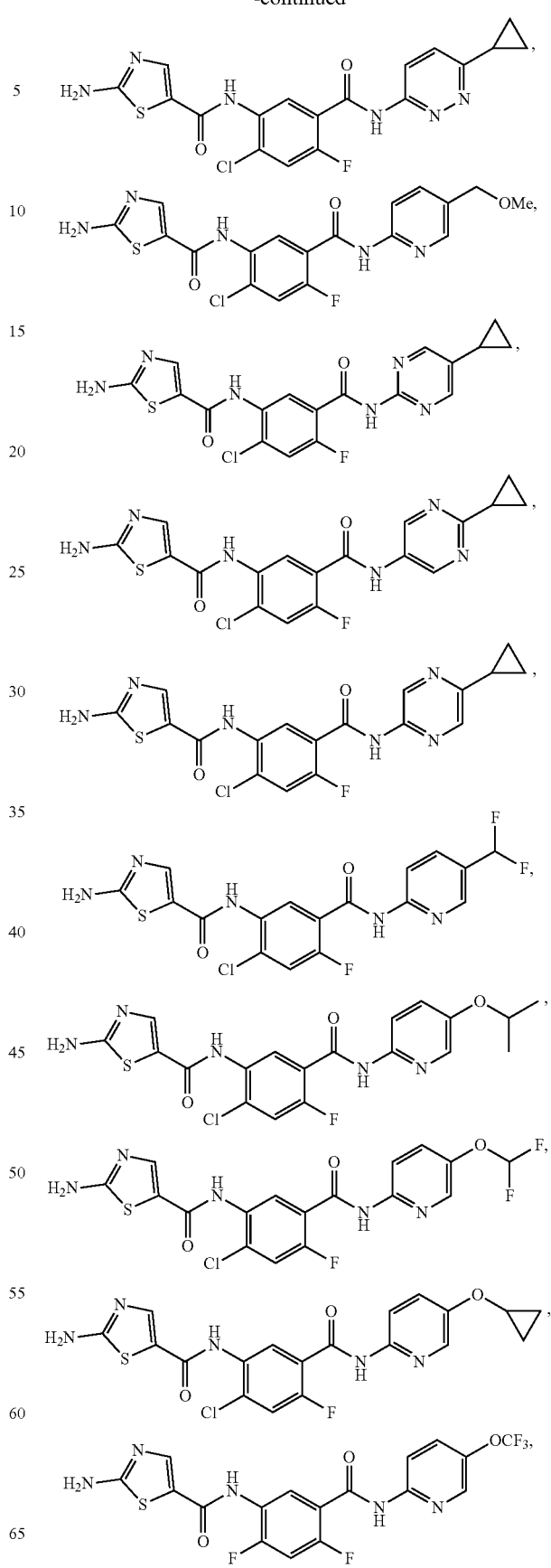

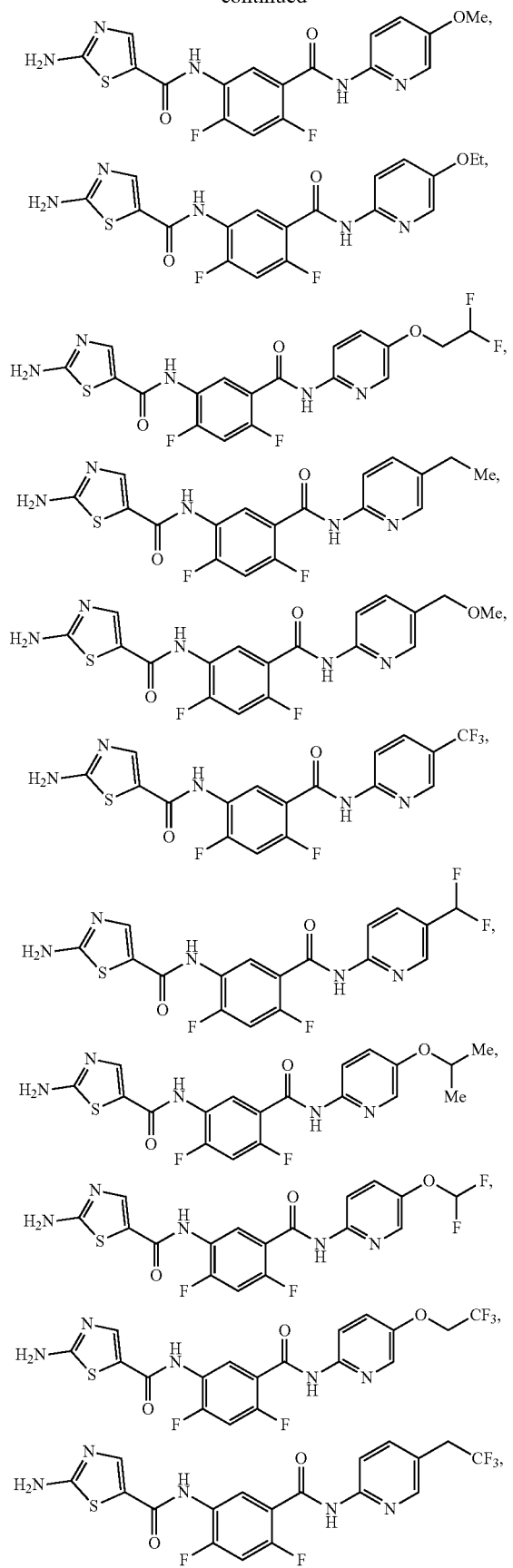
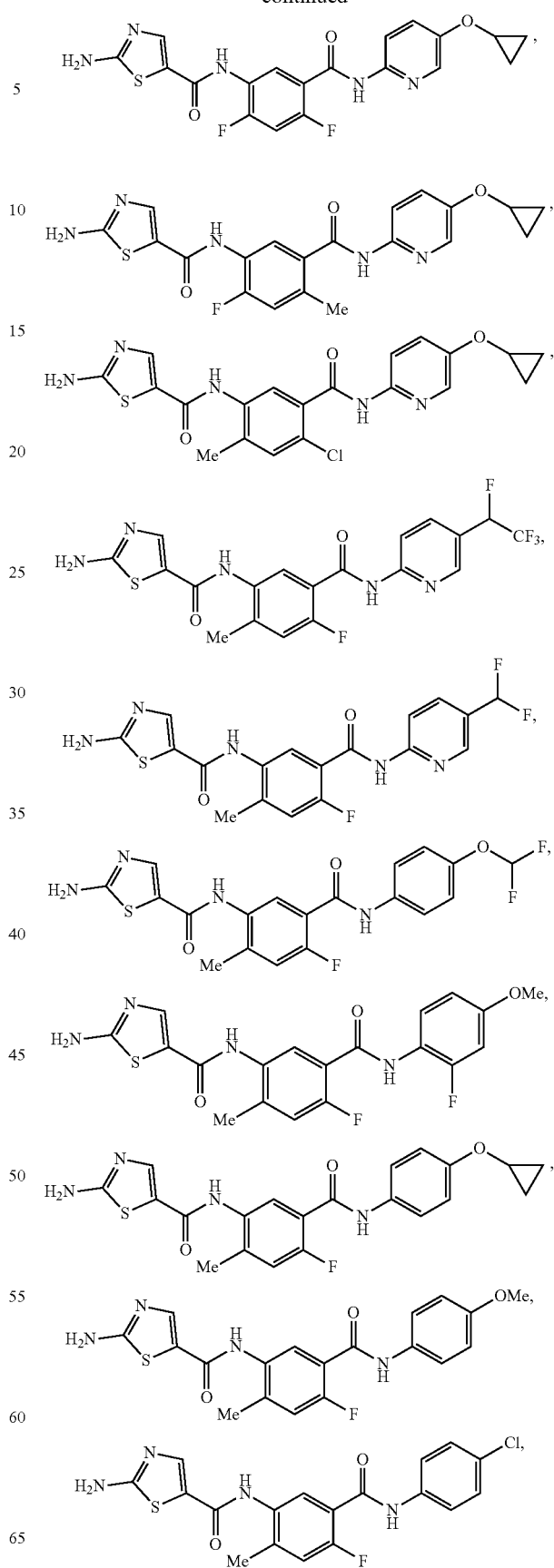

-continued
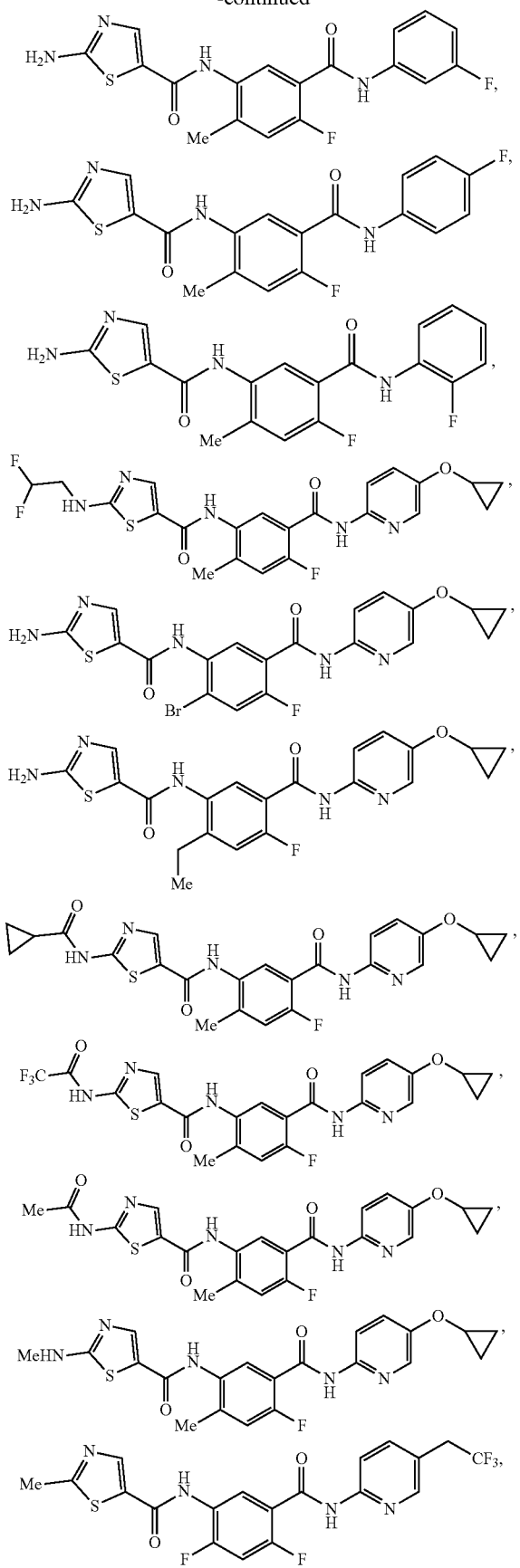
-continued
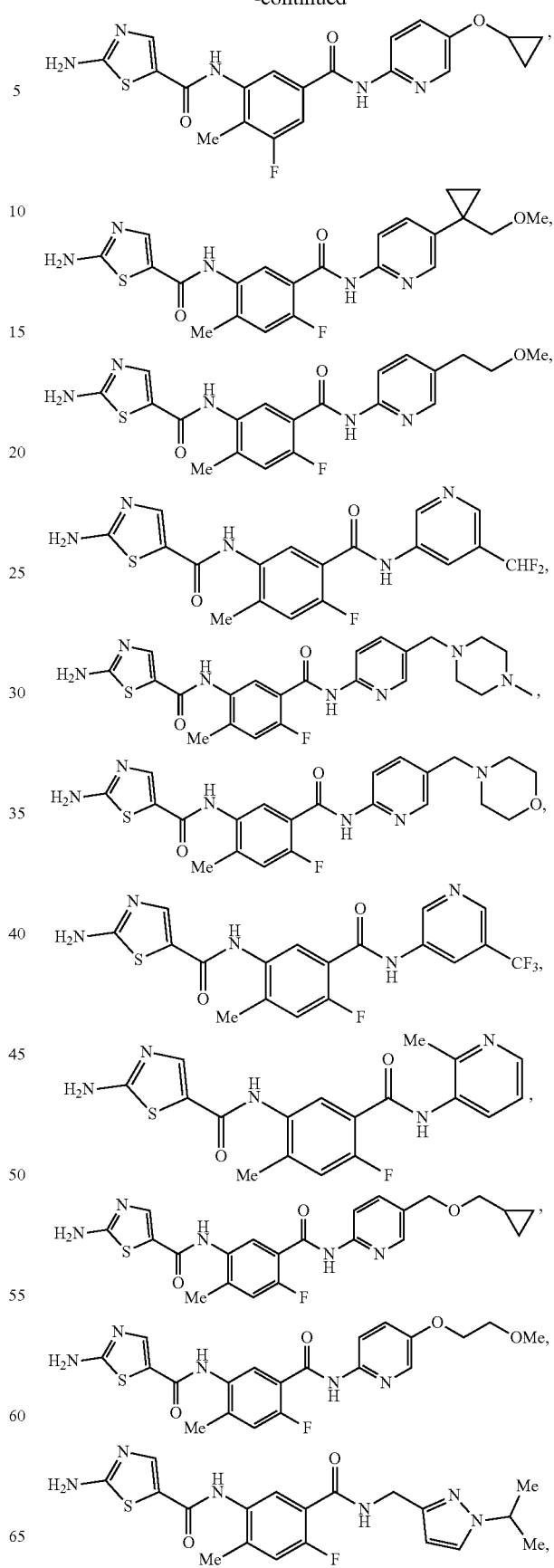

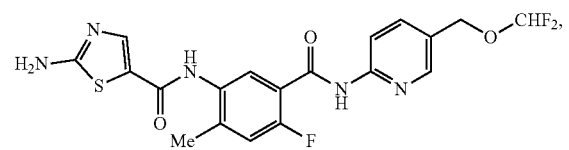
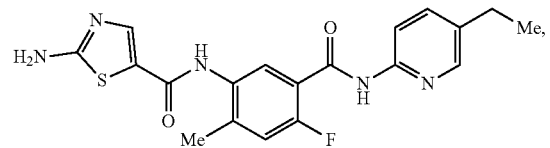
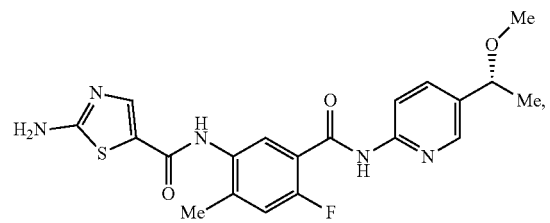
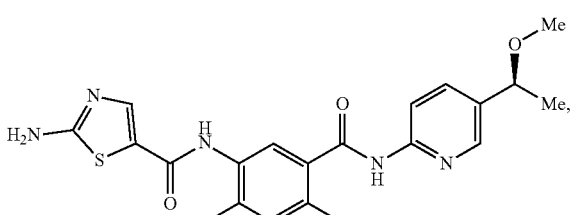
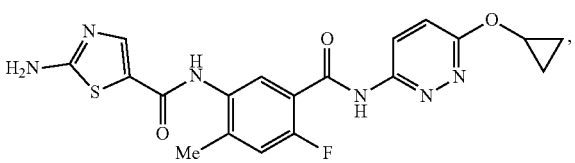
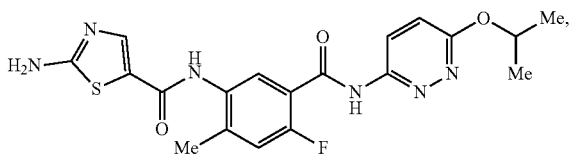
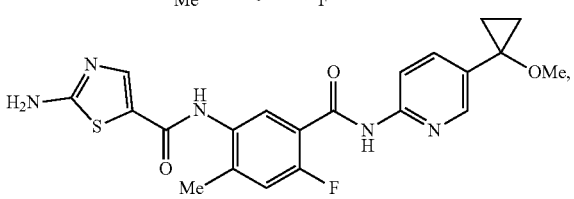
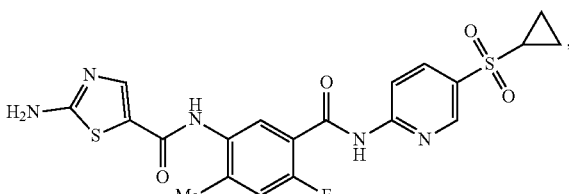
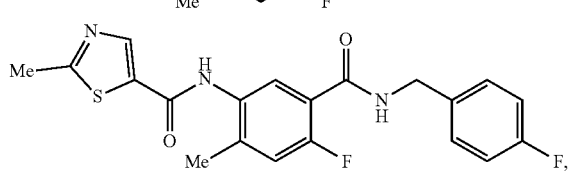

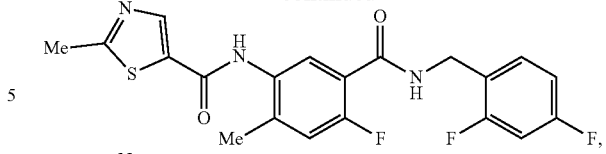
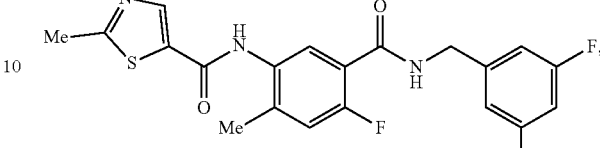
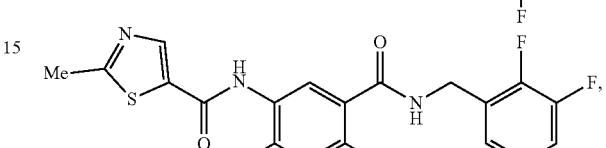
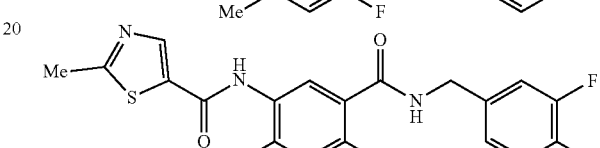
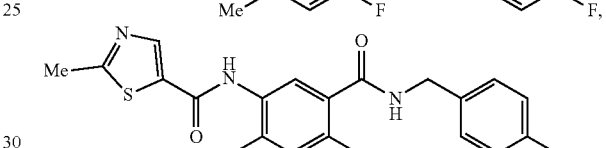
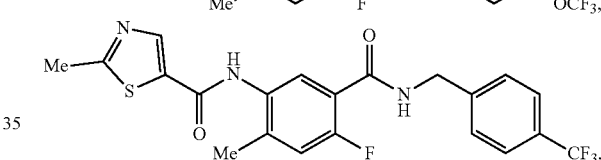
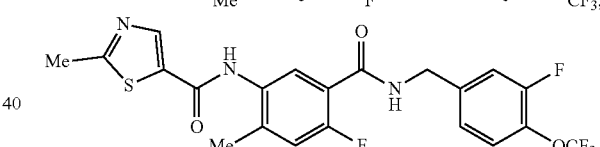

and

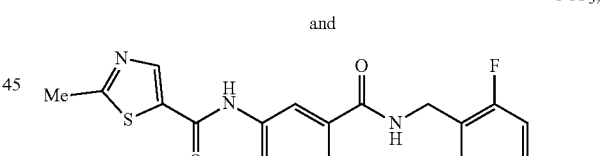

In some embodiments, the compound according to this disclosure is a pharmaceutically acceptable salt of a compound described above or described in the Examples.

Methods of Use

The present disclosure provides methods for using the compounds described herein in the preparation of a medicament for inhibition of KIT. In some embodiments, the medicament is for inhibiting KIT. As used herein, the terms "inhibit", "inhibition" and the like refer to the ability of an antagonist to decrease the function or activity of a particular target, e.g., KIT. The decrease is preferably at least a 50% and may be, for example, at least about 55%, at least about 60%, at least about 65%, at least about 70%, at least about 75%, at least about 80%, at least about 85%, at least about 90%, or at least about 95%. The present disclosure also encompasses the use of the compounds described herein in the preparation of a medicament for the treatment or prevention of diseases, disorders, and/or conditions that would benefit from inhibition of KIT. As one example, the present disclosure encompasses the use of the compounds described herein in the preparation of a medicament for the treatment of an allergic, inflammatory, neuroinflammatory, neurological, autoimmune, dermatological, respiratory, metabolic, cardiovascular or a fibrotic disease, disorder or condition. In some embodiments of the aforementioned methods, the compounds described herein are used in combination with at least one additional therapy, examples of which are set forth elsewhere herein.

In some embodiments, the compounds of this disclosure are inhibitors of wild type KIT. In other embodiments, the compounds are inhibitors of mutant forms of KIT. Exemplary mutant forms of KIT include, but are not limited to, KIT (L576P), KIT (V559D), KIT (V559D, T670I), KIT (V559D, V654A), KIT (D816V), KIT (D816H), and KIT (A829P). In some embodiments, the compounds of the disclosure inhibit both wild type KIT and one or more mutant forms selected from KIT (L576P), KIT (V559D), KIT (V559D, T670I), KIT (V559D, V654A), KIT (D816V), KIT (D816H), and KIT (A829P).

As demonstrated herein, the compounds according to this disclosure potently inhibit the receptor tyrosine kinase (RTK) KIT. Mast cells release proinflammatory and immunomodulatory mediators upon activation via binding of Stem Cell Factor (SCF) to KIT. Mast cells respond to antigens when activated and are often identified by the co-expression of KIT and FcRI. KIT signaling is necessary for mast cell differentiation, maturation and survival. For certain diseases, mast cell activation may play a central role in the onset and progression of the disease. Accordingly, inhibition of KIT may lead to mast cell depletion, and/or reduced mast cell activation, and provide a promising therapeutic approach for mast cell-driven diseases.

Diseases, disorders, and/or conditions that would benefit from KIT inhibition may include those in which mast cells play a contributory or vital role, or which are mediated, at least in part, by mast cell degranulation or mast cell activation.

Accordingly, in some embodiments, the compounds described herein are administered to a subject in need thereof in an amount effective to inhibit KIT. KIT inhibition may be assessed using a peripheral serum sample, blood sample or a tissue sample obtained from the subject. Activity may be determined, for example, by comparison to a previous sample obtained from the subject (i.e., prior to administration of the compound described herein) or by comparison to a reference value for a control group (e.g., standard of care, a placebo, etc.).

Alternatively or in addition, in some embodiments, the compounds described herein are administered to a subject in need thereof in an amount effective to diminish the activity and/or quantity of systemic mast cells in the subject. Mast cell activity and quantity may be assessed using a peripheral serum sample, blood sample or a tissue sample obtained from the subject. Activity may be determined, for example, by comparison to a previous sample obtained from the subject (i.e., prior to administration of the compound) or by comparison to a reference value for a control group (e.g., standard of care, a placebo, etc.). As a specific example, mast cell quantity can be assessed by measuring tryptase levels in a suitable sample (e.g., a blood or serum sample) from a subject to determine mast cell burden on the subject.

In one embodiment, the compounds described herein are administered to a subject identified as having a high mast cell burden.

Alternatively or in addition, in some embodiments, the compounds described herein are administered to a subject in need thereof to treat and/prevent an allergic, inflammatory, neuroinflammatory, neurological, immune, autoimmune, dermatological, respiratory, metabolic, cardiovascular, or fibrotic disease, disorder, or condition. In some embodiments, the compounds described herein are administered in combination with one or more additional therapeutic agents, examples of which are set forth elsewhere herein.

Alternatively or in addition, in some embodiments, the compounds described herein are administered to a subject in need thereof to treat and/prevent a symptom or response associated with an allergic, inflammatory, neuroinflammatory, neurological, immune, autoimmune, dermatological, respiratory, metabolic, cardiovascular, or fibrotic disease, disorder, or condition. In some embodiments, the compounds described herein are administered in combination with one or more additional therapeutic agents, examples of which are set forth elsewhere herein.

Alternatively or in addition, in some embodiments, the compounds described herein are administered to a subject suffering from an allergic, inflammatory, neuroinflammatory, neurological, immune, autoimmune, dermatological, respiratory, metabolic, cardiovascular, or fibrotic disease, disorder, or condition in order to treat and/or prevent a response or symptom associated therewith. In some embodiments, the compounds described herein are administered in combination with one or more additional therapeutic agents, examples of which are set forth elsewhere herein.

Alternatively or in addition, in some embodiments, the compounds described herein are administered to a subject in need thereof to treat and/or prevent cancer or a cancer-related disease, disorder or condition. In some embodiments, the compounds described herein are administered to a subject in need thereof to treat cancer, optionally in combination with at least one additional therapy, examples of which are set forth elsewhere herein.

Inflammatory, Immune, and Autoimmune Indications

In one or more embodiments, the compounds described herein are useful in the treatment and/or prophylaxis of inflammatory, immune, and autoimmune-related diseases, disorders and conditions. Inflammatory, immune and auto-immune-related diseases, disorders and conditions include allergic, neuroinflammatory, neurological, dermatological, respiratory, metabolic, fibrotic, and cardiovascular diseases, disorders and conditions. A non-limiting list of inflammatory, immune, and autoimmune-related diseases, disorders and conditions which may be treated or prevented with the compounds and compositions of the present disclosure include allergies (e.g., food allergy, drug allergy, insect allergy, latex allergy, mold allergy, pet allergy, pollen allergy, hay-fever, ragweed allergy, allergic rhinitis, allergic conjunctivitis, eosinophilic esophagitis, and the like), arthritis (e.g., rheumatoid arthritis, inflammatory arthritis, psoriatic arthritis, osteoarthritis), asthma, eosinophilic asthma, bullous dermatosis, alopecia areata, chronic rhinosinusitis with nasal polyps (CRSwNP), coeliac disease, systemic sclerosis, netherton syndrome, idiopathic anaphylaxis, migraine, chronic graft verse host disease, multiple sclerosis, Alzheimer's disease, autism, psoriasis, inflammatory bowel disease (e.g., Chrohn's disease and ulcerative colitis), irritable bowel syndrome, lupus, Grave's disease, Hashimoto's thyroiditis, ankylosing spondylitis, Sjögren's syndrome (SjS), angioedema, anaphylaxis, atopic dermatitis, urticaria (e.g., chronic spontaneous urticaria (CSU), acute urticaria, or physical urticaria such as popular urticaria, cold urticaria, cholinergic urticaria, solar urticaria, scleroderma, and dermatographic urticaria), mastocytosis, dermographism, systemic mastocytosis, mast cell activation syndrome, mast cell gastrointestinal disease, dermatitis herpetiformis, dermatosis, dermatitis, allergic contact dermatitis, eosinophilic gastrointestinal (GI) disease, type I diabetes, type II diabetes, prurigo nodularis, coronary heart disease, atherosclerosis, myocardial infarction, angina, pulmonary fibrosis, idiopathic pulmonary fibrosis, pulmonary arterial hypertension, primary pulmonary hypertension, chronic obstructive pulmonary disease, acute respiratory distress syndrome, hepatic fibrosis, renal fibrosis, cardiac fibrosis, cystic fibrosis, and bronchitis.

In some embodiments, the inflammatory immune, or autoimmune-related disease, disorder or condition is allergies (e.g., food allergy, drug allergy, insect allergy, latex allergy, mold allergy, pet allergy, pollen allergy, hay-fever, ragweed allergy, allergic rhinitis, allergic conjunctivitis, and eosinophilic esophagitis), allergic asthma, eosinophilic asthma, asthma, multiple sclerosis, inflammatory bowel disease (e.g., Chrohn's disease and ulcerative colitis), lupus, Grave's disease, Hashimoto's thyroiditis, ankylosing spondylitis, Sjögren's syndrome (SjS), urticaria (e.g., chronic spontaneous urticaria (CSU), acute urticaria, or physical urticaria including popular urticaria, cold urticaria, cholinergic urticaria, solar urticaria, scleroderma, and dermatographic urticaria), or anaphylaxis.

In some embodiments, the inflammatory immune, or autoimmune-related disease, disorder, or condition is urticaria (e.g., chronic spontaneous urticaria (CSU), acute urticaria, or physical urticaria including popular urticaria, cold urticaria, cholinergic urticaria, solar urticaria, scleroderma, and dermatographic urticaria), allergic asthma, eosinophilic asthma, atopic dermatitis, allergies (e.g., food allergy, drug allergy, insect allergy, latex allergy, mold allergy, pet allergy, pollen allergy, hay-fever, ragweed allergy, allergic rhinitis, allergic conjunctivitis, and eosinophilic esophagitis), or mastocytosis.

In some embodiments, the inflammatory immune, or autoimmune-related disease, disorder, or condition is urticaria (e.g., chronic spontaneous urticaria (CSU), acute urticaria, or physical urticaria including popular urticaria, cold urticaria, cholinergic urticaria, solar urticaria, scleroderma, and dermatographic urticaria), allergic asthma, eosinophilic asthma, atopic dermatitis, or allergies (e.g., food allergy, drug allergy, insect allergy, latex allergy, mold allergy, pet allergy, pollen allergy, hay-fever, ragweed allergy, allergic rhinitis, allergic conjunctivitis, and eosinophilic esophagitis).

In some embodiments, the inflammatory immune, or autoimmune-related disease, disorder, or condition is urticaria (e.g., chronic spontaneous urticaria (CSU), acute urticaria, or physical urticaria including popular urticaria, cold urticaria, cholinergic urticaria, solar urticaria, scleroderma, and dermatographic urticaria), or allergies (e.g., food allergy, drug allergy, insect allergy, latex allergy, mold allergy, pet allergy, pollen allergy, hay-fever, ragweed allergy, allergic rhinitis, allergic conjunctivitis, and eosinophilic esophagitis).

In some embodiments, the inflammatory immune, or autoimmune-related disease, disorder, or condition is urticaria (e.g., chronic spontaneous urticaria (CSU), acute urticaria, or physical urticaria including popular urticaria, cold urticaria, cholinergic urticaria, solar urticaria, scleroderma, and dermatographic urticaria).

In some embodiments, the inflammatory immune, or autoimmune-related disease, disorder, or condition is allergies (e.g., food allergy, drug allergy, insect allergy, latex allergy, mold allergy, pet allergy, pollen allergy, hay-fever, ragweed allergy, allergic rhinitis, allergic conjunctivitis, and eosinophilic esophagitis).

In some embodiments, the inflammatory immune, or autoimmune-related disease, disorder, or condition is a cardiovascular disease (e.g., coronary heart disease or atherosclerosis).

In some embodiments, the inflammatory immune, or autoimmune-related disease, disorder, or condition is a fibrotic disease (e.g., myocardial infarction, angina, chronic obstructive pulmonary disease, acute respiratory distress syndrome, osteoarthritis, pulmonary fibrosis, idiopathic pulmonary fibrosis, renal fibrosis, cystic fibrosis, bronchitis, or asthma).

In some embodiments, the inflammatory immune, or autoimmune-related disease, disorder or condition is arthritis, asthma, multiple sclerosis, psoriasis, inflammatory bowel disease, (e.g., Chrohn's disease and ulcerative colitis), Grave's disease, Hashimoto's thyroiditis, or ankylosing spondylitis.

In one or more embodiments, the inflammatory immune, or autoimmune-related disease, disorder, or condition is antihistamine-refractory. In some embodiments, the inflammatory immune, or autoimmune-related disease, disorder, or condition is refractory to IgE inhibitor therapy. In some embodiments, the inflammatory immune, or autoimmune-related disease, disorder, or condition is contraindicated or resistant to antihistamines.

Oncology Indications

In one or more embodiments, the compounds described herein are useful in the treatment and/or prophylaxis of cancer (e.g., carcinomas, sarcomas, leukemias, lymphomas, myelomas, etc.). In certain embodiments, the cancer may be locally advanced and/or unresectable, metastatic, or at risk of becoming metastatic. Alternatively, or in addition, the cancer may be recurrent or no longer responding to a treatment, such as a standard of care treatment known to one of skill in the art. Exemplary types of cancer contemplated by this disclosure include melanoma, prostate cancer, pancreatic cancer, squamous cell carcinoma, Hodgkin lymphoma, leukemia (e.g., chronic myeloid leukemia, chronic eosinophilic leukemia, chronic myelomonocytic leukemia, myeloid leukemia, acute myeloid leukemia, acute megakaryoblastic leukemia, mast cell leukemia, acute lymphocytic leukemia), gastric cancer (e.g., gastrointestinal stromal cancer), small bowel cancer, salivary gland cancer, adrenocortical cancer, thyroid cancer, breast cancer, endometrial cancer, cervical cancer, testicular cancer, esophageal cancer, lung cancer (e.g., small cell and non-small cell lung cancer), colorectal cancer, prostate cancer, liver cancer, bile duct cancer, gallbladder cancer, appendiceal cancer, urothelial cancer, neuroendocrine tumors, kidney cancer, head and neck cancer, bone cancer, brain cancer (e.g., glioblastoma, medulloblastoma), mesothelioma, and soft tissue sarcoma.

In the aforementioned embodiments, the methods of the present disclosure may be practiced in an adjuvant setting or neoadjuvant setting. The methods described herein may be indicated as a first line, second line, third line, or greater line of treatment.

The present disclosure also provides methods of treating or preventing other cancer-related diseases, disorders or conditions. The use of the term(s) cancer-related diseases, disorders and conditions is meant to refer broadly to conditions that are associated, directly or indirectly, with cancer and non-cancerous proliferative disease, and includes, e.g., angiogenesis, precancerous conditions such as dysplasia, and non-cancerous proliferative diseases disorders or conditions, such as benign proliferative breast disease and papillomas. For clarity, the term(s) cancer-related disease, disorder and condition do not include cancer per se.

In general, the disclosed methods for treating or preventing cancer, or a cancer-related disease, disorder or condition, in a subject in need thereof comprise administering to the subject a compound according to this disclosure. In some embodiments, the present disclosure provides methods for treating or preventing cancer, or a cancer-related disease, disorder or condition with a compound disclosed herein and at least one additional therapy, examples of which are set forth elsewhere herein.

Routes of Administration

In some embodiments, pharmaceutical compositions containing a compound according to this disclosure may be in a form suitable for oral administration. Oral administration may involve swallowing the formulation thereby allowing the compound to be absorbed into the bloodstream in the gastrointestinal tract. Alternatively, oral administration may involve buccal, lingual or sublingual administration, thereby allowing the compound to be absorbed into the blood stream through oral mucosa.

In another embodiment, the pharmaceutical compositions containing a compound according to this disclosure may be in a form suitable for parenteral administration. Forms of parenteral administration include, but are not limited to, intravenous, intraarterial, intramuscular, intradermal, intraperitoneal, intrathecal, intracisternal, intracerebral, intracerebroventricular, intraventricular, and subcutaneous. Pharmaceutical compositions suitable for parenteral administration may be formulated using suitable aqueous or non-aqueous carriers. Depot injections, which are generally administered subcutaneously or intramuscularly, may also be utilized to release the compounds disclosed herein over a defined period of time.

In another embodiment, the pharmaceutical compositions containing a compound according to this disclosure may be in a form suitable for administration via inhalation. Pharmaceutical compositions suitable for administration via inhalation are formulated such that the compound is dispersed via an aerosol spray, mist, or powder that can be inhaled into the airways. Administration via inhalation may be, for example, via an inhaler, or nebulizer.

In another embodiment, the pharmaceutical compositions containing a compound according to this disclosure may be in a form suitable for topical administration to body surfaces such as the skin or mucous membranes. Forms of topical administration include transdermal, ophthalmic, otic, nasal, intraocular, vaginal, and rectal administration.

Particular embodiments of the present disclosure contemplate oral administration or parenteral administration.

Pharmaceutical Compositions

The compounds of the present disclosure may be in the form of compositions suitable for administration to a subject. In general, such compositions are pharmaceutical compositions comprising a compound according to this disclosure, or a pharmaceutically acceptable salt thereof, and one or more pharmaceutically acceptable excipients. In certain embodiments, the compound may be present in an effective amount. The pharmaceutical compositions may be used in the methods of the present disclosure; thus, for example, the pharmaceutical compositions comprising a compound according to this disclosure, or a pharmaceutically acceptable salt thereof, can be administered to a subject in order to practice the therapeutic and prophylactic methods and uses described herein.

The pharmaceutical compositions of the present disclosure can be formulated to be compatible with the intended method or route of administration. Routes of administration may include those known in the art. Exemplary routes of administration are oral, parenteral, topical, or via inhalation. Furthermore, the pharmaceutical compositions may be used in combination with one or more other therapies described herein in order to treat or prevent the diseases, disorders and conditions as contemplated by the present disclosure. In one embodiment, one or more other therapeutic agents contemplated by this disclosure are included in the same pharmaceutical composition that comprises the compound according to this disclosure. In another embodiment, the one or more other therapeutic agents are in a composition that is separate from the pharmaceutical composition comprising the compound according to this disclosure.

In one aspect, the compounds described herein may be administered orally. Oral administration may be via, for example, capsule or tablets. In making the pharmaceutical compositions that include the compound of Formula I or a pharmaceutically acceptable salt thereof, the tablet or capsule typically includes at least one pharmaceutically acceptable excipient. An oral dosage form may alternatively be formulated as a solution or suspension.

In another aspect, the compounds described herein may be administered parenterally, for example by intravenous injection. A pharmaceutical composition appropriate for parenteral administration may be formulated in solution for injection or may be reconstituted for injection in an appropriate system such as a physiological solution. Such solutions may include sterile water for injection, salts, buffers, and tonicity excipients in amounts appropriate to achieve isotonicity with the appropriate physiology.

In another aspect, the compounds described herein may be administered via inhalation. A pharmaceutical composition appropriate for inhalation may be formulated as an aerosol, dry powder, or other form suitable for administration with nebulizers, pressurized metered-dose inhalers, or dry powder inhalers.

In another aspect, the compounds described herein may be administered topically. Pharmaceutical compositions suitable for topical administration may be formulated as, for example, a lotion, gel, patch, powder, paste, cream, foam, ointment, oil, spray, liniment, aerosol, or liquid.

The pharmaceutical compositions described herein may be stored in an appropriate sterile container or containers. In some embodiments, the container is designed to maintain stability for the pharmaceutical composition over a given period of time.

Administration

In general, the disclosed methods comprise administering a compound of Formula I described herein, or a composition thereof, in an effective amount to a subject in need thereof. An "effective amount" with reference to a KIT inhibitor of the present disclosure means an amount of the compound that is sufficient to engage the target (by inhibiting, or antagonizing the target) at a level that is indicative of the potency of the molecule. For KIT, target engagement can be determined by one or more biochemical or cellular assays resulting in an EC50, ED50, EC90, IC50, or similar value which can be used as one assessment of the potency of the compound. Assays for determining target engagement include, but are not limited to, those described in the Examples. The effective amount may be administered as a single quantity or as multiple, smaller quantities (e.g., as one tablet with "x" amount, as two tablets each with "x/2" amount, etc.).

In some embodiments, the disclosed methods comprise administering a therapeutically effective amount of a compound of Formula I described herein to a subject in need thereof. As used herein, the phrase "therapeutically effective amount" with reference to KIT inhibition means a dose regimen (i.e., amount and interval) of the compound that provides the specific pharmacological effect for which the compound is administered to a subject in need of such treatment. For prophylactic use, a therapeutically effective amount may be effective to eliminate or reduce the risk, lessen the severity, or delay the onset of the disease, including biochemical, histological and/or behavioral signs or symptoms of the disease. For treatment, a therapeutically effective amount may be effective to reduce, ameliorate, or eliminate one or more signs or symptoms associated with a disease, delay disease progression, prolong survival, decrease the dose of other medication(s) required to treat the disease, or a combination thereof. In one embodiment, a therapeutically effective amount may be effective to reduce mast cell burden in the subject. With respect to cancer specifically, a therapeutically effective amount may, for example, result in the killing of cancer cells, reduce cancer cell counts, reduce tumor burden, eliminate tumors or metastasis, or reduce metastatic spread. A therapeutically effective amount of a KIT inhibitor need not always be effective in treating every individual subject to be deemed to be a therapeutically effective amount by those of skill in the art. A therapeutically effective amount may vary based on, for example, one or more of the following: the age and weight of the subject, the subject's overall health, the stage of the subject's disease, the route of administration, and prior or concomitant treatments.

Administration may comprise one or more (e.g., one, two, or three or more) dosing cycles.

In certain embodiments, the compounds of Formula I contemplated by the present disclosure may be administered (e.g., orally, parenterally, topically, via inhalation, etc.) at about 0.01 mg/kg to about 50 mg/kg, or about 1 mg/kg to about 25 mg/kg, of subject's body weight per day, one or more times a day, a week, or a month, to obtain the desired effect. In some embodiments, a suitable weight-based dose of a compound contemplated by the present disclosure is used to determine a dose that is administered independent of a subject's body weight (i.e., a fixed-dose). In certain embodiments, a compound of the present disclosure is administered (e.g., orally, parenterally, etc.) at a fixed dosage levels of about 1 mg to about 1000 mg, particularly 1, 3, 5, 10, 15, 20, 25, 50, 75, 100, 150, 200, 250, 300, 400, 500, 600, 750, 800, 900, or 1000 mg, one or more times a day, a week, or a month, to obtain the desired effect.

In certain embodiments, the compound of Formula I is contained in a "unit dosage form". The phrase "unit dosage form" refers to physically discrete units, each unit containing a predetermined amount of the compound, either alone or in combination with one or more additional agents, sufficient to produce the desired effect. It will be appreciated that the parameters of a unit dosage form will depend on the particular agent and the effect to be achieved.

Combination Therapy

The present disclosure contemplates the use of the KIT inhibitors described herein alone, or in combination with one or more additional therapeutic agents. The use of the KIT inhibitors described herein in combination with one or more additional therapies may have a synergistic therapeutic or prophylactic effect on the underlying disease, disorder, or condition. In addition or alternatively, the combination therapy may allow for a dose reduction of one or more of the therapies, thereby ameliorating, reducing or eliminating adverse effects associated with one or more of the agents.

In embodiments comprising one or more additional therapeutic agents, the KIT inhibitor described herein can be administered before, during, or after treatment with the additional therapeutic agents. In embodiments comprising one or more additional therapeutic agents, the therapeutic agents used in such combination therapy can be formulated as a single composition or as separate compositions. If administered separately, each therapeutic agent in the combination can be given at or around the same time, or at different times. Furthermore, the therapeutic agents are administered "in combination" even if they have different forms of administration (e.g., oral capsule and intravenous), they are given at different dosing intervals, one therapeutic agent is given at a constant dosing regimen while another is titrated up, titrated down or discontinued, or each therapeutic agent in the combination is independently titrated up, titrated down, increased or decreased in dosage, or discontinued and/or resumed during a patient's course of therapy. If the combination is formulated as separate compositions, in some embodiments, the separate compositions are provided together in a kit.

Inflammatory, Immune and Autoimmune-Related Diseases, Disorders and Conditions

The present disclosure contemplates the use of the KIT inhibitors described herein in combination with one or more additional therapies useful in the treatment of inflammatory and immune-related diseases, disorders and conditions, such as those described elsewhere herein.

In some embodiments, one or more of the additional therapies is an additional treatment modality such as, for example, diet modification, physical therapy, skin hydration, oxygen therapy, exercise, plasmapheresis, phototherapy, use of a humidifier, surgery (e.g., coronary artery bypass graft surgery, angioplasty, stent implant, endarterectomy, and thyroidectomy), and behavioral intervention such as avoidance of external triggers (e.g., allergens) or harmful substances.

In one or more embodiments, the compounds according to the disclosure can be combined with one or more anti-inflammatory agents. A non-limiting list of anti-inflammatory agents include non-steroidal anti-inflammatory drugs (NSAIDs) (e.g., ibuprofen, aspirin, naproxen, and celecoxib, etodolac, meloxicam, nabumetone, diclofenac, diflunisal, fenoprofen, and flurbiprofen); corticosteroids (e.g., cortisone, prednisone, prednisolone, methylprednisolone, dexamethasone, deflazacort, betamethasone, hydrocortisone, etc.); disease-modifying antirheumatic drugs (DMARDs) (e.g., methotrexate, sulfasalazine, hydroxychloroquine, and leflunomide); anti-tumor necrosis factor (anti-TNF) agents (e.g., infliximab, adalimumab, and certolizumab pegol); interferons (e.g., interferon alfa); integrin receptor antagonists (e.g., vedolizumab); mast-cell stabilizers (e.g., cromolyn sodium, nedocromil, and lodoxamide); and aminosalicylates (5-ASA) (e.g., balsalazide, mesalazine, olsalazine, and sulfasalazine).

In some embodiments, the additional therapeutic agent comprises an analgesic agent, e.g., acetaminophen, NSAIDs, cyclooxygenase-2 (COX-2) inhibitors (e.g., celecoxib), tramadol, and opiates. In one embodiment, the analgesic agent is acetaminophen.

In some embodiments, the additional therapeutic agent comprises an agent that targets one or more cytokines, such as, e.g., interleukin-4, interleukin-5, interleukin-12, interleukin-13, interleukin-17, and/or interleukin-23. In some embodiments, the agent blocks one or more proinflammatory cytokines (e.g., interleukin-12, interleukin-17, and/or interleukin-23) (e.g., secukinumab, ixekizumab, brodalumab, ustekinumab, guselkumab, tildrakizumab, and risankizumab). In some embodiments, the agent blocks a cytokine that regulates allergic inflammation, e.g., interleukin-4 and/or interleukin 13 (e.g., dupilumab). In some embodiments, the agent blocks a cytokine that mediates eosinophil activation, e.g., interleukin-5 (e.g., benralizumab, mepolizumab, or reslizumab).

In some embodiments, the at least one additional therapeutic agent comprises an agent that targets CD20, e.g., an anti-CD20 antibody (e.g., ocrelizumab)

In one or more embodiments, the additional therapeutic agent comprises one or more immunosuppressants. Exemplary immunosuppressants include, but are not limited to, azathioprine, cyclosporine, leflunomide, JAK-inhibitors (e.g., abrocitinib, baricitinib, tofacitinib, and upadacitinib), and targeted immunosuppressive antibodies (e.g., belimumab).

In some embodiments, the additional therapeutic agent comprises one or more agents that target mast-cell derived immunomodulators, such as, for example, histamines, and/or leukotrienes. Exemplary antihistamines include brompheniramine, cetirizine, chlorpheniramine, clemastine, diphenyldramine, fexofenadine, azelastine, carbinoxamine, cyproheptadine, desloratadine, emedastine, hydroxyzine, levocabastine, levocetirizine, and loratadine. Exemplary leukotriene modifiers include montelukast, zafirlukast, and zileuton.

In one or more embodiments, the additional therapeutic agent comprises a Bruton's tyrosine kinase (BTK) inhibitor. Exemplary BTK inhibitors include ibrutinib, acalabrutinib, remibrutinib, and zanubrutinib.

In one or more embodiments, the additional therapeutic agent comprises an immunoglobulin E (IgE) inhibitor, e.g., an anti-IgE inhibitor (omalizumab, TNX-901, or ligelizumab).

In one or more embodiments, the additional therapeutic agent comprises an agent that targets the cytokine IL-13, e.g., an anti-IL13 antibody (tralokinumab).

In one or more embodiments, the additional therapeutic agent comprises a TSLP antagonist, e.g., an anti-TSLP antibody (Tezepelumab).

In one or more embodiments, the additional therapeutic agent comprises a costimulation inhibitor of CD80 and CD86. Exemplary costimulation inhibitors of CD80 and CD86 include, but are not limited to, abatacept.

In one or more embodiments, the additional therapeutic agent comprises an antagonist of siglec-8, e.g., an anti-siglec-8 antibody (lirentelimab).

In one or more embodiments, the additional therapeutic agent comprises an immunotherapeutic agent. Exemplary immunotherapeutic agents include, but are not limited to, Palforzia©.

In one or more embodiments, the additional therapeutic agent comprises an antagonist of IL-31RA, e.g., an anti-IL-31RA antibody (nemolizumab).

In some embodiments, the additional therapeutic agent comprises an anti-depressant. Exemplary anti-depressants contemplated include, but are not limited to, serotonin and norepinephrine reuptake inhibitors (SNRIs) (e.g., desvenlafaxine, duloxetine, levomilnacipran, milnacipran, and venlafaxine), selective serotonin reuptake inhibitors (SSRIs) (e.g., citalopram, escitalopram, fluoxetine, fluvoxamine, and sertraline), tricyclic antidepressants (e.g., imipramine, nortriptyline, amitriptyline, doxepin, and desipramine), and monoamine oxidase inhibitors (MAOIs) (e.g., tranylcypromine, phenelzine, and isocarboxazid).

In some embodiments, the additional therapeutic agent comprises an antipsychotic. Exemplary antipsychotics include haloperidol, loxapine, thioridazine, molindone, thiothixene, fluphenazine, mesoridazine, trifluoperazine, perphenazine, chlorpromazine, aripiprazole, clozapine, ziprasidone, risperidone, quetiapine, and olanzapine.

In some embodiments, the additional therapeutic agent comprises one or more anti-anxiety agents. Exemplary anti-anxiety agents include alprazolam, chlordiazepoxide, clonazepam, diazepam, lorazepam, and buspirone.

In some embodiments, the additional therapeutic agent comprises one or more anticonvulsants (e.g., valproic acid, phenytoin, clonazepam, and carbamazepine).

In some embodiments, the additional therapeutic agent comprises one or more respiratory agents. In some embodiments, the respiratory agent is a bronchodilator (e.g., adrenergic bronchodilator, anticholinergic bronchodilator, methylxanthines, and combinations thereof), an inhaled corticosteroid (e.g., beclomethasone, fluticasone, ciclesonide, mometasone, and budesonide), a beta adrenergic agonist (e.g., albuterol, metaproterenol, pirbuterol, terbutaline, isoetharine and levalbuterol), or leukotriene modifier (e.g., montelukast, zafirlukast, and zileuton).

In one or more embodiments, the additional therapeutic agent comprises one or more nasal decongestants. Exemplary decongestants include oxymetazoline, phenylephrine, and pseudoephedrine.

In some embodiments, the additional therapeutic agent comprises a cough suppressant. Exemplary cough suppressants include dextromethorphan, guaifenesin, and codeine.

In some embodiments, the compounds according to this disclosure are combined with a proton pump inhibitor (PPI). Exemplary PPIs include lansoprazole, omeprazole, pantoprazole, rebaprazole, and esomeprazole.

In some embodiments, the additional therapeutic agent comprises an agent that modulates cognitive function, e.g., cholinesterase inhibitors (e.g., donepezil, rivastigmine, galantamine), N-methyl-D-aspartate (NMDA) receptor antagonists (e.g., memantine), and agents targeting aggregated soluble and insoluble forms of amyloid beta (e.g., aducanumab).

In some embodiments, the additional therapeutic agent comprises an agent that targets thyroid function, such as, for example, anti-thyroid agents (e.g., radioiodine, propylthiouracil (PTU), and methimazole), or thyroid hormone replacement therapy (e.g., levothyrozine, or cytomel).

In one or more embodiments, the additional therapeutic agent comprises one or more agents useful in the treatment of diabetes, such as, e.g., insulin; synthetic glucagon; hyperglycemic agents (e.g., metformin, sulfonylureas, glinides, thiazolidinediones, dipeptidyl peptidase-4 (DPP-4) inhibitors; anti-hyperglycemic agents (e.g., sodium glucose cotransporter-2 (SGLT2) inhibitors including, e.g., canagliflozin, dapagliflozin, and empagliflozin); and GLP-1 receptor agonists (e.g., semaglutide, exenatide, dulaglutide, liraglutide, or lixisenatide).

In some embodiments, the additional therapeutic agent comprises a diuretic. Exemplary diuretics include spironolactone, bumetanide, torsemide, hydrochlorothiazide, furosemide, and metolazone, and aldosterone antagonists (e.g., spironolactone and eplerenone).

In one or more embodiments, the additional therapeutic agent comprises one or more of an antidiarrheal (e.g., eluxadoline, or alosetron), a laxative (lubiprostone, or a guanylate cyclase-C (GC-C agonist (e.g., linaclotide).

In some embodiments, the additional therapeutic agent comprises a cholinergic modulator, such as a cholinergic agonist (e.g., chantix, pilocarpine, or bethanechol), or an anticholinergic agent (e.g., atropine, belladonna alkaloids, benztropine mesylate, clidinium, cyclopentolate, darifenacin, dicylomine, fesoterodine, flavoxate, glycopyrrolate, homatropine hydrobromide, hyoscyamine, ipratropium, orphenadrine, oxybutynin, propantheline, scopolamine, methscopolamine, solifenacin, tiotropium, tolterodine, trihexphenidyl, and trospium).

In another embodiment, the additional therapeutic agent comprises an antiarrhythmic agent. Antiarrhythmic agents include calcium channel blocking agents (e.g., amlodipine, diltiazem, felodipine, isradipine, nicardipine, nifedipine, nisoldipine, and verapamil), beta-adrenergic blocking agents (i.e., beta blockers) (e.g., atenolol, bisoprolol, carvedilol, labetalol, metoprolol, propranolol, and sotalol), potassium-channel blockers (e.g., amiodarone, dronedarone, dofetilide, ibutilide, azimilide, bretylium, clofilium, nifekalant, tedisamil, and sematilide), adenosine, electrolyte supplements, atropine, and *digitalis* compounds.

In one or more embodiments, the additional therapeutic agent comprises a vasodilator. Exemplary vasodilators include, but are not limited to nitrates (e.g., nitroprusside, nitroglycerine, isosorbide, and amyl nitrate), hydralazine, treprostinil, minoxidil, angiotensin-converting enzyme (ACE) inhibitors (e.g., benazepril, captopril, enalapril, fosinopril, lisinopril, moexipril, perindopril, quinapril, ramipril, and trandolapril), and angiotensin receptor blockers (ARBs) (e.g., azilsartan, candesartan, eprosartan, irbesartan, losartan, olmesartan, telmisartan, and valsartan).

In some embodiments, the additional therapeutic agent comprises a cholesterol modifier. Cholesterol modifiers include statins (atorvastatin, Fluvastatin, lovastatin, pitavastatin, pravastatin, rosuvastatin, and simvastatin), cholesterol absorption inhibitors (e.g., ezetimibe), proprotein convertase subtilisin kexin 9 (PCSK9) inhibitors (e.g., alirocumab, and evolocumab), citrate lyase inhibitors (e.g., bempedoic acid, and benpedoic acid-ezetimibe), bile acid sequestrants (e.g., cholestyramine, colesevelam, and colestipol), fibrates (e.g., fenofibrate, and gemfibrozil), niacin, and omega-3 fatty acids.

In some embodiments, the additional therapeutic agent comprises a thrombolytic agent (e.g., streptokinase, alteplase, reteplase, Tenecteplase, urokinase, prourokinase, and anistreplase).

In another embodiment, the additional therapeutic agent comprises an anticoagulant. Exemplary anticoagulants include rivaroxaban, dabigatran, apixaban, eboxaban, and warfarin.

In some embodiments, the additional therapeutic agent comprises an agent useful in the treatment of fibrosis. Certain such agents include pirfenidone and nintedanib.

In another embodiment, the additional therapeutic agent comprises a targeted agent useful in the treatment of pulmonary arterial hypertension. Targeted agents useful in the treatment of pulmonary arterial hypertension include phosphodiesterase-5 (PDE5) inhibitors (e.g., sildenafil, tadalafil and vardenafil); guanylate cyclase stimulators (GCS) (e.g., adempas, riociguat, vericiguat and verquvo); endothelin receptor antagonists (e.g., bosentan, ambrisentan, and macitentan), and prostacyclin and analogues thereof.

In some embodiments, the additional therapeutic agent includes a mucolytic, e.g., guaifenesin, carbocisteine, erdosteine, mecysteine, bromhexine, hyperosmolar saline, mannitol powder, and dornase alfa.

In some embodiments, the additional therapeutic agent comprises a pancreatic enzyme, e.g., creon.

In some embodiments, the additional therapeutic agent comprises an agent that targets a mutation in the cystic fibrosis transmembrane conductance regulator (CFTR) gene. Exemplary CFTR modulators include ivacaftor, elexacaftor, lumacaftor, and tezacaftor.

In some embodiments, the additional therapeutic agent comprises an antibiotic. Exemplary antibiotics include, but are not limited to phenoxymethylpenicillin, dicloxacillin, amoxicillin, ampicillin, nafcillin, oxacillin, penicillin, cefaclor, cefazolin, cefadroxil, cephalexin, cefuroxime, cefixime, ceroxitin, ceftriaxone, doxycycline, minocycline, sarecycline, erythromycin, clarithromycin, azithromycin, fidaxomicin, roxithromycin, ciprofloxacin, ofloxacin, levofloxacin, moxifloxacin, sulfamethoxazole with trimethoprim, sulfasalazine, sulfacetamide, sulfadiazine silver, vancomycin, dalbavancin, oritavancin, and telavancin.

In some embodiments, the additional therapeutic agent comprises one or more agents selected from the groups consisting of anti-inflammatory agents, analgesic agents, agents that target one or more cytokines, immunosuppressants, agents that targets one or more mast-cell derived immunomodulators, BTK inhibitors, IgE inhibitors, antidepressants, anti-psychotics, anti-anxiety agents, anticonvulsants, respiratory agents, nasal decongestants, cough suppressants, proton pump inhibitors (PPIs), agents that modulate cognitive function, agents that target thyroid function, agents useful in the treatment of diabetes, diuretics, antidiarrheals, laxatives, GC-C agonists, cholinergic modulators, antiarrhythmics, vasodilators, cholesterol modifiers, thrombolytic agents, anticoagulants, agents useful in the treatment of fibrosis, agents useful in the treatment of arterial hypertension, mucolytic agents, pancreatic enzymes, CFTR modulators, and/or antibiotics.

In some embodiments, the additional therapeutic agent comprises one or more agents selected from the group consisting of an anti-inflammatory agent, an analgesic agent, an immunosuppressant, and/or an agent that targets one or more cytokines (e.g., IL-12, IL-17, and/or IL-23).

In some embodiments, the additional therapeutic agent comprises one or more agents selected from the group consisting of a respiratory agent, an anti-inflammatory agent, an agent that targets one or more cytokines (e.g., IL-4 and/or IL-13), a mast-cell stabilizer, and/or an agent that targets a mast-cell derived immunomodulator (e.g., leukotrienes).

In some embodiments, the additional therapeutic agent comprises one or more agents selected from the group consisting of an anti-depressant, an anti-psychotic, an anti-anxiety agent, an anticonvulsant, an agent that modulates cognitive function, an anti-CD20 antibody (e.g., ocrelizumab), an anti-inflammatory, and/or an immunosuppressant.

In some embodiments, the additional therapeutic agent comprises an anti-inflammatory and/or an immunosuppressant.

In some embodiments, the additional therapeutic agent comprises an anti-inflammatory agent, an immunosuppressant, and/or an agent that targets a mast-cell derived immunomodulator (e.g., antihistamine and/or leukotriene modulators).

In some embodiments, the additional therapeutic agent comprises an antihistamine, a BTK inhibitor, and/or an IgE inhibitor.

In some embodiments, the additional therapeutic agent comprises an antihistamine, an anti-inflammatory agent (e.g., a corticosteroid), and IgE inhibitor, and/or an immunosuppressant (e.g., cyclosporine).

In some embodiments, the additional therapeutic agent comprises an anti-inflammatory agent, an immunosuppressive agent, an agent that targets one or more cytokines, or a combination thereof.

In some embodiments, the additional therapeutic agent comprises a cholesterol modifier, a diuretic, an antiarrhythmic, a vasodilator, an anti-inflammatory, an analgesic agent, or any combination thereof.

In one or more embodiments, the compounds described herein are combined with one or more additional therapeutic agents that are considered to be the standard of care (SOC) for one or more of the inflammatory, immune, and/or autoimmune-related indications described herein. Exemplary SOC therapies for the indications described herein are summarized in Table 1 and Table 2 below.

TABLE 1

| Disease/Disorder/ Condition | Non-Biologics | Biologic |
| --- | --- | --- |
| Arthritis | Acetaminophen, non-steroidal anti-inflammatory drugs (NSAIDs), corticosteroids | |
| Rheumatoid arthritis/inflammatory arthritis | NSAIDs, corticosteroids, disease-modifying antirheumatic drugs (DMARDs) methotrexate, immunosuppressants, and JAK-inhibitors | Anti-Tumor Necrosis Factor Agents (TNFs), anti-interleukin (IL)-12, anti-IL-17, & anti-IL-23 |
| Psoriatic arthritis/inflammatory arthritis | NSAIDs, corticosteroids, DMARDs (e.g., methotrexate), immunosuppressants, and JAK-inhibitors | Anti-TNFs, anti- IL-12, anti-IL-17, & anti-IL-23 |
| Osteoarthritis | Acetaminophen, NSAIDs, serotonin and norepinephrine reuptake inhibitors (SNRIs) | |
| Asthma | Bronchodilator, inhaled steroids, oral corticosteroids, leukotriene modifiers, cromolyn sodium | Anti-IL-4/13 (e.g., dupilumab) |
| Multiple sclerosis | Corticosteroids, immunomodulators, and plasmapheresis | Anti-CD20 Mab (e.g., ocrelizumab) |
| Alzheimer's disease | Cholinesterase inhibitors, donepezil, memantine | Aducanumab |
| Autism | Behavioral and cognitive therapy, selective serotonin reuptake inhibitors (SSRIs)/ antidepressants, anti-psychotics, anti-anxiety, anticonvulsants (anti-seizure) | |
| Psoriasis | Topical corticosteroids, vitamin A/D, phototherapy, DMARDs & immunosuppressants (JAK-inhibitors) | Anti-TNFs, anti-IL-12, anti-IL-17, & anti-IL-23 |
| Crohn's disease | Diet modification, corticosteroids and immunomodulators (JAK-inhibitors) | Anti-TNF (e.g.,), integrin receptor antagonists (e.g., vedolizumab), anti-IL-12 (e.g., ustekinumab), & anti-IL-23 |
| Ulcerative Colitis | Diet modification, amino salicylates (5-ASA), corticosteroids, Immunosuppressants, & JAK-inhibitors | Anti-TNF (e.g., infliximab), integrin receptor antagonists (e.g., vedolizumab), anti-IL-12 (e.g., ustekinumab), & anti-IL-23 |
| Irritable bowel syndrome | Diet modification, antidiarrheal, laxatives, selective serotonin reuptake inhibitors (SSRIs), antibiotics, linaclotide, alosetron, eluxadoline, and lubiprostone | |
| Lupus | NSAIDs, corticosteroids, and immunosuppressants | Immunosuppressive MAb (e.g., belimumab) |
| Grave's disease | Radioiodine, beta-blockers and anti-thyroid medications, thyroidectomy | |
| Hashimoto's thyroiditis | T-4 hormone replacement (e.g., levothyroxine), T-3 hormone (e.g., Cytomel) | |
| Ankylosing spondylitis | Physical therapy, NSAIDs, corticosteroids | Anti-TNF & anti-IL-17 (e.g., secukinumab and ixekizumab) |
| Sjögren's syndrome (SjS) | hydroxychloroquine, methotrexate, cyclosporine, pilocarpine, cevimeline | |
| Angioedema | Trigger avoidance, antihistamines, oral corticosteroids, leukotriene modifiers | |
| Allergic asthma | Nasal steroids, antihistamines, inhaled steroids, anticholinergic | IgE inhibitor (e.g., omalizumab) |

TABLE 1-continued

| Disease/Disorder/ Condition | Non-Biologics | Biologic |
|---|---|---|
| Eosinophilic asthma | Inhaled steroids, oral corticosteroids, and leukotriene modifiers | IgE inhibitor, anti-IL-5 (e.g., benralizumab), anti-IL-4/13 (e.g., dupilumab) |
| Anaphylaxis | Epinephrine (EpiPen) Antihistamines, cortisone, beta-agonist (e.g., albuterol) | |
| Atopic dermatitis | Topical corticosteroids, antibiotic cream, oral corticosteroids, phototherapy | Anti-IL-4/13 (e.g., dupilumab) |
| Food allergies | Diet modification/avoidance, antihistamines, corticosteroids, epinephrine (rescue) | |
| Allergic conjunctivitis | Antihistamine eye-drops, oral antihistamines, NSAIDs, corticosteroids, mast cell stabilizers (e.g., lodoxamide and nedocromil) | |
| Allergic rhinitis | Antihistamines, decongestants, corticosteroids, leukotriene modifiers, | IgE inhibitor (e.g., omalizumab) |
| Urticaria (e.g., chronic spontaneous urticaria (CSU) | Antihistamines, corticosteroids, cyclosporine | IgE inhibitor (e.g., omalizumab) |
| Acute/physical urticaria | Avoidance, antihistamines, topical & oral corticosteroids | |
| Mastocytosis | Topical corticosteroids, antihistamines, NSAIDs, leukotriene modifiers, mast cell stabilizers | |
| Dermographism | Skin hydration, antihistamines | |
| Dermatosis/dermatitis | Hydrocortisone, topical corticosteroids, antihistamines, immunosuppressants | |
| Allergic contact dermatitis | Allergen avoidance, hydrocortisone, topical corticosteroids, oral corticosteroids | |
| Eosinophilic GI disease | Proton pump inhibitors (PPIs), swallowed topical steroids, corticosteroids, diet-modification | |
| Eosinophilic esophagitis | Diet modification, proton pump inhibitors (PPIs), swallowed topical steroids, corticosteroids, and esophageal dilation | |
| Type I diabetes | Insulin, diet, synthetic glucagon | |
| Type II diabetes | Diet, exercise, Metformin, Sulfonylureas, Glinides, Thiazolidinediones, DPP-4 inhibitors, GLP-1 receptor agonists, SGLT2 inhibitors, insulin | |
| Prurigo nodularis | Topical corticosteroids, antihistamines, oral corticosteroids, and SSRIs | |

TABLE 2

| Disease/Disorder/ Condition | Non-Biologics | Biologic |
|---|---|---|
| Coronary heart disease | Diet, exercise, cholesterol modifiers (e.g., statins), antiplatelets (e.g., aspirin), beta-blockers, diuretics, calcium channel blockers, nitroglycerin, angiotensin-converting enzyme inhibitors (ACEs), and angiotensin receptor blockers (ARBs), angioplasty, stent implant, and coronary artery bypass | Proprotein convertase subtilisin kexin 9 (PCSK9) inhibitors (e.g., evolocumab and alirocumab) |
| Atherosclerosis | Diet, exercise, cholesterol modifiers (e.g., statins), antiplatelets (e.g., aspirin), beta-blockers, diuretics, calcium channel blockers, ACEs, ARBs, angioplasty, stent implant, endarterectomy, Fibrinolytic therapy, and coronary artery bypass | |
| Myocardial infarction | Oxygen, antiplatelets (e.g., aspirin), anticoagulants, nitroglycerin, thrombolytic medications, anti-arrhythmia medications, beta-blockers, calcium channel blockers, ACEs, and ARBs, | |

TABLE 2-continued

| Disease/Disorder/Condition | Non-Biologics | Biologic |
|---|---|---|
| Angina | Nitrates, antiplatelets (e.g., aspirin), cholesterol modifiers (e.g., statins), anticoagulants, beta-blockers, calcium channel blockers, ACEs, and ARBs | Proprotein convertase subtilisin kexin 9 (PCSK9) inhibitors (e.g., evolocumab and alirocumab) |
| Osteoarthritis | Acetaminophen, NSAIDs, serotonin and norepinephrine reuptake inhibitors (SNRIs) | |
| Pulmonary fibrosis | Oxygen therapy, pulmonary rehabilitation, pirfenidone and nintedanib | |
| Pulmonary arterial hypertension (PAH) | Phosphodiesterase-5 inhibitor (PDE-5i), guanylate cyclase stimulator (GCS), Endothelin receptor antagonist (ERA), Prostacyclin-class therapy | |
| Primary pulmonary hypertension (PH) | Oxygen therapy, vasodilators (e.g., epoprostenol and treprostinil), guanylate cyclase (GSC) stimulators, endothelin receptor antagonists, diuretics, calcium channel blockers, and anticoagulant (e.g., warfarin) | |
| Hepatic fibrosis | Treatments focus on underline driver of fibrosis; e.g., limit alcohol consumption, modify medications causing liver damage, controlling fat/cholesterol/sugars | |
| Renal fibrosis | Focus on overall kidney function | |
| Cardiac fibrosis | ACEs, ARBs, aldosterone antagonist, (e.g., pirfenidone) | |
| Cystic fibrosis | Anti-inflammatoires, mucus-thinners, inhaled steroids, pancreatic enzymes, gene targeting medications (e.g., transmembrane conductance regulator (CFTR) modulators; ivacaftor, elexacaftor, lumacaftor, and tezacaftor) | |
| Bronchitis | Avoid irritants, cough suppressants, humidifier, bronchodilators (e.g., inhaled steroids) | |
| Asthma | Bronchodilator, inhaled steroids, oral corticosteroids, leukotriene modifiers, cromolyn sodium | Anti-IL-4/13 (e.g., dupilumab) |

Cancer Therapies

The present disclosure contemplates the use of the KIT inhibitors described herein in combination with one or more additional therapies useful in the treatment of cancer.

In some embodiments, one or more of the additional therapies is an additional treatment modality. Exemplary treatment modalities include but are not limited to surgical resection of a tumor, bone marrow transplant, radiation therapy, and photodynamic therapy.

In some embodiments, one or more of the additional therapies is a therapeutic agent. Exemplary therapeutic agents include chemotherapeutic agents, radiopharmaceuticals, hormone therapies, epigenetic modulators, ATP-adenosine axis-targeting agents (e.g., CD73 inhibitors, CD39 inhibitors, $A_{2A}R$ inhibitors, and/or $A_{2B}R$ inhibitors), signal transduction inhibitors (e.g., inhibitors of one or more of TYRO3, MERTK, EGFR, FGFR, VEGFR, HER-2, HER-3, BRAF, RET, MET, ABL, ALK, FLT-3, JAK, STAT, NF-kB), RAS signaling inhibitors (e.g., inhibitors of one or more of KRAS, HRAS, RAF, MEK, ERK, PTEN, SOS (e.g., SOS1), mTORC1, SHP2 (PTPN11), and AKT), PI3K inhibitors, arginase inhibitors, HIF inhibitors (e.g., inhibitors of HIF-2α), AXL inhibitors, PAK4 inhibitors, immunotherapeutic agents, cellular therapies, gene therapies, immune checkpoint inhibitors (e.g., inhibitors of one or more of PD-1, PD-L1, TIGIT, CTLA-4, BTLA, LAG-3, and TIM-3), and agonists of stimulatory or co-stimulatory immune checkpoints.

In some embodiments, one or more of the additional therapeutic agents is a chemotherapeutic agent. Examples of chemotherapeutic agents include, but are not limited to, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylolomelamime; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, pornalidomide, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2''-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g., paclitaxel, nab paclitaxel, and docetaxel; chlorambucil; gemcitabine; 6-thioguanine; mercaptopurine; methotrexate; platinum and platinum coordination complexes such as cisplatin, carboplatin and oxaliplatin; vinblastine; etoposide (VP-16); ifosfamide; mitomycin C; mitoxantrone; vincristine; vinorelbine; navelbine; novantrone; teniposide; daunomycin; aminopterin; xeloda; ibandronate; CPT11; proteasome inhibitors such as bortezomib, carfilzomib and ixazomib; topoisomerase inhibitors such as irinotecan, topotecan, etoposide, mitoxantrone, teniposide; difluoromethylornithine (DMFO); retinoic acid; esperamicins; capecitabine; anthracyclines and pharmaceutically acceptable salts, acids or derivatives of any of the above. In certain embodiments, combination therapy comprises a chemotherapy regimen that includes one or more chemotherapeutic agents. In one embodiment, combination therapy comprises a chemotherapeutic regimen comprising FOLFOX (folinic acid, fluorouracil, and oxaliplatin), FOLFIRI (e.g., folinic acid, fluorouracil, and irinotecan), a taxoid (e.g., docetaxel, paclitaxel, nab-paclitaxel, etc.), and gemcitabine.

In some embodiments, one or more of the additional therapeutic agents is an immune checkpoint inhibitor. As used herein, the term "immune checkpoint inhibitor" refers to an antagonist of an inhibitory or co-inhibitory immune checkpoint. The terms "immune checkpoint inhibitor", "checkpoint inhibitor" and "CPJ" may be used herein interchangeably. Immune checkpoint inhibitors may antagonize an inhibitory or co-inhibitory immune checkpoint by interfering with receptor-ligand binding and/or altering receptor signaling. Examples of immune checkpoints (ligands and receptors), some of which are selectively upregulated in various types of cancer cells, that can be antagonized include PD-1 (programmed cell death protein 1); PD-L1 (PD1 ligand); BTLA (B and T lymphocyte attenuator); CTLA-4 (cytotoxic T-lymphocyte associated antigen 4); TIM-3 (T cell immunoglobulin and mucin domain containing protein 3); LAG-3 (lymphocyte activation gene 3); TIGIT (T cell immunoreceptor with Ig and ITIM domains); CD276 (B7-H3), PD-L2, Galectin 9, CEACAM-1, CD69, Galectin-1, CD113, GPR56, VISTA, 2B4, CD48, GARP, PD1H, LAIR1, TIM-1, and TIM-4, and Killer Inhibitory Receptors, which can be divided into two classes based on their structural features: i) killer cell immunoglobulin-like receptors (KIRs), and ii) C-type lectin receptors (members of the type II transmembrane receptor family). Also contemplated are other less well-defined immune checkpoints that have been described in the literature, including both receptors (e.g., the 2B4 (also known as CD244) receptor) and ligands (e.g., certain B7 family inhibitory ligands such B7-H3 (also known as CD276) and B7-H4 (also known as B7-$S_1$, B7x and VCTN1)). [See Pardoll, (April 2012) Nature Rev. Cancer 12:252-64].

In some embodiments, an immune checkpoint inhibitor is a CTLA-4 antagonist. In further embodiments, the CTLA-4 antagonist can be an antagonistic CTLA-4 antibody. Suitable antagonistic CTLA-4 antibodies include, for example, monospecific antibodies such as ipilimumab or tremelimumab, as well as bispecific antibodies such as MEDI5752 and KN046.

In some embodiments, an immune checkpoint inhibitor is a PD-1 antagonist. In further embodiments, the PD-1 antagonist can be an antagonistic PD-1 antibody, small molecule or peptide. Suitable antagonistic PD-1 antibodies include, for example, monospecific antibodies such as balstilimab, budigalimab, camrelizumab, cosibelimab, dostarlimab, cemiplimab, ezabenlimab (BI-754091), MEDI-0680 (AMP-514; WO2012/145493), nivolumab, pembrolizumab, pidilizumab (CT-011), pimivalimab, retifanlimab, sasanlimab, spartalizumab, sintilmab, tislelizumab, toripalimab, and zimberelimab; as well as bi-specific antibodies such as LY3434172. In still further embodiments, the PD-1 antagonist can be a recombinant protein composed of the extracellular domain of PD-L2 (B7-DC) fused to the Fc portion of IgGl (AMP-224). In certain embodiments, an immune checkpoint inhibitor is zimberelimab.

In some embodiments, an immune checkpoint inhibitor is a PD-L1 antagonist. In further embodiments, the PD-L1 antagonist can be an antagonistic PD-L1 antibody. Suitable antagonistic PD-L1 antibodies include, for example, monospecific antibodies such as avelumab, atezolizumab, durvalumab, BMS-936559, and envafolimab as well as bi-specific antibodies such as LY3434172 and KN046.

In some embodiments, an immune checkpoint inhibitor is a TIGIT antagonist. In further embodiments, the TIGIT antagonist can be an antagonistic TIGIT antibody. Suitable antagonistic anti-TIGIT antibodies include monospecific antibodies such as AGEN1327, AB308 (WO2021247591), BMS 986207, COM902, domvanalimab, EOS-448, etigilimab, IBI-929, JS006, M6223, ociperlimab, SEA-TGT, tiragolumab, vibostolimab; as well as bi-specific antibodies such as AGEN1777 and AZD2936. In certain embodiments, an immune checkpoint inhibitor is an antagonistic anti-TIGIT antibody disclosed in WO2017152088 or WO2021247591. In certain embodiments, an immune checkpoint inhibitor is domvanalimab or AB308.

In some embodiments, an immune checkpoint inhibitor is a LAG-3 antagonist. In further embodiments, the LAG-3 antagonist can be an antagonistic LAG-3 antibody. Suitable antagonistic LAG-3 antibodies include, for example, BMS-986016 (WO10/19570, WO14/08218), or IMP-731 or IMP-321 (WO08/132601, WO09/44273).

In certain embodiments, an immune checkpoint inhibitor is a B7-H3 antagonist. In further embodiments, the B7-H3 antagonist is an antagonistic B7-H3 antibody. Suitable antagonist B7-H3 antibodies include, for example, MGA271 (WO11/109400), omburtumab, enoblituzumab, DS-7300a, ABBV-155, and SHR-A1811.

In some embodiments, one or more of the additional therapeutic agents activates a stimulatory or co-stimulatory immune checkpoint. Examples of stimulatory or co-stimulatory immune checkpoints (ligands and receptors) include B7-1, B7-2, CD28, 4-1BB (CD137), 4-1BBL, ICOS, ICOS-L, OX40, OX40L, GITR, GITRL, CD70, CD27, CD40, DR3 and CD2.

In some embodiments, an agent that activates a stimulatory or co-stimulatory immune checkpoint is a CD137

(4-1BB) agonist. In further embodiments, the CD137 agonist can be an agonistic CD137 antibody. Suitable CD137 antibodies include, for example, urelumab and PF-05082566 (WO12/32433). In some embodiments, an agent that activates a stimulatory or co-stimulatory immune checkpoint is a GITR agonist. In further embodiments, the GITR agonist can be an agonistic GITR antibody. Suitable GITR antibodies include, for example, BMS-986153, BMS-986156, TRX-518 (WO06/105021, WO09/009116) and MK-4166 (WO11/028683). In some embodiments, an agent that activates a stimulatory or co-stimulatory immune checkpoint is an OX40 agonist. In further embodiments, the OX40 agonist can be an agonistic OX40 antibody. Suitable OX40 antibodies include, for example, MEDI-6383, MEDI-6469, MEDI-0562, PF-04518600, GSK3174998, BMS-986178, and MOXR0916. In some embodiments, an agent that activates a stimulatory or co-stimulatory immune checkpoint is a CD40 agonist. In further embodiments, the CD40 agonist can be an agonistic CD40 antibody. In some embodiments, an agent that activates a stimulatory or co-stimulatory immune checkpoint is a CD27 agonist. In further embodiments, the CD27 agonist can be an agonistic CD27 antibody. Suitable CD27 antibodies include, for example, varlilumab.

In some embodiments, one or more of the additional therapeutic agents is an ATP-adenosine axis-targeting agent. In certain embodiments, an ATP-adenosine axis-targeting agent is an inhibitor of an ectonucleotidase involved in the conversion of ATP to adenosine or an antagonist of adenosine receptor, e.g., ectonucleoside triphosphate diphosphohydrolase 1 (ENTPD1, also known as CD39 or Cluster of Differentiation 39) and the ecto-5'-nucleotidase (NT5E or 5NT, also known as CD73 or Cluster of Differentiation 73). Exemplary small molecule CD73 inhibitors include CB-708, ORIC-533, LY3475070 and AB680. Exemplary anti-CD39 and anti-CD73 antibodies include ES002023, TTX-030, IPH-5201, SRF-617, CPI-006, oleclumab (MEDI9447), NZV930, IPH5301, GS-1423, uliledlimab (TJD5, TJ004309), BMS-986179, and AB598. In one embodiment, the present disclosure contemplates combination of the compounds described herein with a CD73 inhibitor such as those described in WO 2017/120508, WO 2018/067424, WO 2018/094148, and WO 2020/046813. In further embodiments, the CD73 inhibitor is quemliclustat (AB680). Adenosine can bind to and activate four different G-protein coupled receptors: AiR, A2AR, A2BR, and A3R. A2R antagonists include etrumadenant, inupadenant, taminadenant, caffeine citrate, NUV-1182, TT-702, DZD-2269, INCB-106385, EVOEXS-21546, AZD-4635, imaradenant, RVU-330, ciforadenant, PBF-509, PBF-999, PBF-1129, and CS-3005. In some embodiments, the present disclosure contemplates the combination of the compounds described herein with an A2AR antagonist, an A2BR antagonist, or an antagonist of A2AR and A2BR. In some embodiments, the present disclosure contemplates the combination of the compounds described herein with the adenosine receptor antagonists described in WO 2018/136700, WO 2018/204661, WO 2018/213377, or WO 2020/023846. In one embodiment, the adenosine receptor antagonist is etrumadenant.

In some embodiments, one or more of the additional therapeutic agents is an inhibitor of a hypoxia-inducible factor (HIF) transcription factor, particularly HIF-2a. Exemplary HIF-2a inhibitors include belzutifan, ARO-HIF2, PT-2385, and those described in WO 2021113436, WO 2021188769, and WO 2023077046. In some embodiments, the HIF-2a inhibitor is AB521).

In some embodiments, one or more of the additional therapeutic agents is an inhibitor of anexelekto (AXL). The AXL signaling pathway is associated with tumor growth and metastasis, and is believed to mediate resistance to a variety of cancer therapies. There are a variety of AXL inhibitors under development that also inhibit other kinases in the TAM family (i.e., TYRO3, MERTK), as well as other receptor tyrosine kinases including MET, FLT3, RON and AURORA, among others. Exemplary multikinase inhibitors include sitravatinib, rebastinib, glesatinib, gilteritinib, merestinib, cabozantinib, foretinib, BMS777607, LY2801653, S49076, and RXDX-106. AXL specific inhibitors have also been developed, e.g., small molecule inhibitors including DS-1205, SGI-7079, SLC-391, TP-0903 (i.e., dubermatinib), BGB324 (i.e., bemcentinib), DP3975, and AB801; anti-AXL antibodies such as ADCT-601; and antibody drug conjugates (ADCs) such as BA3011. Another strategy to inhibit AXL signaling involves targeting AXL's ligand, GAS6. For example, batiraxcept (AVB-500) is under development as is a Fc fusion protein that binds the GAS6 ligand thereby inhibiting AXL signaling. In some embodiments, the additional therapeutic agent is an AXL inhibitor described in WO 2022246177, WO 2022246179, or WO 2024006726. In some embodiments, the AXL inhibitor is AB801.

In some embodiments, the additional therapeutic agent comprises chemotherapy, radiation therapy, or both.

In one or more embodiments, the additional therapeutic agent comprises domvanalimab, etrumadenant, quemliclustat, zimberelimab, AB308, AB521, AB598, or AB801, or any combinations thereof.

In one or more embodiments, the additional therapeutic agent comprises one or more of an immune checkpoint inhibitor, an A2R antagonist, a CD73 inhibitor, a HIF-2a inhibitor, a chemotherapeutic agent, radiation therapy, or any combinations thereof. In further embodiments of the above; (a) the immune checkpoint inhibitor comprises one or more inhibitors that block the activity of at least one of PD-1, PD-L1, BTLA, LAG-3, a B7 family member, TIM-3, TIGIT or CTLA-4, (b) the immune checkpoint inhibitor comprises an inhibitor of PD-1 or PD-L1; (c) the immune checkpoint inhibitor is selected from the group consisting of avelumab, atezolizumab, durvalumab, dostarlimab, cemiplimab, nivolumab, pembrolizumab, sintilmab, toripalimab, and zimberelimab; (d) the immune checkpoint inhibitor is zimberelimab; (e) the immune checkpoint inhibitor comprises an inhibitor that blocks the activity of TIGIT; (f) the immune checkpoint inhibitor is domvanalimab or AB308; (g) the A2R antagonist is selected from the group consisting of etrumadenant, inupadenant, taminadenant, caffeine citrate, NUV-1182, TT-702, DZD-2269, INCB-106385, EVOEXS-21546, AZD-4635, imaradenant, RVU-330, ciforadenant, PBF-509, PBF-999, PBF-1129, and CS-3005; (h) the A2R antagonist is etrumadenant; (i) the CD73 inhibitor is selected from the group consisting of CB-708, ORIC-533, LY3475070 and quemliclustat; (j) the CD73 inhibitor is quemliclustat; (k) the HIF-2a inhibitor is selected from the group consisting of belzutifan, ARO-HIF2, PT-2385, and AB521, (l) the inhibitor of HIF-2a is AB521; (m) the at least one additional therapeutic agent comprises a chemotherapeutic agent; (n) the chemotherapeutic agent comprises a platinum-based, taxoid-based, or anthracycline-based chemotherapeutic agent; (o) the chemotherapeutic agent is selected from the group consisting of cisplatin, carboplatin, oxaliplatin, doxorubicin, docetaxel, and paclitaxel; and (p) the at least one additional therapeutic agent comprises radiation therapy.

Selection of the additional therapeutic agent(s) may be informed by current standard of care for a particular cancer and/or mutational status of a subject's cancer and/or stage of disease. Detailed standard of care guidelines are published, for example, by National Comprehensive Cancer Network (NCCN). See, for instance, NCCN Melanoma: Cutaneous v3.2024, NCCN Melanoma: Uveal v1.2024, NCCN Prostate Cancer v4.2024, NCCN Squamous Cell Skin Cancer v1.2024, NCCN Hodgkin Lymphoma v3.2024, NCCN Acute Lymphoblastic Leukemia v2.2024, NCCN Chronic Lymphocytic Leukemia/Small Lymphocytic Lymphoma v1.2025, NCCN Chronic Myeloid Leukemia v1.2025, NCCN Hairy Cell Leukemia v1.2025, NCCN Pediatric Acute Lymphoblastic Leukemia v1.2025, NCNN Small Bowel Adenocarcinoma v5.2024, NCCN Thyroid Carcinoma v4.2024, NCCN Non-Small Cell Lung Cancer v11.2024, NCCN Small Cell Lung Cancer v2.2025, NCCN Breast Cancer v5.2024, NCCN Colon Cancer v5.2024, NCCN Hepatobiliary Cancer v3.2024, NCCN Kidney Cancer, v2.2025, NCCN Pancreatic Adenocarcinoma v3.2024, NCCN Esophageal and Esophagogastric Junction Cancers v4.2024, NCCN Gastric Cancer v4.2024, NCCN Gastrointestinal Stromal Tumors (GIST) v2.2024, NCCN Cervical Cancer v4.2024, NCCN Ovarian Cancer/Fallopian Tube Cancer/Primary Peritoneal Cancer v3.2024, NCCN Testicular Cancer v1.2024, NCCN Kidney Cancer v2.2025, NCCN Head and Neck Cancers v4.2024, NCCN Malignant Peritoneal Mesothelioma v3.2024, NCCN Malignant Pleural Mesothelioma v2.2024, NCCN Soft Tissue Sarcoma v3.2024, and NCCN Bone Cancer v1.2025.

Methods of Synthesis

General Methods for the Preparation of Compounds of the Disclosure

The exemplary molecules described herein and represented in the claims can be synthesized by the methods outlined in the following experimental section, and by various methods that are known to those skilled in the art. The exemplary molecules were synthesized from starting materials that are commercially available or readily prepared by standard synthetic methods. Equation 1 illustrates a retrosynthetic disconnection of the compounds of the disclosure into fragments a, b and c, which are useful for the construction of the compounds according to this disclosure. In general, compounds represented in the claims can be constructed, for example, using methods that consist of three parts, which may be done in any order: modification of the functional groups present in fragments a, b or c; connection of the a and b fragments; and connection of fragments b and c.

Eq. 1

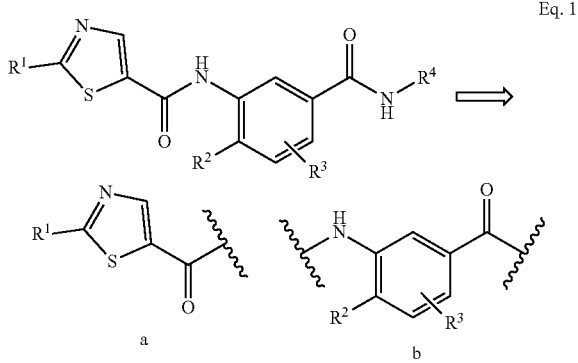

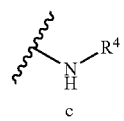

There are several exemplary methods for the preparation of claimed compounds. Equation 2 demonstrates one method of forming the bond between fragments a and b. In the case of Eq. 2, a readily available carboxylic acid derived from fragment a is converted to an activated intermediate, such as an acid chloride or an activated ester, using suitable amide coupling reagent(s). One skilled in the art will recognize that the conversion of carboxylic acids to acid chlorides can be accomplished using a wide range of conditions and reagents, such as oxalyl chloride or thionyl chloride. Alternatively, carboxylic acids are readily converted to activated esters through the use of amide coupling reagents, such as HATU, CDI, EDC, HOBt, POCl$_3$ T3P or various other reagents. The activated ester or acid chloride derived from fragment a can be coupled with a wide variety of amines, including but not limited to anilines (fragment b). The transformation may be assisted or accelerated by heating and/or addition of a base.

Eq. 2

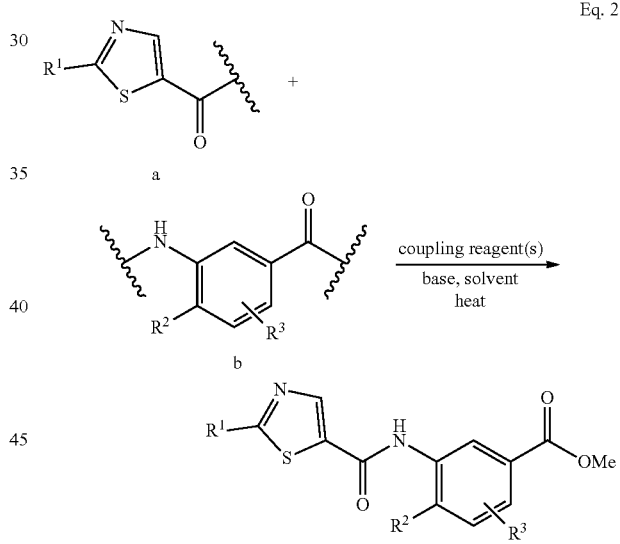

Equation 3 demonstrates one method of forming the bond between previous fragments, such as between fragments b and c. In the case of Eq. 3 where R=H, a readily available carboxylic acid derived is converted to an activated intermediate, such as an acid chloride or an activated ester, using suitable amide coupling reagent(s). One skilled in the art will recognize that the conversion of carboxylic acids to acid chlorides can be accomplished using a wide range of conditions and reagents, such as oxalyl chloride or thionyl chloride. Alternatively, carboxylic acids are readily converted to activated esters through the use of amide coupling reagents, such as HATU, CDI, EDC, HOBt, POCl$_3$ T3P or various other reagents. The activated ester or acid chloride can be coupled with a wide variety of amines, including but not limited to anilines (fragment c). In the case of Eq. 3 where R=Me, the conversion of readily available esters can be accomplished using reagents such as DABAL-Me$_3$ or various other equivalent reagents. The transformation may be assisted or accelerated by heating and/or addition of a base.

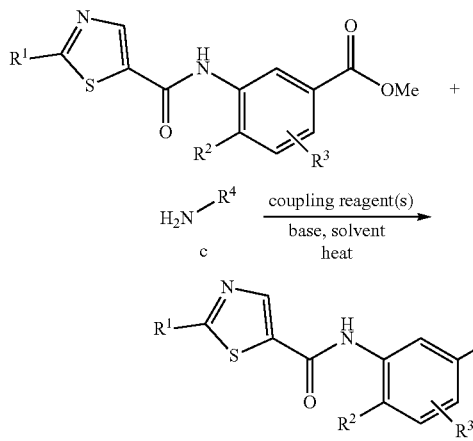

Eq. 3

Equations 4-6 demonstrate useful methods of synthesizing an appropriately substituted aminopyridine suitable for connecting fragments b and c. In the case of Eq. 4, X may be chosen from an appropriate halogen atom, such as Cl, Br and I. The first step is a coupling using benzophenone imine and is mediated by a transition metal catalyst, such as palladium with an appropriate ligand, and may be facilitated by the use of an organic or inorganic base and heating. The second step is the hydrolysis of the imine to afford the corresponding aminopyridine. In the case of Eq. 5, X may be chosen from an appropriate halogen atom, such as Cl, Br and I. The first step is a coupling using tert-butyl carbamate and is mediated by a transition metal catalyst, such as palladium with an appropriate ligand, and may be facilitated by the use of an organic or inorganic base and heating. The second step is the hydrolysis of the carbamate to afford the corresponding aminopyridine. In the case of Eq. 6, X may be chosen from an appropriate halogen atom, such as F, Cl, and Br. The first step is a nucleophilic aromatic substitution of an appropriate nitro-pyridine using various alcohols and amine in the presence of base and under heat. The next step is a reduction of the nitro group to the corresponding amine. One skilled in the art will recognize that there is a wide range of methods available to effect these transformations (e.g., Jang et al. *J. Org. Chem.* 2022, 87, 2, 910-919).

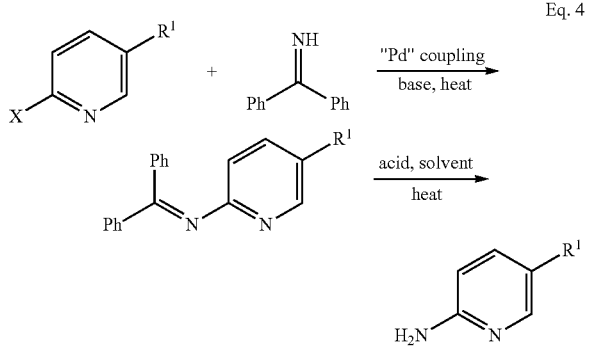

Eq. 4

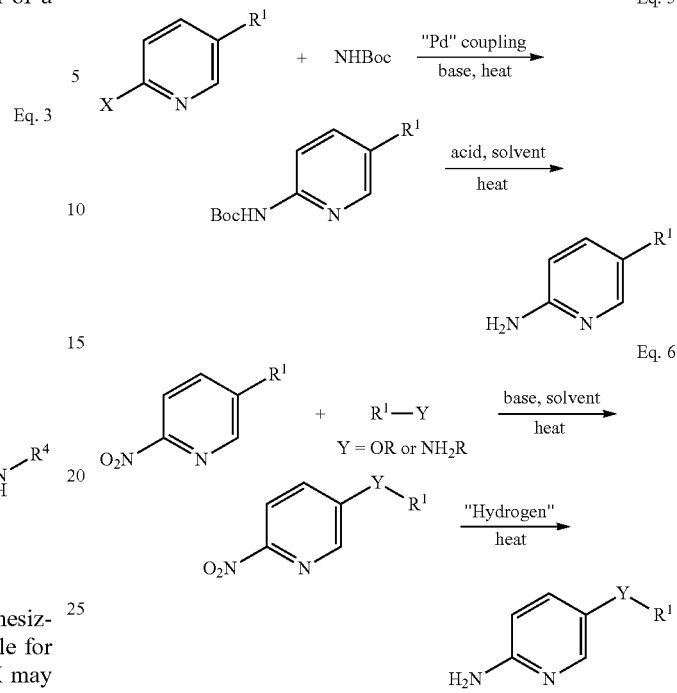

There are other possible combinations and synthetic sequences that will also give rise to the targeted products. Formation of the bond between fragments a and b may occur before or after connection of the b and c fragments, and each of these fragments may be further modified before or after connection of fragments a, b and c. A variety of the methods described above have been used to prepare compounds of the disclosure, some of which are exemplified in the examples.

EXPERIMENTAL

The following examples are put forth so as to provide those of ordinary skill in the art with a complete disclosure and description of how to make and use the present disclosure, and are not intended to limit the scope of what the inventors regard as their invention. Additional compounds within the scope of this disclosure may be made using methods based on those illustrated in these examples, or based on other methods known in the art. Efforts have been made to ensure accuracy with respect to numbers used (e.g., amounts, temperature, etc.), but some experimental errors and deviations should be accounted for.

All reactions were performed using a Teflon-coated magnetic stir bar at the indicated temperature and were conducted under an inert atmosphere when stated. Purchased starting materials and reagents were generally used as received. Reactions were monitored by TLC (silica gel 60 with fluorescence F254, visualized with a short wave/long wave UV lamp) and/or LCMS (Agilent® 1100 or 1200 series LCMS with UV detection at 254 or 280 nm using a binary solvent system [0.1% formic acid in MeCN/0.1% formic acid in $H_2O$] using one of the following columns: Agilent® Eclipse Plus C18 [3.5 µm, 4.6 mm i.d.×100 mm], Waters™ XSelect HSS C18 [3.5 µm, 2.1 mm i.d.×75 mm]). Flash chromatography was conducted on silica gel using an automated system (CombiFlash® RF+manufactured by Teledyne ISCO), with detection wavelengths of 254 and 280 nm, and optionally equipped with an evaporative light scattering detector. Reverse phase preparative HPLC was conducted on an Agilent® 1260 or 1290 Infinity series HPLC. Samples were eluted using a binary solvent system (MeCN/H$_2$O with an acid modifier as needed—for example 0.1% TFA or 0.1% formic acid) with gradient elution on a Gemini C18 110 Å column (21.2 mm i.d. xx 250 mm) with variable wavelength detection. Final compounds obtained through preparative HPLC were concentrated through lyophilization. All assayed compounds were purified to ≥95% purity as determined by $^1$H NMR or LCMS (Agilent® 1100 or 1200 series LCMS with UV detection at 254 or 280 nm using a binary solvent system [0.1% formic acid in MeCN/0.1% formic acid in H$_2$O] using one of the following columns: Agilent® Eclipse Plus C18 [3.5 μm, 4.6 mm i.d.×100 mm], Waters™ XSelectHSS C18 [3.5 μm, 2.1 mm i.d.×75 mm]). $^1$H NMR spectra were recorded on a Varian 400 MHz NMR spectrometer equipped with an Oxford AS400 magnet or a Bruker® AVANCE NEO 400 MHz NMR. Chemical shifts (δ) are reported as parts per million (ppm) relative to residual undeuterated solvent as an internal reference. The abbreviations s, br s, d, t, q, dd, dt, ddd, dddd, and m stand for singlet, broad singlet, doublet, triplet, quartet, doublet of doublets, doublet of triplets, doublet of doublet of doublets, doublet of doublet of doublet of doublet, and multiplet, respectively.

Unless indicated otherwise, parts are parts by weight, molecular weight is average molecular weight, temperature is in degrees Celsius (° C.), and pressure is at or near atmospheric. Standard abbreviations are used, including the following: ATP=adenosine triphosphate; BSA=bovine serum albumin; DCM and CH$_2$Cl$_2$=dichloromethane; DCE=dichloroethane; CH$_2$I$_2$=diiodomethane; DIPEA and i-Pr$_2$NEt=N,N-diisopropylethylamine; DMF=N,N-dimethylformamide; DMSO=dimethyl sulfoxide; DMSO-d$_6$=perdeuterated dimethyl sulfoxide; DMAP=4-dimethylaminopyridine; HPLC=high performance liquid chromatography; rt and RT=room temperature; h or hr=hour(s); min=minute(s); ng=nanogram; μg=microgram; mg=milligram; g=gram; μl or μL=microliter; ml or mL=milliliter; l or L=liter; μM=micromolar; mM=millimolar; M=molar; aq.=aqueous; calcd=calculated; PBS=phosphate-buffered saline; DPBS=Dulbecco's phosphate-buffered saline; SiO$_2$=silica gel; EtOAc=ethyl acetate; equiv.=equivalents; MeOH=methanol; THF=tetrahydrofuran; N$_2$=nitrogen gas; (−)-DIPCl=(−)—B-chlorodiisopinocampheylborane; MeI=iodomethane; TEA=triethylamine; T3P=propylphosphonic anhydride; (CH$_3$)$_2$S·BH$_3$=borane dimethyl sulfide complex; DIAD=diisopropyl azodicarboxylate; DIBAL-H=diisobutylaluminium hydride; Boc2O=di-tert-butyl decarbonate; HATU=N-[(dimethylamino)-1H-1,2,3-triazolo-[4,5-b]pyridin-1-ylmethylene]-N-methylmethanaminium hexafluorophosphate N-oxide; DABAL-Me$_3$=bis(trimethylaluminum)-1,4-diazabicyclo[2.2.2]octane adduct; rac-BINAP=(±)-2,2'-bis(diphenylphosphino)-1,1'-binaphthalene; Methanol-d$_4$=perdeuterated methanol; LAH and LiAlH$_4$=lithium aluminum hydride; TFA=trifluoroacetic acid; TFAA=trifluoroacetic acid anhydride; Et$_3$SiH=triethylsilane; Cs$_2$CO$_3$=cesium carbonate; LiOH·H$_2$O=lithium hydroxide monohydrate; Na(OAc)$_3$BH=sodium triacetoxyborohydride; NaH=sodium hydride; NaOAc=sodium acetate; NaHCO$_3$=sodium bicarbonate; Na$_2$SO$_4$=sodium sulfate; NH$_2$OH HCl=hydroxylamine hydrochloride; TMSCF$_3$=trifluoromethyltrimethylsilane; TBAI=tetrabutylammonium iodide; TBAF=tetra-n-butylammonium fluoride; POCl$_3$=phosphoryl chloride; CDI=1,1'-carbonyldiimidazole; PtO$_2$=platinum dioxide; Pd(dppf)Cl$_2$-[1,1'-bis(diphenylphosphino)ferrocene]dichloropalladium(II); Pd$_2$(dba)$_3$=tris(dibenzylideneacetone)dipalladium(0); PPh3=triphenylphosphine; XPhos=2-dicyclohexylphosphino-2',4',6'-triisopropylbiphenyl; Xantphos=4,5-bis(diphenylphosphino)-9,9-dimethylxanthene, MHz=megahertz; Hz=hertz; ppm=parts per million; HTRF=homogeneous time resolved fluorescence; ESI MS=electrospray ionization mass spectrometry; NMR=nuclear magnetic resonance; TLC=thin layer chromatography; LC/MS=liquid chromatography-mass spectrometry.

Example 1: N-[4-Fluoro-2-methyl-5-[[5-(2,2,2-trifluoroethyl)pyridin-2-yl]carbamoyl]phenyl]-2-methyl-1,3-thiazole-5-carboxamide

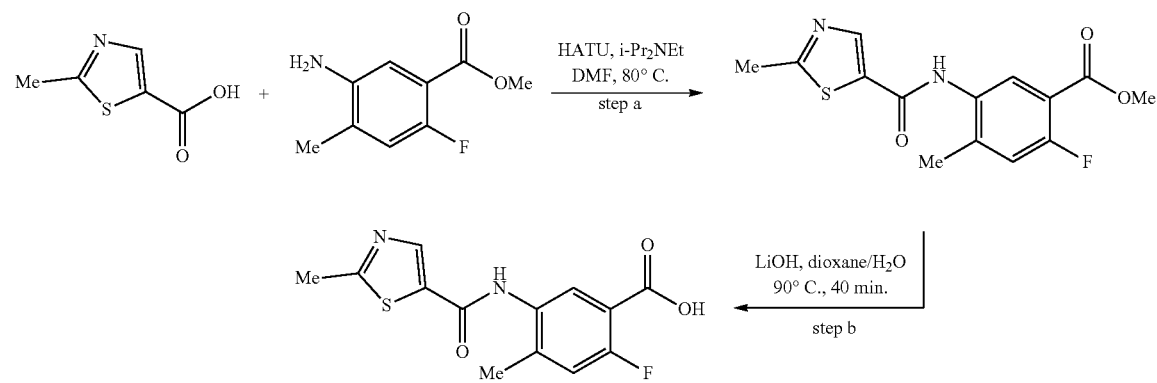

-continued

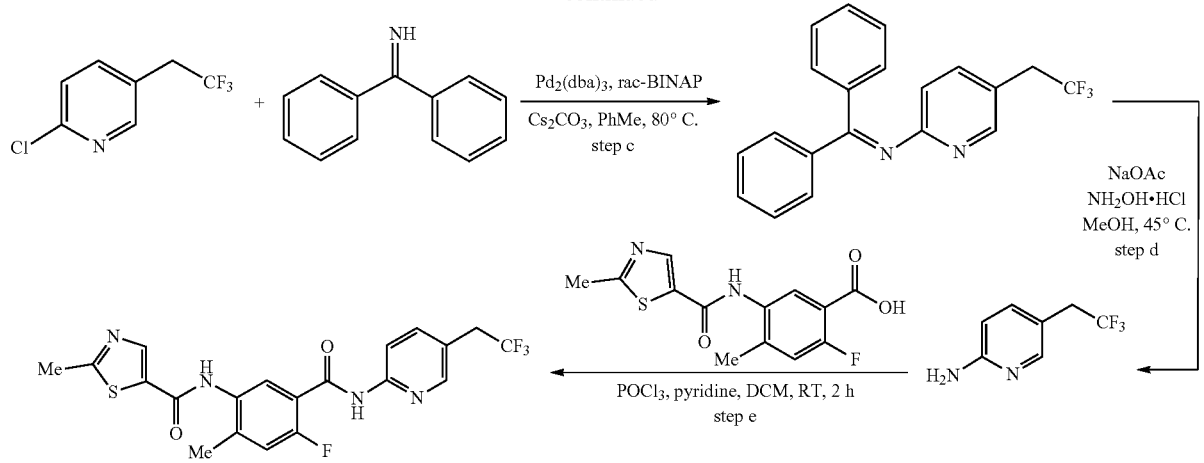

Step a: A round-bottom flask was charged with 2-methyl-1,3-thiazole-5-carboxylic acid (10 g, 69.8 mmol, 1.0 equiv.), methyl 5-amino-2-fluoro-4-methylbenzoate (12.79 g, 69.8 mmol, 1.0 equiv), and HATU (39.82 g, 104.7 mmol, 1.5 equiv). DMF (174 mL, 0.4 M) was added, followed by i-Pr$_2$NEt (36.6 mL, 209.5 mmol, 3.0 equiv). The reaction mixture was stirred at 80° C. for 2 h, at which time LC/MS analysis showed complete consumption of starting material. The reaction mixture was cooled to RT and poured onto ice water (450 mL) with stirring. Stirring was continued for 10 minutes and then the precipitated solid was collected by vacuum filtration, rinsed with water, and dried in vacuo to afford methyl 2-fluoro-4-methyl-5-[(2-methyl-1,3-thiazole-5-carbonyl)amino]benzoate.

Step b: A round-bottom flask was charged with the product of step a (12.94 g, 42.0 mmol, 1.0 equiv), dioxane (140 mL, 0.3 M), and 1 M aqueous LiOH (127 mL, 210 mmol, 5.0 equiv.). The reaction mixture was stirred at 90° C. for 40 minutes, at which time LC/MS analysis indicated complete consumption of starting material. The reaction mixture was cooled to RT and poured onto an ice-cooled solution of 1 M aq. HCl (160 mL) with stirring. The precipitate thus obtained was collected by vacuum filtration, rinsed with water, and dried in vacuo to afford 2-fluoro-4-methyl-5-[(2-methyl-1,3-thiazole-5-carbonyl)amino]benzoic acid.

Step c: A vial was charged with 2-chloro-5-(2,2,2-trifluoroethyl) pyridine (1.0 g, 5.11 mmol, 1.0 equiv.), benzophenone imine (0.95 mL, 5.67 mmol, 1.1 equiv.), rac-BINAP (477 mg, 0.767 mmol, 0.15 equiv.), and Pd$_2$(dba)$_3$ (234 mg, 0.256 mmol, 0.05 equiv.). Toluene (25.6 mL) was then added and the solution was degassed before the addition of Cs$_2$CO$_3$ (2.3 g, 7.15 mmol, 1.4 equiv.). The mixture was stirred at 80° C. under N$_2$ for 16 h. Upon complete conversion, as judged by LC/MS analysis, the reaction mixture was cooled to RT and filtered through a pad of Celite®. The Celite® cake was thoroughly washed with EtOAc. The resulting filtrate was concentrated in vacuo and purified by column chromatography (EtOAc/hexanes, 0% to 10% to 30%) to afford 1,1-diphenyl-N-[5-(2,2,2-trifluoroethyl)pyridin-2-yl]methanimine.

Step d: The product from step c (1.08 g, 3.17 mmol, 1 equiv.) was dissolved in MeOH (33 mL) followed by the addition of NaOAc (651 mg, 7.94 mmol, 2.5 equiv.) and NH$_2$OH HCl (441 mg, 6.34 mmol, 2.0 equiv.). The reaction mixture was heated to 45° C. for 3 h. Upon complete conversion of starting material, the reaction was concentrated in vacuo and the resulting material was purified by column chromatography (MeOH/DCM, 0% to 10%) to afford 5-(2,2,2-trifluoroethyl)pyridin-2-amine.

Step e: A vial was charged with 2-fluoro-4-methyl-5-[(2-methyl-1,3-thiazole-5-carbonyl)amino]benzoic acid (75 mg, 0.25 mmol, 1.0 equiv.), 5-(2,2,2-trifluoroethyl) pyridin-2-amine (44 mg, 0.25 mmol, 1.0 equiv.) and DCM (1.3 mL) under N$_2$ gas. Pyridine (0.2 mL, 2.5 mmol, 10 equiv.) was added and the reaction mixture was allowed to stir at RT. After 5 min., POCl$_3$ (0.47 mL, 0.5 mmol, 2 equiv.) was added dropwise. After LC/MS analysis indicated complete conversion, the reaction was quenched with water and the reaction mixture was concentrated in vacuo. The resulting material was purified by HPLC to provide the title compound. $^1$H NMR (400 MHz, DMSO-d$_6$) δ 10.78 (s, 1H), 10.15 (s, 1H), 8.38 (d, J=22.4 Hz, 2H), 8.20 (d, J=8.6 Hz, 1H), 7.86 (d, J=8.7 Hz, 1H), 7.64 (d, J=6.8 Hz, 1H), 7.31 (d, J=11.0 Hz, 1H), 3.71 (q, J=11.4 Hz, 2H), 2.71 (s, 3H), 2.29 (s, 3H). ESI MS [M+H]$^+$ for C$_{20}$H$_{17}$F$_4$N$_4$O$_2$S$_1$, calcd 453.1, found 453.1.

Example 2: N-[5-[(5-Cyclopropyloxypyridin-2-yl)carbamoyl]-4-fluoro-2-methylphenyl]-2-methyl-1,3-thiazole-5-carboxamide

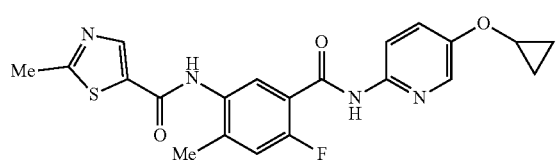 [SMILES: Cc1ncc(C(=O)Nc2cc(C(=O)Nc3ccc(OC4CC4)cn3)c(F)cc2C)s1]

The title compound was prepared from 5-cyclopropyloxy-pyridin-2-amine and 2-fluoro-4-methyl-5-[(2-methyl-1,3-thiazole-5-carbonyl)amino]benzoic acid in a similar fashion to Ex. 1. $^1$H NMR (400 MHz, DMSO-d$_6$) δ 10.55 (s, 1H), 10.14 (s, 1H), 8.40 (s, 1H), 8.15 (s, 1H), 8.11 (d, J=9.0 Hz, 1H), 7.63 (d, J=6.8 Hz, 1H), 7.59 (d, J=9.2 Hz, 1H), 7.30 (d, J=11.1 Hz, 1H), 4.02-3.88 (m, 1H), 2.71 (s, 3H), 2.28 (s, 3H), 0.85-0.77 (m, 2H), 0.72-0.65 (m, 2H). ESI MS [M+H]$^+$ for C$_{21}$H$_{20}$FN$_4$O$_3$S, calcd 427.1, found 427.1.

Example 3: N-[5-[(5-Cyclopropylpyridin-2-yl)carbamoyl]-4-fluoro-2-methylphenyl]-2-methyl-1,3-thiazole-5-carboxamide

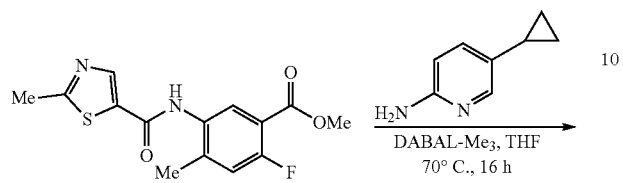

compound. $^1$H NMR (400 MHz, DMSO-$d_6$) δ 10.56 (s, 1H), 10.15 (s, 1H), 8.41 (s, 1H), 8.19 (d, J=2.4 Hz, 1H), 8.05 (d, J=8.6 Hz, 1H), 7.63 (d, J=6.9 Hz, 1H), 7.48 (dd, J=8.6, 2.5 Hz, 1H), 7.29 (d, J=11.1 Hz, 1H), 2.70 (s, 3H), 2.28 (s, 3H), 1.94 (ddd, J=13.5, 8.6, 5.1 Hz, 1H), 1.16-0.89 (m, 2H), 0.80-0.60 (m, 2H). $^{19}$F NMR (376 MHz, DMSO-$d_6$) δ −116.72. ESI MS [M+H]$^+$ for $C_{21}H_{20}FN_4O_2S$, calcd 411.1, found 411.0.

Example 4: N-[5-[[5-(2,2-Difluoropropoxy)pyrazin-2-yl]carbamoyl]-4-fluoro-2-methylphenyl]-2-methyl-1,3-thiazole-5-carboxamide

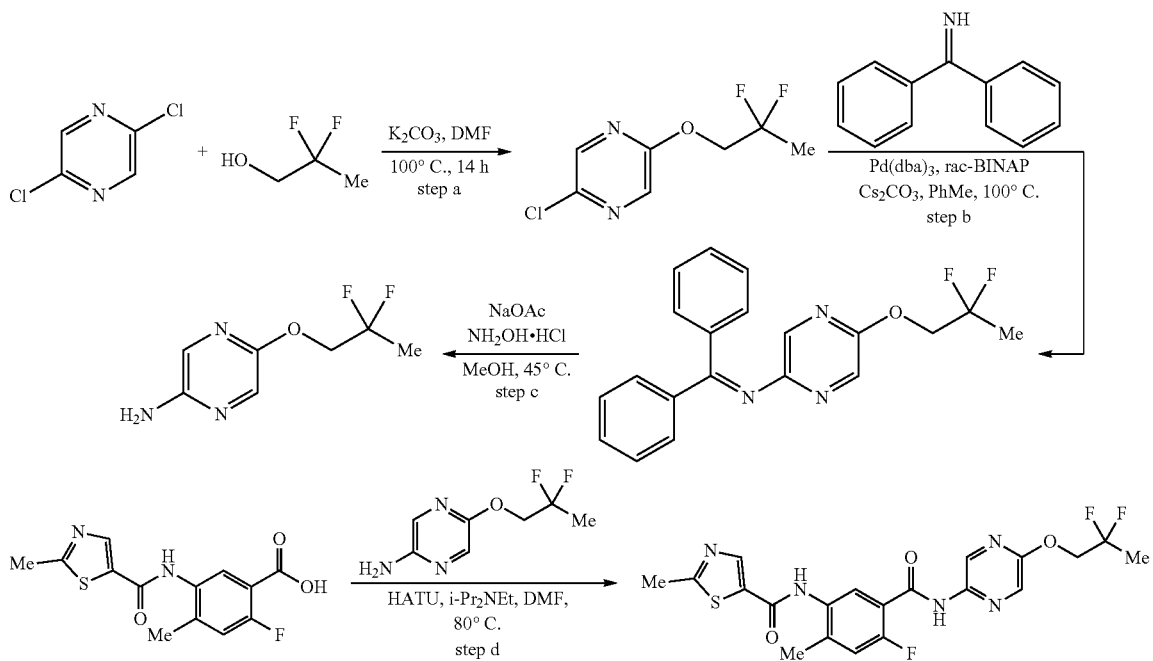

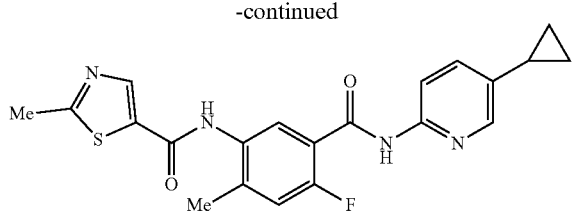

A vial was charged with methyl 2-fluoro-4-methyl-5-(2-methylthiazole-5-carboxamido)benzoate (100 mg, 0.32 mmol, 1.0 equiv., prepared as described in Example 1), 5-cyclopropoxypyridin-2-amine (86 mg, 0.64 mmol, 2.0 equiv.) and THF (4 mL). The solution was degassed with N$_2$ and DABAL-Me$_3$ (180 mg, 0.704 mmol, 2.2 equiv.) was added portion-wise, during which time bubbling was observed. The reaction mixture was allowed to stir overnight at 70° C. After LC/MS analysis indicated complete conversion, the reaction was quenched with aq. 1 M HCl solution and extracted thrice with EtOAc. The combined organic extracts were dried over Na$_2$SO$_4$ and concentrated in vacuo. The crude product was purified by HPLC to provide the title Step a: To a solution of 2,2-difluoroethanol (7.68 g, 80 mmol) and 2,5-dichloropyrazine (5.96 g, 40 mmol) in dioxane (40 mL) at RT was added K$_2$CO$_3$ (11.04 g, 80 mmol) and the resulting reaction mixture was stirred at 100° C. for 14 h. The reaction mixture was allowed to cool to RT and was then filtered and concentrated under reduced pressure to afford the crude product, which was used directly for the next reaction without further purification.

Step b and Step c were performed in an analogous manner to Example 1, steps c and d.

Step d: A vial was charged with the product from step c (0.050 g, 0.26 mmol, 1 equiv.), 2-fluoro-4-methyl-5-[(2-methyl-1,3-thiazole-5-carbonyl)amino]benzoic acid (0.078 g, 0.26 mmol, 1.0 equiv.), HATU (0.2 g, 0.52 mmol, 2 equiv.) and DMF (2 mL). i-Pr$_2$NEt (0.226 mL, 0.1.3 mmol, 5.0 equiv.) was then added dropwise and the reaction mixture was stirred at 80° C. Upon complete conversion, the reaction mixture was cooled to RT, diluted with H$_2$O and extracted three times with EtOAc. The combined organic extracts were dried over Na$_2$SO$_4$, filtered, and concentrated in vacuo to afford the crude product, which was purified by column chromatography (EtOAc/hexanes, 0% to 80%) to provide the title compound. $^1$H NMR (400 MHz, DMSO-$d_6$) δ 10.93 (s, 1H), 10.15 (s, 1H), 8.95 (d, J=1.4 Hz, 1H), 8.41 (s, 1H), 8.28 (d, J=1.4 Hz, 1H), 7.66 (d, J=6.8 Hz, 1H), 7.32 (d, J=11.0 Hz, 1H), 4.62 (t, J=13.1 Hz, 2H), 2.71 (s, 3H), 2.29 (s, 3H), 1.75 (t, J=19.3 Hz, 3H). ESI MS [M+H]$^+$ for $C_{20}H_{19}F_3N_5O_3S_1$, calcd 466.1, found 466.1.

Example 5: N-[5-[[5-(Cyclopropylmethyl)pyridin-2-yl]carbamoyl]-4-fluoro-2-methylphenyl]-2-methyl-1,3-thiazole-5-carboxamide Step c: A vial was charged with the product from step b (0.189 g, 0.89 mmol, 1 equiv.), tert-butyl carbamate (0.125 g, 1.07 mmol, 1.2 equiv.), Xantphos (0.103 g, 0.18 mmol, 0.2 equiv.), $Cs_2CO_3$ (0.868 g, 2.67 mmol, 3 equiv.) and dioxane (20 mL). The mixture was degassed by evacuation and back-filling with nitrogen three times. $Pd_2(dba)_3$ (0.081 g, 0.09 mmol, 10 mol %) was then added. The reaction mixture was stirred at 80° C. and monitored by LC/MS. Upon completion, the reaction mixture was cooled to RT, filtered through a pad of Celite® and the resulting filtrate was concentrated in vacuo. The crude product was purified

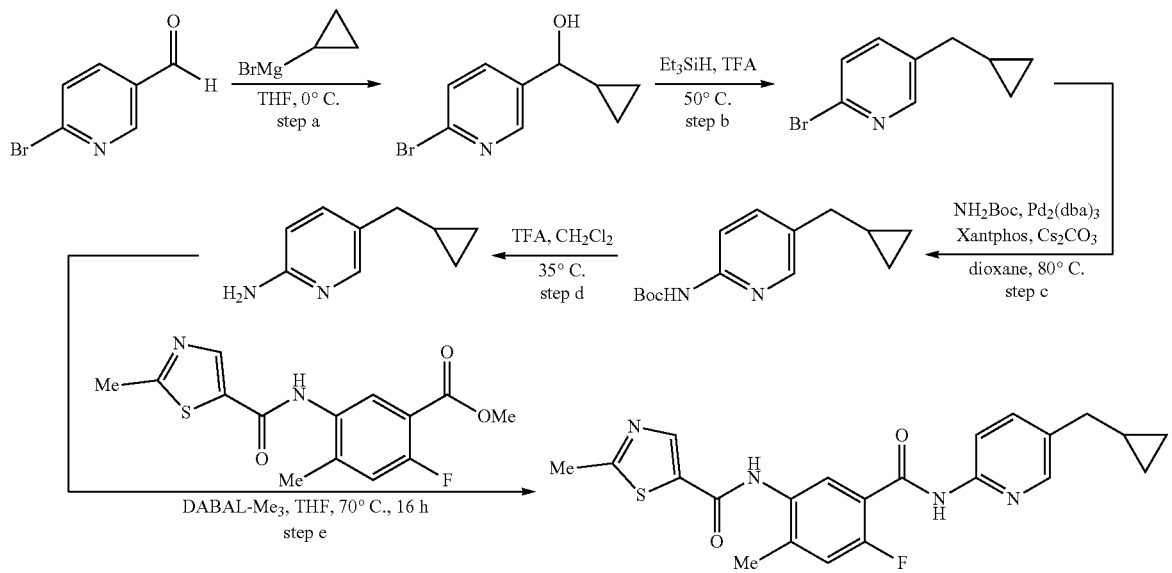

Step a: A vial was charged with 6-bromonicotinaldehyde (0.5 g, 2.69 mmol, 1 equiv.) and THF (10 mL) and the solution was cooled to 0° C. under a nitrogen atmosphere. A solution of cyclopropylmagnesium bromide in THF (1M, 8.07 mL, 8.07 mmol, 3 equiv.) was added dropwise while stirring at 0° C. The reaction was monitored by LC/MS. Upon completion, the reaction was quenched with saturated aq. ammonium chloride solution and the aqueous layer was extracted three times with EtOAc. The combined organic extracts were dried over $Na_2SO_4$, filtered, and concentrated in vacuo. The crude product was purified by column chromatography (EtOAc/hexanes, 10% to 60%) to provide (6-bromopyridin-3-yl)(cyclopropyl)methanol.

Step b: A vial was charged with the product from step a (0.328 g, 1.44 mmol, 1 equiv.) and $Et_3SiH$ (2 mL, 12.55 mmol, 8.7 equiv.), and TFA (2 mL) was added dropwise. The resulting mixture was stirred at 50° C. and the reaction was monitored by LC/MS. Upon completion, the reaction mixture was diluted with $H_2O$ and extracted three times with EtOAc. The combined organic extracts were dried over $Na_2SO_4$, filtered, and concentrated in vacuo. The crude product was purified by column chromatography (EtOAc/hexanes, 0% to 50%) to provide 2-bromo-5-(cyclopropylmethyl)pyridine.

by column chromatography (EtOAc/hexanes, 0% to 50%) to yield tert-butyl N-[5-(cyclopropylmethyl) pyridin-2-yl]carbamate.

Step d: The product from step c (0.101 g, 0.41 mmol) was dissolved in $CH_2Cl_2$ (2.0 mL) and was treated with TFA (1.0 mL). The reaction mixture was stirred at 35° C. and monitored by LC/MS. Upon completion, the reaction mixture was concentrated in vacuo. The residue was dissolved in saturated aq. $NaHCO_3$ solution and extracted three times with EtOAc. The combined organic extracts were dried over $Na_2SO_4$, filtered, and concentrated in vacuo. The crude product was used directly in the next step without further purification.

Step e: The title compound was prepared from 5-(cyclopropylmethyl)pyridin-2-amine and methyl 2-fluoro-4-methyl-5-[(2-methyl-1,3-thiazole-5-carbonyl)amino]benzoate in a similar fashion to Ex. 3. $^1$H NMR (400 MHz, DMSO-$d_6$) δ 10.52 (d, J=2.6 Hz, 1H), 10.10 (s, 1H), 8.35 (s, 1H), 8.18 (dd, J=2.4, 0.8 Hz, 1H), 8.04 (d, J=8.4 Hz, 1H), 7.69 (dd, J=8.5, 2.4 Hz, 1H), 7.58 (d, J=6.9 Hz, 1H), 7.24 (d, J=11.1 Hz, 1H), 2.65 (s, 3H), 2.45-2.43 (m, 2H), 2.22 (s, 3H), 0.96-0.86 (m, 1H), 0.45-0.38 (m, 2H), 0.19-0.12 (m, 2H). ESI MS [M+H]$^+$ for $C_{22}H_{22}F_1N_4O_2S_1$, calcd 425.1, found 425.1.

Example 6: 2-(Azetidine-1-carbonylamino)-N-[5-[(5-cyclopropyloxypyridin-2-yl)carbamoyl]-4-fluoro-2-methylphenyl]-1,3-thiazole-5-carboxamide

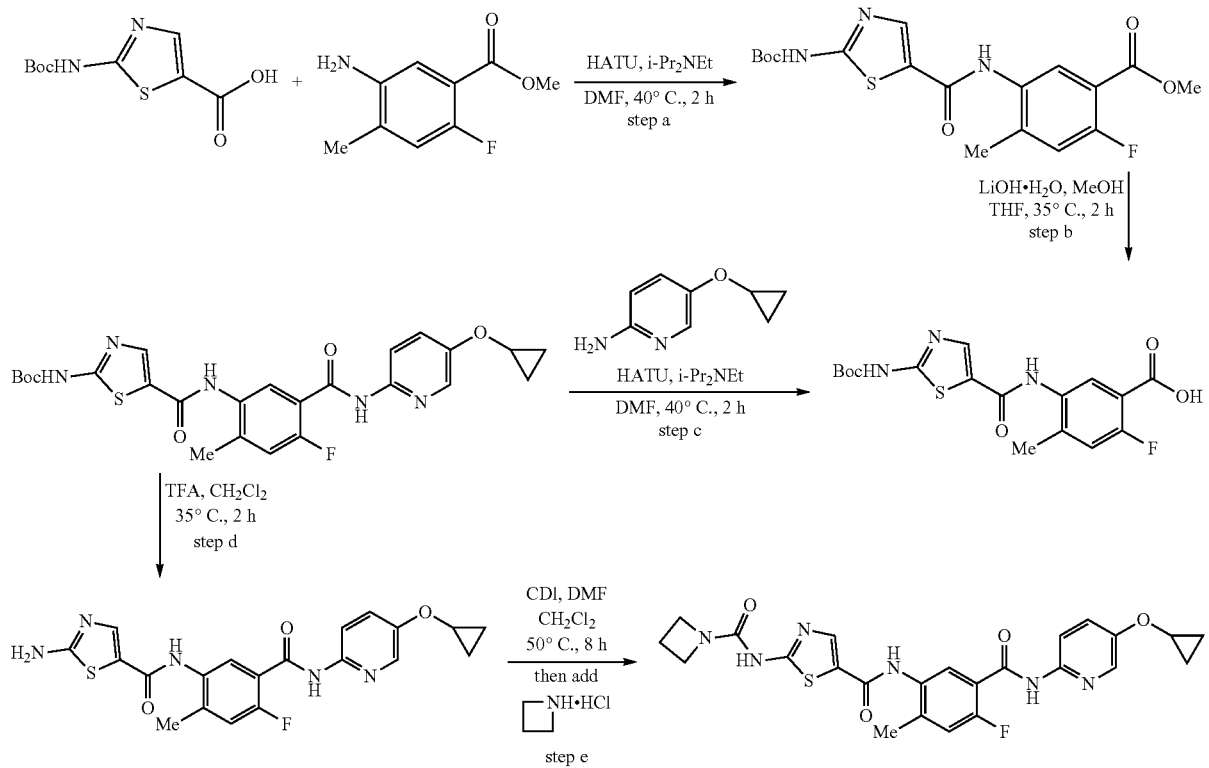

Step a: A round-bottom flask was charged with methyl 5-amino-2-fluoro-4-methylbenzoate (11.2 g, 61.40 mmol, 1.0 equiv.), 2-[(2-methylpropan-2-yl)oxycarbonylamino]-1,3-thiazole-5-carboxylic acid (15.0 g, 61.40 mmol, 1.0 equiv.), and HATU (32.7 g, 85.96 mmol, 1.4 equiv.). DMF (200 mL, 0.3 M) was added, followed by i-Pr$_2$NEt (32.1 mL, 184.2 mmol, 3.0 equiv.). The reaction mixture was stirred at 40° C. for 2 h, at which time LC/MS analysis showed complete consumption of starting material. The reaction mixture was cooled to RT and poured onto ice water (450 mL) with stirring. Stirring was continued for 10 minutes and then the precipitated solid was collected by vacuum filtration, rinsed with water, and dried in vacuo to afford methyl 2-fluoro-4-methyl-5-[[2-[(2-methylpropan-2-yl)oxycarbonylamino]-1,3-thiazole-5-carbonyl]amino]benzoate, which was used directly in the next step without further purification.

Step b: A round-bottom flask was charged with product from step a (25.14 g, 61.40 mmol, 1.0 equiv.), followed by THF (100 mL), MeOH (100 mL) and H$_2$O (50 mL). LiOH·H$_2$O (12.88 g, 307 mmol, 5.0 equiv.) was then added and the reaction mixture was stirred at 35° C. for 2 h, at which time LC/MS analysis indicated complete consumption of starting material. The reaction mixture was cooled to 0° C. and the pH was adjusted to pH=4 with aq. HCl (2 M). The precipitate thus obtained was collected by vacuum filtration, rinsed with water, and extensively dried in vacuo for a few days to afford 2-fluoro-4-methyl-5-[[2-[(2-methylpropan-2-yl)oxycarbonylamino]-1,3-thiazole-5-carbonyl]amino]benzoic acid.

Step c: A round-bottom flask was charged with product from step b (1.18 g, 3.00 mmol, 1.0 equiv.), 5-cyclopropyloxypyridin-2-amine (0.45 g, 3.00 mmol, 1.0 equiv.), and HATU (1.60 g, 4.20 mmol, 1.4 equiv.). DMF (15 mL, 0.2 M) was added, followed by i-Pr$_2$NEt (1.57 mL, 9.00 mmol, 3.0 equiv.). The reaction mixture was stirred at 40° C. for 2 h, at which time LC/MS analysis showed complete consumption of starting material. The reaction mixture was cooled to RT and poured onto ice water with stirring. Stirring was continued for 10 minutes and then the precipitated solid was collected by vacuum filtration, rinsed with water, and dried in vacuo to afford tert-butyl N-[5-[[5-[(5-cyclopropyloxypyridin-2-yl)carbamoyl]-4-fluoro-2-methylphenyl]carbamoyl]-1,3-thiazol-2-yl]carbamate, which was used directly in the next step without further purification.

Step d: A round-bottom flask was charged with product from step c and CH$_2$C$_2$ (4 mL) was added. TFA (2 mL) was then added dropwise and the reaction mixture was stirred at 35° C. for 2 h, at which time LC/MS analysis indicated complete consumption of starting material. The reaction mixture was cooled to RT and the solvents were evaporated. The residue was purified using column chromatography on silica gel (MeOH in CH$_2$Cl$_2$, 0%→5%) to afford 2-amino-N-[5-[(5-cyclopropyloxypyridin-2-yl)carbamoyl]-4-fluoro-2-methylphenyl]-1,3-thiazole-5-carboxamide.

Step e: Product from step d (25 mg, 0.06 mmol, 1.0 equiv.) and CDI (20 mg, 0.12 mmol, 2.0 equiv.) were suspended in CH$_2$Cl$_2$/DMF (2 mL, 4/1, v/v) and the reaction mixture was stirred at 50° C. for 8 h. After complete consumption of the starting material, azetidine hydrochloride (24 mg, 0.24 mmol, 4.0 equiv.) was added and the reaction mixture was stirred at 50° C. for 1 h, then cooled to RT. The solvents were evaporated in vacuo and the crude product was purified by reverse phase HPLC to afford the title compound. $^1$H NMR (400 MHz, DMSO-d$_6$) δ 11.23 (s, 1H), 10.54 (d, J=2.6 Hz, 1H), 9.87 (s, 1H), 8.18 (s, 1H), 8.15 (d, J=3.0 Hz, 1H), 8.14-8.08 (m, 1H), 7.64 (d, J=6.9 Hz, 1H), 7.59 (dd, J=9.0, 3.0 Hz, 1H), 7.28 (d, J=11.2 Hz, 1H), 4.03 (t, J=7.7 Hz, 4H), 3.95 (dq, J=6.1, 3.0 Hz, 1H), 2.29 (s, 3H), 2.21 (p, J=7.5 Hz, 2H), 0.84-0.75 (m, 2H), 0.69 (tq, J=5.4, 3.1 Hz, 2H). ESI MS [M+H]$^+$ for C$_{24}$H$_{24}$F$_1$N$_6$O$_4$S$_1$, calcd 511.2, found 511.2.

Example 7: 2-Amino-N-[5-[[5-(cyclopropylmethyl)pyridin-2-yl]carbamoyl]-4-fluoro-2-methylphenyl]-1,3-thiazole-5-carboxamide

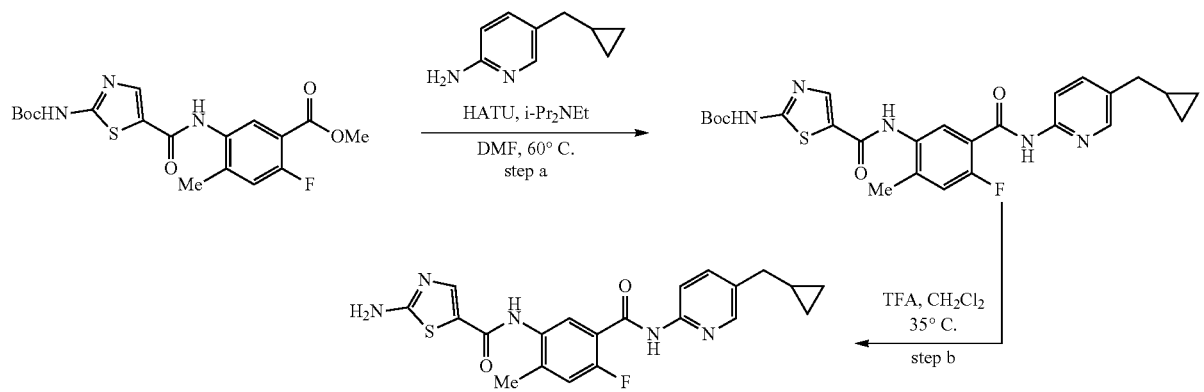

Step a: A vial was charged with the product from Example 6, step b (0.045 g, 0.303 mmol, 1.2 equiv.), 2-fluoro-4-methyl-5-[[2-[(2-methylpropan-2-yl)oxycarbonylamino]-1,3-thiazole-5-carbonyl]amino]benzoic acid (0.100 g, 0.259 mmol, 1.0 equiv.), HATU (0.144 g, 0.379 mmol, 1.5 equiv.) and DMF (2 mL). i-Pr$_2$NEt (0.132 mL, 0.759 mmol, 3.0 equiv.) was then added dropwise and the reaction mixture was stirred at 60° C. Upon completion, the reaction mixture was cooled to RT, diluted with H$_2$O and extracted three times with EtOAc. The combined organic extracts were dried over Na$_2$SO$_4$, filtered, and concentrated in vacuo to afford the crude product, which was purified by column chromatography (EtOAc/hexanes, 0% to 80%) to provide tert-butyl N-[5-[[5-[[5-(cyclopropylmethyl)pyridin-2-yl]carbamoyl]-4-fluoro-2-methylphenyl]carbamoyl]-1,3-thiazol-2-yl]carbamate.

Step b: The product from step a (76 mg, 0.144 mmol) was dissolved in CH$_2$C$_2$ (2.0 mL) and was treated with TFA (1.0 mL). The reaction mixture was stirred at 35° C. and monitored by LC/MS. Upon completion, the reaction mixture was concentrated in vacuo. The residue was purified by reverse phase HPLC to afford the title compound. $^1$H NMR (400 MHz, DMSO-d$_6$) δ 10.54 (d, J=2.7 Hz, 1H), 9.63 (s, 1H), 8.24 (d, J=2.3 Hz, 1H), 8.10 (d, J=8.5 Hz, 1H), 7.85 (s, 1H), 7.75 (dd, J=8.5, 2.4 Hz, 1H), 7.69-7.55 (m, 3H), 7.26 (d, J=11.2 Hz, 1H), 3.33 (s, 2H), 2.27 (s, 3H), 0.97 (td, J=7.4, 3.9 Hz, 1H), 0.53-0.41 (m, 2H), 0.26-0.15 (m, 2H). ESI MS [M+H]$^+$ for C$_{21}$H$_{21}$F$_1$N$_5$O$_2$S$_1$, calcd 426.1, found 426.1.

Example 8: 2-Amino-N-[4-fluoro-2-methyl-5-[[5-(trifluoromethoxy)pyridin-2-yl]carbamoyl]phenyl]-1,3-thiazole-5-carboxamide

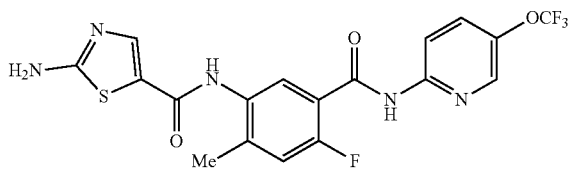 [SMILES: Cc1cc(F)c(C(=O)Nc2ccc(OC(F)(F)F)cn2)cc1NC(=O)c1cnc(N)s1]

The title compound was prepared from 5-(trifluoromethoxy)pyridin-2-amine and 2-fluoro-4-methyl-5-[[2-[(2-methylpropan-2-yl)oxycarbonylamino]-1,3-thiazole-5-carbonyl]amino]benzoic acid in a similar fashion to Ex. 7. $^1$H NMR (400 MHz, DMSO-d$_6$) δ 10.98 (d, J=1.9 Hz, 1H), 9.64 (s, 1H), 8.48 (d, J=3.0 Hz, 1H), 8.30 (d, J=9.2 Hz, 1H), 8.02-7.91 (m, 1H), 7.85 (s, 1H), 7.64 (s, 2H), 7.61 (d, J=6.9 Hz, 1H), 7.28 (d, J=11.2 Hz, 1H), 2.27 (s, 3H). ESI MS [M+H]$^+$ for C$_{18}$H$_{14}$F$_4$N$_5$O$_3$S$_1$, calcd 456.1, found 456.0.

Example 9: 2-Amino-N-[5-[[5-(difluoromethoxy)pyridin-2-yl]carbamoyl]-4-fluoro-2-methylphenyl]-1,3-thiazole-5-carboxamide

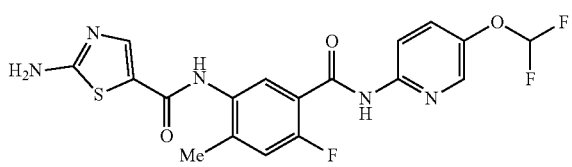 [SMILES: Cc1cc(F)c(C(=O)Nc2ccc(OC(F)F)cn2)cc1NC(=O)c1cnc(N)s1]

The title compound was prepared from 5-(difluoromethoxy)pyridin-2-amine and 2-fluoro-4-methyl-5-[[2-[(2-methylpropan-2-yl)oxycarbonylamino]-1,3-thiazole-5-carbonyl]amino]benzoic acid in a similar fashion to Ex. 7. H NMR (400 MHz, DMSO-d$_6$) δ 10.82 (d, J=2.1 Hz, 1H), 9.64 (s, 1H), 8.29 (d, J=3.0 Hz, 1H), 8.23 (d, J=9.1 Hz, 1H), 7.86 (s, 1H), 7.76 (dd, J=9.1, 3.0 Hz, 1H), 7.66 (s, 2H), 7.61 (d, J=6.9 Hz, 1H), 7.26 (t, J=76 Hz, 1H), 7.27 (d, J=8.1 Hz, 1H), 2.27 (s, 3H). ESI MS [M+H]$^+$ for C$_{18}$H$_{15}$F$_3$N$_5$O$_3$S$_1$, calcd 438.1, found 438.1.

Example 10: 2-Amino-N-[4-fluoro-5-[[5-(methoxymethyl)pyridin-2-yl]carbamoyl]-2-methylphenyl]-1,3-thiazole-5-carboxamide

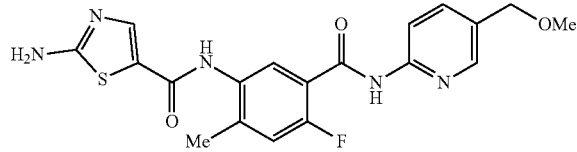 [SMILES: COCc1ccc(NC(=O)c2cc(NC(=O)c3cnc(N)s3)c(C)cc2F)nc1]

The title compound was prepared from 5-(methoxymethyl)pyridin-2-amine and 2-fluoro-4-methyl-5-[[2-[(2-methylpropan-2-yl)oxycarbonylamino]-1,3-thiazole-5-carbonyl]amino]benzoic acid in a similar fashion to Ex. 7. $^1$H NMR (400 MHz, DMSO-$d_6$) δ 10.68 (d, J=2.5 Hz, 1H), 9.67 (s, 1H), 8.32 (d, J=2.3 Hz, 1H), 8.17 (d, J=8.5 Hz, 1H), 7.87 (s, 1H), 7.81 (dd, J=8.6, 2.4 Hz, 1H), 7.77 (s, 2H), 7.61 (d, J=7.0 Hz, 1H), 7.27 (d, J=11.2 Hz, 1H), 4.42 (s, 2H), 3.30 (s, 3H), 2.27 (s, 3H). ESI MS [M+H]$^+$ for $C_{19}H_{19}F_1N_5O_3S_1$, calcd 416.1, found 416.0.

Example 11: 2-Amino-N-[4-fluoro-2-methyl-5-[[5-(2,2,2-trifluoroethyl)pyridin-2-yl]carbamoyl]phenyl]-1,3-thiazole-5-carboxamide

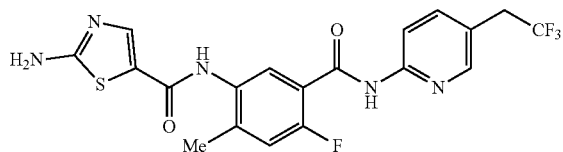 [SMILES: Cc1cc(F)c(C(=O)Nc2ccc(CC(F)(F)F)cn2)cc1NC(=O)c1cnc(N)s1]

The title compound was prepared from 5-(2,2,2-trifluoroethyl) pyridin-2-amine and 2-fluoro-4-methyl-5-[[2-[(2-methylpropan-2-yl)oxycarbonylamino]-1,3-thiazole-5-carbonyl]amino]benzoic acid in a similar fashion to Ex. 7. $^1$H NMR (400 MHz, Methanol-$d_4$) δ 8.51 (s, 1H), 8.31-8.21 (m, 2H), 7.84-7.71 (m, 2H), 7.21 (d, J=11.8 Hz, 1H), 3.53 (q, J=11.0 Hz, 2H), 2.32 (s, 3H). ESI MS [M+H]$^+$ for $C_{19}H_{16}F_4N_5O_2S_1$, calcd 454.1, found 454.1.

Example 12: N-(4-Fluoro-2-methyl-5-((pyridin-3-ylmethyl)carbamoyl)phenyl)-2-methylthiazole-5-carboxamide

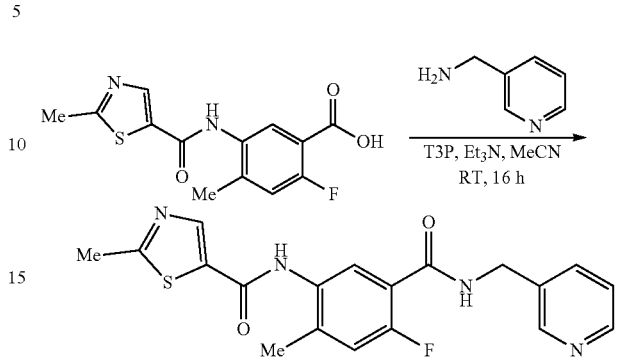

To a mixture of 2-fluoro-4-methyl-5-[(2-methyl-1,3-thiazole-5-carbonyl)amino]benzoic acid (80 mg, 0.27 mmol, 1.0 equiv., prepared according to Example 1), pyridin-3-ylmethanamine (44 mg, 0.41 mmol, 1.5 equiv.) and the Et$_3$N (0.11 mL, 0.82 mmol, 3.0 equiv.) in acetonitrile (1.5 mL) was added T3P (50% in EtOAc, 0.38 mL, 0.54 mmol, 2.0 equiv.) at RT and the resulting mixture was stirred for 16 h. After LC/MS analysis indicated complete conversion, the solvent was concentrated in vacuo and the resulting residue was diluted with H$_2$O and extracted thrice with DCM. The combined organic extracts were dried over Na$_2$SO$_4$ and concentrated in vacuo. The crude product was purified by column chromatography (MeOH/DCM, 5% to 20%) to afford the title compound. $^1$H NMR (400 MHz, DMSO-$d_6$) δ 10.06 (s, 1H), 8.83 (s, 1H), 8.49 (s, 1H), 8.40 (d, J=4.8 Hz, 1H), 8.33 (s, 1H), 7.66 (d, J=8.1 Hz, 1H), 7.52 (d, J=6.9 Hz, 1H), 7.31 (t, J=6.5 Hz, 1H), 7.22 (d, J=11.2 Hz, 1H), 4.42 (d, J=6.0 Hz, 2H), 2.64 (s, 3H), 2.19 (s, 3H). $^{19}$F NMR (376 MHz, DMSO-$d_6$) δ -117.15. ESI MS [M+H]$^+$ for $C_{20}H_{18}F_1N_4O_2S_1$, calcd 386.1, found 386.1.

Example 13: N-[5-[(5-Cyclopropyloxypyrazin-2-yl)carbamoyl]-4-fluoro-2-methylphenyl]-2-methyl-1,3-thiazole-5-carboxamide

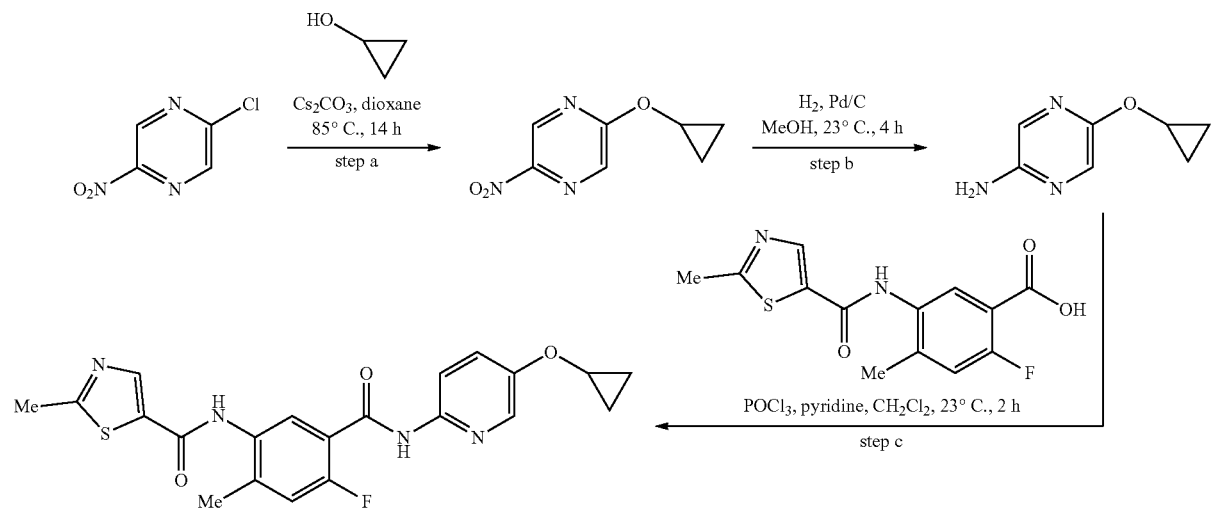

Step a: A mixture of 2-chloro-5-nitropyrazine (320 mg, 2.00 mmol, 1.0 equiv.), Cs₂CO₃ (980 mg, 3.00 mmol, 1.5 equiv.), cyclopropanol (0.9 mL, 14.0 mmol, 7.0 equiv.), and dioxane (4.0 mL) was stirred at 85° C. for 14 h. The reaction mixture was cooled, diluted with EtOAc, filtered to remove solids, and concentrated in vacuo. The crude product was purified by column chromatography (SiO₂, 0% to 100% EtOAc in CH₂Cl₂) to afford 2-cyclopropyloxy-5-nitropyrazine.

Step b: A vial was charged with the product obtained in step a (160 mg, 0.88 mmol, 1.0 equiv.), Pd/C (20 mg, 10 wt. %), and MeOH (2.0 mL). The resulting mixture was stirred under a H₂ balloon at RT for 4 h, at which time LC/MS analysis indicated complete consumption of starting material. The reaction mixture was diluted with MeOH, filtered over Celite®, and concentrated in vacuo to afford 5-cyclopropyloxypyrazin-2-amine, which was used directly in the next step without further purification.

Step c: The title compound was prepared from 2-fluoro-4-methyl-5-[(2-methyl-1,3-thiazole-5-carbonyl)amino]benzoic acid and 5-cyclopropyloxypyrazin-2-amine in a similar fashion to Example 1. ¹H NMR (400 MHz, DMSO-d₆) δ 10.86 (s, 1H), 10.15 (s, 1H), 8.96 (s, 1H), 8.41 (s, 1H), 8.17 (d, J=1.9 Hz, 1H), 7.65 (d, J=6.8 Hz, 1H), 7.32 (d, J=10.9 Hz, 1H), 4.25 (td, J=6.0, 2.9 Hz, 1H), 2.71 (s, 3H), 2.29 (s, 3H), 0.80 (p, J=5.7, 4.9 Hz, 2H), 0.76-0.69 (m, 2H). ESI MS [M+H]⁺ for $C_{20}H_{19}F_1N_5O_3S_1$, calcd 428.1, found 428.1.

Example 14: N-[4-Fluoro-2-methyl-5-[[5-(trifluoromethyl)pyridin-2-yl]carbamoyl]phenyl]-2-methyl-1,3-thiazole-5-carboxamide

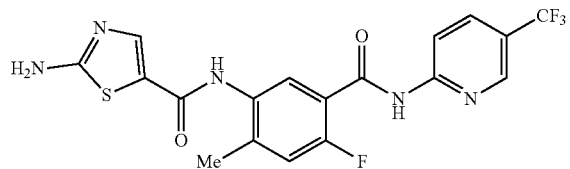 [SMILES: Cc1cc(F)c(C(=O)Nc2ccc(C(F)(F)F)cn2)cc1NC(=O)c1cnc(N)s1]

The title compound was prepared from 2-fluoro-4-methyl-5-[(2-methyl-1,3-thiazole-5-carbonyl)amino]benzoic acid and 5-(trifluoromethyl)pyridin-2-amine in a similar fashion to Example 1. ¹H NMR (400 MHz, DMSO-d₆) δ 11.21 (s, 1H), 10.16 (s, 1H), 8.81-8.70 (m, 1H), 8.41 (s, 1H), 8.38 (d, J=8.8 Hz, 1H), 8.26 (dd, J=8.9, 2.5 Hz, 1H), 7.66 (d, J=6.8 Hz, 1H), 7.33 (d, J=11.1 Hz, 1H), 2.71 (s, 3H), 2.29 (s, 3H). ESI MS [M+H]⁺ for $C_{19}H_{15}F_4N_4O_2S_1$, calcd 439.1, found 439.1.

Example 15: N-[5-[[5-(Difluoromethoxy)pyrazin-2-yl]carbamoyl]-4-fluoro-2-methylphenyl]-2-methyl-1,3-thiazole-5-carboxamide

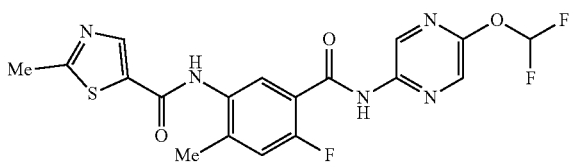 [SMILES: Cc1ncc(C(=O)Nc2cc(C(=O)Nc3cnc(OC(F)F)cn3)c(F)cc2C)s1]

The title compound was prepared from 2-fluoro-4-methyl-5-[(2-methyl-1,3-thiazole-5-carbonyl)amino]benzoic acid and 5-(difluoromethoxy)pyrazin-2-amine in a similar fashion to Example 1. ¹H NMR (400 MHz, DMSO-d₆) δ 11.16 (s, 1H), 10.15 (s, 1H), 9.04 (s, 1H), 8.41 (s, 2H), 7.67 (s, 1H), 7.87-7.46 (m, 1H), 7.33 (d, J=10.7 Hz, 1H), 2.71 (s, 3H), 2.29 (s, 3H). ESI MS [M+H]⁺ for $C_{18}H_{15}F_3N_5O_3S_1$, calcd 438.1, found 438.1.

Example 16: N-[5-[[5-(Difluoromethyl)pyridin-2-yl]carbamoyl]-4-fluoro-2-methylphenyl]-2-methyl-1,3-thiazole-5-carboxamide

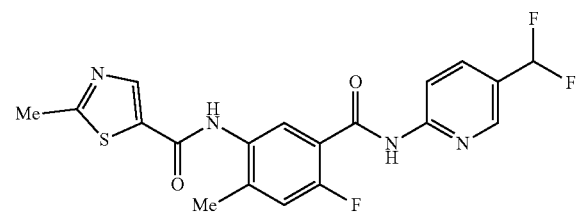 [SMILES: Cc1ncc(C(=O)Nc2cc(C(=O)Nc3ccc(C(F)F)cn3)c(F)cc2C)s1]

The title compound was prepared from 2-fluoro-4-methyl-5-[(2-methyl-1,3-thiazole-5-carbonyl)amino]benzoic acid and 5-(difluoromethyl)pyridin-2-amine in a similar fashion to Example 1. ¹H NMR (400 MHz, DMSO-d₆) δ 11.01 (d, J=1.9 Hz, 1H), 10.15 (s, 1H), 8.58 (d, J=2.2 Hz, 1H), 8.41 (s, 1H), 8.31 (d, J=8.6 Hz, 1H), 8.08 (dd, J=8.8, 2.3 Hz, 1H), 7.65 (d, J=6.9 Hz, 1H), 7.32 (d, J=11.1 Hz, 1H), 7.12 (t, J=55.5 Hz, 1H), 2.71 (s, 3H), 2.29 (s, 3H). ESI MS [M+H]⁺ for $C_{19}H_{16}F_3N_4O_2S_1$, calcd 421.1, found 421.1.

Example 17: N-[5-[(5-Ethoxypyrazin-2-yl)carbamoyl]-4-fluoro-2-methylphenyl]-2-methyl-1,3-thiazole-5-carboxamide

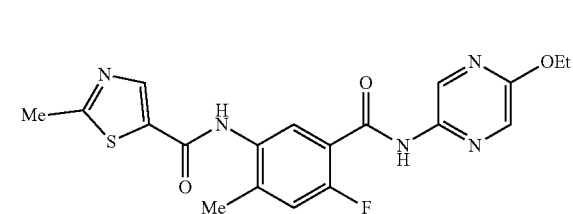 [SMILES: CCOc1cnc(NC(=O)c2cc(NC(=O)c3cnc(C)s3)c(C)cc2F)cn1]

The title compound was prepared from 2-fluoro-4-methyl-5-[(2-methyl-1,3-thiazole-5-carbonyl)amino]benzoic acid and 5-ethoxypyrazin-2-amine in a similar fashion to Example 1. ¹H NMR (400 MHz, DMSO-d₆) δ 10.81 (d, J=1.7 Hz, 1H), 10.14 (s, 1H), 8.91 (s, 1H), 8.41 (s, 1H), 8.13 (d, J=1.3 Hz, 1H), 7.64 (d, J=6.8 Hz, 1H), 7.32 (d, J=10.9 Hz, 1H), 4.35 (qd, J=7.0, 1.1 Hz, 2H), 2.71 (s, 3H), 2.29 (s, 3H), 1.35 (td, J=7.0, 1.0 Hz, 3H). ESI MS [M+H]⁺ for $C_{19}H_{19}F_1N_5O_3S_1$, calcd 416.1, found 416.1.

Example 18: N-[5-[(2-Cyanopyridin-4-yl)carbamoyl]-4-fluoro-2-methylphenyl]-2-methyl-1,3-thiazole-5-carboxamide

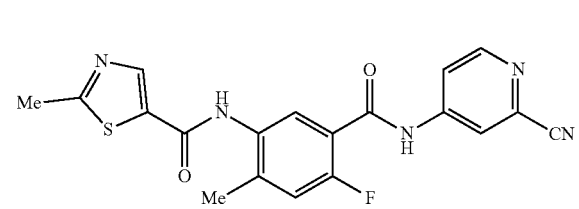 [SMILES: Cc1ncc(C(=O)Nc2cc(C(=O)Nc3ccnc(C#N)c3)c(F)cc2C)s1]

The title compound was prepared from 2-fluoro-4-methyl-5-[(2-methyl-1,3-thiazole-5-carbonyl)amino]benzoic acid and 4-aminopyridine-2-carbonitrile in a similar fashion to Example 1. $^1$H NMR (400 MHz, DMSO-d$_6$) δ 11.12 (s, 1H), 10.19 (s, 1H), 8.65 (d, J=5.6 Hz, 1H), 8.41 (s, 1H), 8.24 (d, J=2.1 Hz, 1H), 7.94 (dd, J=5.7, 2.1 Hz, 1H), 7.65 (d, J=6.8 Hz, 1H), 7.39 (d, J=11.0 Hz, 1H), 2.71 (s, 3H), 2.30 (s, 3H). ESI MS [M+H]$^+$ for C$_{19}$H$_{15}$F$_1$N$_5$O$_2$S$_1$, calcd 396.1, found 396.1.

Example 19: N-[5-[(5-Cyanopyridin-2-yl)carbamoyl]-4-fluoro-2-methylphenyl]-2-methyl-1,3-thiazole-5-carboxamide

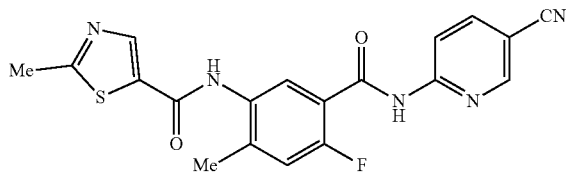 [SMILES: Cc1ncc(C(=O)Nc2cc(C(=O)Nc3ccc(C#N)cn3)c(F)cc2C)s1]

The title compound was prepared from 2-fluoro-4-methyl-5-[(2-methyl-1,3-thiazole-5-carbonyl)amino]benzoic acid and 6-aminopyridine-3-carbonitrile in a similar fashion to Example 1. $^1$H NMR (400 MHz, DMSO-d$_6$) δ 11.28 (s, 1H), 10.15 (s, 1H), 8.84 (t, J=1.6 Hz, 1H), 8.41 (s, 1H), 8.32 (d, J=1.6 Hz, 2H), 7.65 (d, J=6.8 Hz, 1H), 7.33 (d, J=11.1 Hz, 1H), 2.71 (s, 3H), 2.29 (s, 3H). ESI MS [M+H]$^+$ for C$_{19}$H$_{15}$F$_1$N$_5$O$_2$S$_1$, calcd 396.1, found 396.1.

Example 20: N-[5-[[5-(1,1-Difluoroethyl)pyridin-2-yl]carbamoyl]-4-fluoro-2-methylphenyl]-2-methyl-1,3-thiazole-5-carboxamide

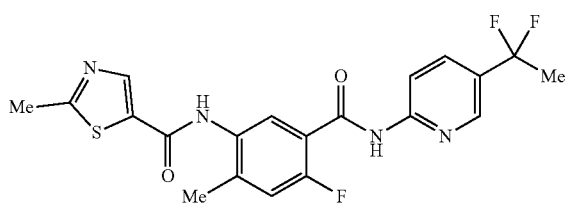 [SMILES: Cc1ncc(C(=O)Nc2cc(C(=O)Nc3ccc(C(C)(F)F)cn3)c(F)cc2C)s1]

The title compound was prepared from 2-fluoro-4-methyl-5-[(2-methyl-1,3-thiazole-5-carbonyl)amino]benzoic acid and 5-(1,1-difluoroethyl)pyridin-2-amine in a similar fashion to Example 1. $^1$H NMR (400 MHz, DMSO-d$_6$) δ 10.99 (s, 1H), 10.15 (s, 1H), 8.61-8.56 (m, 1H), 8.41 (s, 1H), 8.28 (d, J=8.7 Hz, 1H), 8.06 (dd, J=8.9, 2.5 Hz, 1H), 7.65 (d, J=6.9 Hz, 1H), 7.32 (d, J=11.1 Hz, 1H), 2.71 (s, 3H), 2.29 (s, 3H), 2.03 (t, J=19.0 Hz, 3H). ESI MS [M+H]$^+$ for C$_{20}$H$_{18}$F$_3$N$_4$O$_2$S$_1$, calcd 435.1, found 435.1.

Example 21: N-[5-[[2-(Difluoromethoxy)pyridin-4-yl]carbamoyl]-4-fluoro-2-methylphenyl]-2-methyl-1,3-thiazole-5-carboxamide

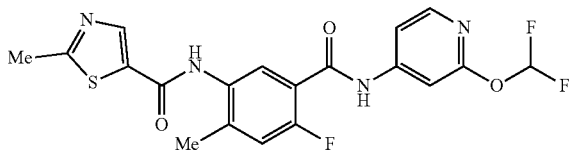 [SMILES: Cc1ncc(C(=O)Nc2cc(C(=O)Nc3ccnc(OC(F)F)c3)c(F)cc2C)s1]

The title compound was prepared from 2-fluoro-4-methyl-5-[(2-methyl-1,3-thiazole-5-carbonyl)amino]benzoic acid and 2-(difluoromethoxy)pyridin-4-amine in a similar fashion to Example 1. $^1$H NMR (400 MHz, DMSO-d$_6$) δ 10.95 (s, 1H), 10.18 (s, 1H), 8.41 (s, 1H), 8.18 (d, J=5.8 Hz, 1H), 7.70 (t, J=72.9 Hz, 1H), 7.63 (d, J=6.9 Hz, 1H), 7.49 (d, J=6.0 Hz, 1H), 7.42 (s, 1H), 7.37 (d, J=10.9 Hz, 1H), 2.71 (s, 3H), 2.30 (s, 3H). ESI MS [M+H]$^+$ for C$_{19}$H$_{16}$F$_3$N$_4$O$_3$S$_1$, calcd 437.1, found 437.1.

Example 22: N-[5-[[2-(Difluoromethyl)pyridin-4-yl]carbamoyl]-4-fluoro-2-methylphenyl]-2-methyl-1,3-thiazole-5-carboxamide

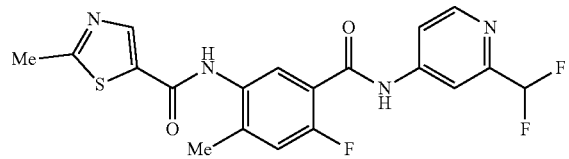 [SMILES: Cc1ncc(C(=O)Nc2cc(C(=O)Nc3ccnc(C(F)F)c3)c(F)cc2C)s1]

The title compound was prepared from 2-fluoro-4-methyl-5-[(2-methyl-1,3-thiazole-5-carbonyl)amino]benzoic acid and 2-(difluoromethyl)pyridin-4-amine in a similar fashion to Example 1. $^1$H NMR (400 MHz, DMSO-d$_6$) δ 10.99 (s, 1H), 10.18 (s, 1H), 8.59 (d, J=5.3 Hz, 1H), 8.41 (s, 1H), 8.06 (s, 1H), 7.81 (d, J=5.4 Hz, 1H), 7.64 (d, J=6.8 Hz, 1H), 7.37 (d, J=11.0 Hz, 1H), 6.94 (dd, J=56.2, 54.4 Hz, 1H), 2.71 (s, 3H), 2.30 (s, 3H). ESI MS [M+H]$^+$ for C$_{19}$H$_{16}$F$_3$N$_4$O$_2$S$_1$, calcd 421.1, found 421.1.

Example 23: N-[4-Fluoro-5-[(5-methoxypyrazin-2-yl)carbamoyl]-2-methylphenyl]-2-methyl-1,3-thiazole-5-carboxamide

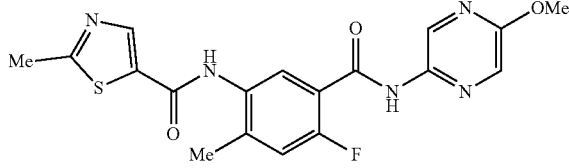 [SMILES: COc1cnc(NC(=O)c2cc(NC(=O)c3cnc(C)s3)c(C)cc2F)cn1]

The title compound was prepared from 2-fluoro-4-methyl-5-[(2-methyl-1,3-thiazole-5-carbonyl)amino]benzoic acid and 5-methoxypyrazin-2-amine in a similar fashion to Example 1. $^1$H NMR (400 MHz, DMSO-d$_6$) δ 10.83 (s, 1H), 10.15 (s, 1H), 8.93 (s, 1H), 8.41 (s, 1H), 8.16 (d, J=1.4 Hz, 1H), 7.65 (d, J=6.8 Hz, 1H), 7.32 (d, J=11.0 Hz, 1H), 3.92 (s, 3H), 2.71 (s, 3H), 2.29 (s, 3H). ESI MS [M+H]$^+$ for $C_{18}H_{17}F_1N_5O_3S_1$, calcd 402.1, found 402.1.

Example 24: N-[5-[(6-Cyclopropylpyridin-3-yl)carbamoyl]-4-fluoro-2-methylphenyl]-2-methyl-1,3-thiazole-5-carboxamide

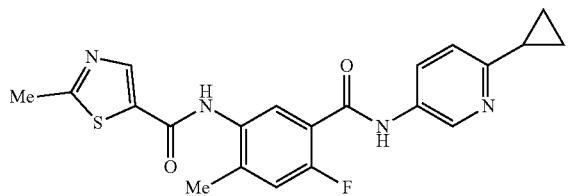 [SMILES: Cc1ncc(C(=O)Nc2cc(C(=O)Nc3ccc(C4CC4)nc3)c(F)cc2C)s1]

The title compound was prepared from 2-fluoro-4-methyl-5-[(2-methyl-1,3-thiazole-5-carbonyl)amino]benzoic acid and 6-cyclopropylpyridin-3-amine in a similar fashion to Example 1. $^1$H NMR (400 MHz, DMSO-d$_6$) δ 10.42 (s, 1H), 10.16 (s, 1H), 8.65 (s, 1H), 8.40 (s, 1H), 7.99 (dd, J=8.4, 2.4 Hz, 1H), 7.60 (d, J=6.9 Hz, 1H), 7.33 (d, J=11.0 Hz, 1H), 7.27 (d, J=8.7 Hz, 1H), 2.70 (s, 3H), 2.28 (s, 3H), 2.12-2.01 (m, 1H), 0.95-0.89 (m, 2H), 0.89-0.83 (m, 2H). ESI MS [M+H]$^+$ for $C_{21}H_{20}F_1N_4O_2S_1$, calcd 411.1, found 411.2.

Example 25: N-[4-Fluoro-2-methyl-5-[[2-(trifluoromethyl)pyridin-4-yl]carbamoyl]phenyl]-2-methyl-1,3-thiazole-5-carboxamide

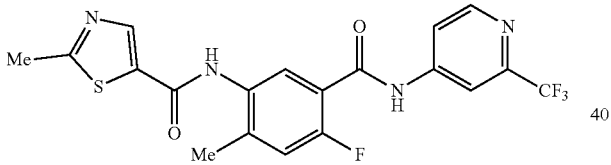

The title compound was prepared from 2-fluoro-4-methyl-5-[(2-methyl-1,3-thiazole-5-carbonyl)amino]benzoic acid and 2-(trifluoromethyl)pyridin-4-amine in a similar fashion to Example 1. $^1$H NMR (400 MHz, DMSO-d$_6$) δ 11.11 (s, 1H), 10.19 (s, 1H), 8.68 (d, J=5.5 Hz, 1H), 8.41 (d, J=1.3 Hz, 1H), 8.22 (t, J=1.7 Hz, 1H), 7.95 (dt, J=5.6, 1.6 Hz, 1H), 7.66 (dd, J=6.9, 1.3 Hz, 1H), 7.45-7.34 (m, 1H), 2.71 (d, J=1.4 Hz, 3H), 2.30 (s, 3H). ESI MS [M+H]$^+$ for $C_{19}H_{15}F_4N_4O_2S_1$, calcd 439.1, found 439.1.

Example 26: N-[4-Fluoro-2-methyl-5-[[6-(trifluoromethyl)pyridin-3-yl]carbamoyl]phenyl]-2-methyl-1,3-thiazole-5-carboxamide

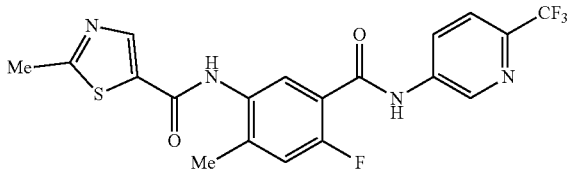 [SMILES: Cc1ncc(C(=O)Nc2cc(C(=O)Nc3ccc(C(F)(F)F)nc3)c(F)cc2C)s1]

The title compound was prepared from 2-fluoro-4-methyl-5-[(2-methyl-1,3-thiazole-5-carbonyl)amino]benzoic acid and 6-(trifluoromethyl)pyridin-3-amine in a similar fashion to Example 1. $^1$H NMR (400 MHz, DMSO-d$_6$) δ 10.96 (s, 1H), 10.18 (s, 1H), 9.00 (d, J=2.4 Hz, 1H), 8.44 (dd, J=8.6, 2.4 Hz, 1H), 8.41 (s, 1H), 7.93 (d, J=8.6 Hz, 1H), 7.66 (d, J=6.8 Hz, 1H), 7.38 (d, J=10.9 Hz, 1H), 2.71 (s, 3H), 2.30 (s, 3H). ESI MS [M+H]$^+$ for $C_{19}H_{15}F_4N_4O_2S_1$, calcd 439.1, found 439.1.

Example 27: N-[5-[(5-ethylpyrazin-2-yl)carbamoyl]-4-fluoro-2-methylphenyl]-2-methyl-1,3-thiazole-5-carboxamide

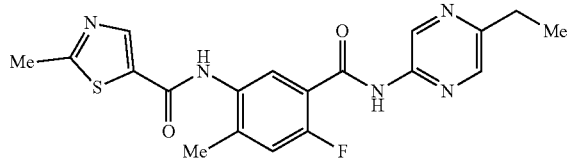 [SMILES: CCc1cnc(NC(=O)c2cc(NC(=O)c3cnc(C)s3)c(C)cc2F)cn1]

The title compound was prepared from 5-ethylpyrazin-2-amine and 2-fluoro-4-methyl-5-[(2-methyl-1,3-thiazole-5-carbonyl)amino]benzoic acid in a similar fashion to Example 1. $^1$H NMR (400 MHz, DMSO-d$_6$) δ 10.78 (s, 1H), 10.17 (s, 1H), 9.22 (s, 1H), 8.31 (d, J=13.6 Hz, 2H), 7.60 (d, J=6.8 Hz, 1H), 7.24 (d, J=11.0 Hz, 1H), 2.71 (q, J=7.7 Hz, 2H), 2.64 (s, 3H), 2.22 (s, 3H), 1.18 (t, J=7.6 Hz, 3H). ESI MS [M+H]$^+$ for $C_{19}H_{19}FN_5O_2S$, calcd 400.1, found 400.1.

Example 28: N-[4-fluoro-2-methyl-5-[(5-propan-2-ylpyrazin-2-yl)carbamoyl]phenyl]-2-methyl-1,3-thiazole-5-carboxamide

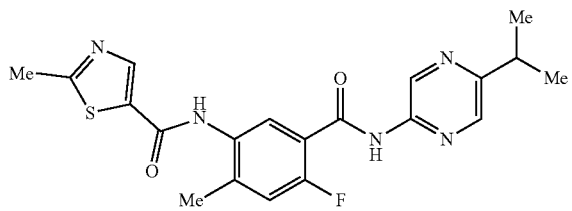 [SMILES: Cc1ncc(C(=O)Nc2cc(C(=O)Nc3cnc(C(C)C)cn3)c(F)cc2C)s1]

The title compound was prepared from 5-propan-2-ylpyrazin-2-amine and 2-fluoro-4-methyl-5-[(2-methyl-1,3-thiazole-5-carbonyl)amino]benzoic acid in a similar fashion to Example 1. $^1$H NMR (400 MHz, DMSO-d$_6$) δ 10.90 (s, 1H), 10.08 (s, 1H), 9.22 (s, 1H), 8.33 (d, J=11.4 Hz, 2H), 7.59 (d, J=6.8 Hz, 1H), 7.26 (d, J=11.0 Hz, 1H), 3.04 (p, J=7.0 Hz, 1H), 2.64 (s, 3H), 2.22 (s, 3H), 1.20 (d, J=6.8 Hz, 6H). ESI MS [M+H]$^+$ for $C_{20}H_{21}FN_5O_2S$, calcd 414.1, found 414.1.

Example 29: N-[4-fluoro-2-methyl-5-[[5-(trifluoromethyl)pyrazin-2-yl]carbamoyl]phenyl]-2-methyl-1,3-thiazole-5-carboxamide

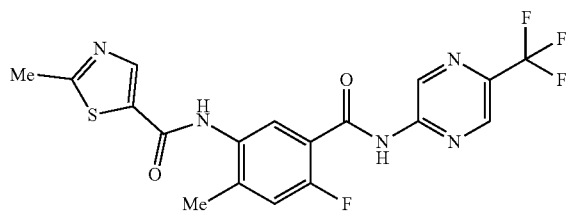 [SMILES: Cc1ncc(C(=O)Nc2cc(C(=O)Nc3cnc(C(F)(F)F)cn3)c(F)cc2C)s1]

The title compound was prepared from 5-(trifluoromethyl)pyrazin-2-amine and 2-fluoro-4-methyl-5-[(2-methyl-1,3-thiazole-5-carbonyl)amino]benzoic acid in a similar fashion to Example 1. $^1$H NMR (400 MHz, DMSO-d$_6$) δ 11.58 (s, 1H), 10.11 (s, 1H), 9.43 (s, 1H), 8.89 (s, 1H), 8.35 (s, 1H), 7.63 (d, J=6.7 Hz, 1H), 7.27 (d, J=11.0 Hz, 1H), 2.64 (s, 3H), 2.23 (s, 3H). ESI MS [M+H]$^+$ for C$_{18}$H$_{14}$F$_4$N$_5$O$_2$S, calcd 440.1, found 440.1.

Example 30: N-[4-Fluoro-2-methyl-5-[[(1S,2R)-2-phenylcyclopropyl]carbamoyl]phenyl]-2-methyl-1,3-thiazole-5-carboxamide

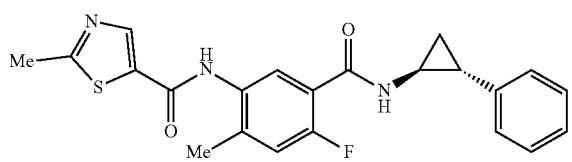 [SMILES: Cc1ncc(C(=O)Nc2cc(C(=O)N[C@H]3C[C@@H]3c3ccccc3)c(F)cc2C)s1]

The title compound was prepared from (1S,2R)-2-phenylcyclopropan-1-amine and 2-fluoro-4-methyl-5-[(2-methyl-1,3-thiazole-5-carbonyl)amino]benzoic acid in a similar fashion to Example 1. $^1$H NMR (400 MHz, Methanol-d$_4$) δ 8.32 (s, 1H), 7.64 (d, J=6.9 Hz, 1H), 7.27 (t, J=7.5 Hz, 3H), 7.21-7.12 (m, 5H), 3.08-3.00 (m, 1H), 2.76 (s, 3H), 2.32 (s, 3H), 2.21-2.13 (m, 1H), 1.35-1.27 (m, 2H). ESI MS [M+H]$^+$ for C$_{22}$H$_{21}$FN$_3$O$_2$S, calcd 410.1, found 410.1.

Example 31: N-[4-Fluoro-2-methyl-5-[[(1R,2S)-2-phenylcyclopropyl]carbamoyl]phenyl]-2-methyl-1,3-thiazole-5-carboxamide

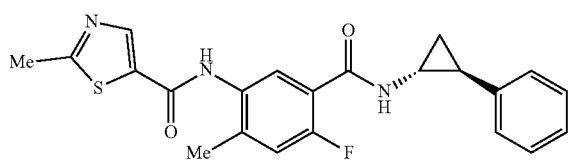 [SMILES: Cc1ncc(C(=O)Nc2cc(C(=O)N[C@@H]3C[C@H]3c3ccccc3)c(F)cc2C)s1]

The title compound was prepared from (1R,2S)-2-phenylcyclopropan-1-amine and 2-fluoro-4-methyl-5-[(2-methyl-1,3-thiazole-5-carbonyl)amino]benzoic acid in a similar fashion to Example 1. $^1$H NMR (400 MHz, Methanol-d$_4$) δ 8.32 (s, 1H), 7.64 (d, J=6.9 Hz, 1H), 7.27 (t, J=7.4 Hz, 3H), 7.22-7.12 (m, 5H), 3.08-3.01 (m, 1H), 2.77 (s, 3H), 2.33 (s, 3H), 2.21-2.13 (m, 1H), 1.37-1.20 (m, 2H). ESI MS [M+H]$^+$ for C$_{22}$H$_{21}$FN$_3$O$_2$S, calcd 410.1, found 410.1.

Example 32: N-[5-[[5-(3,3-difluorocyclobutyl)oxypyrazin-2-yl]carbamoyl]-4-fluoro-2-methylphenyl]-2-methyl-1,3-thiazole-5-carboxamide

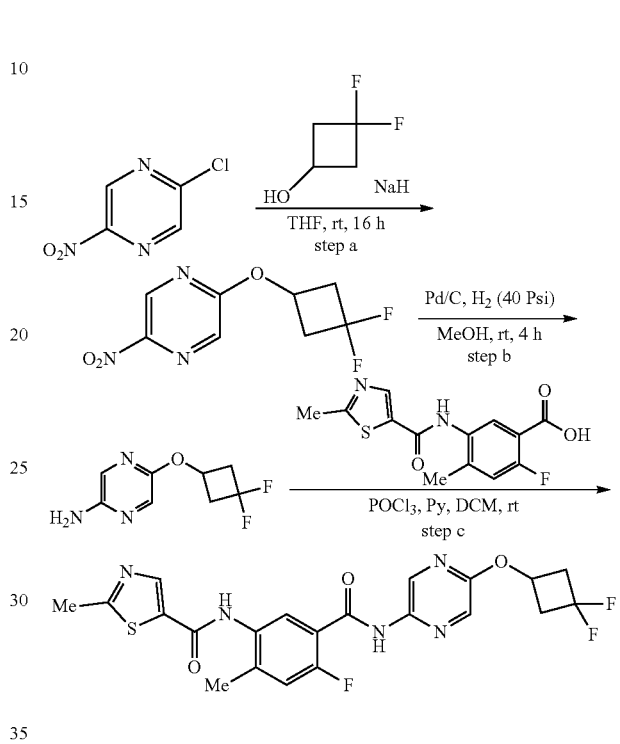

Step a: To the stirred solution of 3,3-difluorocyclobutan-1-ol (1.0 g, 9.4 mmol, 1.5 equiv.) in THF (30 mL, 0.2 M), was added 60% NaH (300 mg, 12.52 mmol, 2 equiv.) in portions at 0° C. After complete addition of NaH, the mixture was stirred for 30 min at rt, and 2-chloro-5-nitropyrazine (1.0 g, 6.26 mmol, 1 equiv.) was added. The resultant mixture was stirred for another 16 h at room temperature, before quenching it with water. The aqueous layer was extracted thrice with EtOAc, and the combined organic extracts were dried over Na$_2$SO$_4$ and concentrated in vacuo. The crude product was purified by column chromatography (EtOAc/hexanes, 0% to 60%) to afford 2-(3,3-difluorocyclobutyl)oxy-5-nitropyrazine.

Step b: To the stirred solution of product from step a (140 mg, 0.6 mmol, 1 equiv.) in MeOH (10 mL), was added 10% Pd/C (50 mg) and stirred under H$_2$ atmosphere (40 Psi) at rt for 4 h. Upon complete conversion, the reaction mixture was filtered through a pad of Celite® and the resulting filtrate was concentrated in vacuo to afford 5-(3,3-difluorocyclobutyl)oxypyrazin-2-amine, which was used directly in the next step without further purification.

Step c: The title compound was prepared from 5-(3,3-difluorocyclobutyl)oxypyrazin-2-amine and 2-fluoro-4-methyl-5-[(2-methyl-1,3-thiazole-5-carbonyl)amino]benzoic acid in a similar fashion to Example 1. $^1$H NMR (400 MHz, Chloroform-d) δ 9.15-9.05 (m, 2H), 8.46 (s, 1H), 8.11 (s, 1H), 8.00-7.93 (m, 2H), 6.97 (d, J=11.8 Hz, 1H), 5.17-5.06 (m, 1H), 3.13 (m, 2H), 2.82-2.64 (m, 5H), 2.26 (s, 3H). ESI MS [M+H]$^+$ for C$_{21}$H$_{19}$F$_3$N$_5$O$_3$S$_1$ calcd 478.1, found 478.1.

Example 33: N-[4-fluoro-2-methyl-5-[[6-(trifluoromethyl)pyrazin-2-yl]carbamoyl]phenyl]-2-methyl-1,3-thiazole-5-carboxamide

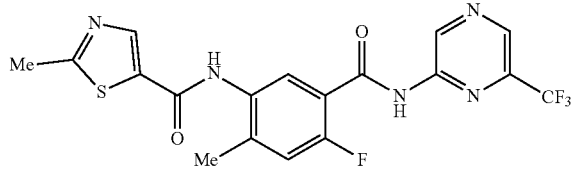 [SMILES: Cc1ncc(C(=O)Nc2cc(C(=O)Nc3cncc(C(F)(F)F)n3)c(F)cc2C)s1]

The title compound was prepared from 6-(trifluoromethyl)pyrazin-2-amine and 2-fluoro-4-methyl-5-[(2-methyl-1,3-thiazole-5-carbonyl)amino]benzoic acid in a similar fashion to Example 1. $^1$H NMR (400 MHz, DMSO-$d_6$) δ 11.64 (s, 1H), 10.14 (s, 1H), 9.70 (s, 1H), 8.93 (s, 1H), 8.41 (s, 1H), 7.69 (d, J=6.9 Hz, 1H), 7.34 (d, J=11.0 Hz, 1H), 2.71 (s, 3H), 2.30 (s, 3H). ESI MS [M+H]$^+$ for $C_{18}H_{14}F_4N_5O_2S_1$ calcd 440.1, found 440.1

Example 34: N-[5-[[6-(cyclopropylmethyl)pyrazin-2-yl]carbamoyl]-4-fluoro-2-methylphenyl]-2-methyl-1,3-thiazole-5-carboxamide Step a: A solution of 6-bromopyrazin-2-amine (2.0 g, 11.49 mmol, 1 equiv.), 4,4,5,5-tetramethyl-2-prop-2-enyl-1,3,2-dioxaborolane (3.9 g, 22.98 mmol, 2 equiv.), and $K_2CO_3$ (4.75 g, 34.47 mmol, 3 equiv.) in 1:1 THF:$H_2O$ (60 mL, 0.2 M) was sparged with nitrogen for 10 min. $PdCl_2$(dppf) (840 mg, 1.15 mmol, 0.1 equiv.) was added and sparging was continued for another 5 min. The mixture was stirred at 100° C. under $N_2$ atmosphere overnight and then cooled to rt. The reaction mixture was diluted with EtOAc and water. The aqueous layer was extracted thrice with EtOAc, and the combined organic extracts were dried over $Na_2SO_4$ and concentrated in vacuo. The crude product was purified by column chromatography (EtOAc/hexanes, 0% to 100%) to afford 6-prop-2-enylpyrazin-2-amine.

Step b: To the stirred solution of product from step a (1.6 g, 11.83 mmol, 1 equiv.) in THF (120 mL, 0.1 M) was added DMAP (433 mg, 3.55 mmol, 0.3 equiv.) and Boc-anhydride (7.74 g, 35.49 mmol, 3 equiv.) at 0° C. The resultant solution was stirred at rt for another 4 h. Solvent was evaporated and the crude product was purified by column chromatography (EtOAc/hexanes, 0% to 60%) to afford tert-butyl N-[(2-methylpropan-2-yl)oxycarbonyl]-N-(6-prop-2-enylpyrazin-2-yl)carbamate.

Step c: To the stirred solution of $Et_2Zn$ (2 M in toluene) (36 mL, 71.5 mmol, 10 equiv.) in DCM (400 mL), was added $CH_2I_2$ (19.2 g, 71.5 mmol, 10 equiv.) very slowly at 0° C. under $N_2$ atmosphere. After stirring for 30 min at 0° C., the product from step b was added and the mixture was stirred for another 2 h at rt. The reaction mixture was quenched with saturated $NH_4Cl$ solution and extracted with EtOAc (3 times). The combined organic extracts were dried over $Na_2SO_4$ and concentrated in vacuo. The crude product was purified by column chromatography (EtOAc/hexanes, 0% to 80%) to afford 6-(cyclopropylmethyl)pyrazin-2-amine.

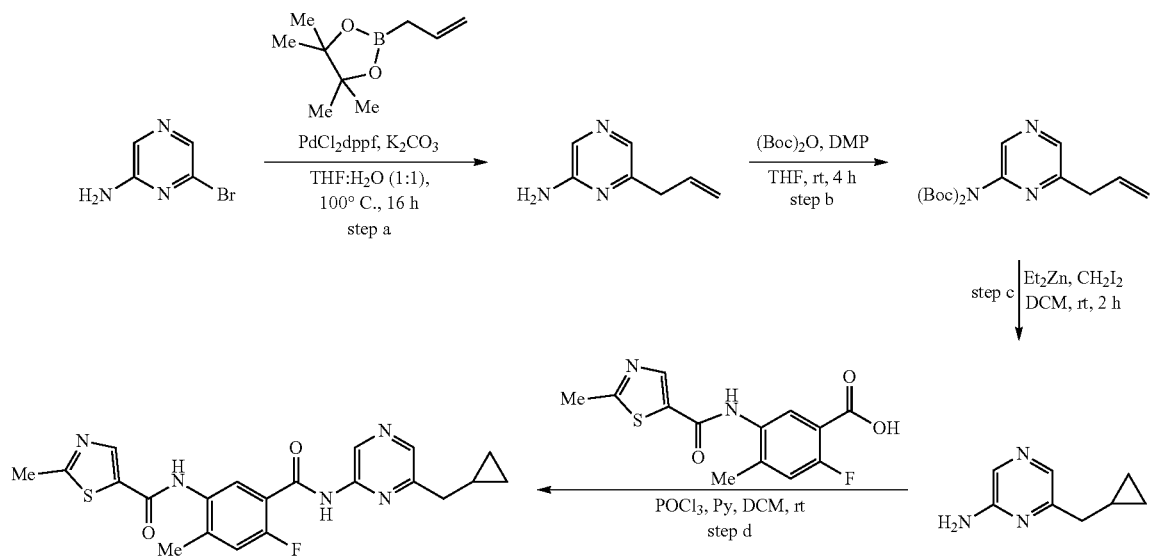

Step d: The title compound was prepared from 6-(cyclopropylmethyl)pyrazin-2-amine and 2-fluoro-4-methyl-5-[(2-methyl-1,3-thiazole-5-carbonyl)amino]benzoic acid in a similar fashion to Example 1. $^1$H NMR (400 MHz, Chloroform-d) δ 9.47 (s, 1H), 9.00 (d, J=13.4 Hz, 1H), 8.35 (s, 1H), 8.18 (d, J=7.3 Hz, 1H), 8.14 (s, 1H), 7.93 (s, 1H), 7.09 (d, J=12.1 Hz, 1H), 2.76 (d, J=1.7 Hz, 3H), 2.65 (d, J=7.0 Hz, 2H), 2.35 (s, 3H), 1.10 (p, J=6.7 Hz, 1H), 0.58 (d, J=7.7 Hz, 2H), 0.26 (d, J=5.0 Hz, 2H). ESI MS [M+H]$^+$ for $C_{21}H_{21}F_1N_5O_2S_1$ calcd 426.1, found 426.1.

Example 35: N-[5-[(6-cyclopropylpyridazin-3-yl)carbamoyl]-4-fluoro-2-methylphenyl]-2-methyl-1,3-thiazole-5-carboxamide

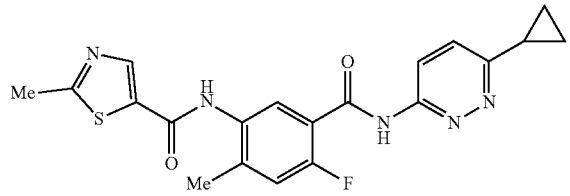 [SMILES: Cc1ncc(C(=O)Nc2cc(C(=O)Nc3ccc(C4CC4)nn3)c(F)cc2C)s1]

The title compound was prepared from 6-cyclopropylpyridazin-3-amine and 2-fluoro-4-methyl-5-[(2-methyl-1,3-thiazole-5-carbonyl)amino]benzoic acid in a similar fashion to Example 1. $^1$H NMR (400 MHz, Methanol-$d_4$) δ 8.40 (d, J=9.3 Hz, 1H), 8.25 (s, 1H), 7.82 (d, J=7.1 Hz, 1H), 7.34 (d, J=9.3 Hz, 1H), 7.15 (d, J=11.7 Hz, 1H), 2.73 (s, 3H), 2.32 (s, 3H), 2.16 (ddd, J=13.1, 8.3, 4.9 Hz, 1H), 1.14-1.08 (m, 2H), 1.06-1.00 (m, 2H). ESI MS [M+H]$^+$ for $C_{20}H_{19}FN_5O_2S_1$, calcd 412.1, found 412.1.

Example 36: N-[5-[[5-(2,2-difluoroethoxy)pyridin-2-yl]carbamoyl]-4-fluoro-2-methylphenyl]-2-methyl-1,3-thiazole-5-carboxamide

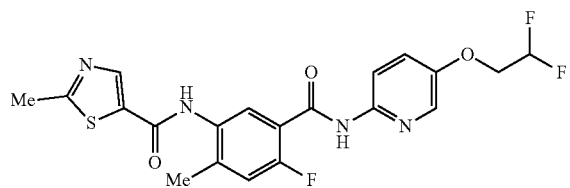 [SMILES: Cc1ncc(C(=O)Nc2cc(C(=O)Nc3ccc(OCC(F)F)cn3)c(F)cc2C)s1]

The title compound was prepared from 5-(2,2-difluoroethoxy)pyridin-2-amine and 2-fluoro-4-methyl-5-[(2-methyl-1,3-thiazole-5-carbonyl)amino]benzoic acid in a similar fashion to Example 1. $^1$H NMR (400 MHz, Methanol-$d_4$) δ 8.25 (s, 1H), 8.20 (d, J=9.1 Hz, 1H), 8.01 (dd, J=3.1, 0.7 Hz, 1H), 7.83 (d, J=7.2 Hz, 1H), 7.39 (dd, J=9.1, 3.1 Hz, 1H), 7.12 (d, J=11.9 Hz, 1H), 6.08 (tt, J=54.9, 3.9 Hz, 1H), 4.22 (td, J=13.3, 3.9 Hz, 2H), 2.72 (s, 3H), 2.31 (s, 3H). ESI MS [M+H]$^+$ for $C_{20}H_{18}F_3N_4O_3S_1$, calcd 451.1, found 451.1.

Example 37: N-[4-fluoro-5-[[5-(methoxymethyl)pyridin-2-yl]carbamoyl]-2-methylphenyl]-2-methyl-1,3-thiazole-5-carboxamide

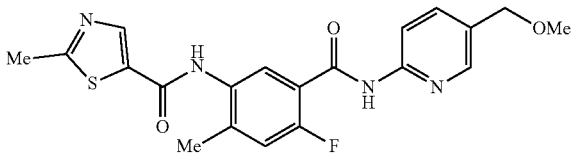 [SMILES: COCc1ccc(NC(=O)c2cc(NC(=O)c3cnc(C)s3)c(C)cc2F)nc1]

The title compound was prepared from 5-(methoxymethyl)pyridin-2-amine and 2-fluoro-4-methyl-5-[(2-methyl-1,3-thiazole-5-carbonyl)amino]benzoic acid in a similar fashion to Example 1. $^1$H NMR (400 MHz, Methanol-$d_4$) δ 8.28-8.21 (m, 3H), 7.85 (d, J=7.2 Hz, 1H), 7.74 (dd, J=8.5, 2.4 Hz, 1H), 7.12 (d, J=12.0 Hz, 1H), 4.42 (s, 2H), 3.36 (s, 3H), 2.72 (s, 3H), 2.31 (s, 3H). ESI MS [M+H]$^+$ for $C_{20}H_{20}FN_4O_3S_1$, calcd 415.1, found 415.1.

Example 38: N-[5-[[5-(difluoromethoxy)pyridin-2-yl]carbamoyl]-4-fluoro-2-methylphenyl]-2-methyl-1,3-thiazole-5-carboxamide

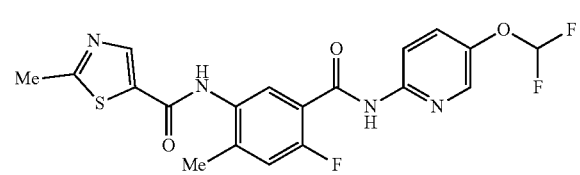 [SMILES: Cc1ncc(C(=O)Nc2cc(C(=O)Nc3ccc(OC(F)F)cn3)c(F)cc2C)s1]

The title compound was prepared from 5-(difluoromethoxy)pyridin-2-amine and 2-fluoro-4-methyl-5-[(2-methyl-1,3-thiazole-5-carbonyl)amino]benzoic acid in a similar fashion to Example 1. $^1$H NMR (400 MHz, Methanol-$d_4$) δ 8.30-8.23 (m, 2H), 8.18-8.12 (m, 1H), 7.82 (d, J=7.2 Hz, 1H), 7.60-7.55 (m, 1H), 7.12 (d, J=11.8 Hz, 1H), 6.64 (t, J=72.9 Hz, 1H), 2.72 (s, 3H), 2.31 (s, 3H). ESI MS [M+H]$^+$ for $C_{19}H_{16}F_3N_4O_3S_1$, calcd 437.1, found 437.1.

Example 39: N-[4-fluoro-2-methyl-5-[[5-(trifluoromethoxy)pyridin-2-yl]carbamoyl]phenyl]-2-methyl-1,3-thiazole-5-carboxamide

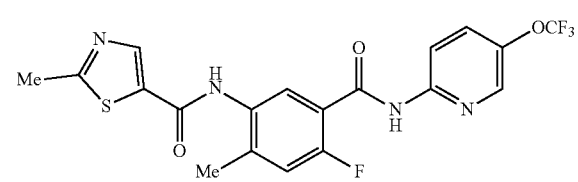 [SMILES: Cc1ncc(C(=O)Nc2cc(C(=O)Nc3ccc(OC(F)(F)F)cn3)c(F)cc2C)s1]

The title compound was prepared from 5-(trifluoromethoxy)pyridin-2-amine and 2-fluoro-4-methyl-5-[(2-methyl-1,3-thiazole-5-carbonyl)amino]benzoic acid in a similar fashion to Example 1. $^1$H NMR (400 MHz, Methanol-$d_4$) δ 8.34 (dd, J=9.1, 0.6 Hz, 1H), 8.26-8.20 (m, 2H), 7.82 (d, J=7.2 Hz, 1H), 7.64 (ddq, J=9.1, 3.0, 1.0 Hz, 1H), 7.11 (d, J=11.8 Hz, 1H), 2.72 (s, 3H), 2.31 (s, 3H). ESI MS [M+H]$^+$ for $C_{19}H_{15}F_4N_4O_3S_1$, calcd 455.1, found 455.1.

Example 40: N-[4-fluoro-2-methyl-5-[(5-propan-2-yloxypyridin-2-yl)carbamoyl]phenyl]-2-methyl-1,3-thiazole-5-carboxamide

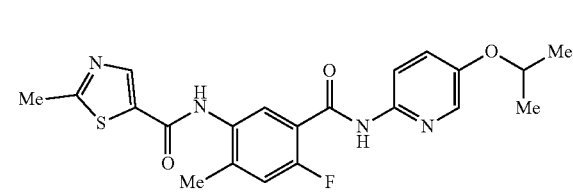 [SMILES: Cc1ncc(C(=O)Nc2cc(C(=O)Nc3ccc(OC(C)C)cn3)c(F)cc2C)s1]

The title compound was prepared from 5-propan-2-yloxypyridin-2-amine and 2-fluoro-4-methyl-5-[(2-methyl-1,3-thiazole-5-carbonyl)amino]benzoic acid in a similar fashion to Example 1. $^1$H NMR (400 MHz, Methanol-$d_4$) δ 8.25 (s, 1H), 8.14 (d, J=9.0 Hz, 1H), 7.92 (dd, J=3.0, 0.6 Hz, 1H), 7.83 (d, J=7.2 Hz, 1H), 7.31 (dd, J=9.1, 3.0 Hz, 1H), 7.11 (d, J=11.9 Hz, 1H), 4.53 (p, J=6.0 Hz, 1H), 2.72 (s, 3H), 2.30 (s, 3H), 1.30 (d, J=6.0 Hz, 6H). ESI MS [M+H]+ for $C_{21}H_{22}FN_4O_3S_1$, calcd 429.1, found 429.1.

Example 41: N-[4-fluoro-2-methyl-5-[[5-(2,2,2-trifluoroethoxy)pyridin-2-yl]carbamoyl]phenyl]-2-methyl-1,3-thiazole-5-carboxamide

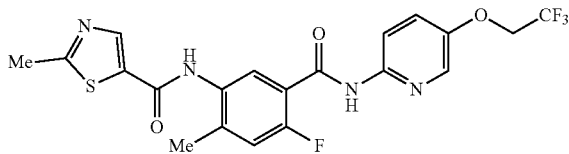 [SMILES: Cc1ncc(C(=O)Nc2cc(C(=O)Nc3ccc(OCC(F)(F)F)cn3)c(F)cc2C)s1]

The title compound was prepared from 5-(2,2,2-trifluoroethoxy)pyridin-2-amine and 2-fluoro-4-methyl-5-[(2-methyl-1,3-thiazole-5-carbonyl)amino]benzoic acid in a similar fashion to Example 1. $^1$H NMR (400 MHz, Methanol-$d_4$) δ 8.26-8.20 (m, 2H), 8.04 (dd, J=3.1, 0.7 Hz, 1H), 7.83 (d, J=7.2 Hz, 1H), 7.42 (dd, J=9.1, 3.1 Hz, 1H), 7.12 (d, J=11.9 Hz, 1H), 4.46 (q, J=8.1 Hz, 2H), 2.72 (s, 3H), 2.31 (s, 3H). ESI MS [M+H]+ for $C_{20}H_{17}F_4N_4O_3S_1$, calcd 469.1, found 469.1.

Example 42: N-[5-[(2-cyclopropylpyrimidin-5-yl)carbamoyl]-4-fluoro-2-methylphenyl]-2-methyl-1,3-thiazole-5-carboxamide

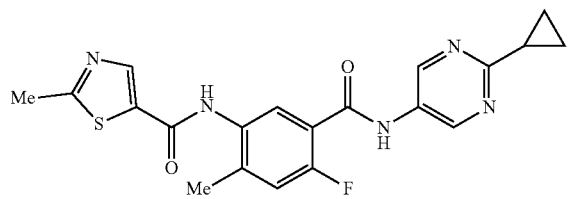 [SMILES: Cc1ncc(C(=O)Nc2cc(C(=O)Nc3cnc(C4CC4)nc3)c(F)cc2C)s1]

The title compound was prepared from 2-cyclopropylpyrimidin-5-amine and 2-fluoro-4-methyl-5-[(2-methyl-1,3-thiazole-5-carbonyl)amino]benzoic acid in a similar fashion to Example 1. $^1$H NMR (400 MHz, Methanol-$d_4$) δ 8.89 (s, 2H), 8.25 (s, 1H), 7.66 (d, J=6.9 Hz, 1H), 7.14-7.06 (m, 1H), 2.72 (s, 3H), 2.31 (s, 3H), 2.21-2.12 (m, 1H), 1.09-0.99 (m, 4H). ESI MS [M+H]+ for $C_{20}H_{19}FN_5O_2S_1$, calcd 412.1, found 412.1.

Example 43: N-[5-[(5-cyclopropylpyrazin-2-yl)carbamoyl]-4-fluoro-2-methylphenyl]-2-methyl-1,3-thiazole-5-carboxamide

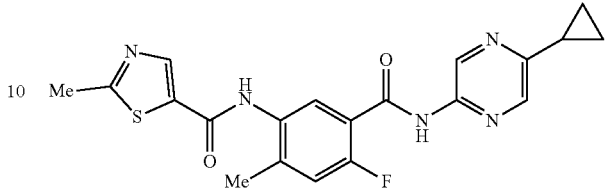

The title compound was prepared from 5-cyclopropylpyrazin-2-amine and 2-fluoro-4-methyl-5-[(2-methyl-1,3-thiazole-5-carbonyl)amino]benzoic acid in a similar fashion to Example 1. $^1$H NMR (400 MHz, Methanol-$d_4$) δ 9.31 (d, J=1.5 Hz, 1H), 8.25 (s, 1H), 8.19 (d, J=1.5 Hz, 1H), 7.80 (d, J=7.1 Hz, 1H), 7.12 (d, J=11.7 Hz, 1H), 2.72 (s, 3H), 2.31 (s, 3H), 2.05 (tt, J=8.1, 5.0 Hz, 1H), 1.06-0.94 (m, 4H). ESI MS [M+H]+ for $C_{20}H_{19}FN_5O_2S_1$, calcd 412.1, found 412.1.

Example 44: N-[5-[(5-cyclopropylpyrimidin-2-yl)carbamoyl]-4-fluoro-2-methylphenyl]-2-methyl-1,3-thiazole-5-carboxamide The title compound was prepared from 5-cyclopropylpyrimidin-2-amine and 2-fluoro-4-methyl-5-[(2-methyl-1,3-thiazole-5-carbonyl)amino]benzoic acid in a similar fashion to Example 1. $^1$H NMR (400 MHz, Methanol-$d_4$) δ 8.35 (s, 2H), 8.25 (d, J=3.1 Hz, 1H), 7.80 (d, J=7.1 Hz, 1H), 7.11 (d, J=11.8 Hz, 1H), 2.72 (s, 3H), 2.30 (s, 3H), 1.85 (tt, J=8.6, 5.1 Hz, 1H), 1.08-1.00 (m, 2H), 0.75-0.70 (m, 2H). ESI MS [M+H]+ for $C_{20}H_{19}FN_5O_2S_1$, calcd 412.1, found 412.1.

Example 45: N-[5-[[5-(2,2-difluoroethyl)pyridin-2-yl]carbamoyl]-4-fluoro-2-methylphenyl]-2-methyl-1,3-thiazole-5-carboxamide

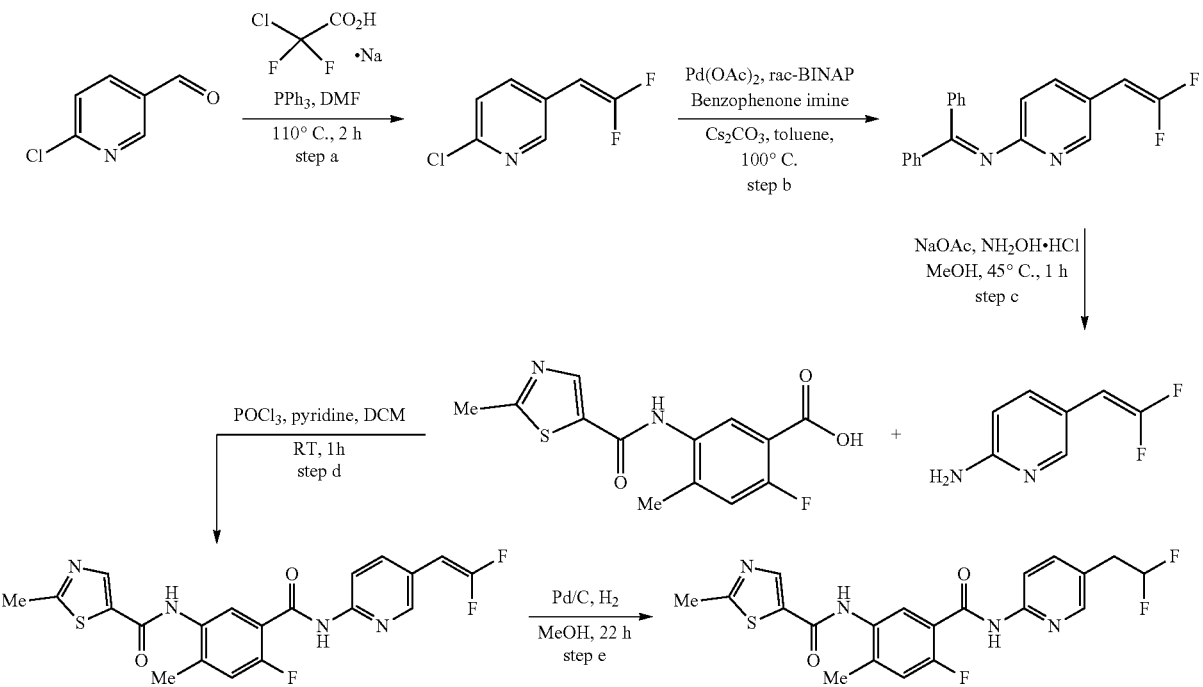

Step a: A round-bottom flask was charged with 6-chloropyridine-3-carbaldehyde (1 g, 7.0 mmol, 1.0 equiv.), PPh$_3$ (2.75 g, 10.5 mmol, 1.5 equiv.), and DMF (20 mL, 0.35 M). Sodium 2-chloro-2,2-difluoroacetate (1.3 g, 8.4 mmol, 1.2 equiv.) was added portionwise and the reaction mixture was warmed up to 110° C. and stirred for 2 h, at which time no further evolution of CO$_2$ gas was observed. The reaction mixture was quenched by water (20 mL), extracted with EtOAc (20 mL×2). The organic layer was collected, dried over Na$_2$SO$_4$ and concentrated in vacuo. The residue was purified using column chromatography on silica gel (EtOAc in hexane, 0%-20%) to afford 2-chloro-5-(2,2-difluoroethenyl)pyridine.

Step b: A round-bottom flask was charged with product from step a (890 mg, 5 mmol, 1.0 equiv.), Pd(OAc)$_2$ (56 mg, 0.25 mmol, 0.05 equiv.), rac-BINAP (311 mg, 0.5 mmol, 0.1 equiv.), benzophenone imine (1.1 g, 6 mmol, 1.2 equiv.), Cs$_2$CO$_3$ (3.26 g, 10 mmol, 2.0 equiv.), and toluene (25 mL, 0.2 M) under N$_2$ gas. The reaction mixture was stirred at 100° C. and cooled down when LC/MS analysis indicated complete consumption of starting material. The reaction mixture was filtrated with Celite® and concentrated in vacuo. The residue was purified using column chromatography on silica gel (EtOAc in hexane, 0%-20%) to afford N-[5-(2,2-difluoroethenyl)pyridin-2-yl]-1,1-diphenylmethanimine.

Step c: A round-bottom flask was charged with product from step b (1.53 g, 4.78 mmol, 1.0 equiv.), NaOAc (980 mg, 12 mmol, 2.5 equiv.), NH$_2$OH·HCl (664 mg, 9.5 mmol, 2.0 equiv.), and MeOH (12 mL, 0.4 M). The reaction mixture was stirred at 45° C. for 1 h, at which time LC/MS analysis showed complete consumption of starting material. The reaction mixture was concentrated in vacuo, purified using column chromatography on silica gel (MeOH in DCM, 0% 10%) to afford 5-(2,2-difluoroethenyl)pyridin-2-amine.

Step d: A vial was charged with product from step c (193 mg, 1.23 mmol, 1.0 equiv.), 2-fluoro-4-methyl-5-[(2-methyl-1,3-thiazole-5-carbonyl)amino]benzoic acid (365 mg, 1.23 mmol, 1.0 equiv.), and DCM (6 mL, 0.2 M) under N$_2$ gas. Pyridine (1 mL, 12.3 mmol, 10 equiv.) was added and the reaction mixture was allowed to stir at RT. After 5 min., POCl$_3$ (0.23 mL, 2.4 mmol, 2 equiv.) was added dropwise. The reaction mixture was continued to stir at RT for 1 h, at which time LC/MS analysis showed complete consumption of starting material. The reaction was quenched with water and concentrated in vacuo. The residue was purified by reverse phase HPLC to afford N-[5-[[5-(2,2-difluoroethenyl)pyridin-2-yl]carbamoyl]-4-fluoro-2-methylphenyl]-2-methyl-1,3-thiazole-5-carboxamide.

Step e: A round-bottom flask was charged with product from step d (90 mg, 0.2 mmol, 1.0 equiv.), followed by MeOH (5 mL, 0.04 M), and Pd/C (20 wt. %, 18 mg). The reaction mixture was shaken under 20 psi of hydrogen gas for 22 h, at which time LC/MS analysis indicated complete consumption of starting material. The reaction mixture was filtered over Celite® and concentrated in vacuo. The residue was purified by reverse phase HPLC to afford the title compound. $^1$H NMR (400 MHz, Methanol-d$_4$) δ 8.27-8.16 (m, 3H), 7.84 (d, J=7.2 Hz, 1H), 7.69 (d, J=8.6 Hz, 1H), 7.14 (d, J=11.9 Hz, 1H), 5.94 (ddd, J=56.3, 52.1, 4.2 Hz, 1H), 3.12 (td, J=17.6, 4.1 Hz, 2H), 2.73 (s, 3H), 2.32 (s, 3H). ESI MS [M+H]$^+$ for C$_{20}$H$_{18}$F$_3$N$_4$O$_2$S$_1$, calcd 435.1, found 435.1.

Example 46: N-[2-chloro-4-fluoro-5-[[5-(2,2,2-trifluoroethyl)pyridin-2-yl]carbamoyl]phenyl]-2-methyl-1,3-thiazole-5-carboxamide

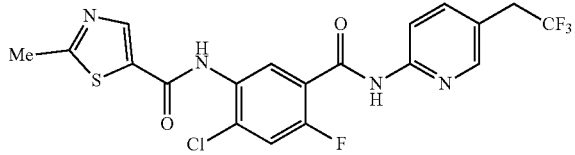

The title compound was prepared from 5-(2,2,2-trifluoroethyl)pyridin-2-amine and 4-chloro-2-fluoro-5-[(2-methyl-1,3-thiazole-5-carbonyl)amino]benzoic acid in a similar fashion to Example 1. $^1$H NMR (400 MHz, Methanol-$d_4$) δ 8.28-8.24 (m, 2H), 8.22 (s, 1H), 8.15 (d, J=7.3 Hz, 1H), 7.76-7.70 (m, 1H), 7.39 (d, J=10.4 Hz, 1H), 3.40 (q, J=10.7 Hz, 2H), 2.73 (s, 3H). ESI MS [M+H]$^+$ for $C_{19}H_{14}ClF_4N_4O_2S_1$, calcd 473.1, found 473.1.

Example 47: N-[2-chloro-4-fluoro-5-[[5-(methoxymethyl)pyridin-2-yl]carbamoyl]phenyl]-2-methyl-1,3-thiazole-5-carboxamide

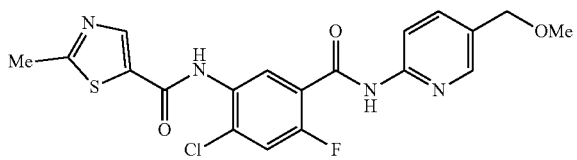 [SMILES: COCc1ccc(NC(=O)c2cc(NC(=O)c3cnc(C)s3)c(Cl)cc2F)nc1]

The title compound was prepared from 5-(methoxymethyl)pyridin-2-amine and 4-chloro-2-fluoro-5-[(2-methyl-1,3-thiazole-5-carbonyl)amino]benzoic acid in a similar fashion to Example 1. $^1$H NMR (400 MHz, Methanol-$d_4$) δ 8.27 (s, 1H), 8.26-8.22 (m, 2H), 8.17 (d, J=7.4 Hz, 1H), 7.75 (dd, J=8.7, 2.2 Hz, 1H), 7.39 (d, J=10.3 Hz, 1H), 4.42 (s, 2H), 3.37 (s, 3H), 2.73 (s, 3H). ESI MS [M+H]$^+$ for $C_{19}H_{17}ClFN_4O_3S_1$, calcd 435.1, found 435.1.

Example 48: N-[2-chloro-4-fluoro-5-[(5-propan-2-yloxypyridin-2-yl)carbamoyl]phenyl]-2-methyl-1,3-thiazole-5-carboxamide

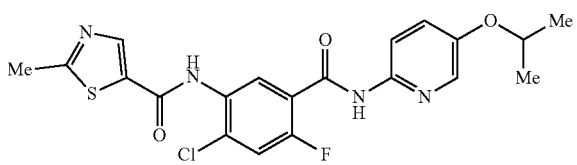 [SMILES: Cc1ncc(C(=O)Nc2cc(C(=O)Nc3ccc(OC(C)C)cn3)c(F)cc2Cl)s1]

The title compound was prepared from 5-propan-2-yloxy-pyridin-2-amine and 4-chloro-2-fluoro-5-[(2-methyl-1,3-thiazole-5-carbonyl)amino]benzoic acid in a similar fashion to Example 1. $^1$H NMR (400 MHz, Methanol-$d_4$) δ 8.27 (s, 1H), 8.14 (t, J=8.3 Hz, 2H), 7.92 (d, J=2.9 Hz, 1H), 7.38 (d, J=10.3 Hz, 1H), 7.31 (dd, J=9.1, 3.0 Hz, 1H), 4.54 (p, J=6.1 Hz, 1H), 2.73 (s, 3H), 1.30 (d, J=6.1 Hz, 6H). ESI MS [M+H]$^+$ for $C_{20}H_{19}ClFN_4O_3S_1$, calcd 449.1, found 449.1.

Example 49: N-[2-chloro-5-[(5-cyclopropyloxypyridin-2-yl)carbamoyl]-4-fluorophenyl]-2-methyl-1,3-thiazole-5-carboxamide

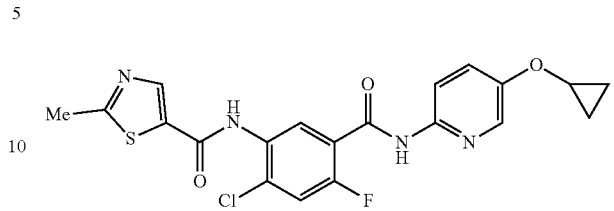

The title compound was prepared from 5-cyclopropyloxy-pyridin-2-amine and 4-chloro-2-fluoro-5-[(2-methyl-1,3-thiazole-5-carbonyl)amino]benzoic acid in a similar fashion to Example 1. $^1$H NMR (400 MHz, Methanol-$d_4$) δ 8.27 (s, 1H), 8.16 (dd, J=8.3, 3.7 Hz, 2H), 8.05 (dd, J=3.0, 0.7 Hz, 1H), 7.46 (dd, J=9.1, 3.0 Hz, 1H), 7.38 (d, J=10.4 Hz, 1H), 3.81-3.75 (m, 1H), 2.73 (s, 3H), 0.82-0.76 (m, 2H), 0.75-0.69 (m, 2H). ESI MS [M+H]$^+$ for $C_{20}H_{17}ClFN_4O_3S_1$, calcd 447.1, found 447.1.

Example 50: N-(5-((6-(cyclopropylmethyl)pyrimidin-4-yl)carbamoyl)-4-fluoro-2-methylphenyl)-2-methylthiazole-5-carboxamide

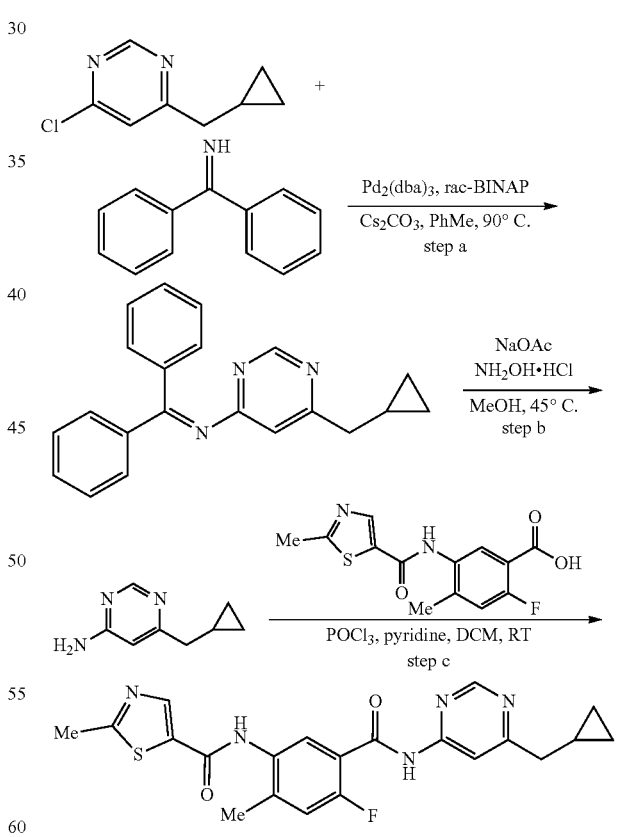

Step a and Step b were performed in an analogous manner to Example 1, steps c and d.

Step c: The title compound was prepared from 6-(cyclopropylmethyl)pyrimidin-4-amine and 2-fluoro-4-methyl-5-[(2-methyl-1,3-thiazole-5-carbonyl)amino]benzoic acid in a similar fashion to Example 1. $^1$H NMR (400 MHz, DMSO-d$_6$) δ 11.04 (s, 1H), 10.09 (s, 1H), 8.75 (s, 1H), 8.34 (s, 1H), 8.10 (s, 1H), 7.58 (d, J=6.8 Hz, 1H), 7.26 (d, J=11.0 Hz, 1H), 2.64 (s, 3H), 2.58 (d, J=7.1 Hz, 2H), 2.22 (s, 3H), 1.08-0.97 (m, 1H), 0.46 (d, J=7.7 Hz, 2H), 0.18 (d, J=5.0 Hz, 2H). $^{19}$F NMR (376 MHz, DMSO-d$_6$) δ −116.41. ESI MS [M+H]$^+$ for C$_{21}$H$_{21}$F$_1$N$_5$O$_2$S$_1$, calcd 426.1, found 426.1.

Example 51: N-(4-fluoro-5-((2-fluorobenzyl)carbamoyl)-2-methylphenyl)-2-methylthiazole-5-carboxamide

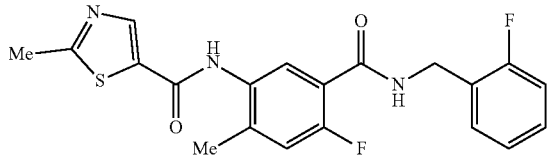 [SMILES: Cc1ncc(C(=O)Nc2cc(C(=O)NCc3ccccc3F)c(F)cc2C)s1]

The title compound was prepared from (2-fluorophenyl)methanamine and 2-fluoro-4-methyl-5-[(2-methyl-1,3-thiazole-5-carbonyl)amino]benzoic acid in a similar fashion to Example 1. $^1$H NMR (400 MHz, Methanol-d$_4$) δ 8.28 (s, 1H), 7.63 (d, J=6.9 Hz, 1H), 7.38 (t, J=7.7 Hz, 1H), 7.26 (q, J=7.2 Hz, 1H), 7.19-7.03 (m, 3H), 4.60 (s, 2H), 2.75-2.68 (m, 3H), 2.29 (s, 3H). ESI MS [M+H]$^+$ for C$_{20}$H$_{18}$F$_2$N$_3$O$_2$S$_1$, calcd 402.1, found 402.1.

Example 52: N-[4-fluoro-2-methyl-5-[[6-(2,2,2-trifluoroethyl)pyridin-2-yl]carbamoyl]phenyl]-2-methyl-1,3-thiazole-5-carboxamide

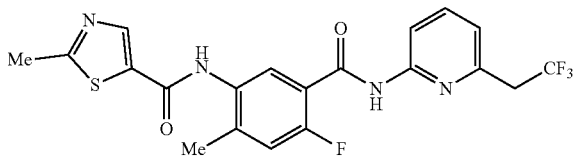 [SMILES: Cc1ncc(C(=O)Nc2cc(C(=O)Nc3cccc(CC(F)(F)F)n3)c(F)cc2C)s1]

The title compound was prepared from 6-(2,2,2-trifluoroethyl)pyridin-2-amine and 2-fluoro-4-methyl-5-[(2-methyl-1,3-thiazole-5-carbonyl)amino]benzoic acid in a similar fashion to Example 1. $^1$H NMR (400 MHz, DMSO-d$_6$) δ 10.69 (s, 1H), 10.08 (s, 1H), 8.34 (s, 1H), 8.10 (d, J=8.3 Hz, 1H), 7.83 (t, J=7.9 Hz, 1H), 7.57 (d, J=6.8 Hz, 1H), 7.21 (dd, J=18.8, 9.3 Hz, 2H), 3.69 (q, J=11.4 Hz, 2H), 2.65 (s, 3H), 2.22 (s, 3H). ESI MS [M+H]$^+$ for C$_{20}$H$_{17}$F$_4$N$_4$O$_2$S$_1$, calcd 453.1, found 453.0.

Example 53: N-[5-[(5-cyclopropylpyridin-3-yl)carbamoyl]-4-fluoro-2-methylphenyl]-2-methyl-1,3-thiazole-5-carboxamide

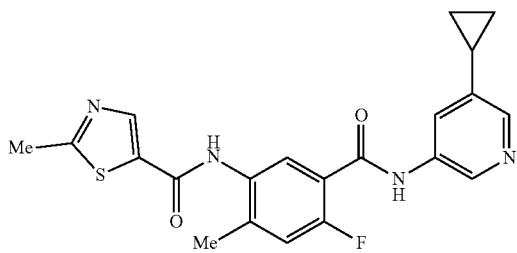 [SMILES: Cc1ncc(C(=O)Nc2cc(C(=O)Nc3cncc(C4CC4)c3)c(F)cc2C)s1]

The title compound was prepared from 5-cyclopropylpyridin-3-amine and 2-fluoro-4-methyl-5-[(2-methyl-1,3-thiazole-5-carbonyl)amino]benzoic acid in a similar fashion to Example 1. $^1$H NMR (400 MHz, DMSO-d$_6$) δ 10.40 (s, 1H), 10.10 (s, 1H), 8.58 (d, J=2.4 Hz, 1H), 8.34 (s, 1H), 8.10 (d, J=2.0 Hz, 1H), 7.71 (d, J=2.2 Hz, 1H), 7.55 (d, J=6.8 Hz, 1H), 7.28 (d, J=10.9 Hz, 1H), 2.65 (s, 3H), 2.44 (t, J=1.9 Hz, 3H), 1.92 (d, J=5.4 Hz, 1H), 0.96 (dd, J=8.4, 2.2 Hz, 2H), 0.65 (dt, J=6.6, 4.6 Hz, 2H). ESI MS [M+H]$^+$ for C$_{21}$H$_{20}$FN$_4$O$_2$S$_1$, calcd 411.1, found 411.0.

Example 54: N-[5-[[6-(difluoromethyl)pyridin-3-yl]carbamoyl]-4-fluoro-2-methylphenyl]-2-methyl-1,3-thiazole-5-carboxamide

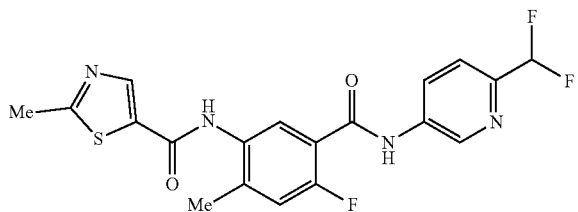 [SMILES: Cc1ncc(C(=O)Nc2cc(C(=O)Nc3ccc(C(F)F)nc3)c(F)cc2C)s1]

The title compound was prepared from 6-(difluoromethyl)pyridin-3-amine and 2-fluoro-4-methyl-5-[(2-methyl-1,3-thiazole-5-carbonyl)amino]benzoic acid in a similar fashion to Example 1. $^1$H NMR (400 MHz, DMSO-d$_6$) δ 10.75 (s, 1H), 10.11 (s, 1H), 8.87 (s, 1H), 8.33 (s, 1H), 8.28 (d, J=8.7 Hz, 1H), 7.65 (d, J=8.6 Hz, 1H), 7.57 (d, J=6.8 Hz, 1H), 7.29 (d, J=10.8 Hz, 1H), 6.86 (t, J=55.1 Hz, 1H), 2.64 (s, 3H), 2.22 (s, 3H). ESI MS [M+H]$^+$ for C$_{19}$H$_{16}$F$_3$N$_4$O$_2$S$_1$, calcd 421.1, found 421.0.

Example 55: N-[4-fluoro-2-methyl-5-[[6-(trifluoromethyl)pyridin-2-yl]carbamoyl]phenyl]-2-methyl-1,3-thiazole-5-carboxamide

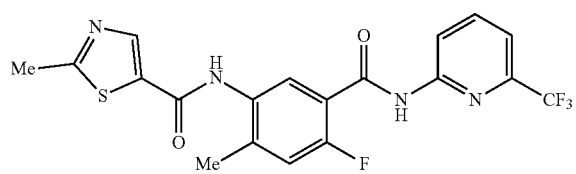 [SMILES: Cc1ncc(C(=O)Nc2cc(C(=O)Nc3cccc(C(F)(F)F)n3)c(F)cc2C)s1]

The title compound was prepared from 6-(trifluoromethyl)pyridin-2-amine and 2-fluoro-4-methyl-5-[(2-methyl-1,3-thiazole-5-carbonyl)amino]benzoic acid in a similar fashion to Example 1. $^1$H NMR (400 MHz, DMSO-d$_6$) δ 11.17 (s, 1H), 10.08 (s, 1H), 8.69-8.27 (m, 2H), 8.08 (t, J=8.0 Hz, 1H), 7.59 (dd, J=10.7, 7.2 Hz, 2H), 7.24 (d, J=11.0 Hz, 1H), 2.64 (s, 3H), 2.22 (s, 3H). ESI MS [M+H]$^+$ for C$_{19}$H$_{15}$F$_4$N$_4$O$_2$S$_1$, calcd 439.1, found 439.1.

Example 56: N-[5-[[5-(difluoromethyl)pyrazin-2-yl]carbamoyl]-4-fluoro-2-methylphenyl]-2-methyl-1,3-thiazole-5-carboxamide

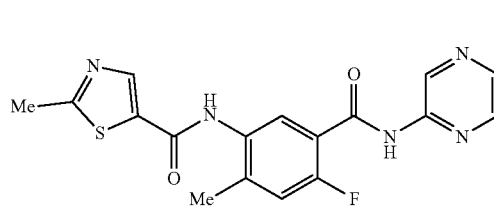

The title compound was prepared from 5-(difluoromethyl)pyrazin-2-amine and 2-fluoro-4-methyl-5-[(2-methyl-1,3-thiazole-5-carbonyl)amino]benzoic acid in a similar fashion to Example 1. $^1$H NMR (400 MHz, DMSO-d$_6$) δ 11.37 (s, 1H), 10.10 (s, 1H), 9.42 (d, J=1.4 Hz, 1H), 8.70 (s, 1H), 8.35 (s, 1H), 7.62 (d, J=6.8 Hz, 1H), 7.28 (d, J=11.0 Hz, 1H), 7.04 (t, J=54.4 Hz, 1H), 2.65 (s, 3H), 2.24 (s, 3H). ESI MS [M+H]$^+$ for C$_{18}$H$_{15}$F$_3$N$_5$O$_2$S$_1$, calcd 422.1, found 422.0.

Example 57: N-[4-Fluoro-2-methyl-5-(3-morpholin-4-ylpropylcarbamoyl)phenyl]-2-methyl-1,3-thiazole-5-carboxamide

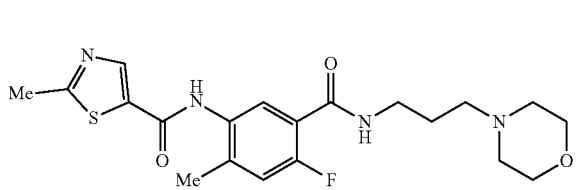 [SMILES: Cc1ncc(C(=O)Nc2cc(C(=O)NCCCN3CCOCC3)c(F)cc2C)s1]

The title compound was prepared from methyl 2-fluoro-4-methyl-5-(2-methylthiazole-5-carboxamido)benzoate and 3-morpholin-4-ylpropan-1-amine in a similar fashion to Example 3. $^1$H NMR (400 MHz, DMSO-d$_6$) δ 10.11 (s, 1H), 8.39 (s, 1H), 8.35-8.25 (m, 1H), 7.54 (d, J=7.1 Hz, 1H), 7.25 (d, J=11.2 Hz, 1H), 3.56 (t, J=4.6 Hz, 4H), 3.28 (q, J=6.4 Hz, 2H), 2.71 (s, 3H), 2.38-2.29 (m, 6H), 2.25 (s, 3H), 1.66 (p, J=7.1 Hz, 2H). ESI MS [M+H]$^+$ for C$_{20}$H$_{26}$F$_1$N$_4$O$_3$S$_1$, calcd 421.2, found 421.2.

Example 58: N-[5-[[5-[[(1S)-2,2-difluorocyclopropyl]methoxy]pyrazin-2-yl]carbamoyl]-4-fluoro-2-methylphenyl]-2-methyl-1,3-thiazole-5-carboxamide

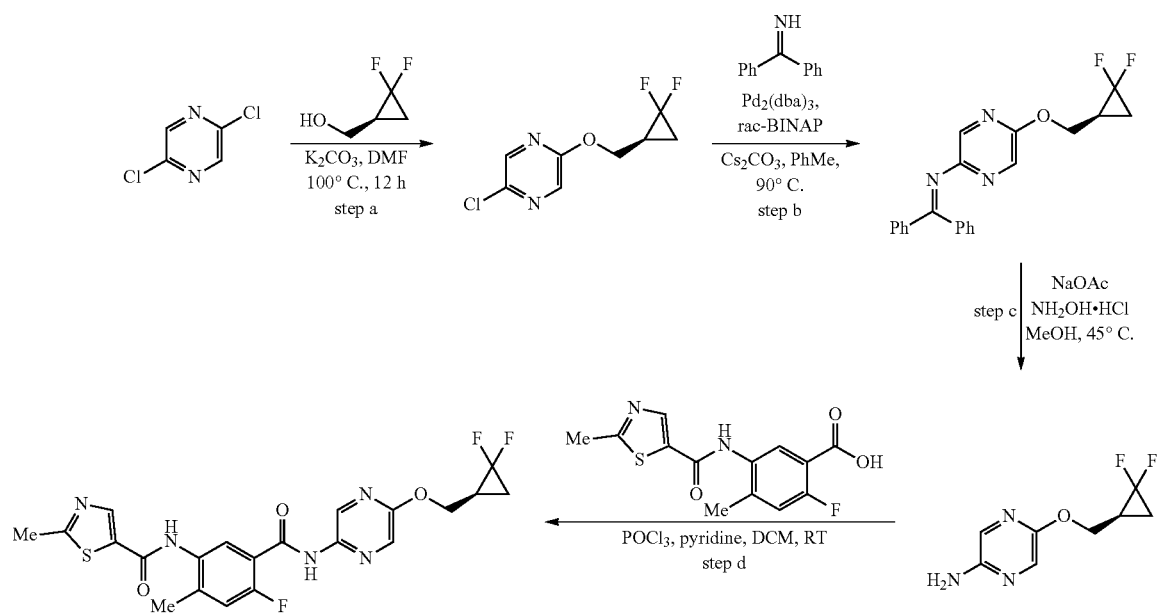

Step a, b and c were performed in an analogous manner to Example 4.

Step d. The title compound was prepared from 5-[[(1S)-2,2-difluorocyclopropyl]methoxy]pyrazin-2-mine and 2-fluoro-4-methyl-5-[(2-methyl-1,3-thiazole-5-carbonyl)amino]benzoic acid in a similar fashion to Example 1. $^1$H NMR (400 MHz, DMSO-$d_6$) δ 10.84 (d, J=1.7 Hz, 1H), 10.13 (s, 1H), 8.93 (d, J=1.5 Hz, 1H), 8.41 (s, 1H), 8.21 (d, J=1.4 Hz, 1H), 7.65 (d, J=6.9 Hz, 1H), 7.32 (d, J=11.0 Hz, 1H), 4.51 (ddd, J=10.1, 6.5, 3.0 Hz, 1H), 4.25 (ddd, J=11.2, 8.7, 1.8 Hz, 1H), 2.71 (s, 3H), 2.29 (s, 3H), 2.22 (m, 1H), 1.73 (dtd, J=12.2, 7.6, 3.9 Hz, 1H), 1.56 (ddd, J=13.8, 7.6, 4.2 Hz, 1H). ESI MS [M+H]$^+$ for $C_{21}H_{19}F_3N_5O_3S$, calcd 478.1, found 478.2.

Example 59: N-[5-[(5-Cyclopropyloxypyridin-2-yl)carbamoyl]-4-fluoro-2-methylphenyl]-2-(difluoromethyl)-1,3-thiazole-5-carboxamide

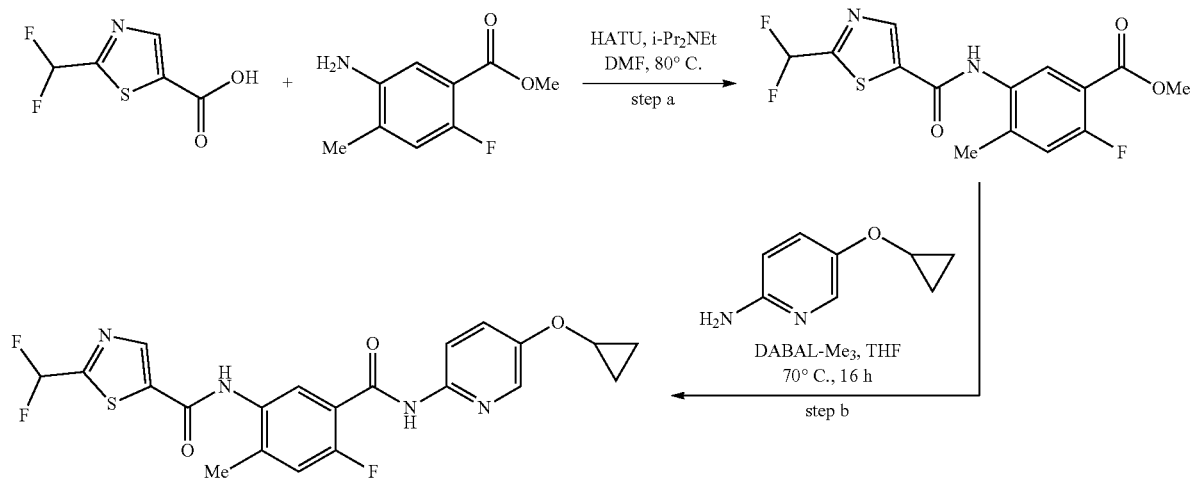 [SMILES: O=C(O)c1cnc(C(F)F)s1 ; COC(=O)c1cc(N)c(C)cc1F ; COC(=O)c1cc(NC(=O)c2cnc(C(F)F)s2)c(C)cc1F ; Nc1ccc(OC2CC2)cn1 ; Cc1cc(F)c(C(=O)Nc2ccc(OC3CC3)cn2)cc1NC(=O)c1cnc(C(F)F)s1]

Step a: A vial was charged with 2-(difluoromethyl)-1,3-thiazole-5-carboxylic acid (76 mg, 0.424 mmol, 1.0 equiv.), methyl 5-amino-2-fluoro-4-methylbenzoate (78 mg, 0.424 mmol, 1.0 equiv.), and HATU (242 mg, 0.636 mmol, 1.5 equiv.). DMF (1.2 mL) was added, followed by i-Pr$_2$NEt (0.23 mL, 1.27 mmol, 3.0 equiv.). The reaction mixture was stirred at 80° C. for 14 h, at which time LC/MS analysis showed complete consumption of starting material. The reaction mixture was cooled to RT and diluted with water. The precipitated solid was collected by vacuum filtration, rinsed with water, and dried in vacuo to afford methyl 5-[[2-(difluoromethyl)-1,3-thiazole-5-carbonyl]amino]-2-fluoro-4-methylbenzoate.

Step b: The title compound was prepared from methyl 5-[[2-(difluoromethyl)-1,3-thiazole-5-carbonyl]amino]-2-fluoro-4-methylbenzoate and 5-cyclopropyloxypyridin-2-amine in a similar fashion to Example 3. $^1$H NMR (400 MHz, DMSO-$d_6$) δ 10.57 (d, J=2.4 Hz, 1H), 10.45 (s, 1H), 8.73 (s, 1H), 8.15 (dd, J=3.0, 0.6 Hz, 1H), 8.11 (d, J=9.0 Hz, 1H), 7.67 (d, J=6.9 Hz, 1H), 7.59 (dd, J=9.0, 3.0 Hz, 1H), 7.41 (t, J=53.9 Hz, 1H), 7.32 (d, J=11.0 Hz, 1H), 3.95 (tt, J=6.0, 2.9 Hz, 1H), 2.30 (s, 3H), 0.88-0.77 (m, 2H), 0.77-0.64 (m, 2H). ESI MS [M+H]$^+$ for $C_{21}H_{18}F_3N_4O_3S_1$, calcd 463.1, found 463.1.

Example 60: 2-Cyclopropyl-N-[5-[(5-cyclopropyloxypyridin-2-yl)carbamoyl]-4-fluoro-2-methylphenyl]-1,3-thiazole-5-carboxamide

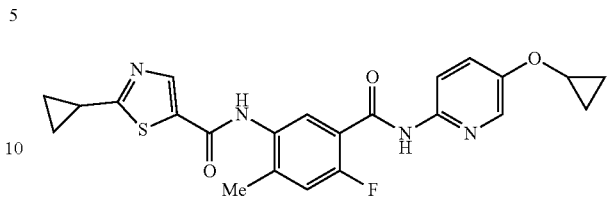

The title compound was prepared from 2-cyclopropyl-1,3-thiazole-5-carboxylic acid, methyl 5-amino-2-fluoro-4-methylbenzoate, and 5-cyclopropyloxypyridin-2-amine in a similar fashion to Example 59. $^1$H NMR (400 MHz, DMSO-$d_6$) δ 10.55 (d, J=2.4 Hz, 1H), 10.11 (s, 1H), 8.36 (s, 1H), 8.15 (d, J=3.0 Hz, 1H), 8.11 (d, J=9.1 Hz, 1H), 7.63-7.56 (m, 2H), 7.29 (d, J=11.1 Hz, 1H), 3.95 (tt, J=6.0, 2.9 Hz, 1H), 2.47 (dd, J=8.1, 4.7 Hz, 1H), 2.27 (s, 3H), 1.18 (dt, J=8.0, 3.3 Hz, 2H), 1.07-1.01 (m, 2H), 0.84-0.77 (m, 2H), 0.75-0.65 (m, 2H). ESI MS [M+H]$^+$ for $C_{23}H_{22}F_1N_4O_3S_1$, calcd 453.1, found 453.1.

Example 61: N-[5-[(1-Cyclobutylpyrazol-3-yl)carbamoyl]-4-fluoro-2-methylphenyl]-2-methyl-1,3-thiazole-5-carboxamide

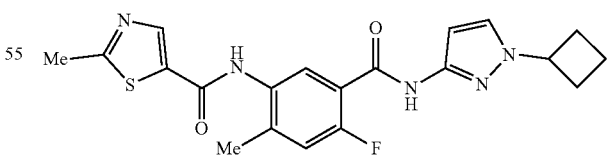

The title compound was prepared from methyl 2-fluoro-4-methyl-5-(2-methylthiazole-5-carboxamido)benzoate and 1-cyclobutylpyrazol-3-amine in a similar fashion to Example 3. $^1$H NMR (400 MHz, DMSO-$d_6$) δ 10.77 (s, 1H), 10.12 (s, 1H), 8.40 (s, 1H), 7.72 (d, J=2.3 Hz, 1H), 7.58 (d, J=6.8 Hz, 1H), 7.27 (d, J=10.9 Hz, 1H), 6.57 (d, J=2.3 Hz, 1H), 4.75 (p, J=8.3 Hz, 1H), 2.71 (s, 3H), 2.44 (td, J=9.5, 2.6

Hz, 2H), 2.36 (ddt, J=11.1, 8.0, 3.4 Hz, 2H), 2.27 (s, 3H), 1.82-1.70 (m, 2H). ESI MS [M+H]⁺ for $C_{20}H_{21}F_1N_5O_2S_1$, calcd 414.1, found 414.2.

Example 62: N-[5-[(5-Cyclopropyloxy-6-methylpyridin-2-yl)carbamoyl]-4-fluoro-2-methylphenyl]-2-methyl-1,3-thiazole-5-carboxamide

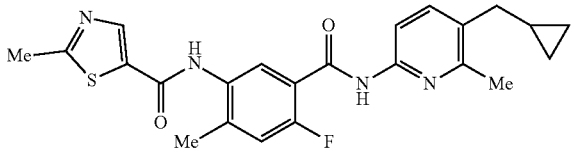 [SMILES: Cc1ncc(C(=O)Nc2cc(C(=O)Nc3ccc(CC4CC4)c(C)n3)c(F)cc2C)s1]

The title compound was prepared from methyl 2-fluoro-4-methyl-5-(2-methylthiazole-5-carboxamido)benzoate and 5-cyclopropyloxy-6-methylpyridin-2-amine in a similar fashion to Example 3. ¹H NMR (400 MHz, DMSO-d₆) δ 10.43 (d, J=2.7 Hz, 1H), 10.13 (s, 1H), 8.41 (s, 1H), 7.99 (d, J=8.8 Hz, 1H), 7.68 (d, J=8.9 Hz, 1H), 7.63 (d, J=6.9 Hz, 1H), 7.28 (d, J=11.1 Hz, 1H), 3.90 (dt, J=6.1, 3.3 Hz, 1H), 2.71 (s, 3H), 2.28 (s, 3H), 2.27 (s, 3H), 0.85-0.77 (m, 2H), 0.72-0.65 (m, 2H). ESI MS [M+H]⁺ for $C_{22}H_{22}F_1N_4O_3S_1$, calcd 441.1, found 441.1.

Example 63: N-[4-Fluoro-2-methyl-5-[(1-propan-2-ylpyrazol-3-yl)carbamoyl]phenyl]-2-methyl-1,3-thiazole-5-carboxamide

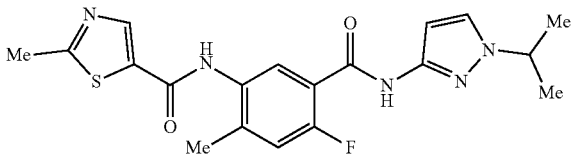 [SMILES: Cc1ncc(C(=O)Nc2cc(C(=O)Nc3ccn(C(C)C)n3)c(F)cc2C)s1]

The title compound was prepared from methyl 2-fluoro-4-methyl-5-(2-methylthiazole-5-carboxamido)benzoate and 1-propan-2-ylpyrazol-3-amine in a similar fashion to Example 3. ¹H NMR (400 MHz, DMSO-d₆) δ 10.73 (s, 1H), 10.12 (s, 1H), 8.40 (s, 1H), 7.68 (d, J=2.3 Hz, 1H), 7.57 (d, J=6.8 Hz, 1H), 7.26 (d, J=10.9 Hz, 1H), 6.56 (d, J=2.3 Hz, 1H), 4.41 (p, J=6.6 Hz, 1H), 2.71 (s, 3H), 2.27 (s, 3H), 1.40 (d, J=6.6 Hz, 6H). ESI MS [M+H]⁺ for $C_{19}H_{21}F_1N_5O_2S_1$, calcd 402.1, found 402.2.

Example 64: N-[4-fluoro-2-methyl-5-[[1-(2-methylpropyl)pyrazol-3-yl]carbamoyl]phenyl]-2-methyl-1,3-thiazole-5-carboxamide

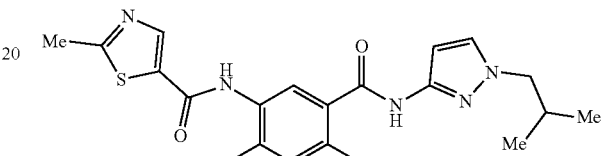

The title compound was prepared from 1-(2-methylpropyl)pyrazol-3-amine and 2-fluoro-4-methyl-5-[(2-methyl-1,3-thiazole-5-carbonyl)amino]benzoic acid in a similar fashion to Example 3. ¹H NMR (400 MHz, DMSO-d₆) δ 10.64 (s, 1H), 10.05 (s, 1H), 8.33 (s, 1H), 7.59-7.45 (m, 2H), 7.19 (d, J=10.9 Hz, 1H), 6.50 (d, J=2.2 Hz, 1H), 3.75 (d, J=7.2 Hz, 2H), 2.63 (s, 3H), 2.19 (s, 3H), 2.08-1.94 (m, 1H), 0.76 (d, J=6.6 Hz, 6H). ESI MS [M+H]⁺ for $C_{20}H_{23}FN_5O_2S$, calcd 416.1, found 416.1.

Example 65: N-[5-[[5-(cyclopropylmethoxy)pyridin-2-yl]carbamoyl]-4-fluoro-2-methylphenyl]-2-methyl-1,3-thiazole-5-carboxamide

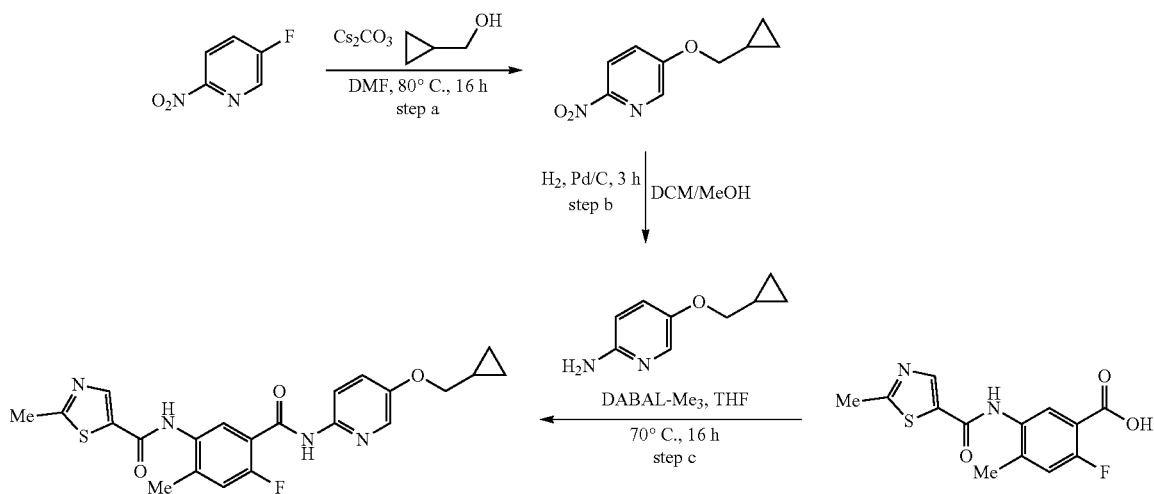

The title compound was prepared from methyl 2-fluoro-4-methyl-5-(2-methylthiazole-5-carboxamido)benzoate and Step a: the mixture of 5-fluoro-2-nitropyridine (0.5 g, 3.5 mmol, 1.0 equiv.), cyclopropylmethanol (279 mg, 3.9 mmol, 1.1 equiv.) and Cs₂CO₃ (1.7 g, 5.3 mmol, 1.5 equiv.) in DMF (7 mL) was heated at 80° C. for 16 h. The resulting reaction mixture was diluted with water and extracted three times with EtOAc. The combined organic layers were washed with water, dried over Na₂SO₄, filtered, and concentrated in vacuo to afford the crude product, which was purified by column chromatography (EtOAc/hexanes, 10% to 60%) to provide 5-(cyclopropylmethoxy)-2-nitropyridine.

Step b: The mixture of 5-(cyclopropylmethoxy)-2-nitropyridine (0.44 g, 2.3 mmol), 10% Pd/C (200 mg) in DCM/MeOH (8 mL/2 mL) was flushed with N₂ three times, followed by H₂ three times. After being stirred with H₂ balloon for 3 h, the reaction mixture was filtered through Celite®. The Celite® plug was washed MeOH. The combined organic layers were concentrated in vacuo to afford the crude product, which was used directly for the next reaction without further purification.

Step c was performed in an analogous manner to Example 3. The crude product was purified by reverse phase HPLC to afford the title compound. ¹H NMR (400 MHz, Methanol-d₄) δ 8.30 (s, 1H), 8.11 (d, J=9.0 Hz, 1H), 7.99 (d, J=2.9 Hz, 1H), 7.77 (d, J=7.0 Hz, 1H), 7.41 (dd, J=9.1, 3.0 Hz, 1H), 7.22 (d, J=11.6 Hz, 1H), 3.87 (d, J=6.9 Hz, 2H), 2.74 (s, 3H), 2.33 (s, 3H), 1.32-1.17 (m, 1H), 0.65-0.54 (m, 2H), 0.41-0.30 (m, 2H). ESI MS [M+H]⁺ for $C_{22}H_{22}F_1N_4O_3S_1$, calcd 441.1, found 441.2.

Example 66: N-[5-[[2-(cyclopropylmethyl)pyrimidin-5-yl]carbamoyl]-4-fluoro-2-methylphenyl]-2-methyl-1,3-thiazole-5-carboxamide

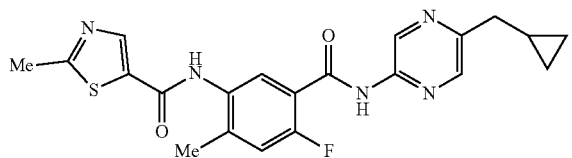 [SMILES: Cc1ncc(C(=O)Nc2cc(C(=O)Nc3cnc(CC4CC4)cn3)c(F)cc2C)s1]

The title compound was prepared from 2-(cyclopropylmethyl)pyrimidin-5-amine and 2-fluoro-4-methyl-5-[(2-methyl-1,3-thiazole-5-carbonyl)amino]benzoic acid in a similar fashion to Example 4. ¹H NMR (400 MHz, DMSO-d₆) δ 10.58 (s, 1H), 10.11 (s, 1H), 8.95 (s, 2H), 8.34 (s, 1H), 7.60 (d, J=6.8 Hz, 1H), 7.30 (d, J=10.9 Hz, 1H), 2.68 (d, J=7.1 Hz, 2H), 2.64 (s, 3H), 2.23 (s, 3H), 1.16-1.05 (m, 1H), 0.39 (d, J=7.8 Hz, 2H), 0.15 (d, J=5.0 Hz, 2H). ESI MS [M+H]⁺ for $C_{21}H_{21}F_1N_5O_2S_1$, calcd 426.1, found 426.1.

Example 67: N-[4-fluoro-2-methyl-5-[[5-[1-(trifluoromethyl)cyclopropyl]pyridin-2-yl]carbamoyl]phenyl]-2-methyl-1,3-thiazole-5-carboxamide

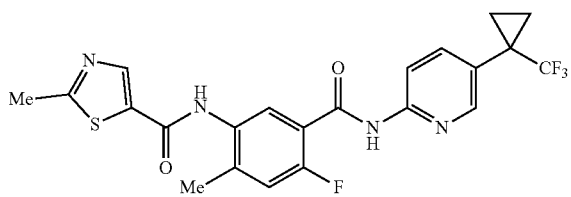 [SMILES: Cc1ncc(C(=O)Nc2cc(C(=O)Nc3ccc(C4(C(F)(F)F)CC4)cn3)c(F)cc2C)s1]

The title compound was prepared from 5-[1-(trifluoromethyl)cyclopropyl]pyridin-2-amine and 2-fluoro-4-methyl-5-[(2-methyl-1,3-thiazole-5-carbonyl)amino]benzoic acid in a similar fashion to Example 4. ¹H NMR (400 MHz, DMSO-d₆) δ 10.77 (s, 1H), 10.10 (s, 1H), 8.36 (d, J=10.1 Hz, 2H), 8.15-8.07 (m, 1H), 7.88 (d, J=8.7 Hz, 1H), 7.58 (d, J=6.8 Hz, 1H), 7.25 (d, J=11.0 Hz, 1H), 2.65 (s, 3H), 2.23 (s, 3H), 1.33-1.28 (m, 2H), 1.15-1.10 (m, 2H). ESI MS [M+H]⁺ for $C_{22}H_{19}F_4N_4O_2S_1$, calcd 479.1, found 479.1.

Example 68: N-[4-Fluoro-5-[(1-fluorocyclobutyl)methylcarbamoyl]-2-methylphenyl]-2-methyl-1,3-thiazole-5-carboxamide

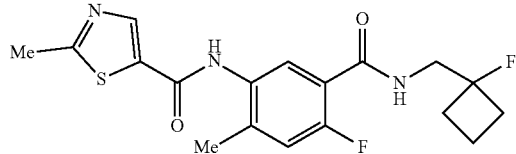 [SMILES: Cc1ncc(C(=O)Nc2cc(C(=O)NCC3(F)CCC3)c(F)cc2C)s1]

The title compound was prepared from (1-fluorocyclobutyl)methanamine hydrochloride and 2-fluoro-4-methyl-5-[(2-methyl-1,3-thiazole-5-carbonyl)amino]benzoic acid in a similar fashion to Example 4. ¹H NMR (400 MHz, DMSO-d₆) δ 10.12 (s, 1H), 8.46 (t, J=6.9 Hz, 1H), 8.39 (s, 1H), 7.52 (d, J=6.9 Hz, 1H), 7.25 (d, J=11.2 Hz, 1H), 3.61 (dd, J=23.2, 6.1 Hz, 2H), 2.71 (s, 3H), 2.25 (s, 3H), 2.25-2.12 (m, 4H), 1.82-1.70 (m, 1H), 1.59-1.46 (m, 1H). ESI MS [M+H]⁺ for $C_{18}H_{20}F_2N_3O_2S_1$, calcd 380.1, found 380.2.

Example 69: N-[5-[[1-(difluoromethyl)pyrazol-3-yl]carbamoyl]-4-fluoro-2-methylphenyl]-2-methyl-1,3-thiazole-5-carboxamide

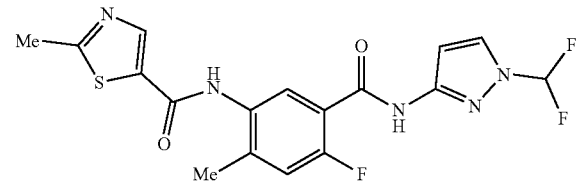 [SMILES: Cc1ncc(C(=O)Nc2cc(C(=O)Nc3ccn(C(F)F)n3)c(F)cc2C)s1]

The title compound was prepared from 1-(difluoromethyl)pyrazol-3-amine and 2-fluoro-4-methyl-5-[(2-methyl-1,3-thiazole-5-carbonyl)amino]benzoic acid in a similar fashion to Example 4. ¹H NMR (400 MHz, DMSO-d₆) δ 11.08 (s, 1H), 10.07 (s, 1H), 8.34 (s, 1H), 8.11 (d, J=2.7 Hz, 1H), 7.82-7.50 (m, 2H), 7.24 (d, J=10.9 Hz, 1H), 6.81 (d, J=2.6 Hz, 1H), 2.65 (s, 3H), 2.22 (s, 3H). ESI MS [M+H]⁺ for $C_{17}H_{15}F_3N_5O_2S$, calcd 410.1, found 410.1.

Example 70: N-[5-[[1-(cyclopropylmethyl)pyrazol-3-yl]carbamoyl]-4-fluoro-2-methylphenyl]-2-methyl-1,3-thiazole-5-carboxamide

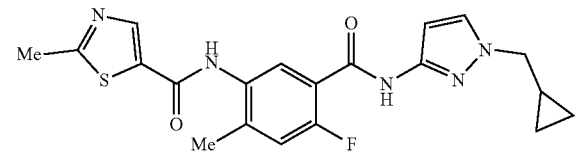 [SMILES: Cc1ncc(C(=O)Nc2cc(C(=O)Nc3ccn(CC4CC4)n3)c(F)cc2C)s1]

The title compound was prepared from 1-(cyclopropylmethyl)pyrazol-3-amine and 2-fluoro-4-methyl-5-[(2-methyl-1,3-thiazole-5-carbonyl)amino]benzoic acid in a similar fashion to Example 4. $^1$H NMR (400 MHz, Chloroform-d) δ 8.95 (d, J=13.1 Hz, 1H), 8.18 (s, 1H), 8.10 (d, J=7.4 Hz, 1H), 7.99 (s, 1H), 7.42 (d, J=2.5 Hz, 1H), 7.03 (d, J=12.0 Hz, 1H), 6.79 (q, J=1.7 Hz, 1H), 3.89 (d, J=7.1 Hz, 2H), 2.76 (d, J=1.7 Hz, 3H), 2.31 (s, 3H), 1.27 (dd, J=12.2, 6.2 Hz, 1H), 0.65 (d, J=7.6 Hz, 2H), 0.36 (d, J=5.1 Hz, 2H). ESI MS [M+H]$^+$ for $C_{20}H_{21}F_1N_5O_2S_1$ calcd 414.1, found 414.1.

Example 71: N-(4-fluoro-5-((5-(3-hydroxyazetidin-1-yl)pyrazin-2-yl)carbamoyl)-2-methylphenyl)-2-methylthiazole-5-carboxamide

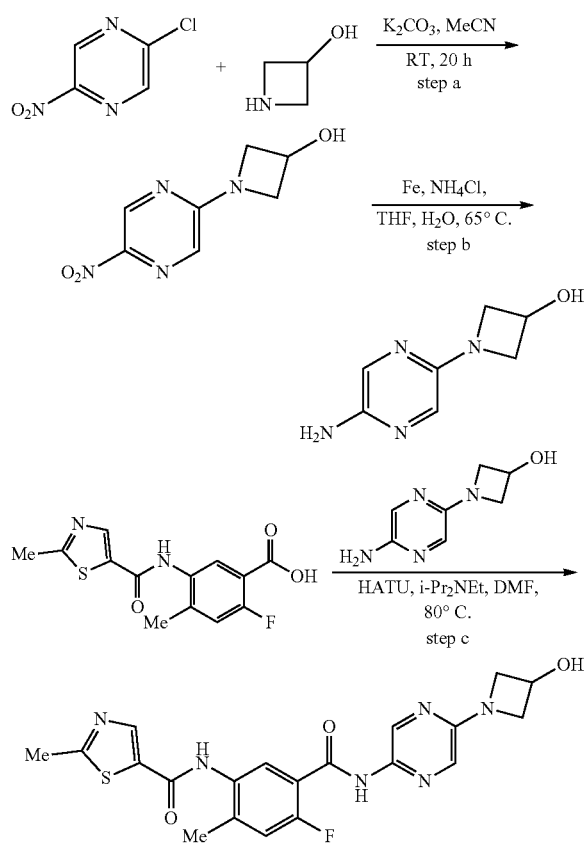

Step a: To a solution of azetidin-3-ol (350 mg, 4.79 mmol, 1.2 equiv.) and 2-chloro-5-nitropyrazine (636 mg, 4.0 mmol, 1.0 equiv.) in acetonitrile (8 mL) at RT was added $K_2CO_3$ (1.1 g, 8.0 mmol, 2.0 equiv.) and the resulting reaction mixture was stirred at RT for 20 h. The reaction mixture was then filtered through a Celite® plug and concentrated under reduced pressure to afford the crude product, which was used directly for the next reaction without further purification.

Step b: The product from step a (100 mg, 0.51 mmol, 1.0 equiv.) was dissolved in a 2:1 mixture of THF and $H_2O$ (0.12 M) followed by addition of $NH_4Cl$ (55 mg, 1.02 mmol, 2.0 equiv.) and iron powder (143 mg, 2.55 mmol, 5.0 equiv.). The resulting mixture was refluxed for 1 hour at which time LC/MS analysis indicated complete consumption of starting material. The reaction mixture was cooled to RT, filtered through a Celite® plug. The plug was subsequently washed with MeOH. The combined filtrate was concentrated in vacuo and the crude product was purified by column chromatography (MeOH/DCM, 0% to 20%) to afford 1-(5-aminopyrazin-2-yl)azetidin-3-ol.

Step c. The title compound was prepared from 1-(5-aminopyrazin-2-yl)azetidin-3-ol and 2-fluoro-4-methyl-5-[(2-methyl-1,3-thiazole-5-carbonyl)amino]benzoic acid in a similar fashion to Example 4. $^1$H NMR (400 MHz, DMSO-d$_6$) δ 10.45 (s, 1H), 10.07 (s, 1H), 8.73 (s, 1H), 8.34 (s, 1H), 7.66 (s, 1H), 7.57 (d, J=6.8 Hz, 1H), 7.23 (d, J=11.1 Hz, 1H), 5.70-5.62 (m, 1H), 4.55 (q, J=6.0 Hz, 1H), 4.17 (t, J=7.6 Hz, 2H), 3.88 (q, J=8.5, 6.5 Hz, 1H), 3.69 (dd, J=8.8, 4.7 Hz, 2H), 2.65 (s, 3H), 2.22 (s, 4H). $^{19}$F NMR (376 MHz, DMSO-d$_6$) δ −116.66. ESI MS [M+H]$^+$ for $C_{20}H_{20}F_1N_6O_3S_1$, calcd 443.1, found 443.1.

Example 72: (R)—N-(4-fluoro-5-((5-(3-hydroxypyrrolidin-1-yl)pyrazin-2-yl)carbamoyl)-2-methylphenyl)-2-methylthiazole-5-carboxamide

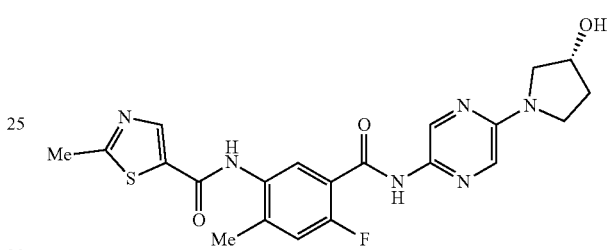

The title compound was prepared from (R)-1-(5-aminopyrazin-2-yl)pyrrolidin-3-ol and 2-fluoro-4-methyl-5-[(2-methyl-1,3-thiazole-5-carbonyl)amino]benzoic acid in a similar fashion to Example 4. $^1$H NMR (400 MHz, DMSO-d$_6$)$^1$H NMR (400 MHz, DMSO-d$_6$) δ 10.34 (s, 1H), 10.08 (s, 1H), 8.70 (s, 1H), 8.34 (s, 1H), 7.69 (s, 1H), 7.57 (d, J=6.7 Hz, 1H), 7.23 (d, J=11.0 Hz, 1H), 4.95 (d, J=3.5 Hz, 1H), 4.34 (s, 1H), 3.54-3.36 (m, 4H), 2.64 (s, 3H), 2.21 (s, 3H), 2.02-1.80 (m, 2H). $^{19}$F NMR (376 MHz, DMSO-d$_6$) δ −116.67. ESI MS [M+H]$^+$ for $C_{21}H_{22}F_1N_6O_3S_1$, calcd 457.1, found 457.1.

Example 73: N-(4-fluoro-5-((5-(3-methoxyazetidin-1-yl)pyrazin-2-yl)carbamoyl)-2-methylphenyl)-2-methylthiazole-5-carboxamide

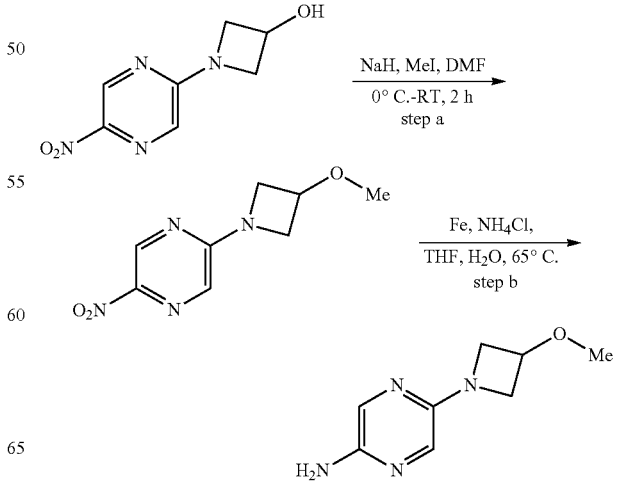

159
-continued

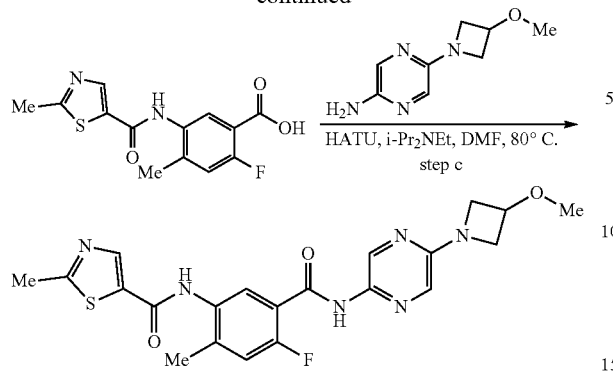

Step a. To a stirred solution of 1-(5-nitropyrazin-2-yl)azetidin-3-ol (196 mg, 1.0 mmol, 1.0 equiv.) in DMF (5 mL) at 0° C. was added NaH (60% in mineral oil, 60 mg, 1.50 mmol, 1.5 equiv.) portion-wise. The reaction mixture was stirred for 20 minutes at 0° C. followed by dropwise addition of MeI (93 µL, 1.5 mmol) and then warmed to RT. After 2 h, the reaction mixture was cooled to 0° C., quenched with H$_2$O and extracted three times with EtOAc. The combined organic extracts were dried over Na$_2$SO$_4$, filtered, and concentrated in vacuo to afford the crude product, which was purified by column chromatography (EtOAc/hexanes, 0% to 50%) to afford the desired compound in 90% yield as a clear colorless oil.

Step b was performed in an analogous manner to Example 71, step b.

Step c. The title compound was prepared from 5-(3-methoxyazetidin-1-yl)pyrazin-2-amine and 2-fluoro-4-methyl-5-[(2-methyl-1,3-thiazole-5-carbonyl)amino]benzoic acid in a similar fashion to Example 4. $^1$H NMR (400 MHz, DMSO-d$_6$) $^1$H NMR (400 MHz, DMSO-d$_6$) δ 10.47 (s, 1H), 10.07 (s, 1H), 8.74 (s, 1H), 8.34 (s, 1H), 7.68 (s, 1H), 7.57 (d, J=6.9 Hz, 1H), 7.24 (d, J=10.7 Hz, 1H), 4.29 (d, J=5.8 Hz, 1H), 4.16 (t, J=7.6 Hz, 2H), 3.77 (dd, J=9.3, 3.9 Hz, 2H), 3.19 (s, 3H), 2.65 (s, 3H), 2.22 (s, 3H). $^{19}$F NMR (376 MHz, DMSO-d$_6$) δ −116.65. ESI MS [M+H]$^+$ for C$_{21}$H$_{22}$F$_1$N$_6$O$_3$S$_1$, calcd 457.1, found 457.1.

160

Example 74: (R)—N-(4-fluoro-5-((5-(3-methoxy-pyrrolidin-1-yl)pyrazin-2-yl)carbamoyl)-2-methylphenyl)-2-methylthiazole-5-carboxamide

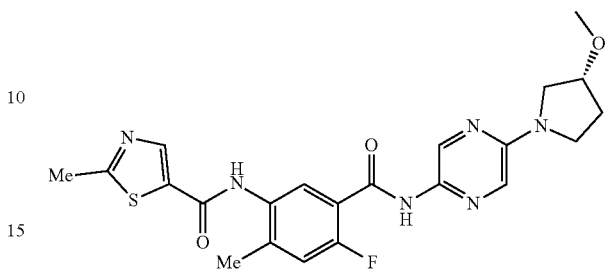

The title compound was prepared from (R)-5-(3-methoxypyrrolidin-1-yl)pyrazin-2-amine and 2-fluoro-4-methyl-5-[(2-methyl-1,3-thiazole-5-carbonyl)amino]benzoic acid in a similar fashion to Example 4. $^1$H NMR (400 MHz, DMSO-d$_6$) $^1$H NMR (400 MHz, DMSO-d$_6$) δ 10.36 (s, 1H), 10.07 (s, 1H), 8.72 (s, 1H), 8.34 (s, 1H), 7.72 (s, 1H), 7.57 (d, J=6.8 Hz, 1H), 7.23 (d, J=11.0 Hz, 1H), 4.03 (d, J=4.5 Hz, 1H), 3.46 (d, J=3.4 Hz, 3H), 3.39-3.30 (m, 1H), 3.21 (s, 3H), 2.64 (s, 3H), 2.22 (s, 3H), 2.00 (dd, J=12.4, 8.1 Hz, 2H). $^{19}$F NMR (376 MHz, DMSO-d$_6$) δ −116.67. ESI MS [M+H]$^+$ for C$_{22}$H$_{23}$F$_1$N$_6$O$_3$S$_1$, calcd 471.1, found 471.1.

Example 75: N-(2,4-dimethyl-5-((5-(2,2,2-trifluoro-ethyl)pyridin-2-yl)carbamoyl)phenyl)-2-methylthiazole-5-carboxamide

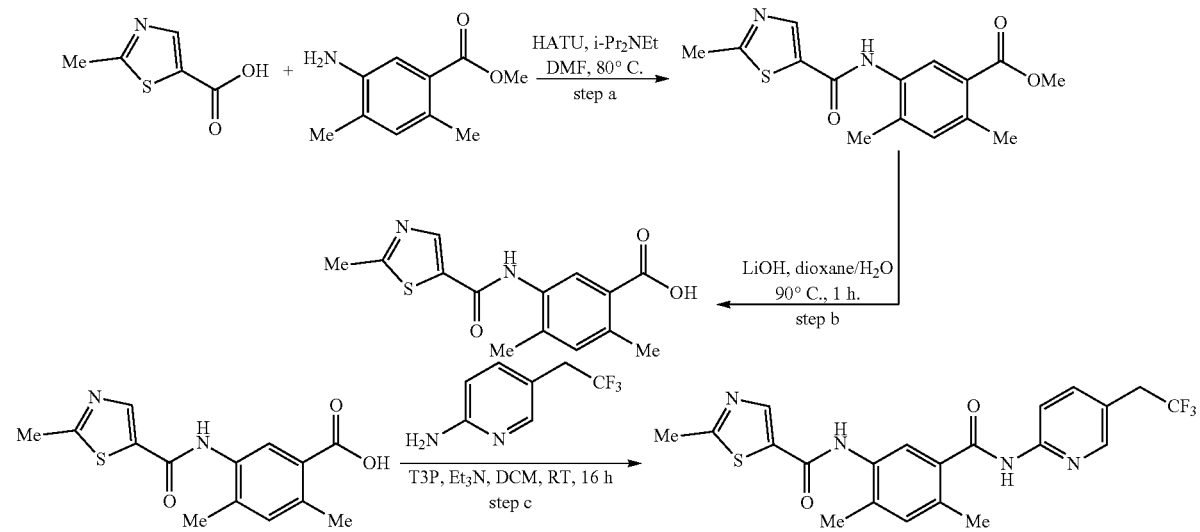

Step a and Step b were performed in an analogous manner to Example 1, steps a and b.

Step c: The title compound was prepared from 5-(2,2,2-trifluoroethyl) pyridin-2-amine and 2,4-dimethyl-5-[(2-methyl-1,3-thiazole-5-carbonyl)amino]benzoic acid in a similar fashion to Example 12. $^1$H NMR (400 MHz, DMSO-d$_6$)$^1$H NMR (400 MHz, DMSO-d$_6$) δ 10.80 (s, 1H), 10.05 (s, 1H), 8.47-8.29 (m, 2H), 8.24-8.16 (m, 1H), 7.83 (dd, J=8.6, 2.3 Hz, 1H), 7.46 (s, 1H), 7.20 (s, 1H), 3.70 (q, J=11.5 Hz, 2H), 2.70 (s, 3H), 2.38 (s, 3H), 2.24 (s, 3H). $^{19}$F NMR (376 MHz, DMSO-d$_6$) δ −64.74. ESI MS [M+H]$^+$ for $C_{21}H_{20}F_3N_4O_2S_1$, calcd 449.1, found 449.1.

Example 76: N-[5-[[5-(difluoromethyl)pyridin-3-yl]carbamoyl]-4-fluoro-2-methylphenyl]-2-methyl-1,3-thiazole-5-carboxamide

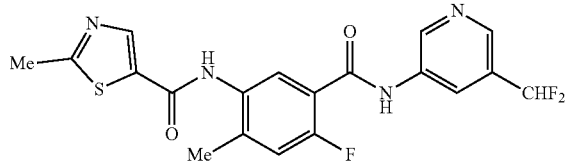 [SMILES: Cc1ncc(C(=O)Nc2cc(C(=O)Nc3cncc(C(F)F)c3)c(F)cc2C)s1]

The title compound was prepared from 5-(difluoromethyl)pyridin-3-amine and 2-fluoro-4-methyl-5-[(2-methyl-1,3-thiazole-5-carbonyl)amino]benzoic acid in a similar fashion to Example 4, step d. $^1$H NMR (400 MHz, DMSO-d$_6$) δ 10.75 (s, 1H), 10.12 (s, 1H), 8.90 (t, J=1.5 Hz, 1H), 8.49-8.44 (m, 1H), 8.36 (d, J=13.9 Hz, 2H), 7.58 (d, J=6.8 Hz, 1H), 7.31 (d, J=10.9 Hz, 1H), 7.13 (t, J=55.2 Hz, 1H), 2.64 (s, 3H), 2.23 (s, 3H). ESI MS [M+H]$^+$ for $C_{19}H_{16}F_3N_4O_2S_1$, calcd 421.1, found 421.1.

Example 77: N-[4-fluoro-2-methyl-5-[[5-(trifluoromethyl)pyridin-3-yl]carbamoyl]phenyl]-2-methyl-1,3-thiazole-5-carboxamide

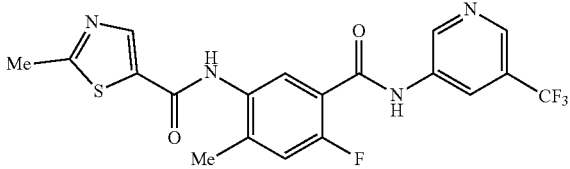 [SMILES: Cc1ncc(C(=O)Nc2cc(C(=O)Nc3cncc(C(F)(F)F)c3)c(F)cc2C)s1]

The title compound was prepared from 5-(trifluoromethyl)pyridin-3-amine and 2-fluoro-4-methyl-5-[(2-methyl-1,3-thiazole-5-carbonyl)amino]benzoic acid in a similar fashion to Example 4, step d. $^1$H NMR (400 MHz, Methanol-d$_4$) δ 9.07 (d, J=1.9 Hz, 1H), 8.69-8.63 (m, 2H), 8.35 (s, 1H), 7.78 (d, J=6.8 Hz, 1H), 7.32-7.26 (m, 1H), 2.79 (s, 3H), 2.39 (s, 3H). ESI MS [M+H]$^+$ for $C_{19}H_{15}F_4N_4O_2S_1$, calcd 439.1, found 439.1.

Example 78: N-[5-[[5-(difluoromethoxymethyl)pyridin-2-yl]carbamoyl]-4-fluoro-2-methylphenyl]-2-methyl-1,3-thiazole-5-carboxamide

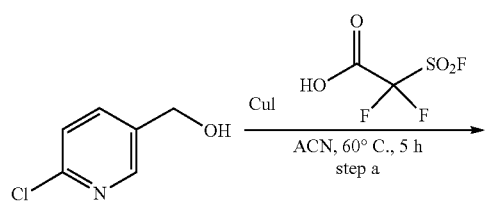

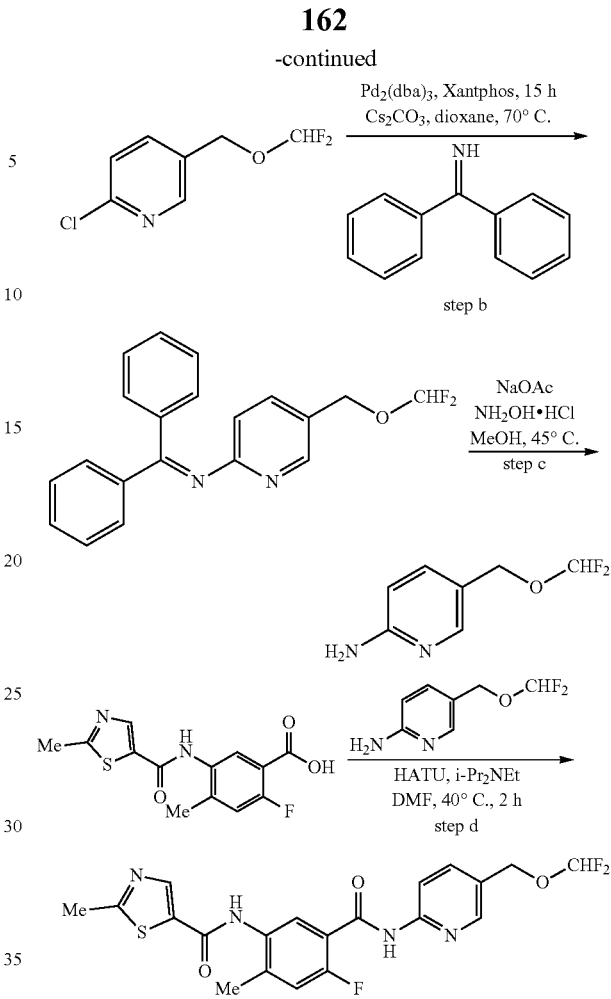

Step a: To a solution of (6-chloropyridin-3-yl)methanol (536.0 mg, 3.7 mmol, 1.0 equiv.) in acetonitrile (20 mL) was added CuI (70.3 mg, 0.37 mmol, 0.1 equiv.) and the resulting reaction mixture was stirred at 60° C. for 10 min. 2,2-Difluoro-2-fluorosulfonylacetic acid (1.0 g, 5.6 mmol, 1.5 equiv.) was added dropwise. After being stirred at 60° C. for 5 h, the reaction mixture was cooled to RT, diluted with H$_2$O and extracted three times with EtOAc. The combined organic extracts were dried over Na$_2$SO$_4$, filtered, and concentrated in vacuo to afford the crude product, which was purified by column chromatography (EtOAc/hexanes, 0% to 40%) to provide 2-chloro-5-(difluoromethoxymethyl)pyridine.

Step b and Step c were performed in an analogous manner to Example 1, steps c and d.

Step d was performed in an analogous manner to Example 4, step d from 2-fluoro-4-methyl-5-[[2-[(2-methylpropan-2-yl)oxycarbonylamino]-1,3-thiazole-5-carbonyl]amino]benzoic acid and the product of step c. The crude product was purified by reverse phase HPLC to afford the title compound $^1$H NMR (400 MHz, DMSO-d$_6$) δ 10.72 (s, 1H), 10.08 (s, 1H), 8.33 (d, J=5.2 Hz, 2H), 8.14 (d, J=8.4 Hz, 1H), 7.82 (d, J=8.7 Hz, 1H), 7.58 (d, J=6.9 Hz, 1H), 7.24 (d, J=11.1 Hz, 1H), 6.75 (t, J=75.4 Hz, 1H), 4.87 (s, 2H), 2.64 (s, 3H), 2.22 (s, 3H). MS [M+H]$^+$ for $C_{20}H_{18}F_3N_4O_3S_1$, calcd 451.1, found 451.1.

Example 79: N-[4-fluoro-2-methyl-5-[(1-propan-2-ylpyrazol-3-yl)methylcarbamoyl]phenyl]-2-methyl-1,3-thiazole-5-carboxamide

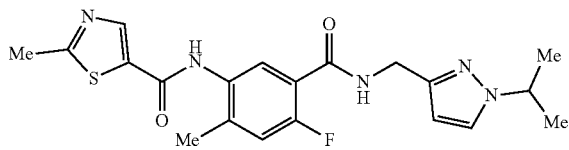 [SMILES: Cc1ncc(C(=O)Nc2cc(C(=O)NCc3ccn(C(C)C)n3)c(F)cc2C)s1]

The title compound was prepared from (1-propan-2-ylpyrazol-3-yl)methanamine and 2-fluoro-4-methyl-5-[(2-methyl-1,3-thiazole-5-carbonyl)amino]benzoic acid in a similar fashion to Example 4, step d. $^1$H NMR (400 MHz, Methanol-$d_4$) δ 8.28 (s, 1H), 7.67 (d, J=7.0 Hz, 1H), 7.57 (d, J=2.3 Hz, 1H), 7.15 (d, J=11.5 Hz, 1H), 6.22 (d, J=2.3 Hz, 1H), 4.53 (s, 2H), 4.46 (hept, J=6.7 Hz, 1H), 2.73 (s, 3H), 2.29 (s, 3H), 1.44 (d, J=6.7 Hz, 6H). ESI MS [M+H]$^+$ for $C_{20}H_{23}F_1N_5O_2S_1$, calcd 416.1, found 416.1.

Example 80: N-[5-[[5-(difluoromethoxymethyl)pyridin-3-yl]carbamoyl]-4-fluoro-2-methylphenyl]-2-methyl-1,3-thiazole-5-carboxamide

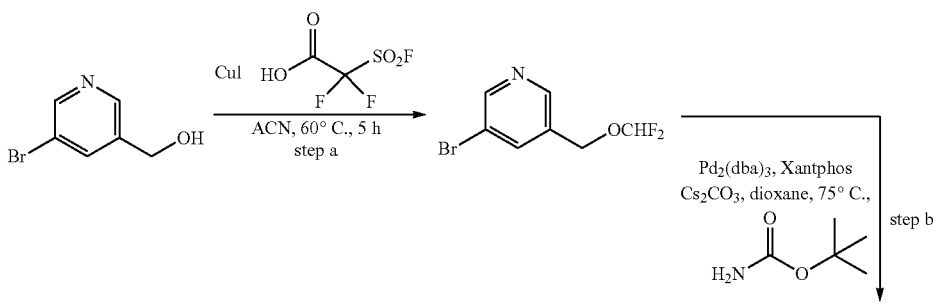

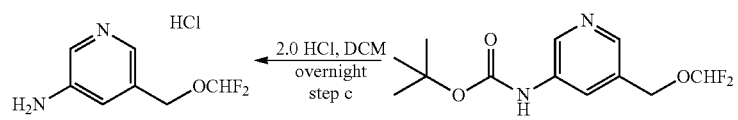

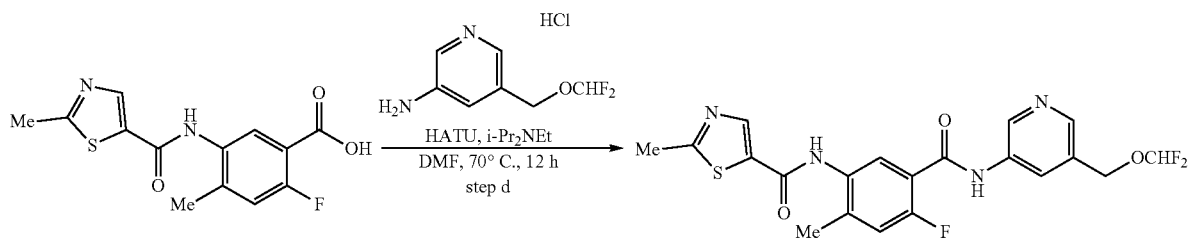

Step a were performed in an analogous manner to Example 78, step a.

Step b and Step c were performed in an analogous manner to Example 244, steps d and e.

Step d was performed in an analogous manner to Example 4, step d. The crude product was purified by reverse phase HPLC to afford the title compound. $^1$H NMR (400 MHz, Methanol-d$_4$) δ 8.80 (s, 1H), 8.38-8.19 (m, 3H), 7.70 (d, J=6.7 Hz, 1H), 7.22 (d, J=11.0 Hz, 1H), 6.52 (t, J=74.4 Hz, 1H), 4.97 (s, 2H), 2.74 (s, 3H), 2.33 (s, 3H). MS [M+H]$^+$ for $C_{20}H_{18}F_3N_4O_3S_1$, calcd 451.1, found 451.1.

Example 81: N-[4-fluoro-2-methyl-5-[[5-(2,2,2-trifluoroethyl)pyridin-3-yl]carbamoyl]phenyl]-2-methyl-1,3-thiazole-5-carboxamide

Example 82: N-[5-[(5-ethylpyridin-2-yl)carbamoyl]-4-fluoro-2-methylphenyl]-2-methyl-1,3-thiazole-5-carboxamide

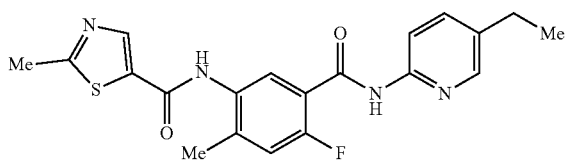 [SMILES: CCc1ccc(NC(=O)c2cc(NC(=O)c3cnc(C)s3)c(C)cc2F)nc1]

The title compound was prepared from 5-ethylpyridin-2-amine and 2-fluoro-4-methyl-5-[(2-methyl-1,3-thiazole-5-carbonyl)amino]benzoic acid in a similar fashion to

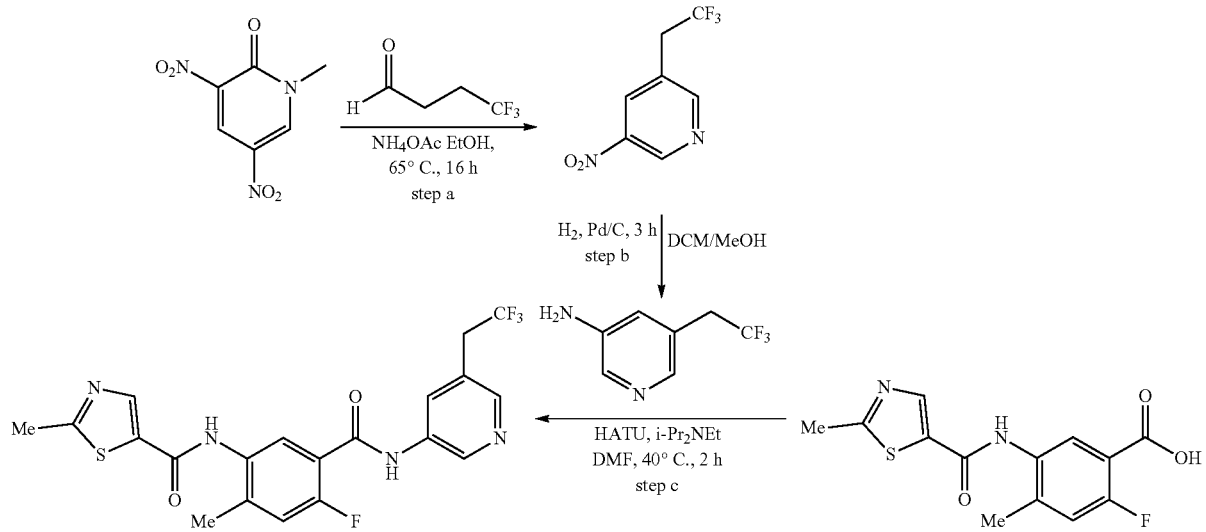

Step a: A mixture of 1-methyl-3,5-dinitropyridin-2-one (1.0 g, 5.0 mmol, 1.0 equiv.), 4,4,4-trifluorobutanal (1.26 g, 10 mmol, 2.0 equiv.) and NH$_4$OAc (5.78 g, 75 mmol, 15 equiv.) in EtOH (100 mL) was heated under N$_2$ at 65° C. for 16 h. The resulting reaction mixture was concentrated in vacuo, diluted with water and extracted three times with EtOAc. The combined organic layers were washed with water, dried over Na$_2$SO$_4$, filtered, and concentrated in vacuo to afford the crude product, which was purified by column chromatography (EtOAc/hexanes, 20% to 100%) to provide the title compound (1.0 g, 4.9 mmol, 97% yield).

Step b was performed in an analogous manner to Example 65, step b.

Step c was performed in an analogous manner to Example 4, step d. The crude product was purified by reverse phase HPLC to afford the title compound. $^1$H NMR (400 MHz, DMSO-d$_6$) δ 10.62 (s, 1H), 10.10 (s, 1H), 8.77 (s, 1H), 8.34 (s, 1H), 8.26 (s, 1H), 8.19 (s, 1H), 7.56 (d, J=6.8 Hz, 1H), 7.29 (d, J=10.8 Hz, 1H), 3.72 (q, J=11.9 Hz, 2H), 2.64 (d, J=1.8 Hz, 3H), 2.22 (s, 3H). ESI MS [M+H]$^+$ for $C_{20}H_{17}F_4N_4O_2S_1$, calcd 453.1, found 453.1.

Example 4, step d. $^1$H NMR (400 MHz, DMSO-d$_6$) δ 10.50 (d, J=2.5 Hz, 1H), 10.07 (s, 1H), 8.33 (s, 1H), 8.18-8.12 (m, 1H), 8.02 (d, J=8.5 Hz, 1H), 7.63 (dd, J=8.5, 2.4 Hz, 1H), 7.56 (d, J=6.9 Hz, 1H), 7.23 (d, J=11.1 Hz, 1H), 2.64 (s, 3H), 2.53 (q, J=7.6 Hz, 2H), 2.21 (s, 3H), 1.12 (t, J=7.6 Hz, 3H). ESI MS [M+H]$^+$ for $C_{20}H_{20}F_1N_4O_2S_1$, calcd 399.1, found 399.2.

Example 83: N-(5-{N-5-[(S)-2-methyl-1-pyrrolidinyl]-2-pyrazinylcarbamoyl}-4-fluoro-2-tolyl)-2-methyl-1,3-thiazole-5-carboxamide

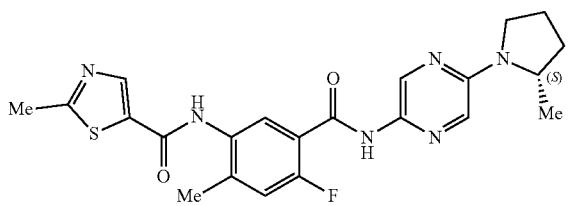

The title compound was prepared from 5-[(2S)-2-methylpyrrolidin-1-yl]pyrazin-2-amine and 2-fluoro-4-methyl-5-[(2-methyl-1,3-thiazole-5-carbonyl)amino]benzoic acid in a similar fashion to Example 4. $^1$H NMR (400 MHz, DMSO-d6) δ 10.32 (s, 1H), 10.07 (s, 1H), 8.69 (s, 1H), 8.33 (s, 1H), 7.68 (s, 1H), 7.55 (d, J=6.8 Hz, 1H), 7.22 (d, J=10.8 Hz, 1H), 4.17-3.99 (m, 2H), 3.46 (t, J=8.6 Hz, 1H), 3.27-3.17 (m, 2H), 2.63 (s, 3H), 2.20 (s, 2H), 2.03-1.83 (m, 3H), 1.09 (d, J=6.2 Hz, 3H). ESI MS [M+H]$^+$ for $C_{22}H_{24}FN_6O_2S_1$, calcd 455.1, found 455.1.

Example 84: N-(5-{N-5-[(R)-2-methyl-1-pyrrolidinyl]-2-pyrazinylcarbamoyl}-4-fluoro-2-tolyl)-2-methyl-1,3-thiazole-5-carboxamide

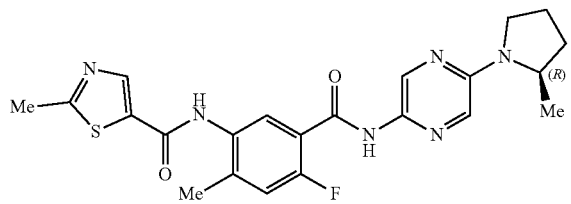

The title compound was prepared from 5-[(2R)-2-methylpyrrolidin-1-yl]pyrazin-2-amine and 2-fluoro-4-methyl-5-[(2-methyl-1,3-thiazole-5-carbonyl)amino]benzoic acid in a similar fashion to Example 4. $^1$H NMR (400 MHz, DMSO-d$_6$) δ 10.32 (s, 1H), 10.06 (s, 1H), 8.68 (s, 1H), 8.33 (s, 1H), 7.69 (s, 1H), 7.55 (d, J=6.8 Hz, 1H), 7.22 (d, J=11.0 Hz, 1H), 4.08 (t, J=6.5 Hz, 2H), 3.46 (t, J=8.7 Hz, 1H), 3.23 (d, J=9.0 Hz, 2H), 2.63 (s, 3H), 2.20 (s, 2H), 2.04-1.80 (m, 3H), 1.09 (d, J=6.2 Hz, 3H). ESI MS [M+H]$^+$ for $C_{22}H_{24}FN_6O_2S_1$, calcd 455.1, found 455.1.

Example 85: N-{5-[N-5-(1-pyrrolidinyl)-2-pyrazinylcarbamoyl]-4-fluoro-2-tolyl}-2-methyl-1,3-thiazole-5-carboxamide

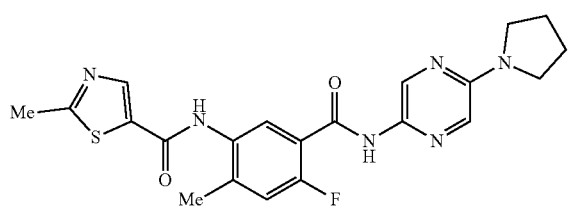 [SMILES: Cc1ncc(C(=O)Nc2cc(C(=O)Nc3cnc(N4CCCC4)cn3)c(F)cc2C)s1]

The title compound was prepared from 5-pyrrolidin-1-ylpyrazin-2-amine and 2-fluoro-4-methyl-5-[(2-methyl-1,3-thiazole-5-carbonyl)amino]benzoic acid in a similar fashion to Example 4. $^1$H NMR (400 MHz, DMSO-d$_6$) δ 10.33 (s, 1H), 10.07 (s, 1H), 8.70 (s, 1H), 8.34 (s, 1H), 7.70 (s, 1H), 7.57 (d, J=6.8 Hz, 1H), 7.23 (d, J=11.0 Hz, 1H), 3.36 (s, 3H), 2.64 (s, 2H), 2.21 (s, 2H), 1.89 (s, 3H). ESI MS [M+H]$^+$ for $C_{21}H_{23}FN_6O_2S_1$, calcd 441.1, found 441.1.

Example 86: N-{5-[N-5-(2,2-difluoroethoxy)-2-pyrazinylcarbamoyl]-4-fluoro-2-tolyl}-2-methyl-1,3-thiazole-5-carboxamide

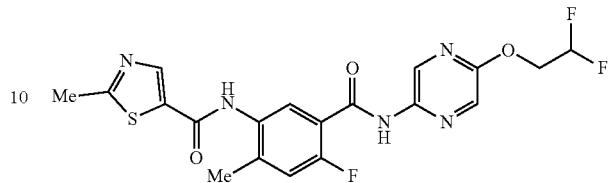

The title compound was prepared from 5-(2,2-difluoroethoxy)pyrazin-2-amine and 2-fluoro-4-methyl-5-[(2-methyl-1,3-thiazole-5-carbonyl)amino]benzoic acid in a similar fashion to Example 4. $^1$H NMR (400 MHz, DMSO-d$_6$) δ 10.85 (s, 1H), 10.07 (s, 1H), 8.88 (s, 1H), 8.33 (s, 1H), 8.20 (s, 1H), 7.58 (d, J=6.8 Hz, 1H), 7.34-7.16 (m, 1H), 6.36 (t, J=54.4 Hz, 1H), 4.55 (td, J=15.2, 3.3 Hz, 2H), 2.64 (s, 3H), 2.22 (s, 3H). ESI MS [M+H]$^+$ for $C_{19}H_{17}F_3N_5O_3S_1$, calcd 452.1, found 452.1.

Example 87: N-[5-(N-5-trifluoromethoxy-2-pyrazinylcarbamoyl)-4-fluoro-2-tolyl]-2-methyl-1,3-thiazole-5-carboxamide

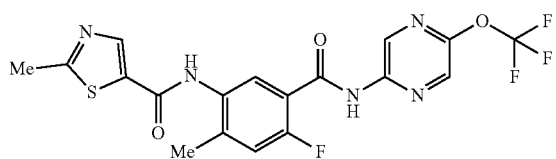 [SMILES: Cc1ncc(C(=O)Nc2cc(C(=O)Nc3cnc(OC(F)(F)F)cn3)c(F)cc2C)s1]

The title compound was prepared from 5-(trifluoromethoxy)pyrazin-2-amine and 2-fluoro-4-methyl-5-[(2-methyl-1,3-thiazole-5-carbonyl)amino]benzoic acid in a similar fashion to Example 4. $^1$H NMR (400 MHz, DMSO-d$_6$) δ 11.31 (s, 1H), 10.10 (s, 1H), 9.10 (s, 1H), 8.53 (s, 1H), 8.35 (s, 1H), 7.60 (d, J=6.8 Hz, 1H), 7.28 (d, J=10.9 Hz, 1H), 2.65 (s, 3H), 2.24 (s, 3H). ESI MS [M+H]$^+$ for $C_{18}H_{14}F_4N_5O_3S_1$, calcd 456.1, found 456.1.

Example 88: N-{5-[N-5-(cyclopropylmethoxy)-2-pyrazinylcarbamoyl]-4-fluoro-2-tolyl}-2-methyl-1,3-thiazole-5-carboxamide

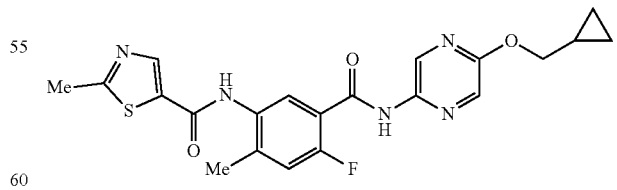

The title compound was prepared from 5-(cyclopropylmethoxy)pyrazin-2-amine and 2-fluoro-4-methyl-5-[(2-methyl-1,3-thiazole-5-carbonyl)amino]benzoic acid in a similar fashion to Example 4. $^1$H NMR (400 MHz, DMSO-d$_6$) δ 10.51 (s, 1H), 10.19 (s, 1H), 8.85 (s, 2H), 8.41 (s, 1H), 7.66 (d, J=6.8 Hz, 1H), 7.36 (d, J=10.9 Hz, 1H), 4.13 (d, J=7.2 Hz, 2H), 2.71 (s, 3H), 2.30 (s, 3H), 1.26 (t, J=7.7 Hz, 1H), 0.56 (d, J=7.9 Hz, 2H), 0.34 (d, J=5.0 Hz, 2H). ESI MS [M+H]+ for $C_{21}H_{21}FN_5O_3S_1$, calcd 442.1, found 442.1.

Example 89: N-{5-[N-5-(2,2,2-trifluoroethoxy)-2-pyrazinylcarbamoyl]-4-fluoro-2-tolyl}-2-methyl-1,3-thiazole-5-carboxamide

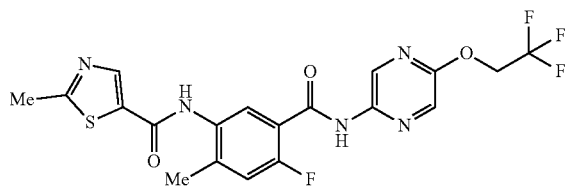 [SMILES: Cc1ncc(C(=O)Nc2cc(C(=O)Nc3cnc(OCC(F)(F)F)cn3)c(F)cc2C)s1]

The title compound was prepared from 5-(2,2,2-trifluoroethoxy)pyrazin-2-amine and 2-fluoro-4-methyl-5-[(2-methyl-1,3-thiazole-5-carbonyl)amino]benzoic acid in a similar fashion to Example 4. $^1$H NMR (400 MHz, DMSO-$d_6$) δ 10.91 (s, 1H), 10.07 (s, 1H), 8.90 (s, 1H), 8.34 (s, 1H), 8.27 (s, 1H), 7.58 (d, J=6.8 Hz, 1H), 7.25 (d, J=10.9 Hz, 1H), 4.03 (d, J=5.4 Hz, 2H), 2.64 (s, 3H), 2.22 (s, 3H). ESI MS [M+H]+ for $C_{19}H_{16}F_4N_5O_3S_1$, calcd 470.1, found 470.1.

Example 90: N-(5-{N-5-[(R)-2-(methoxymethyl)-1-pyrrolidinyl]-2-pyrazinylcarbamoyl}-4-fluoro-2-tolyl)-2-methyl-1,3-thiazole-5-carboxamide

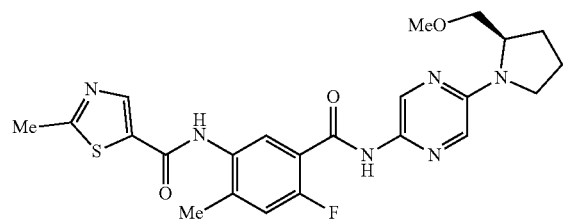 [SMILES: COC[C@H]1CCCN1c1cnc(NC(=O)c2cc(NC(=O)c3cnc(C)s3)c(C)cc2F)cn1]

The title compound was prepared from 5-[(2R)-2-(methoxymethyl)pyrrolidin-1-yl]pyrazin-2-amine and 2-fluoro-4-methyl-5-[(2-methyl-1,3-thiazole-5-carbonyl)amino]benzoic acid in a similar fashion to Example 4. $^1$H NMR (400 MHz, DMSO-$d_6$) δ 10.44 (d, J=2.2 Hz, 1H), 10.16 (s, 1H), 8.77 (s, 1H), 8.41 (s, 1H), 7.82 (d, J=1.5 Hz, 1H), 7.63 (d, J=6.9 Hz, 1H), 7.30 (d, J=11.0 Hz, 1H), 4.19 (d, J=6.2 Hz, 1H), 3.56-3.47 (m, 1H), 3.33-3.29 (m, 1H), 3.27 (s, 3H), 2.89 (s, 1H), 2.73 (s, 1H), 2.71 (s, 3H), 2.28 (s, 3H), 1.94 (d, J=4.5 Hz, 2H), 1.32-1.20 (m, 1H), 0.90-0.80 (m, 1H). ESI MS [M+H]+ for $C_{23}H_{26}FN_6O_3S_1$, calcd 485.1, found 485.1.

Example 91: N-{5-[N-5-(cyclopropylmethyl)-2-pyrazinylcarbamoyl]-4-fluoro-2-tolyl}-2-methyl-1,3-thiazole-5-carboxamide

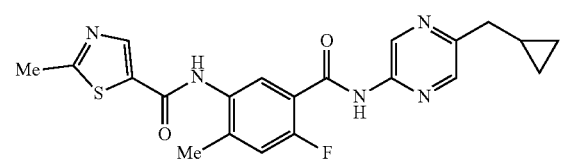 [SMILES: Cc1ncc(C(=O)Nc2cc(C(=O)Nc3cnc(CC4CC4)cn3)c(F)cc2C)s1]

The title compound was prepared from 5-(cyclopropylmethyl)pyrazin-2-amine and 2-fluoro-4-methyl-5-[(2-methyl-1,3-thiazole-5-carbonyl)amino]benzoic acid in a similar fashion to Example 4. $^1$H NMR (400 MHz, DMSO-$d_6$) δ 10.90 (s, 1H), 10.08 (s, 1H), 9.22 (s, 1H), 8.33 (s, 1H), 7.59 (d, J=6.8 Hz, 1H), 7.25 (d, J=11.0 Hz, 1H), 2.64 (s, 2H), 2.60 (d, J=7.1 Hz, 2H), 2.22 (s, 2H), 1.16 (s, 1H), 1.09-0.94 (m, 1H), 0.42 (d, J=7.7 Hz, 2H), 0.18 (d, J=5.0 Hz, 2H). ESI MS [M+H]+ for $C_{21}H_{21}FN_5O_2S_1$, calcd 426.1, found 426.1.

Example 92: N-[5-[[5-(3,3-difluoropyrrolidin-1-yl)pyrazin-2-yl]carbamoyl]-4-fluoro-2-methylphenyl]-2-methyl-1,3-thiazole-5-carboxamide

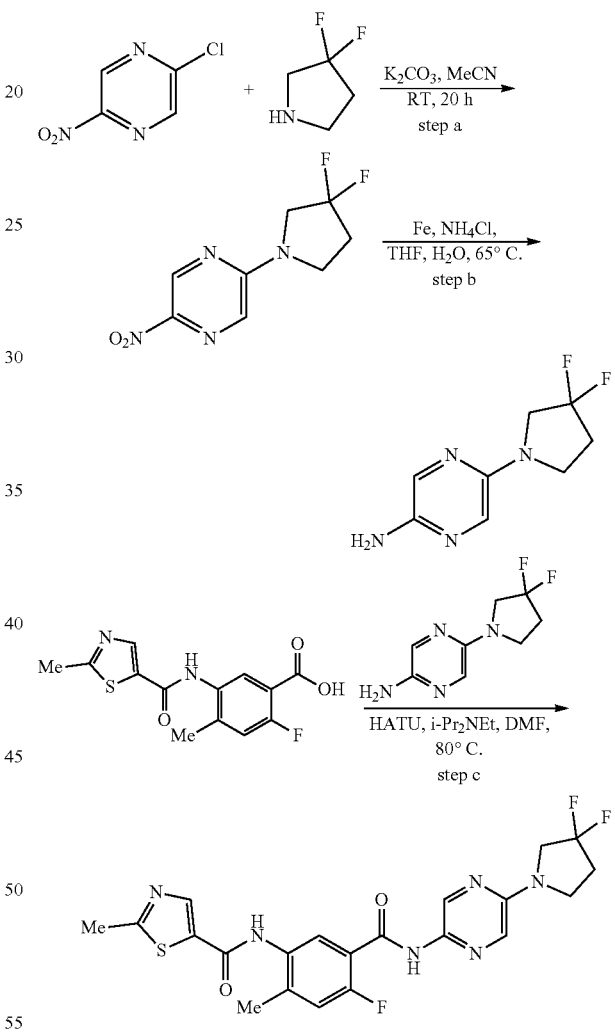

Step a: To a solution of 3,3-difluoropyrrolidine (535 mg, 4.79 mmol, 1.2 equiv.) and 2-chloro-5-nitropyrazine (636 mg, 4.0 mmol, 1.0 equiv.) in acetonitrile (8 mL) at RT was added $K_2CO_3$ (1.1 g, 8.0 mmol, 2.0 equiv.) and the resulting reaction mixture was stirred at RT for 20 h. The reaction mixture was then filtered through a Celite® plug and concentrated under reduced pressure to afford the crude product, which was used directly for the next reaction without further purification.

Step b: The product from step a (400 mg, 0.51 mmol, 1.0 equiv.) was dissolved in a 2:1 mixture of THF and $H_2O$ (0.12

M) followed by addition of NH₄Cl (55 mg, 1.02 mmol, 2.0 equiv.) and iron powder (143 mg, 2.55 mmol, 5.0 equiv.). The resulting mixture was refluxed for 1 hour at which time LC/MS analysis indicated complete consumption of starting material. The reaction mixture was cooled to RT, filtered through a Celite® plug. The plug was subsequently washed with MeOH. The combined filtrate was concentrated in vacuo and the crude product was purified by column chromatography (MeOH/DCM, 0% to 20%) to afford 1-(5-aminopyrazin-2-yl)azetidin-3-ol.

Step c: The title compound was prepared from 5-(3,3-difluoropyrrolidin-1-yl)pyrazin-2-amine and 2-fluoro-4-methyl-5-[(2-methyl-1,3-thiazole-5-carbonyl)amino]benzoic acid in a similar fashion to Example 4, step d. ¹H NMR (400 MHz, DMSO-d₆) δ 10.54 (d, J=2.0 Hz, 1H), 10.12 (s, 1H), 8.85 (s, 1H), 8.40 (s, 1H), 7.89 (d, J=1.6 Hz, 1H), 7.64 (d, J=6.9 Hz, 1H), 7.30 (d, J=11.0 Hz, 1H), 4.01-3.83 (m, 2H), 3.69 (t, J=7.3 Hz, 2H), 2.71 (s, 3H), 2.56 (dt, J=14.3, 7.1 Hz, 2H), 2.29 (s, 3H). ESI MS [M+H]⁺ for C₂₁H₂₀F₃N₆O₂S, calcd 477.2, found 477.3.

Example 93: N-[4-fluoro-5-[[5-[(3S)-3-fluoropyrrolidin-1-yl]pyrazin-2-yl]carbamoyl]-2-methylphenyl]-2-methyl-1,3-thiazole-5-carboxamide

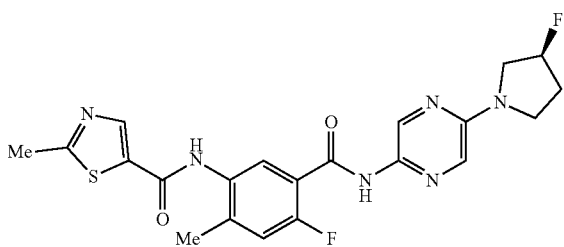 [SMILES: Cc1ncc(C(=O)Nc2cc(C(=O)Nc3cnc(N4CC[C@H](F)C4)cn3)c(F)cc2C)s1]

The title compound was prepared from 5-[(3S)-3-fluoropyrrolidin-1-yl]pyrazin-2-amine (prepared in a similar manner to that described in Example 92, steps a and b) and 2-fluoro-4-methyl-5-[(2-methyl-1,3-thiazole-5-carbonyl)amino]benzoic acid in a similar fashion to Example 4, step d. ¹H NMR (400 MHz, DMSO-d₆) δ 10.45 (d, J=2.2 Hz, 1H), 10.12 (s, 1H), 8.81 (s, 1H), 8.40 (s, 1H), 7.83 (d, J=1.5 Hz, 1H), 7.64 (d, J=6.8 Hz, 1H), 7.29 (d, J=11.1 Hz, 1H), 5.48-5.32 (m, 1H), 3.88-3.55 (m, 3H), 3.55-3.42 (m, 1H), 2.71 (s, 3H), 2.28 (s, 3H), 1.22 (d, J=6.8 Hz, 1H), 1.16 (t, J=7.0 Hz, 1H). ESI MS [M+H]⁺ for C₂₁H₂₁F₂N₆O₂S, calcd 458.2, found 458.3.

Example 94: N-[4-fluoro-5-[[5-[(3R)-3-fluoropyrrolidin-1-yl]pyrazin-2-yl]carbamoyl]-2-methylphenyl]-2-methyl-1,3-thiazole-5-carboxamide

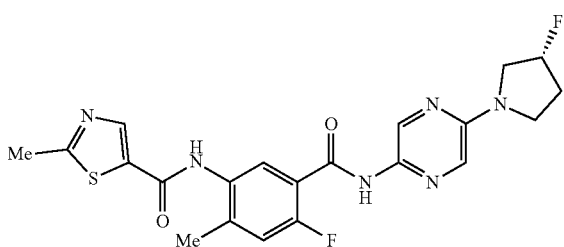 [SMILES: Cc1ncc(C(=O)Nc2cc(C(=O)Nc3cnc(N4CC[C@@H](F)C4)cn3)c(F)cc2C)s1]

The title compound was prepared from 5-[(3R)-3-fluoropyrrolidin-1-yl]pyrazin-2-amine (prepared in a similar manner to that described in Example 92, steps a and b) and 2-fluoro-4-methyl-5-[(2-methyl-1,3-thiazole-5-carbonyl)amino]benzoic acid in a similar fashion to Example 4, step d. ¹H NMR (400 MHz, DMSO-d₆) δ 10.45 (d, J=2.2 Hz, 1H), 10.12 (s, 1H), 8.81 (s, 1H), 8.40 (s, 1H), 7.83 (d, J=1.5 Hz, 1H), 7.64 (d, J=6.8 Hz, 1H), 7.29 (d, J=11.1 Hz, 1H), 5.48-5.32 (m, 1H), 3.88-3.55 (m, 3H), 3.55-3.42 (m, 1H), 2.70 (s, 3H), 2.29 (s, 3H), 1.22 (d, J=6.8 Hz, 1H), 1.15 (t, J=7.0 Hz, 1H). ESI MS [M+H]⁺ for C₂₁H₂₁F₂N₆O₂S, calcd 458.2, found 458.3.

Example 95: N-[4-fluoro-2-methyl-5-[[5-[(2S)-2-(trifluoromethyl)pyrrolidin-1-yl]pyrazin-2-yl]carbamoyl]phenyl]-2-methyl-1,3-thiazole-5-carboxamide

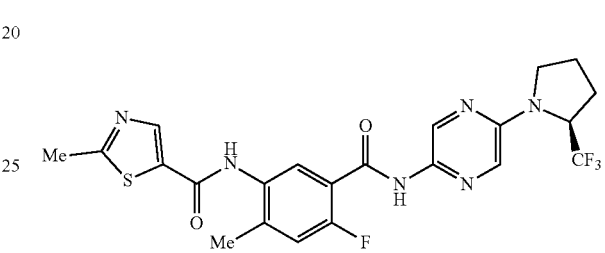

The title compound was prepared from 5-[(2S)-2-(trifluoromethyl)pyrrolidin-1-yl]pyrazin-2-amine (prepared in a similar manner to that described in Example 92, steps a and b) and 2-fluoro-4-methyl-5-[(2-methyl-1,3-thiazole-5-carbonyl)amino]benzoic acid in a similar fashion to Example 4, step d. ¹H NMR (400 MHz, DMSO-d₆) δ 10.60 (d, J=2.0 Hz, 1H), 10.13 (s, 1H), 8.87 (s, 1H), 8.41 (s, 1H), 8.03 (d, J=1.5 Hz, 1H), 7.65 (d, J=6.9 Hz, 1H), 7.30 (d, J=11.0 Hz, 1H), 5.00 (p, J=8.2 Hz, 1H), 3.73 (td, J=6.7, 3.1 Hz, 1H), 3.40 (d, J=8.2 Hz, 1H), 2.71 (s, 3H), 2.29 (s, 3H), 2.10 (dd, J=16.0, 6.6 Hz, 4H). ESI MS [M+H]⁺ for C₂₂H₂₁F₄N₆O₂S, calcd 509.1, found 509.2.

Example 96: N-[4-fluoro-2-methyl-5-[[5-[(2R)-2-(trifluoromethyl)pyrrolidin-1-yl]pyrazin-2-yl]carbamoyl]phenyl]-2-methyl-1,3-thiazole-5-carboxamide

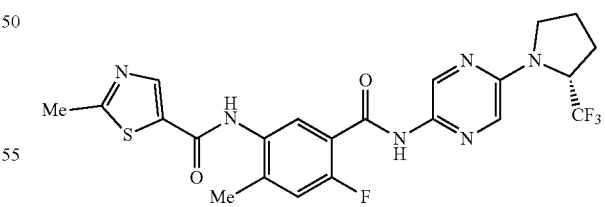

The title compound was prepared from 5-[(2R)-2-(trifluoromethyl)pyrrolidin-1-yl]pyrazin-2-amine (prepared in a similar manner to that described in Example 92, steps a and b) and 2-fluoro-4-methyl-5-[(2-methyl-1,3-thiazole-5-carbonyl)amino]benzoic acid in a similar fashion to Example 4, step d. ¹H NMR (400 MHz, DMSO-d₆) δ 10.54 (d, J=2.0 Hz, 1H), 10.06 (s, 1H), 8.79 (s, 1H), 8.33 (s, 1H), 7.96 (d, J=1.5 Hz, 1H), 7.57 (d, J=6.9 Hz, 1H), 7.23 (d, J=11.0 Hz, 1H), 4.91 (p, J=8.2 Hz, 1H), 3.65 (td, J=6.7, 3.1 Hz, 1H), 3.32 (d, J=8.2 Hz, 1H), 2.63 (s, 3H), 2.21 (s, 3H), 2.03 (dd, J=16.0, 6.6 Hz, 4H). ESI MS [M+H]$^+$ for $C_{22}H_{21}F_4N_6O_2S$, calcd 509.1, found 509.2.

Example 97: N-[4-fluoro-5-[[5-[(2S)-2-(methoxymethyl)pyrrolidin-1-yl]pyrazin-2-yl]carbamoyl]-2-methylphenyl]-2-methyl-1,3-thiazole-5-carboxamide

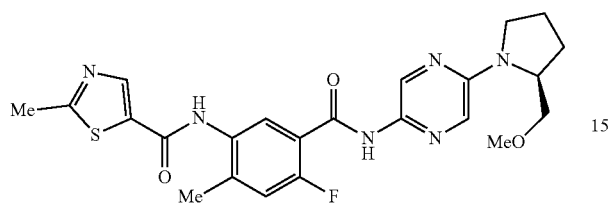

The title compound was prepared from 5-[(2S)-2-(methoxymethyl)pyrrolidin-1-yl]pyrazin-2-amine (prepared in a similar manner to that described in Example 92, steps a and b) and 2-fluoro-4-methyl-5-[(2-methyl-1,3-thiazole-5-carbonyl)amino]benzoic acid in a similar fashion to Example 4, step d. $^1$H NMR (400 MHz, DMSO-d$_6$) δ 10.54 (d, J=2.0 Hz, 1H), 10.16 (s, 1H), 8.77 (s, 1H), 8.42 (s, 1H), 7.85 (d, J=1.5 Hz, 1H), 7.67 (d, J=6.9 Hz, 1H), 7.33 (d, J=11.0 Hz, 1H), 4.19 (p, J=8.2 Hz, 1H), 3.56-3.47 (m, 1H), 3.33-3.29 (m, 1H), 3.27 (s, 3H), 2.89 (s, 1H), 2.73 (s, 1H), 2.71 (s, 3H), 2.28 (s, 3H), 1.94 (dd, J=16.0, 6.6 Hz, 2H), 1.33-1.20 (m, 1H), 0.93-0.85 (m, 1H), ESI MS [M+H]$^+$ for $C_{23}H_{26}FN_6O_3S$, calcd 485.2, found 485.2.

Example 98: N-[4-fluoro-2-methyl-5-[[6-(2,2,2-trifluoroethyl)pyridin-3-yl]carbamoyl]phenyl]-2-methyl-1,3-thiazole-5-carboxamide Step a: In a 40-mL vial, 2-fluoro-4-methyl-5-[(2-methyl-1,3-thiazole-5-carbonyl)amino]benzoic acid from Example 1, step b (59 mg, 0.20 mmol, 1.8 eq.) was dissolved in 2 mL DCM, and 1-chloro-N,N,2-trimethylprop-1-en-1-amine (80 mg, 0.60 mmol, 0.08 mL, 5.5 eq.) was added. The reaction mixture was stirred for 1 h before all volatiles were evaporated. The remaining mixture was further dried in vacuo under high vacuum for 20 min, giving the crude 2-fluoro-4-methyl-5-[(2-methyl-1,3-thiazole-5-carbonyl)amino]benzoyl chloride.

Step b. To a separate vial was added 6-(2,2,2-trifluoroethyl)pyridin-3-amine (20 mg, 0.11 mmol, 1.0 eq.), i-Pr$_2$NEt (74 mg, 0.57 mmol, 0.10 mL, 5.2 eq.), and 1 mL DCM. This DCM solution was slowly added to the vial containing the crude 2-fluoro-4-methyl-5-[(2-methyl-1,3-thiazole-5-carbonyl)amino]benzoyl chloride. After 20 min, all volatiles were evaporated, and the remaining mixture was purified by HPLC to provide the title compound. $^1$H NMR (400 MHz, DMSO-d$_6$) δ 10.60 (s, 1H), 10.14 (s, 1H), 8.81 (s, 1H), 8.38 (s, 1H), 8.15 (d, J=8.6 Hz, 1H), 7.60 (d, J=6.9 Hz, 1H), 7.44 (d, J=8.4 Hz, 1H), 7.33 (d, J=10.8 Hz, 1H), 3.75 (q, J=11.5 Hz, 2H), 2.68 (s, 3H), 2.27 (s, 3H). ESI MS [M+H]$^+$ for $C_{20}H_{17}F_4N_4O_2S$, calcd 453.1, found 453.1.

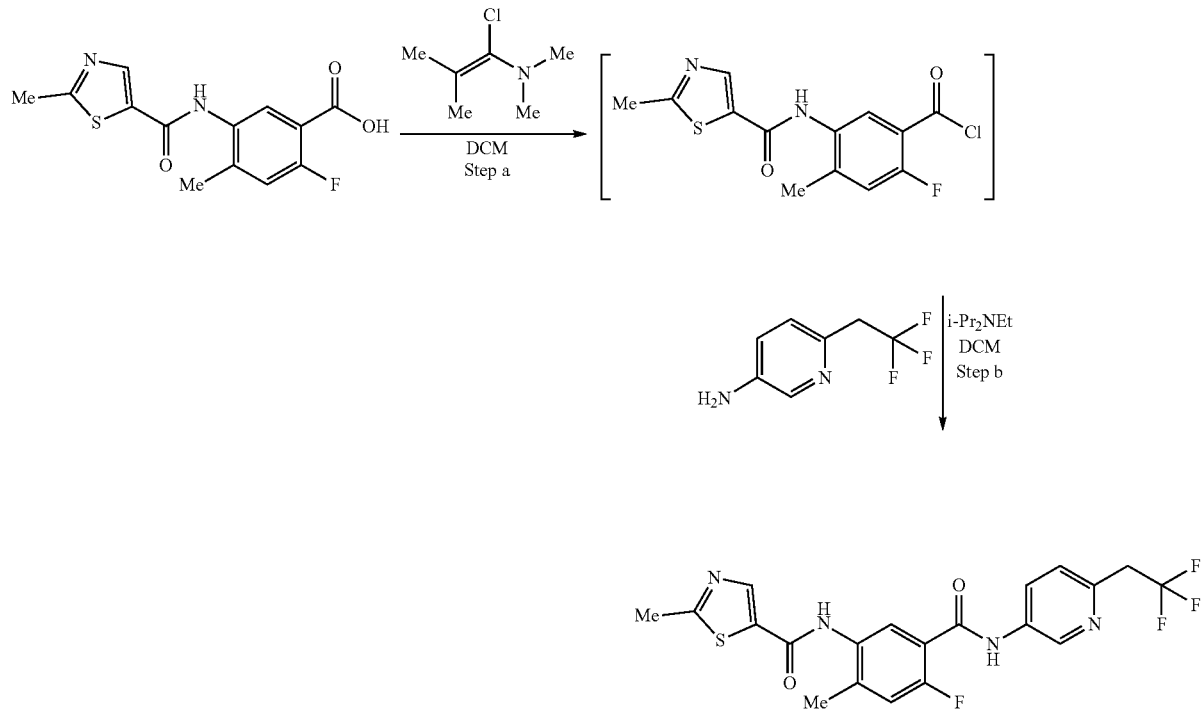

Example 99: N-[4-chloro-2-methyl-5-[[5-(2,2,2-trifluoroethyl)pyridin-2-yl]carbamoyl]phenyl]-2-methyl-1,3-thiazole-5-carboxamide

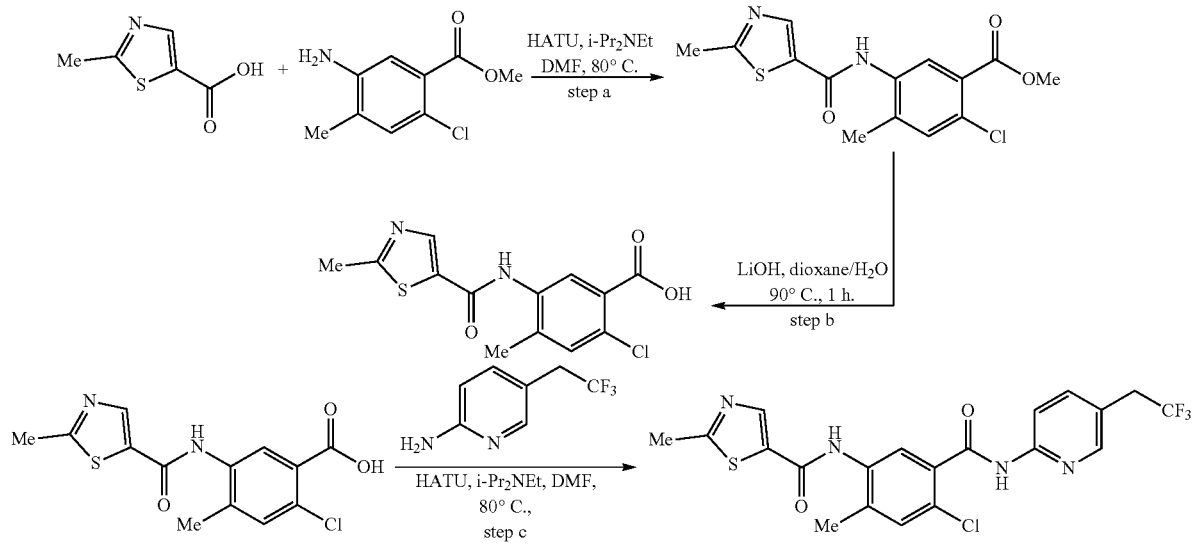

Step a and Step b were performed in an analogous manner to Example 1, steps a and b.

Step c. The title compound was prepared from 5-(2,2,2-trifluoroethyl)pyridin-2-amine (prepared according to Example 1, steps c and d) and 2-chloro-4-methyl-5-[(2-methyl-1,3-thiazole-5-carbonyl)amino]benzoic acid in a similar fashion to Example 4. $^1$H NMR (400 MHz, DMSO-$d_6$) δ 11.09 (s, 1H), 10.15 (s, 1H), 8.42 (s, 1H), 8.34 (d, J=2.3 Hz, 1H), 8.18 (d, J=8.5 Hz, 1H), 7.85 (dd, J=8.6, 2.3 Hz, 1H), 7.55 (s, 1H), 7.49 (d, J=0.8 Hz, 1H), 3.71 (q, J=11.5 Hz, 2H), 2.71 (s, 3H), 2.28 (s, 3H). ESI MS [M+H]$^+$ for $C_{20}H_{17}ClF_3N_4O_2S$, calcd 469.1, found 469.2.

Example 100: N-[5-[[2-(cyclopropylmethyl)pyrimidin-4-yl]carbamoyl]-4-fluoro-2-methylphenyl]-2-methyl-1,3-thiazole-5-carboxamide

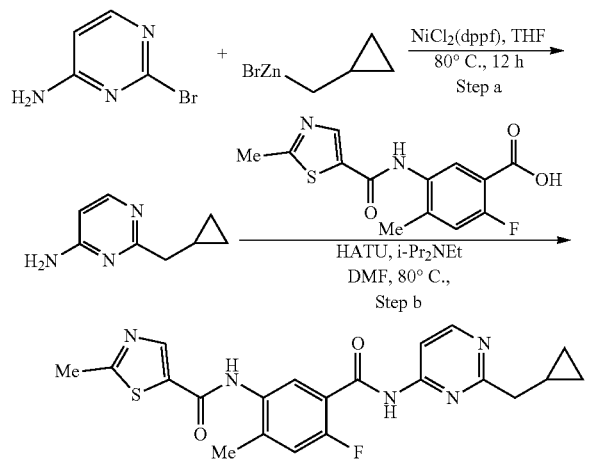

Step a. In a sealed vial under $N_2$, to solution of 2-bromopyrimidin-4-amine (870 mg, 5.0 mmol, 1.0 equiv.) in THF (C=0.2M) was added bromo(cyclopropylmethyl)zinc (0.5M in THF 15.0 mL, 7.5 mmol, 1.5 equiv.) and $NiCl_2$ (dppf) (0.5 mmol, 0.1 equiv.). The resulting reaction mixture was stirred at 80° C. for 12 h. The reaction mixture was then filtered through a Celite® plug and concentrated under reduced pressure to afford the crude product, which was purified by column chromatography using Hexane/EtOAc system.

Step b. The title compound was prepared from 2-(cyclopropylmethyl)pyrimidin-4-amine and 2-fluoro-4-methyl-5-[(2-methyl-1,3-thiazole-5-carbonyl)amino]benzoic acid in a similar fashion to Example 4, step d. $^1$H NMR (400 MHz, DMSO-$d_6$) δ 10.63 (s, 1H), 10.12 (s, 1H), 8.65 (d, J=5.7 Hz, 1H), 8.40 (s, 1H), 7.99 (d, J=5.7 Hz, 1H), 7.64 (d, J=6.8 Hz, 1H), 7.31 (d, J=11.1 Hz, 1H), 6.52 (s, 2H), 6.00-5.78 (m, 2H), 5.42-4.87 (m, 2H), 2.88 (t, J=7.6 Hz, 2H), 2.71 (s, 3H), 2.29 (s, 3H). ESI MS [M+H]$^+$ for $C_{21}H_{21}FN_5O_2S$, calcd 426.1, found 426.2.

Example 101: N-[5-[[(1R,2R)-2-(2-chlorophenyl)cyclopropyl]carbamoyl]-4-fluoro-2-methylphenyl]-2-methyl-1,3-thiazole-5-carboxamide

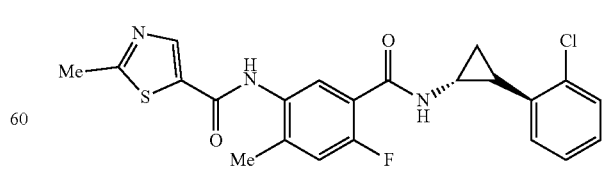

The title compound was prepared from (1R,2R)-2-(2-chlorophenyl)cyclopropan-1-amine and 2-fluoro-4-methyl-5-[(2-methyl-1,3-thiazole-5-carbonyl)amino]benzoic acid in a similar fashion to Example 4, step d. $^1$H NMR (400 MHz, DMSO-d$_6$) δ 10.03 (s, 1H), 8.53 (d, J=5.0 Hz, 1H), 8.31 (s, 1H), 7.43 (d, J=6.8 Hz, 1H), 7.34 (d, J=7.8 Hz, 1H), 7.31-7.08 (m, 3H), 7.12-6.99 (m, 1H), 3.11 (q, J=4.4 Hz, 1H), 2.62 (s, 3H), 2.26 (s, 1H), 2.16 (s, 3H), 1.31 (dt, J=9.9, 5.2 Hz, 1H), 1.14 (q, J=6.7 Hz, 1H). ESI MS [M+H]$^+$ for C$_{22}$H$_2$OClFN$_3$O$_2$S, calcd 444.1, found 444.2.

Example 102: 2-(Azetidine-1-carbonylamino)-N-[4-fluoro-2-methyl-5-[[(3S)-oxolan-3-yl]carbamoyl]phenyl]-1,3-thiazole-5-carboxamide

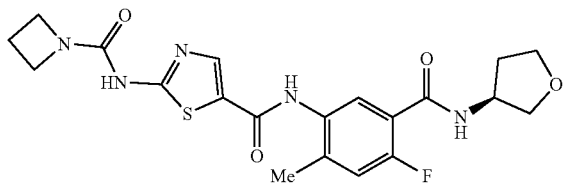 [SMILES: Cc1cc(F)c(C(=O)N[C@H]2CCOC2)cc1NC(=O)c1cnc(NC(=O)N2CCC2)s1]

The title compound was prepared from (3S)-oxolan-3-amine and 2-fluoro-4-methyl-5-[[2-[(2-methylpropan-2-yl)oxycarbonylamino]-1,3-thiazole-5-carbonyl]amino]benzoic acid in a similar fashion to Example 6. $^1$H NMR (400 MHz, DMSO-d$_6$) δ 11.19 (s, 1H), 9.79 (s, 1H), 8.44 (d, J=6.6 Hz, 1H), 8.12 (s, 1H), 7.45 (d, J=6.9 Hz, 1H), 7.22-7.14 (m, 1H), 4.43-4.33 (m, 1H), 3.99 (t, J=7.7 Hz, 4H), 3.85-3.72 (m, 2H), 3.66 (td, J=8.1, 5.6 Hz, 1H), 3.52 (dd, J=8.9, 4.2 Hz, 1H), 2.24-2.19 (m, 3H), 2.22-2.10 (m, 2H), 2.15-2.01 (m, 1H), 1.89-1.76 (m, 1H). ESI MS [M+H]$^+$ for C$_{20}$H$_{23}$FN$_5$O$_4$S, calcd 448.1, found 448.1.

Example 103: 2-(Azetidine-1-carbonylamino)-N-[4-fluoro-5-[(1-fluorocyclopropyl)methylcarbamoyl]-2-methylphenyl]-1,3-thiazole-5-carboxamide

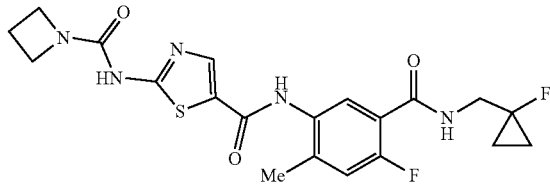 [SMILES: Cc1cc(F)c(C(=O)NCC2(F)CC2)cc1NC(=O)c1cnc(NC(=O)N2CCC2)s1]

The title compound was prepared from (1-fluorocyclopropyl)methanamine and 2-fluoro-4-methyl-5-[[2-[(2-methylpropan-2-yl)oxycarbonylamino]-1,3-thiazole-5-carbonyl]amino]benzoic acid in a similar fashion to Example 6. $^1$H NMR (400 MHz, DMSO-d$_6$) δ 11.21 (s, 1H), 9.81 (s, 1H), 8.53 (s, 1H), 8.13 (d, J=3.9 Hz, 1H), 7.51 (d, J=7.0 Hz, 1H), 7.20 (d, J=11.2 Hz, 1H), 3.99 (d, J=7.9 Hz, 4H), 3.64 (dd, J=20.6, 5.9 Hz, 2H), 2.20 (d, J=19.8 Hz, 5H), 1.02-0.89 (m, 2H), 0.81-0.70 (m, 2H). ESI MS [M+H]$^+$ for C$_{20}$H$_{22}$F$_2$N$_5$O$_3$S, calcd 450.1, found 450.1.

Example 104: 2-(Azetidine-1-carbonylamino)-N-[4-fluoro-5-[(1-fluorocyclobutyl)methylcarbamoyl]-2-methylphenyl]-1,3-thiazole-5-carboxamide

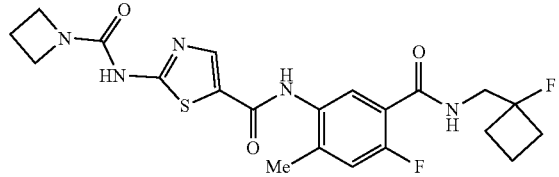 [SMILES: Cc1cc(F)c(C(=O)NCC2(F)CCC2)cc1NC(=O)c1cnc(NC(=O)N2CCC2)s1]

The title compound was prepared from (1-fluorocyclobutyl)methanamine and 2-fluoro-4-methyl-5-[[2-[(2-methylpropan-2-yl)oxycarbonylamino]-1,3-thiazole-5-carbonyl]amino]benzoic acid in a similar fashion to Example 6. $^1$H NMR (400 MHz, DMSO-d$_6$) δ 11.19 (s, 1H), 9.81 (s, 1H), 8.45-8.37 (m, 1H), 8.13 (s, 1H), 7.49 (d, J=7.0 Hz, 1H), 7.23-7.16 (m, 1H), 3.99 (t, J=7.6 Hz, 4H), 3.57 (dd, J=23.1, 6.1 Hz, 2H), 2.24-2.09 (m, 9H), 1.78-1.66 (m, 1H), 1.48 (dtd, J=11.4, 8.9, 2.6 Hz, 1H). ESI MS [M+H]$^+$ for C$_{21}$H$_{24}$F$_2$N$_5$O$_3$S, calcd 450.1, found 450.1.

Example 105: N-[5-[[4-fluoro-2-methyl-5-[[(3S)-oxolan-3-yl]carbamoyl]phenyl]carbamoyl]-1,3-thiazol-2-yl]morpholine-4-carboxamide

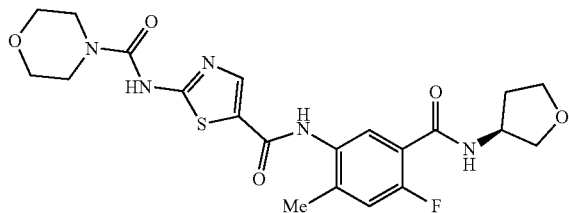 [SMILES: Cc1cc(F)c(C(=O)N[C@H]2CCOC2)cc1NC(=O)c1cnc(NC(=O)N2CCOCC2)s1]

The title compound was prepared in a similar manner to that described in Example 6 using (3S)-oxolan-3-amine in step c, and morpholine in step e. $^1$H NMR (400 MHz, DMSO-d$_6$)$^1$H NMR (400 MHz, DMSO-d$_6$) δ 11.41 (s, 1H), 9.79 (s, 1H), 8.47-8.40 (m, 1H), 8.14 (s, 1H), 7.46 (d, J=6.9 Hz, 1H), 7.19 (d, J=11.0 Hz, 1H), 4.39 (dddd, J=8.0, 6.5, 3.8, 2.1 Hz, 1H), 3.85-3.72 (m, 2H), 3.67 (td, J=8.1, 5.6 Hz, 1H), 3.60-3.45 (m, 9H), 2.22 (s, 3H), 2.10 (dq, J=12.7, 7.7 Hz, 1H), 1.89-1.77 (m, 1H). ESI MS [M+H]$^+$ for C$_{21}$H$_{25}$FN$_5$O$_5$S, calcd 478.1, found 478.1.

Example 106: Cyclobutyl N-[5-[[5-[(4-cyclopropyloxyphenyl)carbamoyl]-4-fluoro-2-methylphenyl]carbamoyl]-1,3-thiazol-2-yl]carbamate

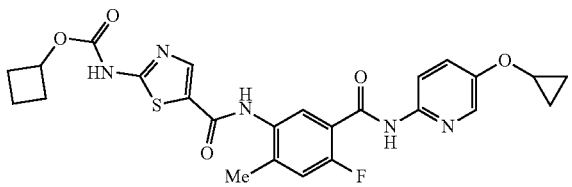 [SMILES: Cc1cc(F)c(C(=O)Nc2ccc(OC3CC3)cn2)cc1NC(=O)c1cnc(NC(=O)OC2CCC2)s1]

The title compound was prepared from cyclobutanol and 2-amino-N-[5-[(5-cyclopropyloxypyridin-2-yl)carbamoyl]-4-fluoro-2-methylphenyl]-1,3-thiazole-5-carboxamide in a similar fashion to Example 6. $^1$H NMR (400 MHz, DMSO-$d_6$) δ 12.09 (s, 1H), 10.51 (d, J=2.6 Hz, 1H), 9.94 (s, 1H), 8.17 (s, 1H), 8.15-8.04 (m, 2H), 7.63-7.51 (m, 2H), 7.25 (d, J=11.1 Hz, 1H), 5.02-4.93 (m, 1H), 3.92 (tt, J=6.0, 2.9 Hz, 1H), 2.36-2.22 (m, 5H), 2.13-1.98 (m, 2H), 1.80-1.67 (m, 1H), 1.66-1.51 (m, 1H), 0.82-0.72 (m, 2H), 0.70-0.61 (m, 2H). ESI MS [M+H]$^+$ for $C_{25}H_{25}FN_5O_5S$, calcd 526.1, found 526.1.

Example 107: N-[5-[(5-cyclopropyloxypyridin-2-yl)carbamoyl]-4-fluoro-2-methylphenyl]-2-[[(3R)-oxolane-3-carbonyl]amino]-1,3-thiazole-5-carboxamide

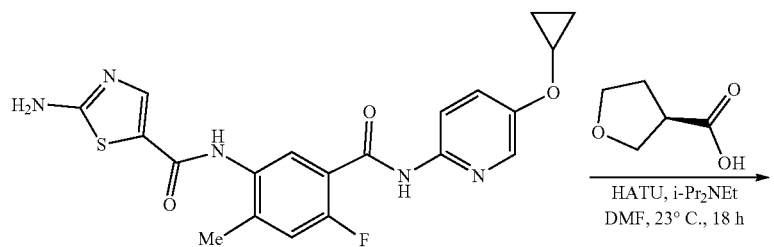

A vial was charged with 2-amino-N-[5-[(5-cyclopropyloxypyridin-2-yl)carbamoyl]-4-fluoro-2-methylphenyl]-1,3-thiazole-5-carboxamide (35 mg, 0.082 mmol, 1.0 equiv., prepared as described in Example 6), (3R)-oxolane-3-carboxylic acid (9.5 mg, 0.082 mmol, 1.0 equiv.), and HATU (46.7 mg, 0.123 mmol, 1.5 equiv.). DMF (1.0 mL, 0.082 M) was added, followed by i-Pr$_2$NEt (0.042 mL, 0.246 mmol, 3.0 equiv.). The reaction mixture was stirred at 23° C. for 16 h, at which time LC/MS analysis showed complete consumption of starting material. The reaction mixture was subjected to purification by reverse phase HPLC to afford the title compound. $^1$H NMR (400 MHz, DMSO-$d_6$) δ 12.53 (s, 1H), 10.51 (d, J=2.5 Hz, 1H), 9.97 (s, 1H), 8.25 (s, 1H), 8.15-8.04 (m, 2H), 7.65-7.51 (m, 2H), 7.26 (d, J=11.1 Hz, 1H), 3.96-3.85 (m, 2H), 3.82-3.70 (m, 2H), 3.67 (dt, J=8.3, 7.0 Hz, 1H), 3.34-3.24 (m, 1H), 2.26 (s, 3H), 2.14-2.02 (m, 2H), 0.82-0.72 (m, 2H), 0.70-0.61 (m, 2H). ESI MS [M+H]$^+$ for $C_{25}H_{25}FN_5O_5S$, calcd 526.1, found 526.1.

Example 108: N-[5-[(5-cyclopropyloxypyridin-2-yl)carbamoyl]-4-fluoro-2-methylphenyl]-2-[[(3S)-oxolane-3-carbonyl]amino]-1,3-thiazole-5-carboxamide

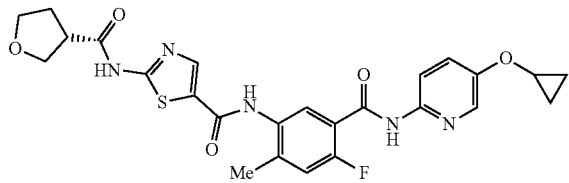

The title compound was prepared from (3S)-oxolane-3-carboxylic acid and 2-amino-N-[5-[(5-cyclopropyloxypyridin-2-yl)carbamoyl]-4-fluoro-2-methylphenyl]-1,3-thiazole-5-carboxamide in a similar fashion to Example 107. $^1$H NMR (400 MHz, DMSO-d$_6$) δ 12.54 (s, 1H), 10.52 (d, J=2.5 Hz, 1H), 9.97 (s, 1H), 8.25 (s, 1H), 8.15-8.04 (m, 2H), 7.64-7.51 (m, 2H), 7.26 (d, J=11.1 Hz, 1H), 3.96-3.85 (m, 2H), 3.81-3.62 (m, 3H), 3.33-3.22 (m, 1H), 2.26 (s, 3H), 2.14-2.01 (m, 2H), 0.82-0.72 (m, 2H), 0.70-0.61 (m, 2H). ESI MS [M+H]$^+$ for C$_{25}$H$_{25}$FN$_5$O$_5$S, calcd 526.2, found 526.2.

Example 109: N-[5-[(5-cyclopropyloxypyridin-2-yl)carbamoyl]-4-fluoro-2-methylphenyl]-2-[(2-hydroxy-2-methylpropanoyl)amino]-1,3-thiazole-5-carboxamide

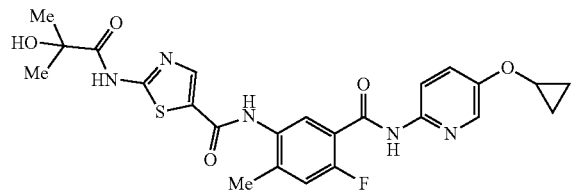 [SMILES: Cc1cc(F)c(C(=O)Nc2ccc(OC3CC3)cn2)cc1NC(=O)c1cnc(NC(=O)C(C)(C)O)s1]

The title compound was prepared from 2-hydroxy-2-methylpropanoic acid and 2-amino-N-[5-[(5-cyclopropyloxypyridin-2-yl)carbamoyl]-4-fluoro-2-methylphenyl]-1,3-thiazole-5-carboxamide in a similar fashion to Example 107. $^1$H NMR (400 MHz, Methanol-d$_4$) δ 8.19 (s, 1H), 8.18-8.08 (m, 2H), 7.78 (d, J=7.0 Hz, 1H), 7.56 (dd, J=9.0, 3.0 Hz, 1H), 7.23 (d, J=11.6 Hz, 1H), 3.87 (dt, J=5.9, 3.0 Hz, 1H), 2.35 (s, 3H), 1.46 (s, 6H), 0.87-0.67 (m, 4H). ESI MS [M+H]$^+$ for C$_{24}$H$_{25}$FN$_5$O$_5$S, calcd 514.2, found 514.2.

Example 110: N-[5-[(5-cyclopropyloxypyridin-2-yl)carbamoyl]-4-fluoro-2-methylphenyl]-2-[[(3R)-oxolane-3-carbonyl]amino]-1,3-thiazole-5-carboxamide

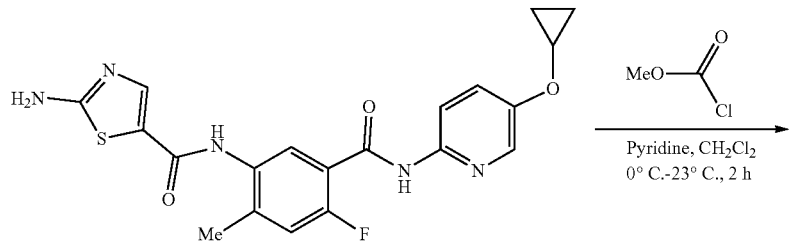

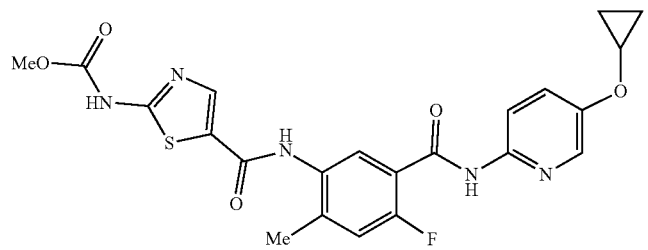

To a solution of 2-amino-N-[5-[(5-cyclopropyloxypyridin-2-yl)carbamoyl]-4-fluoro-2-methylphenyl]-1,3-thiazole-5-carboxamide (38 mg, 0.089 mmol, 1.0 equiv., prepared as described in Example 6) in 1.0 mL of DCM at 0° C. was added pyridine (0.014 mL, 0.179 mmol, 2 equiv.), followed by methyl carbonochloridate (0.0082 mL, 0.106 mmol, 1.2 equiv.). The reaction mixture was stirred at 23° C. for 2 h, at which time LC/MS analysis showed complete consumption of starting material. The reaction mixture was quenched with 1.0 mL of water and concentrated in vacuo. The residue was purified by reverse phase HPLC to afford the title compound. $^1$H NMR (400 MHz, DMSO-d$_6$) δ 10.47 (s, 1H), 8.19-7.98 (m, 3H), 7.66-7.43 (m, 2H), 7.22 (d, J=11.1 Hz, 1H), 6.55 (s, 1H), 6.27 (s, 1H), 3.92 (dt, J=5.9, 3.1 Hz, 1H), 3.60 (s, 3H), 2.25 (s, 3H), 0.82-0.54 (m, 4H). ESI MS [M+H]$^+$ for $C_{22}H_{21}FN_5O_5S$, calcd 486.2, found 486.2.

Example 111: 2-Amino-N-[4-fluoro-2-methyl-5-[[5-(1,1,1-trifluoro-2-hydroxypropan-2-yl)pyridin-2-yl]carbamoyl]phenyl]-1,3-thiazole-5-carboxamide was purified by column chromatography (EtOAc/hexanes, 0% to 100%) to provide tert-butyl N-[5-[[5-[(5-acetylpyridin-2-yl)carbamoyl]-4-fluoro-2-methylphenyl]carbamoyl]-1,3-thiazol-2-yl]carbamate.

Step b: To a solution of product from step a (0.160 g, 0.312 mmol, 1.0 equiv.) in 5.0 mL of THF at 0° C. was added trifluoromethyltrimethylsilane (0.055 mL, 0.374 mmol, 1.2 equiv.), followed by 1.0 M tetrabutylammonium fluoride solution (0.374 mL, 0.374 mmol, 1.2 equiv.). The reaction mixture was stirred at 23° C. for 18 h, at which time LC/MS analysis showed complete consumption of starting material. The reaction was quenched with water and extracted three times with EtOAc. The combined organic extracts were dried over Na$_2$SO$_4$, filtered, and concentrated in vacuo to afford the crude product, which was purified by column chromatography (EtOAc/hexanes, 0% to 100%) to provide tert-butyl N-[5-[[4-fluoro-2-methyl-5-[[5-(1,1,1-trifluoro-2-hydroxypropan-2-yl)pyridin-2-yl]carbamoyl]phenyl]carbamoyl]-1,3-thiazol-2-yl]carbamate.

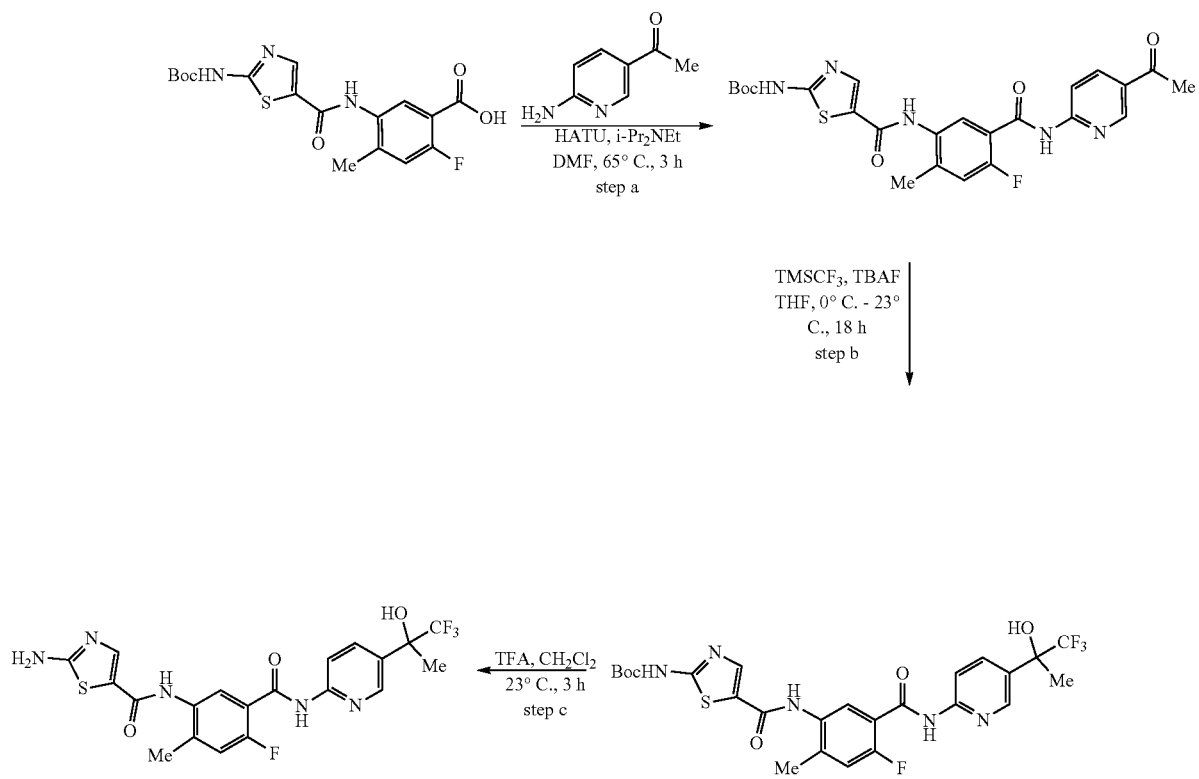

Step a: A vial was charged with 2-fluoro-4-methyl-5-[[2-[(2-methylpropan-2-yl)oxycarbonylamino]-1,3-thiazole-5-carbonyl]amino]benzoic acid (0.150 g, 0.380 mmol, 1.0 equiv., prepared as described in Example 6), 1-(6-aminopyridin-3-yl)ethanone (0.062 g, 0.455 mmol, 1.2 equiv.), HATU (0.216 g, 0.570 mmol, 1.5 equiv.) and DMF (2 mL). i-Pr$_2$NEt (0.198 mL, 1.139 mmol, 3.0 equiv.) was added and the reaction mixture was stirred at 65° C. for 3 h. Upon completion, the reaction mixture was cooled to RT, diluted with water, and extracted three times with EtOAc. The combined organic extracts were dried over Na$_2$SO$_4$, filtered, and concentrated in vacuo to afford the crude product, which Step c: The product from step b (0.136 g, 0.233 mmol) was dissolved in CH$_2$Cl$_2$ (2.0 mL) and was treated with TFA (1.0 mL). The reaction mixture was stirred at 23° C. and monitored by LC/MS. Upon completion, the reaction mixture was concentrated in vacuo. The residue was purified by reverse phase HPLC to afford the title compound. $^1$H NMR (400 MHz, DMSO-d$_6$)$^1$H NMR (400 MHz, DMSO-d$_6$) δ 10.74 (d, J=2.3 Hz, 1H), 9.59 (s, 1H), 8.51 (d, J=2.4 Hz, 1H), 8.16 (dd, J=8.7, 0.8 Hz, 1H), 8.00 (dd, J=8.8, 2.4 Hz, 1H), 7.82 (s, 1H), 7.63-7.54 (m, 3H), 7.23 (d, J=11.2 Hz, 1H), 6.77 (s, 1H), 2.24 (s, 3H), 1.69 (s, 3H). ESI MS [M+H]$^+$ for $C_{20}H_{18}F_4N_5O_3S_1$, calcd 484.1, found 484.1.

Example 112: 2-Amino-N-[5-(1,3-dihydrofuro[3,4-c]pyridin-6-ylcarbamoyl)-4-fluoro-2-methylphenyl]-1,3-thiazole-5-carboxamide

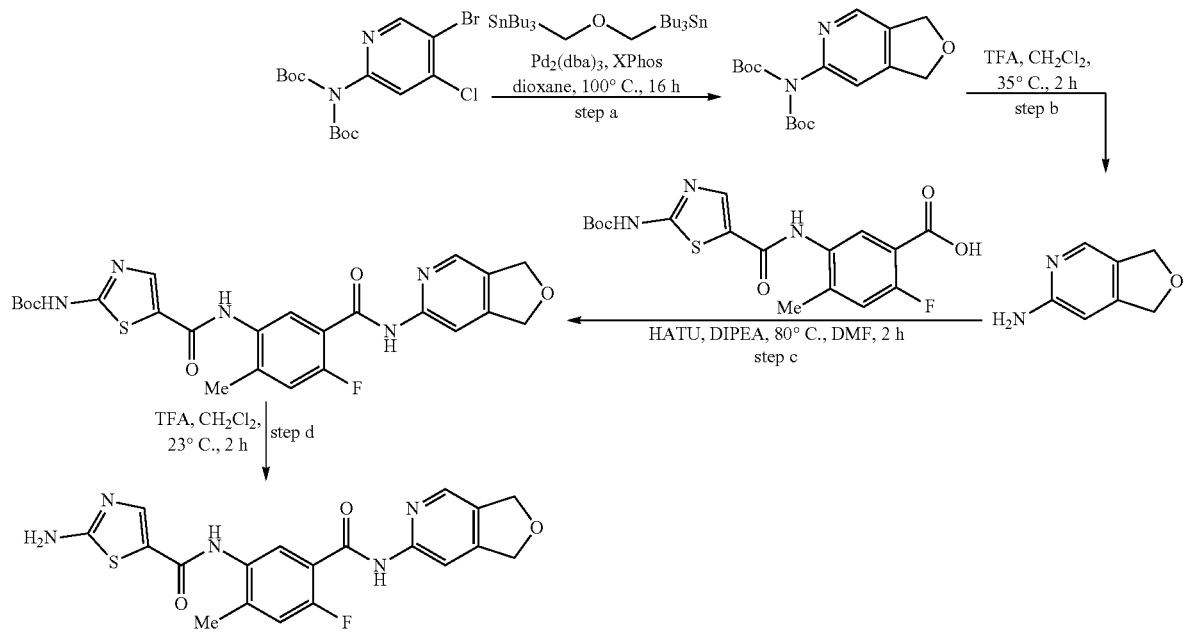

Step a: To a solution of tert-butyl N-(5-bromo-4-chloro-pyridin-2-yl)-N-[(2-methylpropan-2-yl)oxycarbonyl]carbamate (650 mg, 1.59 mmol, 1.0 equiv.) were added successively oxybis(methylene)bis(tributylstannane) (995 mg, 1.59 mmol, 1.0 equiv.) tris(dibenzylideneacetone) dipalladium(0) (293 mg, 0.32 mmol, 0.2 equiv.), 2-dicyclohexylphosphino-2',4',6'-triisopropylbiphenyl (305 mg, 0.64 mmol, 0.4 equiv.) and 1,4-dioxane (16 mL). The reaction mixture was degassed for 15 min. under argon atmosphere. The reaction mixture was stirred at 100° C. for 16 h. After completion of reaction as analyzed by LC/MS, the reaction mixture was filtered through a pad of Celite® and washed with ethyl acetate. The filtrate was concentrated under reduced pressure to obtain crude material, which was further purified using column chromatography on silica gel (hexane/EtOAc, 0%→100%) to obtain tert-butyl N-(1,3-dihydrofuro[3,4-c]pyridin-6-yl)-N-[(2-methylpropan-2-yl)oxycarbonyl]carbamate.

Step b: The product from step a (244 mg, 0.725 mmol, 1.0 equiv.) was dissolved in a mixture of $CH_2Cl_2$ (2.0 mL) and TFA (0.5 mL). The reaction mixture stirred at 35° C. for 2 h. After completion of reaction as analyzed by LC/MS, the reaction mixture was concentrated under reduced pressure to obtain a crude material, which was further purified using column chromatography on silica gel ($CH_2Cl_2$/MeOH, 0%→10%) to obtain 1,3-dihydrofuro[3,4-c]pyridin-6-amine.

Steps c and d were performed in a similar manner to that described in Example 7 from 1,3-dihydrofuro[3,4-c]pyridin-6-amine and 2-fluoro-4-methyl-5-[[2-[(2-methylpropan-2-yl)oxycarbonylamino]-1,3-thiazole-5-carbonyl]amino]benzoic acid. $^1$H NMR (400 MHz, DMSO-$d_6$) δ 10.68 (d, J=2.5 Hz, 1H), 9.69 (s, 1H), 8.26 (d, J=1.0 Hz, 1H), 8.08 (s, 1H), 7.97 (s, 2H), 7.84 (s, 1H), 7.54 (d, J=6.9 Hz, 1H), 7.22 (d, J=11.2 Hz, 1H), 4.97 (d, J=2.3 Hz, 4H), 2.21 (s, 3H). ESI MS [M+H]$^+$ for $C_{19}H_{17}F_1N_5O_3S_1$, calcd 414.1, found 414.0.

Example 113: 2-Amino-N-[4-fluoro-5-[[5-(2-hydroxypropan-2-yl)pyridin-2-yl]carbamoyl]-2-methylphenyl]-1,3-thiazole-5-carboxamide

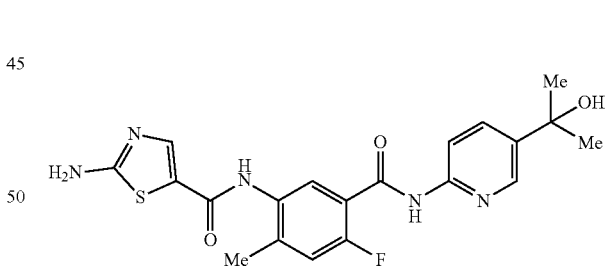

The title compound was prepared from 2-(6-aminopyridin-3-yl)propan-2-ol and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-$d_6$) δ 10.53 (d, J=2.7 Hz, 1H), 9.59 (s, 1H), 8.41 (d, J=2.4 Hz, 1H), 8.06 (d, J=8.6 Hz, 1H), 7.86 (dd, J=8.7, 2.5 Hz, 1H), 7.82 (s, 1H), 7.60 (s, 2H), 7.57 (d, J=7.0 Hz, 1H), 7.22 (d, J=11.3 Hz, 1H), 5.16 (s, 1H), 2.23 (s, 3H), 1.42 (s, 6H). ESI MS [M+H]$^+$ for $C_{20}H_{21}F_1N_5O_3S_1$, calcd 430.1, found 430.1.

Example 114: 2-Amino-N-[5-(6,8-dihydro-5H-pyrano[3,4-b]pyridin-2-ylcarbamoyl)-4-fluoro-2-methylphenyl]-1,3-thiazole-5-carboxamide

The title compound was prepared in a similar manner to Example 7, steps a and b from 2-fluoro-4-methyl-5-[[2-[(2-methylpropan-2-yl)oxycarbonylamino]-1,3-thiazole-5-carbonyl]amino]benzoic acid and 6,8-dihydro-5H-pyrano[3,4-b]pyridin-2-amine prepared from 2-chloro-6,8-dihydro-5H-pyrano[3,4-b]pyridine in a similar manner to Example 1, steps c and d. $^1$H NMR (400 MHz, DMSO-$d_6$) δ 10.55 (d, J=2.7 Hz, 1H), 9.62 (s, 1H), 8.01 (d, J=8.4 Hz, 1H), 7.85 (s, 1H), 7.68 (s, 2H), 7.64-7.58 (m, 2H), 7.24 (d, J=11.3 Hz, 1H), 4.60 (s, 2H), 3.90 (t, J=5.6 Hz, 2H), 2.80 (t, J=5.7 Hz, 2H), 2.26 (s, 3H). ESI MS [M+H]$^+$ for $C_{20}H_{19}F_1N_5O_3S_1$, calcd 428.1, found 428.1.

Example 115: 2-Amino-N-[5-(7,8-dihydro-5H-pyrano[4,3-b]pyridin-2-ylcarbamoyl)-4-fluoro-2-methylphenyl]-1,3-thiazole-5-carboxamide

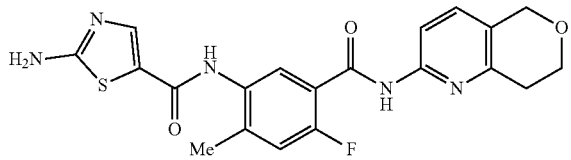 [SMILES: Cc1cc(F)c(C(=O)Nc2ccc3c(n2)CCOC3)cc1NC(=O)c1cnc(N)s1]

The title compound was prepared in a similar manner to Example 7, steps a and b from 2-fluoro-4-methyl-5-[[2-[(2-methylpropan-2-yl)oxycarbonylamino]-1,3-thiazole-5-carbonyl]amino]benzoic acid and 7,8-dihydro-5H-pyrano[4,3-b]pyridin-2-amine prepared from 2-chloro-7,8-dihydro-5H-pyrano[4,3-b]pyridine in a similar manner to Example 1, steps c and d. $^1$H NMR (400 MHz, DMSO-$d_6$) δ 10.56 (d, J=2.7 Hz, 1H), 9.61 (s, 1H), 8.00 (d, J=8.4 Hz, 1H), 7.85 (s, 1H), 7.67 (s, 2H), 7.61 (d, J=7.0 Hz, 1H), 7.53 (d, J=8.4 Hz, 1H), 7.25 (d, J=11.3 Hz, 1H), 4.69 (s, 2H), 3.98 (t, J=5.8 Hz, 2H), 2.82 (t, J=5.8 Hz, 2H), 2.27 (s, 3H). ESI MS [M+H]$^+$ for $C_{20}H_{19}F_1N_5O_3S_1$, calcd 428.1, found 428.1.

Example 116: 2-Amino-N-[4-fluoro-2-methyl-5-[(5-methylsulfonylpyridin-2-yl)carbamoyl]phenyl]-1,3-thiazole-5-carboxamide

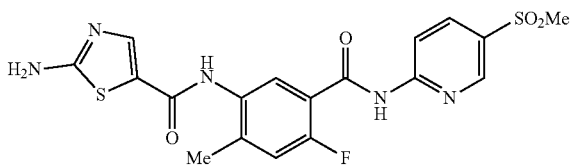 [SMILES: Cc1cc(F)c(C(=O)Nc2ccc(S(C)(=O)=O)cn2)cc1NC(=O)c1cnc(N)s1]

The title compound was prepared from 5-methylsulfonylpyridin-2-amine and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-$d_6$) δ 11.26 (s, 1H), 9.63 (s, 1H), 8.85 (dd, J=2.4, 0.8 Hz, 1H), 8.40-8.31 (m, 2H), 7.85 (s, 1H), 7.64 (s, 1H), 7.63 (s, 2H), 7.29 (d, J=11.1 Hz, 1H), 3.30 (s, 3H), 2.28 (s, 3H). ESI MS [M+H]$^+$ for $C_{18}H_{17}F_1N_5O_4S_2$, calcd 450.1, found 450.1.

Example 117: 2-Amino-N-[4-fluoro-2-methyl-5-[[5-[(3S)-oxolan-3-yl]oxypyridin-2-yl]carbamoyl]phenyl]-1,3-thiazole-5-carboxamide

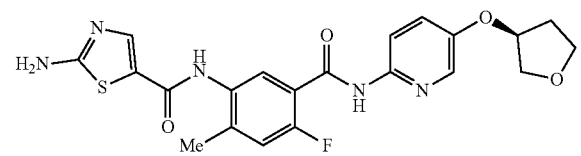 [SMILES: Cc1cc(F)c(C(=O)Nc2ccc(O[C@H]3CCOC3)cn2)cc1NC(=O)c1cnc(N)s1]

The title compound was prepared from (3S)-oxolan-3-ol and 2-fluoro-4-methyl-5-[[2-[(2-methylpropan-2-yl)oxycarbonylamino]-1,3-thiazole-5-carbonyl]amino]benzoic acid in a similar fashion to Example 198. $^1$H NMR (400 MHz, DMSO-$d_6$) δ 10.48 (d, J=2.8 Hz, 1H), 9.61 (s, 1H), 8.10 (d, J=9.1 Hz, 1H), 8.06 (d, J=3.0 Hz, 1H), 7.85 (s, 1H), 7.62 (d, J=1.8 Hz, 2H), 7.60 (s, 1H), 7.49 (dd, J=9.1, 3.1 Hz, 1H), 7.25 (d, J=11.2 Hz, 1H), 5.10 (ddt, J=6.3, 4.1, 1.8 Hz, 1H), 3.92-3.73 (m, 4H), 2.27 (s, 3H), 2.22 (td, J=8.0, 5.8 Hz, 1H), 2.02-1.93 (m, 1H). ESI MS [M+H]$^+$ for $C_{21}H_{21}F_1N_5O_4S_1$, calcd 458.1, found 458.1.

Example 118: 2-Amino-N-[5-[[5-(1-cyanocyclopropyl)pyridin-2-yl]carbamoyl]-4-fluoro-2-methylphenyl]-1,3-thiazole-5-carboxamide

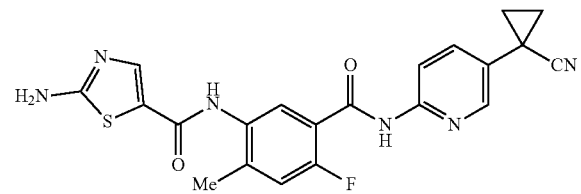 [SMILES: Cc1cc(F)c(C(=O)Nc2ccc(C3(C#N)CC3)cn2)cc1NC(=O)c1cnc(N)s1]

The title compound was prepared in a similar manner to Example 7, steps a and b from 2-fluoro-4-methyl-5-[[2-[(2-methylpropan-2-yl)oxycarbonylamino]-1,3-thiazole-5-carbonyl]amino]benzoic acid and 1-(6-aminopyridin-3-yl)cyclopropane-1-carbonitrile prepared from 1-(6-chloropyridin-3-yl)cyclopropane-1-carbonitrile in a similar manner to Example 1, steps c and d. $^1$H NMR (400 MHz, DMSO-$d_6$) δ 10.81 (d, J=2.2 Hz, 1H), 9.70 (s, 1H), 8.38 (d, J=2.6 Hz, 1H), 8.18 (d, J=8.7 Hz, 1H), 7.85 (s, 2H), 7.89 (s, 1H), 7.82 (dd, J=8.8, 2.6 Hz, 1H), 7.60 (d, J=7.0 Hz, 1H), 7.27 (d, J=11.2 Hz, 1H), 2.27 (s, 3H), 1.81-1.72 (m, 2H), 1.61-1.52 (m, 2H). ESI MS [M+H]$^+$ for $C_{21}H_{18}F_1N_6O_2S_1$, calcd 437.1, found 437.1.

Example 119: 2-Amino-N-[5-[[6-(1-cyanocyclopropyl)pyridazin-3-yl]carbamoyl]-4-fluoro-2-methylphenyl]-1,3-thiazole-5-carboxamide

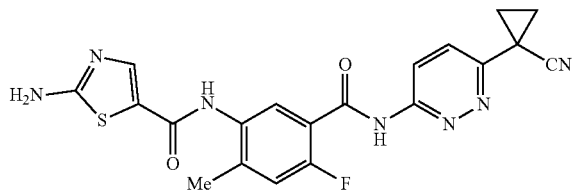 [SMILES: Cc1cc(F)c(C(=O)Nc2ccc(C3(C#N)CC3)nn2)cc1NC(=O)c1cnc(N)s1]

The title compound was prepared in a similar manner to Example 7, steps a and b from 2-fluoro-4-methyl-5-[[2-[(2-methylpropan-2-yl)oxycarbonylamino]-1,3-thiazole-5-carbonyl]amino]benzoic acid and 1-(6-aminopyridazin-3-yl)cyclopropane-1-carbonitrile prepared from 1-(6-chloropyridazin-3-yl)cyclopropane-1-carbonitrile in a similar manner to Example 1, steps c and d. $^1$H NMR (400 MHz, DMSO-d$_6$) δ 11.41 (s, 1H), 9.60 (s, 1H), 8.37 (d, J=9.4 Hz, 1H), 7.82 (s, 1H), 7.75 (d, J=9.4 Hz, 1H), 7.60 (s, 2H), 7.59 (s, 1H), 7.26 (d, J=11.1 Hz, 1H), 2.25 (s, 3H), 1.92-1.86 (m, 2H), 1.80-1.75 (m, 2H). ESI MS [M+H]$^+$ for C$_{20}$H$_{17}$F$_1$N$_7$O$_2$S$_1$, calcd 438.1, found 438.1.

Example 120: 2-Amino-N-[5-(5,7-dihydrofuro[3,4-b]pyridin-2-ylcarbamoyl)-4-fluoro-2-methylphenyl]-1,3-thiazole-5-carboxamide

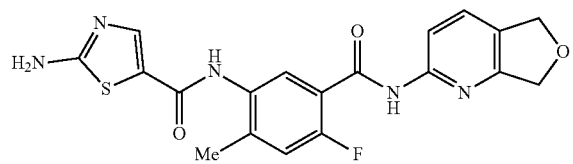 [SMILES: Cc1cc(F)c(C(=O)Nc2ccc3c(n2)COC3)cc1NC(=O)c1cnc(N)s1]

The title compound was prepared in a similar manner to Example 7, steps a and b from 2-fluoro-4-methyl-5-[[2-[(2-methylpropan-2-yl)oxycarbonylamino]-1,3-thiazole-5-carbonyl]amino]benzoic acid and 5,7-dihydrofuro[3,4-b]pyridin-2-amine prepared from 2-chloro-5,7-dihydrofuro[3,4-b]pyridine in a similar manner to Example 1, steps c and d. $^1$H NMR (400 MHz, DMSO-d$_6$) δ 10.65 (s, 1H), 9.61 (s, 1H), 8.04 (d, J=8.3 Hz, 1H), 7.81 (s, 1H), 7.74 (d, J=8.4 Hz, 3H), 7.55 (d, J=6.9 Hz, 1H), 7.20 (d, J=11.2 Hz, 1H), 5.01 (s, 2H), 4.84 (s, 2H), 2.20 (s, 3H). ESI MS [M+H]$^+$ for C$_{19}$H$_{17}$F$_1$N$_5$O$_3$S$_1$, calcd 414.1, found 414.1.

Example 121: 2-Amino-N-[5-[[1-(cyclopropanecarbonyl)azetidin-3-yl]carbamoyl]-4-fluoro-2-methylphenyl]-1,3-thiazole-5-carboxamide

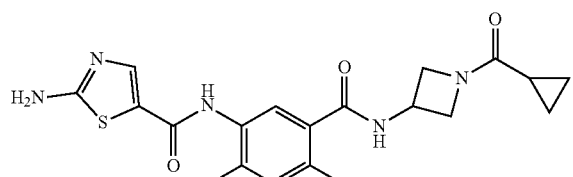

The title compound was prepared from (3-aminoazetidin-1-yl)-cyclopropylmethanone and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-d$_6$) δ 9.58 (s, 1H), 8.89 (dd, J=7.0, 1.7 Hz, 1H), 7.81 (s, 1H), 7.64 (s, 2H), 7.50 (d, J=7.0 Hz, 1H), 7.20 (d, J=11.2 Hz, 1H), 4.73-4.59 (m, 1H), 4.50 (t, J=8.2 Hz, 1H), 4.13 (dd, J=8.7, 5.4 Hz, 1H), 4.09 (dd, J=9.7, 8.0 Hz, 1H), 3.79 (dd, J=9.8, 5.5 Hz, 1H), 2.20 (s, 3H), 1.53-1.46 (m, 1H), 0.71-0.62 (m, 4H). ESI MS [M+H]$^+$ for C$_{19}$H$_{21}$F$_1$N$_5$O$_3$S$_1$, calcd 418.1, found 418.1.

Example 122: 2-Amino-N-[4-fluoro-2-methyl-5-(2,2,2-trifluoroethylcarbamoyl)phenyl]-1,3-thiazole-5-carboxamide

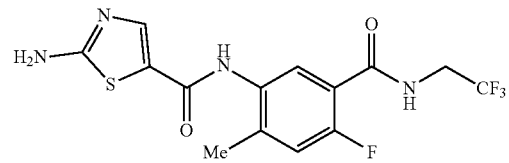 [SMILES: Cc1cc(F)c(C(=O)NCC(F)(F)F)cc1NC(=O)c1cnc(N)s1]

The title compound was prepared from 2,2,2-trifluoroethanamine and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-d$_6$) δ 9.62 (s, 1H), 8.90 (td, J=6.4, 2.2 Hz, 1H), 7.84 (s, 1H), 7.64 (s, 2H), 7.54 (d, J=7.0 Hz, 1H), 7.26 (d, J=11.2 Hz, 1H), 4.07 (qd, J=9.6, 6.3 Hz, 2H), 2.25 (s, 3H). ESI MS [M+H]$^+$ for C$_{14}$H$_{13}$F$_4$N$_4$O$_2$S$_1$, calcd 377.1, found 377.1.

Example 123: 2-Amino-N-[4-fluoro-5-[(3-methoxycyclobutyl)carbamoyl]-2-methylphenyl]-1,3-thiazole-5-carboxamide

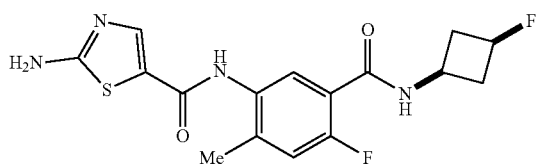 [SMILES: Cc1cc(F)c(C(=O)N[C@H]2C[C@@H](F)C2)cc1NC(=O)c1cnc(N)s1]

The title compound was prepared from cis-3-methoxycyclobutan-1-amine and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-d$_6$) δ 9.58 (s, 1H), 8.52-8.43 (m, 1H), 7.83 (s, 1H), 7.63 (s, 2H), 7.45 (d, J=7.0 Hz, 1H), 7.19 (d, J=11.1 Hz, 1H), 3.98 (ddt, J=16.5, 9.1, 7.5 Hz, 1H), 3.59 (tt, J=7.7, 6.4 Hz, 1H), 3.13 (s, 3H), 2.62-2.53 (m, 2H), 2.23 (s, 3H), 1.93-1.84 (m, 2H). ESI MS [M+H]$^+$ for C$_{17}$H$_{20}$F$_1$N$_4$O$_3$S$_1$, calcd 379.1, found 379.1.

Example 124: 2-Amino-N-[4-fluoro-5-[(3-fluorocyclobutyl)carbamoyl]-2-methylphenyl]-1,3-thiazole-5-carboxamide

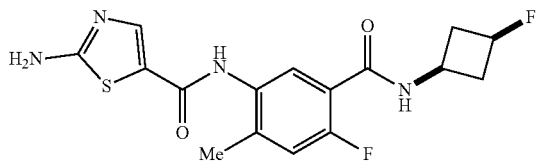 [SMILES: Cc1cc(F)c(C(=O)N[C@H]2C[C@@H](F)C2)cc1NC(=O)c1cnc(N)s1]

The title compound was prepared from cis-3-fluorocyclobutan-1-amine and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-$d_6$) δ 9.55 (s, 1H), 8.58-8.49 (m, 1H), 7.80 (s, 1H), 7.61 (s, 2H), 7.44 (d, J=7.0 Hz, 1H), 7.17 (dd, J=11.0, 0.8 Hz, 1H), 4.81 (dp, J=56.6, 6.8 Hz, 1H), 3.91 (dt, J=8.9, 7.4 Hz, 1H), 2.74-2.63 (m, 2H), 2.27-2.13 (m, 5H). $^1$H NMR (400 MHz, DMSO-$d_6$) δ. ESI MS [M+H]$^+$ for $C_{16}H_{17}F_2N_4O_2S_1$, calcd 367.1, found 367.1.

Example 125: 2-Amino-N-[4-fluoro-2-methyl-5-[(1-pyrimidin-2-ylazetidin-3-yl)carbamoyl]phenyl]-1,3-thiazole-5-carboxamide

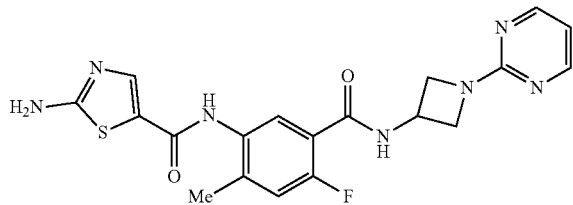 [SMILES: Cc1cc(F)c(C(=O)NC2CN(c3ncccn3)C2)cc1NC(=O)c1cnc(N)s1]

The title compound was prepared from 1-pyrimidin-2-ylazetidin-3-amine and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-$d_6$) δ 9.57 (s, 1H), 8.90 (dd, J=7.0, 1.7 Hz, 1H), 8.32 (d, J=4.8 Hz, 2H), 7.80 (s, 1H), 7.60 (s, 2H), 7.49 (d, J=7.0 Hz, 1H), 7.19 (d, J=11.4 Hz, 1H), 6.66 (t, J=4.8 Hz, 1H), 4.82-4.73 (m, 1H), 4.33-4.24 (m, 2H), 3.96 (dd, J=9.1, 5.5 Hz, 2H), 2.20 (s, 3H). $^1$H NMR (400 MHz, DMSO-$d_6$) δ. ESI MS [M+H]$^+$ for $C_{19}H_{19}F_1N_7O_2S_1$, calcd 428.1, found 428.1.

Example 126: 2-Amino-N-[5-[(3-cyanocyclobutyl)carbamoyl]-4-fluoro-2-methylphenyl]-1,3-thiazole-5-carboxamide

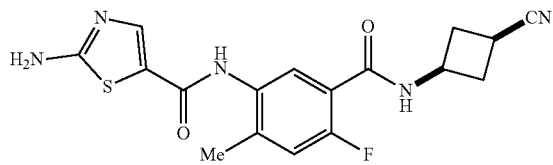 [SMILES: Cc1cc(F)c(C(=O)N[C@H]2C[C@@H](C#N)C2)cc1NC(=O)c1cnc(N)s1]

The title compound was prepared from cis-3-aminocyclobutane-1-carbonitrile and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-$d_6$) δ 9.58 (s, 1H), 8.62 (dd, J=8.0, 2.0 Hz, 1H), 7.83 (s, 1H), 7.62 (s, 2H), 7.50 (d, J=7.0 Hz, 1H), 7.22 (d, J=11.2 Hz, 1H), 4.50-4.38 (m, 1H), 3.07 (tt, J=9.9, 8.1 Hz, 1H), 2.70-2.61 (m, 2H), 2.45-2.32 (m, 2H), 2.24 (s, 3H). $^1$H NMR (400 MHz, DMSO-$d_6$) δ. ESI MS [M+H]$^+$ for $C_{17}H_{17}F_1N_5O_2S_1$, calcd 374.1, found 374.1.

Example 127: 2-Amino-N-[5-[(3-carbamoylcyclobutyl)carbamoyl]-4-fluoro-2-methylphenyl]-1,3-thiazole-5-carboxamide

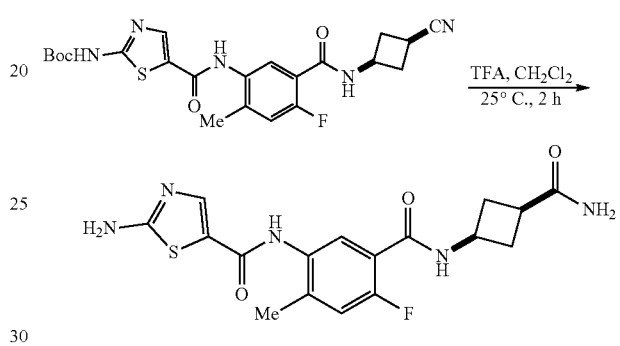

The title compound was prepared from 2-amino-N-[5-[(3-cyanocyclobutyl)carbamoyl]-4-fluoro-2-methylphenyl]-1,3-thiazole-5-carboxamide in a similar fashion to Example 7, step b. $^1$H NMR (400 MHz, DMSO-$d_6$) δ 9.60 (s, 1H), 8.51 (dd, J=7.8, 1.8 Hz, 1H), 7.84 (s, 1H), 7.74 (s, 2H), 7.46 (d, J=7.0 Hz, 1H), 7.25-7.16 (m, 2H), 6.74 (s, 1H), 4.34-4.21 (m, 1H), 2.64 (tt, J=9.6, 7.7 Hz, 1H), 2.39-2.30 (m, 2H), 2.23 (s, 3H), 2.18-2.06 (m, 2H). ESI MS [M+H]$^+$ for $C_{17}H_{19}F_1N_5O_3S_1$, calcd 392.1, found 392.2.

Example 128: 2-Amino-N-[5-[(3-carbamoylcyclobutyl)carbamoyl]-4-fluoro-2-methylphenyl]-1,3-thiazole-5-carboxamide

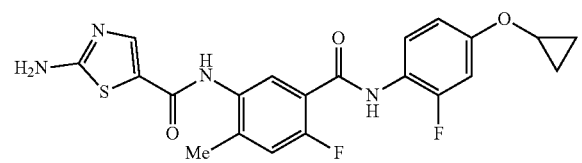

The title compound was prepared from 4-cyclopropyloxy-2-fluoroaniline and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-$d_6$) δ 9.82 (d, J=2.5 Hz, 1H), 9.60 (s, 1H), 7.81 (s, 1H), 7.60 (s, 2H), 7.57 (d, J=6.9 Hz, 1H), 7.51 (t, J=8.9 Hz, 1H), 7.24 (d, J=11.1 Hz, 1H), 6.99 (dd, J=12.2, 2.7 Hz, 1H), 6.92-6.82 (m, 1H), 3.85 (tt, J=6.0, 2.9 Hz, 1H), 2.23 (s, 3H), 0.80-0.72 (m, 2H), 0.66-0.59 (m, 2H). ESI MS [M+H]$^+$ for $C_{21}H_{19}F_2N_4O_3S_1$, calcd 445.1, found 445.1.

Example 129: 2-Amino-N-[5-[(5-cyclopropyloxy-pyridin-2-yl)carbamoyl]-4-fluoro-2-methylphenyl]-1,3-thiazole-5-carboxamide

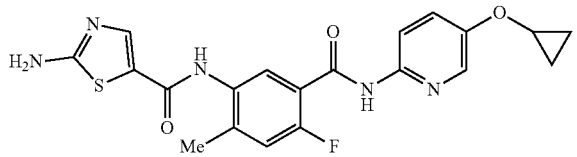

The title compound was prepared from 5-cyclopropyloxy-pyridin-2-amine and 2-fluoro-4-methyl-5-[[2-[(2-methyl-propan-2-yl)oxycarbonylamino]-1,3-thiazole-5-carbonyl]amino]benzoic acid in a similar fashion to Example 7. $^1$H NMR (400 MHz, DMSO-$d_6$) δ 10.51 (d, J=2.7 Hz, 1H), 9.63 (s, 1H), 8.15 (dd, J=3.0, 0.7 Hz, 1H), 8.11 (d, J=9.1 Hz, 1H), 7.85 (s, 1H), 7.67-7.54 (m, 4H), 7.26 (d, J=11.1 Hz, 1H), 3.95 (tt, J=6.0, 3.0 Hz, 1H), 2.27 (s, 3H), 0.85-0.72 (m, 2H), 0.72-0.67 (m, 2H). ESI MS [M+H]$^+$ for $C_{20}H_{19}F_1N_5O_3S_1$, calcd 428.1, found 428.1.

Example 130: 2-Amino-N-[5-[(5-cyclopropylpyri-din-2-yl)carbamoyl]-4-fluoro-2-methylphenyl]-1,3-thiazole-5-carboxamide

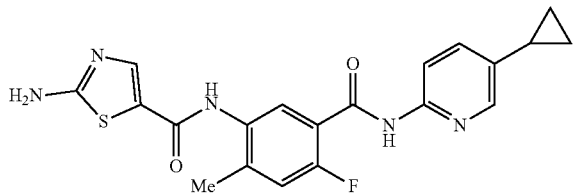 [SMILES: Cc1cc(F)c(C(=O)Nc2ccc(C3CC3)cn2)cc1NC(=O)c1cnc(N)s1]

The title compound was prepared from 5-cyclopropy-lpyridin-2-amine and 2-fluoro-4-methyl-5-[[2-[(2-methyl-propan-2-yl)oxycarbonylamino]-1,3-thiazole-5-carbonyl]amino]benzoic acid in a similar fashion to Example 7. $^1$H NMR (400 MHz, DMSO-$d_6$) δ 10.47 (d, J=2.8 Hz, 1H), 9.58 (s, 1H), 8.16 (d, J=2.4 Hz, 1H), 8.02 (d, J=8.6 Hz, 1H), 7.81 (s, 1H), 7.63-7.53 (m, 3H), 7.45 (dd, J=8.6, 2.5 Hz, 1H), 7.22 (d, J=11.3 Hz, 1H), 2.23 (s, 3H), 1.95-1.87 (m, 1H), 0.97-0.91 (m, 2H), 0.71-0.65 (m, 2H). ESI MS [M+H]$^+$ for $C_{20}H_{19}F_1N_5O_3S_1$, calcd 412.1, found 412.1.

Example 131: 2-Amino-N-[4-fluoro-5-[(5-methoxy-pyridin-2-yl)carbamoyl]-2-methylphenyl]-1,3-thiaz-ole-5-carboxamide

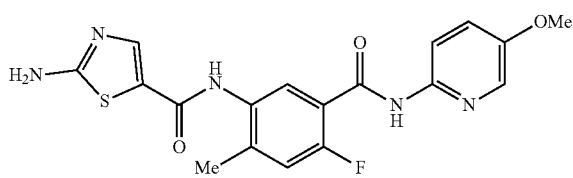 [SMILES: COc1ccc(NC(=O)c2cc(NC(=O)c3cnc(N)s3)c(C)cc2F)nc1]

The title compound was prepared from 5-methoxypyri-din-2-amine and 2-fluoro-4-methyl-5-[[2-[(2-methylpropan-2-yl)oxycarbonylamino]-1,3-thiazole-5-carbonyl]amino] benzoic acid in a similar fashion to Example 7. $^1$H NMR (400 MHz, DMSO-$d_6$) δ 10.45 (d, J=2.7 Hz, 1H), 9.58 (s, 1H), 8.07 (d, J=9.1 Hz, 1H), 8.05 (dd, J=3.1, 0.7 Hz, 1H), 7.81 (s, 1H), 7.59 (s, 2H), 7.57 (d, J=6.9 Hz, 1H), 7.45 (dd, J=9.1, 3.1 Hz, 1H), 7.22 (d, J=11.3 Hz, 1H), 3.79 (s, 3H), 2.23 (s, 3H). ESI MS [M+H]$^+$ for $C_{18}H_{17}F1N_5O_3S_1$, calcd 402.1, found 402.1.

Example 132: 2-Amino-N-[4-fluoro-2-methyl-5-(pyridin-2-ylcarbamoyl)phenyl]-1,3-thiazole-5-car-boxamide

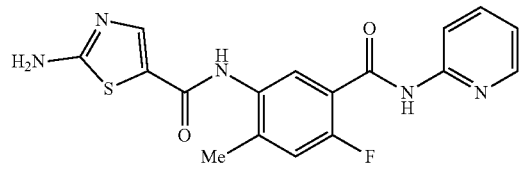 [SMILES: Cc1cc(F)c(C(=O)Nc2ccccn2)cc1NC(=O)c1cnc(N)s1]

The title compound was prepared from pyridin-2-amine and 2-fluoro-4-methyl-5-[[2-[(2-methylpropan-2-yl)oxycar-bonylamino]-1,3-thiazole-5-carbonyl]amino]benzoic acid in a similar fashion to Example 7. $^1$H NMR (400 MHz, DMSO-$d_6$) δ 10.57 (d, J=2.6 Hz, 1H), 9.59 (s, 1H), 8.35-8.30 (m, 1H), 8.14 (d, J=8.4 Hz, 1H), 7.85-7.77 (m, 2H), 7.58 (d, J=7.6 Hz, 3H), 7.23 (d, J=11.3 Hz, 1H), 7.14 (ddd, J=7.4, 4.9, 1.0 Hz, 1H), 2.24 (s, 3H). ESI MS [M+H]$^+$ for $C_{17}H_{15}F_1N_5O_2S_1$, calcd 372.1, found 372.1.

Example 133: 2-Amino-N-[4-fluoro-2-methyl-5-[(5-methylpyridin-2-yl)carbamoyl]phenyl]-1,3-thiazole-5-carboxamide

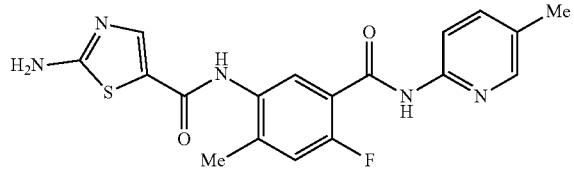 [SMILES: Cc1ccc(NC(=O)c2cc(NC(=O)c3cnc(N)s3)c(C)cc2F)nc1]

The title compound was prepared from 5-methylpyridin-2-amine and 2-fluoro-4-methyl-5-[[2-[(2-methylpropan-2-yl)oxycarbonylamino]-1,3-thiazole-5-carbonyl]amino]ben-zoic acid in a similar fashion to Example 7. $^1$H NMR (400 MHz, DMSO-$d_6$) δ 10.47 (d, J=2.8 Hz, 1H), 9.58 (s, 1H), 8.17-8.15 (m, 1H), 8.04 (d, J=8.4 Hz, 1H), 7.82 (s, 1H), 7.65-7.61 (m, 1H), 7.61-7.56 (m, 3H), 7.22 (d, J=11.2 Hz, 1H), 2.24 (d, J=4.0 Hz, 6H). $^1$H NMR (400 MHz, DMSO-$d_6$) δ. ESI MS [M+H]$^+$ for $C_{18}H_{17}F_1N_5O_2S_1$, calcd 386.1, found 386.1.

Example 134: 2-Amino-N-[5-[(5-cyclobutyloxypyri-din-2-yl)carbamoyl]-4-fluoro-2-methylphenyl]-1,3-thiazole-5-carboxamide

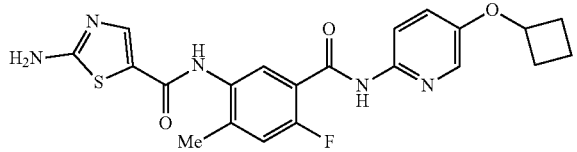 [SMILES: Cc1cc(F)c(C(=O)Nc2ccc(OC3CCC3)cn2)cc1NC(=O)c1cnc(N)s1]

The title compound was prepared from 5-cyclobutyloxy-pyridin-2-amine and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-$d_6$) δ 10.42 (d, J=2.8 Hz, 1H), 9.58 (s, 1H), 8.04 (d, J=9.1 Hz, 1H), 7.95 (dd, J=3.0, 0.7 Hz, 1H), 7.81 (s, 1H), 7.59 (s, 2H), 7.56 (d, J=7.0 Hz, 1H), 7.35 (dd, J=9.0, 3.1 Hz, 1H), 7.22 (d, J=11.2 Hz, 1H), 4.75-4.65 (m, 1H), 2.45-2.35 (m, 2H), 2.23 (s, 3H), 2.08-1.95 (m, 2H), 1.81-1.71 (m, 1H), 1.67-1.54 (m, 1H). ESI MS [M+H]$^+$ for $C_{21}H_{21}F_1N_5O_3S_1$, calcd 442.1, found 442.1.

Example 135: 2-Amino-N-[5-[(6-cyclopropylpyridazin-3-yl)carbamoyl]-4-fluoro-2-methylphenyl]-1,3-thiazole-5-carboxamide

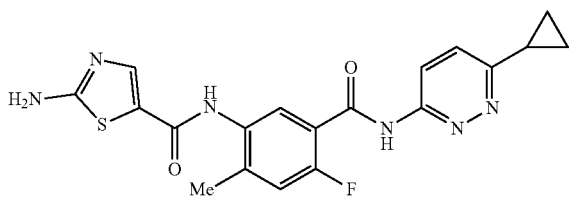

The title compound was prepared from 6-cyclopropylpyridazin-3-amine and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-$d_6$) δ 11.14 (s, 1H), 9.60 (s, 1H), 8.20 (d, J=9.2 Hz, 1H), 7.82 (s, 1H), 7.63 (s, 2H), 7.59 (d, J=6.9 Hz, 1H), 7.51 (d, J=9.2 Hz, 1H), 7.25 (d, J=11.1 Hz, 1H), 2.24 (s, 3H), 2.23-2.16 (m, 1H), 1.07-0.99 (m, 2H), 0.99-0.93 (m, 2H). $^1$H NMR (400 MHz, DMSO-$d_6$) δ. ESI MS [M+H]$^+$ for $C_{19}H_{18}F_1N_6O_2S_1$, calcd 413.1, found 413.1.

Example 136: 2-Amino-N-[4-fluoro-5-[[(1S,2R)-2-fluorocyclopropyl]carbamoyl]-2-methylphenyl]-1,3-thiazole-5-carboxamide

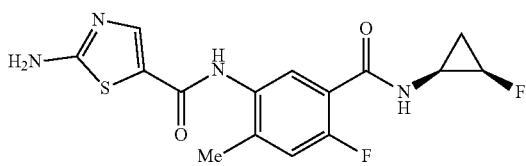 [SMILES: Cc1cc(F)c(C(=O)N[C@H]2C[C@H]2F)cc1NC(=O)c1cnc(N)s1]

The title compound was prepared from (1S,2R)-2-fluorocyclopropan-1-amine and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-$d_6$) δ 9.59 (s, 1H), 8.34 (s, 1H), 7.81 (d, J=0.8 Hz, 1H), 7.66 (s, 2H), 7.45 (d, J=6.9 Hz, 1H), 7.17 (d, J=11.1 Hz, 1H), 4.84-4.58 (m, 1H), 2.83-2.75 (m, 1H), 2.20 (s, 3H), 1.12-0.96 (m, 2H). ESI MS [M+H]$^+$ for $C_{15}H_{15}F_2N_4O_2S_1$, calcd 353.1, found 353.1.

Example 137: 2-Amino-N-[4-fluoro-5-[[(1R,2S)-2-fluorocyclopropyl]carbamoyl]-2-methylphenyl]-1,3-thiazole-5-carboxamide

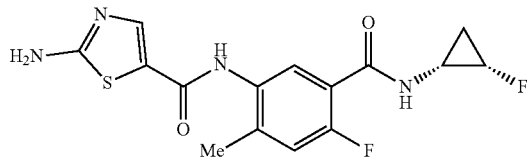 [SMILES: Cc1cc(F)c(C(=O)N[C@@H]2C[C@@H]2F)cc1NC(=O)c1cnc(N)s1]

The title compound was prepared from (1R,2S)-2-fluorocyclopropan-1-amine and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-$d_6$) δ 9.57 (s, 1H), 8.33 (d, J=3.2 Hz, 1H), 7.80 (s, 1H), 7.62 (s, 2H), 7.45 (d, J=6.9 Hz, 1H), 7.17 (d, J=11.0 Hz, 1H), 4.83-4.58 (m, 1H), 2.82-2.75 (m, 1H), 2.20 (s, 3H), 1.12-1.00 (m, 2H). ESI MS [M+H]$^+$ for $C_{15}H_{15}F_2N_4O_2S_1$, calcd 353.1, found 353.1.

Example 138: 2-Amino-N-[4-fluoro-5-[[(1S,2S)-2-fluorocyclopropyl]carbamoyl]-2-methylphenyl]-1,3-thiazole-5-carboxamide

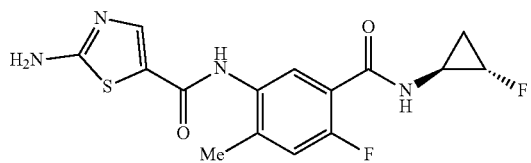 [SMILES: Cc1cc(F)c(C(=O)N[C@H]2C[C@@H]2F)cc1NC(=O)c1cnc(N)s1]

The title compound was prepared from (1S,2S)-2-fluorocyclopropan-1-amine and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-$d_6$) δ 9.56 (s, 1H), 8.28 (s, 1H), 7.80 (s, 1H), 7.66-7.50 (m, 2H), 7.44 (d, J=7.0 Hz, 1H), 7.17 (d, J=11.2 Hz, 1H), 4.83-4.56 (m, 1H), 3.21-3.02 (m, 1H), 2.19 (s, 3H), 1.40-1.27 (m, 1H), 1.04-0.95 (m, 1H). ESI MS [M+H]$^+$ for $C_{15}H_{15}F_2N_4O_2S_1$, calcd 353.1, found 353.0.

Example 139: 2-Amino-N-[5-[[1-(3,3-difluorocyclobutyl)pyrazol-3-yl]carbamoyl]-4-fluoro-2-methylphenyl]-1,3-thiazole-5-carboxamide

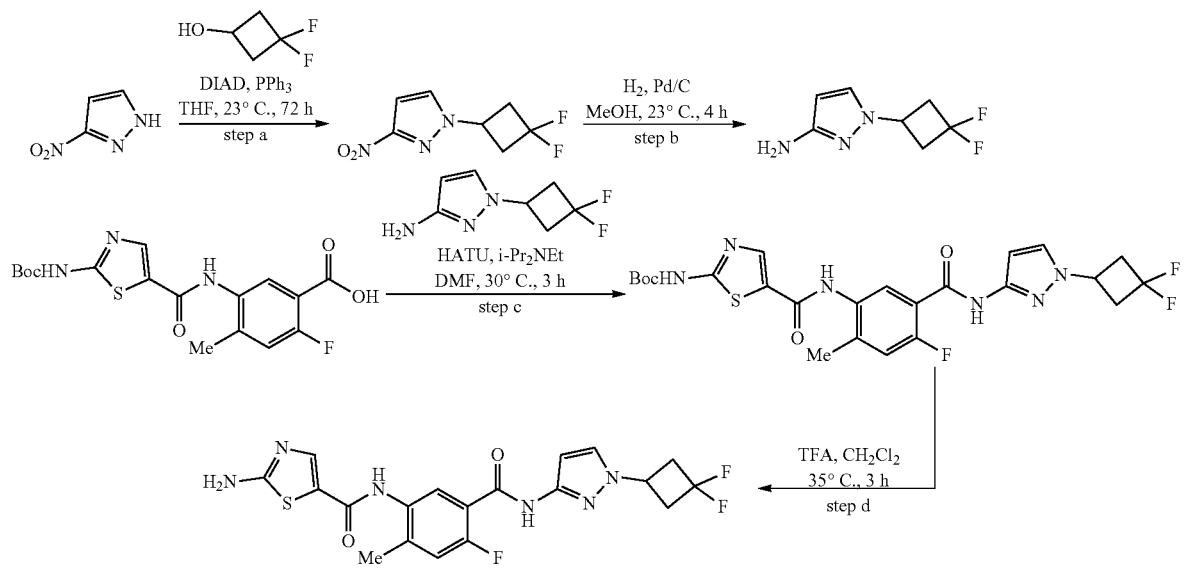

Step a: A vial was charged with 3-nitro-1H-pyrazole (113 mg, 1.00 mmol, 1.0 equiv.), 3,3-difluorocyclobutan-1-ol (108 mg, 1.00 mmol, 1.0 equiv.), PPh₃ (400 mg, 1.50 mmol, 1.5 equiv.) in THF (1.5 mL), and placed under $N_2$ atmosphere. The mixture was cooled to 0° C. to stir for 30 min then DIAD (0.3 mL, 1.50 mmol, 1.5 equiv.) was added dropwise. The resulting mixture was stirred at RT for 3 days. The reaction mixture was then concentrated in vacuo. The crude product was purified by column chromatography ($SiO_2$, 0% to 100% EtOAc in hexanes) to afford 1-(3,3-difluorocyclobutyl)-3-nitropyrazole.

Step b: A vial was charged with the product obtained in step a (100 mg, 0.50 mmol, 1.0 equiv.), Pd/C (10 mg, 10 wt. %), and MeOH (1.0 mL). The resulting mixture was stirred under a $H_2$ balloon at RT for 4 h, at which time LC/MS analysis indicated complete consumption of starting material. The reaction mixture was diluted with MeOH, filtered over Celite®, and concentrated in vacuo to afford 1-(3,3-difluorocyclobutyl)pyrazol-3-amine, which was used directly in the next step without further purification.

Steps c and d were performed in a similar manner to that described in Example 7 using 1-(3,3-difluorocyclobutyl)pyrazol-3-amine and 2-fluoro-4-methyl-5-[[2-[(2-methylpropan-2-yl)oxycarbonylamino]-1,3-thiazole-5-carbonyl]amino]benzoic acid. ¹H NMR (400 MHz, DMSO-$d_6$) δ 10.88 (s, 1H), 10.04 (s, 1H), 8.82 (s, 2H), 8.11 (s, 1H), 7.80 (d, J=2.3 Hz, 1H), 7.55 (d, J=6.8 Hz, 1H), 7.25 (d, J=10.9 Hz, 1H), 6.62 (d, J=2.2 Hz, 1H), 4.87 (q, J=7.4 Hz, 1H), 3.22-3.02 (m, 4H), 2.26 (s, 3H). ESI MS [M+H]⁺ for $C_{19}H_{18}F_3N_6O_2S_1$, calcd 451.1, found 451.1.

Example 140: 2-Amino-N-[4-fluoro-2-methyl-5-[(5-propan-2-yloxypyridin-2-yl)carbamoyl]phenyl]-1,3-thiazole-5-carboxamide

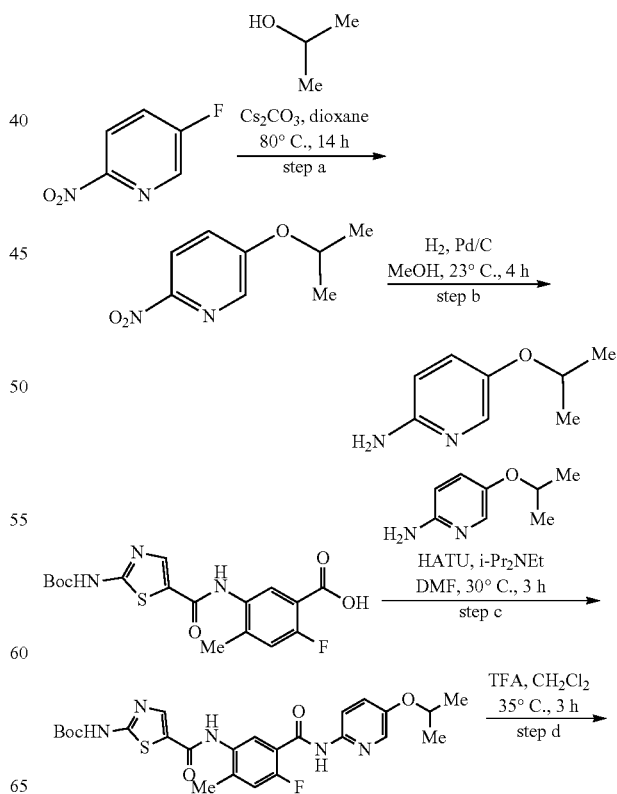

-continued

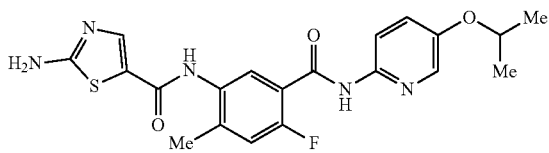

Step a: A mixture of 5-fluoro-2-nitropyridine (142 mg, 1.00 mmol, 1.0 equiv.), $Cs_2CO_3$ (490 mg, 1.50 mmol, 1.5 equiv.), isopropanol (0.42 mL, 7.0 mmol, 7.0 equiv.), and dioxane (1.0 mL) was stirred at 80° C. for 14 h. The reaction mixture was cooled, diluted with EtOAc, filtered to remove solids, and concentrated in vacuo. The crude product was purified by column chromatography ($SiO_2$, 0% to 100% EtOAc in $CH_2Cl_2$) to afford 2-nitro-5-propan-2-yloxypyridine.

Step b: A vial was charged with the product obtained in step a (150 mg, 0.80 mmol, 1.0 equiv.), Pd/C (15 mg, 10 wt. %), and MeOH (1.5 mL). The resulting mixture was stirred under a $H_2$ balloon at RT for 4 h, at which time LC/MS analysis indicated complete consumption of starting material. The reaction mixture was diluted with MeOH, filtered over Celite®, and concentrated in vacuo to afford 5-propan-2-yloxypyridin-2-amine, which was used directly in the next step without further purification.

Steps c and d were performed in a similar manner to that described in Example 7 using 5-propan-2-yloxypyridin-2-amine and 2-fluoro-4-methyl-5-[[2-[(2-methylpropan-2-yl)oxycarbonylamino]-1,3-thiazole-5-carbonyl]amino]benzoic acid. $^1$H NMR (400 MHz, DMSO-$d_6$) δ 10.57 (s, 1H), 10.38-10.17 (m, 1H), 9.23 (s, 2H), 8.32-8.17 (m, 1H), 8.07 (d, J=9.1 Hz, 1H), 8.04 (d, J=3.0 Hz, 1H), 7.60 (d, J=6.9 Hz, 1H), 7.51 (dd, J=9.1, 3.0 Hz, 1H), 7.29 (d, J=11.1 Hz, 1H), 4.66 (hept, J=6.0 Hz, 1H), 2.28 (s, 3H), 1.28 (d, J=6.0 Hz, 6H). ESI MS [M+H]$^+$ for $C_{20}H_{21}F_1N_5O_3S_1$, calcd 430.1, found 430.2.

Example 141: 2-Amino-N-[5-[[(1-tert-butylpyrazol-3-yl)carbamoyl]-4-fluoro-2-methylphenyl]-1,3-thiazole-5-carboxamide

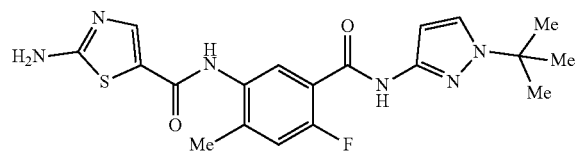 [SMILES: Cc1cc(F)c(C(=O)Nc2ccn(C(C)(C)C)n2)cc1NC(=O)c1cnc(N)s1]

The title compound was prepared from 1-tert-butylpyrazol-3-amine and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-$d_6$) δ 10.80-10.67 (m, 1H), 10.40 (s, 1H), 9.62 (s, 2H), 8.36 (s, 1H), 7.73 (d, J=2.4 Hz, 1H), 7.54 (d, J=6.8 Hz, 1H), 7.24 (d, J=10.9 Hz, 1H), 6.57 (d, J=2.4 Hz, 1H), 2.27 (s, 3H), 1.50 (s, 9H). ESI MS [M+H]$^+$ for $C_{19}H_{22}F_1N_6O_2S_1$, calcd 417.1, found 417.2.

Example 142: 2-Amino-N-[4-fluoro-2-methyl-5-[[1-(2-methylpropyl)pyrazol-3-yl]carbamoyl]phenyl]-1,3-thiazole-5-carboxamide

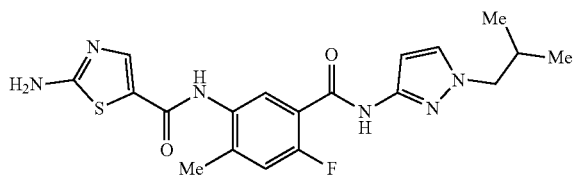 [SMILES: Cc1cc(F)c(C(=O)Nc2ccn(CC(C)C)n2)cc1NC(=O)c1cnc(N)s1]

The title compound was prepared from 1-(2-methylpropyl)pyrazol-3-amine and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-$d_6$) δ 10.70 (s, 1H), 10.20-10.01 (m, 1H), 9.37-8.66 (m, 2H), 8.23-8.05 (m, 1H), 7.63 (d, J=2.3 Hz, 1H), 7.54 (d, J=6.8 Hz, 1H), 7.25 (d, J=11.0 Hz, 1H), 6.56 (d, J=2.2 Hz, 1H), 3.82 (d, J=7.2 Hz, 2H), 2.26 (s, 3H), 2.09 (hept, J=6.9 Hz, 1H), 0.84 (d, J=6.7 Hz, 6H). ESI MS [M+H]$^+$ for $C_{19}H_{22}F_1N_6O_2S_1$, calcd 417.1, found 417.2.

Example 143: 2-Amino-N-[5-[[5-(cyclopropylmethoxy)pyridin-2-yl]carbamoyl]-4-fluoro-2-methylphenyl]-1,3-thiazole-5-carboxamide

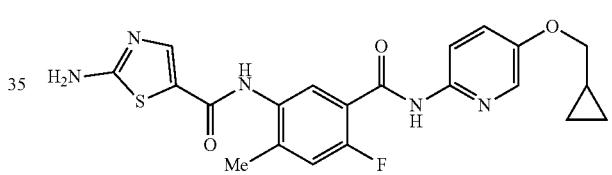

The title compound was prepared from 5-fluoro-2-nitropyridine, cyclopropylmethanol, and 2-fluoro-4-methyl-5-[[2-[(2-methylpropan-2-yl)oxycarbonylamino]-1,3-thiazole-5-carbonyl]amino]benzoic acid in a similar fashion to Example 140. $^1$H NMR (400 MHz, DMSO-$d_6$) δ 10.48 (d, J=2.7 Hz, 1H), 9.63 (s, 1H), 8.13-8.04 (m, 2H), 7.85 (s, 1H), 7.68 (s, 2H), 7.60 (d, J=7.0 Hz, 1H), 7.47 (dd, J=9.0, 3.1 Hz, 1H), 7.25 (d, J=11.3 Hz, 1H), 3.89 (d, J=7.0 Hz, 2H), 2.26 (s, 3H), 1.32-1.18 (m, 1H), 0.64-0.54 (m, 2H), 0.39-0.29 (m, 2H). ESI MS [M+H]$^+$ for $C_{21}H_{21}F_1N_5O_3S_1$, calcd 442.1, found 442.2.

Example 144: 2-Amino-N-[4-fluoro-5-[[1-(2-hydroxyethyl)pyrazol-3-yl]carbamoyl]-2-methylphenyl]-1,3-thiazole-5-carboxamide

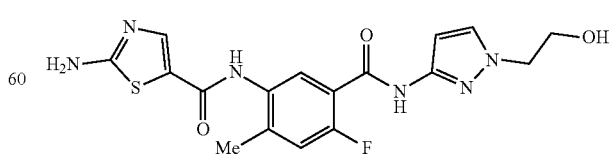

The title compound was prepared from 2-(3-aminopyrazol-1-yl)ethanol and 2-fluoro-4-methyl-5-[[2-[(2-methylpropan-2-yl)oxycarbonylamino]-1,3-thiazole-5-carbonyl]

amino]benzoic acid in a similar fashion to Example 7. $^1$H NMR (400 MHz, DMSO-d$_6$) δ 10.68 (s, 1H), 9.60 (s, 1H), 7.84 (s, 1H), 7.65-7.60 (m, 3H), 7.54 (d, J=6.9 Hz, 1H), 7.23 (d, J=10.9 Hz, 1H), 6.56 (d, J=2.3 Hz, 1H), 4.89 (t, J=5.3 Hz, 1H), 4.05 (t, J=5.6 Hz, 2H), 3.71 (q, J=5.5 Hz, 2H), 2.25 (s, 3H). ESI MS [M+H]$^+$ for $C_{17}H_{18}F_1N_6O_3S_1$, calcd 405.1, found 405.2.

Example 145: 2-Amino-N-[5-(6,7-dihydro-4H-pyrano[4,3-d][1,3]thiazol-2-ylcarbamoyl)-4-fluoro-2-methylphenyl]-1,3-thiazole-5-carboxamide

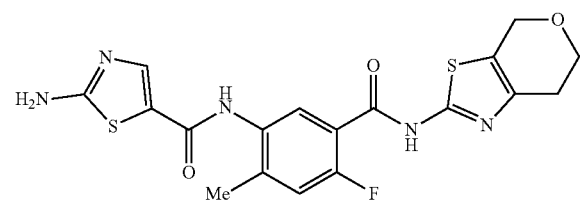 [SMILES: Cc1cc(F)c(C(=O)Nc2nc3c(s2)COCC3)cc1NC(=O)c1cnc(N)s1]

The title compound was prepared from 6,7-dihydro-4H-pyrano[4,3-d][1,3]thiazol-2-amine and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-d$_6$) δ 12.40 (s, 1H), 9.61 (s, 1H), 7.85 (s, 1H), 7.68-7.61 (m, 3H), 7.27 (s, 1H), 4.70 (s, 2H), 3.92 (t, J=5.5 Hz, 2H), 2.72-2.65 (m, 2H), 2.26 (s, 3H). ESI MS [M+H]$^+$ for $C_{18}H_{17}F_1N_5O_3S_2$, calcd 434.1, found 434.1.

Example 146: 2-Amino-N-[4-fluoro-2-methyl-5-[(5-propan-2-yl-1,3-thiazol-2-yl)carbamoyl]phenyl]-1,3-thiazole-5-carboxamide

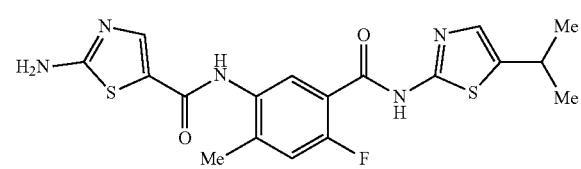 [SMILES: Cc1cc(F)c(C(=O)Nc2ncc(C(C)C)s2)cc1NC(=O)c1cnc(N)s1]

The title compound was prepared from 5-propan-2-yl-1,3-thiazol-2-amine and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-d$_6$) δ 12.32 (s, 1H), 9.63 (s, 1H), 7.85 (s, 1H), 7.64 (s, 2H), 7.61 (d, J=6.9 Hz, 1H), 7.27 (d, J=11.0 Hz, 1H), 7.22 (d, J=1.1 Hz, 1H), 3.20-3.10 (m, 1H), 2.26 (s, 3H), 1.29 (d, J=6.8 Hz, 6H). ESI MS [M+H]$^+$ for $C_{18}H_{19}F_1N_5O_2S_2$, calcd 420.1, found 420.1.

Example 147: 2-Amino-N-[4-fluoro-2-methyl-5-[[5-(1-methylcyclopropyl)oxypyridin-2-yl]carbamoyl]phenyl]-1,3-thiazole-5-carboxamide

The title compound was prepared from 5-fluoro-2-nitropyridine, 1-methylcyclopropan-1-ol, and 2-fluoro-4-methyl-5-[[2-[(2-methylpropan-2-yl)oxycarbonylamino]-1,3-thiazole-5-carbonyl]amino]benzoic acid in a similar fashion to Example 140. $^1$H NMR (400 MHz, DMSO-d$_6$) δ 10.56 (d, J=3.0 Hz, 1H), 10.27-10.08 (m, 1H), 9.05 (s, 2H), 8.25-8.13 (m, 1H), 8.13-8.02 (m, 2H), 7.60 (d, J=6.9 Hz, 1H), 7.56 (dd, J=9.0, 3.1 Hz, 1H), 7.29 (d, J=11.1 Hz, 1H), 2.28 (s, 3H), 1.51 (s, 3H), 0.96-0.89 (m, 2H), 0.80-0.74 (m, 2H). ESI MS [M+H]$^+$ for $C_{21}H_{21}F_1N_5O_3S_1$, calcd 442.1, found 442.2.

Example 148: 2-Amino-N-[5-[[1-(2,2-difluoroethyl)pyrazol-3-yl]carbamoyl]-4-fluoro-2-methylphenyl]-1,3-thiazole-5-carboxamide

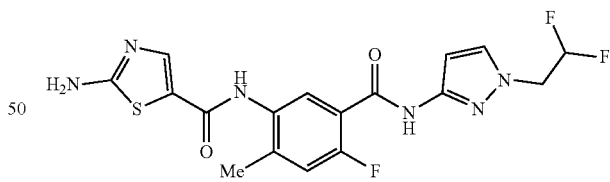

The title compound was prepared from 1-(2,2-difluoroethyl)pyrazol-3-amine and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-d$_6$) δ 10.81 (s, 1H), 10.04 (s, 1H), 8.81 (s, 2H), 8.11 (d, J=3.2 Hz, 1H), 7.73 (d, J=2.4 Hz, 1H), 7.54 (d, J=6.8 Hz, 1H), 7.25 (d, J=10.9 Hz, 1H), 6.66 (d, J=2.3 Hz, 1H), 6.32 (tt, J=55.0, 3.8 Hz, 1H), 4.55 (td, J=15.1, 3.8 Hz, 2H), 2.26 (s, 3H). ESI MS [M+H]$^+$ for $C_{17}H_{16}F_3N_6O_2S_1$, calcd 425.1, found 425.1.

Example 149: 2-Amino-N-[4-fluoro-2-methyl-5-[[1-[(3R)-oxolan-3-yl]pyrazol-3-yl]carbamoyl]phenyl]-1,3-thiazole-5-carboxamide

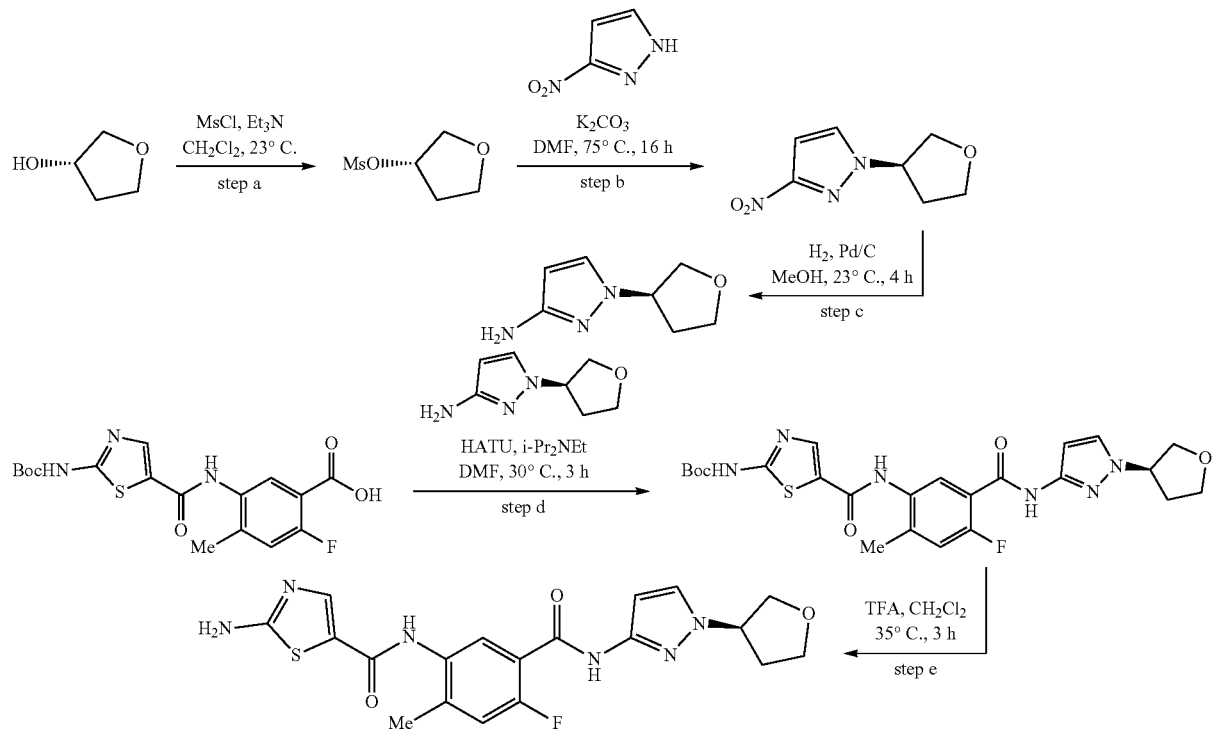

Step a: A vial was charged with (3S)-oxolan-3-ol (88 mg, 1.00 mmol, 1.0 equiv.) and Et₃N (0.28 mL, 2.00 mmol, 2.0 equiv.) in $CH_2C_2$ (1.0 mL). The resulting mixture was cooled to 0° C. and MsCl (0.09 mL, 1.10 mmol, 1.1 equiv.) was added dropwise. The reaction mixture was stirred at RT for 14 h, then diluted with water and $CH_2Cl_2$, and extracted with $CH_2Cl_2$ (3×). The combined organic extracts were dried over $Na_2SO_4$, filtered, and concentrated in vacuo to afford the crude product, which was used directly in the next step without further purification.

Step b: A vial was charged with the crude product obtained in step a (170 mg, 1.00 mmol, 1.0 equiv.), 3-nitro-1H-pyrazole (120 mg, 1.05 mmol, 1.05 equiv.), $K_2CO_3$ (207 mg, 1.50 mmol, 1.5 equiv.), and DMF (1.5 mL). The resulting mixture was stirred at 75° C. for 16 h, then cooled to RT, diluted with water, and extracted with EtOAc (3×). The combined organic extracts were dried over $Na_2SO_4$, filtered, and concentrated in vacuo to afford the crude product, 3-nitro-1-[(3R)-oxolan-3-yl]pyrazole.

Step c: A vial was charged with the crude product obtained in step b (150 mg, 0.83 mmol, 1.0 equiv.), Pd/C (15 mg, 10 wt. %), and MeOH (1.7 mL). The resulting mixture was stirred under a $H_2$ balloon at RT for 4 h, at which time LC/MS analysis indicated complete consumption of starting material. The reaction mixture was diluted with MeOH, filtered over Celite®, and concentrated in vacuo to afford 1-[(3R)-oxolan-3-yl]pyrazol-3-amine, which was used directly in the next step without further purification.

Steps d and e: The title compound was prepared from 1-[(3R)-oxolan-3-yl]pyrazol-3-amine and 2-fluoro-4-methyl-5-[[2-[(2-methylpropan-2-yl)oxycarbonylamino]-1,3-thiazole-5-carbonyl]amino]benzoic acid in a similar fashion to Example 7. $^1H$ NMR (400 MHz, DMSO-$d_6$) δ 10.75 (s, 1H), 9.60 (s, 1H), 7.84 (s, 1H), 7.72 (d, J=2.3 Hz, 1H), 7.63 (s, 2H), 7.54 (d, J=6.9 Hz, 1H), 7.22 (d, J=11.0 Hz, 1H), 6.60 (d, J=2.3 Hz, 1H), 4.95 (ddt, J=8.0, 6.3, 4.0 Hz, 1H), 3.96 (dt, J=9.4, 6.2 Hz, 2H), 3.87 (dd, J=9.3, 3.8 Hz, 1H), 3.80 (td, J=8.2, 5.6 Hz, 1H), 2.35 (dtd, J=13.0, 8.1, 6.9 Hz, 1H), 2.25 (s, 3H), 2.28-2.19 (m, 1H). ESI MS [M+H]⁺ for $C_{19}H_{20}F_1N_6O_3S_1$, calcd 431.1, found 431.2.

Example 150: 2-Amino-N-[4-fluoro-2-methyl-5-[[1-(oxan-4-yl)pyrazol-3-yl]carbamoyl]phenyl]-1,3-thiazole-5-carboxamide

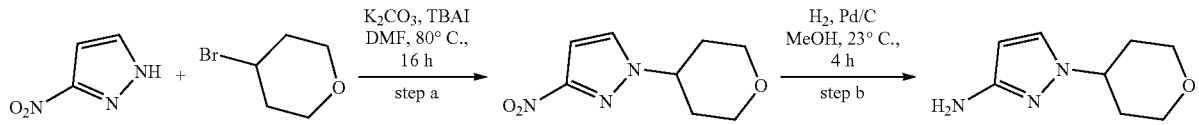

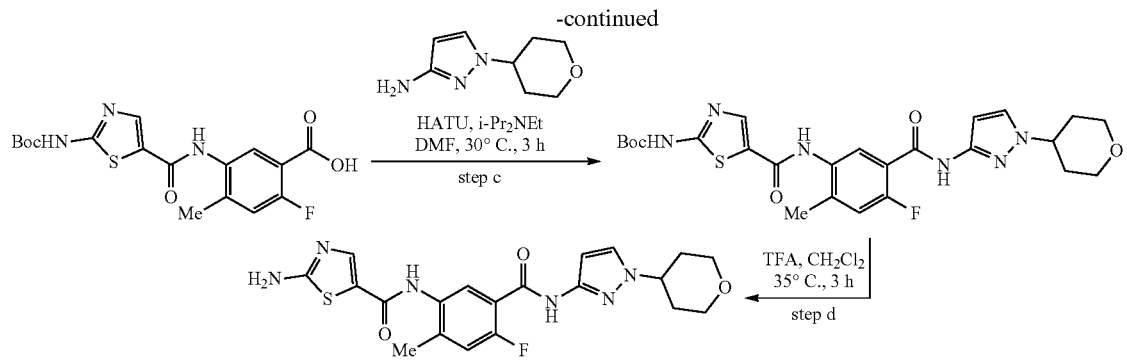

-continued

Step a: A vial was charged with 3-nitro-1H-pyrazole (113 mg, 1.00 mmol, 1.0 equiv.), 4-bromooxane (326 mg, 2.0 mmol, 2.0 equiv.), $K_2CO_3$ (415 mg, 3.0 mmol, 3.0 equiv.), TBAI (55 mg, 0.15 mmol, 0.15 equiv.), and DMF (1.5 mL). The resulting mixture was stirred at 80° C. for 16 h. Upon complete conversion, as judged by LC/MS analysis, the reaction mixture was cooled to RT, diluted with water, and extracted with EtOAc (3×). The combined organic extracts were dried over $Na_2SO_4$, filtered, and concentrated in vacuo to afford the crude product, 3-nitro-1-(oxan-4-yl)pyrazole.

Step b: A vial was charged with the crude product obtained in step a (200 mg, 1.0 mmol, 1.0 equiv.), Pd/C (20 mg, 10 wt. %), and MeOH (2.0 mL). The resulting mixture was stirred under a $H_2$ balloon at RT for 4 h, at which time LC/MS analysis indicated complete consumption of starting material. The reaction mixture was diluted with MeOH, filtered over Celite®, and concentrated in vacuo to afford 1-(oxan-4-yl)pyrazol-3-amine, which was used directly in the next step without further purification.

Steps c and d: The title compound was prepared from 1-(oxan-4-yl)pyrazol-3-amine and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-$d_6$) δ 10.72 (s, 1H), 9.59 (s, 1H), 7.84 (s, 1H), 7.73 (d, J=2.3 Hz, 1H), 7.63 (s, 2H), 7.54 (d, J=6.9 Hz, 1H), 7.22 (d, J=11.0 Hz, 1H), 6.59 (d, J=2.3 Hz, 1H), 4.31 (tt, J=10.6, 5.6 Hz, 1H), 3.99-3.90 (m, 2H), 3.44 (td, J=11.3, 3.9 Hz, 2H), 2.25 (s, 3H), 1.99-1.85 (m, 4H). ESI MS [M+H]$^+$ for $C_{20}H_{22}F_1N_6O_3S_1$, calcd 445.1, found 445.1.

Example 151: 2-Amino-N-[5-[[1-(cyclopropylmethyl)pyrazol-3-yl]carbamoyl]-4-fluoro-2-methylphenyl]-1,3-thiazole-5-carboxamide

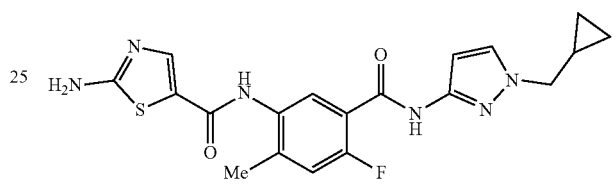

The title compound was prepared from 1-(cyclopropylmethyl)pyrazol-3-amine and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-$d_6$) δ 10.75-10.66 (m, 1H), 10.43-10.31 (m, 1H), 9.52 (s, 2H), 8.42-8.25 (m, 1H), 7.68 (d, J=2.2 Hz, 1H), 7.54 (d, J=6.8 Hz, 1H), 7.25 (d, J=10.9 Hz, 1H), 6.57 (d, J=2.3 Hz, 1H), 3.88 (d, J=7.1 Hz, 2H), 2.27 (s, 3H), 1.21 (pt, J=7.4, 4.7 Hz, 1H), 0.57-0.48 (m, 2H), 0.34 (dt, J=6.3, 4.4 Hz, 2H). ESI MS [M+H]$^+$ for $C_{19}H_{20}F_1N_6O_2S_1$, calcd 415.1, found 415.1.

Example 152: 2-Amino-N-[5-[(5-cyclopropyloxy-6-methylpyridin-2-yl)carbamoyl]-4-fluoro-2-methylphenyl]-1,3-thiazole-5-carboxamide

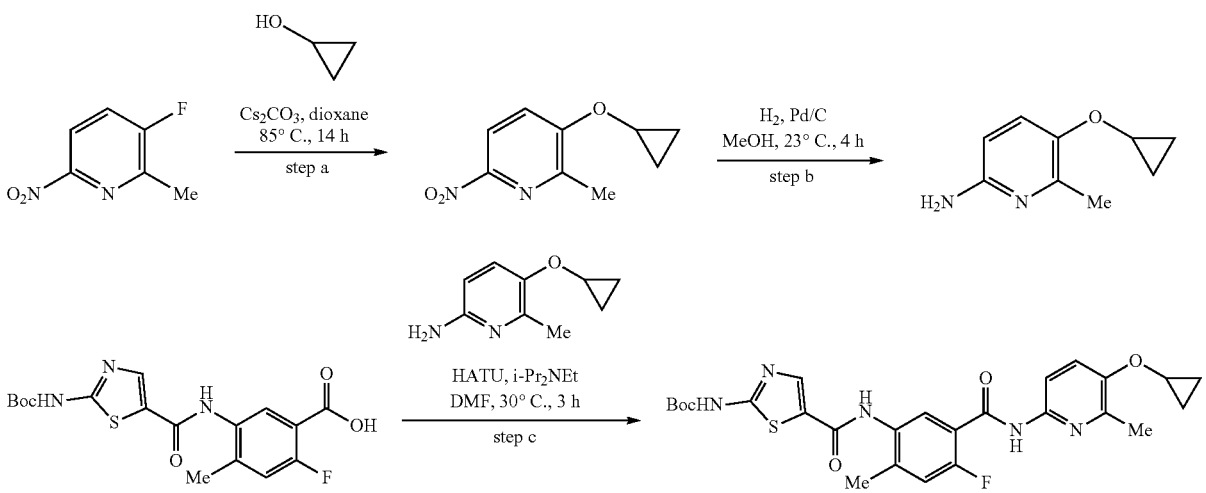

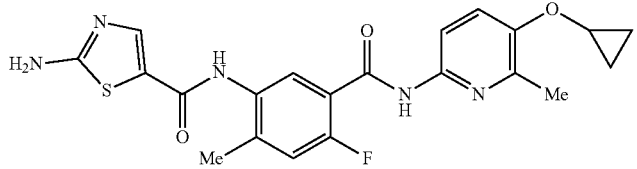

Step a: A mixture of 3-fluoro-2-methyl-6-nitropyridine (160 mg, 1.00 mmol, 1.0 equiv.), $Cs_2CO_3$ (490 mg, 1.50 mmol, 1.5 equiv.), cyclopropanol (0.45 mL, 7.0 mmol, 7.0 equiv.), and dioxane (2.0 mL) was stirred at 85° C. for 14 h. The reaction mixture was cooled, diluted with EtOAc, filtered to remove solids, and concentrated in vacuo. The crude product was purified by column chromatography ($SiO_2$, 0% to 100% EtOAc in $CH_2Cl_2$) to afford 3-cyclopropyloxy-2-methyl-6-nitropyridine.

Step b: A vial was charged with the product obtained in step a (110 mg, 0.57 mmol, 1.0 equiv.), Pd/C (11 mg, 10 wt. %), and MeOH (1.0 mL). The resulting mixture was stirred under a $H_2$ balloon at RT for 4 h, at which time LC/MS analysis indicated complete consumption of starting material. The reaction mixture was diluted with MeOH, filtered over Celite®, and concentrated in vacuo to afford 5-cyclopropyloxy-6-methylpyridin-2-amine, which was used directly in the next step without further purification.

Steps c and d: The title compound was prepared from 5-cyclopropyloxy-6-methylpyridin-2-amine and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-$d_6$) δ 10.44 (s, 1H), 10.29-10.13 (m, 1H), 9.24 (s, 2H), 8.22 (d, J=23.4 Hz, 1H), 7.99 (d, J=8.9 Hz, 1H), 7.70 (dd, J=9.0, 2.3 Hz, 1H), 7.60 (d, J=6.9 Hz, 1H), 7.27 (d, J=11.2 Hz, 1H), 3.91 (tt, J=6.0, 3.0 Hz, 1H), 2.28 (s, 6H), 0.88-0.77 (m, 2H), 0.69 (tt, J=5.2, 3.2 Hz, 2H). ESI MS [M+H]$^+$ for $C_{21}H_{21}F_1N_5O_3S_1$, calcd 442.1, found 442.1.

Example 153: 2-Amino-N-[4-fluoro-5-[[1-(2-hydroxy-2-methylpropyl)pyrazol-3-yl]carbamoyl]-2-methylphenyl]-1,3-thiazole-5-carboxamide

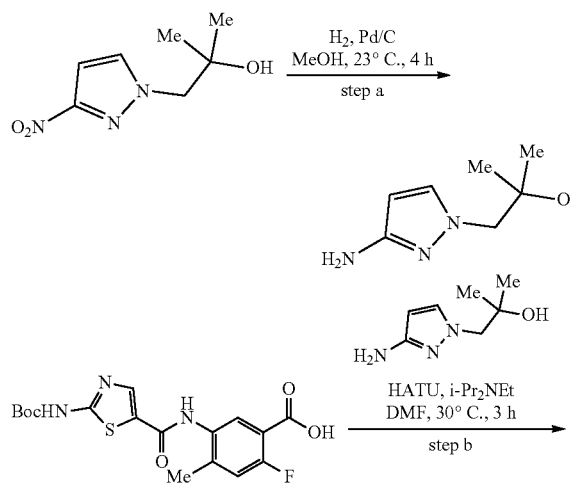

Step a: A vial was charged with 2-methyl-1-(3-nitropyrazol-1-yl)propan-2-ol (50 mg, 0.27 mmol, 1.0 equiv.), Pd/C (5 mg, 10 wt. %), and MeOH (0.6 mL). The resulting mixture was stirred under a $H_2$ balloon at RT for 4 h, at which time LC/MS analysis indicated complete consumption of starting material. The reaction mixture was diluted with MeOH, filtered over Celite®, and concentrated in vacuo to afford 1-(3-aminopyrazol-1-yl)-2-methylpropan-2-ol, which was used directly in the next step without further purification.

Steps b and c: The title compound was prepared from 1-(3-aminopyrazol-1-yl)-2-methylpropan-2-ol and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-$d_6$) δ 10.70 (s, 1H), 9.59 (s, 1H), 7.84 (s, 1H), 7.63 (s, 2H), 7.60 (d, J=2.3 Hz, 1H), 7.54 (d, J=6.9 Hz, 1H), 7.22 (d, J=11.0 Hz, 1H), 6.59 (d, J=2.3 Hz, 1H), 4.70 (s, 1H), 3.92 (s, 2H), 2.25 (s, 3H), 1.07 (s, 6H). ESI MS [M+H]$^+$ for $C_{19}H_{22}F_1N_6O_3S_1$, calcd 433.1, found 433.2.

Example 154: 2-Amino-N-[4-fluoro-5-[[1-(2-methoxyethyl)pyrazol-3-yl]carbamoyl]-2-methylphenyl]-1,3-thiazole-5-carboxamide

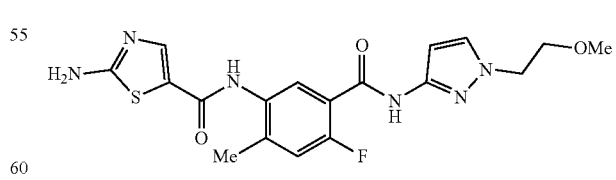

The title compound was prepared from 1-(2-methoxyethyl)pyrazol-3-amine and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-$d_6$) δ 10.68 (s, 1H), 9.61 (s, 1H), 7.85 (s, 1H), 7.67 (s, 2H), 7.63 (d, J=2.3 Hz, 1H), 7.54

(d, J=6.9 Hz, 1H), 7.23 (d, J=11.0 Hz, 1H), 6.56 (d, J=2.2 Hz, 1H), 4.17 (t, J=5.3 Hz, 2H), 3.66 (t, J=5.3 Hz, 2H), 3.23 (s, 3H), 2.25 (s, 3H). ESI MS [M+H]+ for $C_{18}H_{20}F_1N_6O_3S_1$, calcd 419.1, found 419.1.

Example 155: 2-Amino-N-[5-[(1-cyclobutylpyrazol-3-yl)carbamoyl]-4-fluoro-2-methylphenyl]-1,3-thiazole-5-carboxamide

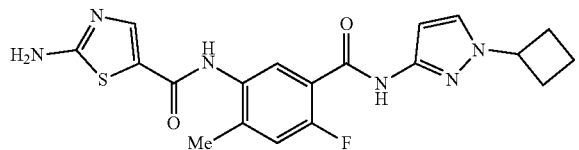 [SMILES: Cc1cc(F)c(C(=O)Nc2ccn(C3CCC3)n2)cc1NC(=O)c1cnc(N)s1]

The title compound was prepared from 1-cyclobutylpyrazol-3-amine and 2-fluoro-4-methyl-5-[[2-[(2-methylpropan-2-yl)oxycarbonylamino]-1,3-thiazole-5-carbonyl]amino] benzoic acid in a similar fashion to Example 7. $^1$H NMR (400 MHz, DMSO-$d_6$) δ 10.73 (d, J=1.4 Hz, 1H), 9.59 (s, 1H), 7.84 (s, 1H), 7.72 (d, J=2.3 Hz, 1H), 7.63 (s, 2H), 7.55 (d, J=6.9 Hz, 1H), 7.22 (d, J=11.0 Hz, 1H), 6.57 (d, J=2.3 Hz, 1H), 4.75 (p, J=8.4 Hz, 1H), 2.48-2.41 (m, 2H), 2.41-2.30 (m, 2H), 2.25 (s, 3H), 1.81-1.71 (m, 2H). ESIMS [M+H]+ for $C_{19}H_{20}F_1N_6O_2S_1$, calcd 415.1, found 415.2.

Example 156: 2-Amino-N-[5-(5,6-dihydro-4H-pyrrolo[1,2-b]pyrazol-2-ylcarbamoyl)-4-fluoro-2-methylphenyl]-1,3-thiazole-5-carboxamide

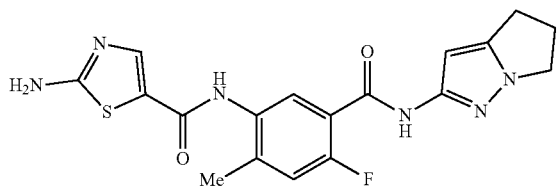 [SMILES: Cc1cc(F)c(C(=O)Nc2cc3n(n2)CCC3)cc1NC(=O)c1cnc(N)s1]

The title compound was prepared from 5,6-dihydro-4H-pyrrolo[1,2-b]pyrazol-2-amine and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-$d_6$) δ 10.54 (s, 1H), 9.60 (s, 1H), 7.84 (s, 1H), 7.63 (s, 2H), 7.53 (d, J=6.9 Hz, 1H), 7.22 (d, J=10.8 Hz, 1H), 6.34 (s, 1H), 3.99 (t, J=7.2 Hz, 2H), 2.84 (t, J=7.3 Hz, 2H), 2.49-2.43 (m, 2H), 2.25 (s, 3H). ESI MS [M+H]+ for $C_{18}H_{18}F_1N_6O_2S_1$, calcd 401.1, found 401.1.

Example 157: 2-Amino-N-[4-fluoro-2-methyl-5-(1H-pyrazol-4-ylcarbamoyl)phenyl]-1,3-thiazole-5-carboxamide

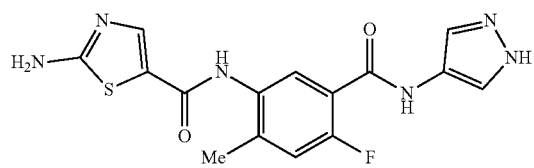

The title compound was prepared from 1H-pyrazol-4-amine and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-$d_6$) δ 10.34 (s, 1H), 10.01 (s, 1H), 8.67 (s, 2H), 8.07 (s, 1H), 7.80 (s, 2H), 7.56 (d, J=7.0 Hz, 1H), 7.29 (d, J=11.1 Hz, 1H), 2.27 (s, 4H). ESI MS [M+H]+ for $C_{15}H_{14}F_1N_6O_2S_1$, calcd 361.1, found 361.1.

Example 158: 2-Amino-N-[4-fluoro-2-methyl-5-[(1-propan-2-ylpyrazol-3-yl)carbamoyl]phenyl]-1,3-thiazole-5-carboxamide

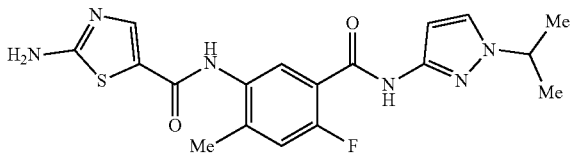 [SMILES: Cc1cc(F)c(C(=O)Nc2ccn(C(C)C)n2)cc1NC(=O)c1cnc(N)s1]

The title compound was prepared from 1-propan-2-ylpyrazol-3-amine and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-$d_6$) δ 10.71 (s, 1H), 10.16-9.90 (m, 1H), 8.88 (s, 3H), 8.11 (d, J=15.7 Hz, 1H), 7.68 (d, J=2.3 Hz, 1H), 7.54 (d, J=6.8 Hz, 1H), 7.24 (d, J=10.9 Hz, 1H), 4.41 (hept, J=6.7 Hz, 1H), 2.26 (s, 3H), 1.39 (d, J=6.6 Hz, 6H). ESI MS [M+H]+ for $C_{18}H_{20}F_1N_6O_2S_1$, calcd 403.1, found 403.2.

Example 159: 2-Amino-N-[5-[(1-cyclopropylpyrazol-3-yl)carbamoyl]-4-fluoro-2-methylphenyl]-1,3-thiazole-5-carboxamide

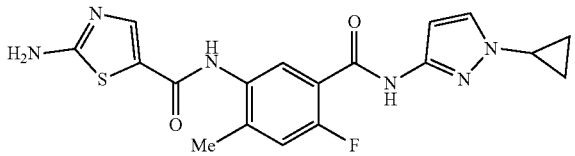 [SMILES: Cc1cc(F)c(C(=O)Nc2ccn(C3CC3)n2)cc1NC(=O)c1cnc(N)s1]

The title compound was prepared from 1-cyclopropylpyrazol-3-amine and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-$d_6$) δ 10.70 (s, 1H), 10.14 (s, 1H), 9.07 (s, 2H), 8.16 (s, 1H), 7.70 (d, J=2.3 Hz, 1H), 7.53 (d, J=6.8 Hz, 1H), 7.25 (d, J=10.9 Hz, 1H), 6.55 (d, J=2.3 Hz, 1H), 3.64 (tt, J=7.3, 3.9 Hz, 1H), 2.26 (s, 3H), 1.02-0.96 (m, 2H), 0.96-0.89 (m, 2H). ESI MS [M+H]+ for $C_{18}H_{18}F_1N_6O_2S_1$, calcd 401.1, found 401.2.

Example 160: 2-Amino-N-[4-fluoro-2-methyl-5-[(5-methyl-1,3-thiazol-2-yl)carbamoyl]phenyl]-1,3-thiazole-5-carboxamide

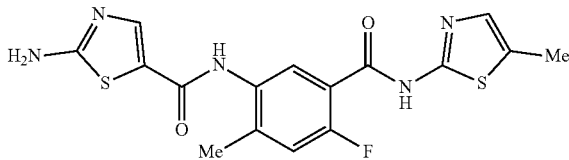 [SMILES: Cc1cnc(NC(=O)c2cc(NC(=O)c3cnc(N)s3)c(C)cc2F)s1]

The title compound was prepared from 5-methyl-1,3-thiazol-2-amine and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-$d_6$) δ 10.28 (s, 1H), 9.25 (s, 2H), 8.25 (s, 1H), 7.62 (d, J=6.8 Hz, 1H), 7.31 (d, J=11.0 Hz, 1H), 7.21 (d, J=1.4 Hz, 1H), 2.68 (d, J=0.7 Hz, 1H), 2.37 (s, 3H), 2.29 (s, 3H). ESI MS [M+H]$^+$ for $C_{16}H_{15}F_1N_5O_2S_2$, calcd 392.1, found 392.1.

Example 161: 2-Amino-N-[5-[(1-cyclopropylpyrazol-4-yl)carbamoyl]-4-fluoro-2-methylphenyl]-1,3-thiazole-5-carboxamide

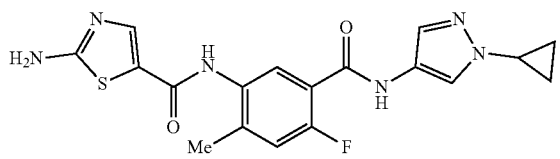

The title compound was prepared from 1-cyclopropylpyrazol-4-amine dihydrochloride and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-$d_6$) δ 10.37 (s, 1H), 10.33 (s, 1H), 9.40 (s, 2H), 8.29 (d, J=6.7 Hz, 1H), 8.03 (d, J=0.7 Hz, 1H), 7.55 (d, J=6.9 Hz, 1H), 7.51 (d, J=0.7 Hz, 1H), 7.29 (d, J=11.0 Hz, 1H), 3.71 (tt, J=7.3, 3.9 Hz, 1H), 2.27 (s, 3H), 1.04-0.97 (m, 2H), 0.97-0.90 (m, 2H). ESI MS [M+H]$^+$ for $C_{18}H_{18}F_1N_6O_2S_1$, calcd 401.1, found 401.2.

Example 162: 2-Amino-N-[4-fluoro-2-methyl-5-[(5-methyl-1,3,4-thiadiazol-2-yl)carbamoyl]phenyl]-1,3-thiazole-5-carboxamide

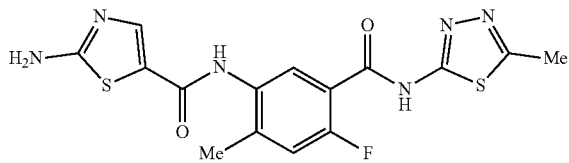 [SMILES: Cc1nnc(NC(=O)c2cc(NC(=O)c3cnc(N)s3)c(C)cc2F)s1]

The title compound was prepared from 5-methyl-1,3,4-thiadiazol-2-amine and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, Methanol-$d_4$) δ 8.02 (s, 1H), 7.78 (d, J=6.7 Hz, 1H), 7.29 (d, J=11.2 Hz, 1H), 2.72 (s, 3H), 2.37 (s, 3H). ESI MS [M+H]$^+$ for $C_{15}H_{14}F_1N_6O_2S_2$, calcd 393.1, found 393.2.

Example 163: 2-Amino-N-[4-fluoro-2-methyl-5-[(1-methylpyrazol-3-yl)carbamoyl]phenyl]-1,3-thiazole-5-carboxamide

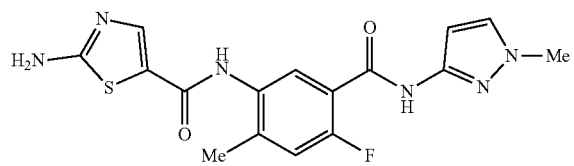 [SMILES: Cc1cc(F)c(C(=O)Nc2ccn(C)n2)cc1NC(=O)c1cnc(N)s1]

The title compound was prepared from 1-methylpyrazol-3-amine and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-$d_6$) δ 10.64 (s, 1H), 10.25 (s, 1H), 9.29 (s, 2H), 8.24 (s, 1H), 7.61 (d, J=2.2 Hz, 1H), 7.54 (d, J=6.8 Hz, 1H), 7.26 (d, J=10.8 Hz, 1H), 6.54 (d, J=2.2 Hz, 1H), 3.76 (s, 3H), 2.27 (s, 3H). ESI MS [M+H]$^+$ for $C_{16}H_{16}F_1N_6O_2S_1$, calcd 375.1, found 375.2.

Example 164: 2-Amino-N-[4-fluoro-2-methyl-5-(3-morpholin-4-ylpropylcarbamoyl)phenyl]-1,3-thiazole-5-carboxamide

The title compound was prepared from 3-morpholin-4-ylpropan-1-amine and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, Methanol-$d_4$) δ 8.09 (s, 1H), 7.74 (d, J=6.4 Hz, 1H), 7.20 (d, J=11.4 Hz, 1H), 4.07 (d, J=12.7 Hz, 2H), 3.82 (t, J=11.9 Hz, 2H), 3.52 (t, J=6.3 Hz, 4H), 3.24 (s, 2H), 3.22-3.10 (m, 2H), 2.34 (s, 3H), 2.10 (s, 2H). ESI MS [M+H]$^+$ for $C_{19}H_{25}F_1N_5O_3S_1$, calcd 422.2, found 422.3.

Example 165: 2-Amino-N-[4-fluoro-5-[2-(4-fluorophenyl)ethylcarbamoyl]-2-methylphenyl]-1,3-thiazole-5-carboxamide

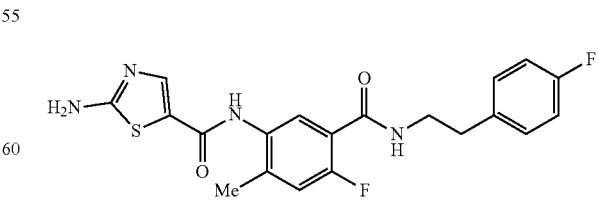

The title compound was prepared from 2-(4-fluorophenyl)ethanamine and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-$d_6$) δ 9.77 (s, 1H), 8.32-8.24 (m, 1H), 8.41-8.04 (m, 2H), 7.94 (s, 1H), 7.49 (d, J=7.0 Hz, 1H), 7.27 (ddd, J=8.9, 5.6, 2.6 Hz, 2H), 7.21 (d, J=11.3 Hz, 1H), 7.16-7.05 (m, 2H), 3.49-3.43 (m, 2H), 2.81 (t, J=7.2 Hz, 2H), 2.23 (s, 3H). ESI MS [M+H]$^+$ for $C_{20}H_{19}F_2N_4O_2S_1$, calcd 417.1, found 417.1.

Example 166: 2-Amino-N-[4-fluoro-2-methyl-5-[(2-methyl-1,3-thiazol-5-yl)carbamoyl]phenyl]-1,3-thiazole-5-carboxamide

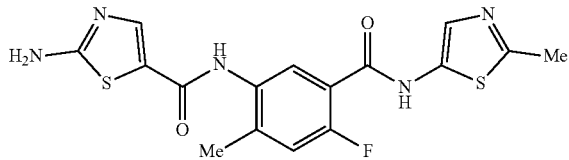 [SMILES: Cc1ncc(NC(=O)c2cc(NC(=O)c3cnc(N)s3)c(C)cc2F)s1]

The title compound was prepared from 2-methyl-1,3-thiazol-5-amine and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-$d_6$) δ 11.64 (s, 1H), 9.94 (s, 1H), 8.44 (s, 2H), 8.06-7.96 (m, 1H), 7.62 (d, J=6.9 Hz, 1H), 7.50 (d, J=1.6 Hz, 1H), 7.34 (d, J=11.0 Hz, 1H), 2.58 (s, 3H), 2.28 (s, 3H). ESI MS [M+H]$^+$ for $C_{16}H_{15}F_1N_5O_2S_2$, calcd 392.1, found 392.1.

Example 167: 2-Amino-N-[4-fluoro-2-methyl-5-[(1-methylpyrazol-4-yl)carbamoyl]phenyl]-1,3-thiazole-5-carboxamide

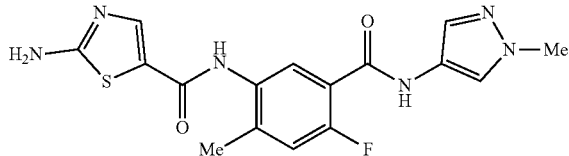 [SMILES: Cc1cc(F)c(C(=O)Nc2cnn(C)c2)cc1NC(=O)c1cnc(N)s1]

The title compound was prepared from 1-methylpyrazol-4-amine hydrochloride and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-$d_6$) δ 10.34 (s, 1H), 10.01 (s, 1H), 8.69 (s, 2H), 8.07 (s, 1H), 7.99 (s, 1H), 7.55 (d, J=6.9 Hz, 1H), 7.52 (d, J=0.7 Hz, 1H), 7.29 (d, J=10.8 Hz, 1H), 3.81 (s, 3H), 2.26 (s, 3H). ESI MS [M+H]$^+$ for $C_{16}H_{16}F_1N_6O_2S_1$, calcd 375.1, found 375.2.

Example 168: 2-Amino-N-[4-fluoro-2-methyl-5-[(1-pyridin-2-ylpyrazol-3-yl)carbamoyl]phenyl]-1,3-thiazole-5-carboxamide

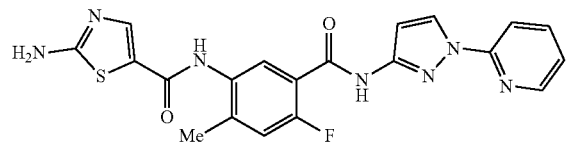 [SMILES: Cc1cc(F)c(C(=O)Nc2ccn(-c3ccccn3)n2)cc1NC(=O)c1cnc(N)s1]

The title compound was prepared from 1-pyridin-2-ylpyrazol-3-amine and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-$d_6$) δ 11.13 (s, 1H), 10.12 (s, 1H), 8.95 (s, 2H), 8.58 (d, J=2.6 Hz, 1H), 8.47 (dd, J=4.7, 1.8 Hz, 1H), 8.23-8.09 (m, 1H), 7.99 (td, J=7.8, 1.9 Hz, 1H), 7.79 (s, 1H), 7.60 (d, J=6.8 Hz, 1H), 7.33 (ddd, J=7.4, 4.8, 0.9 Hz, 1H), 7.29 (d, J=11.0 Hz, 1H), 6.95 (d, J=2.7 Hz, 1H), 2.28 (s, 3H). ESI MS [M+H]$^+$ for $C_{20}H_{17}F_1N_7O_2S_1$, calcd 438.1, found 438.1.

Example 169: N-[5-[(5-Cyclopropyloxypyridin-2-yl)carbamoyl]-4-fluoro-2-methylphenyl]-1,3-thiazole-5-carboxamide

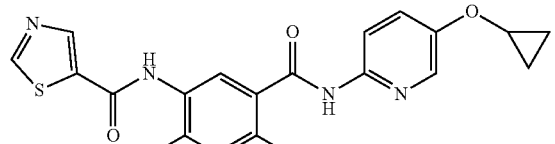

The title compound was prepared from 1,3-thiazole-5-carboxylic acid, methyl 5-amino-2-fluoro-4-methylbenzoate, and 5-cyclopropyloxypyridin-2-amine in a similar fashion to Example 59. $^1$H NMR (400 MHz, DMSO-$d_6$) δ 10.57 (d, J=2.4 Hz, 1H), 10.27 (s, 1H), 9.32 (d, J=0.7 Hz, 1H), 8.67 (s, 1H), 8.15 (dd, J=3.0, 0.7 Hz, 1H), 8.11 (d, J=9.1 Hz, 1H), 7.64 (d, J=6.9 Hz, 1H), 7.59 (dd, J=9.0, 3.0 Hz, 1H), 7.31 (d, J=11.1 Hz, 1H), 3.95 (tt, J=6.0, 2.9 Hz, 1H), 2.29 (s, 3H), 0.85-0.75 (m, 2H), 0.75-0.66 (m, 2H). ESI MS [M+H]$^+$ for $C_{20}H_{18}F_1N_4O_3S_1$, calcd 413.1, found 413.2.

Example 170: 2-Amino-N-[5-[(4-cyclopropyl-1,3-thiazol-2-yl)carbamoyl]-4-fluoro-2-methylphenyl]-1,3-thiazole-5-carboxamide

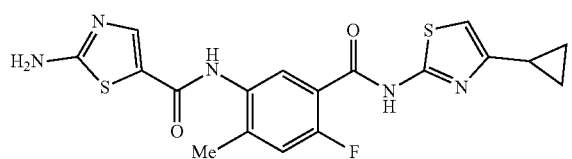 [SMILES: Cc1cc(F)c(C(=O)Nc2nc(C3CC3)cs2)cc1NC(=O)c1cnc(N)s1]

The title compound was prepared from 4-cyclopropyl-1,3-thiazol-2-amine and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-$d_6$) δ 12.40 (s, 1H), 9.60 (s, 1H), 7.84 (s, 1H), 7.68-7.58 (m, 3H), 7.26 (d, J=11.0 Hz, 1H), 6.83 (s, 1H), 2.26 (s, 3H), 1.99 (tt, J=8.4, 4.9 Hz, 1H), 0.85 (ddd, J=8.7, 6.1, 2.6 Hz, 2H), 0.79-0.74 (m, 2H). ESI MS [M+H]$^+$ for $C_{18}H_{17}F_1N_5O_2S_2$, calcd 418.1, found 418.1.

Example 171: 2-Amino-N-[4-fluoro-2-methyl-5-[(2-propan-2-yltriazol-4-yl)carbamoyl]phenyl]-1,3-thiazole-5-carboxamide

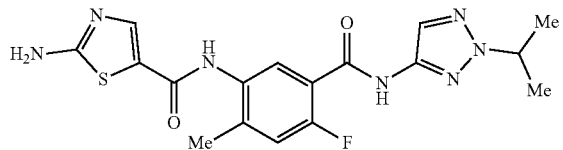 [SMILES: Cc1cc(F)c(C(=O)Nc2cnn(C(C)C)n2)cc1NC(=O)c1cnc(N)s1]

The title compound was prepared from 2-propan-2-yltriazol-4-amine and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-$d_6$) δ 11.22 (s, 1H), 10.20 (s, 1H), 9.06 (s, 2H), 8.31-8.08 (m, 1H), 7.96 (s, 1H), 7.58 (d, J=6.8 Hz, 1H), 7.28 (d, J=10.9 Hz, 1H), 4.74 (hept, J=6.7 Hz, 1H), 2.27 (s, 3H), 1.47 (d, J=6.7 Hz, 6H). ESI MS [M+H]$^+$ for $C_{17}H_{19}F_1N_7O_2S_1$, calcd 404.1, found 404.1.

Example 172: 2-Amino-N-[4-fluoro-2-methyl-5-[(1-phenylpyrazol-3-yl)carbamoyl]phenyl]-1,3-thiazole-5-carboxamide

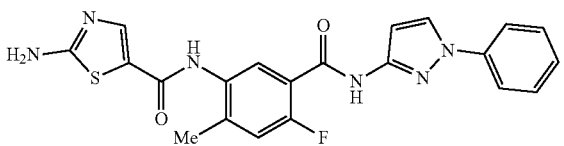 [SMILES: Cc1cc(F)c(C(=O)Nc2ccn(-c3ccccc3)n2)cc1NC(=O)c1cnc(N)s1]

The title compound was prepared from 1-phenylpyrazol-3-amine and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-$d_6$) δ 11.03 (s, 1H), 9.93 (s, 1H), 8.93-8.27 (m, 2H), 8.48 (d, J=2.6 Hz, 1H), 8.03 (s, 1H), 7.80 (d, J=7.7 Hz, 2H), 7.59 (d, J=6.8 Hz, 1H), 7.53-7.45 (m, 2H), 7.31-7.24 (m, 2H), 6.91 (d, J=2.6 Hz, 1H), 2.27 (s, 3H). ESI MS [M+H]$^+$ for $C_{21}H_{18}F_1N_6O_2S_1$, calcd 437.1, found 437.2.

Example 173: 2-Amino-N-[5-[(1,5-dimethyl-1,2,4-triazol-3-yl)carbamoyl]-4-fluoro-2-methylphenyl]-1,3-thiazole-5-carboxamide

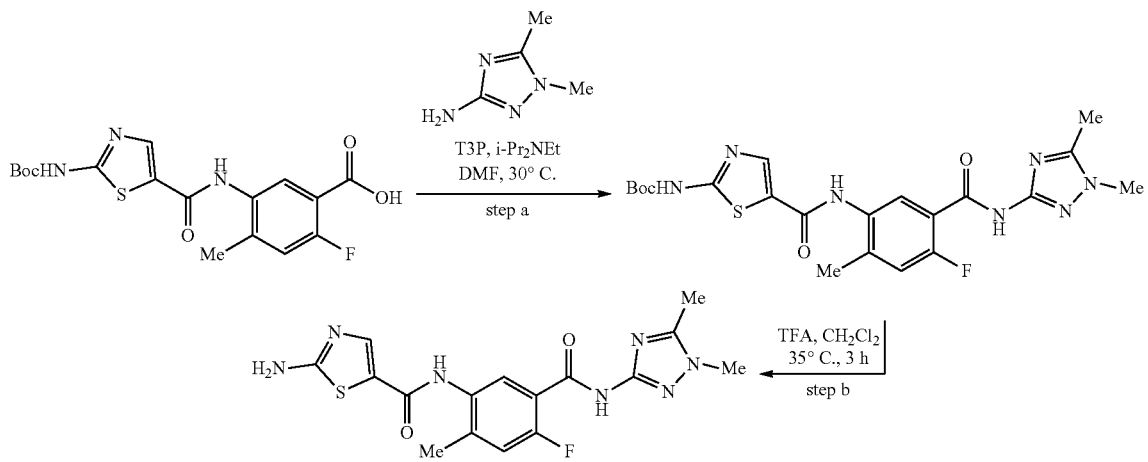 [SMILES: Cc1nc(N)nn1C ; Cc1cc(F)c(C(=O)O)cc1NC(=O)c1cnc(NC(=O)OC(C)(C)C)s1 ; Cc1cc(F)c(C(=O)Nc2nc(C)n(C)n2)cc1NC(=O)c1cnc(NC(=O)OC(C)(C)C)s1 ; Cc1cc(F)c(C(=O)Nc2nc(C)n(C)n2)cc1NC(=O)c1cnc(N)s1]

Step a: A vial was charged with 2-fluoro-4-methyl-5-[[2-[(2-methylpropan-2-yl)oxycarbonylamino]-1,3-thiazole-5-carbonyl]amino]benzoic acid (67 mg, 0.17 mmol, 1.0 equiv.), 1,5-dimethyl-1,2,4-triazol-3-amine (29 mg, 0.26 mmol, 1.5 equiv.), T3P (50% in EtOAc, 0.15 mL, 0.26 mmol, 1.5 equiv.), and DMF (0.5 mL). i-Pr$_2$NEt (0.09 mL, 0.51 mmol, 3.0 equiv.) was then added dropwise and the reaction mixture was stirred at 30° C. Upon complete conversion, as judged by LCMS analysis, the reaction mixture was cooled to RT and diluted with water. The resulting precipitated solid was collected by vacuum filtration, rinsed with water, and dried in vacuo. The crude product was purified by column chromatography (SiO$_2$, 0% to 100% EtOAc in CH$_2$Cl$_2$) to afford tert-butyl N-[5-[[5-[(1,5-dimethyl-1,2,4-triazol-3-yl)carbamoyl]-4-fluoro-2-methylphenyl]carbamoyl]-1,3-thiazol-2-yl]carbamate.

Step b: The title compound was prepared from the product of step a in a similar fashion to step b of Example 7. $^1$H NMR (400 MHz, Methanol-d$_4$) δ 7.80 (s, 1H), 7.69 (d, J=6.9 Hz, 1H), 7.21 (d, J=11.3 Hz, 1H), 3.80 (s, 3H), 2.44 (s, 3H), 2.34 (s, 3H). ESI MS [M+H]$^+$ for C$_{16}$H$_{17}$F$_1$N$_7$O$_2$S$_1$, calcd 390.1, found 390.1.

Example 174: 2-Amino-N-[4-fluoro-2-methyl-5-[(1-methyl-1,2,4-triazol-3-yl)carbamoyl]phenyl]-1,3-thiazole-5-carboxamide

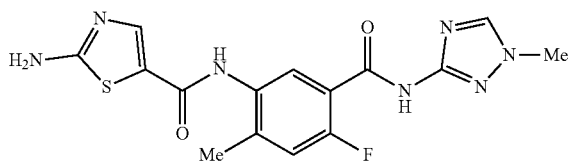 [SMILES: Cc1cc(F)c(C(=O)Nc2ncn(C)n2)cc1NC(=O)c1cnc(N)s1]

The title compound was prepared from 1-methyl-1,2,4-triazol-3-amine and 2-fluoro-4-methyl-5-[[2-[(2-methylpropan-2-yl)oxycarbonylamino]-1,3-thiazole-5-carbonyl]amino]benzoic acid in a similar fashion to Example 173. $^1$H NMR (400 MHz, Methanol-d$_4$) δ 8.46 (d, J=0.7 Hz, 1H), 7.99 (s, 1H), 7.89 (d, J=7.1 Hz, 1H), 7.40 (d, J=11.3 Hz, 1H), 4.10 (d, J=0.4 Hz, 3H), 2.53 (s, 3H). ESI MS [M+H]$^+$ for C$_{15}$H$_{15}$F$_1$N$_7$O$_2$S$_1$, calcd 376.1, found 376.1.

Example 175: 2-Amino-N-[5-[(5-cyclopropyl-1,3,4-thiadiazol-2-yl)carbamoyl]-4-fluoro-2-methylphenyl]-1,3-thiazole-5-carboxamide

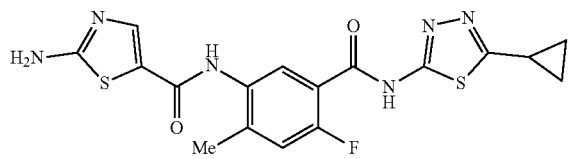 [SMILES: Cc1cc(F)c(C(=O)Nc2nnc(C3CC3)s2)cc1NC(=O)c1cnc(N)s1]

The title compound was prepared from 5-cyclopropyl-1,3,4-thiadiazol-2-amine and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-d$_6$) δ 12.83 (s, 1H), 9.63 (s, 1H), 7.85 (s, 1H), 7.71-7.59 (m, 3H), 7.30 (d, J=11.0 Hz, 1H), 2.42 (ddd, J=13.2, 8.5, 4.9 Hz, 1H), 2.27 (s, 3H), 1.18-1.11 (m, 2H), 1.03-0.98 (m, 2H). ESI MS [M+H]$^+$ for C$_{17}$H$_{16}$F$_1$N$_6$O$_2$S$_2$, calcd 419.1, found 419.1.

Example 176: 2-Amino-N-[5-[(5-cyclopropyl-4H-1,2,4-triazol-3-yl)carbamoyl]-4-fluoro-2-methylphenyl]-1,3-thiazole-5-carboxamide

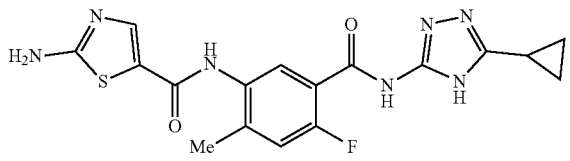 [SMILES: Cc1cc(F)c(C(=O)Nc2nnc(C3CC3)[nH]2)cc1NC(=O)c1cnc(N)s1]

The title compound was prepared from 5-cyclopropyl-4H-1,2,4-triazol-3-amine and 2-fluoro-4-methyl-5-[[2-[(2-methylpropan-2-yl)oxycarbonylamino]-1,3-thiazole-5-carbonyl]amino]benzoic acid in a similar fashion to Example 173. $^1$H NMR (400 MHz, DMSO-d$_6$) δ 10.11 (s, 1H), 8.86 (s, 2H), 8.11 (s, 1H), 7.71 (s, 2H), 7.55 (d, J=6.4 Hz, 1H), 7.32 (d, J=10.5 Hz, 1H), 2.29 (s, 3H), 1.73 (tt, J=8.1, 4.8 Hz, 1H), 0.88-0.80 (m, 2H), 0.77 (dt, J=4.7, 2.9 Hz, 2H). ESI MS [M+H]$^+$ for C$_{17}$H$_{17}$F$_1$N$_7$O$_2$S$_1$, calcd 402.1, found 402.2.

Example 177: 2-Amino-N-[5-[(5-cyclopropyl-1H-pyrazol-3-yl)carbamoyl]-4-fluoro-2-methylphenyl]-1,3-thiazole-5-carboxamide

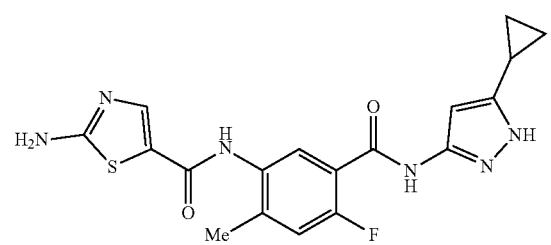 [SMILES: Cc1cc(F)c(C(=O)Nc2cc(C3CC3)[nH]n2)cc1NC(=O)c1cnc(N)s1]

The title compound was prepared from 5-cyclopropyl-1H-pyrazol-3-amine and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-d$_6$) δ 12.17 (s, 1H), 10.48 (s, 1H), 9.60 (s, 1H), 7.84 (s, 1H), 7.63 (s, 2H), 7.52 (d, J=6.9 Hz, 1H), 7.22 (d, J=11.0 Hz, 1H), 6.27 (s, 1H), 2.24 (s, 3H), 1.88 (tt, J=8.5, 5.0 Hz, 1H), 0.99-0.88 (m, 2H), 0.73-0.64 (m, 2H). ESI MS [M+H]$^+$ for C$_{18}$H$_{18}$F$_1$N$_6$O$_2$S$_1$, calcd 401.1, found 401.2.

Example 178: 2-Amino-N-[4-fluoro-2-methyl-5-[[4-(trifluoromethyl)pyridin-2-yl]carbamoyl]phenyl]-1,3-thiazole-5-carboxamide

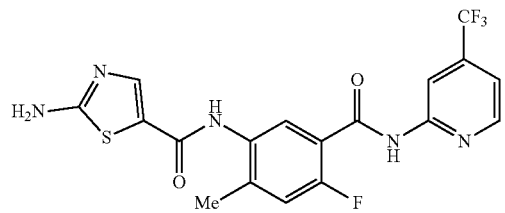 [SMILES: Cc1cc(F)c(C(=O)Nc2cc(C(F)(F)F)ccn2)cc1NC(=O)c1cnc(N)s1]

The title compound was prepared from 4-(trifluoromethyl)pyridin-2-amine and 2-fluoro-4-methyl-5-[[2-[(2-methylpropan-2-yl)oxycarbonylamino]-1,3-thiazole-5-carbonyl]amino]benzoic acid in a similar fashion to Example 173. $^1$H NMR (400 MHz, DMSO-$d_6$) δ 11.23 (s, 1H), 10.19 (d, J=7.4 Hz, 1H), 9.03 (s, 2H), 8.66 (d, J=5.2 Hz, 1H), 8.49 (s, 1H), 8.18 (d, J=5.4 Hz, 1H), 7.62 (d, J=6.8 Hz, 1H), 7.56 (d, J=5.2 Hz, 1H), 7.31 (d, J=11.0 Hz, 1H), 2.29 (s, 3H). ESI MS [M+H]$^+$ for $C_{18}H_{14}F_4N_5O_2S_1$, calcd 440.1, found 440.2.

Example 179: 2-Amino-N-[5-[(1-ethylpyrazol-3-yl)carbamoyl]-4-fluoro-2-methylphenyl]-1,3-thiazole-5-carboxamide

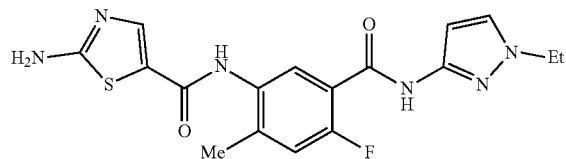 [SMILES: CCn1ccc(NC(=O)c2cc(NC(=O)c3cnc(N)s3)c(C)cc2F)n1]

The title compound was prepared from 1-ethylpyrazol-3-amine and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-$d_6$) δ 10.66 (s, 1H), 9.60 (s, 1H), 7.84 (s, 1H), 7.65 (d, J=2.2 Hz, 1H), 7.63 (s, 2H), 7.54 (d, J=6.9 Hz, 1H), 7.22 (d, J=11.0 Hz, 1H), 6.55 (d, J=2.2 Hz, 1H), 4.05 (q, J=7.2 Hz, 2H), 2.25 (s, 3H), 1.35 (t, J=7.2 Hz, 3H). ESI MS [M+H]$^+$ for $C_{17}H_{18}F_1N_6O_2S_1$, calcd 389.1, found 389.2.

Example 180: 2-Amino-N-[4-fluoro-2-methyl-5-[(5-methyl-6,7-dihydro-4H-pyrazolo[1,5-a]pyrazin-2-yl)carbamoyl]phenyl]-1,3-thiazole-5-carboxamide

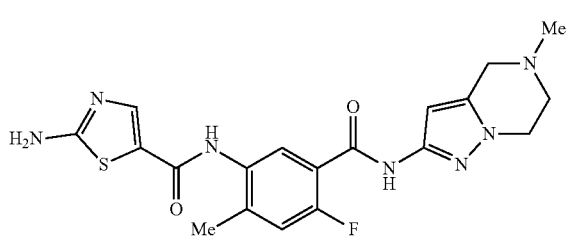 [SMILES: Cc1cc(F)c(C(=O)Nc2cc3n(n2)CCN(C)C3)cc1NC(=O)c1cnc(N)s1]

The title compound was prepared from 5-methyl-6,7-dihydro-4H-pyrazolo[1,5-a]pyrazin-2-amine and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-$d_6$) δ 10.62-10.55 (m, 1H), 9.60 (s, 1H), 7.84 (s, 1H), 7.63 (s, 2H), 7.53 (d, J=6.9 Hz, 1H), 7.22 (d, J=11.0 Hz, 1H), 6.38 (s, 1H), 3.98 (t, J=5.5 Hz, 2H), 3.55 (s, 2H), 2.82 (t, J=5.5 Hz, 2H), 2.38 (s, 3H), 2.25 (s, 3H). ESI MS [M+H]$^+$ for $C_{19}H_{21}F_1N_7O_2S_1$, calcd 430.1, found 430.2.

Example 181: 2-Amino-N-[5-[[1-(difluoromethyl)pyrazol-3-yl]carbamoyl]-4-fluoro-2-methylphenyl]-1,3-thiazole-5-carboxamide

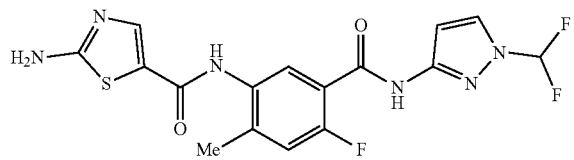 [SMILES: Cc1cc(F)c(C(=O)Nc2ccn(C(F)F)n2)cc1NC(=O)c1cnc(N)s1]

The title compound was prepared from 1-(difluoromethyl)pyrazol-3-amine and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-$d_6$) δ 11.11 (s, 1H), 9.61 (s, 1H), 8.17 (d, J=2.7 Hz, 1H), 7.84 (s, 1H), 7.90-7.53 (m, 2H), 7.63 (s, 2H), 7.26 (d, J=10.8 Hz, 1H), 6.87 (s, 1H), 2.26 (s, 3H). ESI MS [M+H]$^+$ for $C_{16}H_{14}F_3N_6O_2S_1$, calcd 411.1, found 411.1.

Example 182: 2-Amino-N-[5-(6,7-dihydro-4H-pyrazolo[5,1-c][1,4]oxazin-2-ylcarbamoyl)-4-fluoro-2-methylphenyl]-1,3-thiazole-5-carboxamide

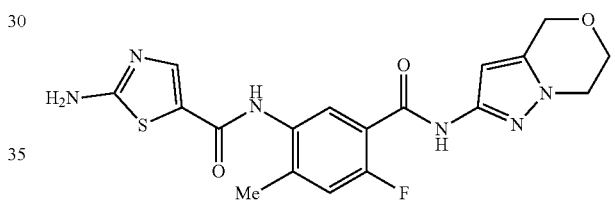

The title compound was prepared from 6,7-dihydro-4H-pyrazolo[5,1-c][1,4]oxazin-2-amine and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-$d_6$) δ 10.66 (s, 1H), 9.60 (s, 1H), 7.84 (s, 1H), 7.63 (s, 2H), 7.54 (d, J=6.9 Hz, 1H), 7.23 (d, J=11.0 Hz, 1H), 6.43 (s, 1H), 4.77 (s, 2H), 4.11-3.96 (m, 4H), 2.25 (s, 3H). ESI MS [M+H]$^+$ for $C_{18}H_{18}F_1N_6O_3S_1$, calcd 417.1, found 417.1.

Example 183: 2-Amino-N-[5-[(3,3-dimethyl-2-oxo-1H-indol-6-yl)carbamoyl]-4-fluoro-2-methylphenyl]-1,3-thiazole-5-carboxamide

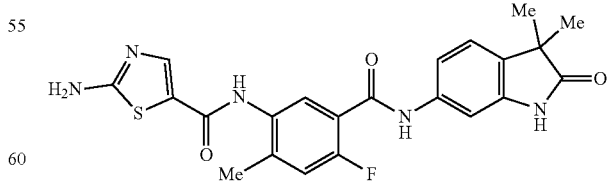

The title compound was prepared from 6-amino-3,3-dimethyl-1H-indol-2-one and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-$d_6$) δ 10.34 (d, J=19.9 Hz, 2H), 9.65 (s, 1H), 7.85 (s, 1H), 7.64 (s, 2H), 7.52 (d, J=6.8 Hz, 1H), 7.46 (d, J=1.7 Hz, 1H), 7.27 (d, J=10.8 Hz, 1H), 7.20 (q, J=8.1 Hz, 2H), 2.26 (s, 3H), 1.23 (s, 6H). ESI MS [M+H]⁺ for $C_{22}H_{21}F_1N_5O_3S_1$, calcd 454.1, found 454.2.

Example 184: 2-Amino-N-[5-[(3,3-dimethyl-2-oxo-1H-indol-5-yl)carbamoyl]-4-fluoro-2-methylphenyl]-1,3-thiazole-5-carboxamide

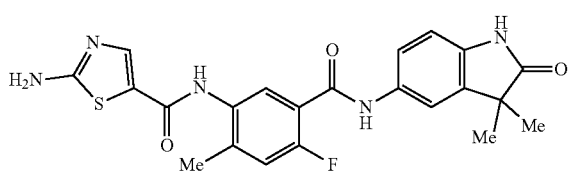 [SMILES: Cc1cc(F)c(C(=O)Nc2ccc3c(c2)C(C)(C)C(=O)N3)cc1NC(=O)c1cnc(N)s1]

The title compound was prepared from 5-amino-3,3-dimethyl-1H-indol-2-one hydrochloride and 2-fluoro-4-methyl-5-[[2-[(2-methylpropan-2-yl)oxycarbonylamino]-1,3-thiazole-5-carbonyl]amino]benzoic acid in a similar fashion to Example 7. ¹H NMR (400 MHz, DMSO-d₆) δ 10.32 (s, 1H), 10.18 (s, 1H), 9.63 (s, 1H), 7.85 (s, 1H), 7.65 (d, J=2.0 Hz, 1H), 7.63 (s, 2H), 7.53 (d, J=6.9 Hz, 1H), 7.44 (dd, J=8.4, 2.1 Hz, 1H), 7.27 (d, J=10.9 Hz, 1H), 6.82 (d, J=8.3 Hz, 1H), 2.26 (s, 3H), 1.25 (s, 6H). ESI MS [M+H]⁺ for $C_{22}H_{21}F_1N_5O_3S_1$, calcd 454.1, found 454.2.

Example 185: 2-Amino-N-[4-fluoro-5-[[1-(cis-3-methoxycyclobutyl)pyrazol-3-yl]carbamoyl]-2-methylphenyl]-1,3-thiazole-5-carboxamide

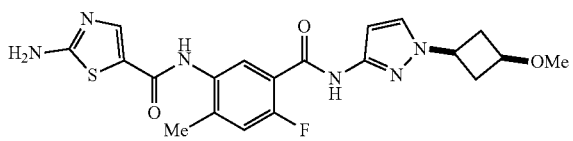 [SMILES: CO[C@H]1C[C@@H](n2ccc(NC(=O)c3cc(NC(=O)c4cnc(N)s4)c(C)cc3F)n2)C1]

The title compound was prepared from trans-3-methoxycyclobutan-1-ol, 3-nitro-1H-pyrazole, and 2-fluoro-4-methyl-5-[[2-[(2-methylpropan-2-yl)oxycarbonylamino]-1,3-thiazole-5-carbonyl]amino]benzoic acid in a similar fashion to Example 149 as the second eluted product. ¹H NMR (400 MHz, DMSO-d₆) δ 10.77 (s, 1H), 9.59 (s, 1H), 7.84 (s, 1H), 7.72 (d, J=2.3 Hz, 1H), 7.63 (s, 2H), 7.54 (d, J=6.9 Hz, 1H), 7.23 (d, J=11.0 Hz, 1H), 6.57 (d, J=2.3 Hz, 1H), 4.41 (p, J=8.3 Hz, 1H), 3.72 (p, J=7.1 Hz, 1H), 3.17 (s, 3H), 2.77-2.68 (m, 2H), 2.33 (dt, J=11.8, 8.9 Hz, 2H), 2.25 (s, 3H). ESI MS [M+H]⁺ for $C_{20}H_{22}F_1N_6O_3S_1$, calcd 445.1, found 445.2.

Example 186: 2-Amino-N-[4-fluoro-5-[[2-(cis-3-methoxycyclobutyl)pyrazol-3-yl]carbamoyl]-2-methylphenyl]-1,3-thiazole-5-carboxamide

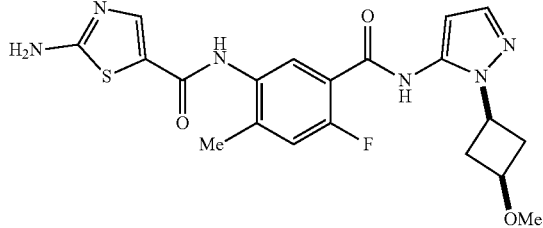 [SMILES: CO[C@H]1C[C@@H](n2nccc2NC(=O)c2cc(NC(=O)c3cnc(N)s3)c(C)cc2F)C1]

The title compound was obtained as the minor regioisomer in the preparation of Example 185 as the first eluted product. ¹H NMR (400 MHz, DMSO-d₆) δ 10.25 (s, 1H), 9.65 (s, 1H), 7.85 (s, 1H), 7.64 (s, 2H), 7.61 (d, J=6.9 Hz, 1H), 7.49 (s, 1H), 7.31 (d, J=11.0 Hz, 1H), 6.25 (s, 1H), 4.40 (p, J=7.5 Hz, 1H), 3.72 (p, J=7.5 Hz, 1H), 3.16 (s, 3H), 2.68 (d, J=8.3 Hz, 2H), 2.44-2.34 (m, 2H), 2.27 (s, 3H). ESI MS [M+H]⁺ for $C_{20}H_{22}F_1N_6O_3S_1$, calcd 445.1, found 445.2.

Example 187: 2-Amino-N-[4-fluoro-5-[[1-(trans-3-methoxycyclobutyl)pyrazol-3-yl]carbamoyl]-2-methylphenyl]-1,3-thiazole-5-carboxamide

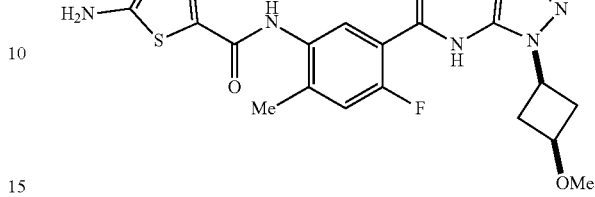

The title compound was prepared from cis-3-methoxycyclobutan-1-ol, 3-nitro-1H-pyrazole, and 2-fluoro-4-methyl-5-[[2-[(2-methylpropan-2-yl)oxycarbonylamino]-1,3-thiazole-5-carbonyl]amino]benzoic acid in a similar fashion to Example 149. ¹H NMR (400 MHz, DMSO-d₆) δ 10.78 (s, 1H), 10.36-10.08 (m, 1H), 9.13 (s, 2H), 8.18 (s, 1H), 7.74 (d, J=2.3 Hz, 1H), 7.54 (d, J=6.8 Hz, 1H), 7.25 (d, J=11.0 Hz, 1H), 6.58 (d, J=2.3 Hz, 1H), 4.88 (ddd, J=14.4, 7.9, 6.1 Hz, 1H), 4.11 (tt, J=6.6, 3.6 Hz, 1H), 3.18 (s, 3H), 2.59 (dt, J=12.9, 6.5 Hz, 2H), 2.42 (ddd, J=12.9, 8.2, 3.6 Hz, 2H), 2.27 (s, 3H). ESI MS [M+H]⁺ for $C_{20}H_{22}F_1N_6O_3S_1$, calcd 445.1, found 445.2.

Example 188: 2-Amino-N-[5-[(3,3-difluoro-2-oxo-1H-indol-5-yl)carbamoyl]-4-fluoro-2-methylphenyl]-1,3-thiazole-5-carboxamide

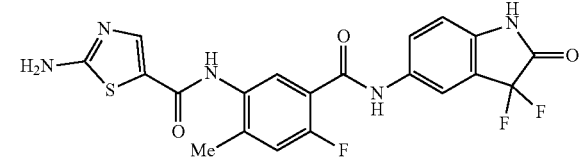 [SMILES: Cc1cc(F)c(C(=O)Nc2ccc3c(c2)C(F)(F)C(=O)N3)cc1NC(=O)c1cnc(N)s1]

The title compound was prepared from 5-amino-3,3-difluoro-1H-indol-2-one and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-$d_6$) δ 11.20 (s, 1H), 10.47 (s, 1H), 9.64 (s, 1H), 8.04 (s, 1H), 7.85 (s, 1H), 7.77 (d, J=8.5 Hz, 1H), 7.64 (s, 2H), 7.56 (d, J=6.8 Hz, 1H), 7.30 (d, J=10.9 Hz, 1H), 7.01 (d, J=8.7 Hz, 1H), 2.27 (s, 3H). ESI MS [M+H]$^+$ for $C_{20}H_{15}F_3N_5O_3S_1$, calcd 462.1, found 462.2.

Example 189: 2-Amino-N-[4-fluoro-5-[(4-methoxy-pyridin-2-yl)carbamoyl]-2-methylphenyl]-1,3-thiazole-5-carboxamide

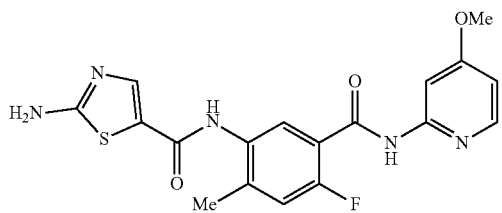 [SMILES: COc1ccnc(NC(=O)c2cc(NC(=O)c3cnc(N)s3)c(C)cc2F)c1]

The title compound was prepared from 4-methoxypyridin-2-amine and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-$d_6$) δ 10.57 (d, J=2.7 Hz, 1H), 9.62 (s, 1H), 8.17 (d, J=5.8 Hz, 1H), 7.85 (s, 1H), 7.80 (d, J=2.4 Hz, 1H), 7.63 (s, 2H), 7.61 (d, J=7.0 Hz, 1H), 7.26 (d, J=11.2 Hz, 1H), 6.78 (dd, J=6.0, 2.4 Hz, 1H), 3.85 (s, 3H), 2.27 (s, 3H). ESI MS [M+H]$^+$ for $C_{18}H_{17}F_1N_5O_3S_1$, calcd 402.1, found 402.1.

Example 190: 2-Amino-N-[5-[(4-cyclopropylpyridin-2-yl)carbamoyl]-4-fluoro-2-methylphenyl]-1,3-thiazole-5-carboxamide

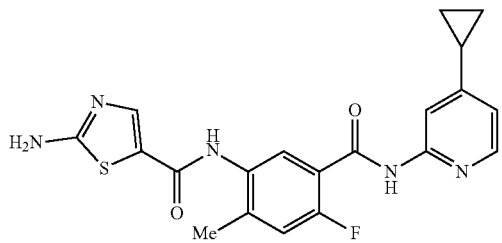 [SMILES: Cc1cc(F)c(C(=O)Nc2cc(C3CC3)ccn2)cc1NC(=O)c1cnc(N)s1]

The title compound was prepared from 4-cyclopropylpyridin-2-amine and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-$d_6$) δ 10.50 (d, J=2.7 Hz, 1H), 9.62 (s, 1H), 8.20-8.14 (m, 1H), 7.93 (t, J=1.1 Hz, 1H), 7.85 (s, 1H), 7.63 (s, 2H), 7.60 (d, J=7.0 Hz, 1H), 7.26 (d, J=11.3 Hz, 1H), 6.85 (dd, J=5.2, 1.6 Hz, 1H), 2.26 (s, 3H), 1.98 (td, J=8.4, 4.3 Hz, 1H), 1.12-1.06 (m, 2H), 0.83-0.76 (m, 2H). ESI MS [M+H]$^+$ for $C_{20}H_{19}F_1N_5O_2S_1$, calcd 412.1, found 412.2.

Example 191: 2-Amino-N-[4-fluoro-2-methyl-5-[[1-[(3S)-oxolan-3-yl]pyrazol-3-yl]carbamoyl]phenyl]-1,3-thiazole-5-carboxamide

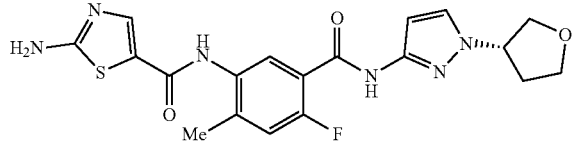 [SMILES: Cc1cc(F)c(C(=O)Nc2ccn([C@H]3CCOC3)n2)cc1NC(=O)c1cnc(N)s1]

The title compound was prepared from (3R)-oxolan-3-ol, 3-nitro-1H-pyrazole, and 2-fluoro-4-methyl-5-[[2-[(2-methylpropan-2-yl)oxycarbonylamino]-1,3-thiazole-5-carbonyl]amino]benzoic acid in a similar fashion to Example 149. $^1$H NMR (400 MHz, DMSO-$d_6$) δ 10.75 (s, 1H), 9.59 (s, 1H), 7.84 (s, 1H), 7.72 (d, J=2.3 Hz, 1H), 7.63 (s, 2H), 7.54 (d, J=6.9 Hz, 1H), 7.22 (d, J=11.0 Hz, 1H), 6.60 (d, J=2.3 Hz, 1H), 4.95 (ddd, J=10.1, 7.7, 4.0 Hz, 1H), 3.96 (dt, J=9.6, 6.3 Hz, 2H), 3.87 (dd, J=9.3, 3.9 Hz, 1H), 3.80 (td, J=8.2, 5.6 Hz, 1H), 2.41-2.30 (m, 1H), 2.25 (s, 3H), 2.29-2.17 (m, 1H). ESI MS [M+H]$^+$ for $C_{19}H_{20}F_1N_6O_3S_1$, calcd 431.1, found 431.2.

Example 192: 2-amino-N-[4-fluoro-5-[(1-fluorocyclobutyl)methylcarbamoyl]-2-methylphenyl]-1,3-thiazole-5-carboxamide

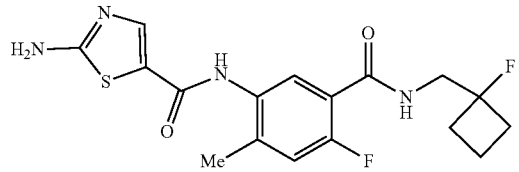 [SMILES: Cc1cc(F)c(C(=O)NCC2(F)CCC2)cc1NC(=O)c1cnc(N)s1]

The title compound was prepared from (1-fluorocyclobutyl)methanamine and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-$d_6$) δ 9.56 (s, 1H), 8.43-8.37 (m, 1H), 7.80 (s, 1H), 7.59 (s, 2H), 7.46 (d, J=7.0 Hz, 1H), 7.21-7.14 (m, 1H), 3.57 (dd, J=23.1, 6.1 Hz, 2H), 2.23-2.09 (m, 6H), 1.72 (td, J=9.8, 9.0, 5.5 Hz, 1H), 1.47 (dtd, J=11.3, 8.9, 2.6 Hz, 2H). ESI MS [M+H]$^+$ for $C_{17}H_{19}F_2N_4O_2S$, calcd 381.1, found 381.1.

Example 193: 2-Amino-N-[4-fluoro-5-[(1-fluorocyclopropyl)methylcarbamoyl]-2-methylphenyl]-1,3-thiazole-5-carboxamide

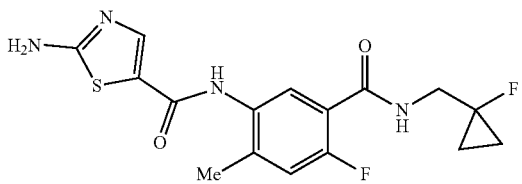 [SMILES: Cc1cc(F)c(C(=O)NCC2(F)CC2)cc1NC(=O)c1cnc(N)s1]

The title compound was prepared from (1-fluorocyclopropyl)methanamine and 2-fluoro-4-methyl-5-[[2-[(2-methylpropan-2-yl)oxycarbonylamino]-1,3-thiazole-5-carbonyl]amino]benzoic acid in a similar fashion to Example 7. ¹H NMR (400 MHz, DMSO-d₆) δ 9.57 (d, J=7.9 Hz, 1H), 8.51 (dt, J=7.0, 3.6 Hz, 1H), 7.80 (d, J=4.7 Hz, 1H), 7.60 (d, J=8.8 Hz, 2H), 7.47 (d, J=7.0 Hz, 1H), 7.18 (d, J=11.2 Hz, 1H), 3.64 (dd, J=20.6, 5.9 Hz, 2H), 2.20 (s, 3H), 1.03-0.89 (m, 2H), 0.83-0.67 (m, 2H). ESI MS [M+H]⁺ for $C_{16}H_{17}F_2N_4O_2S$, calcd 367.1, found 367.1.

Example 194: 2-Amino-N-[4-fluoro-2-methyl-5-[[(3S)-oxolan-3-yl]carbamoyl]phenyl]-1,3-thiazole-5-carboxamide

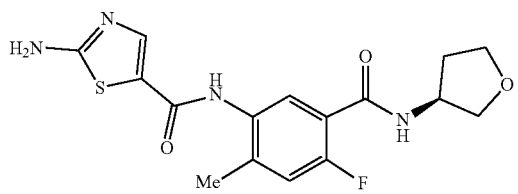 [SMILES: Cc1cc(F)c(C(=O)N[C@H]2CCOC2)cc1NC(=O)c1cnc(N)s1]

The title compound was prepared from (3S)-oxolan-3-amine and 2-fluoro-4-methyl-5-[[2-[(2-methylpropan-2-yl)oxycarbonylamino]-1,3-thiazole-5-carbonyl]amino]benzoic acid in a similar fashion to Example 7. ¹H NMR (400 MHz, DMSO-d₆) δ 9.55 (s, 1H), 8.45-8.38 (m, 1H), 7.79 (s, 1H), 7.60 (s, 2H), 7.42 (d, J=6.9 Hz, 1H), 7.16 (d, J=11.1 Hz, 1H), 4.41-4.33 (m, 1H), 3.84-3.74 (m, 2H), 3.66 (td, J=8.1, 5.6 Hz, 1H), 3.52 (dd, J=8.9, 4.2 Hz, 1H), 2.19 (s, 3H), 2.15-2.03 (m, 1H), 1.82 (ddt, J=12.5, 7.3, 5.1 Hz, 1H). ESI MS [M+H]⁺ for $C_{16}H_{18}FN_4O_3S$, calcd 365.1, found 365.1.

Example 195: 2-Amino-N-[4-fluoro-2-methyl-5-[[5-(propan-2-yloxymethyl)pyridin-2-yl]carbamoyl]phenyl]-1,3-thiazole-5-carboxamide

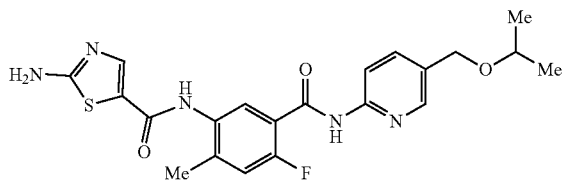 [SMILES: Cc1cc(F)c(C(=O)Nc2ccc(COC(C)C)cn2)cc1NC(=O)c1cnc(N)s1]

The title compound was prepared from 5-(propan-2-yloxymethyl)pyridin-2-amine and 2-fluoro-4-methyl-5-[[2-[(2-methylpropan-2-yl)oxycarbonylamino]-1,3-thiazole-5-carbonyl]amino]benzoic acid in a similar fashion to Example 7. ¹H NMR (400 MHz, DMSO-d₆) δ 10.61 (s, 1H), 9.59 (s, 1H), 8.30-8.24 (m, 1H), 8.12 (d, J=8.5 Hz, 1H), 7.84-7.72 (m, 2H), 7.63-7.54 (m, 3H), 7.23 (d, J=11.2 Hz, 1H), 4.43 (s, 2H), 3.62 (p, J=6.1 Hz, 1H), 2.23 (s, 3H), 1.11 (d, J=6.1 Hz, 6H). ESI MS [M+H]⁺ for $C_{21}H_{23}FN_5O_3S$, calcd 444.1, found 444.1.

Example 196: 2-Amino-N-[5-[[5-(ethoxymethyl)pyridin-2-yl]carbamoyl]-4-fluoro-2-methylphenyl]-1,3-thiazole-5-carboxamide

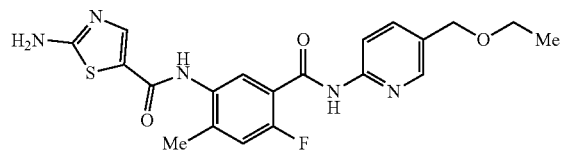 [SMILES: CCOCc1ccc(NC(=O)c2cc(NC(=O)c3cnc(N)s3)c(C)cc2F)nc1]

The title compound was prepared from 5-(ethoxymethyl)pyridin-2-amine and 2-fluoro-4-methyl-5-[[2-[(2-methylpropan-2-yl)oxycarbonylamino]-1,3-thiazole-5-carbonyl]amino]benzoic acid in a similar fashion to Example 7. ¹H NMR (400 MHz, DMSO-d₆) δ 10.63 (d, J=2.6 Hz, 1H), 9.59 (s, 1H), 8.28 (dd, J=2.4, 0.8 Hz, 1H), 8.13 (d, J=8.4 Hz, 1H), 7.84-7.73 (m, 2H), 7.63-7.54 (m, 3H), 7.23 (d, J=11.2 Hz, 1H), 4.42 (s, 2H), 3.46 (q, J=7.0 Hz, 2H), 2.23 (s, 3H), 1.12 (t, J=7.0 Hz, 3H). ESI MS [M+H]⁺ for $C_{20}H_{21}FN_5O_3S$, calcd 430.1, found 430.1.

Example 197: 2-Amino-N-[5-[[5-[cyclopropyl(methoxy)methyl]pyridin-2-yl]carbamoyl]-4-fluoro-2-methylphenyl]-1,3-thiazole-5-carboxamide

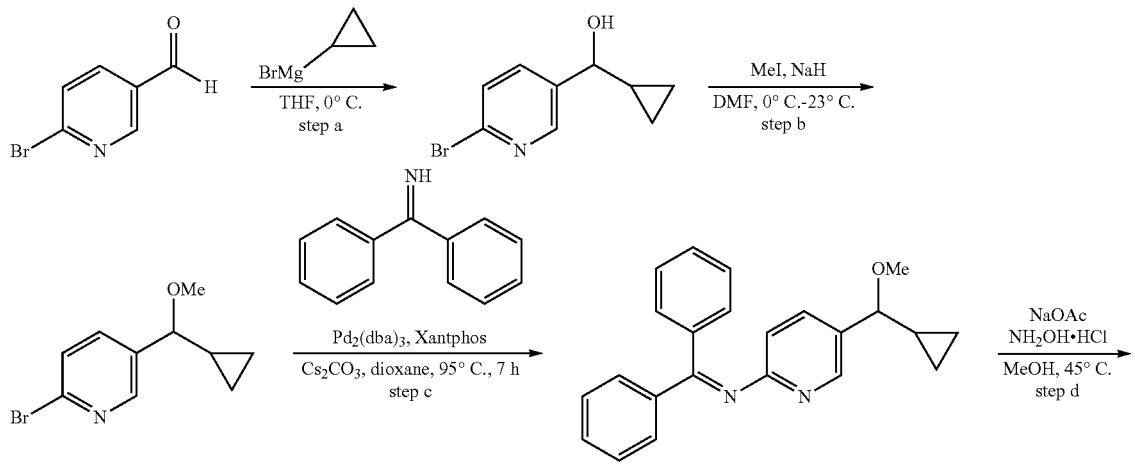

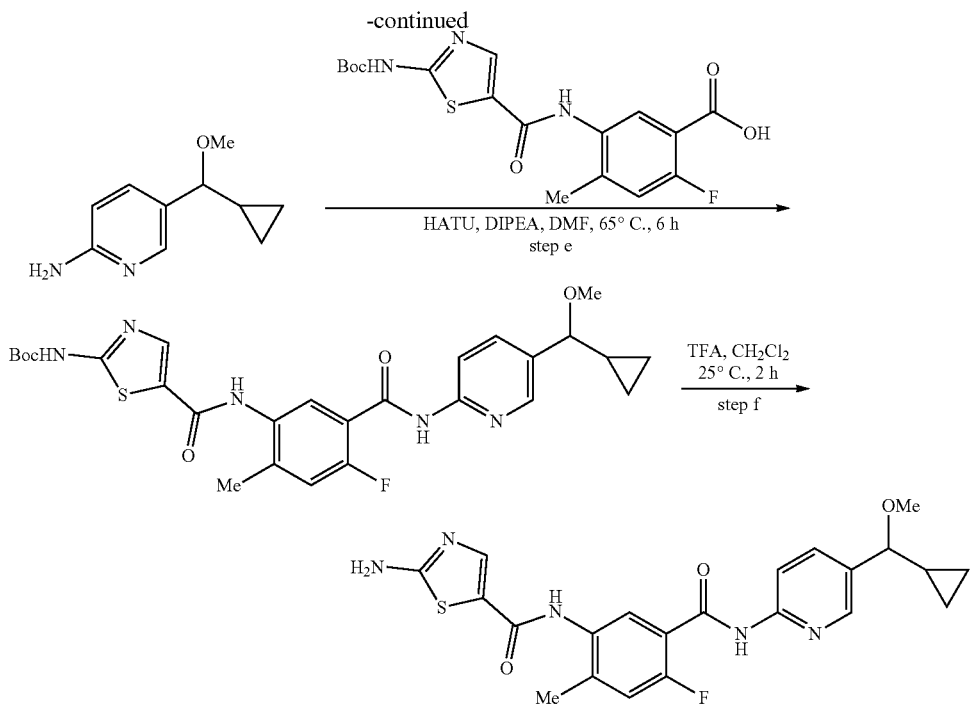

Step a: A vial was charged with 6-bromonicotinaldehyde (0.5 g, 2.69 mmol, 1 equiv.) and THF (10 mL) and the solution was cooled to 0° C. under a nitrogen atmosphere. A solution of cyclopropylmagnesium bromide in THF (1M, 8.07 mL, 8.07 mmol, 3.0 equiv.) was added dropwise while stirring at 0° C. The reaction was monitored by LC/MS. Upon completion, the reaction was quenched with saturated aq. ammonium chloride solution and the aqueous layer was extracted three times with EtOAc. The combined organic extracts were dried over $Na_2SO_4$, filtered, and concentrated in vacuo. The crude product was purified by column chromatography (EtOAc/hexanes, 10% to 60%) to provide (6-bromopyridin-3-yl)(cyclopropyl)methanol.

Step b: To a solution of product from step a (0.526 g, 2.307 mmol, 1.0 equiv.) in 10 mL of DMF at 0° C. was added sodium hydride (60% dispersion in mineral oil, 0.215 g, 3.461 mmol, 1.5 equiv.). The reaction mixture was stirred at 0° C. for 1 h. Iodomethane (0.374 mL, 3.461 mmol, 1.5 equiv.) was added. The reaction mixture was stirred at 23° C. for 3 h, at which time LC/MS analysis showed complete consumption of starting material. The reaction was quenched with water and extracted three times with EtOAc. The combined organic extracts were dried over $Na_2SO_4$, filtered, and concentrated in vacuo to afford the crude product, which was purified by column chromatography (EtOAc/hexanes, 0% to 60%) to provide 2-bromo-5-[cyclopropyl(methoxy)methyl]pyridine.

Step c and Step d were performed in an analogous manner to Example 1, steps c and d.

Step e and Step f were performed in an analogous manner to Example 7, steps a and b to afford the title compound. $^1$H NMR (400 MHz, DMSO-$d_6$) δ 10.60 (d, J=2.5 Hz, 1H), 9.57 (s, 1H), 8.23 (d, J=2.3 Hz, 1H), 8.10 (d, J=8.5 Hz, 1H), 7.81-7.71 (m, 2H), 7.60-7.51 (m, 3H), 7.20 (d, J=11.1 Hz, 1H), 3.57 (d, J=8.1 Hz, 1H), 3.12 (s, 3H), 2.21 (s, 3H), 1.09-0.99 (m, 1H), 0.54 (dt, J=13.0, 6.3 Hz, 1H), 0.41 (dq, J=9.7, 4.9 Hz, 1H), 0.32 (tt, J=9.0, 4.8 Hz, 1H), 0.18 (dt, J=9.8, 5.0 Hz, 1H). ESI MS [M+H]$^+$ for $C_{22}H_{23}FN_5O_3S$, calcd 456.2, found 456.2.

Example 198: 2-Amino-N-[4-fluoro-2-methyl-5-[[5-[(3R)-oxolan-3-yl]oxypyridin-2-yl]carbamoyl]phenyl]-1,3-thiazole-5-carboxamide

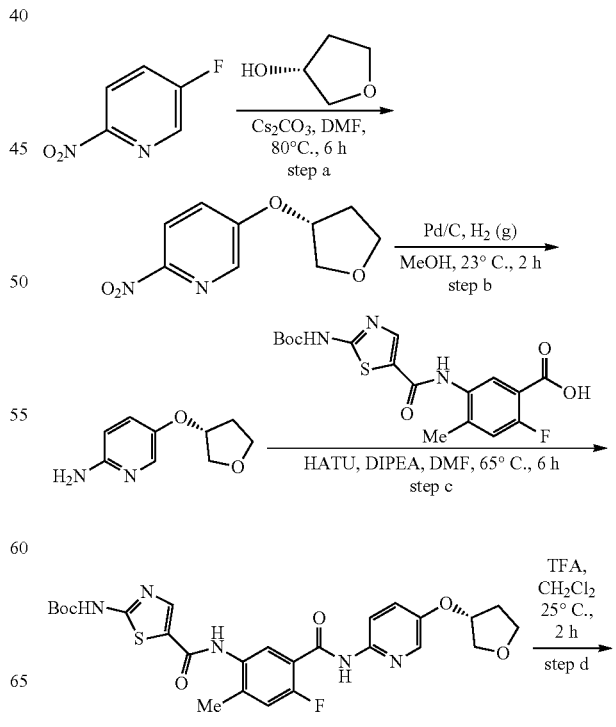

-continued

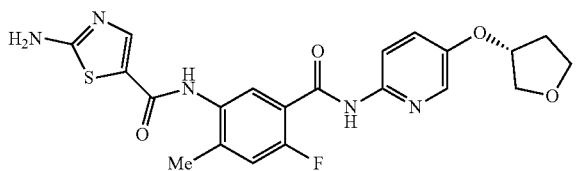

Step a: A mixture of 5-fluoro-2-nitropyridine (1.0 g, 7.04 mmol, 1 equiv.), (3R)-oxolan-3-ol (0.809 mL, 10.56 mmol, 1.5 equiv.), cesium carbonate (4.587 g, 14.08 mmol, 2 equiv.) and 15 mL of DMF was heated at 80° C. for 6 h. The reaction was monitored by LC/MS. Upon completion, the reaction mixture was diluted with water, and extracted three times with EtOAc. The combined organic extracts were dried over $Na_2SO_4$, filtered, and concentrated in vacuo. The crude product was purified by column chromatography (EtOAc/hexanes, 10% to 100%) to provide 2-nitro-5-[(3R)-oxolan-3-yl]oxypyridine.

Step b: A mixture of product from step a (1.387 g, 6.604 mmol, 1.0 equiv.), 10% palladium on carbon (0.700 g, 0.660 mmol, 10 mol %) and 50 mL of MeOH was degassed by flashing $H_2$ (g), then stirred under a $H_2$ atmosphere for 2 h. The reaction was monitored by LC/MS. Upon completion, the reaction mixture was filtered through a pad of Celite®. The filtrate was concentrated in vacuo. The crude product was carried to the next step without further purification.

Step c and Step d were performed in an analogous manner to Example 7, steps a and b to afford the title compound. $^1$H NMR (400 MHz, DMSO-$d_6$) δ 10.44 (d, J=2.8 Hz, 1H), 9.55 (s, 1H), 8.07-7.97 (m, 2H), 7.79 (s, 1H), 7.59-7.51 (m, 3H), 7.43 (dd, J=9.1, 3.1 Hz, 1H), 7.19 (d, J=11.2 Hz, 1H), 5.03 (dd, J=6.2, 4.2 Hz, 1H), 3.87-3.65 (m, 4H), 2.20 (s, 3H), 2.24-2.10 (m, 1H), 1.92 (dt, J=12.8, 5.8 Hz, 1H). ESI MS $[M+H]^+$ for $C_{21}H_{21}FN_5O_4S$, calcd 458.1, found 458.1.

Example 199: 2-Amino-N-[4-fluoro-2-methyl-5-[[5-(4-oxaspiro[2.4]heptan-6-yloxy)pyridin-2-yl]carbamoyl]phenyl]-1,3-thiazole-5-carboxamide

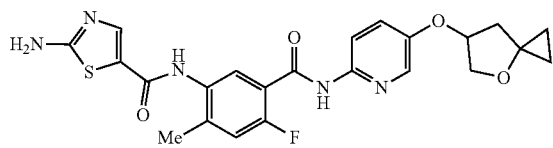 [SMILES: Cc1cc(F)c(C(=O)Nc2ccc(OC3COC4(CC4)C3)cn2)cc1NC(=O)c1cnc(N)s1]

The title compound was prepared from 4-oxaspiro[2.4]heptan-6-ol in a similar fashion to Example 198. $^1$H NMR (400 MHz, Methanol-$d_4$) δ 8.11 (d, J=9.1 Hz, 1H), 8.00 (d, J=3.0 Hz, 1H), 7.86 (s, 1H), 7.75 (d, J=7.0 Hz, 1H), 7.46 (dd, J=9.1, 3.0 Hz, 1H), 7.21 (d, J=11.6 Hz, 1H), 5.16 (ddt, J=6.8, 4.5, 2.0 Hz, 1H), 4.10 (dd, J=10.1, 4.9 Hz, 1H), 3.98 (ddd, J=10.0, 1.9, 0.9 Hz, 1H), 2.46 (dd, J=13.6, 6.6 Hz, 1H), 2.32 (s, 3H), 2.15-2.04 (m, 1H), 0.87 (ddd, J=10.5, 6.4, 4.9 Hz, 1H), 0.78 (ddd, J=11.9, 6.2, 4.8 Hz, 1H), 0.66-0.55 (m, 1H), 0.52 (ddd, J=10.0, 6.5, 4.8 Hz, 1H). ESI MS $[M+H]^+$ for $C_{23}H_{23}FN_5O_4S$, calcd 484.1, found 484.1.

Example 200: 2-Amino-N-[2-chloro-5-(cyclopropylcarbamoyl)-4-fluorophenyl]-1,3-thiazole-5-carboxamide

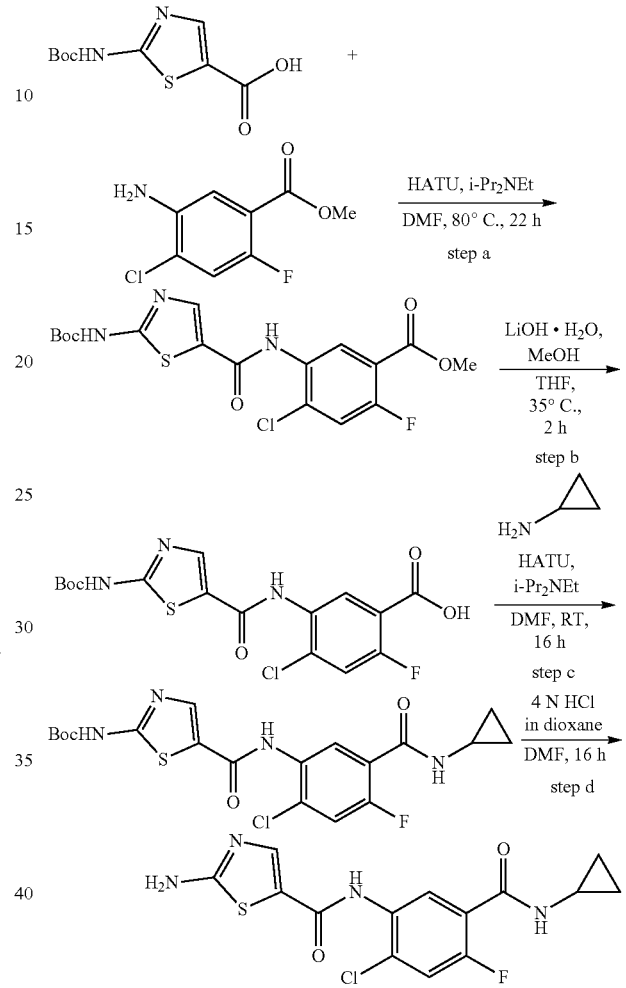

Step a: A round-bottom flask was charged with methyl 5-amino-4-chloro-2-fluorobenzoate (1 g, 4.9 mmol, 1.0 equiv.), 2-[(2-methylpropan-2-yl)oxycarbonylamino]-1,3-thiazole-5-carboxylic acid (1.3 g, 5.3 mmol, 1.1 equiv.), and HATU (2.8 g, 7.3 mmol, 1.5 equiv.). DMF (12 mL, 0.4 M) was added, followed by i-Pr$_2$NEt (2.56 mL, 14.7 mmol, 3.0 equiv.). The reaction mixture was stirred at 80° C. for 22 h, at which time LC/MS analysis showed complete consumption of starting material. The reaction mixture was cooled to RT and poured onto ice water (40 mL) with stirring. Stirring was continued for 10 minutes and then the precipitated solid was collected by vacuum filtration, rinsed with water, and dried in vacuo to afford methyl 4-chloro-2-fluoro-5-[[2-[(2-methylpropan-2-yl)oxycarbonylamino]-1,3-thiazole-5-carbonyl]amino]benzoate, which was used directly in the next step without further purification.

Step b: A round-bottom flask was charged with product from step a (1.6 g, 3.8 mmol, 1.0 equiv.), followed by THF (10.5 mL), and H$_2$O (7 mL). LiOH·H$_2$O (797 mg, 19 mmol, 5.0 equiv.) was then added and the reaction mixture was stirred at 35° C. for 2 h, at which time LC/MS analysis indicated complete consumption of starting material. The reaction mixture was cooled to 0° C. and the pH was adjusted to pH=4 with aq. 2M HCl. The precipitate thus obtained was collected by vacuum filtration, rinsed with water, and extensively dried in vacuo for a few days to afford 4-chloro-2-fluoro-5-[[2-[(2-methylpropan-2-yl)oxycarbonylamino]-1,3-thiazole-5-carbonyl]amino]benzoic acid.

Step c: A round-bottom flask was charged with product from step b (100 mg, 0.24 mmol, 1.0 equiv.), cyclopropanamine (0.02 mL, 0.36 mmol, 1.5 equiv.), and HATU (137 mg, 0.36 mmol, 1.5 equiv.). DMF (2 mL, 0.1 M) was added, followed by i-Pr$_2$NEt (0.125 mL, 0.7 mmol, 3.0 equiv.). The reaction mixture was stirred at RT for 16 h, at which time LC/MS analysis showed complete consumption of starting material. The reaction mixture was cooled to RT and poured onto ice water with stirring. Stirring was continued for 10 minutes and then the precipitated solid was collected by vacuum filtration, rinsed with water, and dried in vacuo to afford tert-butyl N-[5-[[2-chloro-5-(cyclopropylcarbamoyl)-4-fluorophenyl]carbamoyl]-1,3-thiazol-2-yl]carbamate, which was used directly in the next step without further purification.

Step d: A vial was charged with the product from step c (50 mg, 0.11 mmol, 1.0 equiv.). 4N HCl in dioxane (2 mL) was added and the reaction mixture was stirred at RT for 16 h, at which time LC/MS analysis showed complete consumption of starting material. The reaction mixture was concentrated in vacuo. The residue was purified by reverse phase HPLC to afford the title compound. $^1$H NMR (400 MHz, Methanol-d$_4$) δ 7.97 (s, 1H), 7.87 (d, J=7.2 Hz, 1H), 7.29 (d, J=10.0 Hz, 1H), 2.80 (tt, J=7.4, 3.9 Hz, 1H), 0.78 (dd, J=7.3, 5.3 Hz, 2H), 0.62-0.56 (m, 2H). ESI MS [M+H]$^+$ for C$_{14}$H$_{13}$ClFN$_4$O$_2$S$_1$, calcd 355.1, found 355.1.

Example 201: 2-Amino-N-[2-chloro-5-[(6-cyclopropylpyridazin-3-yl)carbamoyl]-4-fluorophenyl]-1,3-thiazole-5-carboxamide

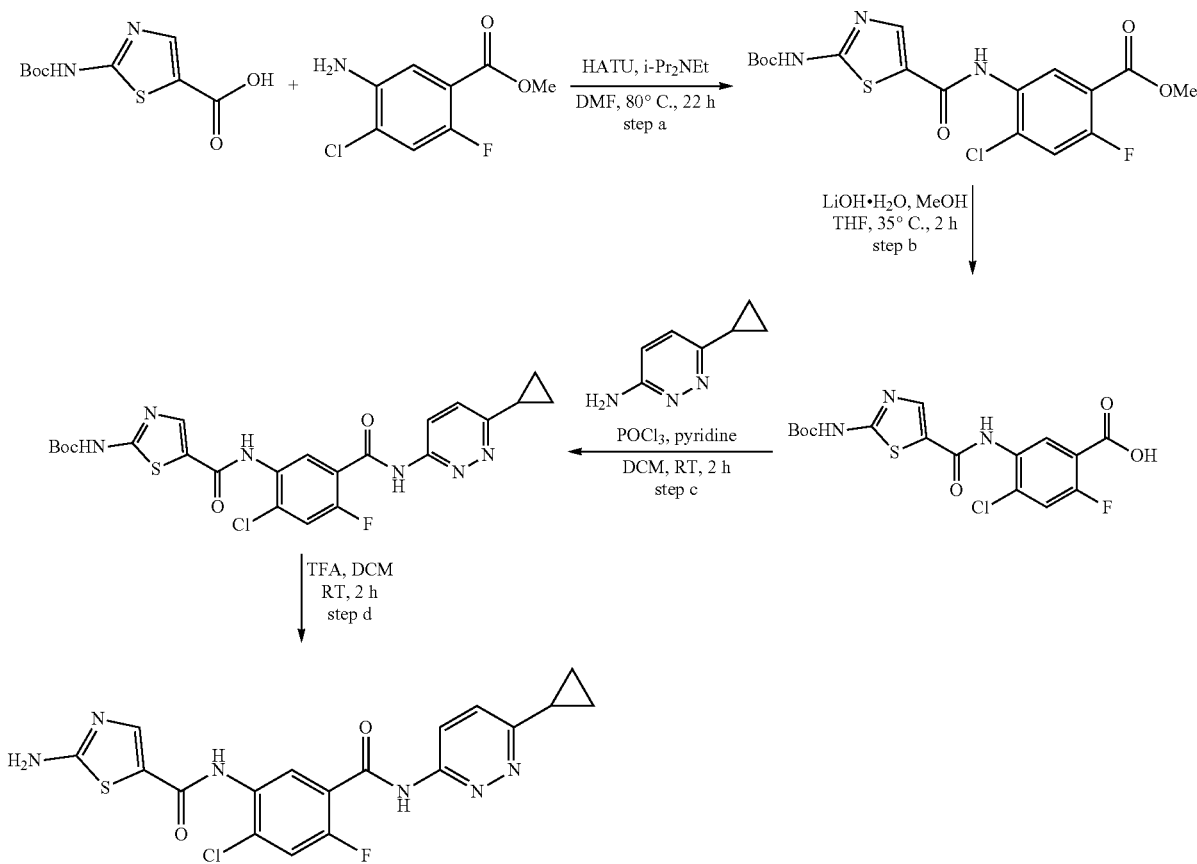

Step a: A round-bottom flask was charged with methyl 5-amino-4-chloro-2-fluorobenzoate (1 g, 4.9 mmol, 1.0 equiv.), 2-[(2-methylpropan-2-yl)oxycarbonylamino]-1,3-thiazole-5-carboxylic acid (1.3 g, 5.3 mmol, 1.1 equiv.), and HATU (2.8 g, 7.3 mmol, 1.5 equiv.). DMF (12 mL, 0.4 M) was added, followed by i-Pr₂NEt (2.56 mL, 14.7 mmol, 3.0 equiv.). The reaction mixture was stirred at 80° C. for 22 h, at which time LC/MS analysis showed complete consumption of starting material. The reaction mixture was cooled to RT and poured onto ice water (40 mL) with stirring. Stirring was continued for 10 minutes and then the precipitated solid was collected by vacuum filtration, rinsed with water, and dried in vacuo to afford methyl 4-chloro-2-fluoro-5-[[2-[(2-methylpropan-2-yl)oxycarbonylamino]-1,3-thiazole-5-carbonyl]amino]benzoate, which was used directly in the next step without further purification.

Step b: A round-bottom flask was charged with product from step a (1.6 g, 3.8 mmol, 1.0 equiv.), followed by THF (10.5 mL), and H₂O (7 mL). LiOH H₂O (797 mg, 19 mmol, 5.0 equiv.) was then added and the reaction mixture was stirred at 35° C. for 2 h, at which time LC/MS analysis indicated complete consumption of starting material. The reaction mixture was cooled to 0° C. and the pH was adjusted to pH=4 with aq. 2M HCl. The precipitate thus obtained was collected by vacuum filtration, rinsed with water, and extensively dried in vacuo for a few days to afford 4-chloro-2-fluoro-5-[[2-[(2-methylpropan-2-yl)oxycarbonylamino]-1,3-thiazole-5-carbonyl]amino]benzoic acid.

Step c: A vial was charged with product from step b (100 mg, 0.24 mmol, 1.0 equiv.), 6-cyclopropylpyridazin-3-amine (49 mg, 3.00 mmol, 1.0 equiv.), and DCM (2 mL) under N₂ gas. Pyridine (0.2 mL, 2.5 mmol, 10 equiv.) was added and the reaction mixture was allowed to stir at RT. After 5 min., POCl₃ (0.045 mL, 0.5 mmol, 2 equiv.) was added dropwise. After LC/MS analysis indicated complete conversion, the reaction was quenched with water and the reaction mixture was concentrated in vacuo, which was used directly in the next step without further purification.

Step d: A vial was charged with product from step c and DCM (1 mL) was added. TFA (1 mL) was then added dropwise and the reaction mixture was stirred at RT for 2 h, at which time LC/MS analysis indicated complete consumption of starting material. The reaction mixture was cooled to RT and the solvents were evaporated in vacuo and the crude product was purified by reverse phase HPLC to afford the title compound. ¹H NMR (400 MHz, Methanol-d₄) δ 8.42 (d, J=9.3 Hz, 1H), 8.11 (d, J=7.2 Hz, 1H), 7.87 (s, 1H), 7.41-7.35 (m, 2H), 2.18 (ddd, J=13.2, 8.3, 4.9 Hz, 1H), 1.17-1.11 (m, 2H), 1.04 (dt, J=7.5, 4.6 Hz, 2H). ESI MS [M+H]⁺ for C₁₈H₁₅ClFN₆O₂S₁, calcd 433.1, found 433.1.

Example 202: 2-Amino-N-[2-chloro-4-fluoro-5-[[5-(methoxymethyl)pyridin-2-yl]carbamoyl]phenyl]-1,3-thiazole-5-carboxamide The title compound was prepared from 5-(methoxymethyl)pyridin-2-amine and 4-chloro-2-fluoro-5-[[2-[(2-methylpropan-2-yl)oxycarbonylamino]-1,3-thiazole-5-carbonyl]amino]benzoic acid in a similar fashion to Example 201. ¹H NMR (400 MHz, Methanol-d₄) δ 8.24 (q, J=4.2 Hz, 3H), 7.76-7.72 (m, 2H), 7.35 (d, J=10.4 Hz, 1H), 4.42 (s, 2H), 3.36 (s, 3H). ESI MS [M+H]⁺ for C₁₈H₁₆ClFN₅O₃S₁, calcd 436.1, found 436.1.

Example 203: 2-Amino-N-[2-chloro-5-[(5-cyclopropylpyrimidin-2-yl)carbamoyl]-4-fluorophenyl]-1,3-thiazole-5-carboxamide

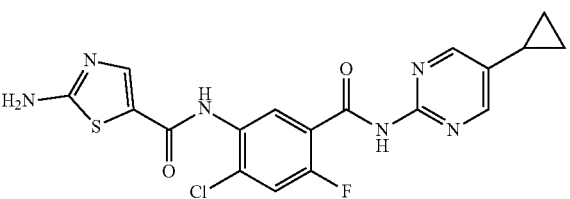 [SMILES: Nc1ncc(C(=O)Nc2cc(C(=O)Nc3ncc(C4CC4)cn3)c(F)cc2Cl)s1]

The title compound was prepared from 5-cyclopropylpyrimidin-2-amine and 4-chloro-2-fluoro-5-[[2-[(2-methylpropan-2-yl)oxycarbonylamino]-1,3-thiazole-5-carbonyl]amino]benzoic acid in a similar fashion to Example 201. ¹H NMR (400 MHz, Methanol-d₄) δ 8.44 (s, 2H), 8.07 (s, 1H), 8.00 (d, J=7.1 Hz, 1H), 7.40 (d, J=10.0 Hz, 1H), 1.95-1.86 (m, 1H), 1.08 (d, J=8.2 Hz, 2H), 0.77 (d, J=6.2 Hz, 2H). ESI MS [M+H]⁺ for C₁₈H₁₅ClFN₆O₂S₁, calcd 433.1, found 433.1.

Example 204: 2-Amino-N-[2-chloro-5-[(2-cyclopropylpyrimidin-5-yl)carbamoyl]-4-fluorophenyl]-1,3-thiazole-5-carboxamide

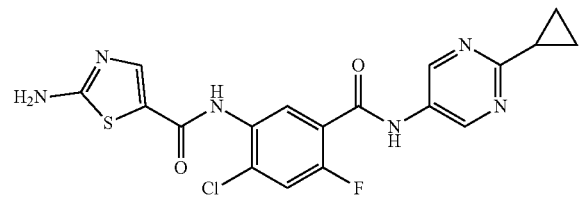 [SMILES: Nc1ncc(C(=O)Nc2cc(C(=O)Nc3cnc(C4CC4)nc3)c(F)cc2Cl)s1]

The title compound was prepared from 2-cyclopropylpyrimidin-5-amine and 4-chloro-2-fluoro-5-[[2-[(2-methylpropan-2-yl)oxycarbonylamino]-1,3-thiazole-5-carbonyl]amino]benzoic acid in a similar fashion to Example 201. ¹H NMR (400 MHz, Methanol-d₄) δ 8.89 (s, 2H), 8.02 (d, J=7.0 Hz, 1H), 7.76 (s, 1H), 7.34 (d, J=9.6 Hz, 1H), 2.16 (ddd, J=13.1, 7.9, 5.1 Hz, 1H), 1.08-1.01 (m, 4H). ESI MS [M+H]⁺ for C₁₈H₁₅ClFN₆O₂S₁, calcd 433.1, found 433.1.

Example 205: 2-Amino-N-[2-chloro-5-[(5-cyclopropylpyrazin-2-yl)carbamoyl]-4-fluorophenyl]-1,3-thiazole-5-carboxamide

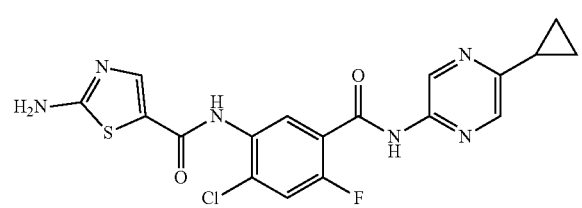 [SMILES: Nc1ncc(C(=O)Nc2cc(C(=O)Nc3cnc(C4CC4)cn3)c(F)cc2Cl)s1]

The title compound was prepared from 5-cyclopropylpyrazin-2-amine and 4-chloro-2-fluoro-5-[[2-[(2-methylpropan-2-yl)oxycarbonylamino]-1,3-thiazole-5-carbonyl]amino]benzoic acid in a similar fashion to Example 201. $^1$H NMR (400 MHz, Methanol-$d_4$) δ 9.29 (d, J=1.5 Hz, 1H), 8.21 (d, J=1.5 Hz, 1H), 8.11 (d, J=7.3 Hz, 1H), 7.76 (s, 1H), 7.37 (d, J=10.1 Hz, 1H), 2.05 (ddd, J=12.8, 8.1, 4.9 Hz, 1H), 1.00 (ddt, J=14.9, 5.1, 2.6 Hz, 4H). ESI MS [M+H]$^+$ for $C_{18}H_{15}ClFN_6O_2S_1$, calcd 433.1, found 433.1.

Example 206: 2-Amino-N-[2-chloro-5-[[5-(difluoromethyl)pyridin-2-yl]carbamoyl]-4-fluorophenyl]-1,3-thiazole-5-carboxamide

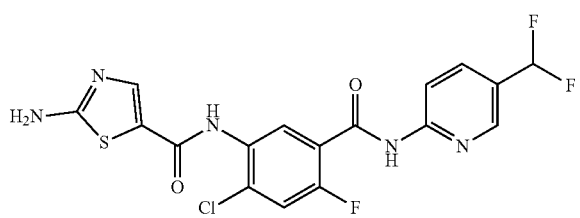 [SMILES: Nc1ncc(C(=O)Nc2cc(C(=O)Nc3ccc(C(F)F)cn3)c(F)cc2Cl)s1]

The title compound was prepared from 5-(difluoromethyl)pyridin-2-amine and 4-chloro-2-fluoro-5-[[2-[(2-methylpropan-2-yl)oxycarbonylamino]-1,3-thiazole-5-carbonyl]amino]benzoic acid in a similar fashion to Example 201. $^1$H NMR (400 MHz, Methanol-$d_4$) δ 8.43 (s, 1H), 8.35 (d, J=8.7 Hz, 1H), 8.17 (d, J=7.3 Hz, 1H), 7.90 (d, J=9.2 Hz, 1H), 7.77 (s, 1H), 7.37 (d, J=10.3 Hz, 1H), 6.71 (t, J=55.8 Hz, 1H). ESI MS [M+H]$^+$ for $C_{17}H_{12}ClF_3N_5O_2S_1$, calcd 442.1, found 442.1.

Example 207: 2-Amino-N-[2-chloro-4-fluoro-5-[(5-propan-2-yloxypyridin-2-yl)carbamoyl]phenyl]-1,3-thiazole-5-carboxamide

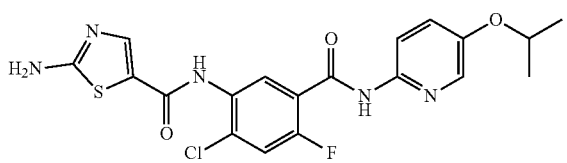 [SMILES: CC(C)Oc1ccc(NC(=O)c2cc(NC(=O)c3cnc(N)s3)c(Cl)cc2F)nc1]

The title compound was prepared from 5-propan-2-yloxypyridin-2-amine and 4-chloro-2-fluoro-5-[[2-[(2-methylpropan-2-yl)oxycarbonylamino]-1,3-thiazole-5-carbonyl]amino]benzoic acid in a similar fashion to Example 201. $^1$H NMR (400 MHz, Methanol-$d_4$) δ 8.18 (d, J=7.4 Hz, 1H), 8.13 (d, J=9.1 Hz, 1H), 7.92 (dd, J=3.0, 0.7 Hz, 1H), 7.74 (s, 1H), 7.35 (d, J=10.3 Hz, 1H), 7.30 (dd, J=9.1, 3.0 Hz, 1H), 4.53 (p, J=6.1 Hz, 1H), 1.30 (d, J=6.1 Hz, 6H). ESI MS [M+H]$^+$ for $C_{19}H_{18}ClFN_5O_3S_1$, calcd 450.1, found 450.1.

Example 208: 2-Amino-N-[2-chloro-5-[[5-(difluoromethoxy)pyridin-2-yl]carbamoyl]-4-fluorophenyl]-1,3-thiazole-5-carboxamide

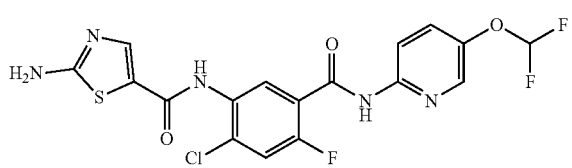 [SMILES: Nc1ncc(C(=O)Nc2cc(C(=O)Nc3ccc(OC(F)F)cn3)c(F)cc2Cl)s1]

The title compound was prepared from 5-(difluoromethoxy)pyridin-2-amine and 4-chloro-2-fluoro-5-[[2-[(2-methylpropan-2-yl)oxycarbonylamino]-1,3-thiazole-5-carbonyl]amino]benzoic acid in a similar fashion to Example 200. $^1$H NMR (400 MHz, Methanol-$d_4$) δ 8.27 (d, J=9.1 Hz, 1H), 8.18 (d, J=7.4 Hz, 1H), 8.15 (d, J=2.8 Hz, 1H), 7.74 (s, 1H), 7.56 (dd, J=9.0, 2.9 Hz, 1H), 7.35 (d, J=10.3 Hz, 1H), 6.61 (t, J=72.9 Hz, 1H). ESI MS [M+H]$^+$ for $C_{17}H_{12}ClF_3N_5O_3S_1$, calcd 458.1, found 458.1.

Example 209: 2-Amino-N-[2-chloro-5-[(5-cyclopropyloxypyridin-2-yl)carbamoyl]-4-fluorophenyl]-1,3-thiazole-5-carboxamide

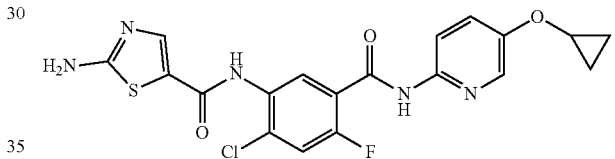

The title compound was prepared from 5-cyclopropyloxypyridin-2-amine and 4-chloro-2-fluoro-5-[[2-[(2-methylpropan-2-yl)oxycarbonylamino]-1,3-thiazole-5-carbonyl]amino]benzoic acid in a similar fashion to Example 200. $^1$H NMR (400 MHz, Methanol-$d_4$) δ 8.18 (d, J=7.4 Hz, 1H), 8.15 (d, J=9.1 Hz, 1H), 8.05 (dd, J=3.0, 0.7 Hz, 1H), 7.74 (s, 1H), 7.46 (dd, J=9.1, 3.0 Hz, 1H), 7.35 (d, J=10.3 Hz, 1H), 3.81-3.75 (m, 1H), 0.82-0.75 (m, 2H), 0.75-0.70 (m, 2H). ESI MS [M+H]$^+$ for $C_{19}H_{16}ClFN_5O_3S_1$, calcd 448.1, found 448.1.

Example 210: 2-Amino-N-[2,4-difluoro-5-[[5-(trifluoromethoxy)pyridin-2-yl]carbamoyl]phenyl]-1,3-thiazole-5-carboxamide

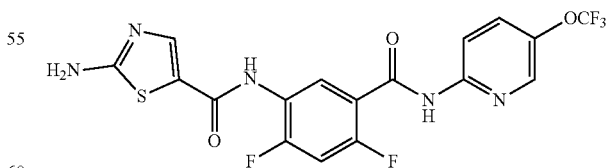

The title compound was prepared from 5-(trifluoromethoxy)pyridin-2-amine, methyl 5-amino-2,4-difluorobenzoate, and 2-[(2-methylpropan-2-yl)oxycarbonylamino]-1,3-thiazole-5-carboxylic acid in a similar fashion to Example 201. $^1$H NMR (400 MHz, Methanol-$d_4$) δ 8.33 (dd, J=9.1, 0.7 Hz, 1H), 8.24 (dt, J=2.9, 0.8 Hz, 1H), 8.15 (t, J=8.1 Hz, 1H), 7.76 (s, 1H), 7.69-7.63 (m, 1H), 7.09 (t, J=10.2 Hz, 1H). ESI MS [M+H]⁺ for $C_{17}H_{11}F_5N_5O_3S_1$, calcd 460.1, found 460.1.

Example 211: 2-Amino-N-[2,4-difluoro-5-[(5-methoxypyridin-2-yl)carbamoyl]phenyl]-1,3-thiazole-5-carboxamide

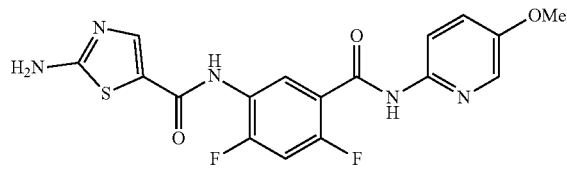 [SMILES: COc1ccc(NC(=O)c2cc(NC(=O)c3cnc(N)s3)c(F)cc2F)nc1]

The title compound was prepared from 5-methoxypyridin-2-amine, methyl 5-amino-2,4-difluorobenzoate, and 2-[(2-methylpropan-2-yl)oxycarbonylamino]-1,3-thiazole-5-carboxylic acid in a similar fashion to Example 201. ¹H NMR (400 MHz, Methanol-d₄) δ 8.20-8.11 (m, 2H), 7.95 (d, J=3.0 Hz, 1H), 7.75 (s, 1H), 7.33 (dd, J=9.1, 3.1 Hz, 1H), 7.07 (t, J=10.2 Hz, 1H), 3.82 (s, 3H). ESI MS [M+H]⁺ for $C_{17}H_{14}F_2N_5O_3S_1$, calcd 406.1, found 406.1.

Example 212: 2-Amino-N-[5-[(5-ethoxypyridin-2-yl)carbamoyl]-2,4-difluorophenyl]-1,3-thiazole-5-carboxamide

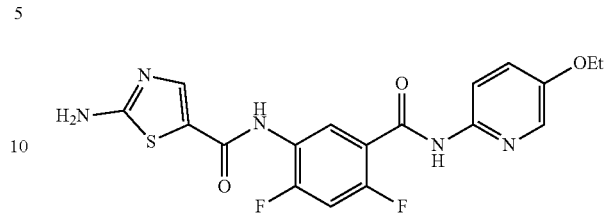

The title compound was prepared from 5-ethoxypyridin-2-amine, methyl 5-amino-2,4-difluorobenzoate, and 2-[(2-methylpropan-2-yl)oxycarbonylamino]-1,3-thiazole-5-carboxylic acid in a similar fashion to Example 201. ¹H NMR (400 MHz, Methanol-d₄) δ 8.20-8.11 (m, 2H), 7.94 (dd, J=3.0, 0.7 Hz, 1H), 7.75 (s, 1H), 7.31 (dd, J=9.1, 3.0 Hz, 1H), 7.11-7.04 (m, 1H), 4.05 (q, J=7.0 Hz, 2H), 1.38 (t, J=7.0 Hz, 3H). ESI MS [M+H]⁺ for $C_{18}H_{16}F_2N_5O_3S_1$, calcd 420.1, found 420.1.

Example 213: 2-Amino-N-[5-[[5-(2,2-difluoroethoxy)pyridin-2-yl]carbamoyl]-2,4-difluorophenyl]-1,3-thiazole-5-carboxamide

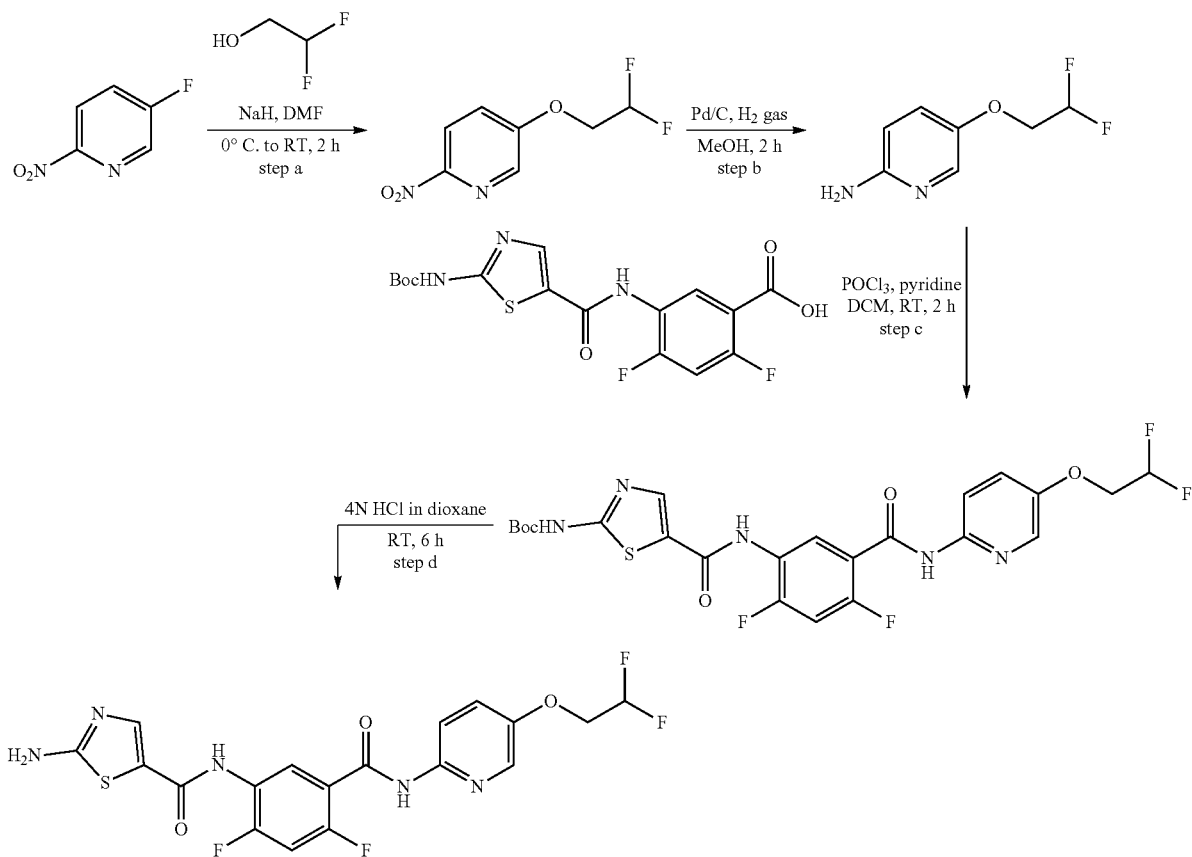

Step a: A round-bottom flask was charged with 5-fluoro-2-nitropyridine (1 g, 7.0 mmol, 1.0 equiv.), 2,2-difluoroethanol (1.15 g, 14 mmol, 2.0 equiv.), and DMF (17.5 mL, 0.4 M). The mixture was cooled on an ice bath, and NaH (60% dispersion in mineral oil, 560 mg, 2.0 equiv.) was added portionwise. The reaction mixture was warmed up to RT and stirred for 2 h, at which time LC/MS analysis showed complete consumption of starting material. The reaction mixture was quenched by water (20 mL), extracted with EtOAc (20 mL×2). The organic layer was collected, dried over Na₂SO₄ and concentrated in vacuo. The residue was purified using column chromatography on silica gel (EtOAc in hexane, 0%→50%) to afford 5-(2,2-difluoroethoxy)-2-nitropyridine.

Step b: A round-bottom flask was charged with product from step a (500 mg, 2.45 mmol, 1.0 equiv.), followed by MeOH (24.5 mL, 0.1 M), and Pd/C (10 wt. %, 50 mg). The reaction mixture was shaken under 20 psi of hydrogen gas for 2 h, at which time LC/MS analysis indicated complete consumption of starting material. The reaction mixture was filtrated with Celite® and concentrated in vacuo, which was used directly in the next step without further purification.

Step c: A vial was charged with the product from step b (66 mg, 0.38 mmol, 1.0 equiv.), 2,4-difluoro-5-[[2-[(2-methylpropan-2-yl)oxycarbonylamino]-1,3-thiazole-5-carbonyl]amino]benzoic acid (101 mg, 0.25 mmol, 0.7 equiv., prepared in similar manner to that described in Example 201, steps a and b), and DCM (2 mL) under N₂ gas. Pyridine (0.2 mL, 2.5 mmol, 7 equiv.) was added and the reaction mixture was allowed to stir at RT. After 5 min., POCl₃ (0.047 mL, 0.5 mmol, 1.4 equiv.) was added dropwise. After LC/MS analysis indicated complete conversion, the reaction was quenched with water and the reaction mixture was concentrated in vacuo, which was used directly in the next step without further purification.

Step d: A vial was charged with the product from step c (138 mg, 0.25 mmol, 1.0 equiv.). 4N HCl in dioxane (2 mL) was added and the reaction mixture was stirred at RT for 6 h, at which time LC/MS analysis showed complete consumption of starting material. The reaction mixture was concentrated in vacuo. The residue was purified by reverse phase HPLC to afford the title compound. ¹H NMR (400 MHz, Methanol-d₄) δ 8.20-8.12 (m, 2H), 8.01 (dd, J=3.1, 0.7 Hz, 1H), 7.75 (d, J=1.0 Hz, 1H), 7.39 (dd, J=9.1, 3.1 Hz, 1H), 7.07 (t, J=10.2 Hz, 1H), 6.08 (tt, J=54.8, 3.9 Hz, 1H), 4.23 (td, J=13.3, 3.8 Hz, 2H). ESI MS [M+H]⁺ for C₁₈H₁₄F₄N₅O₃S₁, calcd 456.1, found 456.1.

Example 214: 2-Amino-N-[5-[(5-ethylpyridin-2-yl)carbamoyl]-2,4-difluorophenyl]-1,3-thiazole-5-carboxamide

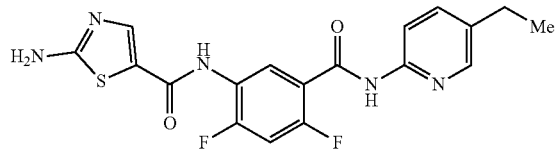 [SMILES: CCc1ccc(NC(=O)c2cc(NC(=O)c3cnc(N)s3)c(F)cc2F)nc1]

The title compound was prepared from 5-ethylpyridin-2-amine, methyl 5-amino-2,4-difluorobenzoate, and 2-[(2-methylpropan-2-yl)oxycarbonylamino]-1,3-thiazole-5-carboxylic acid in a similar fashion to Example 201. ¹H NMR (400 MHz, Methanol-d₄) δ 8.24-8.08 (m, 3H), 7.75 (s, 1H), 7.61 (dd, J=8.4, 2.4 Hz, 1H), 7.07 (t, J=10.3 Hz, 1H), 2.61 (q, J=7.7 Hz, 2H), 1.21 (t, J=7.6 Hz, 3H). ESI MS [M+H]⁺ for C₁₈H₁₆F₂N₅O₂S₁, calcd 404.1, found 404.1.

Example 215: 2-Amino-N-[2,4-difluoro-5-[[5-(methoxymethyl)pyridin-2-yl]carbamoyl]phenyl]-1,3-thiazole-5-carboxamide

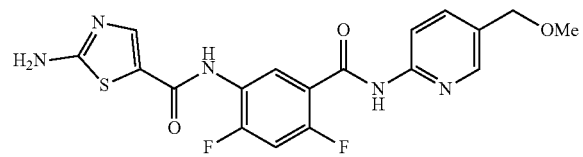

The title compound was prepared from 5-(methoxymethyl)pyridin-2-amine, methyl 5-amino-2,4-difluorobenzoate, and 2-[(2-methylpropan-2-yl)oxycarbonylamino]-1,3-thiazole-5-carboxylic acid in a similar fashion to Example 200. ¹H NMR (400 MHz, Methanol-d₄) δ 8.23-8.15 (m, 3H), 7.90 (s, 1H), 7.77 (dd, J=8.6, 2.3 Hz, 1H), 7.08 (t, J=10.2 Hz, 1H), 4.40 (s, 2H), 3.34 (s, 3H). ESI MS [M+H]⁺ for C₁₈H₁₆F₂N₅O₃S₁, calcd 420.1, found 420.1.

Example 216: 2-Amino-N-[2,4-difluoro-5-[[5-(trifluoromethyl)pyridin-2-yl]carbamoyl]phenyl]-1,3-thiazole-5-carboxamide

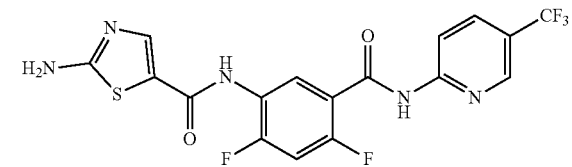 [SMILES: Nc1ncc(C(=O)Nc2cc(C(=O)Nc3ccc(C(F)(F)F)cn3)c(F)cc2F)s1]

The title compound was prepared from 5-(trifluoromethyl)pyridin-2-amine, methyl 5-amino-2,4-difluorobenzoate, and 2-[(2-methylpropan-2-yl)oxycarbonylamino]-1,3-thiazole-5-carboxylic acid in a similar fashion to Example 201. ¹H NMR (400 MHz, Methanol-d₄) δ 8.55 (s, 1H), 8.40 (d, J=8.8 Hz, 1H), 8.18 (t, J=8.1 Hz, 1H), 7.97 (dd, J=8.9, 2.4 Hz, 1H), 7.75 (s, 1H), 7.08 (t, J=10.2 Hz, 1H). ESI MS [M+H]⁺ for C₁₇H₁₁F₅N₅O₂S₁, calcd 444.1, found 444.1.

Example 217: 2-Amino-N-[5-[[5-(difluoromethyl)pyridin-2-yl]carbamoyl]-2,4-difluorophenyl]-1,3-thiazole-5-carboxamide

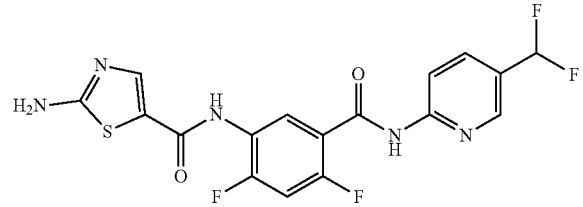

The title compound was prepared from 5-(difluoromethyl)pyridin-2-amine, methyl 5-amino-2,4-difluorobenzoate, and 2-[(2-methylpropan-2-yl)oxycarbonylamino]-1,3-thiazole-5-carboxylic acid in a similar fashion to Example 200. ¹H NMR (400 MHz, Methanol-d₄) δ 8.46 (d, J=24.4 Hz, 1H), 8.35 (d, J=8.7 Hz, 1H), 8.18 (t, J=8.1 Hz, 1H), 7.90 (d, J=8.7 Hz, 1H), 7.76 (s, 1H), 7.09 (t, J=10.2 Hz, 1H), 6.72 (t, J=55.8 Hz, 1H). ESI MS [M+H]⁺ for $C_{17}H_{12}F_4N_5O_2S_1$, calcd 426.1, found 426.1.

Example 218: 2-Amino-N-[2,4-difluoro-5-[(5-propan-2-yloxypyridin-2-yl)carbamoyl]phenyl]-1,3-thiazole-5-carboxamide

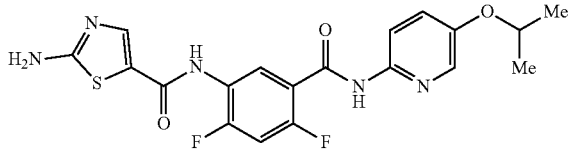 [SMILES: CC(C)Oc1ccc(NC(=O)c2cc(NC(=O)c3cnc(N)s3)c(F)cc2F)nc1]

The title compound was prepared from 5-propan-2-yloxy-pyridin-2-amine, methyl 5-amino-2,4-difluorobenzoate, and 2-[(2-methylpropan-2-yl)oxycarbonylamino]-1,3-thiazole-5-carboxylic acid in a similar fashion to Example 201. ¹H NMR (400 MHz, Methanol-d₄) δ 8.21-8.09 (m, 2H), 7.93-7.89 (m, 1H), 7.74 (s, 1H), 7.30 (dd, J=9.1, 3.0 Hz, 1H), 7.06 (t, J=10.3 Hz, 1H), 4.53 (p, J=6.1 Hz, 1H), 1.30 (d, J=6.0 Hz, 6H). ESI MS [M+H]⁺ for $C_{19}H_{18}F_2N_5O_3S_1$, calcd 434.1, found 434.1.

Example 219: 2-Amino-N-[5-[[5-(difluoromethoxy)pyridin-2-yl]carbamoyl]-2,4-difluorophenyl]-1,3-thiazole-5-carboxamide

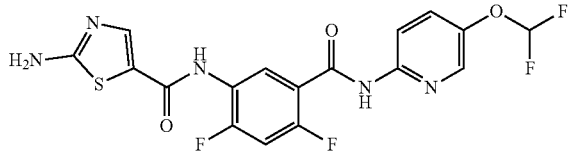

The title compound was prepared from 5-(difluoromethoxy)pyridin-2-amine, methyl 5-amino-2,4-difluorobenzoate, and 2-[(2-methylpropan-2-yl)oxycarbonylamino]-1,3-thiazole-5-carboxylic acid in a similar fashion to Example 200. ¹H NMR (400 MHz, Methanol-d₄) δ 8.27 (d, J=9.1 Hz, 1H), 8.18 (d, J=7.4 Hz, 1H), 8.15 (d, J=2.8 Hz, 1H), 7.74 (s, 1H), 7.56 (dd, J=9.0, 2.9 Hz, 1H), 7.35 (d, J=10.3 Hz, 1H), 6.61 (t, J=72.9 Hz, 1H). ESI MS [M+H]⁺ for $C_{17}H_{12}F_4N_5O_3S_1$, calcd 442.1, found 442.1.

Example 220: 2-Amino-N-[2,4-difluoro-5-[[5-(2,2,2-trifluoroethoxy)pyridin-2-yl]carbamoyl]phenyl]-1,3-thiazole-5-carboxamide

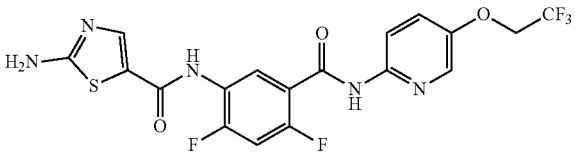 [SMILES: Nc1ncc(C(=O)Nc2cc(C(=O)Nc3ccc(OCC(F)(F)F)cn3)c(F)cc2F)s1]

The title compound was prepared from 5-(2,2,2-trifluoroethoxy)pyridin-2-amine and 2,4-difluoro-5-[[2-[(2-methylpropan-2-yl)oxycarbonylamino]-1,3-thiazole-5-carbonyl]amino]benzoic acid in a similar fashion to Example 213. ¹H NMR (400 MHz, Methanol-d₄) δ 8.25-8.13 (m, 2H), 8.04 (d, J=3.0 Hz, 1H), 7.76 (s, 1H), 7.42 (dd, J=9.1, 3.1 Hz, 1H), 7.07 (t, J=10.2 Hz, 1H), 4.46 (q, J=8.1 Hz, 2H). ESI MS [M+H]⁺ for $C_{18}H_{13}F_5N_5O_3S_1$, calcd 474.1, found 474.1.

Example 221: 2-Amino-N-[2,4-difluoro-5-[[5-(2,2,2-trifluoroethyl)pyridin-2-yl]carbamoyl]phenyl]-1,3-thiazole-5-carboxamide

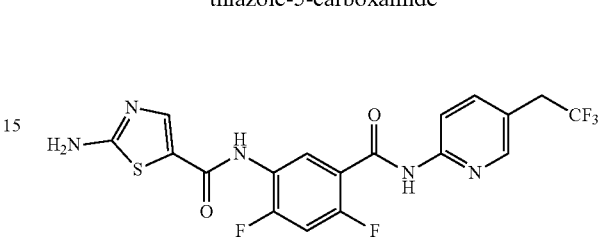

The title compound was prepared from 5-(2,2,2-trifluoroethyl)pyridin-2-amine, methyl 5-amino-2,4-difluorobenzoate, and 2-[(2-methylpropan-2-yl)oxycarbonylamino]-1,3-thiazole-5-carboxylic acid in a similar fashion to Example 201. ¹H NMR (400 MHz, Methanol-d₄) δ 8.29-8.16 (m, 3H), 7.77-7.69 (m, 2H), 7.06 (t, J=10.2 Hz, 1H), 3.39 (q, J=10.8 Hz, 2H). ESI MS [M+H]⁺ for $C_{18}H_{13}F_5N_5O_2S_1$, calcd 458.1, found 458.1.

Example 222: 2-Amino-N-[5-[(5-cyclopropyloxypyridin-2-yl)carbamoyl]-2,4-difluorophenyl]-1,3-thiazole-5-carboxamide

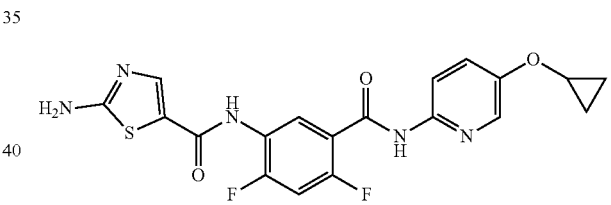

The title compound was prepared from 5-cyclopropyloxy-pyridin-2-amine, methyl 5-amino-2,4-difluorobenzoate, and 2-[(2-methylpropan-2-yl)oxycarbonylamino]-1,3-thiazole-5-carboxylic acid in a similar fashion to Example 200. ¹H NMR (400 MHz, Methanol-d₄) δ 8.20 (t, J=8.1 Hz, 1H), 8.13 (d, J=9.1 Hz, 1H), 8.05 (dd, J=3.0, 0.7 Hz, 1H), 7.93 (s, 1H), 7.53-7.47 (m, 1H), 7.10 (t, J=10.2 Hz, 1H), 3.83-3.74 (m, 1H), 0.82-0.70 (m, 4H). ESI MS [M+H]⁺ for $C_{19}H_{16}F_2N_5O_3S_1$, calcd 432.1, found 432.1.

Example 223: 2-Amino-N-[5-[(5-cyclopropyloxypyridin-2-yl)carbamoyl]-2-fluoro-4-methylphenyl]-1,3-thiazole-5-carboxamide

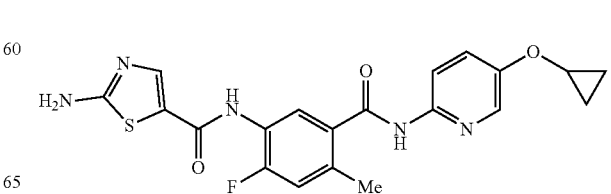

The title compound was prepared from 5-cyclopropyloxy-pyridin-2-amine, methyl 5-amino-4-fluoro-2-methylbenzoate, and 2-[(2-methylpropan-2-yl)oxycarbonylamino]-1,3-thiazole-5-carboxylic acid in a similar fashion to Example 200. $^1$H NMR (400 MHz, Methanol-$d_4$) δ 8.07-8.02 (m, 2H), 7.92 (s, 1H), 7.81 (d, J=7.7 Hz, 1H), 7.52 (dd, J=9.1, 3.0 Hz, 1H), 7.05 (d, J=11.1 Hz, 1H), 3.82-3.75 (m, 1H), 2.44 (s, 3H), 0.83-0.70 (m, 4H). ESI MS [M+H]$^+$ for $C_{20}H_{19}FN_5O_3S_1$, calcd 428.1, found 428.1.

Example 224: 2-Amino-N-[4-chloro-5-[(5-cyclopropyloxypyridin-2-yl)carbamoyl]-2-methylphenyl]-1,3-thiazole-5-carboxamide

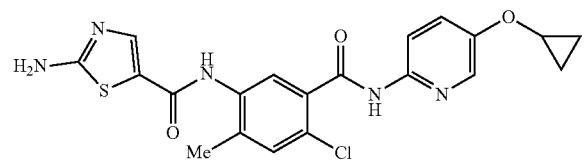

The title compound was prepared from 5-cyclopropyloxy-pyridin-2-amine, methyl 5-amino-2-chloro-4-methylbenzoate, and 2-[(2-methylpropan-2-yl)oxycarbonylamino]-1,3-thiazole-5-carboxylic acid in a similar fashion to Example 200. $^1$H NMR (400 MHz, Methanol-$d_4$) δ 8.11-8.04 (m, 2H), 7.89 (s, 1H), 7.54-7.50 (m, 2H), 7.35 (d, J=0.8 Hz, 1H), 3.82-3.76 (m, 1H), 2.27 (s, 3H), 0.83-0.70 (m, 4H). ESI MS [M+H]$^+$ for $C_{20}H_{19}ClN_5O_3S_1$, calcd 444.1, found 444.1.

Example 225: 2-Amino-N-[4-fluoro-2-methyl-5-[[5-(1,2,2,2-tetrafluoroethyl)pyridin-2-yl]carbamoyl]phenyl]-1,3-thiazole-5-carboxamide

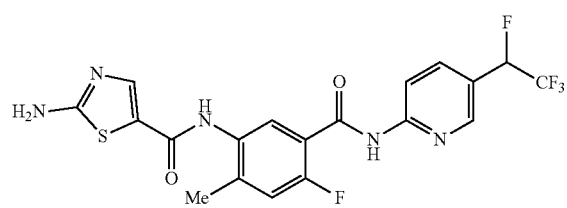 [SMILES: Cc1cc(F)c(C(=O)Nc2ccc(C(F)C(F)(F)F)cn2)cc1NC(=O)c1cnc(N)s1]

The title compound was prepared from 5-(1,2,2,2-tetrafluoroethyl)pyridin-2-amine and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, Methanol-$d_4$) δ 8.37 (d, J=9.0 Hz, 2H), 7.88 (d, J=10.1 Hz, 1H), 7.80 (d, J=7.3 Hz, 1H), 7.72 (s, 1H), 7.11 (d, J=12.0 Hz, 1H), 5.80 (dd, J=43.6, 6.1 Hz, 1H), 2.31 (s, 3H). ESI MS [M+H]$^+$ for $C_{19}H_{15}F_5N_5O_2S_1$, calcd 472.1, found 472.1.

Example 226: 2-Amino-N-[5-[[5-(difluoromethyl)pyridin-2-yl]carbamoyl]-4-fluoro-2-methylphenyl]-1,3-thiazole-5-carboxamide

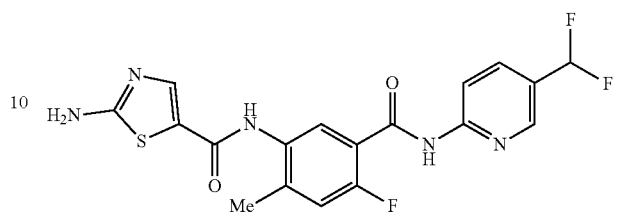

The title compound was prepared from 5, 5-(difluoromethyl)pyridin-2-amine and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, Methanol-$d_4$) δ 8.42 (s, 1H), 8.37 (d, J=8.6 Hz, 1H), 7.89 (d, J=8.7 Hz, 1H), 7.81 (d, J=7.2 Hz, 1H), 7.72 (s, 1H), 6.97 (d, J=9.6 Hz, 1H), 6.71 (t, J=55.8 Hz, 1H), 2.30 (s, 3H). ESI MS [M+H]$^+$ for $C_{18}H_{15}F_3N_5O_2S_1$, calcd 422.1, found 422.1.

Example 227: 2-Amino-N-[5-[[4-(difluoromethoxy)phenyl]carbamoyl]-4-fluoro-2-methylphenyl]-1,3-thiazole-5-carboxamide

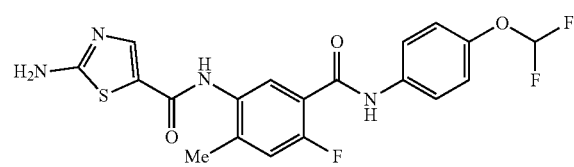 [SMILES: Cc1cc(F)c(C(=O)Nc2ccc(OC(F)F)cc2)cc1NC(=O)c1cnc(N)s1]

The title compound was prepared from 4-(difluoromethoxy)aniline and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, Methanol-$d_4$) δ 7.87 (s, 1H), 7.63 (t, J=7.8 Hz, 3H), 7.08 (dd, J=10.2, 5.9 Hz, 3H), 6.57 (t, J=74.0 Hz, 1H), 2.29 (s, 3H). ESI MS [M+H]$^+$ for $C_{19}H_{16}F_3N_4O_3S_1$, calcd 437.1, found 437.1.

Example 228: 2-Amino-N-[4-fluoro-5-[(2-fluoro-4-methoxyphenyl)carbamoyl]-2-methylphenyl]-1,3-thiazole-5-carboxamide

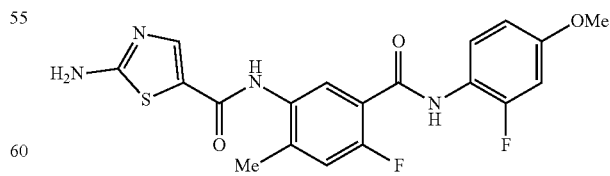

The title compound was prepared from 2-fluoro-4-methoxyaniline and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, Methanol-$d_4$) δ 7.90 (s, 1H), 7.85-7.76 (m, 2H), 7.12 (d, J=11.8 Hz, 1H), 6.75-6.66 (m, 2H), 3.76 (s, 3H), 2.29 (s, 3H). ESI MS [M+H]+ for C19H17F2N4O3S1, calcd 419.1, found 419.1.

Example 229: 2-Amino-N-[5-[(4-cyclopropyloxyphenyl)carbamoyl]-4-fluoro-2-methylphenyl]-1,3-thiazole-5-carboxamide

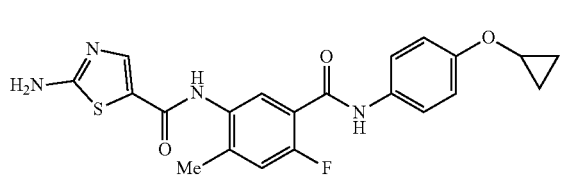

The title compound was prepared from 4-cyclopropyloxyaniline and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, Methanol-d$_4$) δ 7.89 (s, 1H), 7.66 (dd, J=7.1, 1.7 Hz, 1H), 7.51-7.45 (m, 2H), 7.05 (d, J=11.5 Hz, 1H), 7.02-6.95 (m, 2H), 3.72-3.66 (m, 1H), 2.26 (s, 3H), 0.77-0.66 (m, 4H). ESI MS [M+H]+ for C21H20FN4O3S1, calcd 427.1, found 427.1.

Example 230: 2-Amino-N-[4-fluoro-5-[(4-methoxyphenyl)carbamoyl]-2-methylphenyl]-1,3-thiazole-5-carboxamide

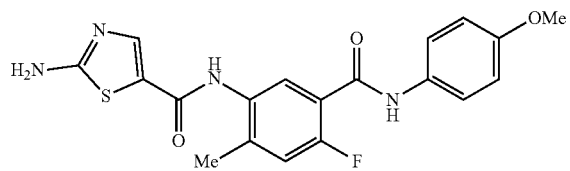 [SMILES: COc1ccc(NC(=O)c2cc(NC(=O)c3cnc(N)s3)c(C)cc2F)cc1]

The title compound was prepared from 4-methoxyaniline and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, Methanol-d$_4$) δ 7.88 (s, 1H), 7.66 (d, J=6.9 Hz, 1H), 7.49 (d, J=7.7 Hz, 2H), 7.07 (d, J=11.3 Hz, 1H), 6.85 (d, J=8.5 Hz, 2H), 3.75 (s, 3H), 2.27 (s, 3H). ESI MS [M+H]+ for C19H18FN4O3S1, calcd 401.1, found 401.1.

Example 231: 2-Amino-N-[5-[(4-chlorophenyl)carbamoyl]-4-fluoro-2-methylphenyl]-1,3-thiazole-5-carboxamide

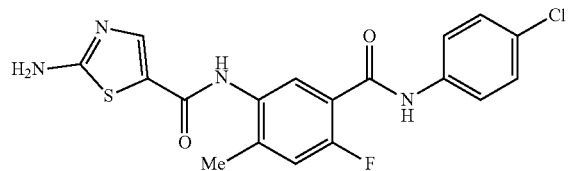 [SMILES: Cc1cc(F)c(C(=O)Nc2ccc(Cl)cc2)cc1NC(=O)c1cnc(N)s1]

The title compound was prepared from 4-chloroaniline and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, Methanol-d$_4$) δ 7.78 (s, 1H), 7.64 (d, J=7.0 Hz, 1H), 7.56 (d, J=8.7 Hz, 2H), 7.25 (d, J=8.7 Hz, 2H), 7.04 (d, J=11.6 Hz, 1H), 2.26 (s, 3H). ESI MS [M+H]+ for C18H15FN4O2S1, calcd 405.1, found 405.1.

Example 232: 2-Amino-N-[4-fluoro-5-[(3-fluorophenyl)carbamoyl]-2-methylphenyl]-1,3-thiazole-5-carboxamide

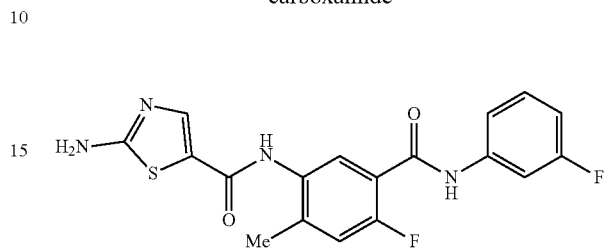

The title compound was prepared from 3-fluoroaniline and 2-fluoro-4-methyl-5-[[2-[(2-methylpropan-2-yl)oxycarbonylamino]-1,3-thiazole-5-carbonyl]amino]benzoic acid in a similar fashion to Example 200. $^1$H NMR (400 MHz, Methanol-d$_4$) δ 7.87 (s, 1H), 7.62 (d, J=6.8 Hz, 1H), 7.55 (dt, J=11.2, 1.9 Hz, 1H), 7.31-7.21 (m, 2H), 7.05 (d, J=11.2 Hz, 1H), 6.83-6.75 (m, 1H), 2.27 (s, 3H). ESI MS [M+H]+ for C18H15F2N4O2S1, calcd 389.1, found 389.1.

Example 233: 2-Amino-N-[4-fluoro-5-[(4-fluorophenyl)carbamoyl]-2-methylphenyl]-1,3-thiazole-5-carboxamide

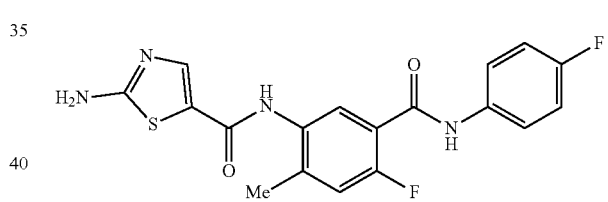

The title compound was prepared from 4-fluoroaniline and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, Methanol-d$_4$) δ 7.82 (s, 1H), 7.64 (d, J=6.9 Hz, 1H), 7.61-7.54 (m, 2H), 7.07 (d, J=11.4 Hz, 1H), 7.00 (t, J=8.7 Hz, 2H), 2.28 (s, 3H). ESI MS [M+H]+ for C18H15F2N4O2S1, calcd 389.1, found 389.1.

Example 234: 2-Amino-N-[4-fluoro-5-[(2-fluorophenyl)carbamoyl]-2-methylphenyl]-1,3-thiazole-5-carboxamide

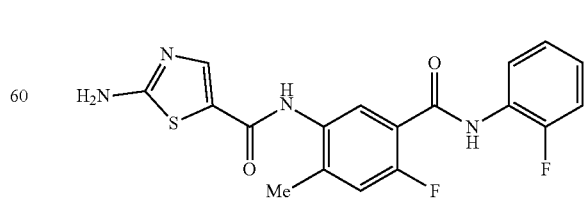

The title compound was prepared from 2-fluoroaniline and 2-fluoro-4-methyl-5-[[2-[(2-methylpropan-2-yl)oxycarbonylamino]-1,3-thiazole-5-carbonyl]amino]benzoic acid in a similar fashion to Example 7. ¹H NMR (400 MHz, Methanol-d₄) δ 8.19 (t, J=7.8 Hz, 1H), 7.81 (d, J=7.1 Hz, 1H), 7.70 (s, 1H), 7.16-7.03 (m, 4H), 2.28 (s, 3H). ESI MS [M+H]⁺ for $C_{18}H_{15}F_2N_4O_2S_1$, calcd 389.1, found 389.1.

Example 235: N-[5-[(5-cyclopropyloxypyridin-2-yl)carbamoyl]-4-fluoro-2-methylphenyl]-2-(2,2-difluoroethylamino)-1,3-thiazole-5-carboxamide and THF (20 mL, 0.2 M). TEA (1.14 mL, 8 mmol, 2.0 equiv.) was added and the reaction mixture was stirred at RT for 16 h, at which time LC/MS analysis indicated complete consumption of starting material. The reaction mixture was diluted with water (20 mL) and extracted with EtOAc (20 mL×2). The organic phase was collected, washed with brine (2×), dried over Na₂SO₄ and concentrated in vacuo, which was used directly in step c.

Step c: A round-bottom flask was charged with product from step b (4.0 mmol, 1.0 equiv.) and THF/H₂O (ratio 3:2,

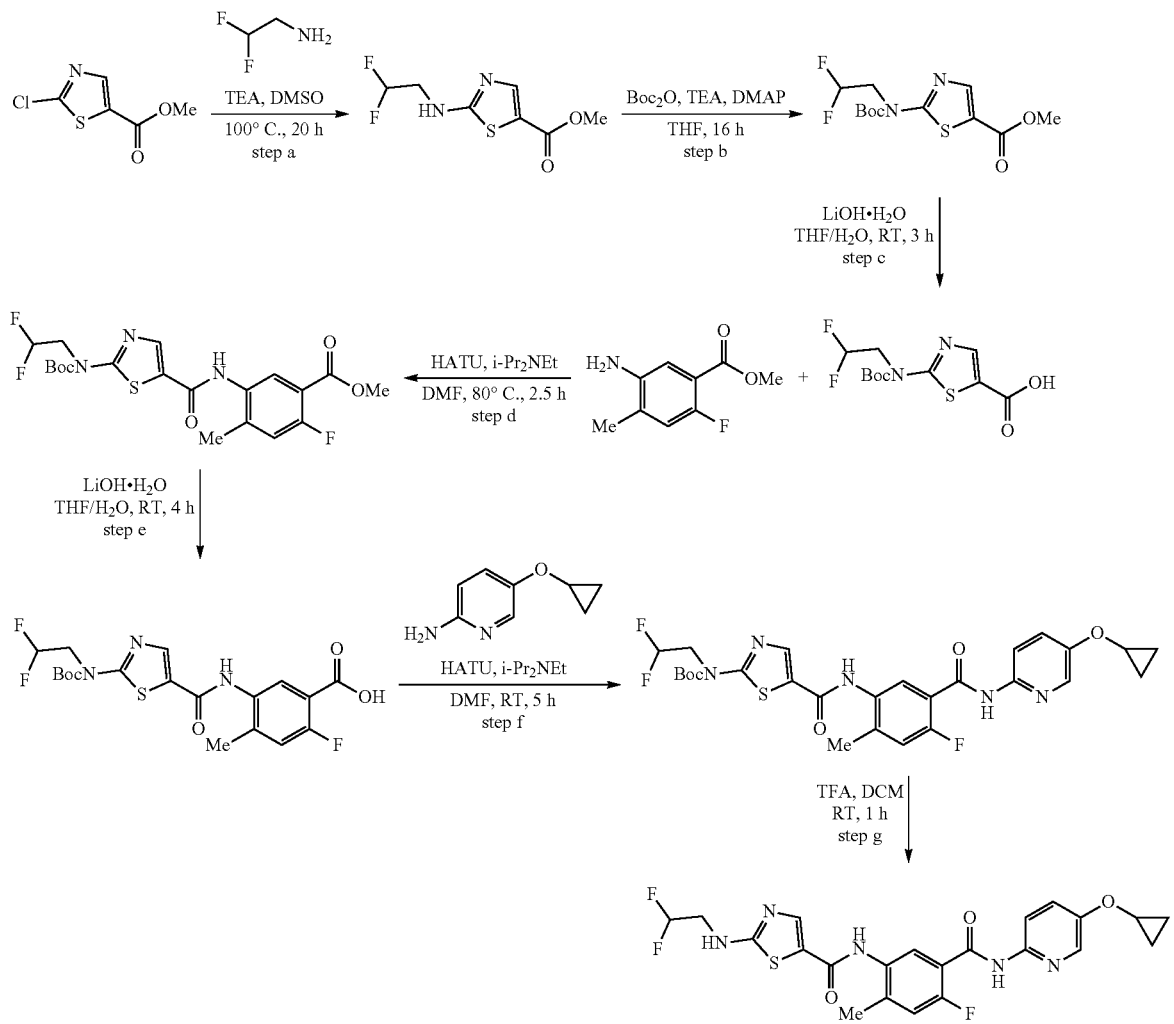

Step a: A round-bottom flask was charged with methyl 2-chloro-1,3-thiazole-5-carboxylate (500 mg, 2.8 mmol, 1.0 equiv.), 2,2-difluoroethanamine (1.14 g, 14 mmol, 5.0 equiv.), triethylamine (2.0 mL, 14 mmol, 5.0 equiv.), and DMSO (7 mL, 0.4 M). The reaction mixture was stirred at 100° C. for 20 h, cooled down to RT and diluted with water (10 mL). The mixture was extracted with EtOAc (10 mL×2) and the organic phase was collected, washed with brine (2×), dried over Na₂SO₄ and concentrated in vacuo. The crude product was purified by column chromatography (EtOAc in hexane, 0%→50%) to provide the desired methyl 2-(2,2-difluoroethylamino)-1,3-thiazole-5-carboxylate.

Step b: A round-bottom flask was charged with product from step a (890 mg, 4 mmol, 1.0 equiv.), Boc₂O (1.75 g, 8 mmol, 2.0 equiv.), DMAP (50 mg, 0.4 mmol, 0.1 equiv.), 20 mL, 0.2 M). LiOH H₂O (839 mg, 20 mmol, 5.0 equiv.) was added and the reaction mixture was stirred at RT for 3 h, at which time LC/MS analysis showed complete consumption of starting material. The reaction mixture was concentrated in vacuo, acidified to pH 4 using 1N aq. HCl. The precipitate thus obtained was collected by vacuum filtration, rinsed with water, and dried in vacuo to afford 2-[2,2-difluoroethyl-[(2-methylpropan-2-yl)oxycarbonyl]amino]-1,3-thiazole-5-carboxylic acid.

Step d: A round-bottom flask was charged with product from step c (956 mg, 3.1 mmol, 1.0 equiv.), methyl 5-amino-2-fluoro-4-methylbenzoate (624 mg, 3.4 mmol, 1.1 equiv), and HATU (1.76 g, 4.65 mmol, 1.5 equiv). DMF (15 mL, 0.2 M) was added, followed by i-Pr₂NEt (1.6 mL, 9.3 mmol, 3.0 equiv). The reaction mixture was stirred at 80° C. for 2.5 h, at which time LC/MS analysis showed complete consumption of starting material. The reaction mixture was cooled to RT and poured onto ice water (50 mL) with stirring. Stirring was continued for 10 minutes and then the precipitated solid was collected by vacuum filtration, rinsed with water, and dried in vacuo to afford methyl 5-[[2-[2,2-difluoroethyl-[(2-methylpropan-2-yl)oxycarbonyl]amino]-1,3-thiazole-5-carbonyl]amino]-2-fluoro-4-methylbenzoate.

Step e: A round-bottom flask was charged with product from step d (1.22 g, 2.58 mmol, 1.0 equiv.) and THF/H$_2$O (ratio 3:2, 12.5 mL, 0.2 M). LiOH·H$_2$O (541 mg, 12.9 mmol, 5.0 equiv.) was added and the reaction mixture was stirred at RT for 4 h, at which time LC/MS analysis showed complete consumption of starting material. The reaction mixture was concentrated in vacuo, acidified to pH 4 using aq. 1N HCl. The precipitate thus obtained was collected by vacuum filtration, rinsed with water, and dried in vacuo to afford 5-[[2-[2,2-difluoroethyl-[(2-methylpropan-2-yl)oxycarbonyl]amino]-1,3-thiazole-5-carbonyl]amino]-2-fluoro-4-methylbenzoic acid.

Step f: A vial was charged with product from step e (220 mg, 0.48 mmol, 1.0 equiv.), 5-cyclopropyloxypyridin-2-amine (79 mg, 0.52 mmol, 1.1 equiv), and HATU (273 mg, 0.72 mmol, 1.5 equiv). DMF (2.5 mL, 0.2 M) was added, followed by i-Pr$_2$NEt (0.25 mL, 1.4 mmol, 3.0 equiv). The reaction mixture was stirred at RT for 5 h, at which time LC/MS analysis showed complete consumption of starting material. The reaction mixture was poured onto ice water (10 mL) with stirring. Stirring was continued for 10 minutes and then the precipitated solid was collected by vacuum filtration, rinsed with water, and dried in vacuo to afford tert-butyl N-[5-[[5-[(5-cyclopropyloxypyridin-2-yl)carbamoyl]-4-fluoro-2-methylphenyl]carbamoyl]-1,3-thiazol-2-yl]-N-(2,2-difluoroethyl)carbamate.

Step g: A vial was charged with product from step f and CH$_2$Cl$_2$ (1 mL) was added. TFA (1 mL) was then added dropwise and the reaction mixture was stirred at RT for 1 h, at which time LC/MS analysis indicated complete consumption of starting material. The solvents were evaporated in vacuo and the crude product was purified by reverse phase HPLC to afford the title compound. $^1$H NMR (400 MHz, Methanol-d$_4$) δ 8.09-8.05 (m, 2H), 7.83 (s, 1H), 7.80 (d, J=7.2 Hz, 1H), 7.61-7.56 (m, 1H), 7.11 (d, J=11.8 Hz, 1H), 5.96 (tt, J=55.7, 3.9 Hz, 1H), 3.84-3.78 (m, 1H), 3.73 (td, J=14.7, 3.9 Hz, 2H), 2.30 (s, 3H), 0.84-0.78 (m, 2H), 0.77-0.71 (m, 2H). ESI MS [M+H]$^+$ for C$_{22}$H$_{21}$F$_3$N$_5$O$_3$S$_1$, calcd 492.1, found 492.1.

Example 236: 2-Amino-N-[2-bromo-5-[(5-cyclopropyloxypyridin-2-yl)carbamoyl]-4-fluorophenyl]-1,3-thiazole-5-carboxamide

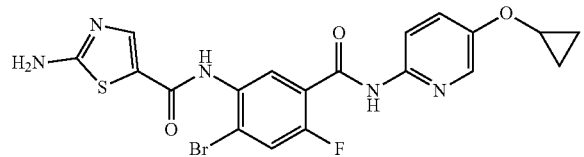 [SMILES: Nc1ncc(C(=O)Nc2cc(C(=O)Nc3ccc(OC4CC4)cn3)c(F)cc2Br)s1]

The title compound was prepared from 5-cyclopropyloxypyridin-2-amine, methyl 5-amino-4-bromo-2-fluorobenzoate, and 2-[(2-methylpropan-2-yl)oxycarbonylamino]-1,3-thiazole-5-carboxylic acid in a similar fashion to Example 200. $^1$H NMR (400 MHz, Methanol-d$_4$) δ 8.19 (d, J=7.4 Hz, 1H), 8.15 (d, J=9.1 Hz, 1H), 8.05 (d, J=2.9 Hz, 1H), 7.73 (s, 1H), 7.50 (d, J 10.1 Hz, 1H), 7.47-7.43 (m, 1H), 3.80-3.74 (m, 1H), 0.78 (ddt, J=5.6, 4.3, 1.3 Hz, 2H), 0.72 (ddd, J=8.2, 6.3, 3.6 Hz, 2H). ESI MS [M+H]$^+$ for C$_{19}$H$_{16}$BrFN$_5$O$_3$S$_1$, calcd 492.1, found 492.1.

Example 237: 2-Amino-N-[5-[(5-cyclopropyloxypyridin-2-yl)carbamoyl]-2-ethyl-4-fluorophenyl]-1,3-thiazole-5-carboxamide

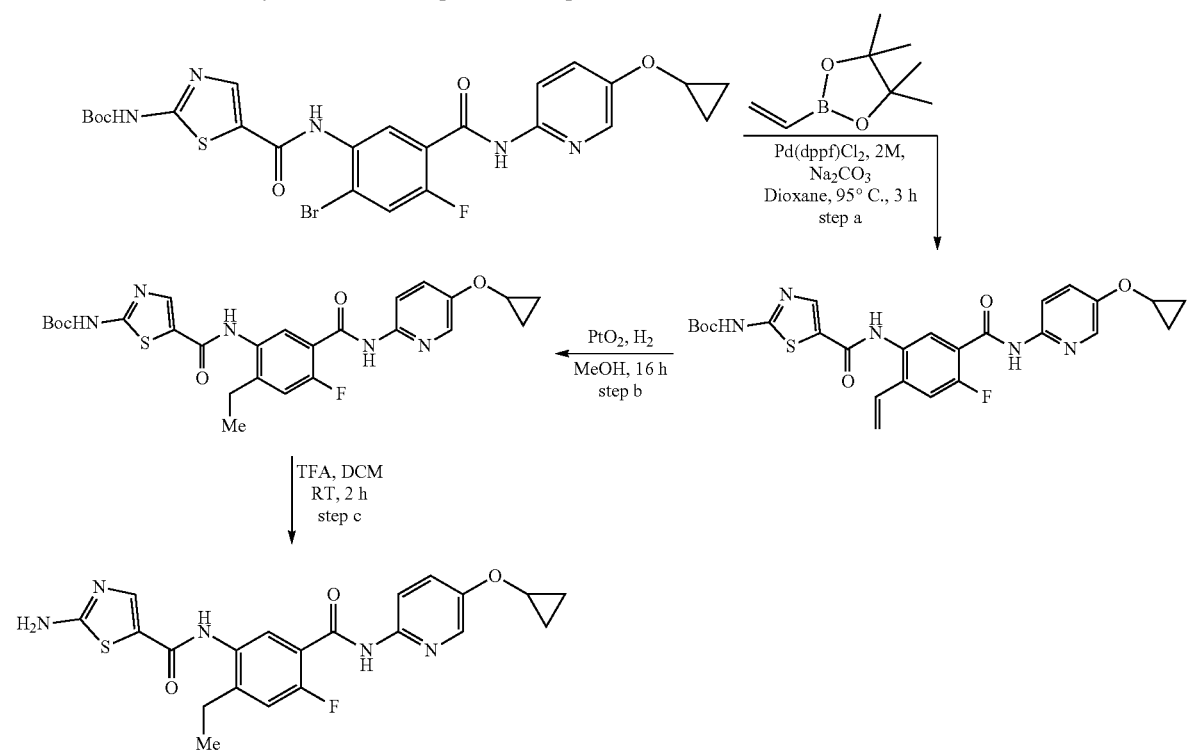

Step a: A vial was charged with tert-butyl N-[5-[[2-bromo-5-[(5-cyclopropyloxypyridin-2-yl)carbamoyl]-4-fluorophenyl]carbamoyl]-1,3-thiazol-2-yl]carbamate, an intermediate for Example 236 (142 mg, 0.24 mmol, 1.0 equiv.), 2-ethenyl-4,4,5,5-tetramethyl-1,3,2-dioxaborolane (44 mg, 0.26 mmol, 1.1 equiv.), Pd(dppf)Cl$_2$ (35 mg, 0.05 mmol, 0.2 equiv.), and degassed dioxane (2 mL, 0.1 M) under N$_2$ gas. 2M aq. Na$_2$CO$_3$ (0.24 mL, 0.48 mmol, 2.0 equiv.) was added and the reaction mixture was stirred at 95° C. for 3 h, at which time LC/MS analysis showed complete consumption of starting material. The reaction mixture was cooled to RT, filtered through Celite® and concentrated in vacuo. The crude material was purified by column chromatography (EtOAc in hexane, 0%→50%) to provide tert-butyl N-[5-[[5-[(5-cyclopropyloxypyridin-2-yl)carbamoyl]-2-ethenyl-4-fluorophenyl]carbamoyl]-1,3-thiazol-2-yl]carbamate.

Step b: A round-bottom flask was charged with product from step a (116 mg, 0.2 mmol, 1.0 equiv.), followed by MeOH (5 mL, 0.04 M), and PtO$_2$ (20 wt. %, 18 mg). The reaction mixture was shaken under 20 psi of hydrogen gas for 16 h, at which time LC/MS analysis indicated complete consumption of starting material. The reaction mixture was filtrated with Celite® and concentrated in vacuo, which was directly used in step c without further purification.

Step c: A vial was charged with product from step b and DCM (1 mL) was added. TFA (1 mL) was then added dropwise and the reaction mixture was stirred at RT for 2 h, at which time LC/MS analysis indicated complete consumption of starting material. The solvents were evaporated in vacuo and the crude product was purified by reverse phase HPLC to afford the title compound. $^1$H NMR (400 MHz, Methanol-d$_4$) δ 8.15 (d, J=9.0 Hz, 1H), 8.07-8.03 (m, 1H), 7.86 (s, 1H), 7.81 (d, J=7.2 Hz, 1H), 7.52-7.46 (m, 1H), 7.14 (d, J=12.3 Hz, 1H), 3.82-3.75 (m, 1H), 2.65 (q, J=7.5 Hz, 2H), 1.20 (t, J=7.5 Hz, 3H), 0.82-0.76 (m, 2H), 0.75-0.70 (m, 2H). ESI MS [M+H]$^+$ for C$_{21}$H$_{21}$FN$_5$O$_3$S$_1$, calcd 442.1, found 442.1.

Example 238: 2-(Cyclopropanecarbonylamino)-N-[5-[(5-cyclopropyloxypyridin-2-yl)carbamoyl]-4-fluoro-2-methylphenyl]-1,3-thiazole-5-carboxamide

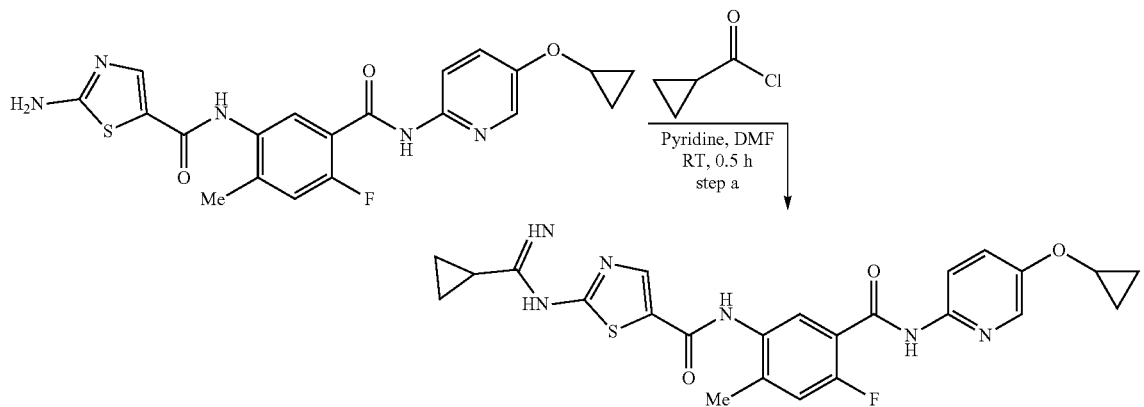

Step a: A vial was charged with 2-amino-N-[5-[(5-cyclopropyloxypyridin-2-yl)carbamoyl]-4-fluoro-2-methylphenyl]-1,3-thiazole-5-carboxamide (57 mg, 0.133 mmol, 1.0 equiv., prepared according to the protocol described in Example 6), and DMF (1.3 mL, 0.1 M), followed by pyridine (0.032 mL, 0.4 mmol, 3.0 equiv.). Cyclopropanecarbonyl chloride (0.036 mL, 0.4 mmol, 3.0 equiv.) was added dropwise and the reaction mixture was stirred at RT for 30 min, at which time LC/MS analysis showed complete consumption of starting material. The reaction mixture was quenched by MeOH (0.5 mL) and the solvents were evaporated in vacuo and the crude product was purified by reverse phase HPLC to afford the title compound. $^1$H NMR (400 MHz, Methanol-$d_4$) δ 8.15 (d, J=9.1 Hz, 1H), 8.10 (s, 1H), 8.07-8.04 (m, 1H), 7.82 (d, J=7.2 Hz, 1H), 7.47 (dd, J=9.1, 3.0 Hz, 1H), 7.12 (d, J=11.9 Hz, 1H), 3.78 (tt, J=6.2, 3.0 Hz, 1H), 2.31 (s, 3H), 1.84 (dq, J=8.3, 4.5, 4.1 Hz, 1H), 1.08 (p, J=4.1 Hz, 2H), 0.96 (dt, J=8.0, 3.5 Hz, 2H), 0.82-0.76 (m, 2H), 0.75-0.70 (m, 2H). ESI MS [M+H]$^+$ for $C_{24}H_{23}FN_5O_4S_1$, calcd 496.1, found 496.1.

Example 239: N-[5-[(5-cyclopropyloxypyridin-2-yl)carbamoyl]-4-fluoro-2-methylphenyl]-2-[(2,2,2-trifluoroacetyl)amino]-1,3-thiazole-5-carboxamide

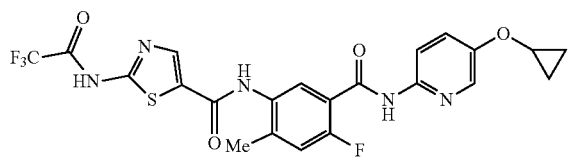 [SMILES: Cc1cc(F)c(C(=O)Nc2ccc(OC3CC3)cn2)cc1NC(=O)c1cnc(NC(=O)C(F)(F)F)s1]

The title compound was prepared from 2-amino-N-[5-[(5-cyclopropyloxypyridin-2-yl)carbamoyl]-4-fluoro-2-methylphenyl]-1,3-thiazole-5-carboxamide and TFAA in a similar fashion to Example 238. $^1$H NMR (400 MHz, Methanol-$d_4$) δ 8.19-8.12 (m, 2H), 8.06 (d, J=2.9 Hz, 1H), 7.83 (d, J=7.3 Hz, 1H), 7.50 (dd, J=9.1, 2.9 Hz, 1H), 7.13 (d, J=11.8 Hz, 1H), 3.82-3.76 (m, 1H), 2.32 (s, 3H), 0.79 (q, J=6.6, 5.6 Hz, 2H), 0.75-0.70 (m, 2H). ESI MS [M+H]$^+$ for $C_{22}H_{18}F_4N_5O_4S_1$, calcd 524.1, found 524.1.

Example 240: 2-Acetamido-N-[5-[(5-cyclopropyloxypyridin-2-yl)carbamoyl]-4-fluoro-2-methylphenyl]-1,3-thiazole-5-carboxamide

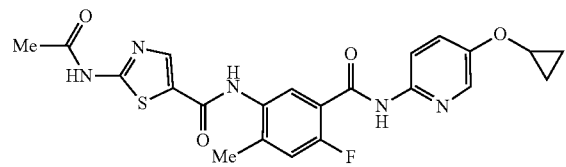 [SMILES: CC(=O)Nc1ncc(C(=O)Nc2cc(C(=O)Nc3ccc(OC4CC4)cn3)c(F)cc2C)s1]

The title compound was prepared from 2-amino-N-[5-[(5-cyclopropyloxypyridin-2-yl)carbamoyl]-4-fluoro-2-methylphenyl]-1,3-thiazole-5-carboxamide and acetyl chloride in a similar fashion to Example 238. $^1$H NMR (400 MHz, Methanol-$d_4$) δ 8.16 (d, J=9.1 Hz, 1H), 8.10 (s, 1H), 8.05 (d, J=3.0 Hz, 1H), 7.82 (d, J=7.2 Hz, 1H), 7.47 (dd, J=9.1, 3.0 Hz, 1H), 7.12 (d, J=11.9 Hz, 1H), 3.81-3.76 (m, 1H), 2.31 (s, 3H), 2.22 (s, 3H), 0.82-0.76 (m, 2H), 0.75-0.70 (m, 2H). ESI MS [M+H]$^+$ for $C_{22}H_{21}FN_5O_4S_1$, calcd 470.1, found 470.1.

Example 241: N-[5-[(5-cyclopropyloxypyridin-2-yl)carbamoyl]-4-fluoro-2-methylphenyl]-2-(methylamino)-1,3-thiazole-5-carboxamide

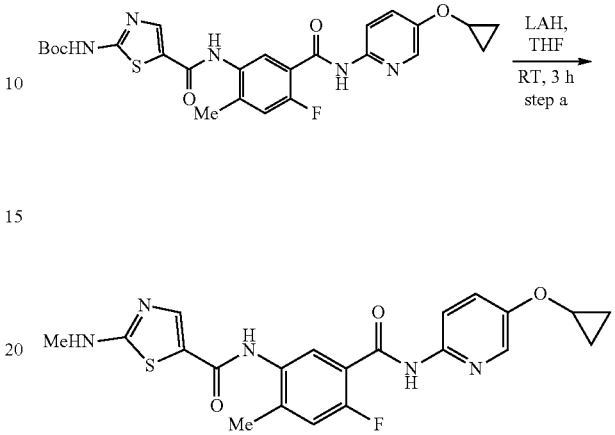

Step a: A vial was charged with tert-butyl N-[5-[[5-[(5-cyclopropyloxypyridin-2-yl)carbamoyl]-4-fluoro-2-methylphenyl]carbamoyl]-1,3-thiazol-2-yl]carbamate (200 mg, 0.38 mmol, 1.0 equiv., prepared according to the protocol described in Example 6), and THF (2 mL, 0.2 M). LAH (43 mg, 1.14 mmol, 3.0 equiv.) was added portionwise and the reaction mixture was stirred at RT for 3 hr, quenched with water (2 mL) and extracted with EtOAc (2 mL×2). The organic phase was collected, washed with brine (2×), dried over $Na_2SO_4$ and concentrated in vacuo. The crude product was purified by reverse phase HPLC to afford the title compound. $^1$H NMR (400 MHz, Methanol-$d_4$) δ 8.12 (d, J=9.1 Hz, 1H), 8.06 (d, J=2.9 Hz, 1H), 7.92 (s, 1H), 7.82 (d, J=7.2 Hz, 1H), 7.55-7.50 (m, 1H), 7.12 (d, J=11.8 Hz, 1H), 3.80 (tt, J=6.2, 2.9 Hz, 1H), 3.02 (s, 3H), 2.30 (s, 3H), 0.83-0.76 (m, 2H), 0.76-0.70 (m, 2H). ESI MS [M+H]$^+$ for $C_{21}H_{21}FN_5O_3S_1$, calcd 442.1, found 442.1.

Example 242: N-[2,4-difluoro-5-[[5-(2,2,2-trifluoroethyl)pyridin-2-yl]carbamoyl]phenyl]-2-methyl-1,3-thiazole-5-carboxamide

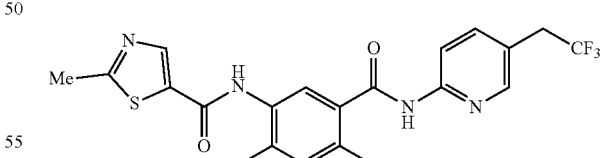

The title compound was prepared from 5-(2,2,2-trifluoroethyl)pyridin-2-amine, methyl 5-amino-2,4-difluorobenzoate, and 2-[(2-methylpropan-2-yl)oxycarbonylamino]-1,3-thiazole-5-carboxylic acid in a similar fashion to Example 1. $^1$H NMR (400 MHz, Methanol-$d_4$) δ 8.32 (t, J=2.5 Hz, 1H), 8.23 (s, 1H), 7.99-7.92 (m, 1H), 7.80 (dd, J=8.2, 2.4 Hz, 1H), 7.39 (d, J=8.2 Hz, 1H), 6.88 (t, J=9.9 Hz, 1H), 3.44 (q, J=10.7 Hz, 2H), 2.71 (s, 3H). ESI MS [M+H]$^+$ for $C_{19}H_{14}F_5N_4O_2S_1$, calcd 457.1, found 457.1.

Example 243: 2-Amino-N-[5-[(5-cyclopropyloxy-pyridin-2-yl)carbamoyl]-3-fluoro-2-methylphenyl]-1,3-thiazole-5-carboxamide

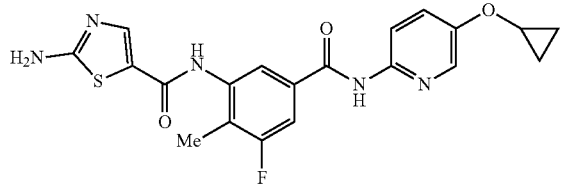 [SMILES: Cc1c(F)cc(C(=O)Nc2ccc(OC3CC3)cn2)cc1NC(=O)c1cnc(N)s1]

The title compound was prepared from 5-cyclopropyloxy-pyridin-2-amine methyl 3-amino-5-fluoro-4-methylbenzoate, and 2-[(2-methylpropan-2-yl)oxycarbonylamino]-1,3-thiazole-5-carboxylic acid in a similar fashion to Example 200. $^1$H NMR (400 MHz, Methanol-$d_4$) δ 8.09-8.03 (m, 2H), 7.94 (s, 1H), 7.71 (t, J=1.3 Hz, 1H), 7.61 (dd, J=9.1, 2.9 Hz, 1H), 7.57 (dd, J=9.6, 1.9 Hz, 1H), 3.84-3.78 (m, 1H), 2.20 (d, J=2.0 Hz, 3H), 0.84-0.78 (m, 2H), 0.77-0.72 (m, 2H). ESI MS [M+H]$^+$ for $C_{20}H_{19}FN_5O_3S_1$, calcd 428.1, found 428.1.

Example 244: 2-Amino-N-[4-fluoro-5-[[5-[1-(methoxymethyl)cyclopropyl]pyridin-2-yl]carbamoyl]-2-methylphenyl]-1,3-thiazole-5-carboxamide

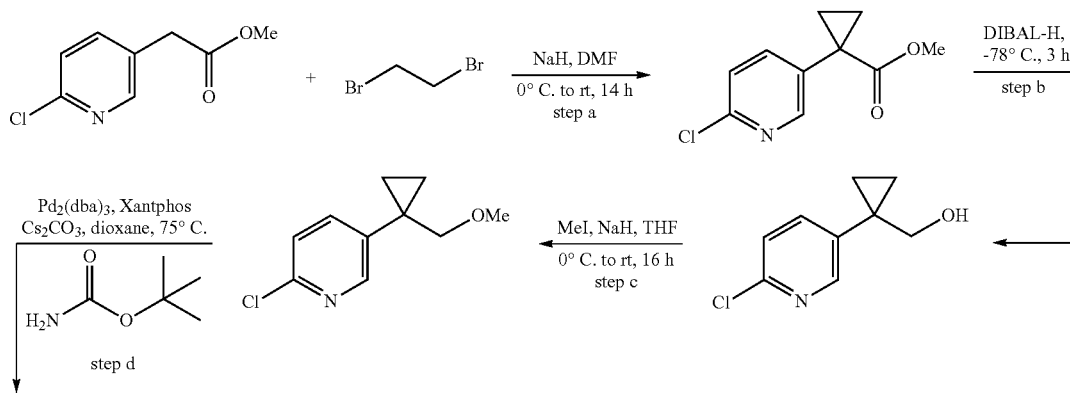

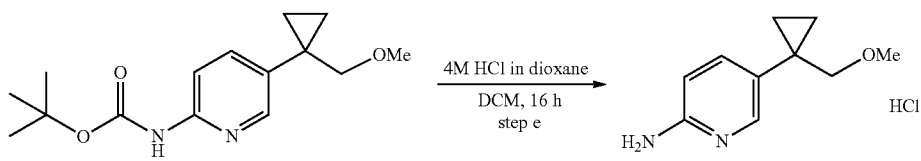

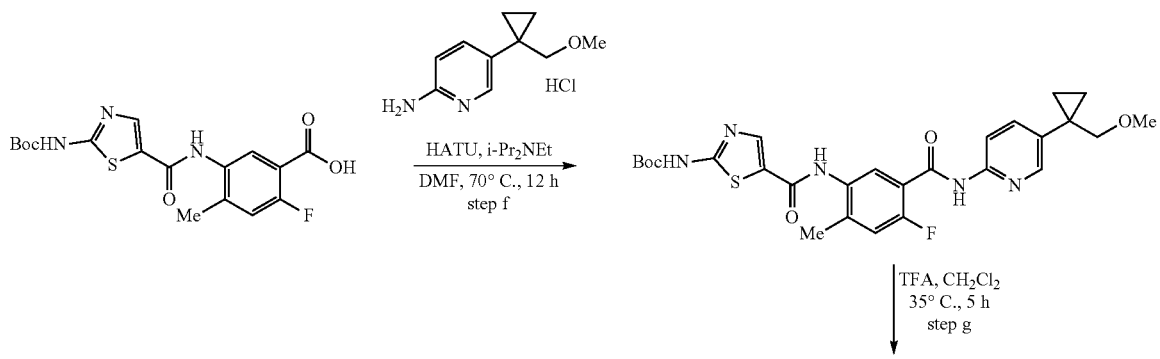

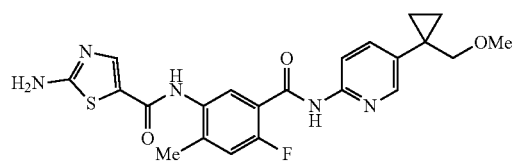

Step a: To a solution of methyl 2-(6-chloropyridin-3-yl)acetate (1.5 g, 8.0 mmol, 1.0 equiv.) in DMF (20 mL) at 0° C. was added NaH (60% in mineral oil, 969 mg, 24 mmol, 3.0 equiv.) and the resulting reaction mixture was stirred at 0° C. for 0.5 h. 1,2-Dibromoethane (1 mL, 12 mmol, 1.5 equiv.) was added. The reaction mixture was stirred for 14 h and allowed to warm to RT. The reaction mixture was then diluted with $H_2O$ and extracted three times with EtOAc. The combined organic extracts were dried over $Na_2SO_4$, filtered, and concentrated in vacuo to afford the crude product, which was purified by column chromatography (EtOAc/hexanes, 10% to 60%) to provide methyl 1-(6-chloropyridin-3-yl)cyclopropane-1-carboxylate.

Step b: To a solution of methyl 1-(6-chloropyridin-3-yl)cyclopropane-1-carboxylate (1.0 g, 4.7 mmol, 1.0 equiv.) in $CH_2Cl_2$ (12 mL) at −78° C. was added DIBAL-H (1.0 M in hexanes, 11.8 mL, 11.8 mmol, 2.5 equiv.) slowly. The resulting reaction mixture was stirred at −78° C. for 3 h and then slowly quenched with 1N NaOH (1 mL). Let it stir for 1 h and warm up to RT. The solid was filtered and washed with EtOAc. The combined organic layers were washed with water, dried over $Na_2SO_4$, filtered, and concentrated in vacuo to afford the crude product, which was used directly for the next reaction without further purification.

Step c: To a solution of [1-(6-chloropyridin-3-yl)cyclopropyl]methanol (0.84 g, 4.6 mmol, 1.0 equiv.) in THF (16 mL) at 0° C. was added NaH (60% in mineral oil, 239 mg, 6.0 mmol, 1.3 equiv.) and the resulting reaction mixture was stirred at 0° C. for 0.5 h. MeI (0.44 mL, 6.9 mmol, 1.5 equiv.) was added. The reaction mixture was stirred for 16 h and allowed to warm to RT. The reaction mixture was then diluted with $H_2O$ and extracted three times with EtOAc. The combined organic extracts were dried over $Na_2SO_4$, filtered, and concentrated in vacuo to afford the crude product, which was purified by column chromatography (EtOAc/hexanes, 0% to 30%) to provide 2-chloro-5-[1-(methoxymethyl)cyclopropyl]pyridine.

Step d was performed in an analogous manner to Example 5, step c.

Step e: Tert-butyl N-[5-[1-(methoxymethyl)cyclopropyl]pyridin-2-yl]carbamate (0.35 g) were combined with 4 mL 4.0 N HCl in dioxane in $CH_2Cl_2$ (4 mL) at RT. After being stirred at RT for 16 h, the resulting reaction mixture was concentrated in vacuo to afford the crude product, which was used directly for the next reaction without further purification.

Step f and Step g were performed in an analogous manner to Example 7. The crude product was purified by reverse phase HPLC to afford the title compound. $^1$H NMR (400 MHz, Methanol-$d_4$) δ 8.27 (d, J=2.4 Hz, 1H), 8.13 (d, J=8.6 Hz, 1H), 7.80-7.71 (m, 3H), 7.20 (d, J=11.7 Hz, 1H), 3.47 (s, 2H), 3.29 (s, 3H), 2.32 (s, 3H), 0.90 (dt, J=8.9, 1.8 Hz, 4H). ESI MS [M+H]$^+$ for $C_{22}H_{23}F_1N_5O_3S_1$, calcd 456.1, found 456.1.

Example 245: 2-Amino-N-[4-fluoro-5-[[5-(2-methoxyethyl)pyridin-2-yl]carbamoyl]-2-methylphenyl]-1,3-thiazole-5-carboxamide

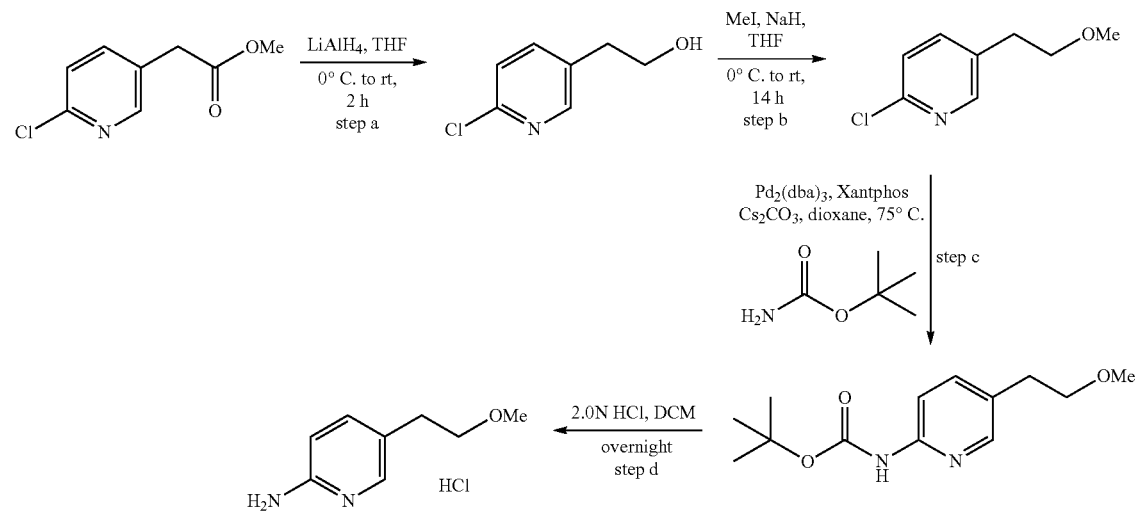

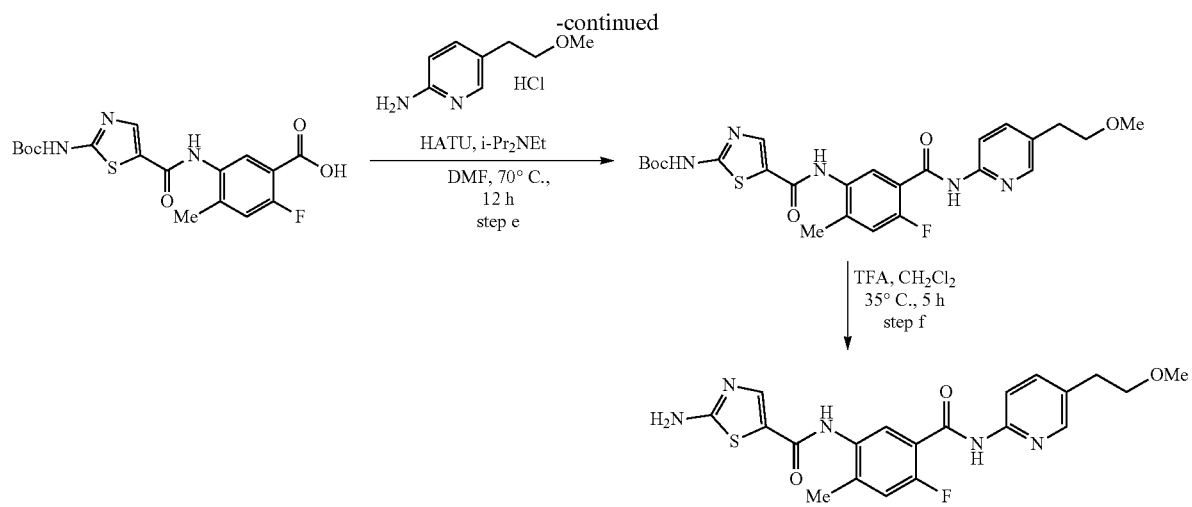

Step a: To a solution of methyl 2-(6-chloropyridin-3-yl) acetate (1.0 g, 5.4 mmol, 1.0 equiv.) in THF (20 mL) at 0° C. was added LiAlH₄ (0.41 g, 10.8 mmol, 2.0 equiv.) slowly. The resulting reaction mixture was stirred at 0° C. for 2 h and then slowly quenched with water (1 mL). The mixture was stirred for 0.5 h and then allowed to warm up to RT. The solid was filtered and washed with EtOAc. The combined organic layers were washed with water, dried over Na₂SO₄, filtered, and concentrated in vacuo to afford the crude product, which was purified by column chromatography (EtOAc/hexanes, 40% to 100%) to provide 2-(6-chloropyridin-3-yl)ethanol.

Step b: To a solution of 2-(6-chloropyridin-3-yl)ethanol (0.62 g, 4.0 mmol, 1.0 equiv.) in THF (15 mL) at 0° C. was added NaH (60% in mineral oil, 205 mg, 5.1 mmol, 1.3 equiv.) and the resulting reaction mixture was stirred at 0° C. for 0.5 h. MeI (0.84 g, 5.9 mmol, 1.5 equiv.) was added. The reaction mixture was stirred for 14 h and allowed to warm to RT. The reaction mixture was then diluted with H₂O and extracted three times with EtOAc. The combined organic extracts were dried over Na₂SO₄, filtered, and concentrated in vacuo to afford the crude product, which was purified by column chromatography (EtOAc/hexanes, 10% to 50%) to provide 2-chloro-5-(2-methoxyethyl)pyridine.

Step c and Step d were performed in an analogous manner to Example 244, steps d and e.

Step e and Step f were performed in an analogous manner to Example 7. The crude product was purified by reverse phase HPLC to afford the title compound. ¹H NMR (400 MHz, Methanol-d₄) δ 8.25 (d, J=2.2, 1H), 8.13 (dd, J=8.8, 2.3 Hz, 1H), 7.93 (s, 1H), 7.86-7.77 (m, 2H), 7.30-7.23 (m, 1H), 3.63 (t, J=6.1 Hz, 2H), 3.31 (s, 3H), 2.94 (t, J=6.1 Hz, 2H), 2.35 (s, 3H). ESI MS [M+H]⁺ for C₂₀H₂₁F₁N₅O₃S₁, calcd 430.1, found 430.2.

Example 246: 2-Amino-N-[5-[[5-(difluoromethyl) pyridin-3-yl]carbamoyl]-4-fluoro-2-methylphenyl]-1,3-thiazole-5-carboxamide

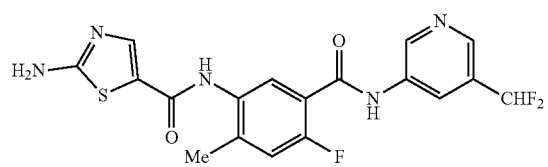 [SMILES: Cc1cc(F)c(C(=O)Nc2cncc(C(F)F)c2)cc1NC(=O)c1cnc(N)s1]

The title compound was prepared from 5-(difluoromethyl)pyridin-3-amine and 2-fluoro-4-methyl-5-[[2-[(2-methylpropan-2-yl)oxycarbonylamino]-1,3-thiazole-5-carbonyl]amino]benzoic acid in a similar fashion to Example 7. ¹H NMR (400 MHz, Methanol-d₄) δ 8.93 (s, 1H), 8.46 (s, 2H), 7.78 (s, 1H), 7.68 (d, J=6.9 Hz, 1H), 7.20 (d, J=11.1 Hz, 1H), 6.91 (t, J=55.4 Hz, 1H), 2.33 (s, 3H). ESI MS [M+H]⁺ for C₁₈H₁₅F₃N₅O₂S₁, calcd 422.1, found 422.1.

Example 247: 2-Amino-N-[4-fluoro-2-methyl-5-[[5-[(4-methylpiperazin-1-yl)methyl]pyridin-2-yl]carbamoyl]phenyl]-1,3-thiazole-5-carboxamide

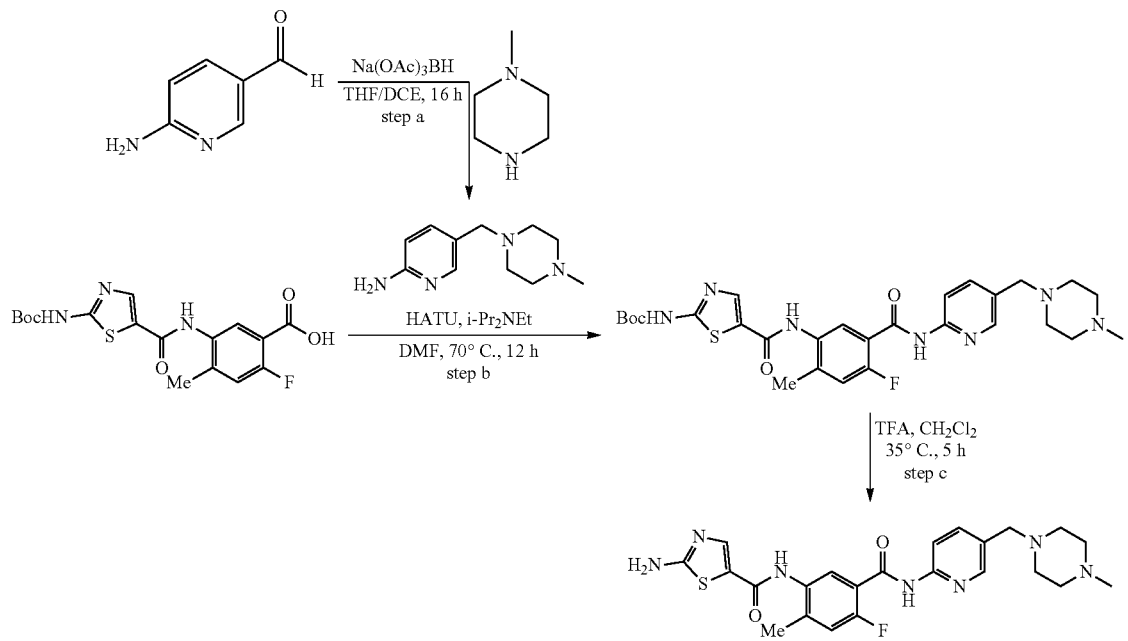

Step a: Methyl 6-aminopyridine-3-carbaldehyde (0.5 g, 4.0 mmol, 1.0 equiv.) and 1-methylpiperazine (0.6 g, 6.0 mmol, 1.5 equiv.) were combined in THF/DCE (12 mL/12 mL) at RT. After being stirred at RT for 2 h, Na(OAc)$_3$BH (1.27 g, 6.0 mmol, 1.5 equiv.) was added slowly. The resulting reaction mixture was stirred at RT for 16 h and then slowly quenched with 1N NaOH (15 mL), extracted three times with EtOAc. The combined organic layers were washed with water, dried over Na$_2$SO$_4$, filtered, and concentrated in vacuo to afford the crude product, which was used directly for the next reaction without further purification.

Step b and Step c were performed in an analogous manner to Example 7. The crude product was purified by reverse phase HPLC to afford the title compound. $^1$H NMR (400 MHz, DMSO-d$_6$) δ 8.33-8.27 (m, 1H), 8.27-8.20 (m, 1H), 7.88-7.81 (m, 2H), 7.77 (d, J=7.0 Hz, 1H), 7.24 (d, J=11.7 Hz, 1H), 3.67 (s, 3H), 3.53-3.39 (m, 2H), 3.20-2.95 (m, 4H), 2.88 (s, 3H), 2.57-2.39 (m, 2H), 2.35 (s, 3H). ESI MS [M+H]$^+$ for C$_{23}$H$_{27}$F$_1$N$_7$O$_2$S$_1$, calcd 484.1, found 484.2.

Example 248: 2-Amino-N-[4-fluoro-2-methyl-5-[[5-(morpholin-4-ylmethyl)pyridin-2-yl]carbamoyl]phenyl]-1,3-thiazole-5-carboxamide

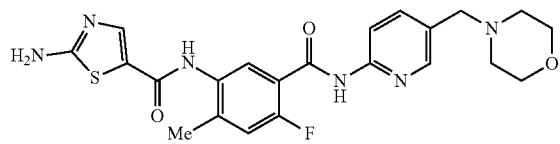 [SMILES: Cc1cc(F)c(C(=O)Nc2ccc(CN3CCOCC3)cn2)cc1NC(=O)c1cnc(N)s1]

The title compound was prepared from morpholine in a similar fashion to Example 247. The crude product was purified by reverse phase HPLC to afford the title compound. $^1$H NMR (400 MHz, Methanol-d$_4$) δ 8.42 (d, J=2.3 Hz, 1H), 8.38-8.31 (m, 1H), 7.94 (dd, J=8.6, 2.4 Hz, 1H), 7.79 (s, 1H), 7.74 (d, J=7.0 Hz, 1H), 7.21 (d, J=11.4 Hz, 1H), 4.26 (s, 2H), 3.85 (br.s, 4H), 3.18 (br.s, 4H), 2.33 (s, 3H). ESI MS [M+H]$^+$ for C$_{22}$H$_{24}$F$_1$N$_6$O$_3$S$_1$, calcd 471.1, found 471.2.

Example 249: 2-Amino-N-[4-fluoro-2-methyl-5-[[5-(trifluoromethyl)pyridin-3-yl]carbamoyl]phenyl]-1,3-thiazole-5-carboxamide

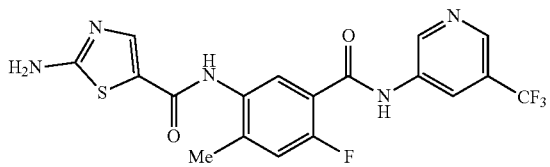 [SMILES: Cc1cc(F)c(C(=O)Nc2cncc(C(F)(F)F)c2)cc1NC(=O)c1cnc(N)s1]

The title compound was prepared from 5-(trifluoromethyl)pyridin-3-amine and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-d$_6$) δ 10.89 (s, 1H), 9.66 (s, 1H), 9.10 (d, J=2.3 Hz, 1H), 8.72 (dd, J=2.1, 1.0 Hz, 1H), 8.62-8.55 (m, 1H), 7.86 (s, 1H), 7.64 (m, 3H), 7.33 (d, J=11.0 Hz, 1H), 2.29 (s, 3H). ESI MS [M+H]$^+$ for C$_{18}$H$_{14}$F$_4$N$_5$O$_2$S$_1$, calcd 440.1, found 440.1.

Example 250: 2-Amino-N-[4-fluoro-2-methyl-5-[(2-methylpyridin-3-yl)carbamoyl]phenyl]-1,3-thiazole-5-carboxamide

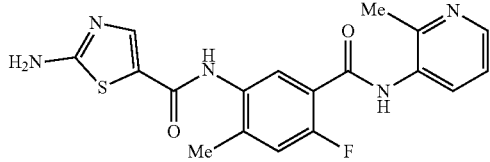 [SMILES: Cc1cc(F)c(C(=O)Nc2cccnc2C)cc1NC(=O)c1cnc(N)s1]

The title compound was prepared from 2-methylpyridin-3-amine and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-$d_6$) δ 10.39-10.34 (m, 1H), 9.62 (s, 1H), 8.31-8.24 (m, 1H), 7.85 (s, 1H), 7.72 (ddd, J=7.6, 1.9, 0.9 Hz, 1H), 7.64-7.56 (m, 3H), 7.29-7.21 (m, 2H), 2.25 (m, 6H). ESI MS [M+H]$^+$ for $C_{18}H_{17}F_1N_5O_2S_1$, calcd 386.1, found 386.1.

Example 251: 2-Amino-N-[5-[[5-(cyclopropylmethoxymethyl)pyridin-2-yl]carbamoyl]-4-fluoro-2-methylphenyl]-1,3-thiazole-5-carboxamide

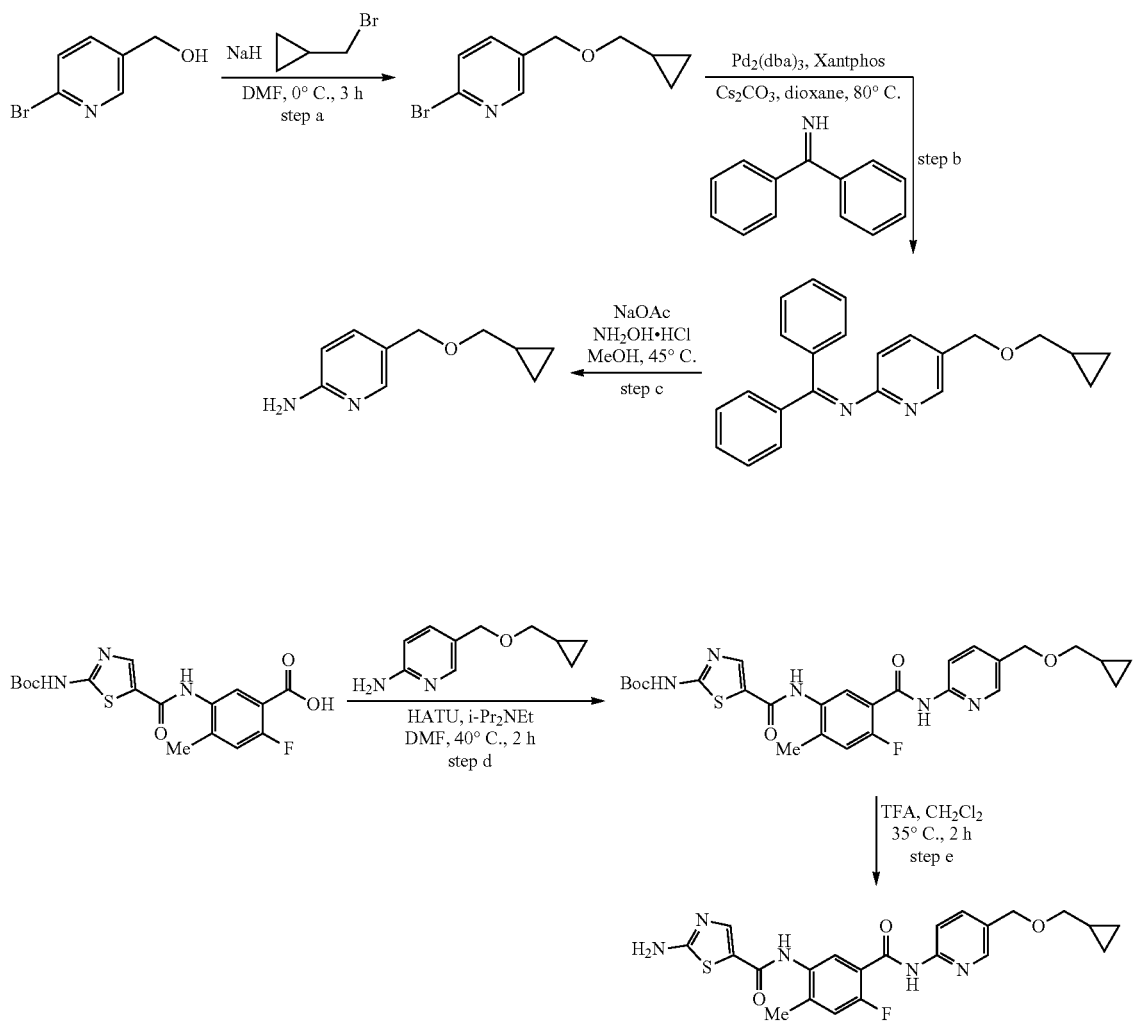

Step a: To a solution of (6-bromopyridin-3-yl)methanol (0.8 g, 4.3 mmol, 1.0 equiv.) in DMF (10 mL) at 0° C. was added NaH (60% in mineral oil, 255 mg, 6.4 mmol, 1.5 equiv.) and the resulting reaction mixture was stirred at 0° C. for 0.5 h. Bromomethylcyclopropane (862 mg, 6.4 mmol, 1.5 equiv.) was added. The reaction mixture was stirred for 3 h and allowed to warm to RT. The reaction mixture was then diluted with $H_2O$ and extracted three times with EtOAc. The combined organic extracts were dried over $Na_2SO_4$, filtered, and concentrated in vacuo to afford the crude product, which was purified by column chromatography (EtOAc/hexanes, 10% to 70%) to provide 2-bromo-5-(cyclopropylmethoxymethyl)pyridine.

Step b and Step c were performed in an analogous manner to Example 1, steps c and d.

Step d and Step e were performed in an analogous manner to Example 7. The crude product was purified by reverse phase HPLC to afford the title compound $^1$H NMR (400 MHz, Methanol-$d_4$) δ 8.30 (d, J=2.2 Hz, 1H), 8.23 (d, J=8.5 Hz, 1H), 7.85-7.72 (m, 3H), 7.21 (d, J=11.7 Hz, 1H), 4.53 (s, 2H), 3.36 (d, J=6.9 Hz, 2H), 2.33 (s, 3H), 1.14-1.04 (m, 1H), 0.57-0.48 (m, 2H), 0.21 (dt, J=6.1, 4.5 Hz, 2H). MS $[M+H]^+$ for $C_{22}H_{23}F_1N_5O_3S_1$, calcd 456.1, found 456.1.

Example 252: 2-Amino-N-[4-fluoro-5-[[5-(2-methoxyethoxy)pyridin-2-yl]carbamoyl]-2-methylphenyl]-1,3-thiazole-5-carboxamide

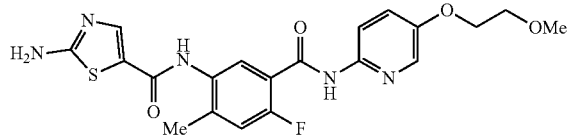 [SMILES: COCCOc1ccc(NC(=O)c2cc(NC(=O)c3cnc(N)s3)c(C)cc2F)nc1]

The title compound was prepared from 2-bromo-5-(2-methoxyethoxy)pyridine in a similar fashion to Example 251, Step b-e. $^1$H NMR (400 MHz, Methanol-$d_4$) δ 8.08-8.01 (m, 2H), 7.92 (s, 1H), 7.78 (d, J=7.0 Hz, 1H), 7.59 (dd, J=9.2, 2.9 Hz, 1H), 7.24 (d, J=11.4 Hz, 1H), 4.24-4.16 (m, 2H), 3.78-3.71 (m, 2H), 3.41 (s, 3H), 2.34 (s, 3H). ESI MS $[M+H]^+$ for $C_{20}H_{21}F_1N_5O_4S_1$, calcd 446.1, found 446.1.

Example 253: 2-Amino-N-[4-fluoro-2-methyl-5-[(1-propan-2-ylpyrazol-3-yl)methylcarbamoyl]phenyl]-1,3-thiazole-5-carboxamide

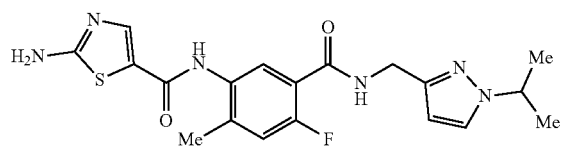 [SMILES: Cc1cc(F)c(C(=O)NCc2ccn(C(C)C)n2)cc1NC(=O)c1cnc(N)s1]

The title compound was prepared from (1-propan-2-ylpyrazol-3-yl)methanamine and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-$d_6$) δ 9.53 (s, 1H), 8.54 (td, J=5.8, 2.9 Hz, 1H), 7.77 (s, 1H), 7.62-7.54 (m, 3H), 7.47 (d, J=7.0 Hz, 1H), 7.14 (d, J=11.2 Hz, 1H), 6.06 (d, J=2.2 Hz, 1H), 4.36 (m, 3H), 2.17 (s, 3H), 1.33 (d, J=6.7 Hz, 6H). ESI MS $[M+H]^+$ for $C_{19}H_{22}F_1N_6O_2S_1$, calcd 417.1, found 417.2.

Example 254: 2-Amino-N-[5-[[5-(difluoromethoxymethyl)pyridin-2-yl]carbamoyl]-4-fluoro-2-methylphenyl]-1,3-thiazole-5-carboxamide

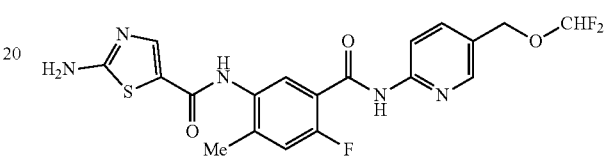

The title compound was prepared from 5-(difluoromethoxymethyl)pyridin-2-amine and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, Methanol-$d_4$) δ 8.26 (d, J=2.2 Hz, 1H), 8.19 (dd, J=8.6, 0.8 Hz, 1H), 7.78 (dd, J=8.6, 2.4 Hz, 1H), 7.74-7.65 (m, 2H), 7.14 (d, J=11.8 Hz, 1H), 6.42 (t, J=74.8 Hz, 1H), 4.84 (s, 2H), 2.26 (s, 3H). ESI MS $[M+H]^+$ for $C_{19}H_{17}F_3N_5O_3S_1$, calcd 452.1, found 452.1.

Example 255: 2-Amino-N-[5-[(5-ethylpyridin-2-yl)carbamoyl]-4-fluoro-2-methylphenyl]-1,3-thiazole-5-carboxamide

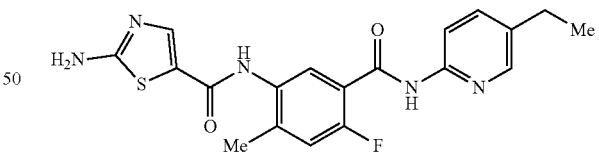

The title compound was prepared from 5-ethylpyridin-2-amine and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, Methanol-$d_4$) δ 8.18-8.09 (m, 2H), 7.80-7.71 (m, 2H), 7.68 (dd, J=8.5, 2.4 Hz, 1H), 7.20 (d, J=11.8 Hz, 1H), 2.64 (q, J=7.6 Hz, 2H), 2.32 (s, 3H), 1.23 (t, J=7.6 Hz, 3H). ESI MS $[M+H]^+$ for $C_{19}H_{19}F_1N_5O_2S_1$, calcd 400.1, found 400.2.

Example 256: 2-Amino-N-[4-fluoro-5-[[5-[(1R)-1-methoxyethyl]pyridin-2-yl]carbamoyl]-2-methylphenyl]-1,3-thiazole-5-carboxamide

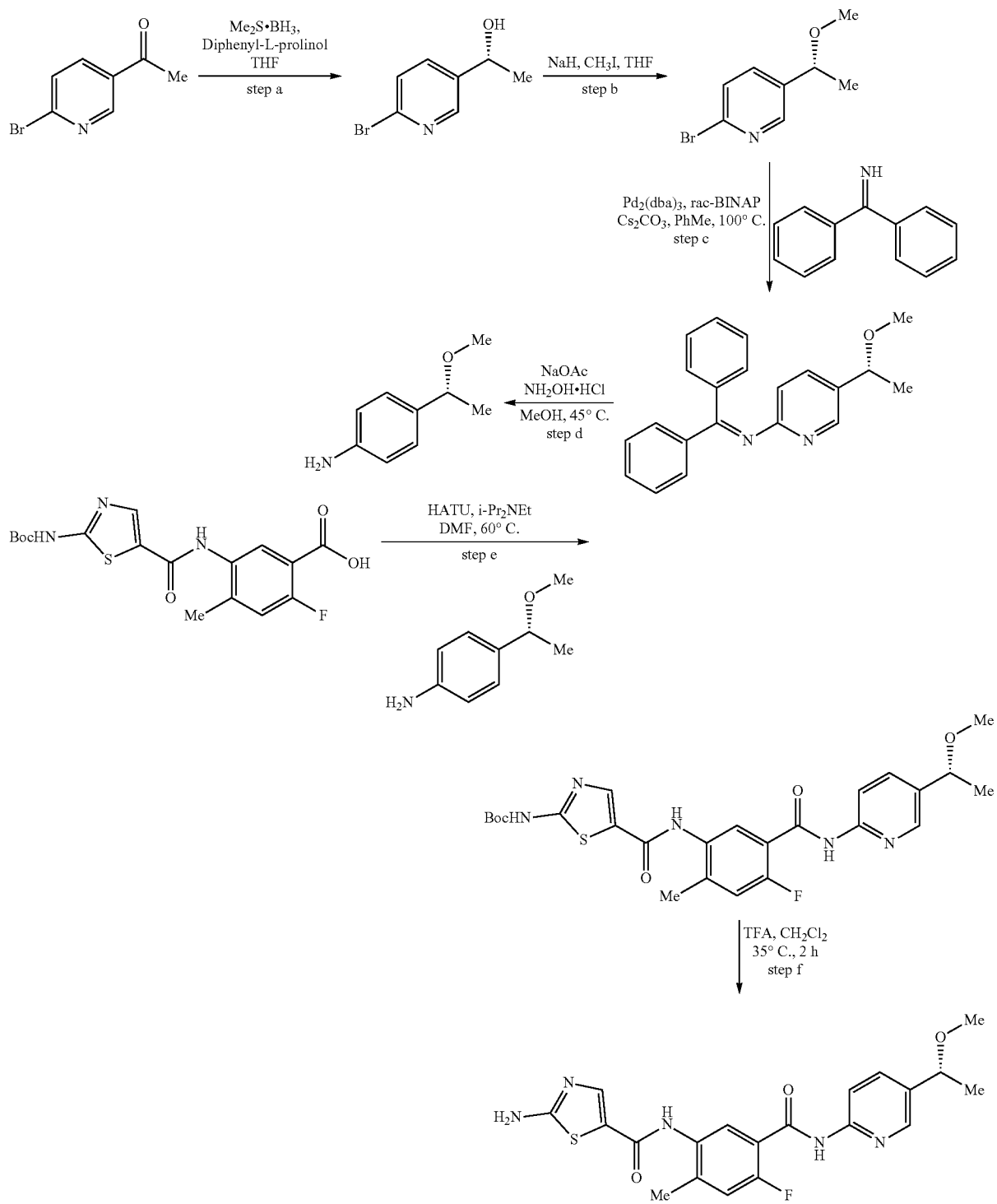

Step a: A vial was charged with (−)-diphenyl-2-prolinol (254.0 mg, 1.0 mmol., 0.2 equiv.) and was dissolved in THF (3.0 mL) and to the solution borane dimethyl sulfide complex (228.0 mg, 3.0 mmol., 0.7 equiv.) dissolved in THF (2.0 mL) was added dropwise under nitrogen. The mixture was stirred at 30° C. for 30 mins after which 1-(6-bromopyridin-3-yl)ethanone (1 g, 5.0 mmol., 1.0 equiv.) dissolved in THF (2.0 mL) was added and the mixture stirred further. After LC/MS analysis indicated complete conversion, the reaction was diluted with water and extracted thrice with EtOAc. The combined organic extracts were dried over $Na_2SO_4$ and concentrated in vacuo to afford the crude product, which was used directly for the next reaction without further purification.

Step b: A vial was charged with NaH (60% in mineral oil) (507 mg, 12.6 mmol., 2.0 equiv.) and dissolved in THF (10.0 mL) and cooled to 0° C. in an ice bath and stirred for 10 mins. The product from step a was dissolved in THF (5.0 mL) and added dropwise to the reaction mixture while maintaining the temperature below 10° C. The reaction mixture was stirred for 30 mins. To the reaction mixture MeI (897 mg, 6.0 mmol., 1.0 equiv.) was added and the resulting mixture stirred for 1 h. After LC/MS analysis indicated complete conversion, the reaction was diluted with water solution and extracted thrice with EtOAc. The combined organic extracts were dried over $Na_2SO_4$ and concentrated in vacuo and was purified by column chromatography (EtOAc/hexanes, 0% to 80%) to provide 1-bromo-4-[(1R)-1-methoxyethyl]benzene.

Step c and Step d were performed in an analogous manner to Example 1, steps c and d.

Step e and Step f: The title compound was prepared from 4-[(1R)-1-methoxyethyl]aniline and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-$d_6$) δ 10.80-10.46 (m, 1H), 9.73 (s, 1H), 8.23 (d, J=2.2 Hz, 1H), 8.09 (d, J=8.6 Hz, 3H), 7.86 (s, 1H), 7.73 (dd, J=8.6, 2.3 Hz, 1H), 7.54 (d, J=6.8 Hz, 1H), 7.21 (d, J=11.1 Hz, 1H), 4.30 (q, J=6.4 Hz, 1H), 2.43 (p, J=1.7 Hz, 3H), 2.20 (s, 3H), 1.30 (d, J=6.4 Hz, 3H). ESI MS [M+H]$^+$ for $C_{20}H_{21}F_1N_5O_3S_1$, calcd 430.1, found 430.0.

Example 257: 2-Amino-N-[4-fluoro-5-[[5-[(1S)-1-methoxyethyl]pyridin-2-yl]carbamoyl]-2-methylphenyl]-1,3-thiazole-5-carboxamide

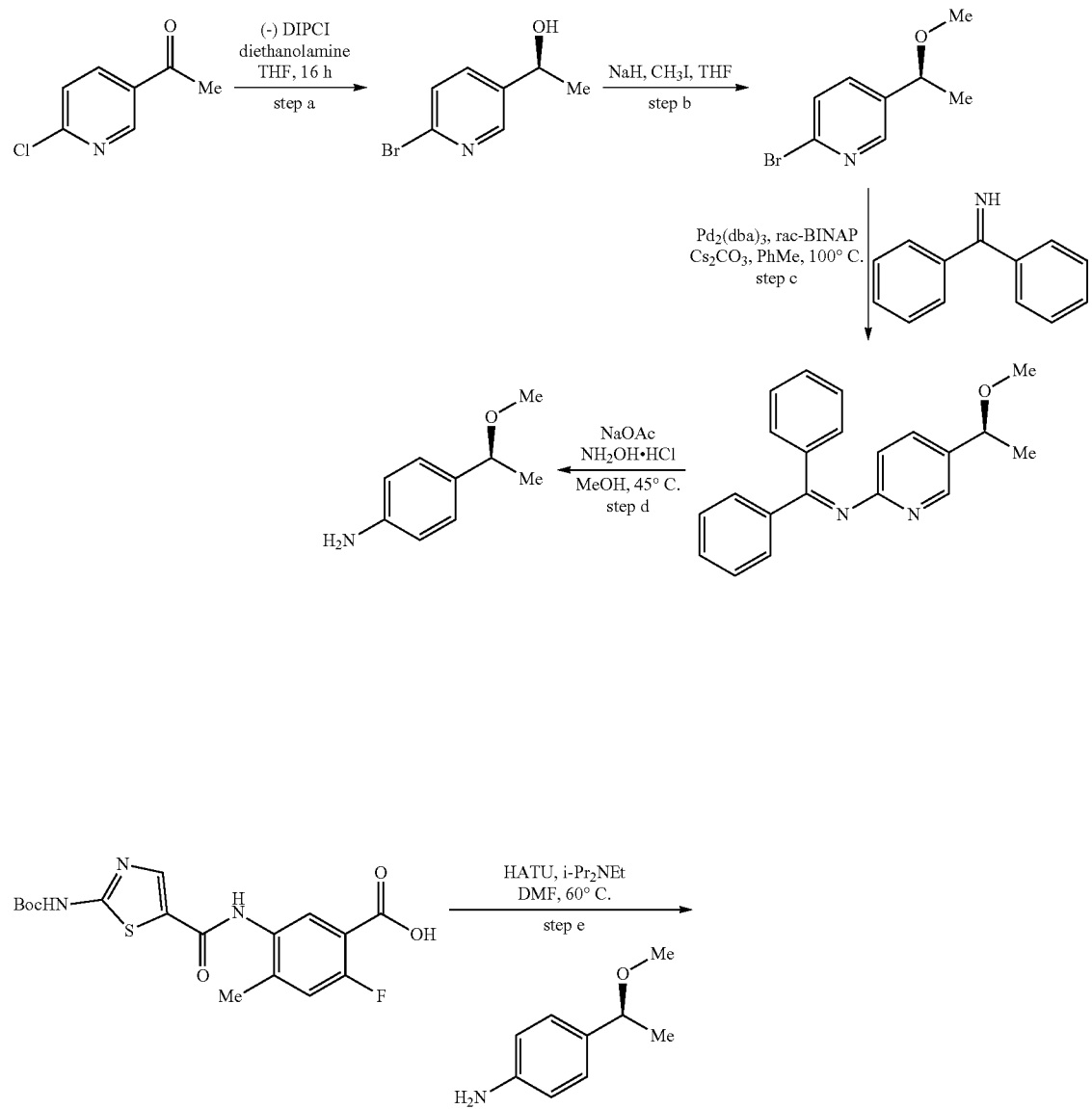

-continued

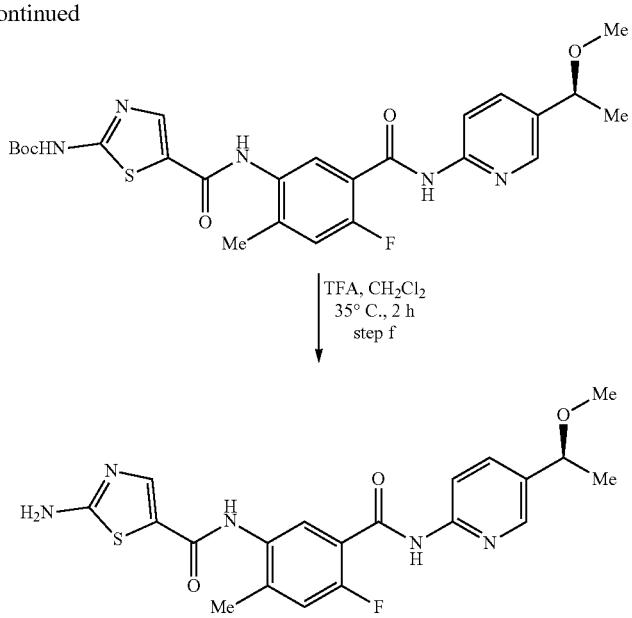

Step a: A vial was charged with (−)-DIPCl (3 g, 9.3 mmol., 1.5 equiv.) in THF (3.0 mL) and cooled to 0° C. To the cooled solution, 1-(6-chloropyridin-3-yl)ethanone (1 g, 6.0 mmol., 1.0 equiv.) dissolved in THF (3.0 mL) was added, and reaction was stirred for 16 h. After LC/MS analysis indicated complete conversion, the solvent was evaporated and to the crude residue, diethyl ether (5.0 mL) followed by diethanolamine was added and stirred at RT for 1 h. The precipitate thus formed was then filtered out, washed with ether multiple times and purified by column chromatography (MeOH/DCM, 0% to 50%) to provide (1S)-1-(4-bromophenyl)ethanol.

Step b was performed in an analogous manner to Example 256, step b.

Step c and Step d were performed in an analogous manner to Example 1, steps c and d.

Step e and Step f: The title compound was prepared from 4-[(1S)-1-methoxyethyl]aniline and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-$d_6$) δ 10.65 (d, J=2.5 Hz, 1H), 9.73 (s, 1H), 8.23 (d, J=2.2 Hz, 1H), 8.09 (dd, J=8.6, 1.8 Hz, 3H), 7.86 (d, J=1.9 Hz, 1H), 7.73 (dd, J=8.6, 2.3 Hz, 1H), 7.54 (dd, J=6.8, 1.9 Hz, 1H), 7.21 (d, J=10.8 Hz, 1H), 4.45-4.16 (m, 1H), 2.43 (p, J=1.8 Hz, 3H), 2.20 (d, J=2.0 Hz, 3H), 1.30 (dd, J=6.7, 2.0 Hz, 3H). ESI MS [M+H]$^+$ for $C_{20}H_{21}FN_5O_3S_1$, calcd 430.1, found 430.0.

Example 258: 2-Amino-N-[5-[(6-cyclopropyloxy-pyridazin-3-yl)carbamoyl]-4-fluoro-2-methylphenyl]-1,3-thiazole-5-carboxamide

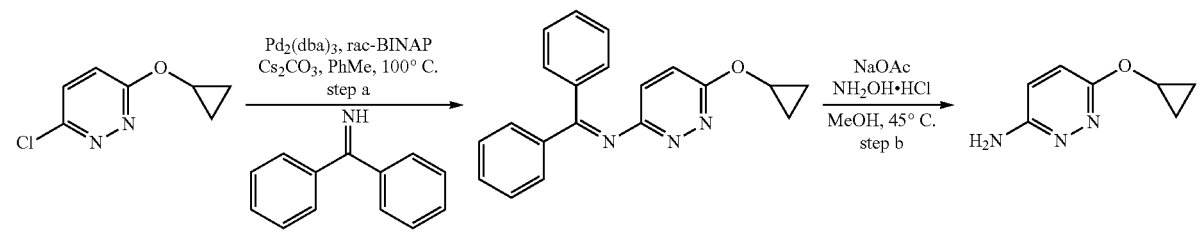

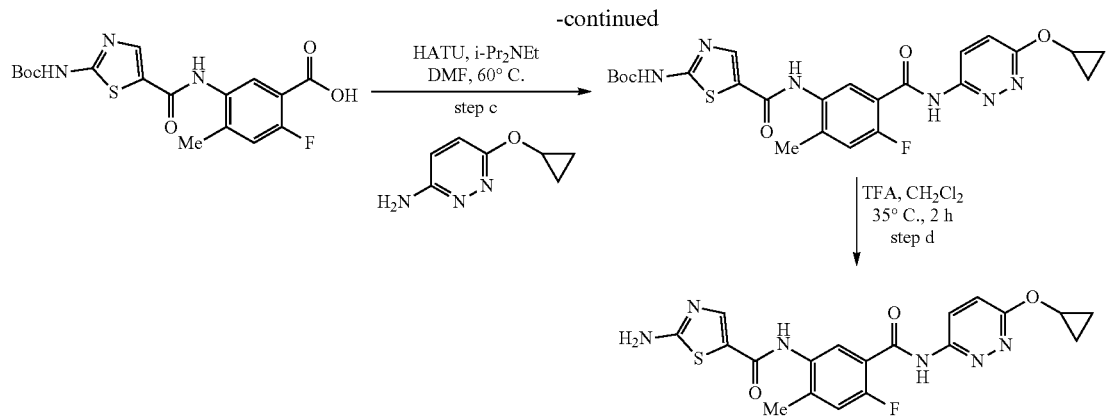

Step a and Step b were performed in an analogous manner to Example 1, steps c and d with 3-chloro-6-cyclopropyloxypyridazine.

Step c and Step d: The title compound was prepared from 6-cyclopropyloxypyridazin-3-amine and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, Methanol-$d_4$) δ 8.44 (d, J=9.6 Hz, 1H), 7.79 (s, 1H), 7.78-7.46 (m, 1H), 7.45-6.74 (m, 2H), 4.55-4.00 (m, 1H), 2.33 (s, 3H), 1.05-0.40 (m, 4H)·ESI MS [M+H]$^+$ for $C_{19}H_{18}FN_6O_3S_1$, calcd 429.1, found 429.0.

Example 259: 2-Amino-N-[4-fluoro-2-methyl-5-[(6-propan-2-yloxypyridazin-3-yl)carbamoyl]phenyl]-1,3-thiazole-5-carboxamide

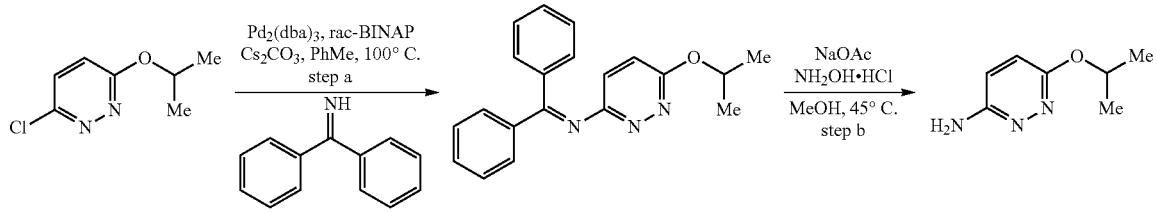

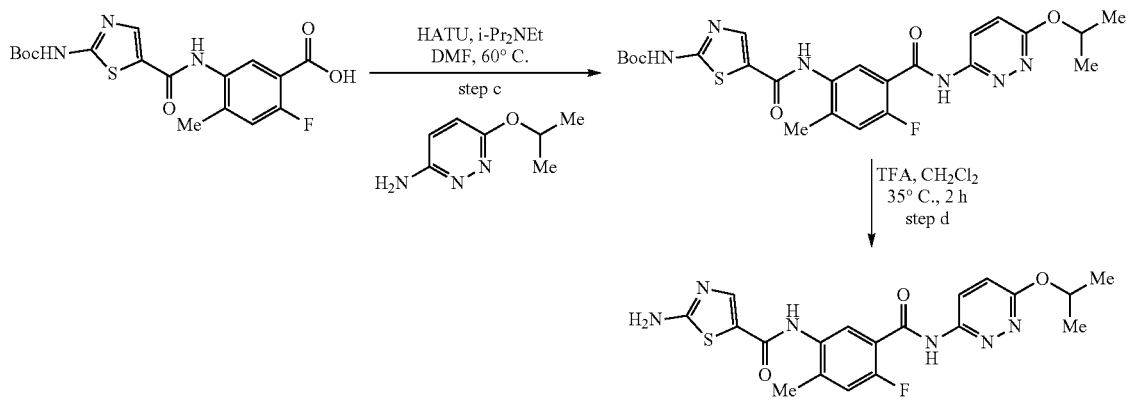

Step a and Step b were performed in an analogous manner to Example 1, steps c and d.

Step c and Step d: The title compound was prepared from 6-propan-2-yloxypyridazin-3-amine and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-$d_6$) δ 11.55-9.98 (m, 1H), 9.74 (s, 1H), 8.22 (d, J=9.5 Hz, 1H), 8.00 (s, 2H), 7.90 (s, 1H), 7.58 (d, J=7.0 Hz, 1H), 7.25 (d, J=11.1 Hz, 1H), 7.19 (d, J=9.5 Hz, 1H), 5.35 (p, J=6.2 Hz, 1H), 2.24 (s, 3H), 1.32 (d, J=6.1 Hz, 6H)·ESI MS [M+H]$^+$ for $C_{19}H_{20}FN_6O_3S_1$, calcd 431.1, found 431.0.

Example 260: 2-Amino-N-[4-fluoro-5-[[5-(1-methoxycyclopropyl)pyridin-2-yl]carbamoyl]-2-methylphenyl]-1,3-thiazole-5-carboxamide

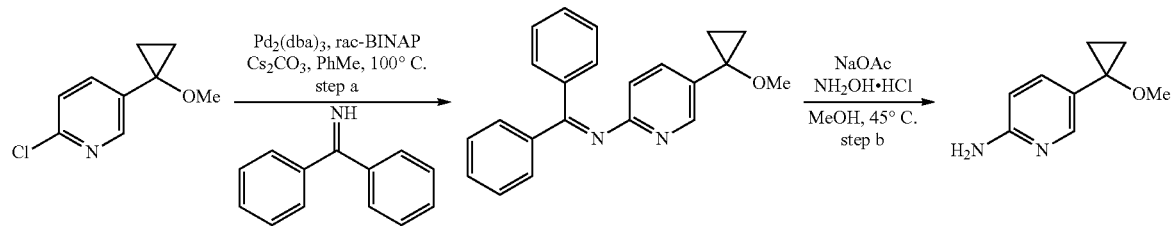

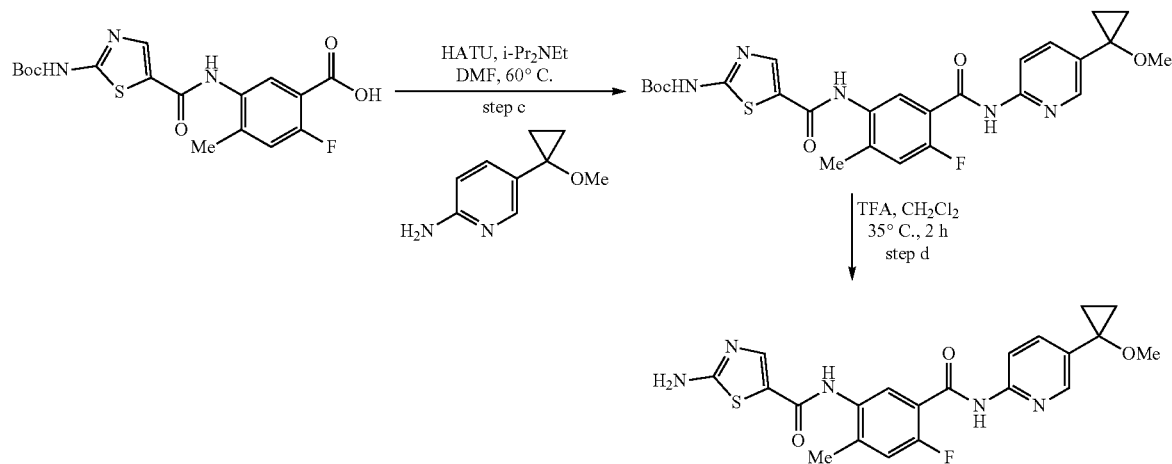

Step a and Step b were performed in an analogous manner to Example 1, steps c and d.

Step c and Step d: The title compound was prepared from 5-(1-methoxycyclopropyl)pyridin-2-amine and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, DMSO-$d_6$) δ 10.64 (d, J=2.5 Hz, 1H), 9.61 (s, 1H), 8.33-8.18 (m, 1H), 8.12 (d, J=8.6 Hz, 1H), 7.80 (d, J=11.3 Hz, 1H), 7.70 (dd, J=8.6, 2.5 Hz, 1H), 7.64-7.38 (m, 2H), 7.23 (d, J=11.2 Hz, 1H), 3.12 (s, 3H), 2.23 (s, 3H), 2.18 (s, 1H), 1.32-1.07 (m, 2H), 1.06-0.82 (m, 2H). ESI MS [M+H]$^+$ for $C_{21}H_{21}FN_5O_3S_1$, calcd 442.1, found 442.0.

Example 261: 2-Amino-N-[5-[(6-cyclopropyloxy-pyridazin-3-yl)carbamoyl]-4-fluoro-2-methylphenyl]-1,3-thiazole-5-carboxamide

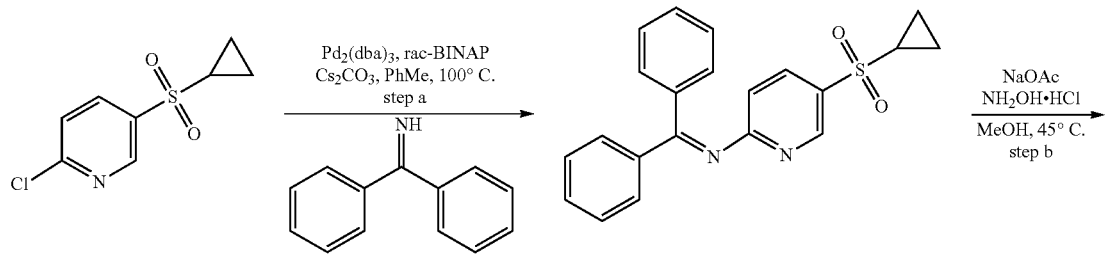

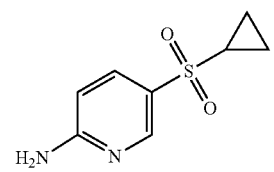

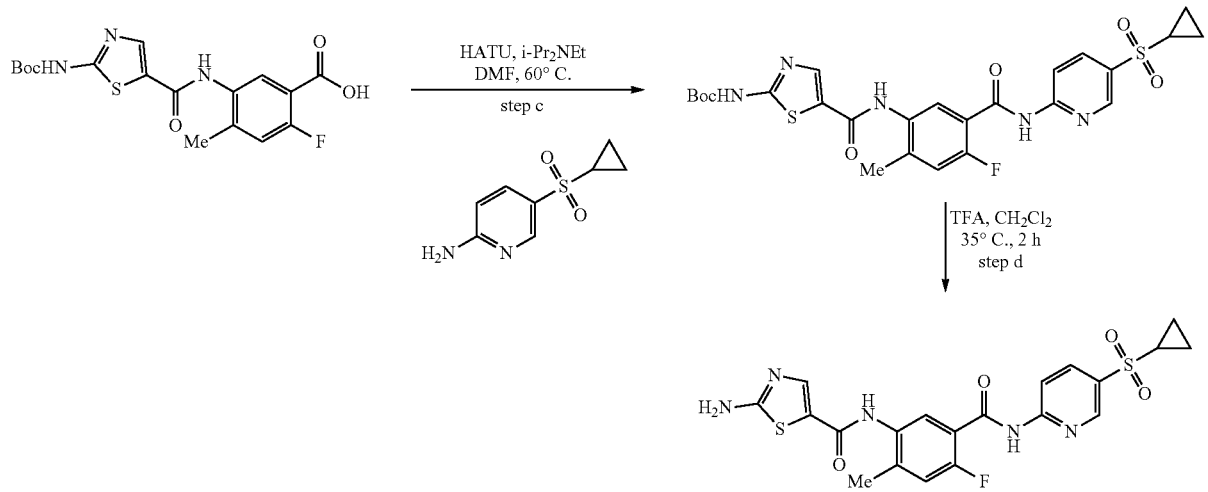

Step a and Step b were performed in an analogous manner to Example 1, steps c and d.

Step c and Step d: The title compound was prepared from 5-cyclopropylsulfonylpyridin-2-amine and 2-fluoro-4-methyl-5-[[2-[(2-methylpropan-2-yl)oxycarbonylamino]-1,3-thiazole-5-carbonyl]amino]benzoic acid in a similar fashion to Example 7. $^1$H NMR (400 MHz, Methanol-d$_4$) δ 8.77 (dt, J=2.5, 0.7 Hz, 1H), 8.47 (dt, J=8.9, 0.6 Hz, 1H), 8.27 (dd, J=8.8, 2.4 Hz, 1H), 7.89 (s, 1H), 7.75 (d, J=6.9 Hz, 1H), 7.23 (d, J=11.5 Hz, 1H), 2.73 (tt, J=7.9, 4.8 Hz, 1H), 2.33 (s, 3H), 1.25 (dd, J=4.8, 2.5 Hz, 2H), 1.08 (dd, J=7.8, 2.6 Hz, 2H). ESI MS [M+H]$^+$ for C$_{20}$H$_{19}$FN$_5$O$_4$S$_2$, calcd 476.1, found 476.1.

Example 262: N-[4-fluoro-5-[(4-fluorophenyl)methylcarbamoyl]-2-methylphenyl]-2-methyl-1,3-thiazole-5-carboxamide

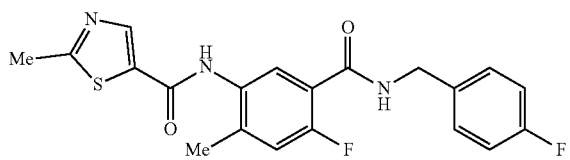 [SMILES: Cc1ncc(C(=O)Nc2cc(C(=O)NCc3ccc(F)cc3)c(F)cc2C)s1]

The title compound was prepared from (4-fluorophenyl)methanamine and 2-fluoro-4-methyl-5-[(2-methyl-1,3-thiazole-5-carbonyl)amino]benzoic acid in a similar fashion to Example 12. $^1$H NMR (400 MHz, Chloroform-d) δ 8.45 (s, 1H), 8.23 (s, 1H), 7.91 (d, J=7.2 Hz, 1H), 7.31-7.26 (m, 2H), 7.13 (dt, J=11.1, 5.7 Hz, 1H), 7.06-6.95 (m, 2H), 6.91 (d, J=12.0 Hz, 1H), 4.60 (d, J=5.6 Hz, 2H), 2.73 (s, 3H), 2.24 (s, 3H). ESI MS [M+H]$^+$ for C$_{20}$H$_{18}$F$_2$N$_3$O$_2$S$_1$ calcd 402.1, found 402.1

Example 263: N-[5-[(2,4-difluorophenyl)methylcarbamoyl]-4-fluoro-2-methylphenyl]-2-methyl-1,3-thiazole-5-carboxamide

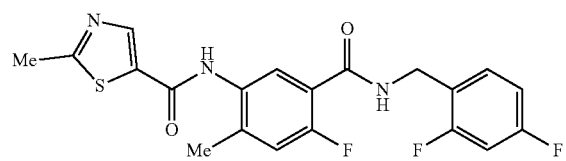 [SMILES: Cc1ncc(C(=O)Nc2cc(C(=O)NCc3ccc(F)cc3F)c(F)cc2C)s1]

The title compound was prepared from (2,4-difluorophenyl)methanamine and 2-fluoro-4-methyl-5-[(2-methyl-1,3-thiazole-5-carbonyl)amino]benzoic acid in a similar fashion to Example 12. $^1$H NMR (400 MHz, Chloroform-d) δ 8.58 (s, 1H), 8.24 (s, 1H), 7.84 (d, J=7.3 Hz, 1H), 7.35 (td, J=8.7, 8.3, 6.3 Hz, 1H), 7.23 (dd, J=11.1, 5.6 Hz, 1H), 6.91-6.83 (m, 1H), 6.83-6.75 (m, 2H), 4.62 (d, J=5.8 Hz, 2H), 2.73 (s, 3H), 2.20 (s, 3H). ESI MS [M+H]$^+$ for C$_{20}$H$_{17}$F$_3$N$_3$O$_2$S$_1$ calcd 420.1, found 420.1

Example 264: N-[5-[(3,5-difluorophenyl)methylcarbamoyl]-4-fluoro-2-methylphenyl]-2-methyl-1,3-thiazole-5-carboxamide

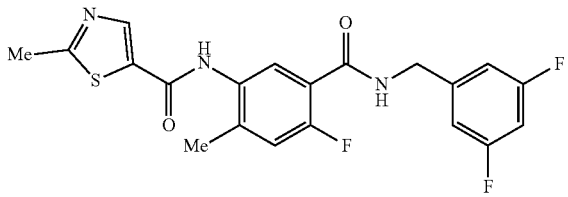 [SMILES: Cc1ncc(C(=O)Nc2cc(C(=O)NCc3cc(F)cc(F)c3)c(F)cc2C)s1]

The title compound was prepared from (3,5-difluorophenyl)methanamine and 2-fluoro-4-methyl-5-[(2-methyl-1,3-thiazole-5-carbonyl)amino]benzoic acid in a similar fashion to Example 12. $^1$H NMR (400 MHz, Chloroform-d) δ 8.19 (s, 1H), 8.07 (s, 1H), 8.01 (d, J=7.3 Hz, 1H), 7.16 (dd, J=11.8, 6.2 Hz, 1H), 6.98 (d, J=12.1 Hz, 1H), 6.84 (d, J=7.0 Hz, 2H), 6.76-6.66 (m, 1H), 4.63 (d, J=5.9 Hz, 2H), 2.75 (s, 3H), 2.28 (s, 3H). ESI MS [M+H]$^+$ for C$_{20}$H$_{17}$F$_3$N$_3$O$_2$S$_1$ calcd 420.1, found 420.1.

Example 265: N-[5-[(2,3-difluorophenyl)methylcarbamoyl]-4-fluoro-2-methylphenyl]-2-methyl-1,3-thiazole-5-carboxamide

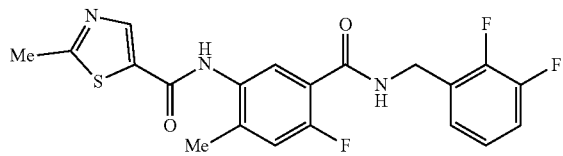 [SMILES: Cc1ncc(C(=O)Nc2cc(C(=O)NCc3cccc(F)c3F)c(F)cc2C)s1]

The title compound was prepared from (2,3-difluorophenyl)methanamine and 2-fluoro-4-methyl-5-[(2-methyl-1,3-thiazole-5-carbonyl)amino]benzoic acid in a similar fashion to Example 12. $^1$H NMR (400 MHz, Chloroform-d) δ 8.19 (s, 1H), 8.04 (s, 1H), 8.00 (d, J=7.3 Hz, 1H), 7.18-7.00 (m, 4H), 6.96 (d, J=12.1 Hz, 1H), 4.75-4.68 (m, 2H), 2.75 (s, 3H), 2.27 (s, 3H). ESI MS [M+H]$^+$ for C$_{20}$H$_{17}$F$_3$N$_3$O$_2$S$_1$ calcd 420.1, found 420.1.

Example 266: N-[5-[(3,4-difluorophenyl)methylcarbamoyl]-4-fluoro-2-methylphenyl]-2-methyl-1,3-thiazole-5-carboxamide

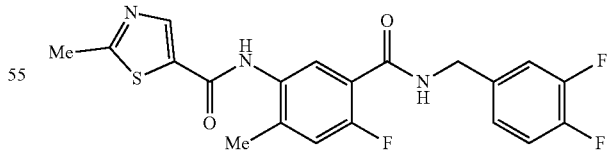

The title compound was prepared from (3,4-difluorophenyl)methanamine and 2-fluoro-4-methyl-5-[(2-methyl-1,3-thiazole-5-carbonyl)amino]benzoic acid in a similar fashion to Example 12. $^1$H NMR (400 MHz, Chloroform-d) δ 8.19 (s, 1H), 8.02 (d, J=7.4 Hz, 2H), 7.18-7.02 (m, 4H), 6.97 (d, J=12.1 Hz, 1H), 4.60 (d, J=5.8 Hz, 2H), 2.75 (s, 3H), 2.29 (s, 3H). ESI MS [M+H]$^+$ for C$_{20}$H$_{17}$F$_3$N$_3$O$_2$S$_1$ calcd 420.1, found 420.1.

Example 267: N-[4-fluoro-2-methyl-5-[[4-(trifluoromethoxy)phenyl]methylcarbamoyl]phenyl]-2-methyl-1,3-thiazole-5-carboxamide

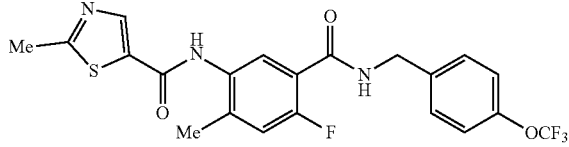 [SMILES: Cc1ncc(C(=O)Nc2cc(C(=O)NCc3ccc(OC(F)(F)F)cc3)c(F)cc2C)s1]

The title compound was prepared from [4-(trifluoromethoxy)phenyl]methanamine and 2-fluoro-4-methyl-5-[(2-methyl-1,3-thiazole-5-carbonyl)amino]benzoic acid in a similar fashion to Example 12. $^1$H NMR (400 MHz, Chloroform-d) δ 9.06 (s, 1H), 8.25 (s, 1H), 7.67 (d, J=7.1 Hz, 1H), 7.50 (dd, J=9.7, 5.3 Hz, 1H), 7.32 (d, J=8.1 Hz, 2H), 7.14 (d, J=8.1 Hz, 2H), 6.75 (d, J=11.6 Hz, 1H), 4.59 (d, J=5.7 Hz, 2H), 2.67 (s, 3H), 2.10 (s, 3H). ESI MS [M+H]$^+$ for $C_{21}H_{18}F_4N_3O_3S_1$ calcd 468.1, found 468.1.

Example 268: N-[4-fluoro-2-methyl-5-[[4-(trifluoromethyl)phenyl]methylcarbamoyl]phenyl]-2-methyl-1,3-thiazole-5-carboxamide

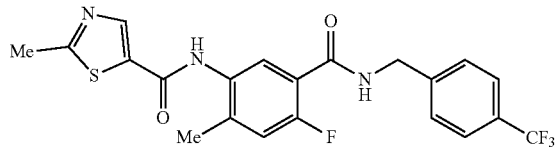 [SMILES: Cc1ncc(C(=O)Nc2cc(C(=O)NCc3ccc(C(F)(F)F)cc3)c(F)cc2C)s1]

The title compound was prepared from [4-(trifluoromethyl)phenyl]methanamine and 2-fluoro-4-methyl-5-[(2-methyl-1,3-thiazole-5-carbonyl)amino]benzoic acid in a similar fashion to Example 12. $^1$H NMR (400 MHz, Chloroform-d) δ 9.02 (s, 1H), 8.24 (s, 1H), 7.67 (d, J=7.0 Hz, 1H), 7.62-7.50 (m, 3H), 7.39 (d, J=8.0 Hz, 2H), 6.75 (d, J=11.7 Hz, 1H), 4.64 (d, J=5.7 Hz, 2H), 2.67 (s, 3H), 2.10 (s, 3H). ESI MS [M+H]$^+$ for $C_{21}H_{18}F_4N_3O_2S_1$ calcd 452.1, found 452.1.

Example 269: N-[4-fluoro-5-[[3-fluoro-4-(trifluoromethoxy)phenyl]methylcarbamoyl]-2-methylphenyl]-2-methyl-1,3-thiazole-5-carboxamide

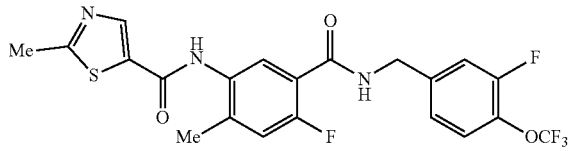 [SMILES: Cc1ncc(C(=O)Nc2cc(C(=O)NCc3ccc(OC(F)(F)F)c(F)c3)c(F)cc2C)s1]

The title compound was prepared from [3-fluoro-4-(trifluoromethoxy)phenyl]methanamine and 2-fluoro-4-methyl-5-[(2-methyl-1,3-thiazole-5-carbonyl)amino]benzoic acid in a similar fashion to Example 12. $^1$H NMR (400 MHz, DMSO-d$_6$) δ 10.13 (s, 1H), 8.91 (q, J=5.5 Hz, 1H), 8.39 (s, 1H), 7.63-7.50 (m, 2H), 7.43 (dd, J=11.4, 2.0 Hz, 1H), 7.33-7.24 (m, 2H), 4.50 (d, J=5.9 Hz, 2H), 2.71 (s, 3H), 2.26 (s, 3H). ESI MS [M+H]$^+$ for $C_{21}H_{17}F_5N_3O_3S_1$ calcd 486.1, found 486.1.

Example 270: N-[4-fluoro-5-[[2-fluoro-4-(trifluoromethoxy)phenyl]methylcarbamoyl]-2-methylphenyl]-2-methyl-1,3-thiazole-5-carboxamide

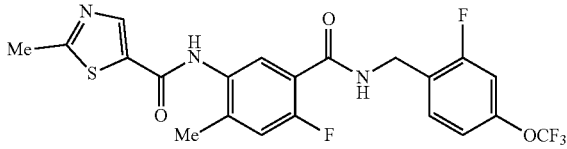 [SMILES: Cc1ncc(C(=O)Nc2cc(C(=O)NCc3ccc(OC(F)(F)F)cc3F)c(F)cc2C)s1]

The title compound was prepared from [2-fluoro-4-(trifluoromethoxy)phenyl]methanamine and 2-fluoro-4-methyl-5-[(2-methyl-1,3-thiazole-5-carbonyl)amino]benzoic acid in a similar fashion to Example 12. $^1$H NMR (400 MHz, DMSO-d$_6$) δ 10.13 (s, 1H), 8.87 (td, J=5.9, 2.5 Hz, 1H), 8.39 (s, 1H), 7.58 (d, J=7.0 Hz, 1H), 7.51 (t, J=8.5 Hz, 1H), 7.39 (dd, J=10.4, 2.3 Hz, 1H), 7.32-7.22 (m, 2H), 4.51 (d, J=5.7 Hz, 2H), 2.71 (s, 3H), 2.26 (s, 3H). ESI MS [M+H]$^+$ for $C_{21}H_{17}F_5N_3O_3S_1$ calcd 486.1, found 486.1.

Biological Example

Inhibition of c-Kit, PDGFRα, PDGFRβ, CSF1R and FLT3 Kinase Activity

Compounds were evaluated to determine the potency with which they inhibit the kinase activity of the following panel of tyrosine kinases: c-Kit (SignalChem, Product #: K06-11BG), PDGFRα (SignalChem, Product #: P12-18G), PDGFRβ (SignalChem, Product #: P13-11G), CSF1R (SignalChem, Product #: C$_{74}$-11G) and FLT3 (Invitrogen, Product #: PR4666C). Activity was determined as a function of phosphorylated biotinylated TK peptide generated by the transfer of phosphate from ATP as measured by the use of the HTRF KinEASE-TK assay kit (Cisbio, Product #: 62TK0PEJ). Levels of phosphorylated biotinylated TK peptide (Part 61TK0BLC of KinEASE assay kit) are quantified by its capture by phosphor-TK-Antibody-Cryptate (Part of KinEASE assay kit) and XL665-labeled Streptavidin (Part 610SAXLG of KinEASE assay kit) followed by measurement of Time-Resolved Fluorescence Resonance Energy Transfer (TR-FRET) signal. On the day of the assay, compounds were solubilized in DMSO and dispensed into a 384-well white Opti-plate (PerkinElmer, catalog #6007290) to generate a 22 point 1:2 titration. Enzyme solution was prepared for each of the tyrosine kinases in 50 mM HEPES, pH 7.4, 5 mM MgCl$_2$ for c-Kit or 10 mM MgCl$_2$ for FLT3, CSF1R, PDGFRα and PDGFRβ, 2 mM MnCl$_2$, 0.01% Brij-35 and 0.01% BSA. Working enzyme concentrations were prepared for c-Kit at 2 nM (2×), PDGFRα and PDGFRβ at 10 nM (2×), CSF1R at 2 nM (2×) and FLT3 at 0.4 nM (2×). Five microliters of enzyme dilution of each tyrosine kinase were added to their respective 384-well white Opti-plate pre-dispensed with compound and allowed to incubate for 1 h at rt. Utilizing the same enzyme buffer recipe, 2× substrate mixes were prepared for each enzyme as follows: For c-Kit, 1.6 µM (2×) TK substrate and 16 µM (2×) ATP (Promega, catalog #V915). For PDGFRα, 3.2 M TK substrate and 1 µM ATP. For PDGFRβ, 3.2 µM TK substrate and 40 M ATP. For CSF1R, 3.2 M TK substrate and 20 M ATP. For FLT3, 3.2 M TK substrate and 100 M ATP. Reactions were initiated by addition of 5 µL of the respective 2× substrate mix to each well of the plates containing the respective tyrosine kinase enzymes and were allowed to proceed for 120 minutes at rt, except for FLT3, the reaction time is 45 min. Following the reaction, 10 L of detection mix consisting of 0.2 M (2×) of Streptavidin-XL665 and 2 M (2×) of TK-Antibody-Cryptate prepared in detection buffer (Part 62SDBRDF of KinEASE assay kit) was added and then allowed to incubate for 60 min. The TR-FRET signal was quantified by measuring the ratio of emission at 665 nm to 620 nm after excitation at 320 nm by reading on a PerkinElmer Envision multimode reader. Compound potencies ($IC_{50}$ values) were determined using a standard 4-parameter non-linear regression fit.

Phospho-KIT (Y703) Cellular Assay in M07e Cells

The day prior to assay, M07e cells (DSMZ, catalog #ACC 104) were serum starved. Cells were centrifuged and cell pellet resuspended in OptiMEM (Gibco, catalog #31985062) to a density of $1 \times 10^6$-$2.5 \times 10^6$ cells per mL. Cells were then incubated overnight at 5% $CO_2$ and 37° C. in an appropriately sized flask. On the day of the experiment, an 11 point, half log titration of test compound was pre-dispensed into 96-well round bottom polypropylene plates (Corning, catalog #3365). The serum starved M07e cells were centrifuged and resuspended to a cell density of $1 \times 10^6$ cells per mL with DPBS (Gibco, catalog #14190-144). Live/Dead Green Fixable viability dye (Invitrogen, catalog #L34970) was added as 1 μL/1 mL of cell suspension. Cells were then incubated in the dark at 4° C. for 30 min. Cells were washed by centrifugation and resuspension with DPBS+0.5% BSA (Gemini Bio Products, catalog #700110/100, 30% BSA solution). Cells were resuspended, separated into two equal volumes and again centrifuged. Cell pellets were resuspended with OptiMEM™ to a cell density of $1 \times 10^6$ cells per mL. Cells were then added to the appropriate compound plate at 100,000 cells per well in 100 μL and mixed. Plates were incubated at 5% $CO_2$ and 37° C. for 50 min. Stem Cell Factor, SCF (R&D Systems, #255-SC/CF) was diluted in OptiMEM to 1 μg/mL and added to all wells as 10 μL for a final concentration of 90.9 ng/mL. Plates were incubated at 5% $CO_2$ and 37° C. for 10 min. Incubation was stopped by addition of 110 μL 4% paraformaldehyde solution in PBS (Life Technologies, catalog #J19943.K2). Plates were incubated at rt for at least 15 min. Plates were then centrifuged and supernatant removed by flicking. Cells were washed once by resuspension in 200 μL DPBS+0.5% BSA, centrifuged, and supernatant removed by flicking. Cells were resuspended in 100 μL 1× Permeabilization buffer (Invitrogen, catalog #88882400) and plates incubated at rt for 30 min. Plates were centrifuged, supernatant removed by flicking, and cells resuspended in 50 μL primary antibody, anti-phospho-c-KIT (Tyr703) (Cell Signaling, catalog #3073), diluted to 1 μg/mL with permeabilization buffer. Plates were incubated at rt for 1 h. Plates were centrifuged, supernatant removed, and cells resuspended with 200 μL DPBS+0.5% BSA. Plates were again centrifuged, supernatant removed by flicking, and cells resuspended in 100 μL secondary antibody, goat anti-rabbit AlexaFluor647 (AF647) (Invitrogen, catalog #A21244) diluted to 1 g/mL with DPBS+0.50% BSA. Plates were incubated at rt for 30 min. followed by centrifugation, supernatant removal, and cell resuspension with 200 μL DPBS+0.5% BSA. Cells were washed again by centrifugation, supernatant removal, and cell resuspension with 200 μL DPBS+0.5% BSA. Samples were then read by flow cytometry. The Forward: Side scatter plot was gated and that population was gated for live cells based on the Live/Dead Green staining. The geometric mean of AF647 of the live cell population was recorded. Percentage maximum activity in each test well was calculated based on DMSO (100% activity) and positive control treated cell wells (000 activity). The potencies ($IC_{50}$ values) of test compounds were determined using a standard 4-parameter non-linear regression fit.

Representative data are shown in Table 3 and Table 4.

TABLE 3

Biochemical and cellular potency of specific examples vs. KIT, PDGFRα, PDGFRβ, CSF1R, and FLT3 ($IC_{50}$: + means >1 μM, ++ means 100 nM to 1 μM, +++ means <100 nM). ND = not determined.

| Ex. | KIT $IC_{50}$ | PDGFRα $IC_{50}$ | PDGFRβ $IC_{50}$ | CSF1R $IC_{50}$ | FLT3 $IC_{50}$ | M07e Cell $IC_{50}$ |
|---|---|---|---|---|---|---|
| 1 | +++ | + | + | + | + | +++ |
| 2 | +++ | + | + | + | + | +++ |
| 3 | +++ | + | + | + | + | +++ |
| 4 | +++ | + | + | + | + | +++ |
| 5 | +++ | + | + | + | + | +++ |
| 6 | +++ | +++ | +++ | +++ | + | ND |
| 7 | +++ | ++ | +++ | ++ | + | +++ |
| 8 | +++ | ++ | ++ | ++ | + | +++ |
| 9 | +++ | + | ++ | ++ | + | +++ |
| 10 | +++ | + | + | + | + | +++ |
| 11 | +++ | ++ | +++ | ++ | + | +++ |

TABLE 4

Biochemical and cellular potency of specific examples vs. KIT, PDGFRα, PDGFRβ, CSF1R, and FLT3 ($IC_{50}$: + means >1 μM, ++ means 100 nM to 1 μM, +++ means <100 nM). ND = not determined.

| Ex. | KIT $IC_{50}$ | PDGFRα $IC_{50}$ | PDGFRβ $IC_{50}$ | CSF1R $IC_{50}$ | FLT3 $IC_{50}$ | M07e Cell $IC_{50}$ |
|---|---|---|---|---|---|---|
| 12 | ++ | + | + | + | ND | ++ |
| 13 | +++ | ND | ND | + | + | +++ |
| 14 | +++ | + | + | + | + | ND |
| 15 | +++ | ND | ND | + | ND | +++ |
| 16 | +++ | + | + | + | ND | ND |
| 17 | +++ | + | + | + | + | +++ |
| 18 | +++ | ND | ND | + | ND | ++ |
| 19 | ++ | ND | ND | + | ND | ++ |
| 20 | +++ | + | + | + | + | +++ |
| 21 | +++ | ND | ND | + | ND | +++ |
| 22 | +++ | ND | ND | + | ND | ++ |
| 23 | +++ | ND | ND | + | ND | ++ |
| 24 | +++ | ND | ND | + | + | +++ |
| 25 | +++ | + | ++ | + | ND | +++ |
| 26 | +++ | + | + | + | ND | ND |
| 27 | +++ | ND | ND | + | ND | +++ |
| 28 | +++ | ND | ND | + | ND | +++ |
| 29 | +++ | ND | ND | + | ND | +++ |
| 30 | ++ | ND | ND | + | ND | +++ |
| 31 | +++ | + | + | + | + | +++ |
| 32 | +++ | + | + | + | ND | +++ |
| 33 | +++ | ND | ND | + | ND | ++ |
| 34 | +++ | ND | ND | + | ND | +++ |
| 35 | +++ | + | + | + | ND | ND |
| 36 | +++ | + | + | + | ND | +++ |
| 37 | ++ | + | + | + | ND | ND |
| 38 | +++ | + | + | + | + | +++ |
| 39 | +++ | + | + | + | ND | +++ |
| 40 | +++ | + | + | + | + | +++ |
| 41 | +++ | + | + | + | ND | ND |
| 42 | +++ | + | + | + | ND | ND |
| 43 | +++ | + | + | + | ND | ND |
| 44 | +++ | + | + | + | + | ND |
| 45 | +++ | + | + | + | + | +++ |
| 46 | +++ | + | + | + | + | +++ |
| 47 | ++ | + | + | + | ND | ND |
| 48 | +++ | + | + | + | ND | +++ |
| 49 | +++ | + | + | + | ND | +++ |
| 50 | +++ | ++ | + | ++ | ND | +++ |
| 51 | ++ | + | + | + | ND | +++ |
| 52 | +++ | + | + | + | ND | +++ |
| 53 | +++ | ND | ND | + | ND | +++ |
| 54 | +++ | ND | ND | ND | ND | |

TABLE 4-continued

Biochemical and cellular potency of specific examples vs. KIT, PDGFRα, PDGFRβ, CSF1R, and FLT3 (IC$_{50}$: + means >1 μM, ++ means 100 nM to 1 μM, +++ means <100 nM). ND = not determined.

| Ex. | KIT IC$_{50}$ | PDGFRα IC$_{50}$ | PDGFRβ IC$_{50}$ | CSF1R IC$_{50}$ | FLT3 IC$_{50}$ | M07e Cell IC$_{50}$ |
|---|---|---|---|---|---|---|
| 55 | +++ | ND | ND | + | ND | +++ |
| 56 | ++ | ND | ND | + | ND | ++ |
| 57 | ++ | + | + | + | ND | ND |
| 58 | +++ | + | + | + | ND | +++ |
| 59 | +++ | + | + | + | ND | ND |
| 60 | ++ | + | + | + | ND | ND |
| 61 | +++ | + | + | + | + | ND |
| 62 | +++ | + | + | + | ND | ND |
| 63 | +++ | + | + | + | + | +++ |
| 64 | +++ | + | + | + | + | +++ |
| 65 | +++ | + | + | + | ND | ND |
| 66 | +++ | ND | ND | + | ND | +++ |
| 67 | +++ | + | ++ | + | + | +++ |
| 68 | ++ | + | + | + | ND | ND |
| 69 | ++ | + | + | + | ND | ND |
| 70 | +++ | + | + | + | ND | +++ |
| 71 | +++ | + | + | + | ND | +++ |
| 72 | +++ | + | + | + | ND | +++ |
| 73 | +++ | + | + | + | ND | +++ |
| 74 | +++ | + | + | + | ND | +++ |
| 75 | ++ | + | + | + | + | ++ |
| 76 | +++ | ND | ND | + | ND | +++ |
| 77 | +++ | ND | ND | + | ND | +++ |
| 78 | +++ | + | + | + | + | +++ |
| 79 | +++ | + | + | + | ND | ND |
| 80 | +++ | + | + | + | + | +++ |
| 81 | +++ | ND | ND | + | ND | +++ |
| 82 | +++ | + | + | + | + | +++ |
| 83 | +++ | + | + | + | + | +++ |
| 84 | +++ | + | + | + | ND | +++ |
| 85 | +++ | + | + | + | ND | +++ |
| 86 | +++ | ++ | + | + | + | +++ |
| 87 | +++ | ND | ND | + | + | +++ |
| 88 | ++ | + | + | + | ND | ++ |
| 89 | +++ | + | + | + | + | +++ |
| 90 | +++ | + | + | + | ND | ++ |
| 91 | +++ | ND | ND | + | + | +++ |
| 92 | +++ | + | + | + | ND | +++ |
| 93 | +++ | + | + | + | ND | +++ |
| 94 | +++ | + | + | + | ND | +++ |
| 95 | +++ | + | + | + | ND | +++ |
| 96 | +++ | + | + | + | + | +++ |
| 97 | +++ | + | + | + | ND | ++ |
| 98 | +++ | ND | ND | + | ND | +++ |
| 99 | ++ | + | + | + | ND | ++ |
| 100 | ++ | + | + | + | ND | ++ |
| 101 | +++ | +++ | ++ | + | ND | +++ |
| 102 | +++ | + | + | ++ | + | ++ |
| 103 | +++ | ++ | ++ | + | + | +++ |
| 104 | +++ | ND | ND | ++ | + | +++ |
| 105 | +++ | + | + | + | + | ND |
| 106 | +++ | + | ++ | + | ND | ND |
| 107 | +++ | + | ++ | + | ND | ND |
| 108 | +++ | + | + | + | ND | ND |
| 109 | ++ | + | + | + | ND | ND |
| 110 | +++ | + | ++ | ND | + | +++ |
| 111 | +++ | +++ | +++ | +++ | ND | ND |
| 112 | +++ | + | ++ | ++ | ND | ND |
| 113 | +++ | ++ | +++ | ++ | ND | ND |
| 114 | +++ | ++ | ++ | ++ | + | +++ |
| 115 | +++ | + | + | ++ | + | +++ |
| 116 | +++ | + | ++ | ++ | ND | ND |
| 117 | +++ | + | + | + | + | +++ |
| 118 | +++ | + | ++ | ++ | + | +++ |
| 119 | +++ | + | ++ | ++ | ND | ND |
| 120 | +++ | + | + | + | + | ND |
| 121 | +++ | + | + | + | ND | ND |
| 122 | +++ | + | + | + | + | +++ |
| 123 | +++ | + | + | + | + | +++ |
| 124 | +++ | + | + | + | + | +++ |
| 125 | +++ | + | + | + | ND | ND |
| 126 | +++ | ++ | + | + | ND | ND |
| 127 | ++ | + | + | + | + | ND |
| 128 | +++ | ++ | +++ | ++ | ND | ND |
| 129 | +++ | + | ++ | ++ | + | +++ |
| 130 | +++ | ++ | ++ | ++ | + | + |
| 131 | +++ | + | + | + | + | +++ |
| 132 | +++ | + | + | + | + | +++ |
| 133 | +++ | + | + | + | + | +++ |
| 134 | +++ | ++ | +++ | ++ | + | +++ |
| 135 | +++ | ++ | +++ | ++ | + | +++ |
| 136 | ++ | ++ | + | + | + | ND |
| 137 | +++ | ++ | + | + | + | ND |
| 138 | +++ | ++ | + | + | + | ND |
| 139 | +++ | ++ | ++ | + | + | +++ |
| 140 | +++ | ++ | ++ | ++ | + | +++ |
| 141 | +++ | +++ | +++ | ++ | ND | ND |
| 142 | +++ | ++ | ++ | + | + | +++ |
| 143 | +++ | + | ++ | + | + | +++ |
| 144 | +++ | + | + | + | ND | ND |
| 145 | +++ | + | ++ | ++ | ND | ND |
| 146 | +++ | +++ | +++ | +++ | ND | ND |
| 147 | +++ | ++ | +++ | ++ | + | +++ |
| 148 | +++ | + | + | + | + | +++ |
| 149 | +++ | + | ++ | + | + | +++ |
| 150 | +++ | + | + | + | + | +++ |
| 151 | +++ | ++ | +++ | ++ | ND | ND |
| 152 | +++ | ++ | ++ | + | + | +++ |
| 153 | +++ | + | + | + | ND | ND |
| 154 | +++ | + | + | ND | + | +++ |
| 155 | +++ | ++ | ++ | + | + | +++ |
| 156 | +++ | + | ++ | + | + | +++ |
| 157 | +++ | + | + | + | ND | ND |
| 158 | +++ | ++ | ++ | + | + | +++ |
| 159 | +++ | + | + | + | + | +++ |
| 160 | +++ | + | ++ | ++ | + | ND |
| 161 | +++ | ++ | ++ | ++ | + | ND |
| 162 | +++ | + | + | ++ | ND | ND |
| 163 | +++ | + | + | + | + | ND |
| 164 | +++ | + | + | + | ND | ND |
| 165 | +++ | ++ | +++ | ++ | ND | ND |
| 166 | +++ | + | ++ | ++ | + | ND |
| 167 | +++ | + | + | + | + | ND |
| 168 | +++ | ND | + | + | + | +++ |
| 169 | +++ | + | + | + | ND | ND |
| 170 | +++ | + | ++ | ++ | + | ND |
| 171 | +++ | ++ | ++ | ++ | + | ND |
| 172 | +++ | + | + | + | + | +++ |
| 173 | ++ | + | + | + | ND | ND |
| 174 | +++ | + | + | + | ND | ND |
| 175 | +++ | ++ | +++ | +++ | ND | ND |
| 176 | ++ | + | + | + | ND | ND |
| 177 | +++ | ++ | ++ | ++ | ND | ND |
| 178 | +++ | +++ | +++ | +++ | ND | ND |
| 179 | +++ | + | + | + | + | +++ |
| 180 | +++ | + | + | + | ND | ND |
| 181 | +++ | + | + | + | + | +++ |
| 182 | +++ | + | ++ | + | ND | ND |
| 183 | +++ | +++ | +++ | ++ | ND | ND |
| 184 | +++ | +++ | +++ | ++ | ND | ND |
| 185 | +++ | + | + | + | + | +++ |
| 186 | ++ | + | + | + | ND | ND |
| 187 | +++ | + | + | + | + | +++ |
| 188 | +++ | +++ | +++ | +++ | ND | ND |
| 189 | +++ | + | ++ | ++ | + | +++ |
| 190 | +++ | +++ | +++ | +++ | ND | ND |
| 191 | +++ | + | + | + | + | +++ |
| 192 | +++ | + | ++ | + | + | +++ |
| 193 | +++ | ND | ND | + | + | +++ |
| 194 | +++ | + | + | + | + | ++ |
| 195 | +++ | + | + | + | ++ | +++ |
| 196 | +++ | + | + | + | + | +++ |
| 197 | +++ | + | ++ | + | + | ND |
| 198 | +++ | + | ++ | + | ND | +++ |
| 199 | +++ | + | + | + | ND | ND |
| 200 | +++ | ++ | + | + | ND | ND |

TABLE 4-continued

Biochemical and cellular potency of specific examples vs. KIT, PDGFRα, PDGFRβ, CSF1R, and FLT3 (IC$_{50}$: + means >1 μM, ++ means 100 nM to 1 μM, +++ means <100 nM). ND = not determined.

| Ex. | KIT IC$_{50}$ | PDGFRα IC$_{50}$ | PDGFRβ IC$_{50}$ | CSF1R IC$_{50}$ | FLT3 IC$_{50}$ | M07e Cell IC$_{50}$ |
|---|---|---|---|---|---|---|
| 201 | +++ | + | ++ | ++ | ND | +++ |
| 202 | +++ | + | + | + | + | +++ |
| 203 | +++ | + | ++ | ++ | + | +++ |
| 204 | +++ | ++ | ++ | ++ | + | +++ |
| 205 | +++ | ++ | +++ | +++ | + | +++ |
| 206 | +++ | + | ++ | ++ | + | +++ |
| 207 | +++ | + | + | ++ | ND | +++ |
| 208 | +++ | + | ++ | ++ | + | +++ |
| 209 | +++ | + | ++ | ++ | + | +++ |
| 210 | +++ | + | ++ | ++ | + | +++ |
| 211 | +++ | + | + | + | ND | ND |
| 212 | +++ | + | + | + | + | +++ |
| 213 | +++ | + | + | + | + | +++ |
| 214 | +++ | + | + | + | ND | +++ |
| 215 | ++ | + | + | + | + | + |
| 216 | +++ | + | + | ++ | + | +++ |
| 217 | +++ | + | + | + | + | +++ |
| 218 | +++ | + | + | + | + | +++ |
| 219 | +++ | + | + | + | + | +++ |
| 220 | +++ | + | + | + | + | +++ |
| 221 | +++ | ND | ND | ++ | ND | +++ |
| 222 | +++ | + | + | ND | + | +++ |
| 223 | ++ | + | + | + | ND | ND |
| 224 | +++ | + | ++ | + | ND | ND |
| 225 | +++ | ++ | +++ | ++ | ND | ND |
| 226 | +++ | + | ++ | ++ | + | +++ |
| 227 | +++ | +++ | +++ | +++ | + | ND |
| 228 | +++ | ++ | ++ | ++ | ND | ND |
| 229 | +++ | +++ | +++ | ++ | + | +++ |
| 230 | +++ | ++ | ++ | ++ | + | +++ |
| 231 | +++ | ++ | ++ | ++ | + | +++ |
| 232 | +++ | + | + | ++ | ND | ND |
| 233 | +++ | + | + | + | ND | +++ |
| 234 | +++ | + | + | + | ND | ND |
| 235 | +++ | + | ++ | + | ND | ND |
| 236 | +++ | + | ++ | ++ | + | ND |
| 237 | ++ | + | + | + | ND | ND |
| 238 | +++ | + | +++ | ++ | + | +++ |
| 239 | +++ | + | ++ | + | + | ND |
| 240 | +++ | + | +++ | + | + | ND |
| 241 | +++ | + | + | + | + | +++ |
| 242 | ++ | + | + | + | ND | ND |
| 243 | +++ | +++ | +++ | +++ | ND | ND |
| 244 | +++ | + | ++ | ++ | + | +++ |
| 245 | +++ | + | + | + | + | +++ |
| 246 | +++ | ND | ND | +++ | ND | +++ |
| 247 | +++ | + | ++ | ++ | ND | ND |
| 248 | +++ | + | + | + | ND | ND |
| 249 | +++ | ND | ND | +++ | ND | +++ |
| 250 | ++ | ND | ND | + | ND | ++ |
| 251 | +++ | + | + | + | + | +++ |
| 252 | +++ | + | + | + | ND | ND |
| 253 | +++ | ++ | ++ | + | ND | ND |
| 254 | +++ | + | +++ | ++ | ND | +++ |
| 255 | +++ | ++ | ++ | ++ | + | +++ |
| 256 | +++ | + | ++ | + | + | +++ |
| 257 | +++ | + | ++ | + | + | +++ |
| 258 | +++ | ++ | ++ | ++ | + | +++ |
| 259 | +++ | ++ | +++ | ++ | + | +++ |
| 260 | +++ | + | ++ | ++ | + | +++ |
| 261 | +++ | + | ++ | + | ND | +++ |
| 262 | ++ | + | + | + | ND | +++ |
| 263 | +++ | + | + | + | ND | +++ |
| 264 | +++ | + | + | + | ND | +++ |
| 265 | +++ | + | + | + | ND | +++ |
| 266 | +++ | + | + | + | ND | +++ |
| 267 | ++ | + | + | + | ND | +++ |
| 268 | +++ | + | + | + | ND | +++ |
| 269 | ++ | + | + | + | ND | +++ |
| 270 | ++ | + | + | + | ND | ++ |

Bioactivation Assessment Procedure

Pooled male Sprague Dawley rat (BioIVT), male beagle dog (BioIVT), male cynomolgus monkey (BioIVT), and a 50-donor pool of cryopreserved human hepatocytes (BioIVT) was thawed in pre-warmed 37° C. InVitroGro™ HT media (BioIVT), centrifuged, and resuspended in the InVitroGro™ HI media (BioIVT). The number of viable cells was determined by the Trypan blue exclusion method. The cells were diluted to a concentration of two million viable cells per milliliter (viability>80%) and seeded into round-bottom 96-well plates. The test articles were dissolved in DMSO and further diluted in 5000 CH$_3$CN and InVitroGro™ HI media with final concentrations of 0.05% DMSO and 0.5% CH$_3$CN in the incubation mixture. Incubation was performed at a final concentration of one million cells per milliliter and 5 μM test compounds with continuous shaking at 1100 rpm in a 37° C., 5/9500 CO$_2$/air incubator with 10000 relative humidity. After 4 hours, the samples were quenched by addition of 3 volumes of CH$_3$CN, vortexed for 15 minutes, and centrifuged at 4200 rpm for 15 minutes at 10° C. (Sorvall Legend XTR centrifuge, Thermo Scientific, Langenselbold, Germany). 80 μL of the resulting supernatant was transferred into a new plate and mixed with 160 μL water followed by liquid chromatography-high resolution mass spectrometry (LC-HIRMS) analysis.

Structural assignments of metabolites were determined through mass spectral analysis. The level of bioactivation was estimated based on the relative peak area of bioactivation products to all identified metabolites. The following equation was used:

$$\% \text{ total metabolism via bioactivation} = \frac{\text{Total peak area of bioactivation products}}{\text{Total peak area of metabolites}}$$

Bioactivation products included glutathione conjugates, imine methides, quinones, diols, and other relevant metabolites.

Representative data are shown in Table 5. The data for a comparative KIT inhibitor compound, labuxtinib, having the structure

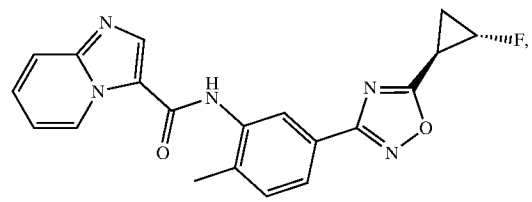 [SMILES: Cc1ccc(-c2noc([C@H]3C[C@@H]3F)n2)cc1NC(=O)c1cnc2ccccn12]

is also included.

TABLE 5

Percent of total metabolism via bioactivation for selected compounds.

| Ex. | Rat hepatocytes | Dog hepatocytes | Monkey hepatocytes | Human hepatocytes |
|---|---|---|---|---|
| 2 | 1-2%[a] | 3-4%[a] | NA | ND[a] |
| 38 | 2% | <1% | NA | ND |
| 3 | <0.1% | 2% | 2% | <0.1% |
| 5 | <1% | 4% | <1% | <1% |
| 4 | <1%[a] | <1%[a] | NA | ND[a] |

TABLE 5-continued

Percent of total metabolism via bioactivation for selected compounds.

| Ex. | Rat hepatocytes | Dog hepatocytes | Monkey hepatocytes | Human hepatocytes |
|---|---|---|---|---|
| 1 | 3-7%[b] | <1%[b] | 4% | <0.1%[b] |
| 242 | 88% | 44% | NA | <1% |
| 46 | 80% | 97% | NA | ND |
| labuxtinib | 45% | 17% | 31% | 24% |

NA = available.
ND = not detected.
[a]Evaluation was done in duplicates.
[b]Evaluation was done four times.

Although the foregoing disclosure has been described in some detail by way of illustration and Example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A compound selected from the group consisting of

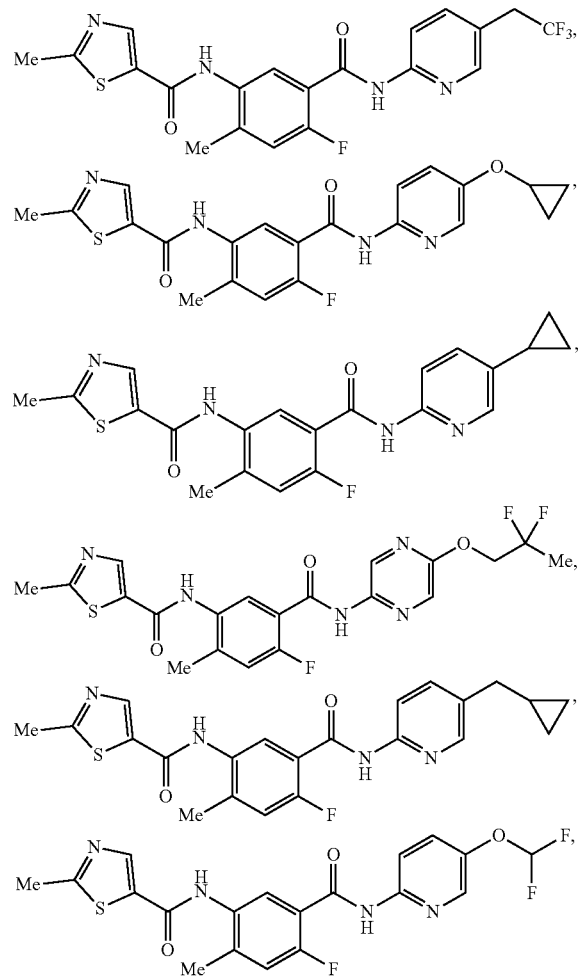

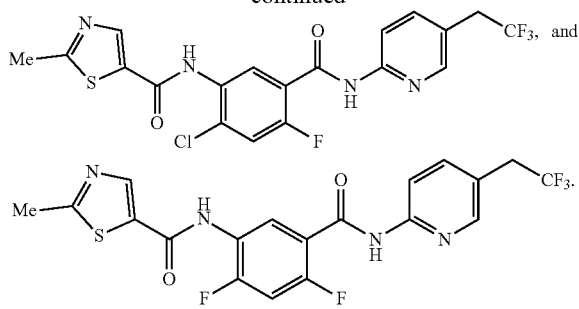

2. The compound of claim 1 selected from the group consisting of

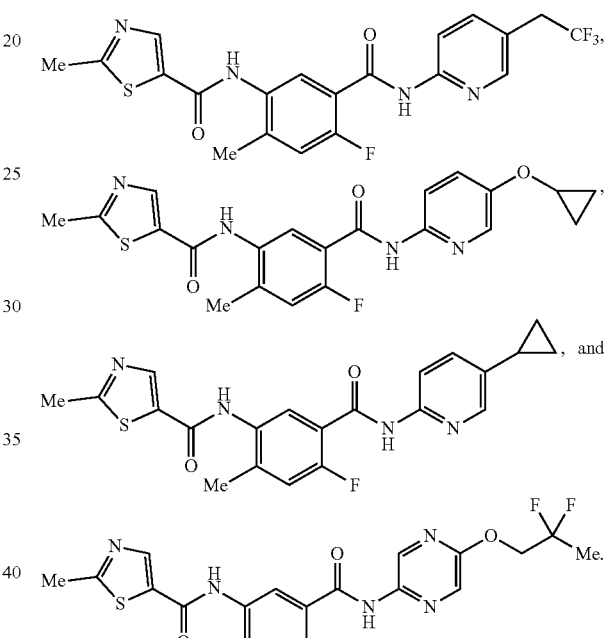

3. The compound of claim 1 selected from the group consisting of

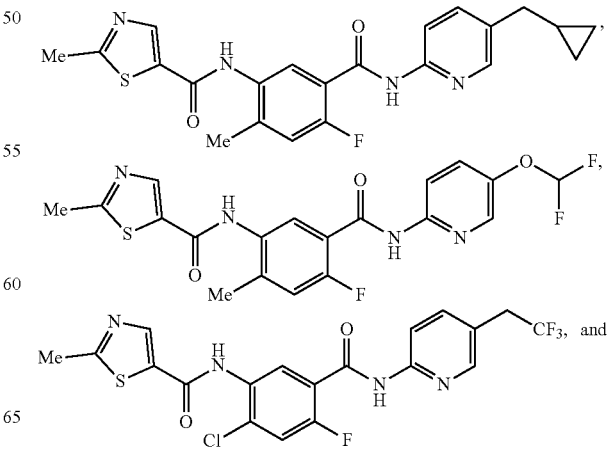

-continued

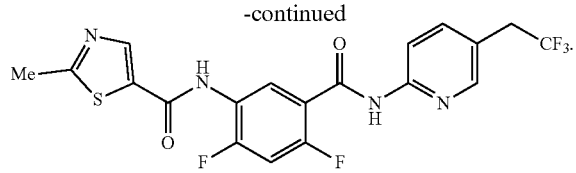

4. The compound of claim 1 having the structure

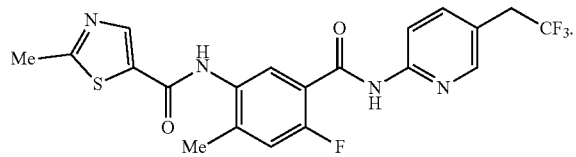

5. The compound of claim 1 having the structure

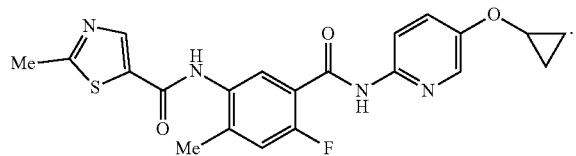 [SMILES: Cc1ncc(C(=O)Nc2cc(C(=O)Nc3ccc(OC4CC4)cn3)c(F)cc2C)s1]

6. The compound of claim 1 having the structure

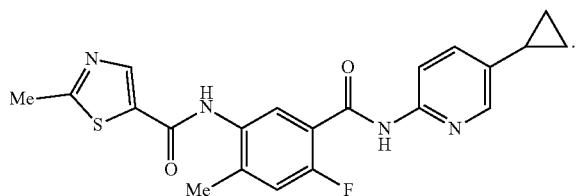 [SMILES: Cc1ncc(C(=O)Nc2cc(C(=O)Nc3ccc(C4CC4)cn3)c(F)cc2C)s1]

7. The compound of claim 1 having the structure

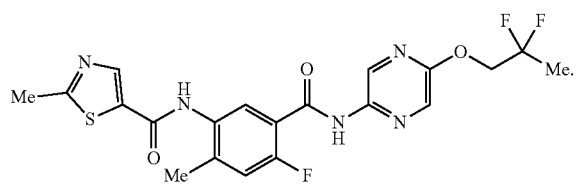 [SMILES: Cc1ncc(C(=O)Nc2cc(C(=O)Nc3cnc(OCC(C)(F)F)cn3)c(F)cc2C)s1]

8. The compound of claim 1 having the structure

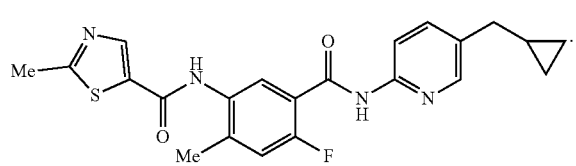 [SMILES: Cc1ncc(C(=O)Nc2cc(C(=O)Nc3ccc(CC4CC4)cn3)c(F)cc2C)s1]

9. The compound of claim 1 having the structure

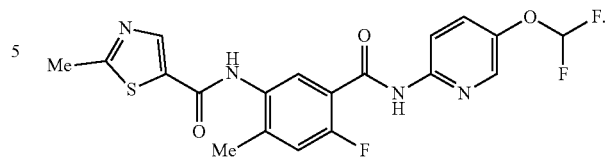

10. The compound of claim 1 having the structure

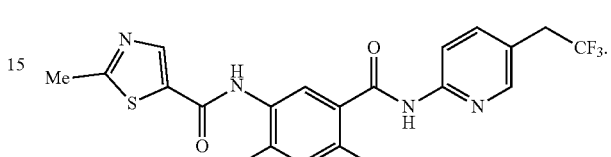

11. The compound of claim 1 having the structure

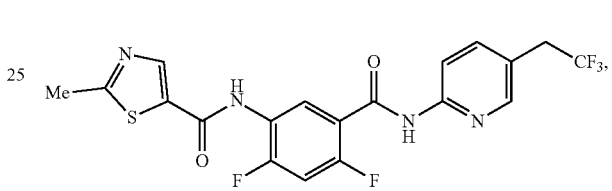

12. A compound having the structure

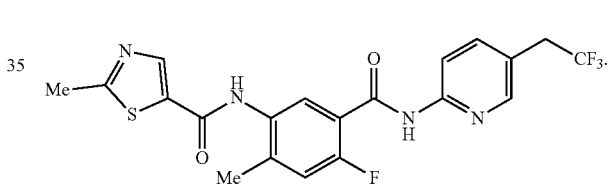

13. A compound having the structure

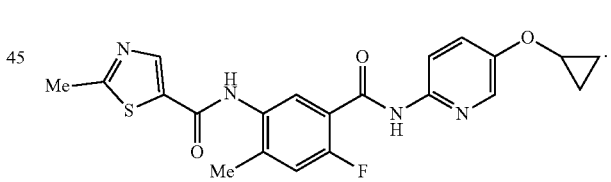

14. A compound having the structure

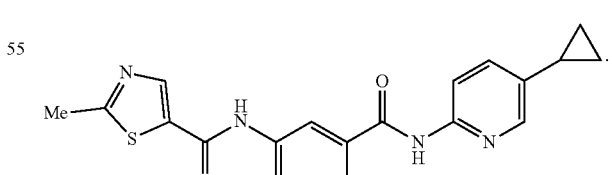

* * * * *